US011572556B2

United States Patent
(12) United States Patent
Abudayyeh et al.
(10) Patent No.: US 11,572,556 B2
(45) Date of Patent: Feb. 7, 2023

(54) SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

(71) Applicant: Massachusetts Institute of Technology, Cambridge, MA (US)

(72) Inventors: Omar Abudayyeh, Cambridge, MA (US); Jonathan Gootenberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/649,308

(22) Filed: Jan. 28, 2022

(65) Prior Publication Data

US 2022/0154224 A1 May 19, 2022

Related U.S. Application Data

(63) Continuation of application No. 17/451,734, filed on Oct. 21, 2021, now abandoned.

(60) Provisional application No. 63/222,550, filed on Jul. 16, 2021, provisional application No. 63/094,803, filed on Oct. 21, 2020.

(51) Int. Cl.

| | |
|---|---|
| ***C12N 15/85*** | (2006.01) |
| ***C12N 15/11*** | (2006.01) |
| ***A61K 31/7105*** | (2006.01) |
| ***C12N 9/12*** | (2006.01) |
| ***C12N 9/22*** | (2006.01) |
| ***C12N 15/10*** | (2006.01) |
| ***C12N 15/113*** | (2010.01) |
| ***C12N 15/90*** | (2006.01) |

(52) U.S. Cl.

CPC ........ *C12N 15/111* (2013.01); *A61K 31/7105* (2013.01); *C12N 9/1276* (2013.01); *C12N 9/22* (2013.01); *C12N 15/102* (2013.01); *C12N 15/113* (2013.01); *C12N 15/85* (2013.01); *C12N 15/907* (2013.01); *C12N 2310/20* (2017.05); *C12N 2310/3519* (2013.01); *C12Y 207/07049* (2013.01)

(58) Field of Classification Search

None

See application file for complete search history.

(56) References Cited

U.S. PATENT DOCUMENTS

| | | | | |
|---|---|---|---|---|
| 9,023,649 | B2 | 5/2015 | Mali et al. | |
| 9,914,939 | B2 | 3/2018 | Church et al. | |
| 10,113,163 | B2 | 10/2018 | Liu et al. | |
| 10,125,361 | B2 | 11/2018 | May et al. | |
| 11,193,123 | B2 | 12/2021 | Halperin | |
| 11,299,731 | B1 * | 4/2022 | Held | C12N 15/1093 |
| 11,352,623 | B2 * | 6/2022 | Halperin | C12N 15/11 |
| 11,447,770 | B1 | 9/2022 | Liu et al. | |
| 2011/0059502 | A1 | 3/2011 | Chalasani | |
| 2014/0186958 | A1 | 7/2014 | Zhang et al. | |
| 2014/0349400 | A1 | 11/2014 | Noah et al. | |
| 2015/0071898 | A1 | 3/2015 | Liu et al. | |
| 2018/0230464 | A1 | 8/2018 | Zhong | |
| 2019/0055543 | A1 | 2/2019 | Tran et al. | |
| 2019/0062734 | A1 | 2/2019 | Cotta-Ramusino et al. | |
| 2019/0330619 | A1 | 10/2019 | Smith et al. | |
| 2020/0109398 | A1 | 4/2020 | Rubens | |
| 2022/0119848 | A1 | 4/2022 | Doudna | |

FOREIGN PATENT DOCUMENTS

| | | | |
|---|---|---|---|
| WO | 2015035139 | A2 | 3/2015 |
| WO | 2015195798 | A1 | 12/2015 |
| WO | 2016205728 | A1 | 12/2016 |
| WO | 2017151719 | A1 | 9/2017 |
| WO | 2018049161 | A1 | 3/2018 |
| WO | 2018049168 | A1 | 3/2018 |
| WO | 2018165629 | A1 | 9/2018 |
| WO | 2019051097 | A1 | 3/2019 |
| WO | 2019118935 | A1 | 6/2019 |
| WO | 2020047124 | A1 | 3/2020 |
| WO | 2020191153 | A2 | 9/2020 |
| WO | 2020191171 | A1 | 9/2020 |
| WO | 2020191233 | A1 | 9/2020 |
| WO | 2020191234 | A1 | 9/2020 |
| WO | 2020191239 | A1 | 9/2020 |

(Continued)

OTHER PUBLICATIONS

Flotte (Human Gene Therapy, 2019, vol. 30, No. 2, pp. 1445-1446). (Year: 2019).*

Anzalone et al. Nature 2019, vol. 576, 149-157, and methods and supplement. (Year: 2019).*

Maeder et al., Development of a Gene-Editing Approach to Restore Vision Loss in Leber Congenital Amaurosis Type 10, Letters, Nature Medicine, 25, 229-233 (2019).

(Continued)

*Primary Examiner* — Celine X Qian

(74) *Attorney, Agent, or Firm* — Laura A. Labeots; Lathrop GPM LLP

(57) ABSTRACT

This disclosure provides systems, methods, and compositions for site-specific genetic engineering using Programmable Addition via Site-Specific Targeting Elements (PASTE). PASTE comprises the addition of an integration site into a target genome followed by the insertion of one or more genes of interest or one or more nucleic acid sequences of interest at the site. PASTE combines gene editing technologies and integrase technologies to achieve unidirectional incorporation of genes in a genome for the treatment of diseases and diagnosis of disease.

23 Claims, 144 Drawing Sheets

Specification includes a Sequence Listing.

(56) References Cited

FOREIGN PATENT DOCUMENTS

| | | | |
|---|---|---|---|
| WO | 2020191241 | A1 | 9/2020 |
| WO | 2020191242 | A1 | 9/2020 |
| WO | 2020191243 | A1 | 9/2020 |
| WO | 2020191245 | A1 | 9/2020 |
| WO | 2020191246 | A1 | 9/2020 |
| WO | 2020191248 | A1 | 9/2020 |
| WO | 2020191249 | A1 | 9/2020 |
| WO | 2020247587 | A1 | 12/2020 |
| WO | 2021046243 | A2 | 3/2021 |
| WO | 2021072328 | A1 | 4/2021 |
| WO | 2021138469 | A1 | 7/2021 |
| WO | 2021188840 | A1 | 9/2021 |
| WO | 2021226558 | A1 | 11/2021 |
| WO | 2022067130 | A2 | 3/2022 |
| WO | 2022087235 | A1 | 4/2022 |
| WO | 2022098885 | A1 | 5/2022 |

OTHER PUBLICATIONS

Anzalone, et al., Genome Editing with CRISPR-Cas Nucleases, Base Editors, Transposases and Prime Editors, Nat. Biotechnol. 38, 824-844 (2020).

Jiang et al., Deletion and Replacement of Long Genomic Sequences Using Prime Editing. Nat. Biotechnol. 1-8 (2021).

Hsu, P. D., Lander, E. S. & Zhang, F. Development and applications of CRISPR-Cas9 for genome engineering. Cell 157, 1262-1278 (2014).

Wright, A. V., Nuñez, J. K. & Doudna, J. A. Biology and Applications of CRISPR Systems: Harnessing Nature's Too1box for Genome Engineering. Cell 164, 29-44 (2016).

Nami, F. et al. Strategies for In Vivo Genome Editing in Nondividing Cells. Trends Biotechnol. 36, 770-786 (2018).

Suzuki, K. et al. In vivo genome editing via CRISPR/Cas9 mediated homology-independent targeted integration. Nature 540, 144-149 (2016).

Mali, P. et al. RNA-guided human genome engineering via Cas9. Science 339, 823-826 (2013).

Cong, L. et al. Multiplex genome engineering using CRISPR/Cas systems. Science 339, 819-823 (2013).

Rouet, P., Smih, F. & Jasin, M. Introduction of double-strand breaks into the genome of mouse cells by expression of a rare-cutting endonuclease. Mol. Cell. Biol. 14, 8096-8106 (1994).

Rudin, N., Sugarman, E. & Haber, J. E. Genetic and physical analysis of double-strand break repair and recombination in *Saccharomyces cerevisiae*. Genetics 122, 519-534 (1989).

Chapman, J. R., Taylor, M. R. G. & Boulton, S. J. Playing the end game: DNA double-strand break repair pathway choice. Mol. Cell 47, 497-510 (2012).

Geisinger, J. M. & Stearns, T. CRISPR/Cas9 treatment causes extended TP53-dependent cell cycle arrest in human cells. Nucleic Acids Res. 48, 9067-9081 (2020).

Wang, H. et al. Development of a Self-Restricting CRISPR-Cas9 System to Reduce Off-Target Effects. Mol Ther Methods Clin Dev 18, 390-401 (2020).

Kanca, O. et al. An efficient CRISPR-based strategy to insert small and large fragments of DNA using short homology arms. Elife 8, (2019).

Gaudelli, N. M. et al. Programmable base editing of A•T to G•C in genomic ONA without DNA cleavage. Nature 551, 464-471 (2017).

Komor, A. C., Kim, Y. B., Packer, M. S., Zuris, J. A. & Liu, D. R. Programmable editing of a target base in genomic DNA without double-stranded DNA cleavage. Nature 533, 420-424 (2016).

Rees, H. A. & Liu, D. R. Base editing: precision chemistry on the genome and transcriptome of living cells. Nat. Rev. Genet. 19, 770-788 (2018).

Anzalone, A. V. et al. Search-and-replace genome editing without double-strand breaks or donor DNA. Nature 576, 149-157 (2019).

Ivics, Z., Hackett, P. B., Plasterk, R. H. & Izsvak, Z. Molecular reconstruction of Sleeping Beauty, a Tc1-like transposon from fish, and its transposition in human cells. Cell 91, 501-510 (1997).

Choi, J. et al. Precise genomic deletions using paired prime editing. Nat. Biotechnol. 1-9 (2021).

Calos, M. P. The C31 Integrase System for Gene Therapy. Curr. Gene Ther. 6, 633-645 (2006).

Mulholland, C. B. et al. A modular open platform for systematic functional studies under physiological conditions. Nucleic Acids Res. 43, e112 (2015).

Ehrhardt, A., Engler, J. A., Xu, H., Cherry, A. M. & Kay, M. A. Molecular Analysis of Chromosomal Rearrangements in Mammalian Cells After øC31-Mediated Integration. Hum. Gene Ther. 17, 1077-1094 (2006).

Liu, J., Jeppesen, I., Nielsen, K. & Jensen, T. G. Phi c31 integrase induces chromosomal aberrations in primary human fibroblasts. Gene Ther. 13, 1188-1190 (2006).

Kovac, A. et al. RNA-guided retargeting of Sleeping Beauty transposition in human cells. Elife 9, (2020).

Ma, S. et al. Enhancing site-specific DNA integration by a Cas9 nuclease fused with a DNA donor-binding domain. Nucleic Acids Res. 48, 10590-10601 (2020).

Chen, S. P. & Wang, H. H. An Engineered Cas-Transposon System for Programmable and Site-Directed DNA Transpositions. CRISPR J 2, 376-394 (2019).

Bhatt, S. & Chalmers, R. Targeted DNA transposition using a dCas9-transposase fusion protein. bioRxiv 571653 (2019) doi:10. 1101/571653.

Hew, B. E., Sato, R., Mauro, D., Stoytchev, I. & Owens, J. B. RNA-guided piggyBac transposition in human cells. Synth. Biol. 4, ysz018 (2019).

Chaikind, B., Bessen, J. L., Thompson, D. B., Hu, J. H. & Liu, D. R. A programmable Cas9-serine recombinase fusion protein that operates on DNA sequences in mammalian cells. Nucleic Acids Res. 44, 9758-9770 (2016).

Akopian, A., He, J., Boocock, M. R. & Stark, W. M. Chimeric recombinases with designed DNA sequence recognition. Proc. Natl. Acad. Sci. U. S. A. 100, 8688-8691 (2003).

Gordley, R. M., Smith, J. D., Graslund, T. & Barbas, C. F., 3rd. Evolution of programmable zinc finger-recombinases with activity in human cells J. Mol. Biol. 367, 802-813 (2007).

Mercer, A. C., Gaj, T., Fuller, R. P. & Barbas, C. F., 3rd. Chimeric TALE recombinases with programmable DNA sequence specificity. Nucleic Acids Res. 40, 11163-11172 (2012).

Gersbach, C. A., Gaj, T., Gordley, R. M., Mercer, A. C. & Barbas, C. F. Targeted plasmid integration into the human genome by an engineered zinc-finger recombinase. Nucleic Acids Res 39, 7868-7878 (2011).

Prorocic, M. M. et al. Zinc-finger recombinase activities in vitro. Nucleic Acids Res. 39, 9316-9328 (2011).

Zhang, Q., Azarin, S. M. & Sarkar, C. A. Model-guided engineering of DNA sequences with predictable site-specific recombination rates. bioRxiv Aug. 2, 2021 454698 (2021) doi:10 1101/2021.08. 02.454698.

Peters, J. E., Makarova, K. S., Shmakov, S. & Koonin, E. V. Recruitment of CRISPR-Cas systems by Tn7-like transposons. Proc. Natl. Acad. Sci. U. S. A. 114, E7358-E7366 (2017).

Strecker, J. et al. RNA-guided DNA insertion with CRISPR-associated transposases. Science (2019) doi:10.1126/science. aax9181.

Klompe, S. E., Vo, P. L. H., Halpin-Healy, T. S. & Sternberg, S. H. Transposon-encoded CRISPR-Cas systems direct RNA-guided DNA integration. Nature 1 (2019).

Xu, Z. et al. Accuracy and efficiency define Bxb1 integrase as the best of fifteen candidate serine recombinases for the integration of DNA into the human genome. BMC Biotechnol. 13, 87 (2013).

Kay, M. A., He, C.-Y. & Chen, Z.-Y. A robust system for production of minicircle DNA vectors. Nat. Biotechnol. 28, 1287-1289 (2010).

Dang, Y. et al. Optimizing sgRNA structure to improve CRISPR-Cas9 knockout efficiency. Genome Biol. 16, 280 (2015).

Oscorbin, I. P., Wong, P. F., Boyarskikh, U. A., Khrapov, E. A. & Filipenko, M. L. The attachment of a DNA-binding Sso7d-like protein improves processivity and resistance to inhibitors of M-MuLV reverse transcriptase. FEBS Lett. 594, 4338-4356 (2020).

(56) References Cited

OTHER PUBLICATIONS

Ghosh, P., Kim, A. I. & Hatfull, G. F. The orientation of mycobacteriophage Bxb1 integration is solely dependent on the central dinucleotide of attP and attB. Mol. Cell 12, 1101-1111 (2003).
Keravala, A. et al. A diversity of serine phage integrases mediate site-specific recombination in mammalian cells. Molecular Genetics and Genomics vol. 276 (2006).
Singh, S., Ghosh, P. & Hatfull, G. F. Attachment site selection and identity in Bxb1 serine integrase-mediated site-specific recombination. PLoS Genet. 9, e1003490 (2013).
Brown et al., "Serine recombinases as tools for genome engineering." Methods, 2011; 53(4):372-9.
Hirano et al., "Site-specific recombinases as tools for heterologous gene integration." Appl. Microbiol. Biotechnol. 2011: 92(2):227-39.
Chavez and Calos, "Therapeutic applications of the ΦC31 integrase system." Curr. Gene Ther. 2011; 11(5):375-81.
Turan and Bode, "Site-specific recombinases: from tag-and-target-to tag-and-exchange-based genomic modifications." FASEB J. 2011; 25(12):4088-107.
Menken and Bellen, "Genome-wide manipulations of *Drosophila melanogaster* with transposons, Flp recombinase, and ΦC31 integrase." Methods Mol. Biol. 2012; 859:203-28.
Murphy, "Phage recombinases and their applications." Adv. Virus Res. 2012; 83:367-414.
Zhang et al., "Conditional gene manipulation: Creating a new biological era." J. Zhejiang Univ. Sci. B. 2012; 13(7):511-24.
Karpenshif and Bernstein, "From yeast to mammals: recent advances in genetic control of homologous recombination." DNA Repair (Amst). 2012; 1; 11(10):781-8.
Groth et al., "Phage integrases: biology and applications." J. Mol. Biol. 2004; 335, 667-678.
Gordley et al., "Synthesis of programmable integrases." Proc. Natl. Acad. Sci. USA. 2009; 106, 5053-5058.
Moss, W. N. et al., RNA Biol. 2011, 8(5), 714-718.
Burke, W. D. et al., Molecular Biology and Evolution 2003, 20(8), 1260-1270).
Wang et al., 2010, Genome Res. 20, 19-27.
Bannert and Kurth, 2006, Proc. Natl. Acad. USA 101, 14572-14579.
Lander et al., 2001, Nature 409, 860-921; Hua-Van et al., 2011, Biol. Dir. 6, 19.
Graham et al. (1973) Virology, 52:456.
Anzalone et al., Programmable Large DNA Deletion, Replacement, Integration, and Inversion with Twin Prime Editing and Site-Specific Recombinases, https://doi.org/10.1101/2021.11.01.466790.
Gaj, et al., Genome-Editing Technologies: Principles and Applications, Cold Spring Harbor Perspectives in Biology 2016;8:a023754.
Anzalone et al, Programmable Deletion, Replacement, Integration and Inversion of Large DNA Sequences with Twin Prime Editing, Nature Biotechnology, Dec. 9, 2021.
Innis et al., A Novel Bxb1 Integrase RMCE System for High Fidelity Site-Specific Integration of mAb Expression Cassette in CHO Cells, Biotechnology and BioEngineering, John Wiley, Hoboken, USA, vol. 114, No. 8, Mar. 14, 2017, pp. 1837-1846.
Merrick, et al., Serine Integrases: Advancing Synthetic Biology, ACS Synthetic Biology, vol. 7, No. 2, Jan. 9, 2018, pp. 299-310.
Lee et al., Conditional Targeting of Ispd Using Paired Cas9 Nickase and a Single DNA Template in Mice, FEBS Open Bio, vol. 4, No. 1, Jul. 1, 2014, pp. 637-642.
PCT Application No. PCT/US2021/056006, International Search Report and Written Opinion, dated Feb. 23, 2022, 20 pages.
Jusiak, B. et al. Comparison of Integrases Identifies Bxb1-GA Mutant as the Most Efficient Site-Specific Integrase System in Mammalian Cells. ACS Synth. Biol. 8, 16-24 (2019).
Schwinn, M. K. et al. CRISPR-Mediated Tagging of Endogenous Proteins with a Luminescent Peptide. ACS Chem. Biol. 13, 467-474 (2018).
Lin, S., Staahl, B. T., Alla, R. K. & Doudna, J. A. Enhanced homology-directed human genome engineering by controlled timing of CRISPR/Cas9 delivery. Elife 3, e04766 (2014).
Schnepp, B. C., Jensen, R. L., Chen, C.-L., Johnson, P. R. & Clark, K. R. Characterization of adeno-associated virus genomes isolated from human tissues. J. Virol. 79, 14793-14803 (2005).
Wold, W. S. M. & Toth, K. Adenovirus vectors for gene therapy, vaccination and cancer gene therapy. Curr. Gene Ther. 13, 421-433 (2013).
Wesselhoeft, R. A., Kowalski, P. S. & Anderson, D. G. Engineering circular RNA for potent and stable translation in eukaryotic cells. Nat. Commun. 9, 2629 (2018).
Azuma, H. et al. Robust expansion of human hepatocytes in Fah-/-/Rag2-/-/Il2rg-/-mice. Nat. Biotechnol. 25, 903-910 (2007).
Bateman, A. et al. UniProt: the universal protein knowledgebase in 2021. Nucleic Acids Res. (2020).
Amberger, J. S., Bocchini, C. A., Schiettecatte, F., Scott, A. F. & Hamosh, A. OMIM.org: Online Mendelian Inheritance in Man (OMIM®), an online catalog of human genes and genetic disorders. Nucleic Acids Res 43, D789-98 (2015).
Ruan, J. et al. Efficient Gene Editing at Major CFTR Mutation Loci. Mol. Ther. Nucleic Acids 16, 73-81 (2019).
Mackay, D. S. et al. Screening of a large cohort of leber congenital amaurosis and retinitis pigmentosa patients identifies novel LCA5 mutations and new genotype-phenotype correlations. Hum. Mutat. 34, 1537-1546 (2013).
Marson, F. A. L., Bertuzzo, C. S. & Ribeiro, J. D. Classification of CFTR mutation classes. The Lancet. Respiratory medicine vol. 4 e37-e38 (2016).
Eyquem, J. et al. Targeting a CAR to the TRAC locus with CRISPR/Cas9 enhances tumour rejection. Nature 543, 113-117(2017).
Tareen, A. & Kinney, J. B. Logomaker: beautiful sequence logos in Python. Bioinformatics 36, 2272-2274 (2020).
Su, Q., Sena-Esteves, M. & Gao, G. Purification of the recombinant Adenovirus by cesium chloride gradient centrifugation. Cold Spring Harb. Protoc. 2019, db.prot095547 (2019).
Anzalone, A., et al., "Programmable deletion, replacement, integration and inversion of large DNA sequences with twin prime editing," Nat. Biotechnol., 2022, 40(5):731-740.
Chen, P., et al., "Enhanced prime editing systems by manipulating cellular determinants of editing outcomes," Cell, 2021, 184(22):5635-5652.e29.
Guilinger, J., et al., "Fusion of catalytically inactive Cas9 to FokI nuclease improves the specificity of genome modification," Nat. Biotechnol., 2014, 32(6):577-582.
Halperin, S., et al., "CRISPR-guided DNA polymerases enable diversification of all nucleotides in a tunable window," Nature, 2018, 560(7717):248-252. doi: 10.1038/s41586-018-0384-8.
Ioannidi, E., et al., "Drag-and-drop genome insertion without DNA cleavage with CRISPR-directed integrases," bioRxiv, 2021. doi: 10.1101/2021.11.01.466786.
Jiang, T., et al., "Deletion and replacement of long genomic sequences using prime editing," Nat. Biotechnol., 2022, 40(2):227-234.
Krzywkowski, T., et al., "Limited reverse transcriptase activity of phi29 DNA polymerase," Nucleic Acids Res., 2018, 46(7):3625-3632.
Lee, H. K., et al., "Simultaneous targeting of linked loci in mouse embryos using base editing," Sci. Rep., 2019, 9(1):1662.
Lin, Q., et al., "High-efficiency prime editing with optimized, paired pegRNAs in plants," Nat. Biotechnol., 2021, 39(8):923-927.
Marzec, M., et al., "Prime Editing: A New Way for Genome Editing," Trends Cell Biol., 2020, 30(4):257-259.
Mohr, G., et al., "A Reverse Transcriptase-Cas1 Fusion Protein Contains a Cas6 Domain Required for Both CRISPR RNA Biogenesis and RNA Spacer Acquisition," Molecular Cell, 2018, 72(4):700-714, available at https://doi.org/10.1016/j.molcel.2018.09.013.
Nelson, J., et al., "Engineered pegRNAs improve prime editing efficiency," Nat. Biotechnol., 2022, 40(3):402-410. https://doi.org/10.1038/s41587-021-01039-7.
Pallarès-Masmitjà, M., et al., "Find and cut-and-transfer (FiCAT) mammalian genome engineering," Nat. Commun., 2021, 12(1):7071. https://doi.org/10.1038/s41467-021-27183-x.

(56) References Cited

OTHER PUBLICATIONS

Ran, F. A., et al., "Double Nicking by RNA-Guided CRISPR Cas9 for Enhanced Genome Editing Specificity," Cell, 2013, 154(6):1380-89.
Sharon, E., et al., "Functional Genetic Variants Revealed by Massively Parallel Precise Genome Editing," Cell, 2018, 175(2):544-557.e16.
Su, Y., et al., "Human DNA polymerase η has reverse transcriptase activity in cellular environments," J. Biol. Chem., 2019, 294(15):6073-6081.
Wang, J., et al., "Efficient targeted insertion of large DNA fragments without DNA donors," Nat. Methods, 2022, 19(3):331-340. https://doi.org/10.1038/s41592-022-01399-1.
Wang, Z., et al., "Optimized paired-sgRNA/Cas9 cloning and expression cassette triggers high-efficiency multiplex genome editing in kiwifruit," Plant Biotechnol. J., 2018, 16(8):1424-1433.
Xu, W., et al., "Multiplex Nucleotide Editing by High-Fidelity Cas9 Variants with Improved Efficiency in Rice," BMC Plant Biol., 2019, 19(1):511.
Yang, L., et al., "One Prime for All Editing," Cell, 2019, 179(7):1448-1450.

* cited by examiner

FIG. 26A
PASTE
25
20
15
10
5
0
% EGFP Editing
+ Bxb1
– Bxb1
PBS 13 13
RT 29 29
guide ACTB NT

SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

CROSS REFERENCE TO RELATED APPLICATIONS

This application is a continuation of U.S. application Ser. No. 17/451,734, filed Oct. 21, 2021, which claims the benefit of U.S. Provisional Patent Application Ser. No. 63/222,550, filed Jul. 16, 2021 and U.S. Provisional Patent Application Ser. No. 63/094,803, filed Oct. 21, 2020. The entire contents of the above-referenced patent applications are incorporated by reference in their entirety herein.

GOVERNMENT INTEREST

This invention was made with government support under EB031057 by the National Institutes of Health. The government has certain rights in the invention.

FIELD OF DISCLOSURE

The subject matter disclosed herein is generally directed to systems, methods, and compositions for site-specific genetic engineering using Programmable Addition via Site-Specific Targeting Elements (PASTE) for the treatment of diseases and diagnostics.

BACKGROUND

Editing genomes using the RNA-guided DNA targeting principle of CRISPR-Cas (Clustered Regularly Interspaced Short Palindromic Repeats-CRISPR associated proteins) immunity has been widely exploited and has become a powerful genome editing means for a wide variety of applications. The main advantage of CRISPR-Cas system lies in the minimal requirement for programmable DNA interference: an endonuclease, such as a Cas9, Cas12, or any programmable nucleases, guided by a customizable dual-RNA structure. Cas9 is a multi-domain enzyme that uses an HNH nuclease domain to cleave the target strand. The CRISPR/Cas9 protein-RNA complex is localized on the target by a guide RNA (guide RNA), then cleaved to generate a DNA double strand break (dsDNA break, DSB). After cleavage, DNA repair mechanisms are activated to repair the cleaved strand. Repair mechanisms are generally from one of two types: non-homologous end joining (NHEJ) or homologous recombination (HR). In general, NHEJ dominates the repair, and, being error prone, generates random indels (insertions or deletions) causing frame shift mutations, among others. In contrast, HR has a more precise repairing capability and is potentially capable of incorporating the exact substitution or insertion. To enhance HR, several techniques have been tried, for example: combination of fusion proteins of Cas9 nuclease with homology-directed repair (HDR) effectors to enforce their localization at DSBs, introducing an overlapping homology arm, or suppression of NHEJ. Most of these techniques rely on the host DNA repair systems.

Recently, new guided editors have been developed, such as guided prime editors (PE) PE1, PE2, and PE3, e.g., Liu, D. et al., Nature 2019, 576, 149-157. These PEs are reverse transcriptase (RT) fused with Cas 9 H 840A nickase (Cas9n (H840A)), and the genome editing is achieved using a prime-editing guide RNA (pegRNA). Despite these developments, programmable gene integration is still generally dependent on cellular pathways or repair processes.

Therefore, there is a need for more effective tools for gene editing and delivery.

SUMMARY

The present disclosure provides a method of site-specific integration of a nucleic acid into a cell genome. The method comprises incorporating an integration site at a desired location in the cell genome by introducing into the cell a DNA binding nuclease linked to a reverse transcriptase domain, wherein the DNA binding nuclease comprises a nickase activity; and a guide RNA (gRNA) comprising a primer binding sequence linked to an integration sequence, wherein the gRNA interacts with the DNA binding nuclease and targets the desired location in the cell genome, wherein the DNA binding nuclease nicks a strand of the cell genome and the reverse transcriptase domain incorporates the integration sequence of the gRNA into the nicked site, thereby providing the integration site at the desired location of the cell genome. The method further comprises integrating the nucleic acid into the cell genome by introducing into the cell a DNA or RNA strand comprising the nucleic acid linked to a sequence that is complementary or associated to the integration site, and an integration enzyme, wherein the integration enzyme incorporates the nucleic acid into the cell genome at the integration site by integration, recombination, or reverse transcription of the sequence that is complementary or associated to the integration site, thereby introducing the nucleic acid into the desired location of the cell genome of the cell.

In some embodiments, the gRNA can be hybridized to a complementary strand of the cell genome to the genomic strand that is nicked by the DNA binding nuclease.

In some embodiments, the integration enzyme can be introduced as a peptide or a nucleic acid encoding the same.

In some embodiments, the DNA binding nuclease can be introduced as a peptide or a nucleic acid encoding the same.

In some embodiments, the DNA or RNA strand comprising the nucleic acid can be introduced into the cell as a minicircle, a plasmid, mRNA or a linear DNA.

In some embodiments, the DNA or RNA strand comprising the nucleic acid can be between 1000 bp and 10,000 bp.

In some embodiments, the DNA or RNA strand comprising the nucleic acid can be more than 10,000 bp.

In some embodiments, the DNA or RNA strand comprising the nucleic acid can be less than 1000 bp.

In some embodiments, the DNA comprising the nucleic acid can be introduced into the cell as a minicircle.

In some embodiment, the minicircle cannot comprise sequences of a bacterial origin.

In some embodiments, the DNA binding nuclease can be linked to a reverse transcriptase domain and the integration enzyme can be linked via a linker. The linker can be cleavable. The linker can be non-cleavable. The linker can be replaced by two associating binding domains of the DNA binding nuclease linked to a reverse transcriptase.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the integration site can be selected from an attB site, an attP site, an attL site, an attR site, a lox71 site a Vox site, or a FRT site.

In some embodiments, the DNA binding nuclease comprising a nickase activity can be selected from Cas9-D10A, Cas9-H840A, and Cas12a/b nickase.

In some embodiments, the reverse transcriptase domain can be selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium rectale* maturase RT (MarathonRT).

In some embodiments, the reverse transcriptase domain can comprise a mutation relative to the wild-type sequence.

In some embodiments, the M-MLV reverse transcriptase domain can comprise one or more mutations selected from the group consisting of D200N, T306K, W313F, T330P and L603W.

In some embodiments, the method can further comprise introducing a second nicking guide RNA (ngRNA). The ngRNA can direct nicking at 90 bases downstream of the gRNA nick on a complementary strand.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced into a cell in a single reaction.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced using a virus, a RNP, an mRNA, a lipid, or a polymeric nanoparticle.

In some embodiments, the nucleic acid can be a reporter gene. The reporter gene can be a fluorescent protein.

In some embodiments, the cell can be a dividing cell.

In some embodiments, the cell can be a non-dividing cell.

In some embodiments, the desired location in the cell genome can be the locus of a mutated gene.

In some embodiments, the nucleic acid can be a degradation tag for programmable knockdown of proteins in the presence of small molecules.

In some embodiments, the cell can be a mammalian cell, a bacterial cell or a plant cell.

In some embodiments, nucleic acid can be a T-cell receptor (TCR), a chimeric antigen receptor (CAR), an interleukin, a cytokine, or an immune checkpoint gene for integration into a T-cell or natural killer (NK) cell. The TCR, the CAR, the interleukin, the cytokine, or the immune checkpoint gene can be incorporated into the target site of the T-cell or NK cell genome using a minicircle DNA.

In some embodiments, the nucleic acid can be a beta hemoglobin (HBB) gene and the cell can be a hematopoietic stem cell (HSC). The HBB gene can be incorporated into the target site in the HSC genome using a minicircle DNA. The nucleic acid can be a gene responsible for beta thalassemia or sickle cell anemia.

In some embodiments, the nucleic acid can be a metabolic gene. The metabolic gene can be involved in alpha-1 antitrypsin deficiency or ornithine transcarbamylase (OTC) deficiency. The metabolic gene can be a gene involved in inherited diseases.

In some embodiments, the nucleic acid can be a gene involved in an inherited disease or an inherited syndrome. The inherited disease can be cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

The present disclosure provides a vector comprising a nucleic acid encoding a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the linker can comprise two associating binding domains of the DNA binding nuclease linked to a reverse transcriptase.

In some embodiments, the integration enzyme can comprise a conditional activation domain or conditional expression domain.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, MarathonRT, or a RTX. The reverse transcriptase can be a modified M-MLV reverse transcriptase relative to the wildtype M-MLV reverse transcriptase. The M-MLV reverse transcriptase domain can comprise one or more of the mutations selected from the group consisting of D200N, T306K, W313F, T330P and L603W.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the recombinase or integrase can be Bxb1 or a mutant thereof.

The present disclosure provides a cell comprising a vector comprising a nucleic acid encoding a DNA binding nuclease comprising a nickase activity C-terminally linked to a reverse transcriptase linked to an integration enzyme via a linker. The cell further comprises a gRNA comprising a primer binding sequence, an integration sequence, and a guide sequence, wherein the gRNA can interact with the encoded nuclease comprising a nickase activity. The cell further comprising a DNA minicircle comprising a nucleic acid and a sequence recognized by the encoded integrase, recombinase, or reverse transcriptase. The cell further comprising a nicking guide RNA (ngRNA) capable of binding the encoded nuclease comprising a nickase activity, and wherein the ngRNA targets a sequence away from the gRNA.

In some embodiments, the minicircle cannot comprise a sequence of bacterial origin.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA binding nuclease comprising a nickase activity can be selected from the group consisting of Cas9-D10A, Cas9-H840A and Cas12a.

In some embodiments, the reverse transcriptase can be a M-MLV reverse transcriptase. The reverse transcriptase can be a modified M-MLV reverse transcriptase. The amino acid sequence of the M-MLV reverse transcriptase can comprise one or more mutations selected from the group consisting of D200N, T306K, W313F, T330P, and L603W.

In some embodiments, the cell can further comprise introducing ngRNA to the cell. The ngRNA can be a +90 ngRNA. The +90 ngRNA can direct nicking at 90 bases downstream of the gRNA nick on a complementary strand.

The present disclosure provides a polypeptide comprising a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, a MarathonRT, or a XRT. The reverse transcriptase can be a modified M-MLV relative to a wild-type M-MLV reverse transcriptase. The M-MLV reverse transcriptase domain can comprise one or more of mutations selected from the group consisting of D200N, T306K, W313F, T330P, and L603W.

In some embodiments, the integration enzyme can be selected from group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

The present disclosure provides a gRNA that specifically binds to a DNA binding nuclease comprising nickase activity, the gRNA comprising a primer binding site, which hybridizes to a nicked DNA strand, a recognition site for an integration enzyme, and a target recognition sequence recognizing a target site in a cell genome and hybridizing to a genomic strand complementary to the strand that is nicked by the DNA binding nuclease.

In some embodiments, the DNA binding nuclease comprising a nickase activity can be selected from the group consisting of Cas9-D10A, Cas9-H840A, and Cas12a/b.

In some embodiments, the primer binding site can hybridize to the 3' end of the nicked DNA strand.

In some embodiments, the recognition site for the integration enzyme can be selected from an attB site, an attP site, an attL site, an attR site, a lox71 site, and a FRT site.

In some embodiments, the recognition site for the integration enzyme can be a Bxb1 site.

The present disclosure provides a method of site-specific integration of two or more nucleic acids into a cell genome. The method comprises incorporating two integration sites at desired locations in the cell genome by introducing into the cell a DNA binding nuclease linked to a reverse transcriptase domain, wherein the DNA binding nuclease comprises a nickase activity, and two guide RNAs (gRNAs), each comprising, a primer binding sequence, linked to a unique integration sequence, wherein the gRNA interacts with the DNA binding nuclease and targets the desired locations in the cell genome, wherein the DNA binding nuclease nicks a strand of the cell genome and the reverse transcriptase domain incorporates each of the integration sequence of the gRNA into the nicked site, thereby providing the integration site at the desired locations of the cell genome. The method further comprises integrating the nucleic acid by introducing into the cell two or more DNA or RNA comprising the nucleic acids, wherein each DNA is flanked by orthogonal integration sites, and an integration enzyme, wherein the integration enzyme incorporates the nucleic acids into the cell genome at the integration sites by integrase, recombinase, or reverse transcriptase of the sequence that is complementary or associated to the integration site, thereby introducing the nucleic acids into the desired locations of the cell genome of the cell.

In some embodiments, each of the two different integration sites inserted into the cell genome can be attB sequences comprising different palindromic or non-palindromic central dinucleotide.

In some embodiments, each of the two different integration sites inserted into the cell genome can be attP sequences comprising different palindromic or non-palindromic central dinucleotide.

In some embodiments, the integration enzyme can enable each of the two or more DNA or RNA comprising the nucleic acids to directionally enable integration of the nucleic acids into a genome via recombination of a pair of orthogonal attB site sequence and an attP site sequence.

In some embodiments, the integration enzyme can be selected from the group consisting of Cre, Dre, Vika, Bxb1, φC31, RDF, FLP, φBT1, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R1, R2, R3, R4, R5, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA comprising genes can be genes involved in a cell maintenance pathway, cell-division, or a signal transduction pathway.

In some embodiments, the reverse transcriptase domain can comprise Moloney Murine Leukemia Virus (M-MLV) reverse transcriptase domain, transcription xenopolymerase (RTX), avian myeloblastosis virus reverse transcriptase (AMV-RT), or *Eubacterium rectale* maturase RT (MarathonRT).

In some embodiments, the DNA binding nuclease comprising a nickase activity can be selected from the group consisting of Cas9-D10A, Cas9-H840A, and Cas12a/b.

In some embodiments, the pair of an attB site sequence and an attP site sequence can be selected from the group consisting of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34 and SEQ ID NO: 35 and SEQ ID NO: 36.

The present disclosure provides a cell comprising a vector comprising a nucleic acid encoding a DNA binding nuclease comprising a nickase activity, wherein the DNA binding nuclease is C-terminally linked to a reverse transcriptase, wherein the reverse transcriptase is linked to a recombinase or integrase via a linker. The cell further comprises two guide RNAs (gRNAs) comprising a primer binding sequence, an integration sequence and a guide sequence, wherein the gRNA can interact with the encoded DNA binding nuclease comprising a nickase activity. The cell further comprises two or more DNA or RNA strands comprising a nucleic acid and a pair of flanking attB site sequence and an attP site sequence recognized by the encoded integrase or recombinase. The cell optionally further comprises a nicking guide RNA (ngRNA) capable of binding the encoded nuclease comprising a nickase activity, and wherein the ngRNA targets a sequence away from the gRNA.

The present disclosure provides a cell comprising a modified genome, wherein the modification comprises incorporation of two orthogonal integration sites within the cell genome by introducing into the cell a: vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA.

The present disclosure provides a method of integrating two or more nucleic acids into the cell genome of cell of claim 90, the method comprising introducing into the cell: two or more DNA, each comprising a nucleic acid and a pair of flanking orthogonal integration site sequences; an integration enzyme that can recognize the integration site sequence enabling directional linking of the two or more DNA comprising nucleic acid; and enabling incorporation of the nucleic acids into the cell genome by integrating the 5' orthogonal integration sequence of the first DNA with the first genomic integration sequence and 3' orthogonal integration sequence of the last DNA with the last genomic integration sequence, thereby incorporating the two or more nucleic acids into the cell genome.

The present disclosure provides a cell comprising a modified genome, wherein the modification comprises incorporation of two orthogonal integration sites within the cell genome by introducing into the cell: a vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA; two or more DNA or RNA comprising the nucleic acids, wherein each DNA is flanked by orthogonal integration sites; and an integration enzyme, wherein the integration enzyme incorporates the nucleic acids into the cell genome at the integration sites.

BRIEF DESCRIPTION OF THE DRAWINGS

Aspects, features, benefits and advantages of the embodiments described herein will be apparent with regard to the following description, appended claims, and accompanying drawings where:

FIG. 29E discloses: a first portion of the PASTE guide RNA, SEQ ID NO:428 (gacgagcgcg gcgauaucau caucca uggc cggaugaucc ugacgacgga gaccgccguc gucgacaagc cggccugagc ugcgagaa), comprising the RT, AttB site, and PBS, presented 5' to 3' from right to left in the figure; a second portion of the PASTE gRNA (pegRNA) comprising the genomic targeting spacer, SEQ ID NO:431 (accacucgac gcucuuaucg), presented 3' to 5' from right to left in the figure; separate nicking guide SEQ ID NO:429 (gaagccggcc uugcacaugc) presented 5' to 3' from right to left in the figure; a portion of the ACTB exon 1 genomic locus shown double stranded, with top strand SEQ ID NO:430 (gcgcgcccgg ctattctcgc agctcaccat ggatgatgat atcgccgcgc tcgtcgtcga caacggctcc ggcatgtgca aggccggctt cgcgg) presented 5' to 3' left to right in the figure;

FIG. 40C shows the validation of ddPCR assays for detecting editing at predicted PASTE ACTB Cas9 guide off-target sites using synthetic amplicons according to embodiments of the present teachings;

FIG. 40D shows the validation of ddPCR assays for detecting editing at predicted HITI ACTB Cas9 guide off-target sites using synthetic amplicons according to embodiments of the present teachings;

FIG. 41A shows a number of significant differentially regulated genes in HEK293FT cells expressing Bxb1 integrase, PASTE targeting ACTB integration of EGFP, or Prime editing targeting ACTB for EGFP insertion without Bxb1 expression according to embodiments of the present teachings;

Figure 41A:
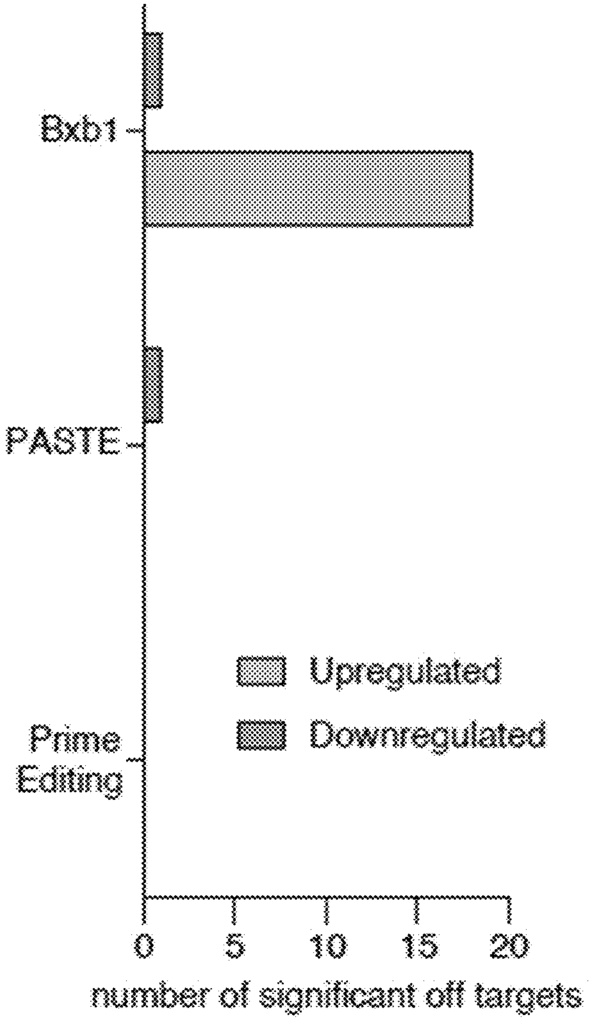
Figure 41B:
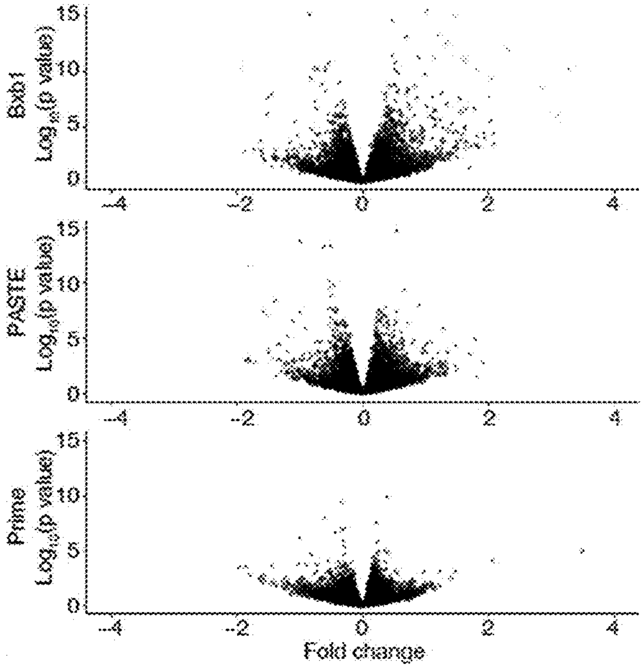
Figure 41C:
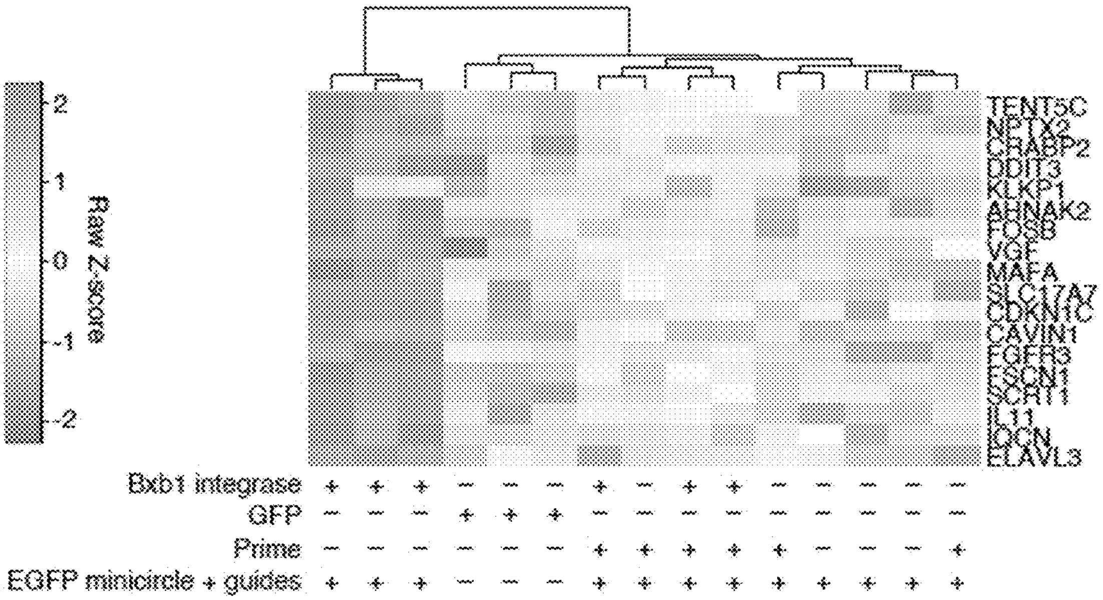
Figure 42A:
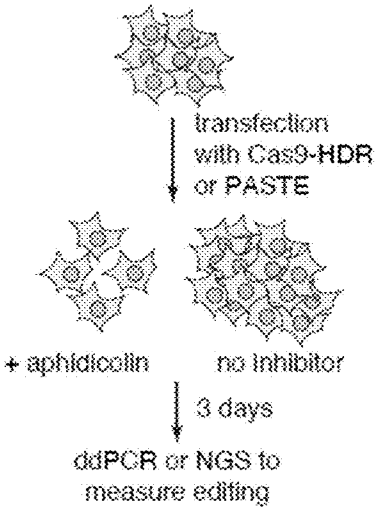
Figure 42B:
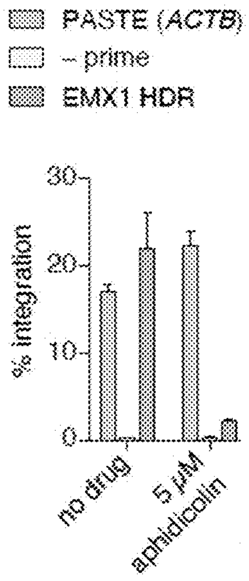
Figure 42C:
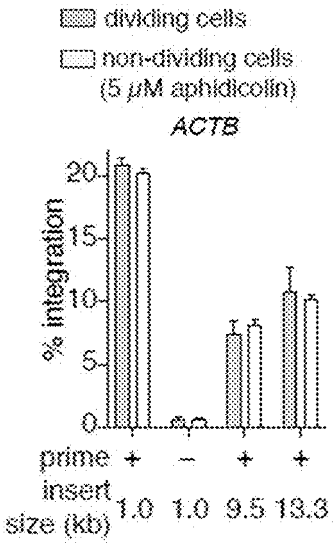
Figure 42D:
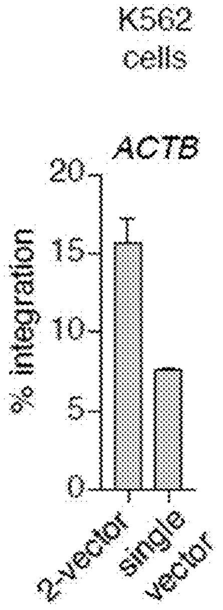
Figure 42E:
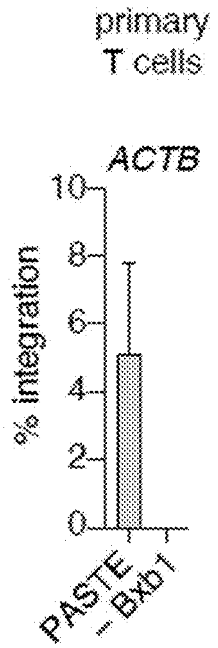
Figure 42F:
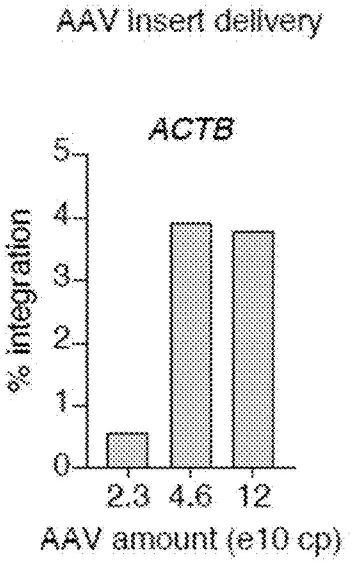
Figure 42G:
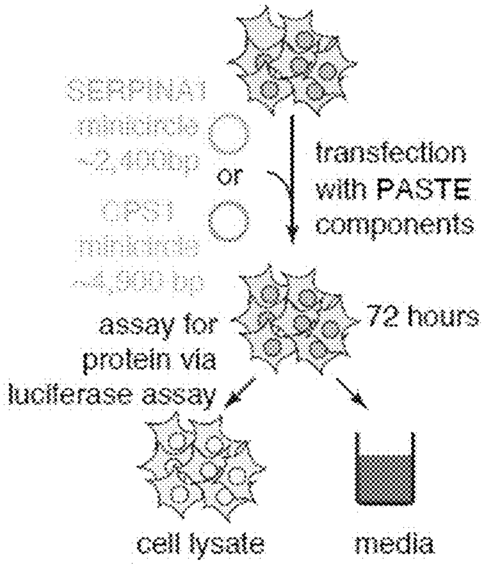
Figure 42H:
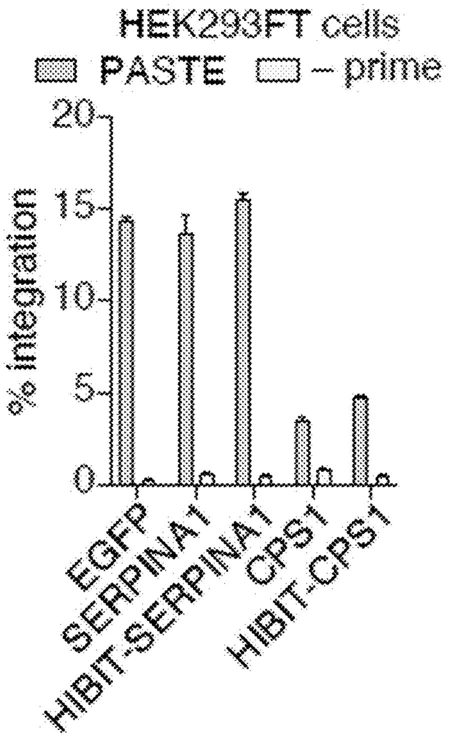
Figure 42I:
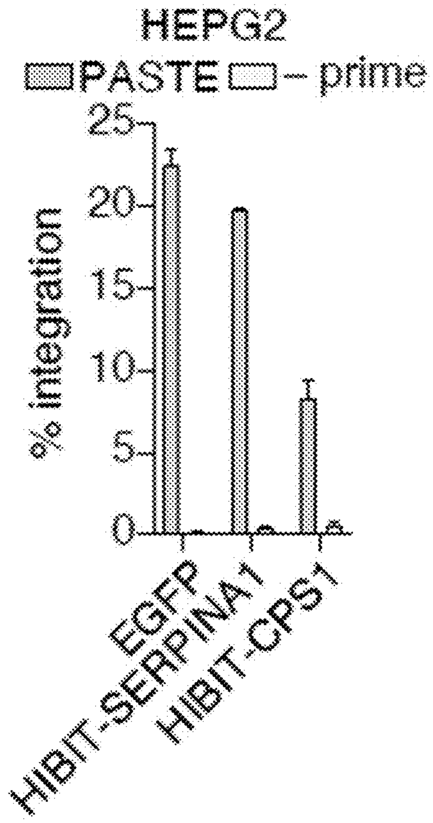
Figure 42J:
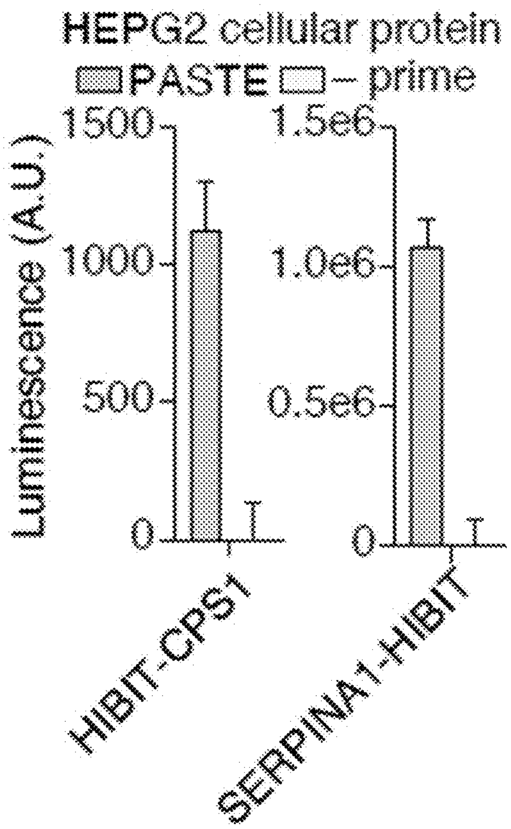
Figure 42K:
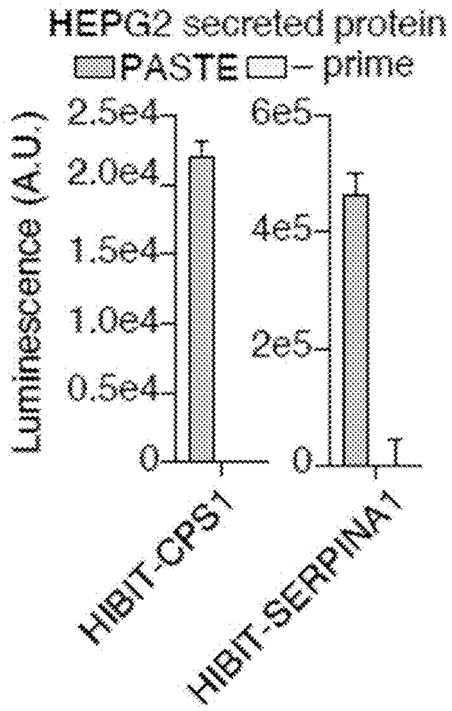
Figure 43A:
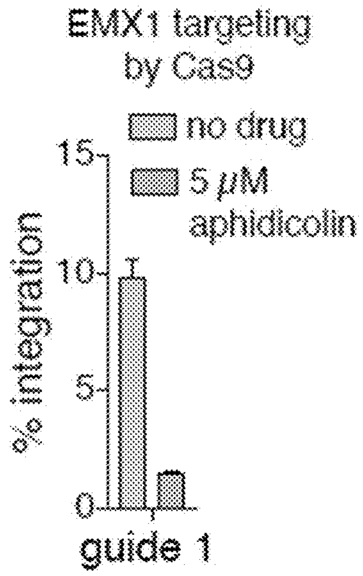
Figure 43B:
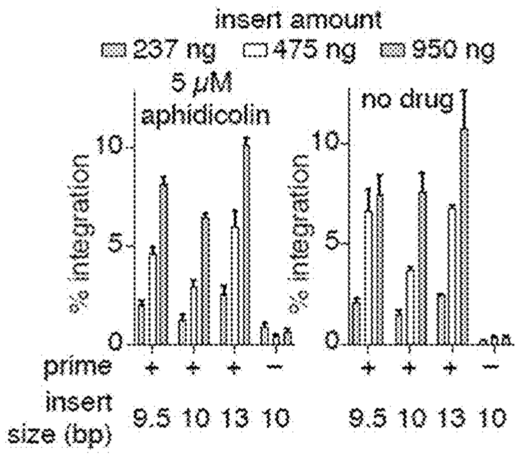
Figure 43C:
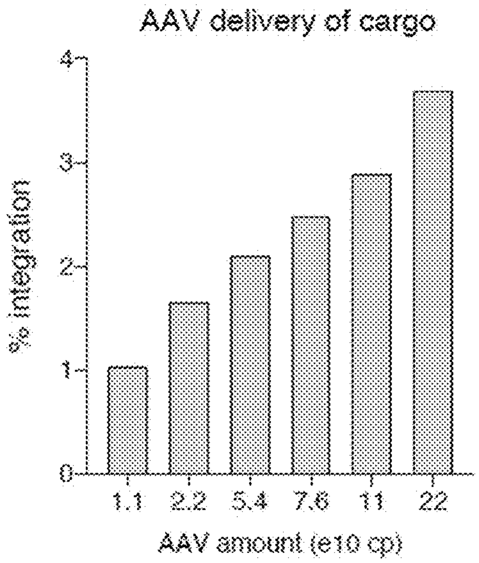
Figure 44A:
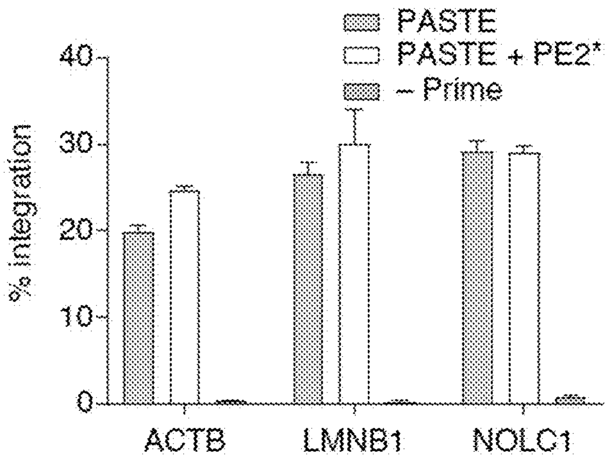
Figure 44B:
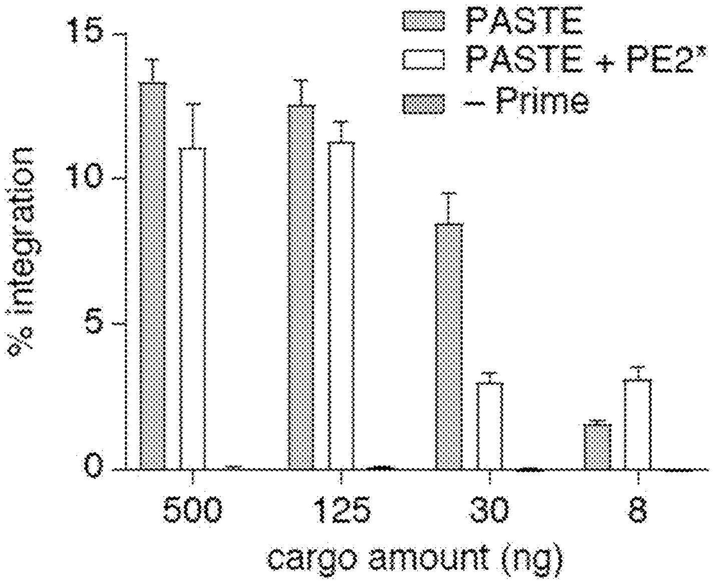
Figure 45:
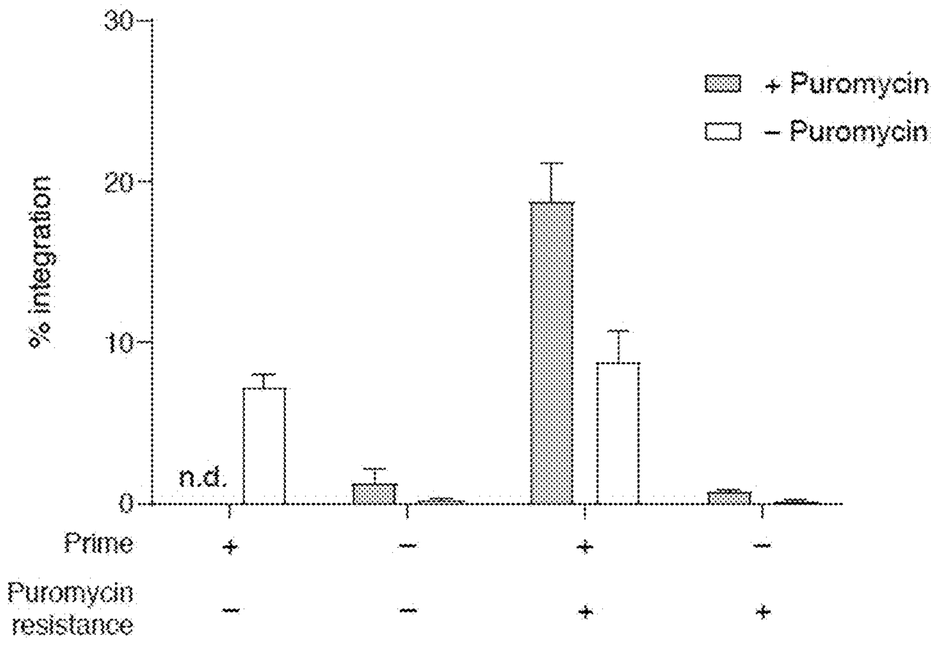
Figure 46A:
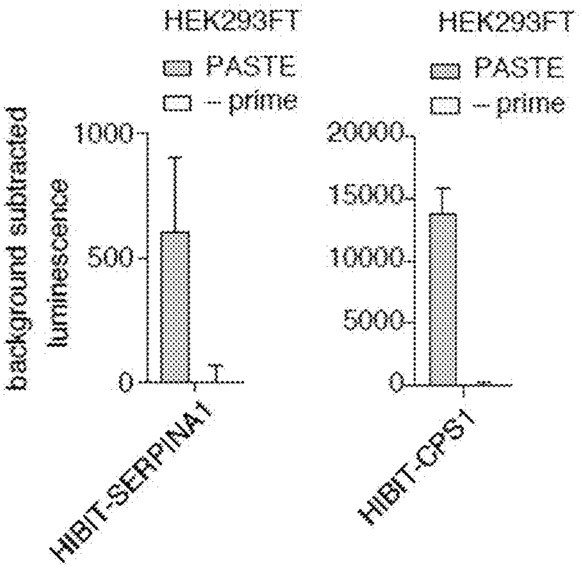
Figure 46B:
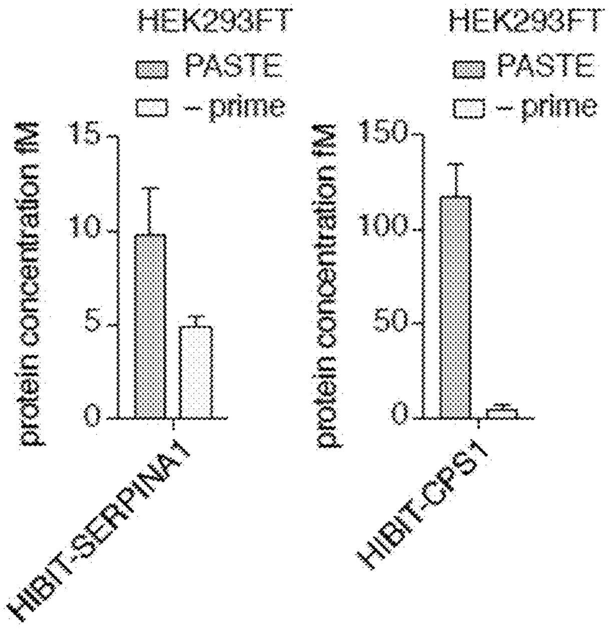
Figure 47A:
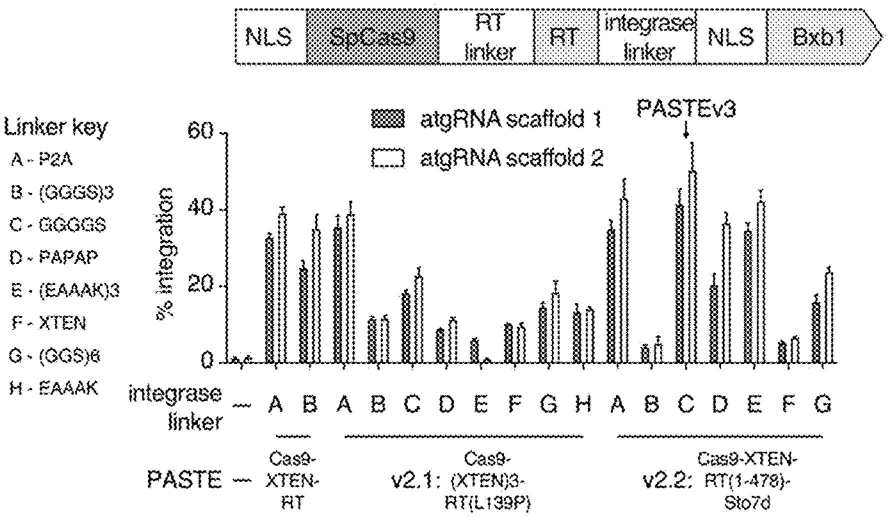
Figure 47B:
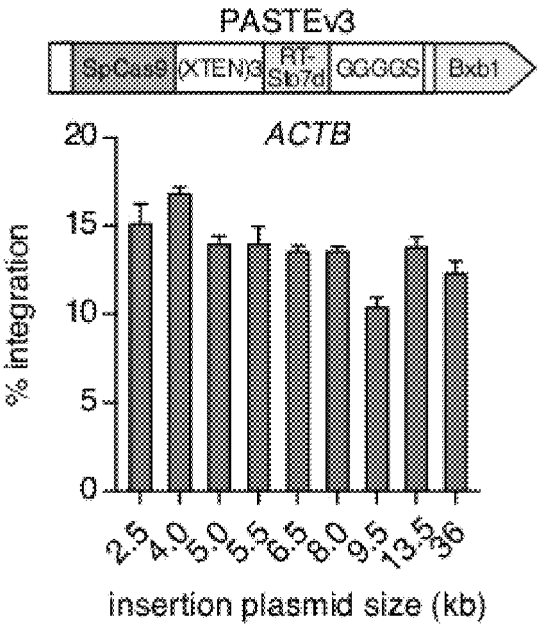
Figure 48A:
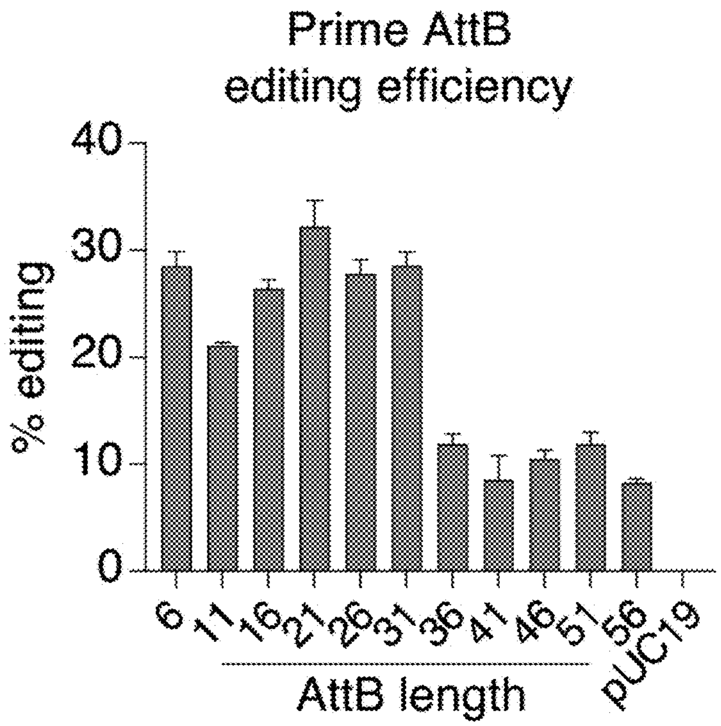
Figure 48B:
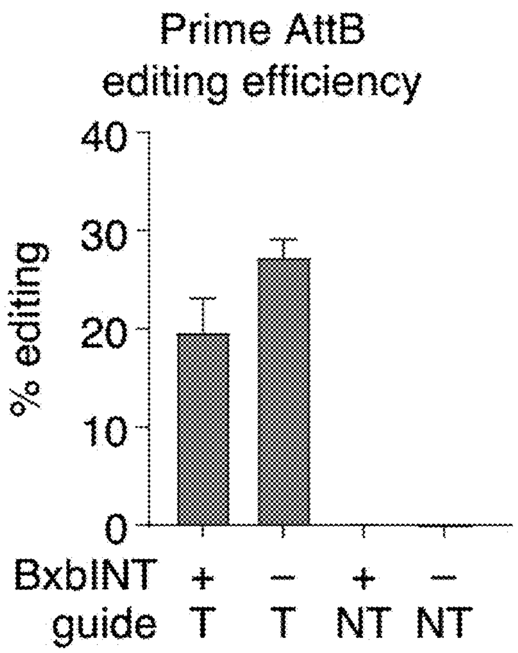
Figure 48C:
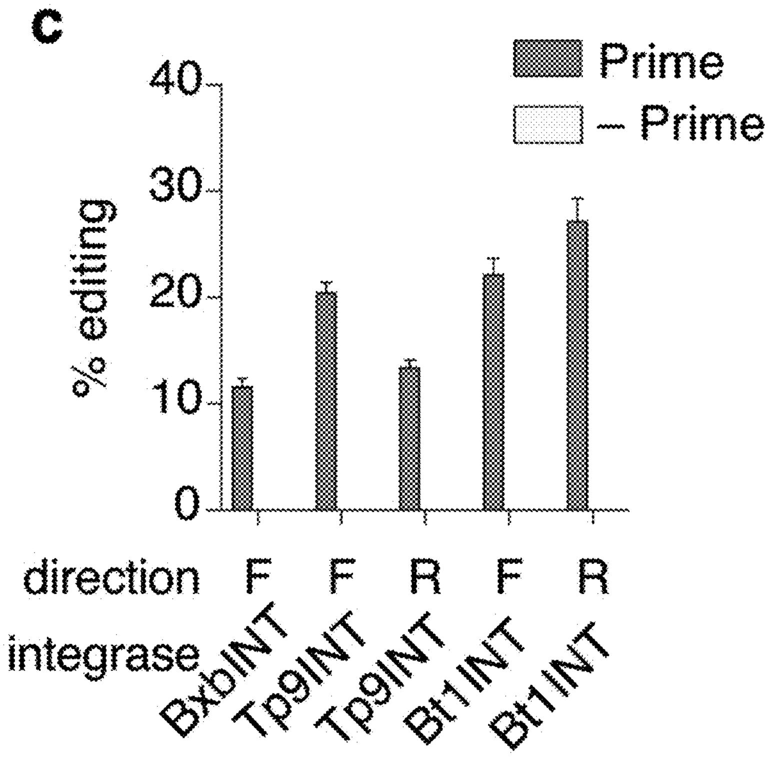
Figure 48D:
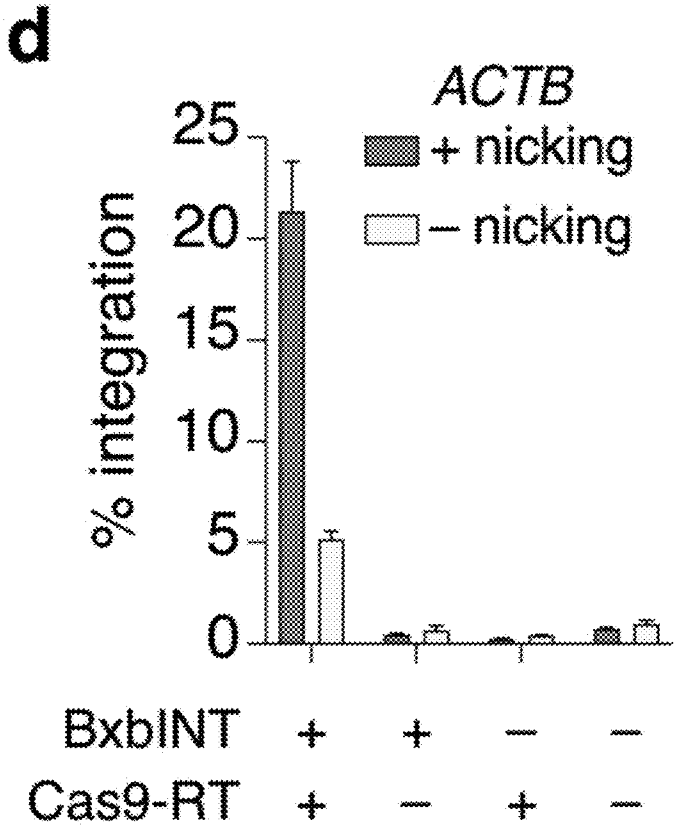
Figures 49A, 49B, 49C, 49D, 49E, 49F:
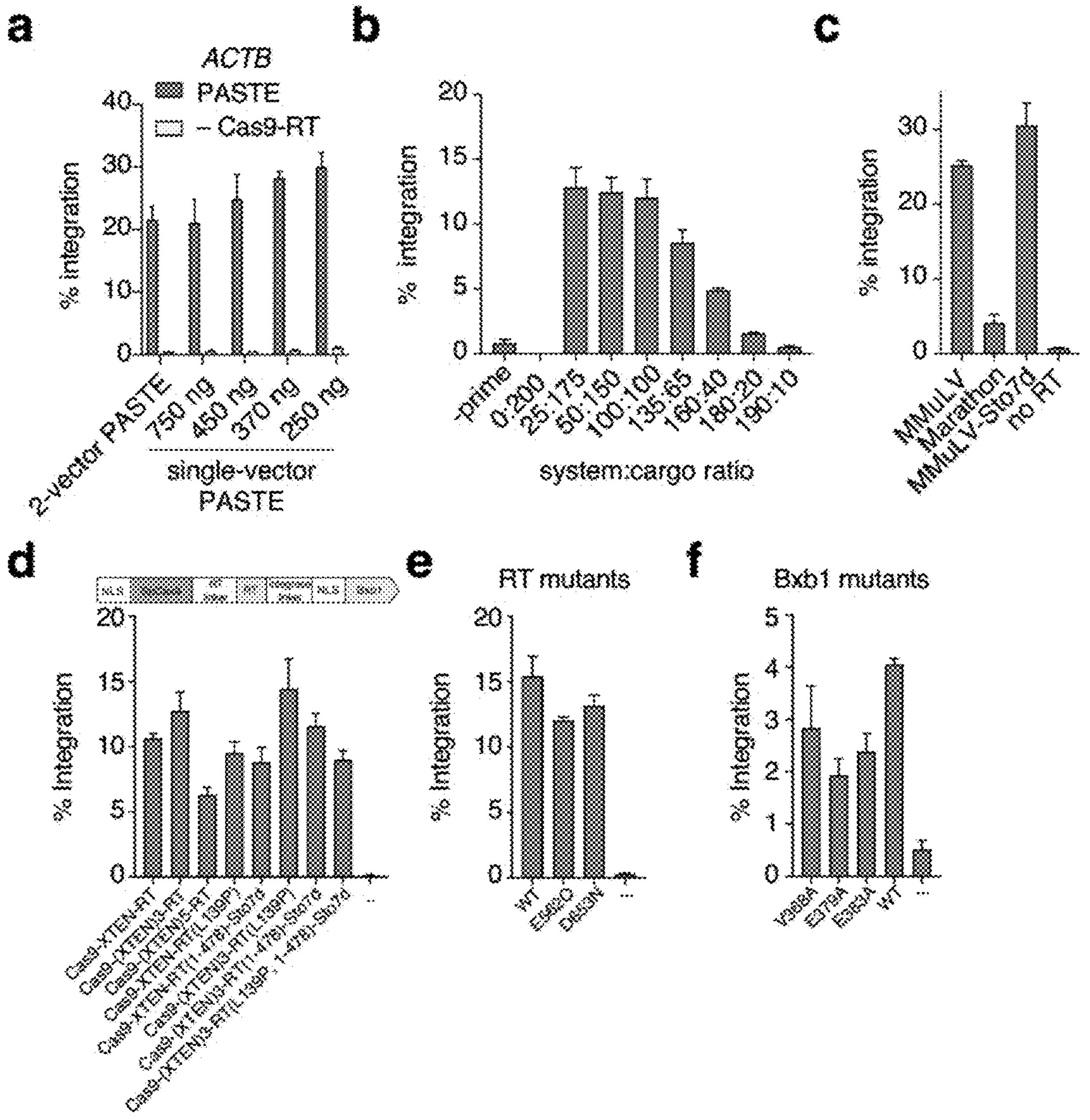

FIG. 41B shows Volcano plots depicting the fold expression change of sequenced mRNAs versus significance (p-value), wherein each dot represents a unique mRNA transcript and significant transcripts are shaded according to either upregulation (red) or downregulation (blue), and wherein fold expression change is measured against ACTB-targeting guide-only expression (including cargo) according to embodiments of the present teachings;

FIG. 41C shows top significantly upregulated and downregulated genes for Bxb1-only conditions, wherein genes are shown with their corresponding Z-scores of counts per million (cpm) for Bxb1 only expression, GFP-only expression, PASTE targeting ACTB for EGFP insertion, Prime targeting ACTB for EGFP expression without Bxb1, and guide/cargo only according to embodiments of the present teachings;

FIG. 42A shows a schematic of PASTE performance in the presence of cell cycle inhibition, wherein cells are transfected with plasmids for insertion with PASTE or Cas9-induced HDR and treated with aphidicolin to arrest cell division, and wherein the efficiency of PASTE and HDR are read out with ddPCR or amplicon sequencing respectively according to embodiments of the present teachings;

FIG. 42B shows the editing efficiency of single mutations by HDR at EMX1 locus with two Cas9 guides in the presence or absence of cell division read out with amplicon sequencing according to embodiments of the present teachings;

FIG. 42C shows the integration efficiency of various sized GFP inserts up to 13.3 kb at the ACTB locus with PASTE in the presence or absence of cell division according to embodiments of the present teachings;

FIG. 42D shows the PASTE editing efficiency with two vector (PE2 and Bxb1) and single vector (PE2-P2A-Bxb1) designs in K562 cells according to embodiments of the present teachings;

FIG. 42E shows the PASTE editing efficiency with single vector (PE2-P2A-Bxb1) designs in primary human T cells according to embodiments of the present teachings;

FIG. 42F shows the integration efficiency of therapeutically relevant genes at the ACTB locus according to embodiments of the present teachings;

FIG. 42G shows a schematic of protein production assay for PASTE-integrated transgene, wherein SERPINA1 and CPS1 transgenes are tagged with HIBIT luciferase for readout with both ddPCR and luminescence according to embodiments of the present teachings;

FIG. 42H shows the integration efficiency of SERPINA1 and CPS1 transgenes in HEK293FT cells at the ACTB locus according to embodiments of the present teachings;

FIG. 42I shows the integration efficiency of SERPINA1 and CPS1 transgenes in HepG2 cells at the ACTB locus according to embodiments of the present teachings;

FIG. 42J shows the intracellular levels of SERPINA1-HIBIT and CPS1-HIBIT in HepG2 cells according to embodiments of the present teachings;

FIG. 42K shows the secreted levels of SERPINA1-HIBIT and CPS1-HIBIT in HepG2 cells according to embodiments of the present teachings;

FIG. 43A shows the HDR mediated editing of the EMX1 locus that is significantly diminished in non-dividing HEK293FT cells blocked by 5 μM aphidicolin treatment according to embodiments of the present teachings;

FIG. 43B shows the effect of insert minicircle DNA amount on PASTE-mediated insertion at the ACTB locus in dividing and nondividing HEK293FT cells blocked by 5 μM aphidicolin treatment according to embodiments of the present teachings;

FIG. 43C shows the PASTE integration of GFP at the ACTB locus with the GFP template delivered via AAV, showing dose dependence of integration efficiency according to embodiments of the present teachings;

FIG. 44A shows the PASTE integration activity at three endogenous loci comparing the normal PASTE SV40 NLS to a c-Myc NLS/variable bi-partite SV40 NLS design according to embodiments of the present teachings;

FIG. 44B shows the PASTE integration activity at the ACTB locus with different GFP minicircle template amounts comparing the normal PASTE SV40 NLS to a c-Myc NLS/variable bi-partite SV40 NLS design according to embodiments of the present teachings;

FIG. 45 shows the improvement of the PASTE editing activity using a puromycin growth selection marker according to embodiments of the present teachings;

FIG. 46A shows the integration of SERPINA1 and CPS1 genes that are HIBIT tagged as measured by a protein expression luciferase assay according to embodiments of the present teachings;

FIG. 46B shows the integration of SERPINA1 and CPS1 genes that are HIBIT tagged as measured by a protein expression luciferase assay normalized to a standardized HIBIT ladder, enabling accurate quantification of protein levels according to embodiments of the present teachings;

FIG. 47A shows optimization of PASTE constructs with a panel of linkers and reverse transcriptase (RT) modifications for EGFP integration at the ACTB locus, according to embodiments of the present teachings;

FIG. 47B shows the effect of cargo size on PASTE insertion efficiency at the endogenous ACTB target. Cargos were transfected with fixed molar amounts, according to embodiments of the present teachings;

FIG. 48A shows prime editing efficiency for the insertion of different length BxbINT AttB sites at ACTB, according to embodiments of the present teachings;

FIG. 48B shows prime editing efficiency for the insertion of a BxbINT AttB site at ACTB with targeting and non-targeting guides, according to embodiments of the present teachings;

FIG. 48C shows prime editing efficiency for the insertion of different integrases' (Bxb1, Tp9, and Bt1) AttB sites at ACTB. Both orientations of landing sites are profiled (F, forward; R, reverse), according to embodiments of the present teachings;

FIG. 48D shows PASTE editing efficiency for the insertion of EGFP at ACTB with and without a nicking guide, according to embodiments of the present teachings; and FIG. 49A shows optimization of PASTE editing by dosage titration and protein optimization. PASTE integration efficiency of EGFP at ACTB measured with different doses of a single-vector delivery of components.

FIG. 49B PASTE integration efficiency of EGFP at ACTB measured with different ratios of a single-vector delivery of components to the EGFP template vector.

FIG. 49C PASTE integration efficiency of EGFP at ACTB with different RT domain fusions.

FIG. 49D PASTE integration efficiency of EGFP at ACTB with different RT domain fusions and linkers.

FIG. 49E PASTE integration efficiency of EGFP at ACTB with mutant RT domains.

FIG. 49F PASTE integration efficiency of EGFP at ACTB with mutated BxbINT domains.

Figures 50A, 50B, 50C, 50D, 50E, 50F, 50G, 50H, 50I:
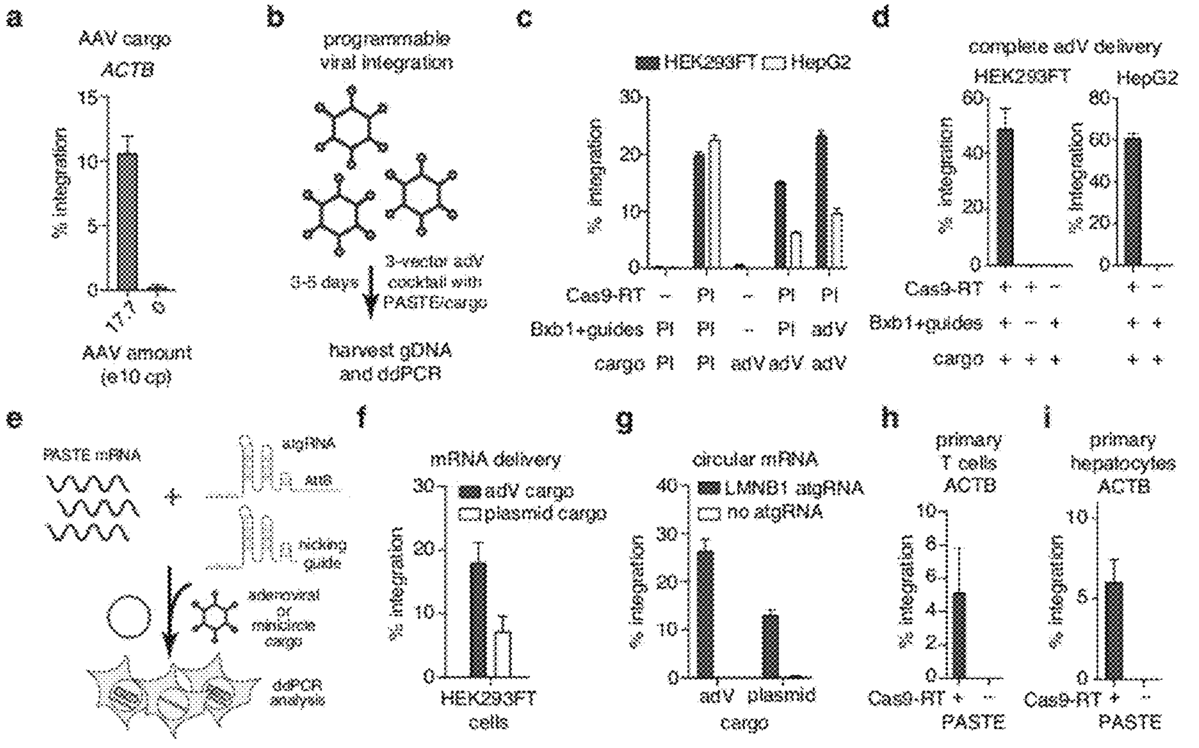

FIG. 50A Insertion templates delivered via AAV transduction. PASTE editing machinery was delivered via transfection, and templates were co-delivered via AAV dosing at levels indicated.

FIG. 50B Schematic of AdV delivery of the complete PASTE system with three viral vectors.

FIG. 50C Integration efficiency of AdV delivery of integrase, guides, and cargo in HEK293FT and HepG2 cells. BxbINT and guide RNAs or cargo were delivered either via plasmid transfection (P1), AdV transduction (AdV), or omitted (-). SpCas9-RT was only delivered as plasmid or omitted.

FIG. 50D AdV delivery of all PASTE components in HEK293FT and HepG2 cells.

FIG. 50E Schematic of mRNA and synthetic guide delivery of PASTE components.

FIG. 50F Delivery of PASTE system components with mRNA and synthetic guides, paired with either AdV or plasmid cargo.

FIG. 50G Delivery of circular mRNA with synthetic guides and either AdV or plasmid cargo.

FIG. 50H PASTE editing efficiency with single vector designs in primary human T cells.

FIG. 50I PASTE editing efficiency with single vector designs in primary human hepatocytes.

Figure 51A:
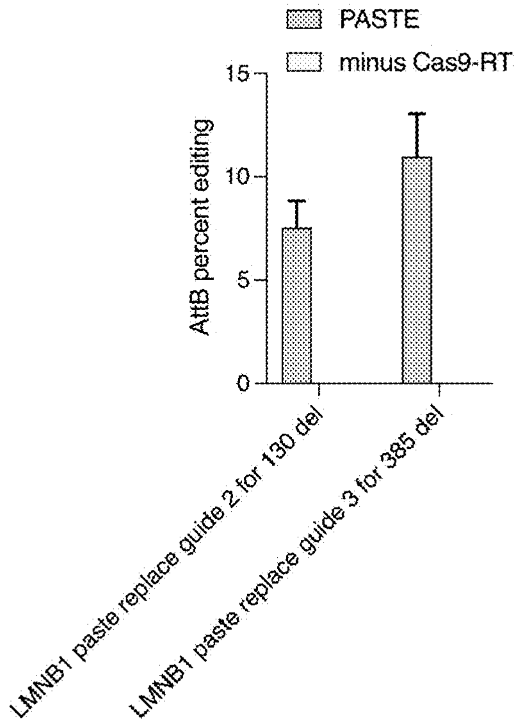

FIG. 51A PASTE editing efficiency at the LMNB1 locus with 130 bp and 385 bp deletions of the first exon of LMNB1 with combined insertion of an attB sequence.

Figure 51B:
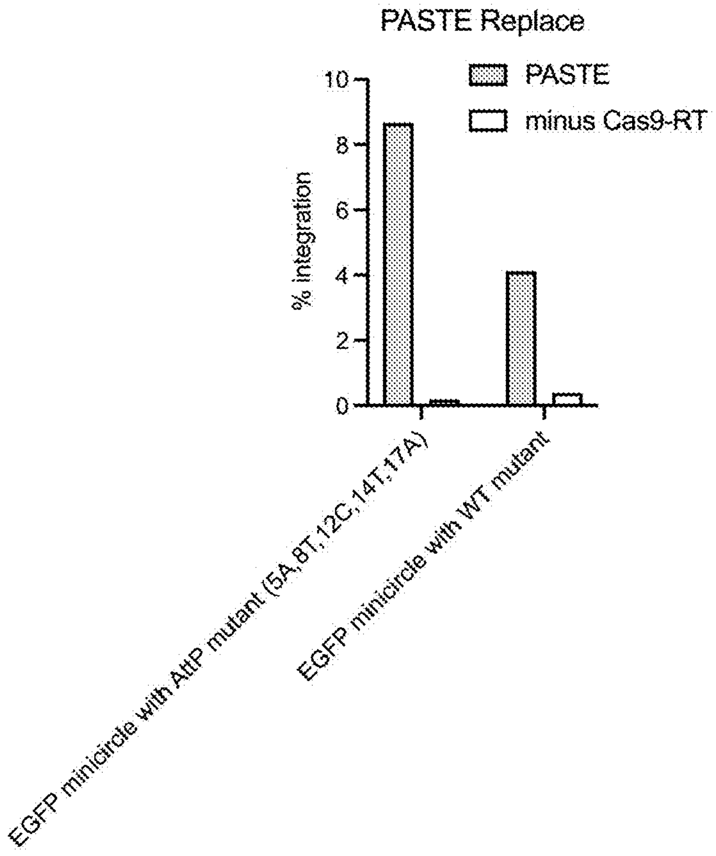

FIG. 51B PASTE editing efficiency with a 130 bp deletion of the first exon of LMNB1 with a combined insertion of a 967 bp cargo using the PASTE system.

DETAILED DESCRIPTION

It will be appreciated that for clarity, the following discussion will describe various aspects of embodiments of the applicant's teachings. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular feature, structures or characteristics may be combined in any suitable manner, as would be apparent to a person skilled in the art from this disclosure, in one or more embodiments.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise. Thus, for example, reference to "a cell" includes a plurality of such cells.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosure. It is to be understood that the value to which the modifier "about" or "approximately" refers is itself also specifically, and preferably, disclosed.

It is noted that all publications and references cited herein are expressly incorporated herein by reference in their entirety. The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

Overview

Figure 1:
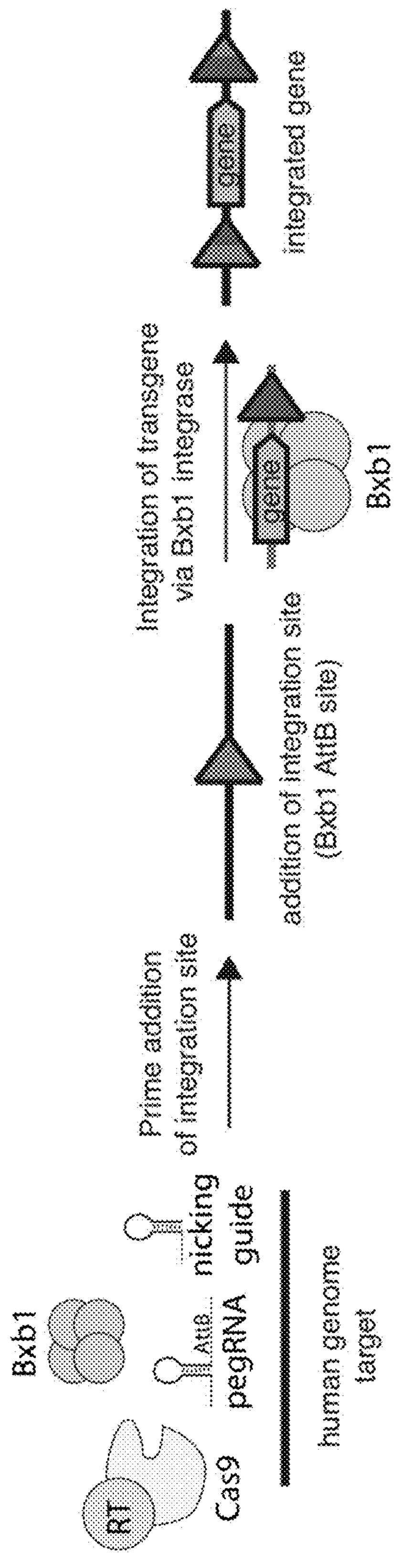
FIG. 1 shows a schematic diagram of a concept of Programmable Addition via Site-Specific Targeting Elements (PASTE) according to embodiments of the present teachings.

The embodiments disclosed herein provide non-naturally occurring or engineered systems, methods, and compositions for site-specific genetic engineering using Programmable Addition via Site-Specific Targeting Elements (PASTE). A schematic diagram illustrating the concept of PASTE is shown in FIG. 1. As discussed in more details below, PASTE comprises the addition of an integration site into a target genome followed by the insertion of one or more genes of interest or one or more nucleic acid sequences of interest at the site. This process can be done as one or more reactions in a cell. The addition of the integration site into the target genome is done using gene editing technologies that include for example, without limitation, prime editing, recombinant adeno-associated virus (rAAV)-mediated nucleic acid integration, transcription activator-like effector nucleases (TALENS), and zinc finger nucleases (ZFNs). The integration of the transgene at the integration site is done using integrase technologies that include for example, without limitation, integrases, recombinases and reverse transcriptases. The necessary components for the site-specific genetic engineering disclosed herein comprise at least one or more nucleases, one or more gRNA, one or more integration enzymes, and one or more sequences that are complementary or associated to the integration site and linked to the one or more genes of interest or one or more nucleic acid sequences of interest to be inserted into the cell genome.

An advantage of the non-naturally occurring or engineered systems, methods, and compositions for site-specific genetic engineering disclosed herein is programmable insertion of large elements without reliance on DNA damage responses.

Another advantage of the non-naturally occurring or engineered systems, methods, and compositions for site-specific genetic engineering disclosed herein is facile multiplexing, enabling programmable insertion at multiple sites.

Another advantage of the non-naturally occurring or engineered systems, methods, and compositions for site-specific genetic engineering disclosed herein is scalable production and delivery through minicircle templates.

Prime Editing

The present disclosure provides non-naturally occurring or engineered systems, methods, and compositions for site-specific genetic engineering using gene editing technologies, such as prime editing, to add an integration site into a target genome. Prime editing will be discussed in more details below.

Figure 2:
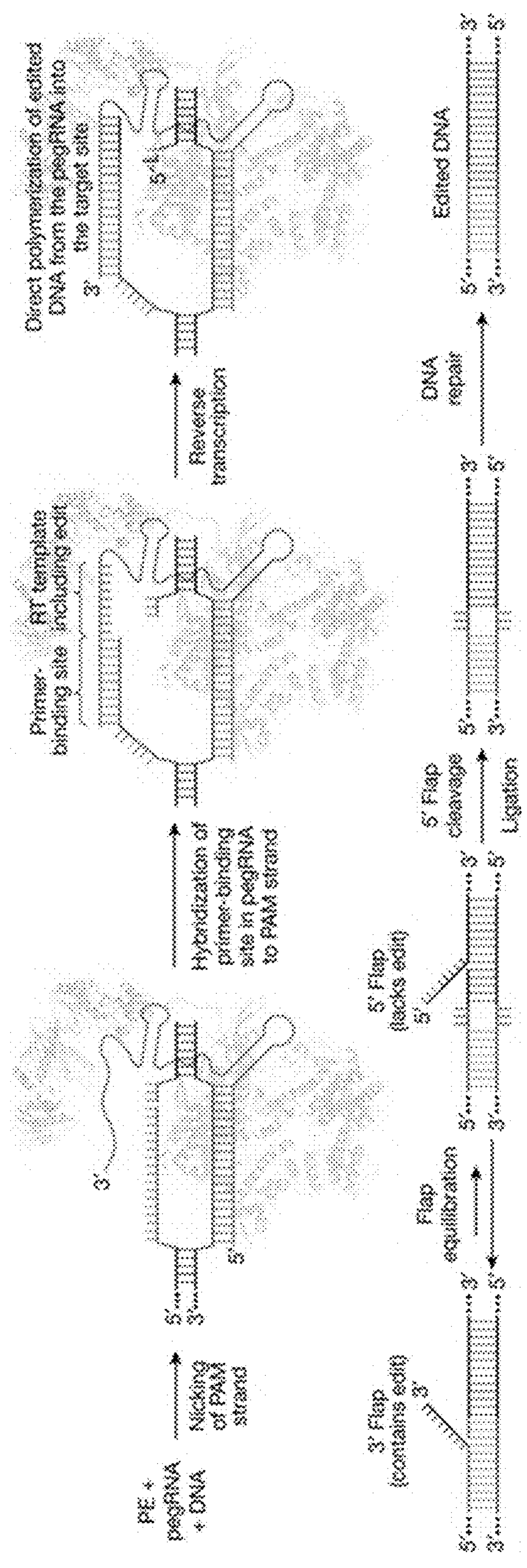
FIG. 2 shows a schematic diagram of a prime editing process according to embodiments of the present teachings.

Prime editing is a versatile and precise genome editing method that directly writes new genetic information into a specified DNA site. A schematic diagram illustrating the concept of prime editing is shown in FIG. 2. See, Anzalone, A. V., et al. "Search-and-replace genome editing without double-strand breaks or donor DNA," *Nature* 576, 149-157 (2019). Prime editing uses a catalytically-impaired Cas9 endonuclease that is fused to an engineered reverse transcriptase (RT) and programmed with a prime-editing guide RNA (pegRNA). The skilled person in the art would appreciate that the pegRNA both specifies the target site and encodes the desired edit. The catalytically-impaired Cas9 endonuclease also comprises a Cas9 nickase that is fused to the reverse transcriptase. During genetic editing, the Cas9 nickase part of the protein is guided to the DNA target site by the pegRNA. The reverse transcriptase domain then uses the pegRNA to template reverse transcription of the desired edit, directly polymerizing DNA onto the nicked target DNA strand. The edited DNA strand replaces the original DNA strand, creating a heteroduplex containing one edited strand and one unedited strand. Afterward, the prime editor (PE) guides resolution of the heteroduplex to favor copying the edit onto the unedited strand, completing the process.

The prime editors refer to a Moloney Murine Leukemia Virus (M-MLV) reverse transcriptase (RT) fused to a Cas9 H840A nickase. Fusing the RT to the C-terminus of the Cas9 nickase may result in higher editing efficiency. Such a complex is called PE1. The Cas9(H840A) can also be linked to a non-M-MLV reverse transcriptase such as a AMV-RT or XRT (Cas9(H840A)-AMV-RT or XRT). In some embodiments, Cas 9(H840A) can be replaced with Cas12a/b or Cas9(D10A). A Cas9 (wild type), Cas9(H840A), Cas9 (D10A) or Cas 12a/b nickase fused to a pentamutant of M-MLV RT (D200N/L603W/T330P/T306K/W313F), having up to about 45-fold higher efficiency is called PE2. In some embodiments, the M-MLV RT comprise one or more of the mutations: Y8H, P51L, S56A, S67R, E69K, V129P, L139P, T197A, H204R, V223H, T246E, N249D, E286R, Q291I, E302K, E302R, F309N, M320L, P330E, L435G, L435R, N454K, D524A, D524G, D524N, E562Q, D583N, H594Q, E607K, D653N, and L671P. In some embodiments, the reverse transcriptase can also be a wild-type or modified transcription xenopolymerase (RTX), avian myeloblastosis virus reverse transcriptase (AMV-RT), Feline Immunodeficiency Virus reverse transcriptase (FIV-RT), FeLV-RT (Feline leukemia virus reverse transcriptase), HIV-RT (Human Immunodeficiency Virus reverse transcriptase), or *Eubacterium rectale* maturase RT (MarathonRT). PE3 involves nicking the non-edited strand, potentially causing the cell to remake that strand using the edited strand as the template to induce HR. The nicking of the non-edited strand can involve the use of a nicking guide RNA (ngRNA).

Nicking the non-edited strand can increase editing efficiency. For example, nicking the non-edited strand can increase editing efficiency by about 1.1 fold, about 1.3 fold, about 1.5 fold, about 1.7 fold, about 1.9 fold, about 2.1 fold, about 2.3 fold, about 2.5 fold, about 2.7 fold, about 2.9 fold, about 3.1 fold, about 3.3 fold, about 3.5 fold, about 3.7 fold, about 3.9 fold, 4.1 fold, about 4.3 fold, about 4.5 fold, about 4.7 fold, about 4.9 fold, or any range that is formed from any two of those values as endpoints.

Although the optimal nicking position varies depending on the genomic site, nicks positioned 3' of the edit about 40-90 bp from the pegRNA-induced nick can generally increase editing efficiency without excess indel formation. The prime editing practice allows starting with non-edited strand nicks about 50 bp from the pegRNA-mediated nick, and testing alternative nick locations if indel frequencies exceed acceptable levels.

As used herein, the term "guide RNA" (gRNA) and the like refer to a RNA that guide the insertion or deletion of one or more genes of interest or one or more nucleic acid sequences of interest into a target genome. The gRNA can also refer to a prime editing guide RNA (pegRNA), a nicking guide RNA (ngRNA), and a single guide RNA (sgRNA). In some embodiments, the term "gRNA molecule" refers to a nucleic acid encoding a gRNA. In some embodiments, the gRNA molecule is naturally occurring. In some embodiments, a gRNA molecule is non-naturally occurring. In some embodiments, a gRNA molecule is a synthetic gRNA molecule. A gRNA can target a nuclease or a nickase such as Cas9, Cas 12a/b, Cas9 (H840A) or Cas9 (D10A) molecule to a target nucleic acid or sequence in a genome. In some embodiments, the gRNA can bind to a DNA nickase bound to a reverse transcriptase domain. A "modified gRNA," as used herein, refers to a gRNA molecule that has an improved half-life after being introduced into a cell as compared to a non-modified gRNA molecule after being introduced into a cell. In some embodiments, the guide RNA can facilitate the addition of the insertion site sequence for recognition by integrases, transposases, or recombinases.

Figure 24A:
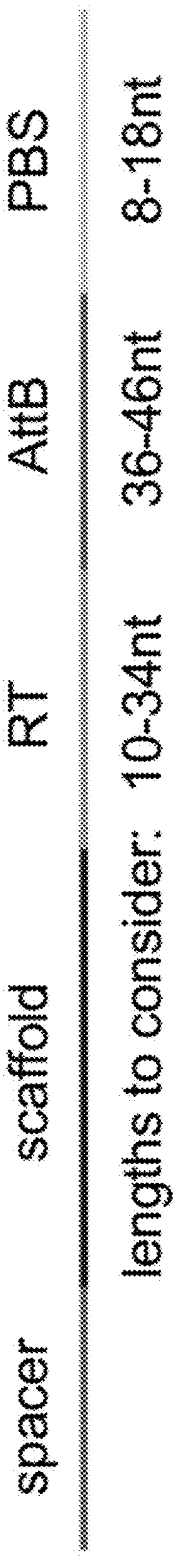
FIG. 24A shows a schematic of the design parameters for the pegRNA according to embodiments of the present teachings.

As used herein, the term "prime-editing guide RNA" (pegRNA) and the like refer to an extended single guide RNA (sgRNA) comprising a primer binding site (PBS), a reverse transcriptase (RT) template sequence, and an integration site sequence that can be recognized by recombinases, integrases, or transposases. Exemplary design parameters for pegRNA are shown in FIG. 24A. For example, the PBS can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or more nt. For example, the PBS can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or any range that is formed from any two of those values as endpoints. For example, the RT template sequence can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or more nt. For example, the RT template sequence can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or any range that is formed from any two of those values as endpoints.

During genome editing, the primer binding site allows the 3' end of the nicked DNA strand to hybridize to the pegRNA, while the RT template serves as a template for the synthesis of edited genetic information. The pegRNA is capable for instance, without limitation, of (i) identifying the target nucleotide sequence to be edited and (ii) encoding new genetic information that replaces the targeted sequence. In some embodiments, the pegRNA is capable of (i) identifying the target nucleotide sequence to be edited and (ii) encoding an integration site that replaces the targeted sequence.

Figure 24B:
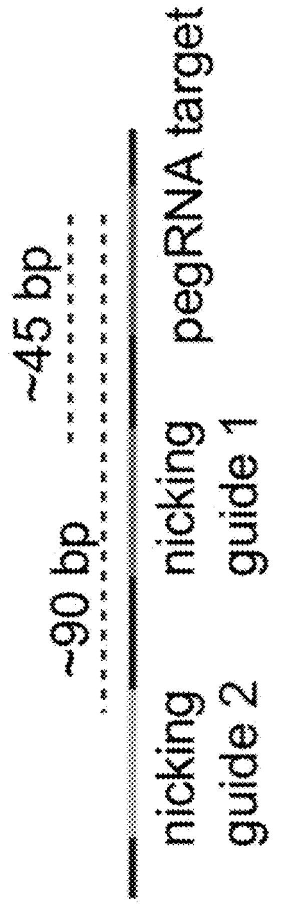
FIG. 24B shows a schematic of the design parameters for nicking guide RNA according to embodiments of the present teachings.

As used herein, the term "nicking guide RNA" (ngRNA) and the like refer to an RNA sequence that can nick a strand such as an edited strand and a non-edited strand. Exemplary design parameters for ngRNA are shown in FIG. 24B. The ngRNA can induce nicks at about 1 or more nt away from the site of the gRNA-induced nick. For example, the ngRNA can nick at least at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more nt away from the site of the gRNA induced nick. In some embodiments, the ngRNA comprises SEQ ID NO: 75 with guide sequence SEQ ID NO: 74. As used herein, the terms "reverse transcriptase" and "reverse transcriptase domain" refer to an enzyme or an enzymatically active domain that can reverse a RNA transcribe into a complementary DNA. The reverse transcriptase or reverse transcriptase domain is a RNA dependent DNA polymerase. Such reverse transcriptase domains encompass, but are not limited, to a M-MLV reverse transcriptase, or a modified reverse transcriptase such as, without limitation, Superscript® reverse transcriptase (Invitrogen; Carlsbad, Calif.), Superscript® VILO™ cDNA synthesis (Invitrogen; Carlsbad, Calif.), RTX, AMV-RT, and Quantiscript Reverse Transcriptase (Qiagen, Hilden, Germany).

The pegRNA-PE complex disclosed herein recognizes the target site in the genome and the Cas9 for example nicks a protospacer adjacent motif (PAM) strand. The primer binding site (PBS) in the pegRNA hybridizes to the PAM strand. The RT template operably linked to the PBS, containing the edit sequence, directs the reverse transcription of the RT template to DNA into the target site. Equilibration between the edited 3' flap and the unedited 5' flap, cellular 5' flap cleavage and ligation, and DNA repair results in stably edited DNA. To optimize base editing, a Cas9 nickase can be used to nick the non-edited strand, thereby directing DNA repair to that strand, using the edited strand as a template.

Integrase Technologies

The present disclosure provides non-naturally occurring or engineered systems, methods, and compositions for site-specific genetic engineering using integrase technologies. Integrase technologies will be discussed in more details below.

The integrase technologies used herein comprise proteins or nucleic acids encoding the proteins that direct integration of a gene of interest or nucleic acid sequence of interest into an integration site via a nuclease such as a prime editing nuclease. The protein directing the integration can be an enzyme such as integration enzyme. The integration enzyme can be an integrase that incorporates the genome or nucleic acid of interest into the cell genome at the integration site by integration. The integration enzyme can be a recombinase that incorporates the genome or nucleic acid of interest into the cell genome at the integration site by recombination. The integration enzyme can be a reverse transcriptase that incorporates the genome or nucleic acid of interest into the cell genome at the integration site by reverse transcription. The integration enzyme can be a retrotransposase that incorporates the genome or nucleic acid of interest into the cell genome at the integration site by retrotransposition.

As used herein, the term "integration enzyme" refers to an enzyme or protein used to integrate a gene of interest or nucleic acid sequence of interest into a desired location or at the integration site, in the genome of a cell, in a single reaction or multiple reactions. Example of integration enzymes include for example, without limitation, Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, and retrotransposases encoded by R2, L1, Tol2 Tc1, Tc3, Mariner (Himar 1), Mariner (mos 1), and Minos. In some embodiments, the term "integration enzyme" refers to a nucleic acid (DNA or RNA) encoding the above-mentioned enzymes. In some embodiments, the Cre recombinase is expressed from a Cre recombinase expression plasmid (SEQ ID NO: 71).

Mammalian expression plasmids can be found in Table 1 below.

TABLE 1

| Name | Full Description | SEQ ID NOS: |
|---|---|---|
| PE2-Bxbl Single Vector | pCMV-PE2-P2A- Bxbl | (SEQ ID NO: 381) |
| PE2 prime editor | pCMV-PE2/ Addgene #132775 | (SEQ ID NO: 382) |
| PE2*-Bxb1 Single Vector | New NLS pCMV- PE2-P2A-Bxbl | (SEQ ID NO: 383) |
| PASTEv3 | pCMV-SpCas9-XTEN-RT(1-478)-Sto7d-GGGGS-BxbINT | (SEQ ID NO: 384) |
| ACTB pegRNA | ACTB N-term PBS 13 RT 29 attB 46 pegRNA | (SEQ ID NO: 385) |
| ACTB Nicking +48 | ACTB N-term Nicking guide 1 +48 guide | (SEQ ID NO: 386) |
| Bxbl integrase | pCAG-NLS-HA-Bxblintegrase/ Addgene #51271 | (SEQ ID NO: 387) |
| TP901-1 Integrase | TP901-1 Integrase | (SEQ ID NO: 388) |
| PhiBT Integrase | PhiBT Integrase | (SEQ ID NO: 389) |
| HDR sgRNA guide | Minicircle U6-sgRNA EFS-SpCas9 | (SEQ ID NO: 390) |
| HDR EGFP cargo | Cas9 HDR template site with EGFP | (SEQ ID NO: 391) |
| AAV helper plasmid | PDF6 AAV helper plasmid | (SEQ ID NO: 392) |
| AAV EGFP donor | GFP AAV donor plasmid | (SEQ ID NO: 393) |
| AAV2/8 | AAV2/8 capsid protein | (SEQ ID NO: 394) |

Minicircle cargo gene maps can be found in Table 2 below.

TABLE 2

| Name | Full Description | SEQ ID NOS: |
|---|---|---|
| Cargo EGFP | Parent minicircle plasmid - Cargo EGFP with attP Bxbl site | (SEQ ID NO: 76) |
| Cargo EGFP post cleavage | Cargo EGFP with attP Bxbl site - post minicircle cleavage | (SEQ ID NO: 395) |
| Cargo EGFP for fusion | Parent minicircle plasmid - Cargo EGFP with attP Bxbl site for fusion | (SEQ ID NO: 396) |
| mCherry Cargo post cleavage | Cargo mCherry with attP Bxbl site - post minicircle cleavage | (SEQ ID NO: 397) |
| YFP Cargo post cleavage | Cargo YFP with attP Bxbl site - post minicircle cleavage | (SEQ ID NO: 398) |

TABLE 2-continued

| Name | Full Description | SEQ ID NOS: |
|---|---|---|
| SERPINA1 Cargo post cleavage | Cargo SERPINA1 with attP Bxbl site - post minicircle cleavage | (SEQ ID NO: 399) |
| CPS1 Cargo post cleavage | Cargo CPS1 with attP Bxbl site - post minicircle cleavage | (SEQ ID NO: 400) |
| CFTR Cargo | Parent minicircle plasmid - Cargo CFTR with attP Bxbl site | (SEQ ID NO: 401) |
| NYESO TCR Cargo post cleavage | Cargo NYESO TCR with attP Bxbl site - post minicircle cleavage | (SEQ ID NO: 402) |

In some embodiments, the serine integrase φC31 from φC31 phage is use as integration enzyme. The integrase φC31 in combination with a pegRNA can be used to insert the pseudo attP integration site (SEQ ID NO: 78). A DNA minicircle containing a gene or nucleic acid of interest and attB (SEQ ID NO: 3) site can be used to integrate the gene or nucleic acid of interest into the genome of a cell. This integration can be aided by a co-transfection of an expression vector having the φC31 integrase.

As used herein, the term "integrase" refers to a bacteriophage derived integrase, including wild-type integrase and any of a variety of mutant or modified integrases. As used herein, the term "integrase complex" may refer to a complex comprising integrase and integration host factor (IF). As used herein, the term "integrase complex" and the like may also refer to a complex comprising an integrase, an integration host factor, and a bacteriophage X-derived excisionase (Xis).

As used herein, the term "recombinase" and the like refer to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R1, R2, R3, R4, R5, φRV1, φFC1, MR11, A118, U153, and gp29. Examples of serine recombinases also include, without limitation, recombinases Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, and BxZ2 from Mycobacterial phages. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange.

Recombinases have numerous applications, including the creation of gene knockouts/knock-ins and gene therapy applications. See, e.g., Brown et al., "Serine recombinases as tools for genome engineering."*Methods,* 2011; 53(4):372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12): 4088-107; Venken and Bellen, "Genome-wide manipulations of *Drosophila melanogaster* with transposons, Flp recombinase, and ΦC31 integrase."*Methods Mol. Biol.* 2012; 859:203-28; Murphy, "Phage recombinases and their applications."*Adv. Virus Res.* 2012; 83:367-414; Zhang et al., "Conditional gene manipulation: Creating a new biological era." J. Zhejiang Univ. Sci. B. 2012; 13(7):511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety.

The recombinases provided herein are not meant to be exclusive examples of recombinases that can be used in embodiments of the disclosure. The methods and compositions of the disclosure can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety).

Other examples of recombinases that are useful in the systems, methods, and compositions described herein are known to those of skill in the art, and any new recombinase that is discovered or generated is expected to be able to be used in the different embodiments of the disclosure.

As used herein, the term "retrotransposase" and the like refer to an enzyme, or combination of one or more enzymes, wherein at least one enzyme has a reverse transcriptase domain. Retrotransposases are capable of inserting long sequences (e.g., over 3000 nucleotides) of heterologous nucleic acid into a genome. Examples of retrotransposases include for example, without limitation, retrotransposases encoded by elements such as R2, L1, Tol2 Tc1, Tc3, Mariner (Himar 1), Mariner (mos 1), Minos, and any mutants thereof.

In some embodiments, the one or more genes of interest or one or more nucleic acid sequences of interest are inserted into a desired location in a genome using a RNA fragment, such as a retrotransposon, encoding the nucleic acid linked to a complementary or associated integration site. The insertion of the nucleic acid of interest into a location in the desired location in the genome using a retrotransposon is aided by a retrotransposase.

The gene and nucleic acid sequence of interest disclosed herein can be any gene and nucleic acid sequence that are known in the art. The gene and nucleic acid sequence of interest can be for therapeutic and/or diagnostic uses. Examples of genes of interest include, without limitation, GBA, BTK, ADA, CNGB3, CNGA3, ATF6, GNAT2, ABCA1, ABCA7, APOE, CETP, LIPC, MMP9, PLTP, VTN, ABCA4, MFSD8, TLR3, TLR4, ERCC6, HMCN1, HTRA1, MCDR4, MCDR5, ARMS2, C2, C3, CFB, CFH, JAG1, NOTCH2, CACNA1F, SERPINA1, TTR, GSN, B2M, APOA2, APOA1, OSMR, ELP4, PAX6, ARG, ASL, PITX2, FOXC1, BBS1, BBS10, BBS2, BBS9, MKKS, MKS1, BBS4, BBS7, TTC8, ARL6, BBS5, BBS12, TRIM32, CEP290, ADIPOR1, BBIP1, CEP19, IFT27, LZTFL1, DMD, BEST1, HBB, CYP4V2, AMACR, CYP7B1, HSD3B7, AKR1D1, OPN1SW, NR2F1, RLBP1, RGS9, RGS9BP, PROM1, PRPH2, GUCY2D, CACD, CHM, ALAD, ASS1, SLC25A13, OTC, ACADVL, ETFDH, TMEM67, CC2D2A, RPGRIP1L, KCNV2, CRX, GUCA1A, CERKL, CDHR1, PDE6C, TTLL5, RPGR, CEP78, C21orf2, C8ORF37, RPGRIP1, ADAM9, POC1B, PITPNM3, RAB28, CACNA2D4, AIPL1, UNC119, PDE6H, OPN1LW, RIMS1, CNNM4, IFT81, RAX2, RDH5, SEMA4A, CORD17, PDE6B, GRK1, SAG, RHO, CABP4, GNB3, SLC24A1, GNAT1, GRM6, TRPM1, LRIT3, TGFBI, TACSTD2, KRT12, OVOL2, CPS1, UGT1A1, UGT1A9, UGT1A8, UGT1A7, UGT1A6, UGT1A5, UGT1A4, CFTR, DLD, EFEMP1, ABCC2, ZNF408, LRP5, FZD4, TSPAN12, EVR3, APOB, SLC2A2, LOC106627981, GBA1, NR2E3, OAT, SLC40A1, F8, F9, UROD, CPDX, HFE, JH, LDLR, EPHX1, TJP2, BAAT, NBAS, LARS1, HAMP, HJV, RS1, ADAMTS18, LRAT, RPE65, LCA5, MERTK, GDF6, RD3, CCT2, CLUAP1, DTHD1, NMNAT1, SPATA7, IFT140, IMPDH1, OTX2, RDH12, TULP1, CRB1, MT-ND4, MT-ND1, MT-ND6, BCKDHA, BCKDHB, DBT, MMAB, ARSB, GUSB, NAGS, NPC1, NPC2, NDP, OPA1, OPA3, OPA4, OPA5, RTN4IP1, TMEM126A, OPA6, OPA8, ACO2, PAH, PRKCSH, SEC63, GAA, UROS, PPDX, HPX, HMOX1, HMBS, MIR223, CYP1B1, LTBP2, AGXT, ATP8B1, ABCB11, ABCB4, FECH, ALAS2, PRPF31, RP1, EYS, TOPORS, USH2A, CNGA1, C2ORF71, RP2, KLHL7, ORF1, RP6, RP24, RP34, ROM1, ADGRA3, AGBL5, AHR, ARHGEF18, CA4, CLCC1, DHDDS, EMC1, FAM161A, HGSNAT, HK1, IDH3B, KIAA1549, KIZ, MAK, NEUROD1, NRL, PDE6A, PDE6G, PRCD, PRPF3, PRPF4, PRPF6, PRPF8, RBP3, REEP6, SAMD11, SLC7A14, SNRNP200, SPP2, ZNF513, NEK2, NEK4, NXNL1, OFD1, RP1L1, RP22, RP29, RP32, RP63, RP9, RGR, POMGNT1, DHX38, ARL3, COL2A1, SLCO1B1, SLCO1B3, KCNJ13, TIMP3, ELOVL4, TFR2, FAH, HPD, MYO7A, CDH23, PCDH15, DFNB31, GPR98, USH1C, USH1G, CIB2, CLRN1, HARS, ABHD12, ADGRV1, ARSG, CEP250, IMPG1, IMPG2, VCAN, G6PC1, ATP7B and any derivatives thereof.

As used here, the terms "retrotransposons," "jumping genes," "jumping nucleic acids," and the like refer to cellular movable genetic elements dependent on reverse transcription. The retrotransposons are of non-replication competent cellular origin, and are capable of carrying a foreign nucleic acid sequence. The retrotransposons can act as parasites of retroviruses, retaining certain classical hallmarks, such as long terminal repeats (LTR), retroviral primer binding sites, and the like. However, the naturally occurring retrotransposons usually do not contain functional retroviral structure genes, which would normally be capable of recombining to yield replication competent viruses. Some retrotransposons are examples of so-called "selfish DNA", or genetic information, which encodes nothing except the ability to replicate itself. The retrotransposon may do so by utilizing the occasional presence of a retrovirus or a retrotransposase within the host cell, efficiently packaging itself within the viral particle, which transports it to the new host genome, where it is expressed again as RNA. The information encoded within that RNA is potentially transported with the jumping gene. A retrotransposon can be a DNA transposon or a retrotransposon, including a LTR retrotransposon or a non-LTR retrotransposon.

Non-long terminal repeat (LTR) retrotransposons are a type of mobile genetic elements that are widespread in eukaryotic genomes. They include two classes: the apurinic/apyrimidinic endonuclease (APE)-type and the restriction enzyme-like endonuclease (RLE)-type. The APE class retrotransposons are comprised of two functional domains: an endonuclease/DNA binding domain, and a reverse transcriptase domain. The RLE class are comprised of three functional domains: a DNA binding domain, a reverse transcription domain, and an endonuclease domain. The reverse transcriptase domain of non-LTR retrotransposon functions by binding an RNA sequence template and reverse transcribing it into the host genome's target DNA. The RNA sequence template has a 3' untranslated region which is specifically bound to the transposase, and a variable 5' region generally having Open Reading Frame(s) ("ORF") encoding transposase proteins. The RNA sequence template may also comprise a 5' untranslated region which specifically binds the retrotransposase. In some embodiments, a non-LTR transposons can include a LINE retrotransposon, such as L1, and a SINE retrotransposon, such as an Alu sequence. Other examples include for example, without limitation, R1, R2, R3, R4, and R5 retro-transposons (Moss, W. N. et al., *RNA Biol.* 2011, 8(5), 714-718; and Burke, W. D. et al., *Molecular Biology and Evolution* 2003, 20(8), 1260-1270). The transposon can be autonomous or non-autonomous.

LTR retrotransposons, which include retroviruses, make up a significant fraction of the typical mammalian genome, comprising about 8% of the human genome and 10% of the mouse genome. Lander et al., 2001, *Nature* 409, 860-921; Waterson et al., 2002, *Nature* 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and retrotransposase.

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, *Genome Res.* 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, *Nature* 409, 860-921; Hua-Van et al., 2011, Biol. Dir. 6, 19.

Integration Site

The present disclosure provides non-naturally occurring or engineered systems, methods, and compositions for site-specific genetic engineering via the addition of an integration site into a target genome. The integration site will be discussed in more details below.

As used herein, the term "integration site" refers to the site within the target genome where one or more genes of interest or one or more nucleic acid sequences of interest are inserted. Examples of integration sites include for example, without limitation, a lox71 site (SEQ ID NO: 1), attB sites (SEQ ID NO: 3 and SEQ ID NO: 43), attP sites (SEQ ID NO: 4 and SEQ ID NO: 44), an attL site (SEQ ID NO: 67), an attR site (SEQ ID NO: 68), a Vox site (SEQ ID NO: 69), a FRT site (SEQ ID NO: 70), or a pseudo attP site (SEQ ID NO: 78). The integration site can be inserted into the genome or a fragment thereof of a cell using a nuclease, a gRNA, and/or an integration enzyme. The integration site can be inserted into the genome of a cell using a prime editor such as, without limitation, PE1, PE2, and PE3, wherein the integration site is carried on a pegRNA. The pegRNA can target any site that is known in the art. Examples of cites targeted by the pegRNA include, without limitation, ACTB, SUPT16H, SRRM2, NOLC1, DEPDC4, NES, LMNB1, AAVS1 locus, CC10, CFTR, SERPINA1, ABCA4, and any derivatives thereof. The complementary integration site may be operably linked to a gene of interest or nucleic acid sequence of interest in an exogenous DNA or RNA. In some embodiments, one integration site is added to a target genome. In some embodiments, more than one integration sites are added to a target genome.

To insert multiple genes or nucleic acids of interest, two or more integration sites are added to a desired location. Multiple DNA comprising nucleic acid sequences of interest are flanked orthogonal to the integration sequences, such as, without limitation, attB and attP. An integration site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when there is recognition of each other's attB or attP site sequences.

The lack of recognition of integration sites or pairs of sites by the same recombinase or a different recombinase can be less than about 30%. In some embodiments, the lack of recognition of integration sites or pairs of sites by the same recombinase or a different recombinase can be less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, about 1%, or any range that is formed from any two of those values as endpoints. The crosstalk can be less than about 30%. In some embodiments, the crosstalk is less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, less than about 1%, or any range that is formed from any two of those values as endpoints.

In some embodiments, the attB and/or attP site sequences comprise a central dinucleotide sequence. It has been shown that, for example, the central dinucleotide can be changed to GA from GT and that only GA containing attB/attP sites interact and will not cross react with GT containing sequences. In some embodiments, the central dinucleotide is selected from the group consisting of AG, AC, TG, TC, CA, CT, GA, AA, TT, CC, GG, AT, TA, GC, CG and GT.

As used herein, the term "pair of an attB and attP site sequences" and the like refer to attB and attP site sequences that share the same central dinucleotide and can recombine. This means that in the presence of one serine integrase as many as six pairs of these orthogonal att sites can recombine (attPTT will specifically recombine with attBTT, attPTC will specifically recombine with attBTC, and so on).

In some embodiments, the central dinucleotide is nonpalindromic. In some embodiments, the central dinucleotide is palindromic. In some embodiments, a pair of an attB site sequence and an attP site sequence are used in different DNA encoding genes of interest or nucleic acid sequences of interest for inducing directional integration of two or more different nucleic acids.

The Table 3 below shows examples of pairs of attB site sequence and attP site sequence with different central dinucleotide (CD).

TABLE 3

| Pair | attB | attP | CD |
|---|---|---|---|
| 1 | SEQ ID NO: 5 | SEQ ID NO: 6 | TT |
| 2 | SEQ ID NO: 7 | SEQ ID NO: 8 | AA |
| 3 | SEQ ID NO: 9 | SEQ ID NO: 10 | CC |
| 4 | SEQ ID NO: 11 | SEQ ID NO: 12 | GG |
| 5 | SEQ ID NO: 13 | SEQ ID NO: 14 | TG |
| 6 | SEQ ID NO: 15 | SEQ ID NO: 16 | GT |
| 7 | SEQ ID NO: 17 | SEQ ID NO: 18 | CT |
| 8 | SEQ ID NO: 19 | SEQ ID NO: 20 | CA |
| 9 | SEQ ID NO: 21 | SEQ ID NO: 22 | TC |
| 10 | SEQ ID NO: 23 | SEQ ID NO: 24 | GA |
| 11 | SEQ ID NO: 25 | SEQ ID NO: 26 | AG |
| 12 | SEQ ID NO: 27 | SEQ ID NO: 28 | AC |
| 13 | SEQ ID NO: 29 | SEQ ID NO: 30 | AT |
| 14 | SEQ ID NO: 31 | SEQ ID NO: 32 | GC |
| 15 | SEQ ID NO: 33 | SEQ ID NO: 34 | CG |
| 16 | SEQ ID NO: 35 | SEQ ID NO: 36 | TA |

Paste

The present disclosure provides non-naturally occurring or engineered systems, methods, and compositions for site-specific genetic engineering using PASTE. PASTE will be discussed in more details below.

The site-specific genetic engineering disclosed herein is for the insertion of one or more genes of interest or one or more nucleic acid sequences of interest into a genome of a cell. In some embodiments, the gene of interest is a mutated gene implicated in a genetic disease such as, without limitation, a metabolic disease, cystic fibrosis, muscular dystrophy, hemochromatosis, Tay-Sachs, Huntington disease, Congenital Deafness, Sickle cell anemia, Familial hypercholesterolemia, adenosine deaminase (ADA) deficiency, X-linked SCID (X-SCID), and Wiskott-Aldrich syndrome (WAS). In some embodiments, the gene of interest or nucleic acid sequence of interest can be a reporter gene upstream or downstream of a gene for genetic analyses such as, without limitation, for determining the expression of a gene. In some embodiments, the reporter gene is a GFP template (SEQ ID NO: 76) or a *Gaussia* Luciferase (G-Luciferase) template (SEQ ID NO: 77) In some embodiments, the gene of interest or nucleic acid sequence of interest can be used in plant genetics to insert genes to enhance drought tolerance, weather hardiness, and increased yield and herbicide resistance in plants. In some embodiments, the gene of interest or nucleic acid sequence of interest can be used for site-specific insertion of a protein (e.g., a lysosomal enzyme), a blood factor (e.g., Factor I, II, V, VII, X, XI, XII or XIII), a membrane protein, an exon, an intracellular protein (e.g., a cytoplasmic protein, a nuclear protein, an organellar protein such as a mitochondrial protein or lysosomal protein), an extracellular protein, a structural protein, a signaling protein, a regulatory protein, a transport protein, a sensory protein, a motor protein, a defense protein, or a storage protein, an anti-inflammatory signaling molecules into cells for treatment of immune diseases, including but not limited to arthritis, psoriasis, lupus, coeliac disease, glomerulonephritis, hepatitis, and inflammatory bowel disease.

The size of the inserted gene or nucleic acid can vary from about 1 bp to about 50,000 bp. In some embodiments, the size of the inserted gene or nucleic acid can be about 1 bp, 10 bp, 50 bp, 100 bp, 150 bp, 200 bp, 250 bp, 300 bp, 350 bp, 400 bp, 600 bp, 800 bp, 1000 bp, 1200 bp, 1400 bp, 1600 bp, 1800 bp, 2000 bp, 2200 bp, 2400 bp, 2600 bp, 2800 bp, 3000 bp, 3200 bp, 3400 bp, 3600 bp, 3800 bp, 4000 bp, 4200 bp, 4400 bp, 4600 bp, 4800 bp, 5000 bp, 5200 bp, 5400 bp, 5600 bp, 5800 bp, 6000 bp, 6200, 6400 bp, 6600 bp, 6800 bp, 7000 bp, 7200 bp, 7400 bp, 7600 bp, 7800 bp, 8000 bp, 8200 bp, 8400 bp, 8600 bp, 8800 bp, 9000 bp, 9200 bp, 9400 bp, 9600 bp, 9800 bp, 10,000 bp, 10,200 bp, 10,400 bp, 10,600 bp, 10,800 bp, 11,000 bp, 11,200 bp, 11,400 bp, 11,600 bp, 11,800 bp, 12,000 bp, 14,000 bp, 16,000 bp, 18,000 bp, 20,000 bp, 30,000 bp, 40,000 bp, 50,000 bp, or any range that is formed from any two of those values as endpoints.

In some embodiments, the site-specific engineering using the gene of interest or nucleic acid sequence of interest disclosed herein is for the engineering of T cells and NKs for tumor targeting or allogeneic generation. These can involve the use of receptor or CAR for tumor specificity, anti-PD1 antibody, cytokines like IFN-gamma, TNF-alpha, IL-15, IL-12, IL-18, IL-21, and IL-10, and immune escape genes.

In the present disclosure, the site-specific insertion of the gene of interest or nucleic acid of interest is performed through Programmable Addition via Site-Specific Targeting Elements (PASTE). Components for inserting a gene of interest or a nucleic acid of interest using PASTE are for example, without limitation, a nuclease, a gRNA adding the integration site, a DNA or RNA strand comprising the gene or nucleic acid linked to a sequence that is complementary or associated to the integration site, and an integration enzyme. Components for inserting a gene of interest or a nucleic acid of interest using PASTE are for example, without limitation, a prime editor expression, pegRNA adding the integration site, nicking guide RNA, integration enzyme (Cre or serine recombinase), transgene vector comprising the gene of interest or nucleic acid sequence of interest with gene and integration signal. The nuclease and prime editor integrate the integration site into the genome. The integration enzyme integrates the gene of interest into the integration site. In some embodiments, the transgene vector comprising the gene or nucleic acid sequence of interest with gene and integration signal is a DNA minicircle devoid of bacterial DNA sequences. In some embodiments, the transgenic vector is a eukaryotic or prokaryotic vector.

As used herein, the term "vector" or "transgene vector" refers to a recombinant DNA molecule containing a desired coding sequence and appropriate nucleic acid sequences necessary for the expression of the operably linked coding sequence in a host organism. Nucleic acid sequences necessary for expression in prokaryotes usually include for example, without limitation, a promoter, an operator (optional), a ribosome binding site, and/or other sequences. Eukaryotic cells are generally known to utilize promoters (constitutive, inducible or tissue specific), enhancers, and termination and polyadenylation signals, although some elements may be deleted and other elements added without sacrificing the necessary expression. The transgenic vector may encode the PE and the integration enzyme, linked to each other via a linker. The linker can be a cleavable linker. For example, transgenic vector encoding the PE and the integration enzyme, linked to each other via a linker is pCMV PE2 P2A Cre comprises SEQ ID NO: 73. In some embodiments, the linker can be a non-cleavable linker. In some embodiments the nuclease, prime editor, and/or integration enzyme can be encoded in different vectors.

Figure 12:
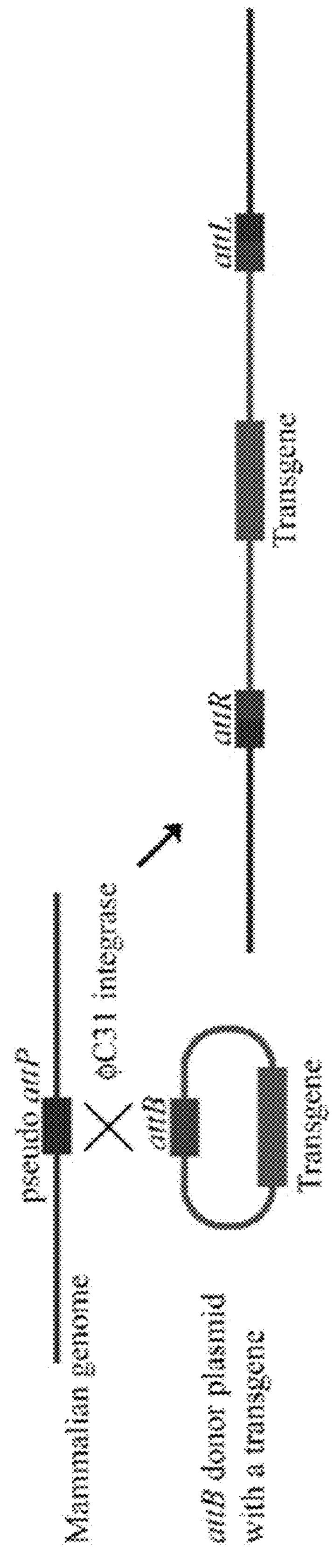
FIG. 12 shows a schematic diagram of the using φC31 as the integration enzyme, according to embodiments of the present teachings.
Figure 13:
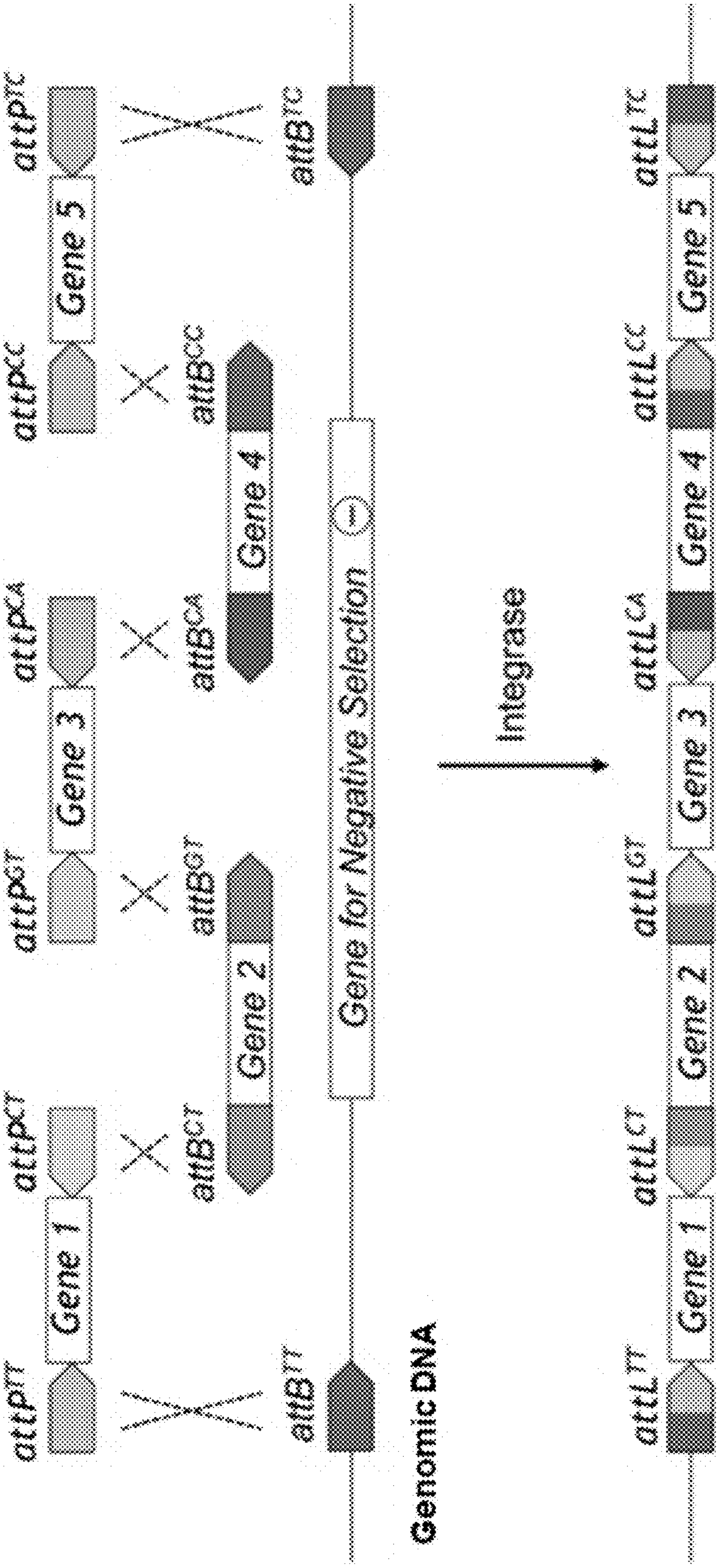
FIG. 13 shows a schematic diagram of multiplexing involving inserting multiple genes of interest in multiple loci using unique guide RNAs that incorporated exterior flanking attB sites according to embodiments of the present teachings.

A method of inserting multiple genes or nucleic acid sequences of interest into a single site according to embodiments of the present disclosure is illustrated in FIG. 12. In some embodiments, multiplexing involves inserting multiple genes of interest in multiple loci using unique pegRNA as illustrated in FIG. 13 (Merrick, C. A. et al., *ACS Synth. Biol.* 2018, 7, 299-310). The insertion of multiple genes of interest or nucleic acids of interest into a cell genome, referred herein as "multiplexing," is facilitated by incorporation of the complementary 5' integration site to the 5' end of the DNA or RNA comprising the first nucleic acid and 3' integration site to the 3' end of the DNA or RNA comprising the last nucleic acid. In some embodiments, the number of genome of interest or amino acid sequences of interest that are inserted into a cell genome using multiplexing can be about 1, 2, 3, 4, 5, 6, 7, 8, 9 10, 11, 12, 13, 14, 15, 16, 17, 18, 19, 20, 21, 22, 23, 24, 25, or any range that is formed from any two of those values as endpoints.

In some embodiments, multiplexing allows integration of for example, signaling cascade, over-expression of a protein of interest with its cofactor, insertion of multiple genes mutated in a neoplastic condition, or insertion of multiple CARs for treatment of cancer.

In some embodiments, the integration sites may be inserted into the genome using non-prime editing methods such as rAAV mediated nucleic acid integration, TALENS and ZFNs. A number of unique properties make AAV a promising vector for human gene therapy (Muzyczka, CURRENT TOPICS IN MICROBIOLOGY AND IMMUNOLOGY, 158:97-129 (1992)). Unlike other viral vectors, AAVs have not been shown to be associated with any known human disease and are generally not considered pathogenic. Wild type AAV is capable of integrating into host chromosomes in a site-specific manner M. Kotin et al., PROC. NATL. ACAD. SCI, USA, 87:2211-2215 (1990); R. J. Samulski, EMBO 10(12):3941-3950 (1991)). Instead of creating a double-stranded DNA break, AAV stimulates endogenous homologous recombination to achieve the DNA modification. Further, transcription activator-like effector nucleases (TALENs) and Zinc-finger nucleases (ZFNs) for genome editing and introducing targeted DSBs. The specificity of TALENs arises from two polymorphic amino acids, the so-called repeat variable diresidues (RVDs) located at positions 12 and 13 of a repeated unit. TALENS are linked to FokI nucleases, which cleaves the DNA at the desired locations. ZFNs are artificial restriction enzymes for custom site-specific genome editing. Zinc fingers themselves are transcription factors, where each finger recognizes 3-4 bases. By mixing and matching these finger modules, researchers can customize which sequence to target.

As used herein, the terms "administration," "introducing," or "delivery" into a cell, a tissue, or an organ of a plasmid, nucleic acids, or proteins for modification of the host genome refers to the transport for such administration, introduction, or delivery that can occur in vivo, in vitro, or ex vivo. Plasmids, DNA, or RNA for genetic modification can be introduced into cells by transfection, which is typically accomplished by chemical means (e.g., calcium phosphate transfection, polyethyleneimine (PEI) Or lipofection), physical means (electroporation or microinjection), infection (this typically means the introduction of an infectious agent such as a virus (e.g., a baculovirus expressing the AAV Rep gene)), transduction (in microbiology, this refers to the stable infection of cells by viruses, or the transfer of genetic material from one microorganism to another by viral factors (e.g., bacteriophages)). Vectors for the expression of a recombinant polypeptide, protein or oligonucleotide may be obtained by physical means (e.g., calcium phosphate transfection, electroporation, microinjection, or lipofection) in a cell, a tissue, an organ or a subject. The vector can be delivered by preparing the vector in a pharmaceutically acceptable carrier for the in vitro, ex vivo, or in vivo delivery to the carrier.

As used herein, the term "transfection" refers to the uptake of an exogenous nucleic acid molecule by a cell. A cell is "transfected" when an exogenous nucleic acid has been introduced into the cell membrane. The transfection can be a single transfection, co-transfection, or multiple transfection. Numerous transfection techniques are generally known in the art. See, for example, Graham et al. (1973) Virology, 52: 456. Such techniques can be used to introduce one or more exogenous nucleic acid molecules into a suitable host cell.

In some embodiments, the exogenous nucleic acid molecule and/or other components for gene editing are combined and delivered in a single transfection. In other embodiments, the exogenous nucleic acid molecule and/or other components for gene editing are not combined and delivered in a single transfection. In some embodiments, exogenous nucleic acid molecule and/or other components for gene editing are combined and delivered in a single transfection to comprise for example, without limitation, a prime editing vector, a landing site such as a landing site containing pegRNA, a nicking guide such as a nicking guide for stimulating prime editing, an expression vector such as an expression vector for a corresponding integrase or recombinase, a minicircle DNA cargo such as a minicircle DNA cargo encoding for green fluorescent protein (GFP), any derivatives thereof, and any combinations thereof. In some embodiments, the gene of interest or amino acid sequence of interest can be introduced using liposomes. In some embodiments, the gene of interest or amino acid sequence of interest can be delivered using suitable vectors for instance, without limitation, plasmids and viral vectors. Examples of viral vectors include, without limitation, adeno-associated viruses (AAV), lentiviruses, adenoviruses, other viral vectors, derivatives thereof, or combinations thereof. The proteins and one or more guide RNAs can be packaged into one or more vectors, e.g., plasmids or viral vectors. In some embodiments, the delivery is via nanoparticles or exosomes. For example, exosomes can be particularly useful in delivery RNA.

In some embodiments, the prime editing inserts the landing site with efficiencies of at least about 1%, at least about 5%, at least about 10%, at least about 15%, at least about, at least about 20%, at least about 25%, at least about 30%, at least about 35%, at least about 40%, at least about 45%, or at least about 50%. In some embodiments, the prime editing inserts the landing site(s) with efficiencies of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or any range that is formed from any two of those values as endpoints.

Sequences

Sequences of enzymes, guides, integration sites, and plasmids can be found in Table 4 below.

TABLE 4

| SEQ ID NO/ DESCRIPTION/ SOURCE | SEQUENCE |
|---|---|
| SEQ ID NO: 1 Lox71 (Artificial sequence) | ATAACTTCGTATAATGTATGCTATACGAACGGTA |
| SEQ ID NO: 2 Lox66 (Artificial sequence) | TACCGTTCGTATAATGTATGCTATACGAAGTTAT |
| SEQ ID NO: 3 attB (Artificial sequence) | GGCCGGCTTGTCGACGACGGCGGTCTCCGTCGTCAGGATCATCCG G |
| SEQ ID NO: 4 attP (Artificial Sequence) | CCGGATGATCCTGACGACGGAGACCGCCGTCGTCGACAAGCCGGC C |
| SEQ ID NO: 5 attB-TT (Artificial Sequence) | GGCTTGTCGACGACGGCGTTCTCCGTCGTCAGGATCAT |
| SEQ ID NO: 6 attP-TT (Artificial Sequence) | GTGGTTTGTCTGGTCAACCACCGCGTTCTCAGTGGTGTACGGTACA AACCCA |
| SEQ ID NO: 7 attB-AA (Artificial Sequence) | GGCTTGTCGACGACGGCGAACTCCGTCGTCAGGATCAT |
| SEQ ID NO: 8 attP-AA (Artificial Sequence) | GTGGTTTGTCTGGTCAACCACCGCGAACTCAGTGGTGTACGGTAC AAACCCA |
| SEQ ID NO: 9 attB-CC (Artificial Sequence) | GGCTTGTCGACGACGGCGCCCTCCGTCGTCAGGATCAT |
| SEQ ID NO: 10 attP-CC (Artificial Sequence) | GTGGTTTGTCTGGTCAACCACCGCGCCCTCAGTGGTGTACGGTACA AACCCA |
| SEQ ID NO: 11 attB-GG (Artificial Sequence) | GGCTTGTCGACGACGGCGGGCTCCGTCGTCAGGATCAT |
| SEQ ID NO: 12 attP-GG (Artificial Sequence) | GTGGTTTGTCTGGTCAACCACCGCGGGCTCAGTGGTGTACGGTAC AAACCCA |
| SEQ ID NO: 13 attB-TG (Artificial Sequence) | GGCTTGTCGACGACGGCGTGCTCCGTCGTCAGGATCAT |
| SEQ ID NO: 14 attP-TG (Artificial Sequence) | GTGGTTTGTCTGGTCAACCACCGCGTGCTCAGTGGTGTACGGTACA AACCCA |
| SEQ ID NO: 15 attB-GT (Artificial Sequence) | GGCTTGTCGACGACGGCGGTCTCCGTCGTCAGGATCAT |
| SEQ ID NO: 16 attP-GT (Artificial Sequence) | GTGGTTTGTCTGGTCAACCACCGCGGTCTCAGTGGTGTACGGTACA AACCCA |

TABLE 4-continued

| SEQ ID NO/ DESCRIPTION/ SOURCE | SEQUENCE |
|---|---|
| SEQ ID NO: 17 attB-CT (Artificial Sequence) | GGCTTGTCGACGACGGCGCTCTCCGTCGTCAGGATCAT |
| SEQ ID NO: 18 attP-CT (Artificial Sequence) | GTGGTTTGTCTGGTCAACCACCGCGCTCTCAGTGGTGTACGGTACA AACCCA |
| SEQ ID NO: 19 attB-CA (Artificial Sequence) | GGCTTGTCGACGACGGCGCACTCCGTCGTCAGGATCAT |
| SEQ ID NO: 20 attP-CA (Artificial Sequence) | GTGGTTTGTCTGGTCAACCACCGCGCACTCAGTGGTGTACGGTACA AACCCA |
| SEQ ID NO: 21 attB-TC (Artificial Sequence) | GGCTTGTCGACGACGGCGTCCTCCGTCGTCAGGATCAT |
| SEQ ID NO: 22 attP-TC (Artificial Sequence) | GTGGTTTGTCTGGTCAACCACCGCGTCCTCAGTGGTGTACGGTACA AACCCA |
| SEQ ID NO: 23 attB-GA (Artificial Sequence) | GGCTTGTCGACGACGGCGGACTCCGTCGTCAGGATCAT |
| SEQ ID NO: 24 attP-GA (Artificial Sequence) | GTGGTTTGTCTGGTCAACCACCGCGGACTCAGTGGTGTACGGTAC AAACCCA |
| SEQ ID NO: 25 attB-AG (Artificial Sequence) | GGCTTGTCGACGACGGCGAGCTCCGTCGTCAGGATCAT |
| SEQ ID NO: 26 attP-AG (Artificial Sequence) | GTGGTTTGTCTGGTCAACCACCGCGAGCTCAGTGGTGTACGGTAC AAACCCA |
| SEQ ID NO: 27 attB-AC (Artificial Sequence) | GGCTTGTCGACGACGGCGACCTCCGTCGTCAGGATCAT |
| SEQ ID NO: 28 attP-AC (Artificial Sequence) | GTGGTTTGTCTGGTCAACCACCGCGACCTCAGTGGTGTACGGTACA AACCCA |
| SEQ ID NO: 29 attB-AT (Artificial Sequence) | GGCTTGTCGACGACGGCGATCTCCGTCGTCAGGATCAT |
| SEQ ID NO: 30 attP-AT (Artificial Sequence) | GTGGTTTGTCTGGTCAACCACCGCGATCTCAGTGGTGTACGGTACA AACCCA |
| SEQ ID NO: 31 attB-GC (Artificial Sequence | GGCTTGTCGACGACGGCGGCCTCCGTCGTCAGGATCAT |
| SEQ ID NO: 32 attP-GC (Artificial Sequence) | GTGGTTTGTCTGGTCAACCACCGCGGCCTCAGTGGTGTACGGTACA AACCCA |
| SEQ ID NO: 33 attB-CG (Artificial Sequence) | GGCTTGTCGACGACGGCGCGCTCCGTCGTCAGGATCAT |
| SEQ ID NO: 34 attP-CG (Artificial Sequence) | GTGGTTTGTCTGGTCAACCACCGCGCGCTCAGTGGTGTACGGTACA AACCCA |
| SEQ ID NO: 35 attB-TA (Artificial Sequence) | GGCTTGTCGACGACGGCGTACTCCGTCGTCAGGATCAT |

TABLE 4-continued

| SEQ ID NO/ DESCRIPTION/ SOURCE | SEQUENCE |
|---|---|
| SEQ ID NO: 36 attP-TA (Artificial Sequence) | GTGGTTTGTCTGGTCAACCACCGCGTACTCAGTGGTGTACGGTACA AACCCA |
| SEQ ID NO: 37 C31-attB (Artificial Sequence) | TGCGGGTGCCAGGGCGTGCCCTTGGGCTCCCCGGGCGCGTACTCC |
| SEQ ID NO: 38 C31-attP (Artificial Sequence) | GTGCCCCAACTGGGGTAACCTTTGAGTTCTCTCAGTTGGGGG |
| SEQ ID NO: 39 R4-attB (Artificial Sequence) | GCGCCCAAGTTGCCCATGACCATGCCGAAGCAGTGGTAGAAGGGC ACCGGCAGACAC |
| SEQ ID NO: 40 R4-attP (Artificial Sequence) | AGGCATGTTCCCCAAAGCGATACCACTTGAAGCAGTGGTACTGCT TGTGGGTACACTCTGCGGGTGATGA |
| SEQ ID NO: 41 BT1-attB (Artificial Sequence) | GTCCTTGACCAGGTTTTTGACGAAAGTGATCCAGATGATCCAGCTC CACACCCCGAACGC |
| SEQ ID NO: 42 BT1-attP (Artificial Sequence) | GGTGCTGGGTTGTTGTCTCTGGACAGTGATCCATGGGAAACTACTC AGCACCACCAATGTTCC |
| SEQ ID NO: 43 Bxb-attB (Artificial Sequence) | TCGGCCGGCTTGTCGACGACGGCGGTCTCCGTCGTCAGGATCATCC GGGC |
| SEQ ID NO: 44 Bxb-attP (Artificial Sequence) | GTCGTGGTTTGTCTGGTCAACCACCGCGGTCTCAGTGGTGTACGGT ACAAACCCCGAC |
| SEQ ID NO: 45 TG1-attB (Artificial Sequence) | GATCAGCTCCGCGGGCAAGACCTTCTCCTTCACGGGGTGGAAGGT C |
| SEQ ID NO: 46 TG1-attP (Artificial Sequence) | TCAACCCCGTTCCAGCCCAACAGTGTTAGTCTTTGCTCTTACCCAG TTGGGCGGGATAGCCTGCCCG |
| SEQ ID NO: 47 C1-attB (Artificial Sequence) | AACGATTTTCAAAGGATCACTGAATCAAAAGTATTGCTCATCCAC GCGAAATTTTTC |
| SEQ ID NO: 48 C1-attP (Artificial Sequence) | AATATTTTAGGTATATGATTTTGTTTATTAGTGTAAATAACACTAT GTACCTAAAAT |
| SEQ ID NO: 49 C370-attB (Artificial Sequence) | TGTAAAGGAGACTGATAATGGCATGTACAACTATACTCGTCGGTA AAAAGGCA |
| SEQ ID NO: 50 C370-attP (Artificial Sequence) | TAAAAAAATACAGCGTTTTTCATGTACAACTATACTAGTTGTAGTG CCTAAA |
| SEQ ID NO: 51 K38-attB (Artificial Sequence) | GAGCGCCGGATCAGGGAGTGGACGGCCTGGGAGCGCTACACGCT GTGGCTGCGGTC |
| SEQ ID NO: 52 K38-attP (Artificial Sequence) | CCCTAATACGCAAGTCGATAACTCTCCTGGGAGCGTTGACAACTT GCGCACCCTGA |
| SEQ ID NO: 53 RB-attB (Artificial Sequence) | TCTCGTGGTGGTGGAAGGTGTTGGTGCGGGGTTGGCCGTGGTCGA GGTGGGGTGGTGGTAGCCATTCG |
| SEQ ID NO: 54 RV-attP (Artificial Sequence) | GCACAGGTGTAGTGTATCTCACAGGTCCACGGTTGGCCGTGGACT GCTGAAGAACATTCCACGCCAGGA |

TABLE 4-continued

| SEQ ID NO/ DESCRIPTION/ SOURCE | SEQUENCE |
|---|---|
| SEQ ID NO: 55 SPBC-attB (Artificial Sequence) | AGTGCAGCATGTCATTAATATCAGTACAGATAAAGCTGTATCTCCT GTGAACACAATGGGTGCCA |
| SEQ ID NO: 56 SPBC-attP (Artificial Sequence) | AAAGTAGTAAGTATCTTAAAAAACAGATAAAGCTGTATATTAAGA TACTTACTAC |
| SEQ ID NO: 57 TP901-attB (Artificial Sequence) | TGATAATTGCCAACACAATTAACATCTCAATCAAGGTAAATGCTTT TTCGTTTT |
| SEQ ID NO: 58 TP901-attP (Artificial Sequence) | AATTGCGAGTTTTTATTTCGTTTATTTCAATTAAGGTAACTAAAAA ACTCCTTT |
| SEQ ID NO: 59 Wβ-attB (Artificial Sequence) | AAGGTAGCGTCAACGATAGGTGTAACTGTCGTGTTTGTAACGGTA CTTCCAACAGCTGGCGTTTCAGT |
| SEQ ID NO: 60 Wβ-attP (Artificial Sequence) | TAGTTTTAAAGTTGGTTATTAGTTACTGTGATATTTATCACGGTAC CCAATAACCAATGAATATTTGA |
| SEQ ID NO: 61 A118-attB (Artificial Sequence) | TGTAACTTTTTCGGATCAAGCTATGAAGGACGCAAAGAGGGAACT AAACACTTAATT |
| SEQ ID NO: 62 A118-attP (Artificial Sequence) | TTGTTTAGTTCCTCGTTTTCTCTCGTTGGAAGAAGAAGAAACGAGA AACTAAAATTA |
| SEQ ID NO: 63 BL3-attB (Artificial Sequence) | CAACCTGTTGACATGTTTCCACAGACAACTCACGTGGAGGTAGTC ACGGCTTTTACGTTAGTT |
| SEQ ID NO: 64 BL3-attP (Artificial Sequence) | GAGAATACTGTTGAACAATGAAAAACTAGGCATGTAGAAGTTGTT TGTGCACTAACTTTAA |
| SEQ ID NO: 65 MR11-attB (Artificial Sequence) | ACAGGTCAACACATCGCAGTTATCGAACAATCTTCGAAAATGTAT GGAGGCACTTGTATCAATATAGGATGTATACCTTCGAAGACACTT GTACATGATGGATTAGAAGGCAAATCCTTT |
| SEQ ID NO: 66 MR11-attP (Artificial Sequence) | CAAAATAAAAAACATTGATTTTTATTAACTTCTTTTGTGCGGAACT ACGAACAGTTCATTAATACGAAGTGTACAAACTTCCATACAAAAA TAACCACGACAATTAAGACGTGGTTTCTA |
| SEQ ID NO: 67 attL (Artificial Sequence) | ATTATTTCTCACCCTGA |
| SEQ ID NO: 68 attR (Artificial Sequence) | ATCATCTCCCACCCGGA |
| SEQ ID NO: 69 Vox (Artificial Sequence) | AATAGGTCTG AGAACGCCCA TTCTCAGACG TATT |
| SEQ ID NO: 70 FRT (Artificial Sequence) | GAAGTTCCTATAC TTTCTAGA GAATAGGAACTTC |
| SEQ ID NO: 71 Cre recombinase expression plasmid (Artificial Sequence) | GGTCGACATTGATTATTGACTAGTTATTAATAGTAATCAATTACGG GGTCATTAGTTCATAGCCCATATATGGAGTTCCGCGTTACATAACT TACGGTAAATGGCCCGCCTGGCTGACCGCCCAACGACCCCCGCCC ATTGACGTCAATAATGACGTATGTTCCCATAGTAACGCCAATAGG GACTTTCCATTGACGTCAATGGGTGGAGTATTTACGGTAAACTGCC CACTTGGCAGTACATCAAGTGTATCATATGCCAAGTACGCCCCCTA TTGACGTCAATGACGGTAAATGGCCCGCCTGGCATTATGCCCAGT ACATGACCTTATGGGACTTTCCTACTTGGCAGTACATCTACGTATT AGTCATCGCTATTACCATGGTCGAGGTGAGCCCCACGTTCTGCTTC ACTCTCCCCATCTCCCCCCCCTCCCCACCCCCAATTTTGTATTTATT TATTTTTTAATTATTTTGTGCAGCGATGGGGGCGGGGGGGGGGG |

TABLE 4-continued

| SEQ ID NO/ DESCRIPTION/ SOURCE | SEQUENCE |
|---|---|
| | GGCGCGCGCCAGGCGGGGGGGGGGGGGGGGGGGGGGGGGGGG<br>GGGGGGGCGGGGGGGGGCGGCGGCAGCCAATCAGAGCGGCGCGC<br>TCCGAAAGTTTCCTTTTATGGCGAGGCGGCGGCGGCGGCGGCCCT<br>ATAAAAAGCGAAGCGCGCGGCGGGCGGGAGTCGCTGCGCGCTGC<br>CTTCGCCCCGTGCCCCGCTCCGCCGCCGCCTCGCGCCGCCCGCCCC<br>GGCTCTGACTGACCGCGTTACTCCCACAGGTGAGCGGGCGGGACG<br>GCCCTTCTCCTCCGGGCTGTAATTAGCGCTTGGTTTAATGACGGCT<br>TGTTTCTTTTCTGTGGCTGCGTGAAAGCCTTGAGGGGCTCCGGGAG<br>GGCCCTTTGTGCGGGGGGAGCGGCTCGGGGGGTGCGTGCGTGTGT<br>GTGTGCGTGGGGAGCGCCGCGTGCGGCTCCGCGCTGCCCGGCGGC<br>TGTGAGCGCTGCGGGCGCGGCGCGGGGCTTTGTGCGCTCCGCAGT<br>GTGCGCGAGGGGAGCGCGGCCGGGGGCGGTGCCCCGCGGTGCGG<br>GGGGGGCTGCGAGGGGAACAAAGGCTGCGTGCGGGGTGTGTGCG<br>TGGGGGGGTGAGCAGGGGGTGTGGGCGCGTCGGTCGGGCTGCAA<br>CCCCCCCTGCACCCCCCTCCCCGAGTTGCTGAGCACGGCCCGGCTT<br>CGGGTGCGGGGCTCCGTACGGGGCGTGGCGCGGGGCTCGCCGTGC<br>CGGGCGGGGGGTGGCGGCAGGTGGGGGTGCCGGGCGGGGCGGGG<br>CCGCCTCGGGCCGGGGAGGGCTCGGGGGAGGGGCGCGGCGGCCC<br>CCGGAGCGCCGGCGGCTGTCGAGGCGCGGCGAGCCGCAGCCATTG<br>CCTTTTATGGTAATCGTGCGAGAGGGCGCAGGGACTTCCTTTGTCC<br>CAAATCTGTGCGGAGCCGAAATCTGGGAGGCGCCGCCGCACCCCC<br>TCTAGCGGGCGCGGGGCGAAGCGGTGCGGCGCCGGCAGGAAGGA<br>AATGGGCGGGGAGGGCCTTCGTGCGTCGCCGCGCCGCCGTCCCCT<br>TCTCCCTCTCCAGCCTCGGGGCTGTCCGCGGGGGGACGGCTGCCTT<br>CGGGGGGGACGGGGCAGGGCGGGGTTCGGCTTCTGGCGTGTGACC<br>GGCGGCTCTAGAGCCTCTGCTAACCATGTTCATGCCTTCTTCTTTTT<br>CCTACAGCTCCTGGGCAACGTGCTGGTTATTGTGCTGTCTCATCAT<br>TTTGGCAAAGAATTCTGAGCCGCCACCATGGCCAATTTACTGACC<br>GTACACCAAAATTTGCCTGCATTACCGGTCGATGCAACGAGTGAT<br>GAGGTTCGCAAGAACCTGATGGACATGTTCAGGGATCGCCAGGCG<br>TTTTCTGAGCATACCTGGAAAATGCTTCTGTCCGTTTGCCGGTCGT<br>GGGCGGCATGGTGCAAGTTGAATAACCGGAAATGGTTTCCCGCAG<br>AACCTGAAGATGTTCGCGATTATCTTCTATATCTTCAGGCGCGCGG<br>TCTGGCAGTAAAAACTATCCAGCAACATTTGGGCCAGCTAAACAT<br>GCTTCATCGTCGGTCCGGGCTGCCACGACCAAGTGACAGCAATGC<br>TGTTTCACTGGTTATGCGGCGGATCCGAAAAGAAAACGTTGATGC<br>CGGTGAACGTGCAAAACAGGCTCTAGCGTTCGAACGCACTGATTT<br>CGACCAGGTTCGTTCACTCATGGAAAATAGCGATCGCTGCCAGGA<br>TATACGTAATCTGGCATTTCTGGGGATTGCTTATAACACCCTGTTA<br>CGTATAGCCGAAATTGCCAGGATCAGGGTTAAAGATATCTCACGT<br>ACTGACGGTGGGAGAATGTTAATCCATATTGGCAGAACGAAAACG<br>CTGGTTAGCACCGCAGGTGTAGAGAAGGCACTTAGCCTGGGGGTA<br>ACTAAACTGGTCGAGCGATGGATTTCCGTCTCTGGTGTAGCTGATG<br>ATCCGAATAACTACCTGTTTTGCCGGGTCAGAAAAAATGGTGTTG<br>CCGCGCCATCTGCCACCAGCCAGCTATCAACTCGCGCCCTGGAAG<br>GGATTTTTGAAGCAACTCATCGATTGATTTACGGCGCTAAGGATG<br>ACTCTGGTCAGAGATACCTGGCCTGGTCTGGACACAGTGCCCGTG<br>TCGGAGCCGCGCGAGATATGGCCCGCGCTGGAGTTTCAATACCGG<br>AGATCATGCAAGCTGGTGGCTGGACCAATGTAAATATTGTCATGA<br>ACTATATCCGTAACCTGGATAGTGAAACAGGGGCAATGGTGCGCC<br>TGCTGGAAGATGGCGATGGACCGGTGGAACAAAAACTTATTTCTG<br>AAGAAGATCTGTGATAGCGGCCGCACTCCTCAGGTGCAGGCTGCC<br>TATCAGAAGGTGGTGGCTGGTGTGGCCAATGCCCTGGCTCACAAA<br>TACCACTGAGATCTTTTTCCCTCTGCCAAAAATTATGGGGACATCA<br>TGAAGCCCCTTGAGCATCTGACTTCTGGCTAATAAAGGAAATTTAT<br>TTTCATTGCAATAGTGTGTTGGAATTTTTTGTGTCTCTCACTCGGAA<br>GGACATATGGGAGGGCAAATCATTTAAAACATCAGAATGAGTATT<br>TGGTTTAGAGTTTGGCAACATATGCCCATATGCTGGCTGCCATGAA<br>CAAAGGTTGGCTATAAAGAGGTCATCAGTATATGAAACAGCCCCC<br>TGCTGTCCATTCCTTATTCCATAGAAAAGCCTTGACTTGAGGTTAG<br>ATTTTTTTTATATTTTGTTTTGTGTTATTTTTTTCTTTAACATCCCTA<br>AAATTTTCCTTACATGTTTTACTAGCCAGATTTTTCCTCCTCTCCTG<br>ACTACTCCCAGTCATAGCTGTCCCTCTTCTCTTATGGAGATCCCTC<br>GACCTGCAGCCCAAGCTTGGCGTAATCATGGTCATAGCTGTTTCCT<br>GTGTGAAATTGTTATCCGCTCACAATTCCACACAACATACGAGCC<br>GGAAGCATAAAGTGTAAAGCCTGGGGTGCCTAATGAGTGAGCTAA<br>CTCACATTAATTGCGTTGCGCTCACTGCCCGCTTTCCAGTCGGGAA<br>ACCTGTCGTGCCAGCGGATCCGCATCTCAATTAGTCAGCAACCAT<br>AGTCCCGCCCCTAACTCCGCCCATCCCGCCCCTAACTCCGCCCAGT<br>TCCGCCCATTCTCCGCCCCATGGCTGACTAATTTTTTTTATTTATGC<br>AGAGGCCGAGGCCGCCTCGGCCTCTGAGCTATTCCAGAAGTAGTG<br>AGGAGGCTTTTTTGGAGGCCTAGGCTTTTGCAAAAAGCTAACTTGT<br>TTATTGCAGCTTATAATGGTTACAAATAAAGCAATAGCATCACAA<br>ATTTCACAAATAAAGCATTTTTTTCACTGCATTCTAGTTGTGGTTTG<br>TCCAAACTCATCAATGTATCTTATCATGTCTGGATCCGCTGCATTA<br>ATGAATCGGCCAACGCGCGGGGAGAGGCGGTTTGCGTATTGGGCG |

TABLE 4-continued

| SEQ ID NO/ DESCRIPTION/ SOURCE | SEQUENCE |
|---|---|
| | CTCTTCCGCTTCCTCGCTCACTGACTCGCTGCGCTCGGTCGTTCGG CTGCGGCGAGCGGTATCAGCTCACTCAAAGGCGGTAATACGGTTA TCCACAGAATCAGGGGATAACGCAGGAAAGAACATGTGAGCAAA AGGCCAGCAAAAGGCCAGGAACCGTAAAAAGGCCGCGTTGCTGG CGTTTTTCCATAGGCTCCGCCCCCCTGACGAGCATCACAAAAATCG ACGCTCAAGTCAGAGGTGGCGAAACCCGACAGGACTATAAAGAT ACCAGGCGTTTCCCCCTGGAAGCTCCCTCGTGCGCTCTCCTGTTCC GACCCTGCCGCTTACCGGATACCTGTCCGCCTTTCTCCCTTCGGGA AGCGTGGCGCTTTCTCATAGCTCACGCTGTAGGTATCTCAGTTCGG TGTAGGTCGTTCGCTCCAAGCTGGGCTGTGTGCACGAACCCCCCGT TCAGCCCGACCGCTGCGCCTTATCCGGTAACTATCGTCTTGAGTCC AACCCGGTAAGACACGACTTATCGCCACTGGCAGCAGCCACTGGT AACAGGATTAGCAGAGCGAGGTATGTAGGCGGTGCTACAGAGTTC TTGAAGTGGTGGCCTAACTACGGCTACACTAGAAGAACAGTATTT GGTATCTGCGCTCTGCTGAAGCCAGTTACCTTCGGAAAAAGAGTT GGTAGCTCTTGATCCGGCAAACAAACCACCGCTGGTAGCGGTGGT TTTTTTGTTTGCAAGCAGCAGATTACGCGCAGAAAAAAAGGATCT CAAGAAGATCCTTTGATCTTTTCTACGGGGTCTGACGCTCAGTGGA ACGAAAACTCACGTTAAGGGATTTTGGTCATGAGATTATCAAAAA GGATCTTCACCTAGATCCTTTTAAATTAAAAATGAAGTTTTAAATC AATCTAAAGTATATATGAGTAAACTTGGTCTGACAGTTACCAATG CTTAATCAGTGAGGCACCTATCTCAGCGATCTGTCTATTTCGTTCA TCCATAGTTGCCTGACTCCCCGTCGTGTAGATAACTACGATACGGG AGGGCTTACCATCTGGCCCCAGTGCTGCAATGATACCGCGAGACC CACGCTCACCGGCTCCAGATTTATCAGCAATAAACCAGCCAGCCG GAAGGGCCGAGCGCAGAAGTGGTCCTGCAACTTTATCCGCCTCCA TCCAGTCTATTAATTGTTGCCGGGAAGCTAGAGTAAGTAGTTCGCC AGTTAATAGTTTGCGCAACGTTGTTGCCATTGCTACAGGCATCGTG GTGTCACGCTCGTCGTTTGGTATGGCTTCATTCAGCTCCGGTTCCC AACGATCAAGGCGAGTTACATGATCCCCCATGTTGTGCAAAAAAG CGGTTAGCTCCTTCGGTCCTCCGATCGTTGTCAGAAGTAAGTTGGC CGCAGTGTTATCACTCATGGTTATGGCAGCACTGCATAATTCTCTT ACTGTCATGCCATCCGTAAGATGCTTTTCTGTGACTGGTGAGTACT CAACCAAGTCATTCTGAGAATAGTGTATGCGGCGACCGAGTTGCT CTTGCCCGGCGTCAATACGGGATAATACCGCGCCACATAGCAGAA CTTTAAAAGTGCTCATCATTGGAAAACGTTCTTCGGGGCGAAAAC TCTCAAGGATCTTACCGCTGTTGAGATCCAGTTCGATGTAACCCAC TCGTGCACCCAACTGATCTTCAGCATCTTTTACTTTCACCAGCGTTT CTGGGTGAGCAAAAACAGGAAGGCAAAATGCCGCAAAAAAGGGA ATAAGGGCGACACGGAAATGTTGAATACTCATACTCTTCCTTTTTC AATATTATTGAAGCATTTATCAGGGTTATTGTCTCATGAGCGGATA CATATTTGAATGTATTTAGAAAAATAAACAAATAGGGGTTCCGCG CACATTTCCCCGAAAAGTGCCACCTG |
| SEQ ID NO: 72 GFP-Lox66 Cre expression plasmid (Artificial Sequence) | AGCTCTGATCAAGAGACAGGATGAGGATCGTTTCGCATGATTGAA CAAGATGGATTGCACGCAGGTTCTCCGGCCGCTTGGGTGGAGAGG CTATTCGGCTATGACTGGGCACAACAGACAATCGGCTGCTCTGAT GCCGCCGTGTTCCGGCTGTCAGCGCAGGGGCGCCCGGTTCTTTTTG TCAAGACCGACCTGTCCGGTGCCCTGAATGAACTGCAAGACGAGG CAGCGCGGCTATCGTGGCTGGCCACGACGGGCGTTCCTTGCGCAG CTGTGCTCGACGTTGTCACTGAAGCGGGAAGGGACTGGCTGCTAT TGGGCGAAGTGCCGGGGCAGGATCTCCATGTCATCTACACCTTGC TCCTGCCGAGAAAGTATCCATCATGGCTGATGCAATGCGGCGGCT GCATACGCTTGATCCGGCTACCTGCCCATTCGACCACCAAGCGAA ACATCGCATCGAGCGAGCACGTACTCGGATGGAAGCCGGTCTTGT CGATCAGGATGATCTGGACGAAGAGCATCAGGGGCTCGCGCCAGC CGAACTGTTCGCCAGGCTCAAGGCGAGCATGCCCGACGGCGAGGA TCTCGTCGTGACCCATGGCGATGCCTGCTTGCCGAATATCATGGTG GAAAATGGCCGCTTTTCTGGATTCATCGACTGTGGCCGGCTGGGTG TGGCGGACCGCTATCAGGACATAGCGTTGGCTACCCGTGATATTG CTGAAGAGCTTGGCGGCGAATGGGCTGACCGCTTCCTCGTGCTTTA CGGTATCGCCGCTCCCGATTCGCAGCGCATCGCCTTCTATCGCCTT CTTGACGAGTTCTTCTGAATTATTAACTCGAGATCCACTAGAGTGT GGCGGCCGCATTCTTATAATCAGCATCATGATGTGGTACCACATCA TGATGCTGATTACCCCCAACTGAGAGAACTCAAAGGTTACCCCAG TTGGGGCGGGCCCACAAATAAAGCAATAGCATCACAAATTTCACA AATAAAGCATTTTTTTCACTGCATTCTAGTTGTGGTTTGTCCAAAC TCATCGAGCTCGAGATCTGGCGAAGGCGATGGGGGTCTTGAAGGC GTGCTGGTACTCCACGATGCCCAGCTCGGTGTTGCTGTGCAGCTCC TCCACGCGGCGGAAGGCGAACATGGGGCCCCCGTTCTGCAGGATG CTGGGGTGGATGGCGCTCTTGAAGTGCATGTGGCTGTCCACCACG AAGCTGTAGTAGCCGCCGTCGCGCAGGCTGAAGGTGCGGGCGAAG CTGCCCACCAGCACGTTATCGCCCATGGGGTGCAGGTGCTCCACG GTGGCGTTGCTGCGGATGATCTTGTCGGTGAAGATCACGCTGTCCT CGGGGAAGCCGGTGCCCACCACCTTGAAGTCGCCGATCACGCGGC CGGCCTCGTAGCGGTAGCTGAAGCTCACGTGCAGCACGCCGCCGT |

TABLE 4-continued

| SEQ ID NO/ DESCRIPTION/ SOURCE | SEQUENCE |
|---|---|
| | CCTCGTACTTCTCGATGCGGGTGTTGGTGTAGCCGCCGTTGTTGAT GGCGTGCAGGAAGGGGTTCTCGTAGCCGCTGGGGTAGGTGCCGAA GTGGTAGAAGCCGTAGCCCATCACGTGGCTCAGCAGGTAGGGGCT GAAGGTCAGGGCGCCTTTGGTGCTCTTCATCTTGTTGGTCATGCGG CCCTGCTCGGGGGTGCCCTCTCCGCCGCCCACCAGCTCGAACTCCA CGCCGTTCAGGGTGCCGGTGATGCGGCACTCGATCTTCATGGCGG GCATGGTGGCGACCGGTAGCGCTAGCGGCTTCGGATAACTTCGTA TAGCATACATTATACGAACGGTAAGCGCTACCGCCGGCATACCCA AGTGAAGTTGCTCGCAGCTTATAGTCGCGCCCGGGGAGCCCAAGG GCACGCCCTGGCACCGCGGCCGCTGAGTCTCGACCATCATCATCA TCATCATTGAGTTTATCTGGGATAACAGGGTAATGTCATCTAGGGA TAACAGGGTATGTCATCTGGGATAACAGGGTAATGTATCTAGGGA TAACAGGGTAATGTCATCTGGGATAACAGGGTAATGTCATCTAGG GATAACAGGGTATGTCATCTGGGATAACAGGGTAATGTATCTAGG GATAACAGGGTAATGTCATCTGGGATAACAGGGTAATGTCATCTA GGGATAACAGGGTATGTCATCTGGGATAACAGGGTAATGTATCTA GGGATAACAGGGTAATGTCATCTGGGATAACAGGGTAATGTCATC TAGGGATAACAGGGTATGTCATCTGGGATAACAGGGTAATGTATC TAGGGATAACAGGGTAATGTCATCTGGGATAACAGGGTAATGTCA TCTAGGGATAACAGGGTATGTCATCTGGGATAACAGGGTAATGTA TCTAGGGATAACAGGGTAATGTCATCTGGGATAACAGGGTAATGT CATCTAGGGATAACAGGGTATGTCATCTGGGATAACAGGGTAATG TATCTAGGGATAACAGGGTAATGTCATCTGGGATAACAGGGTAAT GTCATCTAGGGATAACAGGGTAAATGTCATCTAGGGATAACAGGG TAATGTCATCTAGGGATAACAGGGTAATGTCATCTGGGATAACAG GGTAATGTCATCTAGGGATAACAGGGTAATGTATCGCCAGCGTCG CACAGCATGTTTGCTTGTCGCCGTCGCGTCTGTCACATCTTTTCCG CCAGCAGTTAGGGATTAGCGTCTTAAGCTGGCGCGAGGACCAACG TATCAGCCAGGCGAAGCTGCTTTTGAGCACCACCCGGATGCCTAT CGCCACCGTCGGTCGCAATGTTGGTTTTGACGATCAACTCTATTTC TCGCGGGTATTTAAAAAATGCACCGGGGCCAGCCCGAGCGAGTTC CGTGCCGGTTGTGAAGAAAAAGTGAATGATGTAGCCGTCAAGTTG TCATAATTGGTAACGAATCAGACAATTGACGGCTTGACGGAGTAG CATAGGGTTTGCAGAATCCCTGCTTCGTCCATTTGACAGGCACATT ATGCATGCCGCTTCGCCTTCGCGCGCGAATTGATCTGCTGCCTCGC GCGTTTCGGTGATGACGGTGAAAACCTCTGACACATGCAGCTCCC GGAGACGGTCACAGCTTGTCTGTAAGCGGATGCCGGGAGCAGACA AGCCCGTCAGGGCGCGTCAGCGGGTGTTGGCGGGTGTCGGGGCGC AGCCATGACCCAGTCACGTAGCGATAGCGGAGTGTATACTGGCTT AACTATGCGGCATCAGAGCAGATTGTACTGAGAGTGCACCATATG CGGTGTGAAATACCGCACAGATGCGTAAGGAGAAAATACCGCATC AGGCGCTCTTCCGCTTCCTCGCTCACTGACTCGCTGCGCTCGGTCG TTCGGCTGCGGCGAGCGGTATCAGCTCACTCAAAGGCGGTAATAC GGTTATCCACAGAATCAGGGGATAACGCAGGAAAGAACATGTGA GCAAAAGGCCAGCAAAAGGCCAGGAACCGTAAAAAGGCCGCGTT GCTGGCGTTTTTCCATAGGCTCCGCCCCCCTGACGAGCATCACAAA AATCGACGCTCAAGTCAGAGGTGGCGAAACCCGACAGGACTATAA AGATACCAGGCGTTTCCCCCTGGAAGCTCCCTCGTGCGCTCTCCTG TTCCGACCCTGCCGCTTACCGGATACCTGTCCGCCTTTCTCCCTTCG GGAAGCGTGGCGCTTTCTCATAGCTCACGCTGTAGGTATCTCAGTT CGGTGTAGGTCGTTCGCTCCAAGCTGGGCTGTGTGCACGAACCCC CCGTTCAGCCCGACCGCTGCGCCTTATCCGGTAACTATCGTCTTGA GTCCAACCCGGTAAGACACGACTTATCGCCACTGGCAGCAGCCAC TGGTAACAGGATTAGCAGAGCGAGGTATGTAGGCGGTGCTACAGA GTTCTTGAAGTGGTGGCCTAACTACGGCTACACTAGAAGGACAGT ATTTGGTATCTGCGCTCTGCTGAAGCCAGTTACCTTCGGAAAAAGA GTTGGTAGCTCTTGATCCGGCAAACAAACCACCGCTGGTAGCGGT GGTTTTTTTGTTTGCAAGCAGCAGATTACGCGCAGAAAAAAAGGA TCTCAAGAAGATCCTTTGATCTTTTCTACGGGGTCTGACGCTCAGT GGAACGAAAACTCACGTTAAGGGATTTTGGTCATGAGCGGATACA TATTTGAATGTATTTAGAAAAATAAACAAAAGAGTTTGTAGAAAC GCAAAAAGGCCATCCGTCAGGATGGCCTTCTGCTTAATTTGATGCC TGGCAGTTTATGGCGGGCGTCCTGCCCGCCACCCTCCGGGCCGTTG CTTCGCAACGTTCAAATCCGCTCCCGGCGGATTTGTCCTACTCAGG AGAGCGTTCACCGACAAACAACAGATAAAACGAAAGGCCCAGTC TTTCGACTGAGCCTTTCGTTTTATTTGATGCCTGGCAGTTCCCTACT CTCGCATGGGGAGACCCCACACTACCATCGGCGCTACGGCGTTTC ACTTCTGAGTTCGGCATGGGGTCAGGTGGGACCACCGCGCTACTG CCGCCAGGCAAATTCTGTTTTATCAGACCGCTTCTGCGTTCTGATT TAATCTGTATCAGGCTGAAAATCTTCTCTCATCCGCCAAAACAGCC AAGCTGGAGACCGTTTGGCCCCCCTCGAGCACGTAGAAAGCCAGT CCGCAGAAACGGTGCTGACCCCGGATGAATGTCAGCTACTGGGCT ATCTGGACAAGGGAAAACGCAAGCGCAAAGAGAAAGCAGGTAGC TTGCAGTGGGCTTACATGGCGATAGCTAGACTGGGCGGTTTTATG GACAGCAAGCGAACCGGAATTGCCAGCTGGGGCGCCCTCTGGTAA |

TABLE 4-continued

| SEQ ID NO/<br>DESCRIPTION/<br>SOURCE | SEQUENCE |
|---|---|
| | GGTTGGGAAGCCCTGCAAAGTAAACTGGATGGCTTTCTCGCCGCC<br>AAGGATCTGATGGCGCAGGGGATCA |
| SEQ ID NO: 73<br>pCMV PE2 P2A Cre<br>plasmid<br>(Artificial Sequence) | ACGCGTTGACATTGATTATTGACTAGTTATTAATAGTAATCAATTA<br>CGGGGTCATTAGTTCATAGCCCATATATGGAGTTCCGCGTTACATA<br>ACTTACGGTAAATGGCCCGCCTGGCTGACCGCCCAACGACCCCCG<br>CCCATTGACGTCAATAATGACGTATGTTCCCATAGTAACGCCAATA<br>GGGACTTTCCATTGACGTCAATGGGTGGAGTATTTACGGTAAACT<br>GCCCACTTGGCAGTACATCAAGTGTATCATATGCCAAGTACGCCC<br>CCTATTGACGTCAATGACGGTAAATGGCCCGCCTGGCATTATGCCC<br>AGTACATGACCTTATGGGACTTTCCTACTTGGCAGTACATCTACGT<br>ATTAGTCATCGCTATTACCATGGTGATGCGGTTTTGGCAGTACATC<br>AATGGGCGTGGATAGCGGTTTGACTCACGGGGATTTCCAAGTCTC<br>CACCCCATTGACGTCAATGGGAGTTTGTTTTGGCACCAAAATCAAC<br>GGGACTTTCCAAAATGTCGTAACAACTCCGCCCCATTGACGCAAA<br>TGGGCGGTAGGCGTGTACGGTGGGAGGTCTATATAAGCAGAGCTG<br>GTTTAGTGAACCGTCAGATCCGCTAGAGATCCGCGGCCGCTAATA<br>CGACTCACTATAGGGAGAGCCGCCACCATGAAACGGACAGCCGAC<br>GGAAGCGAGTTCGAGTCACCAAAGAAGAAGCGGAAAGTCGACAA<br>GAAGTACAGCATCGGCCTGGACATCGGCACCAACTCTGTGGGCTG<br>GGCCGTGATCACCGACGAGTACAAGGTGCCCAGCAAGAAATTCAA<br>GGTGCTGGGCAACACCGACCGGCACAGCATCAAGAAGAACCTGAT<br>CGGAGCCCTGCTGTTCGACAGCGGCGAAACAGCCGAGGCCACCCG<br>GCTGAAGAGAACCGCCAGAAGAAGATACACCAGACGGAAGAACC<br>GGATCTGCTATCTGCAAGAGATCTTCAGCAACGAGATGGCCAAGG<br>TGGACGACAGCTTCTTCCACAGACTGGAAGAGTCCTTCCTGGTGG<br>AAGAGGATAAGAAGCACGAGCGGCACCCCATCTTCGGCAACATCG<br>TGGACGAGGTGGCCTACCACGAGAAGTACCCCACCATCTACCACC<br>TGAGAAAGAAACTGGTGGACAGCACCGACAAGGCCGACCTGCGG<br>CTGATCTATCTGGCCCTGGCCCACATGATCAAGTTCCGGGGCCACT<br>TCCTGATCGAGGGCGACCTGAACCCCGACAACAGCGACGTGGACA<br>AGCTGTTCATCCAGCTGGTGCAGACCTACAACCAGCTGTTCGAGG<br>AAAACCCCATCAACGCCAGCGGCGTGGACGCCAAGGCCATCCTGT<br>CTGCCAGACTGAGCAAGAGCAGACGGCTGGAAAATCTGATCGCCC<br>AGCTGCCCGGCGAGAAGAAGAATGGCCTGTTCGGAAACCTGATTG<br>CCCTGAGCCTGGGCCTGACCCCCAACTTCAAGAGCAACTTCGACC<br>TGGCCGAGGATGCCAAACTGCAGCTGAGCAAGGACACCTACGACG<br>ACGACCTGGACAACCTGCTGGCCCAGATCGGCGACCAGTACGCCG<br>ACCTGTTTCTGGCCGCCAAGAACCTGTCCGACGCCATCCTGCTGAG<br>CGACATCCTGAGAGTGAACACCGAGATCACCAAGGCCCCCCTGAG<br>CGCCTCTATGATCAAGAGATACGACGAGCACCACCAGGACCTGAC<br>CCTGCTGAAAGCTCTCGTGCGGCAGCAGCTGCCTGAGAAGTACAA<br>AGAGATTTTCTTCGACCAGAGCAAGAACGGCTACGCCGGCTACAT<br>TGACGGCGGAGCCAGCCAGGAAGAGTTCTACAAGTTCATCAAGCC<br>CATCCTGGAAAAGATGGACGGCACCGAGGAACTGCTCGTGAAGCT<br>GAACAGAGAGGACCTGCTGCGGAAGCAGCGGACCTTCGACAACG<br>GCAGCATCCCCCACCAGATCCACCTGGGAGAGCTGCACGCCATTC<br>TGCGGCGGCAGGAAGATTTTTACCCATTCCTGAAGGACAACCGGG<br>AAAAGATCGAGAAGATCCTGACCTTCCGCATCCCCTACTACGTGG<br>GCCCTCTGGCCAGGGGAAACAGCAGATTCGCCTGGATGACCAGAA<br>AGAGCGAGGAAACCATCACCCCCTGGAACTTCGAGGAAGTGGTGG<br>ACAAGGGCGCTTCCGCCCAGAGCTTCATCGAGCGGATGACCAACT<br>TCGATAAGAACCTGCCCAACGAGAAGGTGCTGCCCAAGCACAGCC<br>TGCTGTACGAGTACTTCACCGTGTATAACGAGCTGACCAAAGTGA<br>AATACGTGACCGAGGGAATGAGAAAGCCCGCCTTCCTGAGCGGCG<br>AGCAGAAAAAGGCCATCGTGGACCTGCTGTTCAAGACCAACCGGA<br>AAGTGACCGTGAAGCAGCTGAAAGAGGACTACTTCAAGAAAATC<br>GAGTGCTTCGACTCCGTGGAAATCTCCGGCGTGGAAGATCGGTTC<br>AACGCCTCCCTGGGCACATACCACGATCTGCTGAAAATTATCAAG<br>GACAAGGACTTCCTGGACAATGAGGAAAACGAGGACATTCTGGA<br>AGATATCGTGCTGACCCTGACACTGTTTGAGGACAGAGAGATGAT<br>CGAGGAACGGCTGAAAACCTATGCCCACCTGTTCGACGACAAAGT<br>GATGAAGCAGCTGAAGCGGCGGAGATACACCGGCTGGGGCAGGC<br>TGAGCCGGAAGCTGATCAACGGCATCCGGGACAAGCAGTCCGGCA<br>AGACAATCCTGGATTTCCTGAAGTCCGACGGCTTCGCCAACAGAA<br>ACTTCATGCAGCTGATCCACGACGACAGCCTGACCTTTAAAGAGG<br>ACATCCAGAAAGCCCAGGTGTCCGGCCAGGGCGATAGCCTGCACG<br>AGCACATTGCCAATCTGGCCGGCAGCCCCGCCATTAAGAAGGGCA<br>TCCTGCAGACAGTGAAGGTGGTGGACGAGCTCGTGAAAGTGATGG<br>GCCGGCACAAGCCCGAGAACATCGTGATCGAAATGGCCAGAGAG<br>AACCAGACCACCCAGAAGGGACAGAAGAACAGCCGCGAGAGAAT<br>GAAGCGGATCGAAGAGGGCATCAAAGAGCTGGGCAGCCAGATCC<br>TGAAAGAACACCCCGTGGAAAACACCCAGCTGCAGAACGAGAAG<br>CTGTACCTGTACTACCTGCAGAATGGGCGGGATATGTACGTGGAC<br>CAGGAACTGGACATCAACCGGCTGTCCGACTACGATGTGGACGCT<br>ATCGTGCCTCAGAGCTTTCTGAAGGACGACTCCATCGACAACAAG |

TABLE 4-continued

| SEQ ID NO/ DESCRIPTION/ SOURCE | SEQUENCE |
|---|---|
| | GTGCTGACCAGAAGCGACAAGAACCGGGGCAAGAGCGACAACGT |
| | GCCCTCCGAAGAGGTCGTGAAGAAGATGAAGAACTACTGGCGGC |
| | AGCTGCTGAACGCCAAGCTGATTACCCAGAGAAAGTTCGACAATC |
| | TGACCAAGGCCGAGAGAGGCGGCCTGAGCGAACTGGATAAGGCC |
| | GGCTTCATCAAGAGACAGCTGGTGGAAACCCGGCAGATCACAAAG |
| | CACGTGGCACAGATCCTGGACTCCCGGATGAACACTAAGTACGAC |
| | GAGAATGACAAGCTGATCCGGGAAGTGAAAGTGATCACCCTGAA |
| | GTCCAAGCTGGTGTCCGATTTCCGGAAGGATTTCCAGTTTTACAAA |
| | GTGCGCGAGATCAACAACTACCACCACGCCCACGACGCCTACCTG |
| | AACGCCGTCGTGGGAACCGCCCTGATCAAAAAGTACCCTAAGCTG |
| | GAAAGCGAGTTCGTGTACGGCGACTACAAGGTGTACGACGTGCGG |
| | AAGATGATCGCCAAGAGCGAGCAGGAAATCGGCAAGGCTACCGC |
| | CAAGTACTTCTTCTACAGCAACATCATGAACTTTTTCAAGACCGAG |
| | ATTACCCTGGCCAACGGCGAGATCCGGAAGCGGCCTCTGATCGAG |
| | ACAAACGGCGAAACCGGGGAGATCGTGTGGGATAAGGGCCGGGA |
| | TTTTGCCACCGTGCGGAAAGTGCTGAGCATGCCCCAAGTGAATAT |
| | CGTGAAAAAGACCGAGGTGCAGACAGGCGGCTTCAGCAAAGAGT |
| | CTATCCTGCCCAAGAGGAACAGCGATAAGCTGATCGCCAGAAAGA |
| | AGGACTGGGACCCTAAGAAGTACGGCGGCTTCGACAGCCCCACCG |
| | TGGCCTATTCTGTGCTGGTGGTGGCCAAAGTGGAAAAGGGCAAGT |
| | CCAAGAAACTGAAGAGTGTGAAAGAGCTGCTGGGGATCACCATCA |
| | TGGAAAGAAGCAGCTTCGAGAAGAATCCCATCGACTTTCTGGAAG |
| | CCAAGGGCTACAAAGAAGTGAAAAAGGACCTGATCATCAAGCTG |
| | CCTAAGTACTCCCTGTTCGAGCTGGAAAACGGCCGGAAGAGAATG |
| | CTGGCCTCTGCCGGCGAACTGCAGAAGGGAAACGAACTGGCCCTG |
| | CCCTCCAAATATGTGAACTTCCTGTACCTGGCCAGCCACTATGAGA |
| | AGCTGAAGGGCTCCCCCGAGGATAATGAGCAGAAACAGCTGTTTG |
| | TGGAACAGCACAAGCACTACCTGGACGAGATCATCGAGCAGATCA |
| | GCGAGTTCTCCAAGAGAGTGATCCTGGCCGACGCTAATCTGGACA |
| | AAGTGCTGTCCGCCTACAACAAGCACCGGGATAAGCCCATCAGAG |
| | AGCAGGCCGAGAATATCATCCACCTGTTTACCCTGACCAATCTGG |
| | GAGCCCCTGCCGCCTTCAAGTACTTTGACACCACCATCGACCGGA |
| | AGAGGTACACCAGCACCAAAGAGGTGCTGGACGCCACCCTGATCC |
| | ACCAGAGCATCACCGGCCTGTACGAGACACGGATCGACCTGTCTC |
| | AGCTGGGAGGTGACTCTGGAGGATCTAGCGGAGGATCCTCTGGCA |
| | GCGAGACACCAGGAACAAGCGAGTCAGCAACACCAGAGAGCAGT |
| | GGCGGCAGCAGCGGCGGCAGCAGCACCCTAAATATAGAAGATGA |
| | GTATCGGCTACATGAGACCTCAAAAGAGCCAGATGTTTCTCTAGG |
| | GTCCACATGGCTGTCTGATTTTCCTCAGGCCTGGGCGGAAACCGG |
| | GGGCATGGGACTGGCAGTTCGCCAAGCTCCTCTGATCATACCTCTG |
| | AAAGCAACCTCTACCCCCGTGTCCATAAAACAATACCCCATGTCA |
| | CAAGAAGCCAGACTGGGGATCAAGCCCCACATACAGAGACTGTTG |
| | GACCAGGGAATACTGGTACCCTGCCAGTCCCCCTGGAACACGCCC |
| | CTGCTACCCGTTAAGAAACCAGGGACTAATGATTATAGGCCTGTC |
| | CAGGATCTGAGAGAAGTCAACAAGCGGGTGGAAGACATCCACCC |
| | CACCGTGCCCAACCCTTACAACCTCTTGAGCGGGCTCCCACCGTCC |
| | CACCAGTGGTACACTGTGCTTGATTTAAAGGATGCCTTTTTCTGCC |
| | TGAGACTCCACCCCACCAGTCAGCCTCTCTTCGCCTTTGAGTGGAG |
| | AGATCCAGAGATGGGAATCTCAGGACAATTGACCTGGACCAGACT |
| | CCCACAGGGTTTCAAAAACAGTCCCACCCTGTTTAATGAGGCACT |
| | GCACAGAGACCTAGCAGACTTCCGGATCCAGCACCCAGACTTGAT |
| | CCTGCTACAGTACGTGGATGACTTACTGCTGGCCGCCACTTCTGAG |
| | CTAGACTGCCAACAAGGTACTCGGGCCCTGTTACAAACCCTAGGG |
| | AACCTCGGGTATCG0GCCTCGGCCAAGAAAGCCCAAATTTGCCAG |
| | AAACAGGTCAAGTATCTGGGGTATCTTCTAAAAGAGGGTCAGAGA |
| | TGGCTGACTGAGGCCAGAAAAGAGACTGTGATGGGGCAGCCTACT |
| | CCGAAGACCCCTCGACAACTAAGGGAGTTCCTAGGGAAGGCAGGC |
| | TTCTGTCGCCTCTTCATCCCTGGGTTTGCAGAAATGGCAGCCCCCC |
| | TGTACCCTCTCACCAAACCGGGGACTCTGTTTAATTGGGGCCCAGA |
| | CCAACAAAAGGCCTATCAAGAAATCAAGCAAGCTCTTCTAACTGC |
| | CCCAGCCCTGGGGTTGCCAGATTTGACTAAGCCCTTTGAACTCTTT |
| | GTCGACGAGAAGCAGGGCTACGCCAAAGGTGTCCTAACGCAAAA |
| | ACTGGGACCTTGGCGTCGGCCGGTGGCCTACCTGTCCAAAAAGCT |
| | AGACCCAGTAGCAGCTGGGTGGCCCCCTTGCCTACGGATGGTAGC |
| | AGCCATTGCCGTACTGACAAAGGATGCAGGCAAGCTAACCATGGG |
| | ACAGCCACTAGTCATTCTGGCCCCCCATGCAGTAGAGGCACTAGT |
| | CAAACAACCCCCCGACCGCTGGCTTTCCAACGCCCGGATGACTCA |
| | CTATCAGGCCTTGCTTTTGGACACGGACCGGGTCCAGTTCGGACCG |
| | GTGGTAGCCCTGAACCCGGCTACGCTGCTCCCACTGCCTGAGGAA |
| | GGGCTGCAACACAACTGCCTTGATATCCTGGCCGAAGCCCACGGA |
| | ACCCGACCCGACCTAACGGACCAGCCGCTCCCAGACGCCGACCAC |
| | ACCTGGTACACGGATGGAAGCAGTCTCTTACAAGAGGGACAGCGT |
| | AAGGCGGGAGCTGCGGTGACCACCGAGACCGAGGTAATCTGGGCT |
| | AAAGCCCTGCCAGCCGGGACATCCGCTCAGCGGGCTGAACTGATA |
| | GCACTCACCCAGGCCCTAAAGATGGCAGAAGGTAAGAAGCTAAAT |
| | GTTTATACTGATAGCCGTTATGCTTTTGCTACTGCCCATATCCATG |

TABLE 4-continued

| SEQ ID NO/ DESCRIPTION/ SOURCE | SEQUENCE |
|---|---|
| | GAGAAATATACAGAAGGCGTGGGTGGCTCACATCAGAAGGCAAA<br>GAGATCAAAAATAAAGACGAGATCTTGGCCCTACTAAAAGCCCTC<br>TTTCTGCCCAAAAGACTTAGCATAATCCATTGTCCAGGACATCAAA<br>AGGGACACAGCGCCGAGGCTAGAGGCAACCGGATGGCTGACCAA<br>GCGGCCCGAAAGGCAGCCATCACAGAGACTCCAGACACCTCTACC<br>CTCCTCATAGAAAATTCATCACCCTCTGGCGGCTCAAAAAGAACC<br>GCCGACGGCAGCGAATTCGAGCCCAAGAAGAAGAGGAAAGTCGG<br>AAGCGGAGCTACTAACTTCAGCCTGCTGAAGCAGGCTGGCGACGT<br>GGAGGAGAACCCTGGACCTAATTTACTGACCGTACACCAAAATTT<br>GCCTGCATTACCGGTCGATGCAACGAGTGATGAGGTTCGCAAGAA<br>CCTGATGGACATGTTCAGGGATCGCCAGGCGTTTTCTGAGCATACC<br>TGGAAAATGCTTCTGTCCGTTTGCCGGTCGTGGGCGGCATGGTGCA<br>AGTTGAATAACCGGAAATGGTTTCCCGCAGAACCTGAAGATGTTC<br>GCGATTATCTTCTATATCTTCAGGCGCGCGGTCTGGCAGTAAAAAC<br>TATCCAGCAACATTTGGGCCAGCTAAACATGCTTCATCGTCGGTCC<br>GGGCTGCCACGACCAAGTGACAGCAATGCTGTTTCACTGGTTATG<br>CGGCGGATCCGAAAAGAAAACGTTGATGCCGGTGAACGTGCAAA<br>ACAGGCTCTAGCGTTCGAACGCACTGATTTCGACCAGGTTCGTTCA<br>CTCATGGAAAATAGCGATCGCTGCCAGGATATACGTAATCTGGCA<br>TTTCTGGGGATTGCTTATAACACCCTGTTACGTATAGCCGAAATTG<br>CCAGGATCAGGGTTAAAGATATCTCACGTACTGACGGTGGGAGAA<br>TGTTAATCCATATTGGCAGAACGAAAACGCTGGTTAGCACCGCAG<br>GTGTAGAGAAGGCACTTAGCCTGGGGGTAACTAAACTGGTCGAGC<br>GATGGATTTCCGTCTCTGGTGTAGCTGATGATCCGAATAACTACCT<br>GTTTTGCCGGGTCAGAAAAAATGGTGTTGCCGCGCCATCTGCCAC<br>CAGCCAGCTATCAACTCGCGCCCTGGAAGGGATTTTTGAAGCAAC<br>TCATCGATTGATTTACGGCGCTAAGGATGACTCTGGTCAGAGATA<br>CCTGGCCTGGTCTGGACACAGTGCCCGTGTCGGAGCCGCGCGAGA<br>TATGGCCCGCGCTGGAGTTTCAATACCGGAGATCATGCAAGCTGG<br>TGGCTGGACCAATGTAAATATTGTCATGAACTATATCCGTAACCTG<br>GATAGTGAAACAGGGGCAATGGTGCGCCTGCTGGAAGATGGCGAT<br>TAATTTAAACCCGCTGATCAGCCTCGACTGTGCCTTCTAGTTGCCA<br>GCCATCTGTTGTTTGCCCCTCCCCCGTGCCTTCCTTGACCCTGGAA<br>GGTGCCACTCCCACTGTCCTTTCCTAATAAAATGAGAAAATTGCAT<br>CGCATTGTCTGAGTAGGTGTCATTCTATTCTGGGGGGTGGGGTGGG<br>GCAGGACAGCAAGGGGGAGGATTGGGAAGACAATAGCAGGCATG<br>CTGGGGATGCGGTGGGCTCTATGGCTTCTGAGGCGGAAAGAACCA<br>GCTGGGGCTCGATACCGTCGACCTCTAGCTAGAGCTTGGCGTAAT<br>CATGGTCATAGCTGTTTCCTGTGTGAAATTGTTATCCGCTCACAAT<br>TCCACACAACATACGAGCCGGAAGCATAAAGTGTAAAGCCTAGGG<br>TGCCTAATGAGTGAGCTAACTCACATTAATTGCGTTGCGCTCACTG<br>CCCGCTTTCCAGTCGGGAAACCTGTCGTGCCAGCTGCATTAATGAA<br>tcggccaacgcgcggggagaggcggtttgcgtattgggcgctctt<br>CCGCTTCCTCGCTCACTGACTCGCTGCGCTCGGTCGTTCGGCTGCG<br>GCGAGCGGTATCAGCTCACTCAAAGGCGGTAATACGGTTATCCAC<br>AGAATCAGGGGATAACGCAGGAAAGAACATGTGAGCAAAAGGCC<br>AGCAAAAGGCCAGGAACCGTAAAAAGGCCGCGTTGCTGGCGTTTT<br>TCCATAGGCTCCGCCCCCCTGACGAGCATCACAAAAATCGACGCT<br>CAAGTCAGAGGTGGCGAAACCCGACAGGACTATAAAGATACCAG<br>GCGTTTCCCCCTGGAAGCTCCCTCGTGCGCTCTCCTGTTCCGACCC<br>TGCCGCTTACCGGATACCTGTCCGCCTTTCTCCCTTCGGGAAGCGT<br>GGCGCTTTCTCATAGCTCACGCTGTAGGTATCTCAGTTCGGTGTAG<br>GTCGTTCGCTCCAAGCTGGGCTGTGTGCACGAACCCCCCGTTCAGC<br>CCGACCGCTGCGCCTTATCCGGTAACTATCGTCTTGAGTCCAACCC<br>GGTAAGACACGACTTATCGCCACTGGCAGCAGCCACTGGTAACAG<br>GATTAGCAGAGCGAGGTATGTAGGCGGTGCTACAGAGTTCTTGAA<br>GTGGTGGCCTAACTACGGCTACACTAGAAGAACAGTATTTGGTAT<br>CTGCGCTCTGCTGAAGCCAGTTACCTTCGGAAAAAGAGTTGGTAG<br>CTCTTGATCCGGCAAACAAACCACCGCTGGTAGCGGTGGTTTTTTT<br>GTTTGCAAGCAGCAGATTACGCGCAGAAAAAAAGGATCTCAAGA<br>AGATCCTTTGATCTTTTCTACGGGGTCTGACGCTCAGTGGAACGAA<br>AACTCACGTTAAGGGATTTTGGTCATGAGATTATCAAAAAGGATC<br>TTCACCTAGATCCTTTTAAATTAAAAATGAAGTTTTAAATCAATCT<br>AAAGTATATATGAGTAAACTTGGTCTGACAGTTACCAATGCTTAAT<br>CAGTGAGGCACCTATCTCAGCGATCTGTCTATTTCGTTCATCCATA<br>GTTGCCTGACTCCCCGTCGTGTAGATAACTACGATACGGGAGGGC<br>TTACCATCTGGCCCCAGTGCTGCAATGATACCGCGAGACCCACGC<br>TCACCGGCTCCAGATTTATCAGCAATAAACCAGCCAGCCGGAAGG<br>GCCGAGCGCAGAAGTGGTCCTGCAACTTTATCCGCCTCCATCCAGT<br>CTATTAATTGTTGCCGGGAAGCTAGAGTAAGTAGTTCGCCAGTTA<br>ATAGTTTGCGCAACGTTGTTGCCATTGCTACAGGCATCGTGGTGTC<br>ACGCTCGTCGTTTGGTATGGCTTCATTCAGCTCCGGTTCCCAACGA<br>TCAAGGCGAGTTACATGATCCCCCATGTTGTGCAAAAAAGCGGTT<br>AGCTCCTTCGGTCCTCCGATCGTTGTCAGAAGTAAGTTGGCCGCAG<br>TGTTATCACTCATGGTTATGGCAGCACTGCATAATTCTCTTACTGT<br>CATGCCATCCGTAAGATGCTTTTCTGTGACTGGTGAGTACTCAACC |

TABLE 4-continued

| SEQ ID NO/<br>DESCRIPTION/<br>SOURCE | SEQUENCE |
|---|---|
| | AAGTCATTCTGAGAATAGTGTATGCGGCGACCGAGTTGCTCTTGCC<br>CGGCGTCAATACGGGATAATACCGCGCCACATAGCAGAACTTTAA<br>AAGTGCTCATCATTGGAAAACGTTCTTCGGGGCGAAAACTCTCAA<br>GGATCTTACCGCTGTTGAGATCCAGTTCGATGTAACCCACTCGTGC<br>ACCCAACTGATCTTCAGCATCTTTTACTTTCACCAGCGTTTCTGGG<br>TGAGCAAAAACAGGAAGGCAAAATGCCGCAAAAAAGGGAATAAG<br>GGCGACACGGAAATGTTGAATACTCATACTCTTCCTTTTTCAATAT<br>TATTGAAGCATTTATCAGGGTTATTGTCTCATGAGCGGATACATAT<br>TTGAATGTATTTAGAAAAATAAACAAATAGGGGTTCCGCGCACAT<br>TTCCCCGAAAAGTGCCACCTGACGTCGACGGATCGGGAGATCGAT<br>CTCCCGATCCCCTAGGGTCGACTCTCAGTACAATCTGCTCTGATGC<br>CGCATAGTTAAGCCAGTATCTGCTCCCTGCTTGTGTGTTGGAGGTC<br>GCTGAGTAGTGCGCGAGCAAAATTTAAGCTACAACAAGGCAAGGC<br>TTGACCGACAATTGCATGAAGAATCTGCTTAGGGTTAGGCGTTTTG<br>CGCTGCTTCGCGATGTACGGGCCAGATAT |
| SEQ ID NO: 74<br>+90 ngRNA guide<br>sequence<br>(Artificial Sequence) | GTCAACCAGTATCCCGGTGC |
| SEQ ID NO: 75<br>+90 ngRNA<br>(Artificial Sequence) | GTCAACCAGTATCCCGGTGCGTTTTAGAGCTAGAAATAGCAAGTT<br>AAAATAAGGCTAGTCCGTTATCAACTTGAAAAAGTGGCACCGAGT<br>CGGTGC |
| SEQ ID NO: 76<br>GFP minicircle<br>template (before<br>cleavage into a<br>minicircle)<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT |

TABLE 4-continued

| SEQ ID NO/ DESCRIPTION/ SOURCE | SEQUENCE |
|---|---|
| | TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCAGCTACCGG<br>TCGCCACCATGCCCGCCATGAAGATCGAGTGCCGCATCACCGGCA<br>CCCTGAACGGCGTGGAGTTCGAGCTGGTGGGCGGCGGAGAGGGC<br>ACCCCCGAGCAGGGCCGCATGACCAACAAGATGAAGAGCACCAA<br>AGGCGCCCTGACCTTCAGCCCCTACCTGCTGAGCCACGTGATGGG<br>CTACGGCTTCTACCACTTCGGCACCTACCCCAGCGGCTACGAGAA<br>CCCCTTCCTGCACGCCATCAACAACGGCGGCTACACCAACACCCG<br>CATCGAGAAGTACGAGGACGGCGGCGTGCTGCACGTGAGCTTCAG<br>CTACCGCTACGAGGCCGGCCGCGTGATCGGCGACTTCAAGGTGGT<br>GGGCACCGGCTTCCCCGAGGACAGCGTGATCTTCACCGACAAGAT<br>CATCCGCAGCAACGCCACCGTGGAGCACCTGCACCCCATGGGCGA<br>TAACGTGCTGGTGGGCAGCTTCGCCCGCACCTTCAGCCTGCGCGA<br>CGGCGGCTACTACAGCTTCGTGGTGGACAGCCACATGCACTTCAA<br>GAGCGCCATCCACCCCAGCATCCTGCAGAACGGGGGCCCCATGTT<br>CGCCTTCCGCCGCGTGGAGGAGCTGCACAGCAACACCGAGCTGGG<br>CATCGTGGAGTACCAGCACGCCTTCAAGACCCCCATCGCCTTCGCC<br>AGATCTCGAGCTCGATGAGTTTGGACAAACCACAACTAGAATGCA<br>GTGAAAAAAATGCTTTATTTGTGAAATTTGTGATGCTATTGCTTTA<br>TTTGTGGGCCCGCCCCAACTGGGGTAACCTTTGAGTTCTCTCAGTT<br>GGGGGTAATCAGCATCATGATGTGGTACCACATCATGATGCTGAT<br>TATAAGAATGCGGCCGCCACACTCTAGTGGATCTCGAGTTAATAA<br>TTCAGAAGAACTCGTCAAGAAGGCGATAGAAGGCGATGCGCTGCG<br>AATCGGGAGCGGCGATACCGTAAAGCACGAGGAAGCGGTCAGCC<br>CATTCGCCGCCAAGCTCTTCAGCAATATCACGGGTAGCCAACGCT<br>ATGTCCTGATAGCGGTCCGCCACACCCAGCCGGCCACAGTCGATG<br>AATCCAGAAAAGCGGCCATTTTCCACCATGATATTCGGCAAGCAG<br>GCATCGCCATGGGTCACGACGAGATCCTCGCCGTCGGGCATGCTC<br>GCCTTGAGCCTGGCGAACAGTTCGGCTGGCGCGAGCCCCTGATGC<br>TCTTCGTCCAGATCATCCTGATCGACAAGACCGGCTTCCATCCGAG<br>TACGTGCTCGCTCGATGCGATGTTTCGCTTGGTGGTCGAATGGGCA<br>GGTAGCCGGATCAAGCGTATGCAGCCGCCGCATTGCATCAGCCAT<br>GATGGATACTTTCTCGGCAGGAGCAAGGTGTAGATGACATGGAGA<br>TCCTGCCCCGGCACTTCGCCCAATAGCAGCCAGTCCCTTCCCGCTT<br>CAGTGACAACGTCGAGCACAGCTGCGCAAGGAACGCCCGTCGTGG<br>CCAGCCACGATAGCCGCGCTGCCTCGTCTTGCAGTTCATTCAGGGC<br>ACCGGACAGGTCGGTCTTGACAAAAAGAACCGGGCGCCCCTGCGC<br>TGACAGCCGGAACACGGCGGCATCAGAGCAGCCGATTGTCTGTTG<br>TGCCCAGTCATAGCCGAATAGCCTCTCCACCCAAGCGGCCGGAGA<br>ACCTGCGTGCAATCCATCTTGTTCAATCATGCGAAACGATCCTCAT<br>CCTGTCTCTTGATCAGAGCT |
| SEQ ID NO: 77<br>*Gaussia* Luciferase minicircle template (Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT |

TABLE 4-continued

| SEQ ID NO/ DESCRIPTION/ SOURCE | SEQUENCE |
|---|---|
| | TATTTTTCTAAATACATTCAAATATGTATCCGCTCATGACCAAAAT |
| | CCCTTAACGTGAGTTTTCGTTCCACTGAGCGTCAGACCCCGTAGAA |
| | AAGATCAAAGGATCTTCTTGAGATCCTTTTTTTCTGCGCGTAATCT |
| | GCTGCTTGCAAACAAAAAAACCACCGCTACCAGCGGTGGTTTGTT |
| | TGCCGGATCAAGAGCTACCAACTCTTTTTCCGAAGGTAACTGGCTT |
| | CAGCAGAGCGCAGATACCAAATACTGTCCTTCTAGTGTAGCCGTA |
| | GTTAGGCCACCACTTCAAGAACTCTGTAGCACCGCCTACATACCTC |
| | GCTCTGCTAATCCTGTTACCAGTGGCTGCTGCCAGTGGCGATAAGT |
| | CGTGTCTTACCGGGTTGGACTCAAGACGATAGTTACCGGATAAGG |
| | CGCAGCGGTCGGGCTGAACGGGGGGTTCGTGCACACAGCCCAGCT |
| | TGGAGCGAACGACCTACACCGAACTGAGATACCTACAGCGTGAGC |
| | TATGAGAAAGCGCCACGCTTCCCGAAGGGAGAAAGGCGGACAGG |
| | TATCCGGTAAGCGGCAGGGTCGGAACAGGAGAGCGCACGAGGGA |
| | GCTTCCAGGGGGAAACGCCTGGTATCTTTATAGTCCTGTCGGGTTT |
| | CGCCACCTCTGACTTGAGCGTCGATTTTTGTGATGCTCGTCAGGGG |
| | GGCGGAGCCTATGGAAAAACGCCAGCAACGCGGCCTTTTTACGGT |
| | TCCTGGCCTTTTGCTGGCCTTTTGCTCACATGTTCTTTCCTGCGTTA |
| | TCCCCTGATTCTGTGGATAACCGTATTACCGCCTTTGAGTGAGCTG |
| | ATACCGCTCGCCGCAGCCGAACGACCGAGCGCAGCGAGTCAGTGA |
| | GCGAGGAAGCGGAAGAGCGCCTGATGCGGTATTTTCTCCTTACGC |
| | ATCTGTGCGGTATTTCACACCGCATATGGTGCACTCTCAGTACAAT |
| | CTGCTCTGATGCCGCATAGTTAAGCCAGTATACACTCCGCTATCGC |
| | TACGTGACTGGGTCATGGCTGCGCCCCGACACCCGCCAACACCCG |
| | CTGACGCGCCCTGACGGGCTTGTCTGCTCCCGGCATCCGCTTACAG |
| | ACAAGCTGTGACCGTCTCCGGGAGCTGCATGTGTCAGAGGTTTTC |
| | ACCGTCATCACCGAAACGCGCGAGGCAGCAGATCAATTCGCGCGC |
| | GAAGGCGAAGCGGCATGCATAATGTGCCTGTCAAATGGACGAAGC |
| | AGGGATTCTGCAAACCCTATGCTACTCCGTCAAGCCGTCAATTGTC |
| | TGATTCGTTACCAATTATGACAACTTGACGGCTACATCATTCACTT |
| | TTTCTTCACAACCGGCACGGAACTCGCTCGGGCTGGCCCCGGTGC |
| | ATTTTTTAAATACCCGCGAGAAATAGAGTTGATCGTCAAAACCAA |
| | CATTGCGACCGACGGTGGCGATAGGCATCCGGGTGGTGCTCAAAA |
| | GCAGCTTCGCCTGGCTGATACGTTGGTCCTCGCGCCAGCTTAAGAC |
| | GCTAATCCCTAACTGCTGGCGGAAAAGATGTGACAGACGCGACGG |
| | CGACAAGCAAACATGCTGTGCGACGCTGGCGATACATTACCCTGT |
| | TATCCCTAGATGACATTACCCTGTTATCCCAGATGACATTACCCTG |
| | TTATCCCTAGATGACATTACCCTGTTATCCCTAGATGACATTTACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATAAACTCAA |
| | TGATGATGATGATGATGGTCGAGACTCAGCGGCCGCGGTGCCAGG |
| | GCGTGCCCTTGGGCTCCCCGGGCGCGACTATAAGCTGCGAGCAAC |
| | TTCACTTGGGTATGCCGGCGGTAGCGCTTACCGTTCGTATAATGTA |
| | TGCTATACGAAGTTATCCGAAGCCGCTAGCGGTGGTTTGTCTGGTC |
| | AACCACCGCGGTCTCAGTGGTGTACGGTACAAACCCACTACCGGT |
| | CGCCACCATGGGAGTCAAAGTTCTGTTTGCCCTGATCTGCATCGCT |
| | GTGGCCGAGGCCAAGCCCACCGAGAACAACGAAGACTTCAACATC |
| | GTGGCCGTGGCCAGCAACTTCGCGACCACGGATCTCGATGCTGAC |
| | CGCGGGAAGTTGCCCGGCAAGAAGCTGCCGCTGGAGGTGCTCAAA |
| | GAGATGGAAGCCAATGCCCGGAAAGCTGGCTGCACCAGGGGCTGT |
| | CTGATCTGCCTGTCCCACATCAAGTGCACGCCCAAGATGAAGAAG |
| | TTCATCCCAGGACGCTGCCACACCTACGAAGGCGACAAAGAGTCC |
| | GCACAGGGCGGCATAGGCGAGGCGATCGTCGACATTCCTGAGATT |
| | CCTGGGTTCAAGGACTTGGAGCCCATGGAGCAGTTCATCGCACAG |
| | GTCGATCTGTGTGTGGACTGCACAACTGGCTGCCTCAAAGGGCTT |
| | GCCAACGTGCAGTGTTCTGACCTGCTCAAGAAGTGGCTGCCGCAA |
| | CGCTGTGCGACCTTTGCCAGCAAGATCCAGGGCCAGGTGGACAAG |
| | ATCAAGGGGGCCGGTGGTGACTAAGCGGAGCTCGATGAGTTTGGA |
| | CAAACCACAACTAGAATGCAGTGAAAAAAATGCTTTATTTGTGAA |
| | ATTTGTGATGCTATTGCTTTATTTGTGGGCCCGCCCCAACTGGGGT |
| | AACCTTTGAGTTCTCTCAGTTGGGGGTAATCAGCATCATGATGTGG |
| | TACCACATCATGATGCTGATTATAAGAATGCGGCCGCCACACTCT |
| | AGTGGATCTCGAGTTAATAATTCAGAAGAACTCGTCAAGAAGGCG |
| | ATAGAAGGCGATGCGCTGCGAATCGGGAGCGGCGATACCGTAAA |
| | GCACGAGGAAGCGGTCAGCCCATTCGCCGCCAAGCTCTTCAGCAA |
| | TATCACGGGTAGCCAACGCTATGTCCTGATAGCGGTCCGCCACAC |

TABLE 4-continued

| SEQ ID NO/ DESCRIPTION/ SOURCE | SEQUENCE |
|---|---|
| | CCAGCCGGCCACAGTCGATGAATCCAGAAAAGCGGCCATTTTCCA CCATGATATTCGGCAAGCAGGCATCGCCATGGGTCACGACGAGAT CCTCGCCGTCGGGCATGCTCGCCTTGAGCCTGGCGAACAGTTCGG CTGGCGCGAGCCCCTGATGCTCTTCGTCCAGATCATCCTGATCGAC AAGACCGGCTTCCATCCGAGTACGTGCTCGCTCGATGCGATGTTTC GCTTGGTGGTCGAATGGGCAGGTAGCCGGATCAAGCGTATGCAGC CGCCGCATTGCATCAGCCATGATGGATACTTTCTCGGCAGGAGCA AGGTGTAGATGACATGGAGATCCTGCCCCGGCACTTCGCCCAATA GCAGCCAGTCCCTTCCCGCTTCAGTGACAACGTCGAGCACAGCTG CGCAAGGAACGCCCGTCGTGGCCAGCCACGATAGCCGCGCTGCCT CGTCTTGCAGTTCATTCAGGGCACCGGACAGGTCGGTCTTGACAA AAAGAACCGGGCGCCCCTGCGCTGACAGCCGGAACACGGCGGCA TCAGAGCAGCCGATTGTCTGTTGTGCCCAGTCATAGCCGAATAGC CTCTCCACCCAAGCGGCCGGAGAACCTGCGTGCAATCCATCTTGTT CAATCATGCGAAACGATCCTCATCCTGTCTCTTGATCAGAGCT |
| SEQ ID NO: 78 pseudo attP site (Artificial sequence) | CCCCAACTGGGGTAACCTTTGAGTTCTCTCAGTTGGGG |
| SEQ ID NO: 79 Albumin-pegRNA-SERPIN (Artificial Sequence) | GACTGAAACTTCACAGAATAGTTTTAGAGCTAGAAATAGCAAGTT AAAATAAGGCTAGTCCGTTATCAACTTGAAAAAGTGGCACCGAGT CGGTGCTTGGGATAGTTATGAATTCAATCTTCAACCCTATCCGGAT GATCCTGACGACGGAGACCGCCGTCGTCGACAAGCCGGCCTCTGT GAAGTTTCAGTCA |
| SEQ ID NO: 80 Albumin-pegRNA-CPS1 (Artificial Sequence) | GACTGAAACTTCACAGAATAGTTTTAGAGCTAGAAATAGCAAGTT AAAATAAGGCTAGTCCGTTATCAACTTGAAAAAGTGGCACCGAGT CGGTGCTTGGGATAGTTATGAATTCAATCTTCAACCCTATCCGGAT GATCCTGACGACGGAGACCGCCGTCGTCGACAAGCCGGCCTCTGT GAAGTTTC |
| SEQ ID NO: 81 34 bp lox71 pegRNA (Artificial Sequence) | GGCCCAGACTGAGCACGTGAGTTTTAGAGCTAGAAATAGCAAGTT AAAATAAGGCTAGTCCGTTATCAACTTGAAAAAGTGGCACCGAGT CGGTGCTGGAGGAAGCAGGGCTTCCTTTCCTCTGCCATCATACCGT TCGTATAGCATACATTATACGAAGTTATCGTGCTCAGTCTG |
| SEQ ID NO: 82 34 bp lox66 pegRNA (Artificial Sequence) | GGCCCAGACTGAGCACGTGAGTTTTAGAGCTAGAAATAGCAAGTT AAAATAAGGCTAGTCCGTTATCAACTTGAAAAAGTGGCACCGAGT CGGTGCTGGAGGAAGCAGGGCTTCCTTTCCTCTGCCATCAATAACT TCGTATAGCATACATTATACGAACGGTACGTGCTCAGTCTG |
| SEQ ID NO: 83 gRNA (Artificial Sequence) | GGCCCAGACTGAGCACGTGA |
| SEQ ID NO: 84 ACTB N-term PBS 13 RT 29 attB 46 (original length) pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGACCGCCGTCGTCGACAAGCCGGCCTGAGCTGCGA GAA |
| SEQ ID NO: 85 ACTB N-term PBS_13_RT_29_with TP901-1 minimal attB f pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCACAATTAACATCTCAATCAAGGTAAATGCTTGAGCTGCGAG AA |
| SEQ ID NO: 86 ACTB N-term PBS_13_RT_29_with TP901-1 minimal attB rc pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGAGCATTTACCTTGATTGAGATGTTAATTGTGTGAGCTGCGAGA A |
| SEQ ID NO: 87 ACTB N-term PBS_13_RT_29_with PhiBT1 minimal attB f pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCAGGTTTTTGACGAAAGTGATCCAGATGATCCAGTGAGCTGC GAGAA |
| SEQ ID NO: 88 ACTB N-term | GCTATTCTCGCAGCTCACCAGTTTTAGAGCTAGAAATAGCAAGTT AAAATAAGGCTAGTCCGTTATCAACTTGAAAAAGTGGCACCGAG |

TABLE 4-continued

| SEQ ID NO/ DESCRIPTION/ SOURCE | SEQUENCE |
|---|---|
| PBS 13 RT_29_with PhiBT1 minimal attB rc pegRNA (Artificial Sequence) | TCGGTGCGAGTCGGTGCGACGAGCGCGGCGATATCATCATCCATGGCTGGATCATCTGGATCACTTTCGTCAAAAACCTGTGAGCTGCGAGAA |
| SEQ ID NO: 89 ACTB N-term Nicking guide 1 +48 guide (Artificial Sequence) | GAAGCCGGCCTTGCACATGCGTTTTAGAGCTAGAAATAGCAAGTTAAAATAAGGCTAGTCCGTTATCAACTTGAAAAAGTGGCACCGAGTCGGTGC |
| SEQ ID NO: 90 ACTB N-term PBS_18_RT_16_with_ Lox71_Cre pegRNA (Artificial Sequence) | GAAGCCGGCCTTGCACATGCGTTTTAGAGCTAGAAATAGCAAGTTAAAATAAGGCTAGTCCGTTATCAACTTGAAAAAGTGGCACCGAGTCGGTGCATATCATCATCCATGGTACCGTTCGTATAGCATACATTATACGAAGTTATTGAGCTGCGAGAATAGCC |
| SEQ ID NO: 91 ACTB N-term PBS_13_RT_29_with_ Lox71_Cre pegRNA (Artificial Sequence) | GAAGCCGGCCTTGCACATGCGTTTTAGAGCTAGAAATAGCAAGTTAAAATAAGGCTAGTCCGTTATCAACTTGAAAAAGTGGCACCGAGTCGGTGCGACGAGCGCGGCGATATCATCATCCATGGTACCGTTCGTATAGCATACATTATACGAAGTTATTGAGCTGCGAGAA |
| SEQ ID NO: 92 ACTB N-term PBS 13 RT 34 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCTCGACGACGAGCGCGGCGATATCATCATCCATGGCCGGATGATCCTGACGACGGAGACCGCCGTCGTCGACAAGCCGGCCTGAGCTGCGAGAA |
| SEQ ID NO: 93 ACTB N-term PBS 13 RT 26 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCGAGCGCGGCGATATCATCATCCATGGCCGGATGATCCTGACGACGGAGACCGCCGTCGTCGACAAGCCGGCCTGAGCTGCGAGAA |
| SEQ ID NO: 94 ACTB N-term PBS 13 RT 23 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCCGCGGCGATATCATCATCCATGGCCGGATGATCCTGACGACGGAGACCGCCGTCGTCGACAAGCCGGCCTGAGCTGCGAGAA |
| SEQ ID NO: 95 ACTB N-term PBS 13 RT 20 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCGGCGATATCATCATCCATGGCCGGATGATCCTGACGACGGAGACCGCCGTCGTCGACAAGCCGGCCTGAGCTGCGAGAA |
| SEQ ID NO: 96 ACTB N-term PBS 13 RT 16 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCATATCATCATCCATGGCCGGATGATCCTGACGACGGAGACCGCCGTCGTCGACAAGCCGGCCTGAGCTGCGAGAA |
| SEQ ID NO: 97 ACTB N-term PBS 18 RT 34 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCTCGACGACGAGCGCGGCGATATCATCATCCATGGCCGGATGATCCTGACGACGGAGACCGCCGTCGTCGACAAGCCGGCCTGAGCTGCGAGAATAGCC |
| SEQ ID NO: 98 ACTB N-term PBS 18 RT 29 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCGACGAGCGCGGCGATATCATCATCCATGGCCGGATGATCCTGACGACGGAGACCGCCGTCGTCGACAAGCCGGCCTGAGCTGCGAGAATAGCC |
| SEQ ID NO: 99 ACTB N-term PBS 18 RT 16 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCATATCATCATCCATGGCCGGATGATCCTGACGACGGAGACCGCCGTCGTCGACAAGCCGGCCTGAGCTGCGAGAATAGCC |
| SEQ ID NO: 100 LMNB1 N-term PBS 13 RT 39 pegRNA (Artificial Sequence) | GCTGTCTCCGCCGCCCGCCAGTTTTAGAGCTAGAAATAGCAAGTTAAAATAAGGCTAGTCCGTTATCAACTTGAAAAAGTGGCACCGAGTCGGTGCCTGCCCATCCGCGGCGGCACGGGGGTCGCAGTCGCCATGCCGGATGATCCTGACGACGGAGACCGCCGTCGTCGACAAGCCGGCCCGGGCGGCGGAGA |
| SEQ ID NO: 101 LMNB1 N-term PBS | GCTGTCTCCGCCGCCCGCCAGTTTTAGAGCTAGAAATAGCAAGTTAAAATAAGGCTAGTCCGTTATCAACTTGAAAAAGTGGCACCGAG |

TABLE 4-continued

| SEQ ID NO/ DESCRIPTION/ SOURCE | SEQUENCE |
|---|---|
| 13 RT 34 pegRNA (Artificial Sequence) | TCGGTGCCATCCGCGGCGGCACGGGGGTCGCAGTCGCCATGCCG GATGATCCTGACGACGGAGACCGCCGTCGTCGACAAGCCGGCCC GGGCGGCGGAGA |
| SEQ ID NO: 102 LMNB1 N-term PBS 13 RT 29 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGCGGCGGCACGGGGGTCGCAGTCGCCATGCCGGATGA TCCTGACGACGGAGACCGCCGTCGTCGACAAGCCGGCCCGGGCG GCGGAGA |
| SEQ ID NO: 103 LMNB1 N-term PBS 13 RT 24 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGCACGGGGGTCGCAGTCGCCATGCCGGATGATCCTG ACGACGGAGACCGCCGTCGTCGACAAGCCGGCCCGGGCGGCGGA GA |
| SEQ ID NO: 104 LMNB1 N-term PBS 13 RT 19 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGGGGTCGCAGTCGCCATGCCGGATGATCCTGACGAC GGAGACCGCCGTCGTCGACAAGCCGGCCCGGGCGGCGGAGA |
| SEQ ID NO: 105 LMNB1 N-term PBS 18 RT 39 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCTGCCCATCCGCGGCGGCACGGGGGTCGCAGTCGCCA TGCCGGATGATCCTGACGACGGAGACCGCCGTCGTCGACAAGCC GGCCCGGGCGGCGGAGACAGCG |
| SEQ ID NO: 106 LMNB1 N-term PBS 18 RT 34 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCATCCGCGGCGGCACGGGGGTCGCAGTCGCCATGCCG GATGATCCTGACGACGGAGACCGCCGTCGTCGACAAGCCGGCCC GGGCGGCGGAGACAGCG |
| SEQ ID NO: 107 LMNB1 N-term PBS 18 RT 29 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGCCGGATGATC CTGACGACGGAGACCGCCGTCGTCGACAAGCCGGCCCGGGCGGCG GAGACAGCG |
| SEQ ID NO: 108 LMNB1 N-term PBS 18 RT 24 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGCACGGGGGTCGCAGTCGCCATGCCGGATGATCCTG ACGACGGAGACCGCCGTCGTCGACAAGCCGGCCCGGGCGGCGGA GACAGCG |
| SEQ ID NO: 109 LMNB1 N-term PBS 18 RT 19 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGGGGGTCGCAGTCGCCATGCCGGATGATCCTGACGAC GGAGACCGCCGTCGTCGACAAGCCGGCCCGGGCGGCGGAGACAG CG |
| SEQ ID NO: 110 LMNB1 N-term Nicking guide 1 +46 (Artificial Sequence) | GCGTGGTGGGGCCGCCAGCGGTTTTAGAGCTAGAAATAGCAAGT TAAAATAAGGCTAGTCCGTTATCAACTTGAAAAAGTGGCACCGA GTCGGTGC |
| SEQ ID NO: 111 ACTB N-term PBS 13 RT 29 attB 42 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGGATGATCCTG ACGACGGAGACCGCCGTCGTCGACAAGCCGGTGAGCTGCGAGAA |
| SEQ ID NO: 112 ACTB N-term PBS 13 RT 29 attB 40 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGATGATCCTGA CGACGGAGACCGCCGTCGTCGACAAGCCGTGAGCTGCGAGAA |
| SEQ ID NO: 113 ACTB N-term PBS 13 RT 29 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGATGATCCTGAC GACGGAGACCGCCGTCGTCGACAAGCCTGAGCTGCGAGAA |
| SEQ ID NO: 114 ACTB N-term PBS | GCTATTCTCGCAGCTCACCAGTTTTAGAGCTAGAAATAGCAAGTTA AAATAAGGCTAGTCCGTTATCAACTTGAAAAAGTGGCACCGAGTC |

TABLE 4-continued

| SEQ ID NO/ DESCRIPTION/ SOURCE | SEQUENCE |
|---|---|
| 13 RT 29 attB 36 pegRNA (Artificial Sequence) | GGTGCGACGAGCGCGGCGATATCATCATCCATGGTGATCCTGACG ACGGAGACCGCCGTCGTCGACAAGCTGAGCTGCGAGAA |
| SEQ ID NO: 115 LMNB1 N-term PBS 13 RT 29 attB 44 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGCGGATGATCC TGACGACGGAGACCGCCGTCGTCGACAAGCCGGCCGGGCGGCGG AGA |
| SEQ ID NO: 116 LMNB1 N-term PBS 13 RT 29 attB 42 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGGGATGATCCT GACGACGGAGACCGCCGTCGTCGACAAGCCGGCGGGCGGCGGAG A |
| SEQ ID NO: 117 LMNB1 N-term PBS 13 RT 29 attB 40 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGGATGATCCTG ACGACGGAGACCGCCGTCGTCGACAAGCCGCGGGCGGCGGAGA |
| SEQ ID NO: 118 LMNB1 N-term PBS 13 RT 29 attB 38 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGATGATCCTGA CGACGGAGACCGCCGTCGTCGACAAGCCCGGGCGGCGGAGA |
| SEQ ID NO: 119 NOLC1 N-term PBS 18 RT 29 attB 46 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCCCGGATG ATCCTGACGACGGAGACCGCCGTCGTCGACAAGCCGGCCTCCTC CAGGCAATACGCG |
| SEQ ID NO: 120 NOLC1 N-term PBS 13 RT 29 attB 46 pegRNA (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAGT CGGTGCGAACCACGCGGCGAATGCCGGCGTCCGCCCCGGATGATC CTGACGACGGAGACCGCCGTCGTCGACAAGCCGGCCTCCTCCAGG CAAT |
| SEQ ID NO: 121 NOLC1 N-term PBS 13 RT 29 attB 44 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCCGGATGA TCCTGACGACGGAGACCGCCGTCGTCGACAAGCCGGCTCCTCCA GGCAAT |
| SEQ ID NO: 122 NOLC1 N-term PBS 13 RT 29 attB 42 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCGGATGAT CCTGACGACGGAGACCGCCGTCGTCGACAAGCCGGTCCTCCAGG CAAT |
| SEQ ID NO: 123 NOLC1 N-term PBS 13 RT 29 attB 40 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCGATGATC CTGACGACGGAGACCGCCGTCGTCGACAAGCCGTCCTCCAGGCA AT |
| SEQ ID NO: 124 NOLC1 N-term PBS 13 RT 29 attB 38 pegRNA (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAG TCGGTGCGAACCACGCGGCGAATGCCGGCGTCCGCCATGATCCT GACGACGGAGACCGCCGTCGTCGACAAGCCTCCTCCAGGCAAT |
| SEQ ID NO: 125 NOLC1 nicking guide-43 (Artificial Sequence) | GAGCCGAGCACGAGGGGATACGTTTTAGAGCTAGAAATAGCAAGT TAAAATAAGGCTAGTCCGTTATCAACTTGAAAAAGTGGCACCGAG TCGGTGC |
| SEQ ID NO: 126 ACTB N-term PBS 13 RT 20 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGGCGATATCATCATCCATGGATGATCCTGACGACGGAGAC CGCCGTCGTCGACAAGCCTGAGCTGCGAGAA |

TABLE 4-continued

| SEQ ID NO/ DESCRIPTION/ SOURCE | SEQUENCE |
|---|---|
| SEQ ID NO: 127 ACTB N-term PBS 13 RT 15 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTATCATCATCCATGGATGATCCTGACGACGGAGACCGCCG TCGTCGACAAGCCTGAGCTGCGAGAA |
| SEQ ID NO: 128 ACTB N-term PBS 13 RT 10 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCATCCATGGATGATCCTGACGACGGAGACCGCCGTCGTC GACAAGCCTGAGCTGCGAGAA |
| SEQ ID NO: 129 ACTB N-term PBS 9 RT 20 attB 38 pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGGCGATATCATCATCCATGGATGATCCTGACGACGGAG ACCGCCGTCGTCGACAAGCCTGAGCTGCG |
| SEQ ID NO: 130 ACTB N-term PBS 9 RT 15 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTATCATCATCCATGGATGATCCTGACGACGGAGACCGCCG TCGTCGACAAGCCTGAGCTGCG |
| SEQ ID NO: 131 ACTB N-term PBS 9 RT 10 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCATCCATGGATGATCCTGACGACGGAGACCGCCGTCGTC GACAAGCCTGAGCTGCG |
| SEQ ID NO: 132 LMNB1 N-term PBS 13 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCGGGGGTCGCAGTCGCCATGATGATCCTGACGACGGA GACCGCCGTCGTCGACAAGCCCGGGCGGCGGAGA |
| SEQ ID NO: 133 LMNB1 N-term PBS 13 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCGGAGA |
| SEQ ID NO: 134 LMNB1 N-term PBS 13 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCAGTCGCCATGATGATCCTGACGACGGAGACCGCCGTC GTCGACAAGCCCGGGCGGCGGAGA |
| SEQ ID NO: 135 LMNB1 N-term PBS 9 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCCGGGGGTCGCAGTCGCCATGATGATCCTGACGACGGAGA CCGCCGTCGTCGACAAGCCCGGGCGGCG |
| SEQ ID NO: 136 LMNB1 N-term PBS 9 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCG |
| SEQ ID NO: 137 LMNB1 N-term PBS 9 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCAGTCGCCATGATGATCCTGACGACGGAGACCGCCGTCGT CGACAAGCCCGGGCGGCG |
| SEQ ID NO: 138 SUPT16H N-term PBS 13 RT 24 Bxb1-GT_Initial length (Artificial Sequence) | GAGAAGCGGCGTCCGGGGCTAGTTTTAGAGCTAGAAATAGCAAGT TAAAATAAGGCTAGTCCGTTATCAACTTGAAAAAGTGGCACCGAG TCGGTGCTCTTTGTCCAGAGTCACAGCCATACCGGATGATCCTGAC GACGGAGACCGCCGTCGTCGACAAGCCGGCCCCCCGGACGCCGC |
| SEQ ID NO: 139 SRRM2 N-term PBS 13 RT 24 Bxb1 | GGGCACGGGGCCATGTACAAGTTTTAGAGCTAGAAATAGCAAGT TAAAATAAGGCTAGTCCGTTATCAACTTGAAAAAGTGGCACCGA GTCGGTGCGGCGTCGGCAGCCCGATCCCGTTGCCGGATGATCCT |

TABLE 4-continued

| SEQ ID NO/ DESCRIPTION/ SOURCE | SEQUENCE |
|---|---|
| Initial length (Artificial Sequence) | GACGACGGAGACCGCCGTCGTCGACAAGCCGGCCTACATGGCCC CGT |
| SEQ ID NO: 140 DEPDC4 N-term PBS 18 RT 24 Bxb1 Initial length (Artificial Sequence) | GTGTCAGGTGGGGCGGGGCTAGTTTTAGAGCTAGAAATAGCAAG TTAAAATAAGGCTAGTCCGTTATCAACTTGAAAAAGTGGCACCG AGTCGGTGCGCTGGCTCCTCCCCTGGCACCATACCGGATGATCCT GACGACGGAGACCGCCGTCGTCGACAAGCCGGCCCCCCGCCCCA CCTGACAC |
| SEQ ID NO: 141 NES N-term PBS 13 RT 29 Bxb1 Initial length (Artificial Sequence) | GAGTGGGTCAGACGAGCAGGAGTTTTAGAGCTAGAAATAGCAAGT TAAAATAAGGCTAGTCCGTTATCAACTTGAAAAAGTGGCACCGAG TCGGTGCGATGGAGGGCTGCATGGGGGAGGAGTCGCCGGATGATC CTGACGACGGAGACCGCCGTCGTCGACAAGCCGGCCTGCTCGTCT GACC |
| SEQ ID NO: 142 SUPT16H nicking guide-53 (Artificial Sequence) | GCAGCCACCCGCTCTCGGCCCGTTTTAGAGCTAGAAATAGCAAG TTAAAATAAGGCTAGTCCGTTATCAACTTGAAAAAGTGGCACCG AGTCGGTGC |
| SEQ ID NO: 143 SRRM2 N-term nicking guide 1 +87 (Artificial Sequence) | GTGTAGTCAGGCCGCTCACCCGTTTTAGAGCTAGAAATAGCAAG TTAAAATAAGGCTAGTCCGTTATCAACTTGAAAAAGTGGCACCG AGTCGGTGC |
| SEQ ID NO: 144 DEPDC4 N-term Nicking guide 1 +59 (Artificial Sequence) | GCTGACAAGTCTACGGAACCTGTTTTAGAGCTAGAAATAGCAAG TTAAAATAAGGCTAGTCCGTTATCAACTTGAAAAAGTGGCACCG AGTCGGTGC |
| SEQ ID NO: 145 NES N-term Nicking guide 2 + 9 (Artificial Sequence) | GCTCCTCCAGCGCCTTGACCGTTTTAGAGCTAGAAATAGCAAGTTA AAATAAGGCTAGTCCGTTATCAACTTGAAAAAGTGGCACCGAGTC GGTGC |
| SEQ ID NO: 146 HITI_ACTB_guide (Artificial Sequence) | GCTATTCTCGCAGCTCACCA |
| SEQ ID NO: 147 HITI_SUPTH16_guide (Artificial Sequence) | AGAAGCGGCGTCCGGGGCTA |
| SEQ ID NO: 148 HITI_SRRM2_guide (Artificial Sequence) | GGGCACGGGGCCATGTACAA |
| SEQ ID NO: 149 HITI_NOLC1_guide (Artificial Sequence) | GCGTATTGCCTGGAGGATGG |
| SEQ ID NO: 150 HITI_DEPDC4_guide (Artificial Sequence) | TGTCAGGTGGGGCGGGGCTA |
| SEQ ID NO: 151 HITI_NES_guide (Artificial Sequence) | AGTGGGTCAGACGAGCAGGA |
| SEQ ID NO: 152 HITI_LMNB1_guide (Artificial Sequence) | GCTGTCTCCGCCGCCCGCCA |
| SEQ ID NO: 153 HDR Cas9 ACTB guide (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGC |
| SEQ ID NO: 154 ACTB N-term PBS 13 RT 29 attB original length pegRNAs for dinucleotides (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAG**XX**CGCCGTCGTCGACAAGCCGGCCTGAGCTGCGA GAA **XX**: CG, GC, AT, TA, GG, TT, GA, AG, CC, TC, CT, AA, TG, GT, CA, or AC |

TABLE 4-continued

| SEQ ID NO/ DESCRIPTION/ SOURCE | SEQUENCE |
|---|---|
| SEQ ID NO: 155 ACTB N-term PBS 13 RT 29 pegRNA with attB 46 GT for fusion (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGCCGGATGATCCT GACGACGGAGACCGCCGTCGTCGACAAGCCGGCCTGAGCTGCGAG AA |
| SEQ ID NO: 156 ACTB N-term PBS 13 RT 29 pegRNA with attB 46 CT for multiplexing (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGCCGGATGATCCT GACGACGGAGAGCGCCGTCGTCGACAAGCCGGCCTGAGCTGCGA GAA |
| SEQ ID NO: 157 NOLC1 N-term PBS 18 RT 29 pegRNA with attB 46 GA for multiplexing (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAGT CGGTGCGAACCACGCGGCGAATGCCGGCGTCCGCCCCGGATGATC CTGACGACGGAGTCCGCCGTCGTCGACAAGCCGGCCTCCTCCAGG CAATACGCG |
| SEQ ID NO: 158 LMNB1 N-term PBS 18 RT 29 pegRNA with attB 46 AG for multiplexing (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGCCGGATGATC CTGACGACGGAGCTCGCCGTCGTCGACAAGCCGGCCCGGGCGGCG GAGACAGCG |
| SEQ ID NO: 159 EMX1 Cas9 guide 1 (Artificial Sequence) | GTCACCTCCAATGACTAGGG |
| SEQ ID NO: 160 EMX1 Cas9 guide 2 (Artificial Sequence) | GGGCAACCACAAACCCACGA |
| SEQ ID NO: 161 ACTB N-term PBS 13 RT 29 attB 56 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCTATGCCGGAT GATCCTGACGACGGAGTCCGCCGTCGTCGACAAGCCGGCCCTAGC TGAGCTGCGAGAA |
| SEQ ID NO: 162 ACTB N-term PBS 13 RT 29 attB 51 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGCCGGATGAT CCTGACGACGGAGTCCGCCGTCGTCGACAAGCCGGCCCTATGAGC TGCGAGAA |
| SEQ ID NO: 163 ACTB N-term PBS 13 RT 29 attB 46 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGTCCGCCGTCGTCGACAAGCCGGCCTGAGCTGCGA GAA |
| SEQ ID NO: 164 ACTB N-term PBS 13 RT 29 attB 41 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGGATGATCCTG ACGACGGAGTCCGCCGTCGTCGACAAGCCGTGAGCTGCGAGAA |
| SEQ ID NO: 165 ACTB N-term PBS 13 RT 29 attB 36 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGATCCTGACG ACGGAGTCCGCCGTCGTCGACAAGCTGAGCTGCGAGAA |
| SEQ ID NO: 166 ACTB N-term PBS 13 RT 29 attB 31 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGATCCTGACGAC GGAGTCCGCCGTCGTCGACATGAGCTGCGAGAA |

TABLE 4-continued

| SEQ ID NO/ DESCRIPTION/ SOURCE | SEQUENCE |
|---|---|
| SEQ ID NO: 167 ACTB N-term PBS 13 RT 29 attB 26 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCTGACGACGG AGTCCGCCGTCGTCGTGAGCTGCGAGAA |
| SEQ ID NO: 168 ACTB N-term PBS 13 RT 29 attB 21 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGACGACGGAG TCCGCCGTCGTGAGCTGCGAGAA |
| SEQ ID NO: 169 ACTB N-term PBS 13 RT 29 attB 16 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGACGACGGAGTC CGCCGTGAGCTGCGAGAA |
| SEQ ID NO: 170 ACTB N-term PBS 13 RT 29 attB 11 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGACGGAGTCCG TGAGCTGCGAGAA |
| SEQ ID NO: 171 ACTB N-term PBS 13 RT 29 attB 6 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCGGAGTTGAGC TGCGAGAA |
| SEQ ID NO: 172 ACTB N-term PBS_18_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAATAG CC |
| SEQ ID NO: 173 ACTB N-term PBS_18_RT_29_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCGACGAGCGCGGCGATATCATCATCCATGGTACCGTTCGT ATAGCATACATTATACGAAGTTATTGAGCTGCGAGAATAGCC |
| SEQ ID NO: 174 ACTB N-term PBS_13_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAA |
| SEQ ID NO: 175 ACTB N-term PBS_13_RT_16_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCATATCATCATCCATGGTACCGTTCGTATAGCATACATTAT ACGAAGTTATTGAGCTGCGAGAA |
| SEQ ID NO: 176 ACTB N-term Nicking guide 2 +93 guide (Artificial Sequence) | CCCCACGATGGAGGGGAAGAGTTTTAGAGCTAGAAATAGCAAGTT AAAATAAGGCTAGTCCGTTATCAACTTGAAAAAGTGGCACCGAGT CGGTGC |
| SEQ ID NO: 177 LMNB1 N-term Nicking guide 2 +87 guide (Artificial Sequence) | CCTTCTCCTGGAGCCGCGACGTTTTAGAGCTAGAAATAGCAAGTT AAAATAAGGCTAGTCCGTTATCAACTTGAAAAAGTGGCACCGAGT CGGTGC |

Sequences of insertion sites can be found in Table 4 below.

TABLE 4

| | FORWARD SEQUENCE (5'-3') | | REVERSE SEQUENCE (5'-3') | |
|---|---|---|---|---|
| DESCRIPTION/ SOURCE | SEQ ID NO | Sequence | SEQ ID NO | Sequence |
| Bxb1_attP_GT_ original_site (Artificial Sequence) | 178 | GTGGTTTGTCTGGTC AACCACCGCGGTCT CAGTGGTGTACGGT ACAAACCCA | 179 | TGGGTTTGTACCGTA CACCACTGAGACCG CGGTGGTTGACCAG ACAAACCAC |
| Bxb1_attP_CG_ site (Artificial Sequence) | 180 | GTGGTTTGTCTGGTC AACCACCGCGCGCT CAGTGGTGTACGGT ACAAACCCA | 181 | TGGGTTTGTACCGTA CACCACTGAGCGCG CGGTGGTTGACCAG ACAAACCAC |
| Bxb1_attP_GC_ site (Artificial Sequence) | 182 | GTGGTTTGTCTGGTC AACCACCGCGGCCT CAGTGGTGTACGGT ACAAACCCA | 183 | TGGGTTTGTACCGTA CACCACTGAGGCCG CGGTGGTTGACCAG ACAAACCAC |
| Bxb1_attP_AT_ site (Artificial Sequence) | 184 | GTGGTTTGTCTGGTC AACCACCGCGATCT CAGTGGTGTACGGT ACAAACCCA | 185 | TGGGTTTGTACCGTA CACCACTGAGATCG CGGTGGTTGACCAG ACAAACCAC |
| Bxb1_attP_TA_ site (Artificial Sequence) | 186 | GTGGTTTGTCTGGTC AACCACCGCGTACT CAGTGGTGTACGGT ACAAACCCA | 187 | TGGGTTTGTACCGTA CACCACTGAGTACG CGGTGGTTGACCAG ACAAACCAC |
| Bxb1_attP_GG_ site (Artificial Sequence) | 188 | GTGGTTTGTCTGGTC AACCACCGCGGGCT CAGTGGTGTACGGT ACAAACCCA | 189 | TGGGTTTGTACCGTA CACCACTGAGCCCG CGGTGGTTGACCAG ACAAACCAC |
| Bxb1_attP_TT_ site (Artificial Sequence) | 190 | GTGGTTTGTCTGGTC AACCACCGCGTTCTC AGTGGTGTACGGTA CAAACCCA | 191 | TGGGTTTGTACCGTA CACCACTGAGAACG CGGTGGTTGACCAG ACAAACCAC |
| Bxb1_attP_GA_ site (Artificial Sequence) | 192 | GTGGTTTGTCTGGTC AACCACCGCGGACT CAGTGGTGTACGGT ACAAACCCA | 193 | TGGGTTTGTACCGTA CACCACTGAGTCCG CGGTGGTTGACCAG ACAAACCAC |
| Bxb1_attP_AG_ site (Artificial Sequence) | 194 | GTGGTTTGTCTGGTC AACCACCGCGAGCT CAGTGGTGTACGGT ACAAACCCA | 195 | TGGGTTTGTACCGTA CACCACTGAGCTCG CGGTGGTTGACCAG ACAAACCAC |
| Bxb1_attP_CC_ site (Artificial Sequence) | 196 | GTGGTTTGTCTGGTC AACCACCGCGCCCT CAGTGGTGTACGGT ACAAACCCA | 197 | TGGGTTTGTACCGTA CACCACTGAGGGCG CGGTGGTTGACCAG ACAAACCAC |
| Bxb1_attP_TC_ site (Artificial Sequence) | 198 | GTGGTTTGTCTGGTC AACCACCGCGTCCTC AGTGGTGTACGGTA CAAACCCA | 199 | TGGGTTTGTACCGTA CACCACTGAGGACG CGGTGGTTGACCAG ACAAACCAC |
| Bxb1_attP_CT_ site (Artificial Sequence) | 200 | GTGGTTTGTCTGGTC AACCACCGCGCTCTC AGTGGTGTACGGTA CAAACCCA | 201 | TGGGTTTGTACCGTA CACCACTGAGAGCG CGGTGGTTGACCAG ACAAACCAC |
| Bxb1_attP_AA_ site (Artificial Sequence) | 202 | GTGGTTTGTCTGGTC AACCACCGCGAACT CAGTGGTGTACGGT ACAAACCCA | 203 | TGGGTTTGTACCGTA CACCACTGAGTTCGC GGTGGTTGACCAGA CAAACCAC |
| Bxb1_attP_C A_site (Artificial Sequence) | 204 | GTGGTTTGTCTGGTC AACCACCGCGCACT CAGTGGTGTACGGT ACAAACCCA | 205 | TGGGTTTGTACCGTA CACCACTGAGTGCG CGGTGGTTGACCAG ACAAACCAC |
| Bxb1_attP_AC_ site | 206 | GTGGTTTGTCTGGTC AACCACCGCGACCT | 207 | TGGGTTTGTACCGTA CACCACTGAGGTCG |

TABLE 4-continued

| | FORWARD SEQUENCE (5'-3') | | REVERSE SEQUENCE (5'-3') | |
|---|---|---|---|---|
| DESCRIPTION/ SOURCE | SEQ ID NO | Sequence | SEQ ID NO | Sequence |
| (Artificial Sequence) | | CAGTGGTGTACGGT ACAAACCCA | | CGGTGGTTGACCAG ACAAACCAC |
| Bxb1_attP_TG_ site (Artificial Sequence) | 208 | GTGGTTTGTCTGGTC AACCACCGCGTGCT CAGTGGTGTACGGT ACAAACCCA | 209 | TGGGTTTGTACCGTA CACCACTGAGCACG CGGTGGTTGACCAG ACAAACCAC |
| Bxb1_attB_46_ GT_original_ site (Artificial Sequence) | 210 | GGCCGGCTTGTCGA CGACGGCGGTCTCC GTCGTCAGGATCATC CGG | 211 | CCGGATGATCCTGA CGACGGAGACCGCC GTCGTCGACAAGCC GGCC |
| Bxb1_attB_46_ AA_site (Artificial Sequence) | 212 | GGCCGGCTTGTCGA CGACGGCGAACTCC GTCGTCAGGATCATC CGG | 213 | CCGGATGATCCTGA CGACGGAGTTCGCC GTCGTCGACAAGCC GGCC |
| Bxb1_attB_46_ GA_site (Artificial Sequence) | 214 | GGCCGGCTTGTCGA CGACGGCGGACTCC GTCGTCAGGATCATC CGG | 215 | CCGGATGATCCTGA CGACGGAGTCCGCC GTCGTCGACAAGCC GGCC |
| Bxb1_attB_46_ CA_site (Artificial Sequence) | 216 | GGCCGGCTTGTCGA CGACGGCGCACTCC GTCGTCAGGATCATC CGG | 217 | CCGGATGATCCTGA CGACGGAGTGCGCC GTCGTCGACAAGCC GGCC |
| Bxb1_attB_46_ TA_site (Artificial Sequence) | 218 | GGCCGGCTTGTCGA CGACGGCGTACTCC GTCGTCAGGATCATC CGG | 219 | CCGGATGATCCTGA CGACGGAGTACGCC GTCGTCGACAAGCC GGCC |
| Bxb1_attB_46_ AG_site (Artificial Sequence) | 220 | GGCCGGCTTGTCGA CGACGGCGAGCTCC GTCGTCAGGATCATC CGG | 221 | CCGGATGATCCTGA CGACGGAGCTCGCC GTCGTCGACAAGCC GGCC |
| Bxb1_attB_46_ GG_site (Artificial Sequence) | 222 | GGCCGGCTTGTCGA CGACGGCGGGCTCC GTCGTCAGGATCATC CGG | 223 | CCGGATGATCCTGA CGACGGAGCCCGCC GTCGTCGACAAGCC GGCC |
| Bxb1_attB_46_ CG_site (Artificial Sequence) | 224 | GGCCGGCTTGTCGA CGACGGCGCGCTCC GTCGTCAGGATCATC CGG | 225 | CCGGATGATCCTGA CGACGGAGCGCGCC GTCGTCGACAAGCC GGCC |
| Bxb1_attB_46_ TG_site (Artificial Sequence) | 226 | GGCCGGCTTGTCGA CGACGGCGTGCTCC GTCGTCAGGATCATC CGG | 227 | CCGGATGATCCTGA CGACGGAGCACGCC GTCGTCGACAAGCC GGCC |
| Bxb1_attB_46_ AC_site (Artificial Sequence) | 228 | GGCCGGCTTGTCGA CGACGGCGACCTCC GTCGTCAGGATCATC CGG | 229 | CCGGATGATCCTGA CGACGGAGGTCGCC GTCGTCGACAAGCC GGCC |
| Bxb1_attB_46_ GC_site (Artificial Sequence) | 230 | GGCCGGCTTGTCGA CGACGGCGGCCTCC GTCGTCAGGATCATC CGG | 231 | CCGGATGATCCTGA CGACGGAGGCCGCC GTCGTCGACAAGCC GGCC |
| Bxb1_attB_46_ CC_site (Artificial Sequence) | 232 | GGCCGGCTTGTCGA CGACGGCGCCCTCC GTCGTCAGGATCATC CGG | 233 | CCGGATGATCCTGA CGACGGAGGGCGCC GTCGTCGACAAGCC GGCC |
| Bxb1_attB_46_ TC_site (Artificial Sequence) | 234 | GGCCGGCTTGTCGA CGACGGCGTCCTCC GTCGTCAGGATCATC CGG | 235 | CCGGATGATCCTGA CGACGGAGGACGCC GTCGTCGACAAGCC GGCC |

TABLE 4-continued

| DESCRIPTION/ SOURCE | FORWARD SEQUENCE (5'-3') SEQ ID NO | Sequence | REVERSE SEQUENCE (5'-3') SEQ ID NO | Sequence |
|---|---|---|---|---|
| Bxb1_attB_46_ AT_site (Artificial Sequence) | 236 | GGCCGGCTTGTCGA CGACGGCGATCTCC GTCGTCAGGATCATC CGG | 237 | CCGGATGATCCTGA CGACGGAGATCGCC GTCGTCGACAAGCC GGCC |
| Bxb1_attB_46_ CT_site (Artificial Sequence) | 238 | GGCCGGCTTGTCGA CGACGGCGCTCTCC GTCGTCAGGATCATC CGG | 239 | CCGGATGATCCTGA CGACGGAGAGCGCC GTCGTCGACAAGCC GGCC |
| Bxb1_attB_46_ TT_site (Artificial Sequence) | 240 | GGCCGGCTTGTCGA CGACGGCGTTCTCCG TCGTCAGGATCATCC GG | 241 | CCGGATGATCCTGA CGACGGAGAACGCC GTCGTCGACAAGCC GGCC |
| Bxb1_attB_38_ GT_site (Artificial Sequence) | 242 | GGCTTGTCGACGAC GGCGGTCTCCGTCGT CAGGATCAT | 243 | ATGATCCTGACGAC GGAGACCGCCGTCG TCGACAAGCC |
| Bxb1_attB_38_ AA_site (Artificial Sequence) | 244 | GGCTTGTCGACGAC GGCGAACTCCGTCG TCAGGATCAT | 245 | ATGATCCTGACGAC GGAGTTCGCCGTCGT CGACAAGCC |
| Bxb1_attB_38_ GA_site (Artificial Sequence) | 246 | GGCTTGTCGACGAC GGCGGACTCCGTCG TCAGGATCAT | 247 | ATGATCCTGACGAC GGAGTCCGCCGTCG TCGACAAGCC |
| Bxb1_attB_38_ CA_site (Artificial Sequence) | 248 | GGCTTGTCGACGAC GGCGCACTCCGTCGT CAGGATCAT | 249 | ATGATCCTGACGAC GGAGTGCGCCGTCG TCGACAAGCC |
| Bxb1_attB_38_ TA_site (Artificial Sequence) | 250 | GGCTTGTCGACGAC GGCGTACTCCGTCGT CAGGATCAT | 251 | ATGATCCTGACGAC GGAGTACGCCGTCG TCGACAAGCC |
| Bxb1_attB_38_ AG_site (Artificial Sequence) | 252 | GGCTTGTCGACGAC GGCGAGCTCCGTCG TCAGGATCAT | 253 | ATGATCCTGACGAC GGAGCTCGCCGTCG TCGACAAGCC |
| Bxb1_attB_38_ GG_site (Artificial Sequence) | 254 | GGCTTGTCGACGAC GGCGGGCTCCGTCG TCAGGATCAT | 255 | ATGATCCTGACGAC GGAGCCCGCCGTCG TCGACAAGCC |
| Bxb1_attB_38_ CG_site (Artificial Sequence) | 256 | GGCTTGTCGACGAC GGCGCGCTCCGTCGT CAGGATCAT | 257 | ATGATCCTGACGAC GGAGCGCGCCGTCG TCGACAAGCC |
| Bxb1_attB_38_ TG_site (Artificial Sequence) | 258 | GGCTTGTCGACGAC GGCGTGCTCCGTCGT CAGGATCAT | 259 | ATGATCCTGACGAC GGAGCACGCCGTCG TCGACAAGCC |
| Bxb1_attB_38_ AC_site (Artificial Sequence) | 260 | GGCTTGTCGACGAC GGCGACCTCCGTCGT CAGGATCAT | 261 | ATGATCCTGACGAC GGAGGTCGCCGTCG TCGACAAGCC |
| Bxb1_attB_38_ GC_site (Artificial Sequence) | 262 | GGCTTGTCGACGAC GGCGGCCTCCGTCGT CAGGATCAT | 263 | ATGATCCTGACGAC GGAGGCCGCCGTCG TCGACAAGCC |
| Bxb1_attB_38_ CC_site (Artificial Sequence) | 264 | GGCTTGTCGACGAC GGCGCCCTCCGTCGT CAGGATCAT | 265 | ATGATCCTGACGAC GGAGGGCGCCGTCG TCGACAAGCC |

TABLE 4-continued

| | FORWARD SEQUENCE (5'-3') | | REVERSE SEQUENCE (5'-3') | |
|---|---|---|---|---|
| DESCRIPTION/ SOURCE | SEQ ID NO | Sequence | SEQ ID NO | Sequence |
| Bxb1_attB_38_ TC_site (Artificial Sequence) | 266 | GGCTTGTCGACGAC GGCGTCCTCCGTCGT CAGGATCAT | 267 | ATGATCCTGACGAC GGAGGACGCCGTCG TCGACAAGCC |
| Bxb1_attB_38_ AT_site (Artificial Sequence) | 268 | GGCTTGTCGACGAC GGCGATCTCCGTCGT CAGGATCAT | 269 | ATGATCCTGACGAC GGAGATCGCCGTCG TCGACAAGCC |
| Bxb1_attB_38_ CT_site (Artificial Sequence) | 270 | GGCTTGTCGACGAC GGCGCTCTCCGTCGT CAGGATCAT | 271 | ATGATCCTGACGAC GGAGAGCGCCGTCG TCGACAAGCC |
| Bxb1_attB_38_ TT_site (Artificial Sequence) | 272 | GGCTTGTCGACGAC GGCGTTCTCCGTCGT CAGGATCAT | 273 | ATGATCCTGACGAC GGAGAACGCCGTCG TCGACAAGCC |
| Cre Lox 66 site (Artificial Sequence) | 274 | TACCGTTCGTATAAT GTATGCTATACGAA GTTAT | 275 | ATAACTTCGTATAGC ATACATTATACGAA CGGTA |
| Cre Lox 71 site (Artificial Sequence) | 276 | ATAACTTCGTATAAT GTATGCTATACGAA CGGTA | 277 | TACCGTTCGTATAGC ATACATTATACGAA GTTAT |
| TP901-1 minimal attB site (Artificial Sequence) | 278 | TTTACCTTGATTGAG ATGTTAATTGTG | 279 | CACAATTAACATCTC AATCAAGGTAAA |
| TP901-1 minimal attP site (Artificial Sequence) | 280 | GCGAGTTTTTATTTC GTTTATTTCAATTAA GGTAACTAAAAAAC TCCTTT | 281 | AAAGGAGTTTTTTAG TTACCTTAATTGAAA TAAACGAAATAAAA ACTCGC |
| PhiBT1 minimal attB site (Artificial Sequence) | 282 | CTGGATCATCTGGAT CACTTTCGTCAAAAA CCTG | 283 | CAGGTTTTTGACGAA AGTGATCCAGATGA TCCAG |
| PhiBT1 minimal attP site (Artificial Sequence) | 284 | TTCGGGTGCTGGGTT GTTGTCTCTGGACAG TGATCCATGGGAAA CTACTCAGCACCA | 285 | TGGTGCTGAGTAGTT TCCCATGGATCACTG TCCAGAGACAACAA CCCAGCACCCGAA |

Sequences of Bxb1 and RT mutants can be found in Table 6 below.

TABLE 6

| SEQ ID NO/ DESCRIPTION/ SOURCE | FORWARD SEQUENCE (5'-3') |
|---|---|
| SEQ ID NO: 286 Bxb1_mut_V368A (Artificial Sequence) | AAAAGTGTGGGCTGCAGGATCTGA |
| SEQ ID NO: 287 Bxb1_mut_E379A (Artificial Sequence) | GGAGCTGGCAGCTGTCAATGCC |

TABLE 6-continued

| SEQ ID NO/ DESCRIPTION/ SOURCE | FORWARD SEQUENCE (5'-3') |
|---|---|
| SEQ ID NO: 288 Bxb1_mut_E383A (Artificial Sequence) | AGTCAATGCCGCTCTCGTGGA |
| SEQ ID NO: 403 RT_mut_L139P (Artificial Sequence) | TTGAGCGGGCCCCCACCGT |
| SEQ ID NO: 289 RT_mut_E562Q (Artificial Sequence) | CAGCGGGCTCAGCTGATAGCA |
| SEQ ID NO: 290 RT_mut_D653N (Artificial Sequence) | CGGATGGCTAACCAAGCGGCC |
| SEQ ID NO: 404 RT(1-478)_Sto7d fusion | atgactcactatcaggccttgcttaggacacggaccgggtccagttcggaccggtggtagccctgaaccc ggctacgctgctcccactgcctgaggaagggctgcaacacaactgccttgatGGGACAGGTGG CGGTGGTGTCACCGTCAAGTTCAAGTACAAGGGTGAGGAACTT GAAGTTGATATTAGCAAAATCAAGAAGGTTTGGCGCGTTGGTA AAATGATATCTTTTACTTATGACGACAACGGCAAGACAGGTAG AGGGGCAGTGTCTGAGAAAGACGCCCCCAAGGAGCTGTTGCAA ATGTTGGAAAAGTCTGGGAAAAAGtctggcggctcaaaaagaaccgccgacgg cagcgaattcgagcccaagaagaagaggaaagtc |

Sequences of primers, probes and restriction enzymes used in ddPCR readout can be found in Table 7 below.

TABLE 7

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | GFP (pDY0186) | 291 | CCCG GCTTC CTTTG TCC | 292 | GAAC TCCAC GCCG TTCA | /56-FAM/C C GGC TTG T/ZEN/ C GAC GAC GGC G/3IAB kFQ/ | 405 | Eco91I, HindIII |
| ACTB | TP90-1 GFP (pDY0333) | 293 | CCCG GCTTC CTTTG TCC | 294 | AACC ACAA CTAG AATG CAGT GA | /56-FAM/T G CTA TTG C/ZEN/ T TTA TTT GTG GGC CCG /3IABk FQ/ | 406 | None |
| ACTB | TP90-1 rc GFP (pDY0334) | 295 | CCCG GCTTC CTTTG TCC | 296 | GAAC TCCAC GCCG TTCA | /56-FAM/ CC ATG AAG A/ZEN/ T CGA GTG CCG CAT CA/3I ABkF Q/ | 407 | None |

TABLE 7-continued

| Locus | Cargo | SEQ ID NO: | Forward Primer | SEQ ID NO: | Reverse Primer | Probe | SEQ ID NO: | Restrict-ion Enzymes |
|---|---|---|---|---|---|---|---|---|
| ACTB | PhiBT1 GFP (pDY0367) | 297 | CCCG GCTTC CTTTG TCC | 298 | AACC ACAA CTAG AATG CAGT GA | /56-FAM/T G CTA TTG C/ZEN/T TTA TTT GTG GGC CCG /3IABkFQ/ | 406 | None |
| ACTB | PhiBT1 rc GFP (pDY0368) | 299 | CCCG GCTTC CTTTG TCC | 300 | GAAC TCCAC GCCG TTCA | /56-FAM/CC ATG AAG A/ZEN/T CGA GTG CCG CAT CA/3IABkFQ/ | 407 | None |
| LMNB1 | GFP (pDY0186) | 301 | TCCTT ATCA CGGT CCCG CTCG | 302 | GAAC TCCAC GCCG TTCA | /56-FAM/CC ATG AAG A/ZEN/T CGA GTG CCG CAT CA/3IABkFQ/ | 407 | Eco91I, HindIII |
| NOLC1 | GFP (pDY0186) | 303 | CGTC GACA ACGG TAGT G | 304 | GAAC TCCAC GCCG TTCA | /56-FAM/CC ATG AAG A/ZEN/T CGA GTG CCG CAT CA/3IABkFQ/ | 407 | Eco91I, HindIII |
| SUPT16 H | GFP pDY0186) | 305 | TCGC GTGA TTCTC GGAA C | 306 | GAAC TCCA CGCC GTTC A | /56-FAM/C C ATG AAG A/ZEN/T CGA GTG CCG CAT CA/31ABkFQ/ | 407 | Eco91I, HindIII |
| SRRM2 | GFP (pDY0186) | 307 | GGGC GGTA AGTG GTTA GTTT | 308 | GAAC TCCAC GCCG TTCA | /56-FAM/CC ATG AAG A/ZEN/ | 407 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | T CGA GTG CCG CAT CA/3I ABkF Q/ | | |
| DEPDC4 | GFP (pDY0186) | 309 | AAGA GGCG GAGC CAGT A | 310 | GAAC TCCAC GCCG TTCA | /56-FAM/ CC ATG AAG A/ZEN/ T CGA GTG CCG CAT CA/3I ABkF Q/ | 407 | Eco91I, HindIII |
| NES | GFP (pDY0186) | 311 | CTCCC TTCTC CCGG TGCCC | 312 | GAAC TCCAC GCCG TTCA | /56-FAM/C C GGC TTG T/ZEN/ C GAC GAC GGC G/3IAB kFQ/ | 405 | Eco91I, HindIII |
| ACTB | ACTB HITI template GFP (pDY0219) | 313 | CCCG GCTTC CTTTG TCC | 314 | GAAC TCCAC GCCG TTCA | /56-FAM/ CC ATG AAG A/ZE N/T CGA GTG CCG CAT CA/3I ABkF Q/ | 407 | Eco91I |
| SRRM2 | SRRM2 HITI template GFP (aRY0182_ A2) | 315 | GGGC GGTA AGTG GTTA GTTT | 316 | GAAC TCCAC GCCG TTCA | /56-FAM/ CC ATG AAG A/ZE N/T CGA GTG CCG CAT CA/3I ABkF Q/ | 407 | Eco91I |
| NOLC1 | NOLC1 HITI template GFP (aRY0182_ A3) | 317 | CGTC GACA ACGG TAGT G | 318 | GAAC TCCAC GCCG TTCA | /56-FAM/ CC ATG AAG A/ZE N/T CGA GTG CCG CAT | 407 | Eco91I |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | CA/3IABkFQ/ | | |
| DEPDC4 | DEPDC4 HITI template GFP (aRY0182_A5) | 319 | AAGAGGCGGAGCCAGTA | 320 | GAACTCCACGCCGTTCA | /56-FAM/CCATGAAGA/ZEN/TCGAGTGCCGCATCA/3IABkFQ/ | 407 | Eco91I |
| NES | NES HITI template GFP (aRY0182_A7) | 321 | CTCCCTTCTCCCGGTGCCC | 322 | GAACTCCACGCCGTTCA | /56-FAM/CCATGAAGA/ZEN/TCGAGTGCCGCATCA/3IABkFQ/ | 407 | Eco91I |
| LMNB1 | LMNB1 HITI template GFP (aRY0182_A4) | 323 | TCCTTATCACGGTCCCGCTCG | 324 | GAACTCCACGCCGTTCA | /56-FAM/CCATGAAGA/ZEN/TCGAGTGCCGCATCA/3IABkFQ/ | 407 | Eco91I |
| ACTB | SERPINA (pDY0298) | 325 | CCCGGCTTCCTTTGTCC | 326 | GGCCTGCCAGCAGGAGGA | /56-FAM/CCGGCTTGT/ZEN/CGACGACGGCG/3IABkFQ/ | 405 | EcoRI, XhoI, HindIII |
| ACTB | CPS1 (pDY299) | 327 | CCCGGCTTCCTTTGTCC | 328 | GGTGTGCAGTCACATTGGTAAAGCC | /56-FAM/ACAGCTTTC/ZEN/AAAGTGGTGAGGACACT/3IA | 408 | XhoI, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | BkFQ / | | |
| ACTB | CFTR (pDY0373) | 329 | CCCG GCTTC CTTTG TCC | 330 | GATG GGTCT AGTC CAGC TAAA G | /56-FAM/ TAC GGT ACA/ ZEN/ AAC CC ACC CGA GAG A/3I ABkF Q/ | 409 | Eco91I, HindIII |
| ACTB | NYESO TRAC (pDY0318) | 331 | CCCG GCTTC CTTTG TCC | 332 | GAGA GACA AGGC TGCA CA | /56-FAM/ TAC GGT ACA/ ZEN/ AAC CC ACC CGA GAG A/3I ABkF Q/ | 409 | Eco47III, HindIII |
| NC_ 000003 | GFP (pDY0186) | 333 | CCAG GTGA GAGT CAGG GTAG TGTTC A | 334 | GAAC TCCAC GCCG TTCA | /56-FAM/ CC GGC TTG T/ZEN/ C GAC GAC GGC G/3I ABkF Q/ | 405 | Eco91I, HindIII |
| NC_ 000002 | GFP (pDY0186) | 335 | AGGG ACCTT TGCCT GTGT GAGT C | 336 | GAAC TCCAC GCCG TTCA | /56-FAM/ CC GGC TTG T/ZEN/ C GAC GAC GGC G/3I ABkF Q/ | 405 | Eco91I, HindIII |
| NC_ 000009 | GFP (pDY0186) | 337 | TCAG CTCTG TGCTG AGGC GAA | 338 | GAAC TCCAC GCCG TTCA | /56-FAM/ CC GGC TTG T/ZEN/ C GAC GAC GGC G/3I ABkF Q/ | 405 | Eco91I, HindIII |

TABLE 7-continued

| Locus | Cargo | SEQ ID NO: | Forward Primer | SEQ ID NO: | Reverse Primer | Probe | SEQ ID NO: | Restrict-ion Enzymes |
|---|---|---|---|---|---|---|---|---|
| chr6: 149045959 | GFP (pDY0186) | 339 | AAGCCATCTCCCAGAATATCTGCTTAGAAATG | 340 | GAACTCCACGCCGTTCA | /56-FAM/CCGGCTTGT/ZEN/CGACGACGGCG/3IABkFQ/ | 405 | Eco91I, HindIII |
| chr16: 18607730 | GFP (pDY0186) | 341 | GAGAGGAGCAACAGTGAGCATGATG | 342 | GAACTCCACGCCGTTCA | /56-FAM/CCGGCTTGT/ZEN/CGACGACGGCG/3IABkFQ/ | 405 | Eco91I, HindIII |
| chr6: 149045959 | ACTB HITI template GFP (pDY0219) | 343 | AAGCCATCTCCCAGAATATCTGCTTAGAAATG | 344 | GAACTCCACGCCGTTCA | /56-FAM/CCGGCTTGT/ZEN/CGACGACGGCG/3IABkFQ/ | 405 | Eco91I |
| chr16: 18607730 | ACTB HITI template GFP (pDY0219) | 345 | GAGAGGAGCAACAGTGAGCATGATG | 346 | GAACTCCACGCCGTTCA | /56-FAM/CCGGCTTGT/ZEN/CGACGACGGCG/3IABkFQ/ | 405 | Eco91I |
| ACTB | CAG_Kozak_bGH_thera-peutic_genes generic minicircle | 347 | CCCGGCTTCCTTTGTCC | 348 | GGCTATGAACTAATGACCCCGT | /56-FAM/CCGGCTTGT/ZEN/CGACGACGGCG/3IABkFQ/ | 405 | Eco91I, HindIII |
| ACTB | Hibit-SERPINA (pDY045) | 349 | CCCGGCTTCCTTTGTCC | 350 | GGCCTGCCAGCAGGAGGA | /56-FAM/CCGGCTTG | 405 | EcoRI, XhoI, HindIII |

TABLE 7-continued

| Locus | Cargo | SEQ ID NO: | Forward Primer | SEQ ID NO: | Reverse Primer | Probe | SEQ ID NO: | Restrict-ion Enzymes |
|---|---|---|---|---|---|---|---|---|
| | | | | | | T/ZE N/C GAC GAC GGC G/3I ABkF Q/ | | |
| ACTB | Hibit-CPS1 (pDY406) | 351 | CCCG GCTTC CTTTG TCC | 352 | GGTG TGCA GTCA CATTG GTAA AGCC | /56-FAM/ AC AGC TTT C/ZE N/A AAG TGG TGA GGA CAC T/3IA BkFQ / | 408 | XhoI, HindIII |

Sequences of primers used for NGS readout can be found in Table 8 below.

TABLE 8

| SEQ ID NO/ DESCRIPTION/ SOURCE | ID | SEQUENCE (5'-3') |
|---|---|---|
| SEQ ID NO: 353 N-term ACTB Tn5 readout F 1 (Artificial Sequence) | PD0966 | ACACTCTTTCCCTACACGACGCTCTTCCGATCTCCGAC CTCGGC TCACAGCG |
| SEQ ID NO: 354 N-term ACTB Tn5 readout F 2 (Artificial Sequence) | PD0967 | ACACTCTTTCCCTACACGACGCTCTTCCGATCTACCGA CCTCGG CTCACAGCG |
| SEQ ID NO: 355 N-term ACTB Tn5 readout F 3 (Artificial Sequence) | PD0968 | ACACTCTTTCCCTACACGACGCTCTTCCGATCTGACCG ACCTCG GCTCACAGCG |
| SEQ ID NO: 356 N-term ACTB Tn5 readout F 4 (Artificial Sequence) | PD0969 | ACACTCTTTCCCTACACGACGCTCTTCCGATCTTGACC GACCTC GGCTCACAGCG |
| SEQ ID NO: 357 N-term ACTB Tn5 readout F 5 (Artificial Sequence) | PD0970 | ACACTCTTTCCCTACACGACGCTCTTCCGATCTCTGAC CGACCT CGGCTCACAGCG |
| SEQ ID NO: 358 N-term ACTB Tn5 readout F 6 (Artificial Sequence) | PD0971 | ACACTCTTTCCCTACACGACGCTCTTCCGATCTACTGA CCGACC TCGGCTCACAGCG |
| SEQ ID NO: 359 N-term ACTB Tn5 readout F 7 (Artificial Sequence) | PD0972 | ACACTCTTTCCCTACACGACGCTCTTCCGATCTTACTG ACCGAC CTCGGCTCACAGCG |
| SEQ ID NO: 360 N-term ACTB Tn5 readout F 8 (Artificial Sequence) | PD0973 | ACACTCTTTCCCTACACGACGCTCTTCCGATCTGTACT GACCGA CCTCGGCTCACAGCG |

TABLE 8-continued

| SEQ ID NO/ DESCRIPTION/ SOURCE | ID | SEQUENCE (5'-3') |
|---|---|---|
| SEQ ID NO: 361 ACTB N-term NGS R for Cas14 indels (Artificial Sequence) | FP0952 | GTGACTGGAGTTCAGACGTGTGCTCTTCCGATCTCCAC CCAGCC AGCTCCC |
| SEQ ID NO: 362 NGS EMX1 Forward 1 (Artificial Sequence) | PD0313 | ACACTCTTTCCCTACACGACGCTCTTCCGATCTCCGGT GGCGCAT TGCCAC |
| SEQ ID NO: 363 NGS EMX1 Forward 2 (Artificial Sequence) | PD0314 | ACACTCTTTCCCTACACGACGCTCTTCCGATCTACCGG TGGCGCA TTGCCAC |
| SEQ ID NO: 364 NGS EMX1 Forward 3 (Artificial Sequence) | PD0315 | ACACTCTTTCCCTACACGACGCTCTTCCGATCTGACCG GTGGCGC ATTGCCAC |
| SEQ ID NO: 365 NGS EMX1 Forward 4 (Artificial Sequence) | PD0316 | ACACTCTTTCCCTACACGACGCTCTTCCGATCTTGACC GGTGGCG CATTGCCAC |
| SEQ ID NO: 366 NGS EMX1 Forward 5 (Artificial Sequence) | PD0317 | ACACTCTTTCCCTACACGACGCTCTTCCGATCTCTGAC CGGTGGC GCATTGCCAC |
| SEQ ID NO: 367 NGS EMX1 Forward 6 (Artificial Sequence) | PD0318 | ACACTCTTTCCCTACACGACGCTCTTCCGATCTACTGA CCGGTGG CGCATTGCCAC |
| SEQ ID NO: 368 NGS EMX1 Forward 7 (Artificial Sequence) | PD0319 | ACACTCTTTCCCTACACGACGCTCTTCCGATCTTACTG ACCGGTG GCGCATTGCCAC |
| SEQ ID NO: 369 NGS EMX1 Forward 8 (Artificial Sequence) | PD0320 | ACACTCTTTCCCTACACGACGCTCTTCCGATCTGTACT GACCGG GGCGCATTGCCAC |
| SEQ ID NO: 370 NGS EMX1 Reverse (Artificial Sequence) | PD0321 | GTGACTGGAGTTCAGACGTGTGCTCTTCCGATCTCAGA GTCCAGC TTGGGCCCA |

Sequences of off-target sites can be found in Table 9 below.

TABLE 9

| SEQ ID NO/ DESCRIPTION/ SOURCE | SEQUENCE (5'-3') |
|---|---|
| SEQ ID NO: 371 Cas9_chr6:149045959 (Artificial Sequence) | GATATTTTCCCAGCTCACCA |
| SEQ ID NO: 372 Cas9_chr16:18607730 (Artificial Sequence) | TCTATTCTCCCAGCTCCCCA |
| SEQ ID NO: 373 Bxb1_NC_000002 (Artificial Sequence) | AGCGGCTTCTGTCTCTGTGAGTGAGCTGGCGGTCTCCGTC |

TABLE 9-continued

| SEQ ID NO/ DESCRIPTION/ SOURCE | SEQUENCE (5'-3') |
|---|---|
| SEQ ID NO: 374 Bxb1_NC_000003 (Artificial Sequence) | GACTAGCCCACGCTCCGGTTCTGAGCCGCGACGGCGGTCTCCG |
| SEQ ID NO: 375 Bxb1_NC_000009 (Artificial Sequence) | CCCAGGGTCCCATGCGCTCCCCGGCCCTGACGGCGGTCTCC |

Linker sequences in Table 10 below.

TABLE 10

| Description | Sequence (5'-3') | Amino acid sequence |
|---|---|---|
| A-P2A | GGAAGCGGAGCTACTAACTTCAGCCT GCTGAAGCAGGCTGGCGACGTGGAGG AGAACCCTGGACCT (SEQ ID NO: 410) | GSGATNFSLLKQAGDVEENPGP (SEQ ID NO: 418) |
| B-(GGGS)3 | GGGGGAGGAGGTTCTGGAGGCGGAGG CTCCGGAGGCGGAGGGTCA (SEQ ID NO: 411) | GGGGSGGGGSGGGGS (SEQ ID NO: 419) |
| C-GGGGS | GGAGGTGGCGGGAGC (SEQ ID NO: 412) | GGGGS (SEQ ID NO: 420) |
| D-PAPAP | CCCGCACCAGCGCCT (SEQ ID NO: 413) | PAPAP (SEQ ID NO: 421) |
| E-(EAAAK)3 | GAGGCAGCTGCCAAGGAAGCCGCT GCCAAGGAGGCGGCCGCAAAG (SEQ ID NO: 414) | EAAAKEAAAKEAAAK (SEQ ID NO: 422) |
| F-XTEN | AGTGGGAGCGAGACCCCTGGGACT AGCGAGTCAGCTACACCCGAAAGC (SEQ ID NO: 415) | SGSETPGTSESATPES (SEQ ID NO: 423) |
| G-(GGS)6 | GGGGGGTCAGGTGGATCCGGCGG AAGTGGCGGATCCGGTGGATCTGG CGGCAGT (SEQ ID NO: 416) | GGSGGSGGSGGSGGSGGS (SEQ ID NO 424) |
| H-EAAAK | GAAGCTGCTGCTAAG (SEQ ID NO: 417) | EAAAK (SEQ ID NO: 425) |

Exemplary fusion sequences in Table 11 below.

| Description | Sequence |
|---|---|
| SpCas9-XTEN-RT(1-478)-Sto7d-GGGGS-BxbINT Amino acid SEQ ID NO: 376 | MKRTADGSEFESPKKKRKVDKKYSIGLDIGTNSVGWAVITDEYKVPS<br>KKFKVLGNTDRHSIKKNLIGALLFDSGETAEATRLKRTARRRYTRR<br>KNRICYLQEIFSNEMAKVDDSFFHRLEESFLVEEDKKHERHPIFGNI<br>VDEVAYHEKYPTIYHLRKKLVDSTDKADLRLIYLALAHMIKFRGHF<br>LIEGDLNPDNSDVDKLFIQLVQTYNQLFEENPINASGVDAKAILSAR<br>LSKSRRLENLIAQLPGEKKNGLFGNLIALSLGLTPNFKSNFDLAEDA<br>KLQLSKDTYDDDLDNLLAQIGDQYADLFLAAKNLSDAILLSDILRVN<br>TEITKAPLSASMIKRYDEHHQDLTLLKALVRQQLPEKYKEIFFDQS<br>KNGYAGYIDGGASQEEFYKFIKPILEKMDGTEELLVKLNREDLLRK<br>QRTFDNGSIPHQIHLGELHAILRRQEDFYPFLKDNREKIEKILTFRIP<br>YYVGPLARGNSRFAWMTRKSEETITPWNFEEVVDKGASAQSFIER<br>MTNFDKNLPNEKVLPKIISLLYEYFTVYNELTKVKYVTEGMRKPAF<br>LSGEQKKAIVDLLFKTNRKVTVKQLKEDYFKKIECFDSVEISGVED<br>RFNASLGTYHDLLKIIKDKDFLDNEENEDILEDIVLTLTLFEDREMIE<br>ERLKTYAHLFDDKVMKQLICRRRYTGWGRLSRKLINGIRDKQSGK<br>TILDFLKSDGFANRNFMQLIHDDSLTFKEDIQKAQVSGQGDSLHEHI<br>ANLAGSPAIKKGILQTVKVVDELVKVMGRHKPENIVIEMARENQTT<br>QKGQKNSRERMKRIEEGIKELGSQILKEHPVENTQLQNEKLYLYYL<br>QNGRDMYVDQELDINRLSDYDVDAIVPQSFLKDDSIDNKVLTRSDK<br>NRGKSDNVPSEEVVKKMKNYWRQLLNAKLITQRKFDNLTKAERG |

-continued

| Description | Sequence |
|---|---|
| | **GLSELDKAGFIKRQLVETRQITKHVAQILDSRMNTKYDENDKLIRE**<br>**VKVITLKSKLVSDFRKDFQFYKVREINNYHHAHDAYLNAVVGTALI**<br>**KKYPKLESEFVYGDYKVYDVRKMIAKSEQEIGKATAKYFFYSNIMN**<br>**FFKTEITLANGEIRKRPLIETNGETGEIVWDKGRDFATVRKVLSMP**<br>**QVNIVKKTEVQTGGFSKESILPKRNSDKLIARKKDWDPKKYGGFDS**<br>**PTVAYSVLVVAKVEKGKSKKLKSVKELLGITIMERSSFEKNPIDFLE**<br>**AKGYKEVKKDLIIKLPKYSLFELENGRKRMLASAGELQKGNELAL**<br>**PSKYVNFLYLASHYEKLKGSPEDNEQKQLFVEQHKHYLDEHEQISE**<br>**FSKRVILADANLDKVLSAYNKHRDKPIREQAENIIHLFTLTNLGAPA**<br>**AFKYFDTTIDRKRYTSTKEVLDATLIHQSITGLYETRIDLSQLGGD**S<br>GGSSGGSSGSETPGTSESATPESSGSETPGTSESATPESSGSETPGTSESAT<br>PESSGGSSGGSST**LNIEDEYRLHETSKEPDVSLGSTWLSDFPQAWAET**<br>**GGMGLAVRQAPLIIPLKATSTPVSIKQVPMSQEARLGIKPHIQRLLD**<br>**QGILVPCQSPWNTPLLPVKKPGTNDYRPVQDLREVNKRVEDIHPTV**<br>**PNPYNLLSGPPPSHQWYTVLDLKDAFFCLRLHPTSQPLFAFEWRDP**<br>**EMGISGQLTWTRLPQGFKNSPTLFNEALHRDLADFRIQHPDLILLQ**<br>**YVDDLLLAATSELDCQQGTRALLQTLGNLGYRASAKKAQKQKQV**<br>**KYLGYLLKEGQRWLTEARKETVMGQPTPKTPRQLREFLGKAGFC**<br>**RLFIPGFAEMAAPLYPLTKPGTLFNWGPDQQKAYQEIKQALLTAPA**<br>**LGLPDLTKPFELFVDEKQGYAKGVLTQKLGPWRRPVAYLSKKLDP**<br>**VAAGWPPCLRMVAAIAVLTKDAGKLTMGQPLVILAPHAVEALVK**<br>**QPPDRWLSNARNITHYQALLLDTDRVQFGPVVALNPATLLPLPEEG**<br>**LQIINCLDGTGGGGVTVKFKYKGEELEVDISKIKKVWRVGKNIISFT**<br>**YDDNGKTGRGAVSEKDAPKELLQMLEKSGKKSGGSKRTADGS**EFE<br>PKKKRKVGGGGSPKKKRKVYPYDVPDYAG**SRALVVIRLSRVTDATTS**<br>**PERQLESCQQLCAQRGWDVVGVAEDLDVSGAVDPFDRKRRPNLAR**<br>**WLAFEEQPFDVIVAYRVDRLTRSIRHLQQLVHWAEDHKKLVVSAT**<br>**EAHFDTTTPFAAVVIALMGTVAQMELEAIKERNRSAAHFNIRAGKY**<br>**RGSLPPWGYLPTRVDGEWRLVPDPVQRERILEVYHRVVDNHEPLH**<br>**LVAHDLNRRGVLSPKDYFAQLQGREPQGREWSATALKRSMISEAM**<br>**LGYATLNGKTVRDDDGAPLVRAEPILTREQLEALRAELVKTSRAKP**<br>**AVSTPSLLLRVLFCAVCGEPAYKFAGGGRKHPRYRCRSMGFPKHC**<br>**GNGTVAMAEWDAFCEEQVLDLLGDAERLEKVWVAGSDSAVELAE**<br>**VNAELVDLTSLIGSPAYRAGSPQREALDARIAALAARQEELEGLEAR**<br>**PSGWEWRETGQRFGDWWREQDTAAKNTWLRSMNVRLTFDVRGG**<br>**LTRTIDFGDLQEYEQHLRLGSVVERLHTGMS** |
| SpCas9-XTEN-<br>RT(1-478)-Sto7d-<br>GGGGS-BxbINT<br>Nucleic acid<br>SEQ ID NO: 377 | ATGAAACGGACAGCCGACGGAAGCGAGTTCGAGTCACCAAAGAAG<br>AAGCGGAAAGTCGACAAGAAGTACAGCATCGGCCTGGACATCGGCA<br>CCAACTCTGTGGGCTGGGCCGTGATCACCGACGAGTACAAGGTGCC<br>CAGCAAGAAATTCAAGGTGCTGGGCAACACCGACCGGCACAGCATC<br>AAGAAGAACCTGATCGGAGCCCTGCTGTTCGACAGCGGCGAAACAG<br>CCGAGGCCACCCGGCTGAAGAGAACCGCCAGAAGAAGATACACCA<br>GACGGAAGAACCGGATCTGCTATCTGCAAGAGATCTTCAGCAACGA<br>GATGGCCAAGGTGGACGACAGCTTCTTCCACAGACTGGAAGAGTCC<br>TTCCTGGTGGAAGAGGATAAGAAGCACGAGCGGCACCCCATCTTCG<br>GCAACATCGTGGACGAGGTGGCCTACCACGAGAAGTACCCCACCAT<br>CTACCACCTGAGAAAGAAACTGGTGGACAGCACCGACAAGGCCGAC<br>CTGCGGCTGATCTATCTGGCCCTGGCCCACATGATCAAGTTCCGGGG<br>CCACTTCCTGATCGAGGGCGACCTGAACCCCGACAACAGCGACGTG<br>GACAAGCTGTTCATCCAGCTGGTGCAGACCTACAACCAGCTGTTCGA<br>GGAAAACCCCATCAACGCCAGCGGCGTGGACGCCAAGGCCATCCTG<br>TCTGCCAGACTGAGCAAGAGCAGACGGCTGGAAAATCTGATCGCCC<br>AGCTGCCCGGCGAGAAGAAGAATGGCCTGTTCGGAAACCTGATTGC<br>CCTGAGCCTGGGCCTGACCCCCAACTTCAAGAGCAACTTCGACCTGG<br>CCGAGGATGCCAAACTGCAGCTGAGCAAGGACACCTACGACGACGA<br>CCTGGACAACCTGCTGGCCCAGATCGGCGACCAGTACGCCGACCTG<br>TTTCTGGCCGCCAAGAACCTGTCCGACGCCATCCTGCTGAGCGACAT<br>CCTGAGAGTGAACACCGAGATCACCAAGGCCCCCCTGAGCGCCTCT<br>ATGATCAAGAGATACGACGAGCACCACCAGGACCTGACCCTGCTGA<br>AAGCTCTCGTGCGGCAGCAGCTGCCTGAGAAGTACAAAGAGATTTT<br>CTTCGACCAGAGCAAGAACGGCTACGCCGGCTACATTGACGGCGGA<br>GCCAGCCAGGAAGAGTTCTACAAGTTCATCAAGCCCATCCTGGAAA<br>AGATGGACGGCACCGAGGAACTGCTCGTGAAGCTGAACAGAGAGG<br>ACCTGCTGCGGAAGCAGCGGACCTTCGACAACGGCAGCATCCCCCA<br>CCAGATCCACCTGGGAGAGCTGCACGCCATTCTGCGGCGGCAGGAA<br>GATTTTTACCCATTCCTGAAGGACAACCGGGAAAAGATCGAGAAGA<br>TCCTGACCTTCCGCATCCCCTACTACGTGGGCCCTCTGGCCAGGGGA<br>AACAGCAGATTCGCCTGGATGACCAGAAAGAGCGAGGAAACCATCA<br>CCCCCTGGAACTTCGAGGAAGTGGTGGACAAGGGCGCTTCCGCCCA<br>GAGCTTCATCGAGCGGATGACCAACTTCGATAAGAACCTGCCCAAC<br>GAGAAGGTGCTGCCCAAGCACAGCCTGCTGTACGAGTACTTCACCG<br>TGTATAACGAGCTGACCAAAGTGAAATACGTGACCGAGGGAATGAG<br>AAAGCCCGCCTTCCTGAGCGGCGAGCAGAAAAAGGCCATCGTGGAC<br>CTGCTGTTCAAGACCAACCGGAAAGTGACCGTGAAGCAGCTGAAAG<br>AGGACTACTTCAAGAAAATCGAGTGCTTCGACTCCGTGGAAATCTCC<br>GGCGTGGAAGATCGGTTCAACGCCTCCCTGGGCACATACCACGATC |

-continued

| Description | Sequence |
|---|---|
| | TGCTGAAAATTATCAAGGACAAGGACTTCCTGGACAATGAGGAAAA<br>CGAGGACATTCTGGAAGATATCGTGCTGACCCTGACACTGTTTGAGG<br>ACAGAGAGATGATCGAGGAACGGCTGAAAACCTATGCCCACCTGTT<br>CGACGACAAAGTGATGAAGCAGCTGAAGCGGCGGAGATACACCGG<br>CTGGGGCAGGCTGAGCCGGAAGCTGATCAACGGCATCCGGGACAAG<br>CAGTCCGGCAAGACAATCCTGGATTTCCTGAAGTCCGACGGCTTCGC<br>CAACAGAAACTTCATGCAGCTGATCCACGACGACAGCCTGACCTTT<br>AAAGAGGACATCCAGAAAGCCCAGGTGTCCGGCCAGGGCGATAGCC<br>TGCACGAGCACATTGCCAATCTGGCCGGCAGCCCCGCCATTAAGAA<br>GGGCATCCTGCAGACAGTGAAGGTGGTGGACGAGCTCGTGAAAGTG<br>ATGGGCCGGCACAAGCCCGAGAACATCGTGATCGAAATGGCCAGAG<br>AGAACCAGACCACCCAGAAGGGACAGAAGAACAGCCGCGAGAGAA<br>TGAAGCGGATCGAAGAGGGCATCAAAGAGCTGGGCAGCCAGATCCT<br>GAAAGAACACCCCGTGGAAAACACCCAGCTGCAGAACGAGAAGCT<br>GTACCTGTACTACCTGCAGAATGGGCGGGATATGTACGTGGACCAG<br>GAACTGGACATCAACCGGCTGTCCGACTACGATGTGGACGCTATCG<br>TGCCTCAGAGCTTTCTGAAGGACGACTCCATCGACAACAAGGTGCT<br>GACCAGAAGCGACAAGAACCGGGGCAAGAGCGACAACGTGCCCTC<br>CGAAGAGGTCGTGAAGAAGATGAAGAACTACTGGCGGCAGCTGCTG<br>AACGCCAAGCTGATTACCCAGAGAAAGTTCGACAATCTGACCAAGG<br>CCGAGAGAGGCGGCCTGAGCGAACTGGATAAGGCCGGCTTCATCAA<br>GAGACAGCTGGTGGAAACCCGGCAGATCACAAAGCACGTGGCACA<br>GATCCTGGACTCCCGGATGAACACTAAGTACGACGAGAATGACAAG<br>CTGATCCGGGAAGTGAAAGTGATCACCCTGAAGTCCAAGCTGGTGT<br>CCGATTTCCGGAAGGATTTCCAGTTTTACAAAGTGCGCGAGATCAAC<br>AACTACCACCACGCCCACGACGCCTACCTGAACGCCGTCGTGGGAA<br>CCGCCCTGATCAAAAAGTACCCTAAGCTGGAAAGCGAGTTCGTGTA<br>CGGCGACTACAAGGTGTACGACGTGCGGAAGATGATCGCCAAGAGC<br>GAGCAGGAAATCGGCAAGGCTACCGCCAAGTACTTCTTCTACAGCA<br>ACATCATGAACTTTTTCAAGACCGAGATTACCCTGGCCAACGGCGA<br>GATCCGGAAGCGGCCTCTGATCGAGACAAACGGCGAAACCGGGGA<br>GATCGTGTGGGATAAGGGCCGGGATTTTGCCACCGTGCGGAAAGTG<br>CTGAGCATGCCCCAAGTGAATATCGTGAAAAAGACCGAGGTGCAGA<br>CAGGCGGCTTCAGCAAAGAGTCTATCCTGCCCAAGAGGAACAGCGA<br>TAAGCTGATCGCCAGAAAGAAGGACTGGGACCCTAAGAAGTACGGC<br>GGCTTCGACAGCCCCACCGTGGCCTATTCTGTGCTGGTGGTGGCCAA<br>AGTGGAAAAGGGCAAGTCCAAGAAACTGAAGAGTGTGAAAGAGCT<br>GCTGGGGATCACCATCATGGAAAGAAGCAGCTTCGAGAAGAATCCC<br>ATCGACTTTCTGGAAGCCAAGGGCTACAAAGAAGTGAAAAAGGACC<br>TGATCATCAAGCTGCCTAAGTACTCCCTGTTCGAGCTGGAAAACGGC<br>CGGAAGAGAATGCTGGCCTCTGCCGGCGAACTGCAGAAGGGAAACG<br>AACTGGCCCTGCCCTCCAAATATGTGAACTTCCTGTACCTGGCCAGC<br>CACTATGAGAAGCTGAAGGGCTCCCCCGAGGATAATGAGCAGAAAC<br>AGCTGTTTGTGGAACAGCACAAGCACTACCTGGACGAGATCATCGA<br>GCAGATCAGCGAGTTCTCCAAGAGAGTGATCCTGGCCGACGCTAAT<br>CTGGACAAAGTGCTGTCCGCCTACAACAAGCACCGGGATAAGCCCA<br>TCAGAGAGCAGGCCGAGAATATCATCCACCTGTTTACCCTGACCAAT<br>CTGGGAGCCCCTGCCGCCTTCAAGTACTTTGACACCACCATCGACCG<br>GAAGAGGTACACCAGCACCAAAGAGGTGCTGGACGCCACCCTGATC<br>CACCAGAGCATCACCGGCCTGTACGAGACACGGATCGACCTGTCTC<br>AGCTGGGAGGTGACTCTGGAGGATCTAGCGGAGGATCCTCTGGCAG<br>CGAGACACCAGGAACAAGCGAGTCAGCAACACCAGAGAGCTCTGGT<br>AGCGAGACACCCGGTACCAGTGAAAGCGCCACGCCAGAAAGCAGT<br>GGGAGTGAGACTCCGGGTACATCTGAATCAGCGACACCGGAATCAA<br>GTGGCGGCAGCAGCGGCGGCAGCAGCACCCTAAATATAGAAGATGA<br>GTATCGGCTACATGAGACCTCAAAAGAGCCAGATGTTTCTCTAGGGT<br>CCACATGGCTGTCTGATTTTCCTCAGGCCTGGGCGGAAACCGGGGGC<br>ATGGGACTGGCAGTTCGCCAAGCTCCTCTGATCATACCTCTGAAAGC<br>AACCTCTACCCCCGTGTCCATAAAACAATACCCCATGTCACAAGAA<br>GCCAGACTGGGGATCAAGCCCCACATACAGAGACTGTTGGACCAGG<br>GAATACTGGTACCCTGCCAGTCCCCCTGGAACACGCCCCTGCTACCC<br>GTTAAGAAACCAGGGACTAATGATTATAGGCCTGTCCAGGATCTGA<br>GAGAAGTCAACAAGCGGGTGGAAGACATCCACCCCACCGTGCCCAA<br>CCCTTACAACCTCTTGAGCGGGCCCCCACCGTCCCACCAGTGGTACA<br>CTGTGCTTGATTTAAAGGATGCCTTTTTCTGCCTGAGACTCCACCCC<br>ACCAGTCAGCCTCTCTTCGCCTTTGAGTGGAGAGATCCAGAGATGGG<br>AATCTCAGGACAATTGACCTGGACCAGACTCCCACAGGGTTTCAAA<br>AACAGTCCCACCCTGTTTAATGAGGCACTGCACAGAGACCTAGCAG<br>ACTTCCGGATCCAGCACCCAGACTTGATCCTGCTACAGTACGTGGAT<br>GACTTACTGCTGGCCGCCACTTCTGAGCTAGACTGCCAACAAGGTAC<br>TCGGGCCCTGTTACAAACCCTAGGGAACCTCGGGTATCGGGCCTCG<br>GCCAAGAAAGCCCAAATTTGCCAGAAACAGGTCAAGTATCTGGGGT<br>ATCTTCTAAAAGAGGGTCAGAGATGGCTGACTGAGGCCAGAAAAGA<br>GACTGTGATGGGGCAGCCTACTCCGAAGACCCCTCGACAACTAAGG<br>GAGTTCCTAGGGAAGGCAGGCTTCTGTCGCCTCTTCATCCCTGGGTT<br>TGCAGAAATGGCAGCCCCCCTGTACCCTCTCACCAAACCGGGGACT<br>CTGTTTAATTGGGGCCCAGACCAACAAAAGGCCTATCAAGAAATCA |

-continued

| Description | Sequence |
|---|---|
| | AGCAAGCTCTTCTAACTGCCCCAGCCCTGGGGTTGCCAGATTTGACT<br>AAGCCCTTTGAACTCTTTGTCGACGAGAAGCAGGGCTACGCCAAAG<br>GTGTCCTAACGCAAAAACTGGGACCTTGGCGTCGGCCGGTGGCCTA<br>CCTGTCCAAAAAGCTAGACCCAGTAGCAGCTGGGTGGCCCCCTTGC<br>CTACGGATGGTAGCAGCCATTGCCGTACTGACAAAGGATGCAGGCA<br>AGCTAACCATGGGACAGCCACTAGTCATTCTGGCCCCCCATGCAGTA<br>GAGGCACTAGTCAAACAACCCCCCGACCGCTGGCTTTCCAACGCCC<br>GGATGACTCACTATCAGGCCTTGCTTTTGGACACGGACCGGGTCCAG<br>TTCGGACCGGTGGTAGCCCTGAACCCGGCTACGCTGCTCCCACTGCC<br>TGAGGAAGGGCTGCAACACAACTGCCTTGATGGGACAGGTGGCGGT<br>GGTGTCACCGTCAAGTTCAAGTACAAGGGTGAGGAACTTGAAGTTG<br>ATATTAGCAAAATCAAGAAGGTTTGGCGCGTTGGTAAAATGATATC<br>TTTTACTTATGACGACAACGGCAAGACAGGTAGAGGGGCAGTGTCT<br>GAGAAAGACGCCCCCAAGGAGCTGTTGCAAATGTTGGAAAAGTCTG<br>GGAAAAAGTCTGGCGGCTCAAAAAGAACCGCCGACGGCAGCGAATT<br>CGAGCCCAAGAAGAAGAGGAAAGTCGGAGGTGGCGGGAGCCCAAA<br>AAAGAAAAGAAAAGTGTATCCCTATGATGTCCCCGATTATGCCGGT<br>TCAAGAGCCCTGGTCGTGATTAGACTGAGCCGAGTGACAGACGCCA<br>CCACAAGTCCCGAGAGACAGCTGGAATCATGCCAGCAGCTCTGTGC<br>TCAGCGGGGTTGGGATGTGGTCGGCGTGGCAGAGGATCTGGACGTG<br>AGCGGGGCCGTCGATCCATTCGACAGAAAGAGGAGGCCCAACCTGG<br>CAAGATGGCTCGCTTTCGAGGAACAGCCCTTTGATGTGATCGTCGCC<br>TACAGAGTGGACCGGCTGACCCGCTCAATTCGACATCTCCAGCAGCT<br>GGTGCATTGGGCTGAGGACCACAAGAAACTGGTGGTCAGCGCAACA<br>GAAGCCCACTTCGATACTACCACACCTTTTGCCGCTGTGGTCATCGC<br>ACTGATGGGCACTGTGGCCCAGATGGAGCTCGAAGCTATCAAGGAG<br>CGAAACAGGAGCGCAGCCCATTTCAATATTAGGGCCGGTAAATACA<br>GAGGCTCCCTGCCCCCTTGGGGATATCTCCCTACCAGGGTGGATGGG<br>GAGTGGAGACTGGTGCCAGACCCCGTCCAGAGAGAGCGGATTCTGG<br>AAGTGTACCACAGAGTGGTCGATAACCACGAACCACTCCATCTGGT<br>GGCACACGACCTGAATAGACGCGGCGTGCTCTCTCCAAAGGATTAT<br>TTTGCTCAGCTGCAGGGAAGAGAGCCACAGGGAAGAGAATGGAGTG<br>CTACTGCACTGAAGAGATCTATGATCAGTGAGGCTATGCTGGGTTAC<br>GCAACACTCAATGGCAAAACTGTCCGGGACGATGACGGAGCCCCTC<br>TGGTGAGGGCTGAGCCTATTCTCACCAGAGAGCAGCTCGAAGCTCT<br>GCGGGCAGAACTGGTCAAGACTAGTCGCGCCAAACCTGCCGTGAGC<br>ACCCCAAGCCTGCTCCTGAGGGTGCTGTTCTGCGCCGTCTGTGGAGA<br>GCCAGCATACAAGTTTGCCGGCGGAGGGCGCAAACATCCCCGCTAT<br>CGATGCAGGAGCATGGGGTTCCCTAAGCACTGTGGAAACGGGACAG<br>TGGCCATGGCTGAGTGGGACGCCTTTTGCGAGGAACAGGTGCTGGA<br>TCTCCTGGGTGACGCTGAGCGGCTGGAAAAAGTGTGGGTGGCAGGA<br>TCTGACTCCGCTGTGGAGCTGGCAGAAGTCAATGCCGAGCTCGTGG<br>ATCTGACTTCCCTCATCGGATCTCCTGCATATAGAGCTGGGTCCCCA<br>CAGAGAGAAGCTCTGGACGCACGAATTGCTGCACTCGCTGCTAGAC<br>AGGAGGAACTGGAGGGCCTGGAGGCCAGGCCCTCTGGATGGGAGTG<br>GCGAGAAACCGGACAGAGGTTTGGGGATTGGTGGAGGGAGCAGGA<br>CACCGCAGCCAAGAACACATGGCTGAGATCCATGAATGTCCGGCTC<br>ACATTCGACGTGCGCGGTGGCCTGACTCGAACCATCGATTTTGGCGA<br>CCTGCAGGAGTATGAACAGCACCTGAGACTGGGGTCCGTGGTCGAA<br>AGACTGCACACTGGGATGTCC |
| SpCas9<br>Amino acid<br>SEQ ID NO: 378 | DKKYSIGLDIGTNSVGWAVITDEYKVPSKKFKVLGNTDRHSIKKNLIGA<br>LLFDSGETAEATRLKRTARRRYTRRKNRICYLQEIFSNEMAKVDDSFFH<br>RLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLN<br>REDLLRKQRTFDNGSIPHQIHLGELHAILRRQEDFYPFLKDNREKIEKILT<br>FRIPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFA<br>NRNFMQLIHDDSLTFKEDIQKAQVSGQGDSLHEHIANLAGSPAIKKGIL<br>QTVKVVDELVKVMGRHKPENIVIEMARENQTTQKGQKNSRERMKRIE<br>EGIKELGSQILKEHPVENTQLQNEKLYLYYLQNGRDMYVDQELDINRL<br>SDYDVDAIVPQSFLKDDSIDNKVLTRSDKNRGKSDNVPSEEVVKKMKN<br>YWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKK<br>DWDPKKYGGFDSPTVAYSVLVVAKVEKGKSKKLKSVKELLGITIMERS<br>SFEKNPIDFLEAKGYKEVKKDLIIKLPKYSLFELENGRKRMLASAGELQ<br>KGNELALPSKYVNFLYLASHYEKLKGSPEDNEQKQLFVEQHKHYLDEII |

-continued

| Description | Sequence |
|---|---|
| | EQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD |
| RT(1-478)-Sto7d<br>Amino acid<br>SEQ ID NO: 379 | LNIEDEYRLHETSKEPDVSLGSTWLSDFPQAWAETGGMGLAVRQAPLII<br>PLKATSTPVSIKQYPMSQEARLGIKPHIQRLLDQGILVPCQSPWNTPLLP<br>VKKPGTNDYRPVQDLREVNKRVEDIHPTVPNPYNLLSGPPPSHQWYTV<br>LDLKDAFFCLRLHPTSQPLFAFEWRDPEMGISGQLTWTRLPQGFKNSPT<br>LFNEALHRDLADFRIQHPDLILLQYVDDLLLAATSELDCQQGTRALLQT<br>LGNLGYRASAKKAQICQKQVKYLGYLLKEGQRWLTEARKETVMGQPT<br>PKTPRQLREFLGKAGFCRLFIPGFAEMAAPLYPLTKPGTLFNWGPDQQK<br>AYQEIKQALLTAPALGLPDLTKPFELFVDEKQGYAKGVLTQKLGPWRR<br>PVAYLSKKLDPVAAGWPPCLRMVAAIAVLTKDAGKLTMGQPLVILAP<br>HAVEALVKQPPDRWLSNARMTHYQALLLDTDRVQFGPVVALNPATLL<br>PLPEEGLQHNCLDGTGGGGVTVKFKYKGEELEVDISKIKKVWRVGKMI<br>SFTYDDNGKTGRGAVSEKDAPKELLQMLEKSGKKSGGSKRTADGS |
| BxbINT<br>Amino acid<br>SEQ ID NO: 380 | SRALVVIRLSRVTDATTSPERQLESCQQLCAQRGWDVVGVAEDLDVSG<br>AVDPFDRKRRPNLARWLAFEEQPFDVIVAYRVDRLTRSIRHLQQLVHW<br>AEDHKKLVVSATEAHFDTTTPFAAVVIALMGTVAQMELEAIKERNRSA<br>AHFNIRAGKYRGSLPPWGYLPTRVDGEWRLVPDPVQRERILEVYHRVV<br>DNHEPLHLVAHDLNRRGVLSPKDYFAQLQGREPQGREWSATALKRSM<br>ISEAMLGYATLNGKTVRDDDGAPLVRAEPILTREQLEALRAELVKTSRA<br>KPAVSTPSLLLRVLFCAVCGEPAYKFAGGGRKHPRYRCRSMGFPKHCG<br>NGTVAMAEWDAFCEEQVLDLLGDAERLEKVWVAGSDSAVELAEVNA<br>ELVDLTSLIGSPAYRAGSPQREALDARIAALAARQEELEGLEARPSGWE<br>WRETGQRFGDWWREQDTAAKNTWLRSMNVRLTFDVRGGLTRTIDFG<br>DLQEYEQHLRLGSVVERLHTGMS |

EXAMPLES

While several experimental Examples are contemplated, these Examples are intended to be non-limiting.

Example 1

CRE Integration Efficiency

Figure 3:
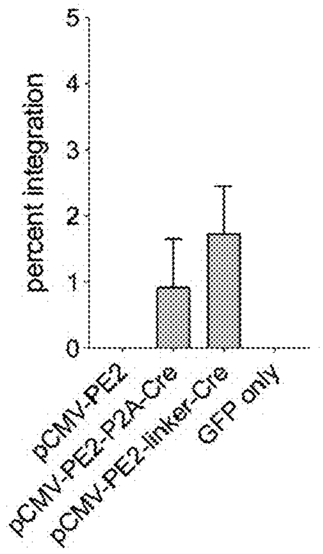
FIG. 3 shows the percent integration of green fluorescent protein (GFP) in the lentiviral integrated lox71 site in HEK293FT cell line in the presence of various plasmids according to embodiments of the present teachings.

The efficiency of the CRE integration was tested. In order to test the efficacy of PASTE with GFP using lox71/lox66/Cre recombinase system, a clonal HEK293FT cell line with lox71 sequence (SEQ ID NO: 1) integrated into the genome using lentivirus was developed. The integration of GFP was tested by transfection of modified HEK293FT cell line with: (1) plus/minus SEQ ID NO: 71 comprising a Cre recombinase expression plasmid, and (2) SEQ ID NO: 72 comprising a GFP template and a lox 66 Cre site of SEQ ID NO: 2. After 72 hours, the percent integration of GFP into the lox71 site was probed. FIG. 3 shows the percent integration of GFP in the lentiviral integrated lox71 site in HEK293FT cell line in the presence of various plasmids. It was observed that pCMV PE2 P2A Cre (SEQ ID NO: 73), a mammalian expression vector with prime editing complex and Cre recombinase linked to PE2 via a cleavable linker or a non-cleavable linker, shows integration of GFP.

Example 2

Figure 4:
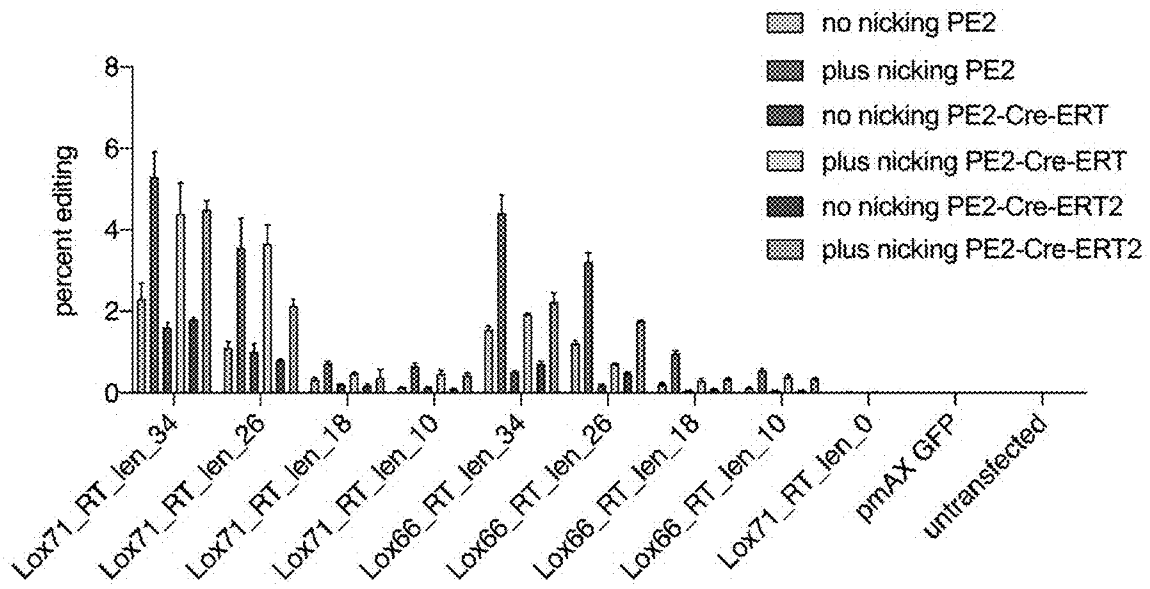
FIG. 4 shows the percent editing of the HEK293FT genome for incorporation of various lengths of lox71 or lox66 according to embodiments of the present teachings.

Programmable Addition Via Site-Specific Targeting Elements (PASTE) with Cre Recombinase—Addition of Lox Site The lox71 (SEQ ID NO: 1) or lox66 (SEQ ID NO: 2) sequence was inserted into the HEK293FT cell genome using prime editing to test integration of GFP into the HEK293FT genome. In order to insert lox71 or lox66 sequence into HEK293FT cell genome, a pegRNA with PBS length of 13 base pairs operably linked to RT region of varying lengths was used. The following plasmids were used in the transfection of HEK293FT cells. The cells were transfected with (1) prime editing construct (PE2) or PE2 with conditional Cre expression, (2) Lox71 or Lox66 pegRNA targeting the HEK3 locus, and (3) plus/minus +90 HEK3 nicking second guide RNA targeting the HEK3 locus (+90 ngRNA). After 72 hours, the percent editing of the HEK293FT genome at the HEK3 locus was probed for incorporation of various lengths of lox71 or lox66 (see FIG. 4). It was observed that 34 base pair lox71 (HEK3 locus guide, SEQ ID NO: 83; and Lox71 pegRNA with RT 34 and PBS 13, SEQ ID NO: 81) with +90 ngRNA (SEQ ID NO: 75) and 34 base pair lox66 (HEK3 locus guide, SEQ ID NO: 83; and Lox66 pegRNA with RT 34 and PBS 13, SEQ ID NO: 82) with +90 ngRNA (SEQ ID NO: 75) had the highest percent editing.

Example 3

PASTE with Cre Recombinase—Integration of Gene

Figure 5A:
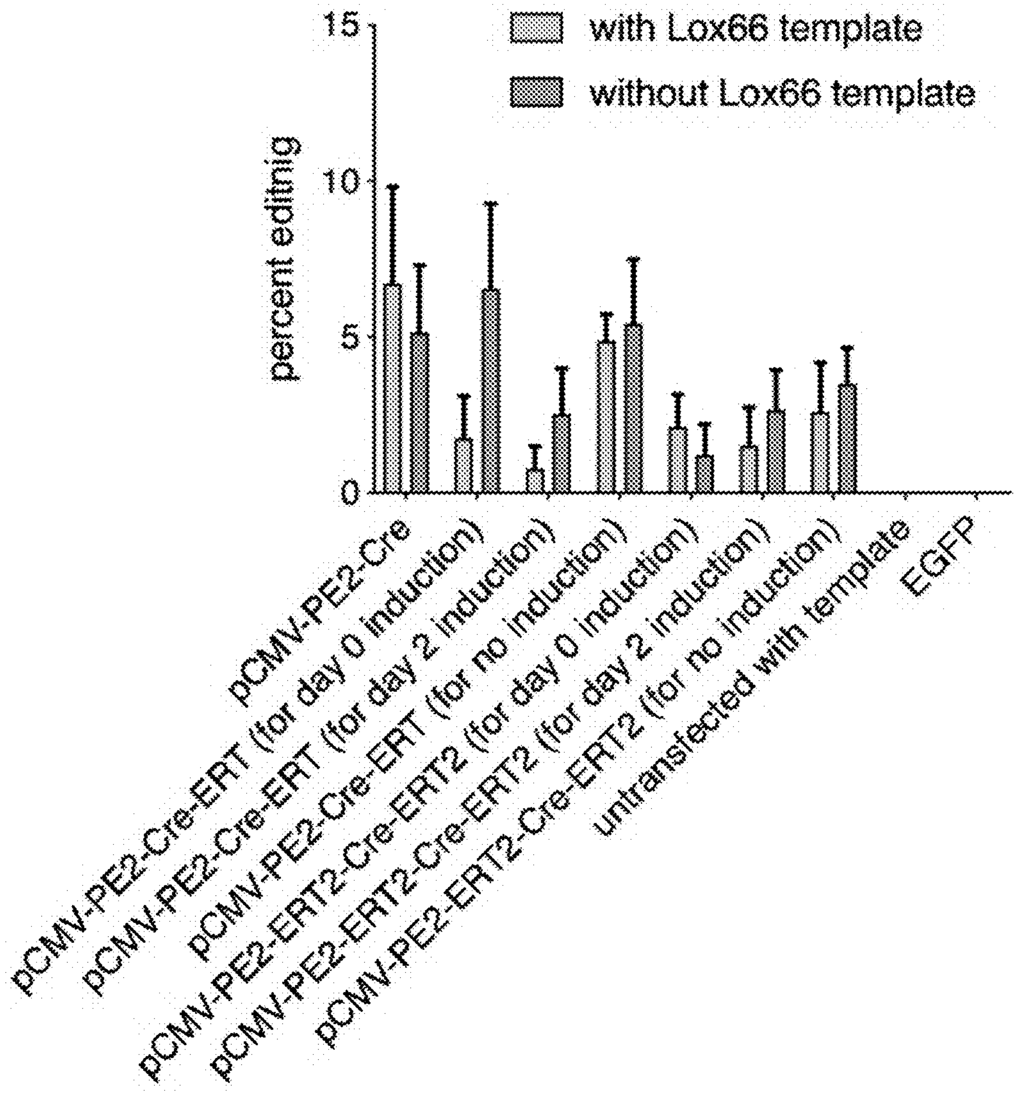
FIG. 5A shows the percent editing of lox71 site with different PE/Cre vectors according to embodiments of the present teachings.
Figure 5B:
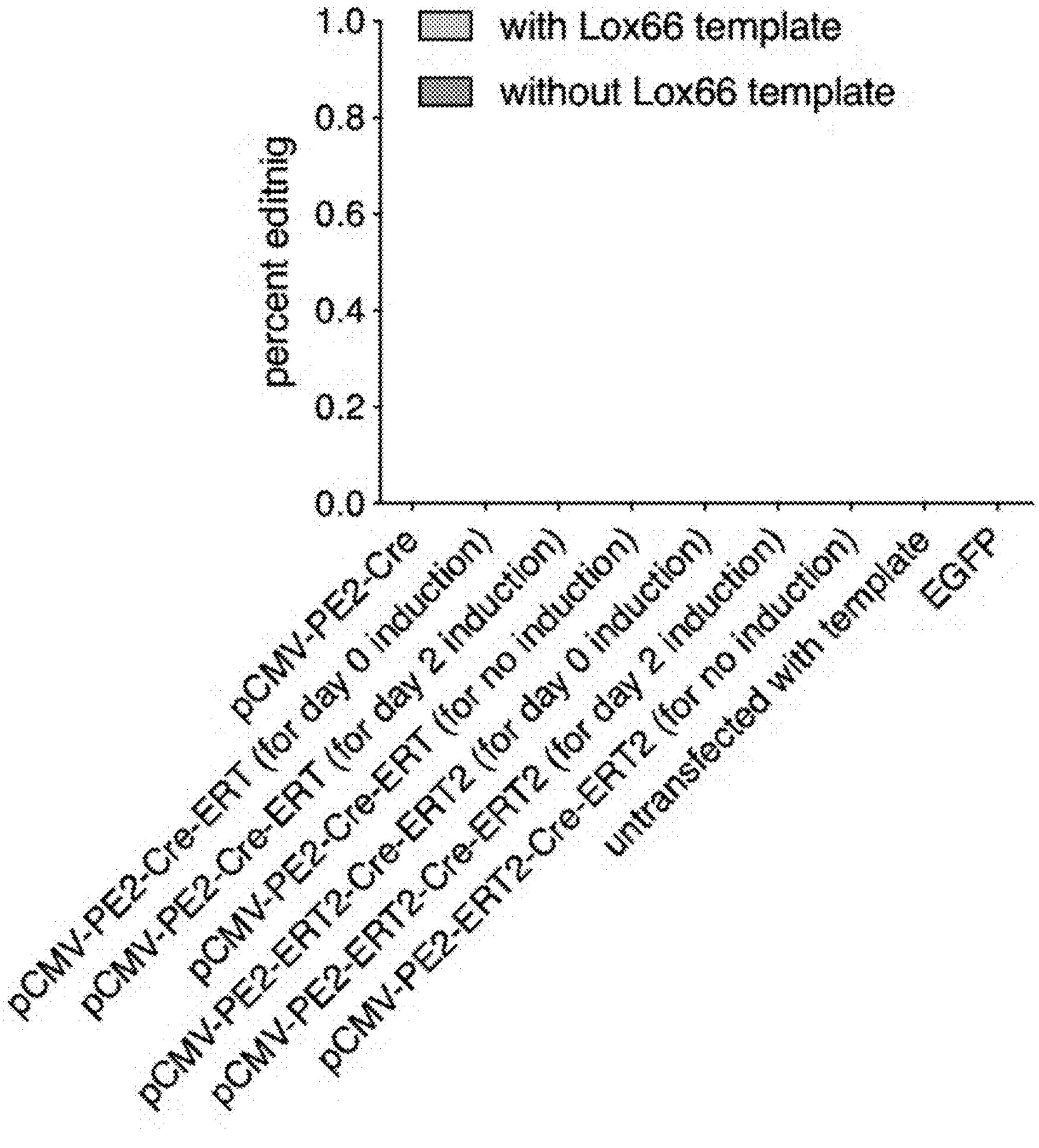
FIG. 5B shows the percent integration of GFP at the lox71 site in HEK293FT cell genome according to embodiments of the present teachings.

The lox71 or lox66 pegRNAs having PBS length of 13 base pairs and insert length of 34 base pairs were used to probe integration of GFP in the HEK293F genome. The PE and Cre were delivered in an inducible expression vectors and induced at day 2. The HEK293FT cells were transfected with the following plasmids: (1) prime editing construct (PE2 or PE2 with conditional Cre expression); (2) Lox71 pegRNA; (3) plus/minus +90 HEK3 nicking guide RNA; and (4) EGFP template with Lox66 site. After 72 hours, the percent editing of lox71 site and percent integration of GFP was probed with or without lox66 site in the presence of various PE/Cre constructs. FIG. 5A summarizes the percent editing of lox71 site with different PE/Cre vectors. FIG. 5B summarizes the percent integration of GFP at the lox71 site in HEK293FT cell genome. It was observed that although the lox71 site was edited in the presence of inducible or non-inducible PE/Cre expression system, there was no GFP integration.

Example 4

Bxb1 Integration Data Lenti Reporter

Figure 6:
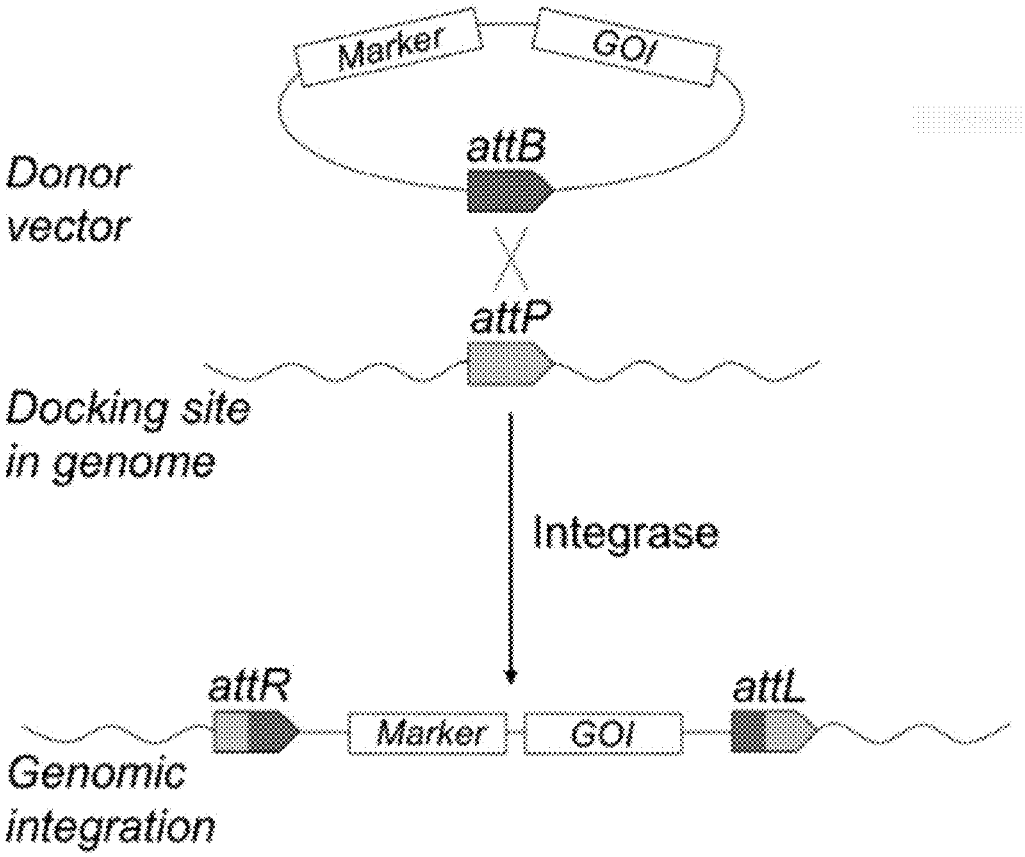
FIG. 6 shows a schematic representation of using Bxb1 to integrate a nucleic acid into the genome according to embodiments of the present teachings.

The integration system was switched to an integrase system that could result in an integration of target genes into a genome with higher efficiency. Serine integrase Bxb1 has been shown to be more active than Cre recombinase and highly efficient in bacteria and mammalian cells for irreversible integration of target genes. FIG. 6 shows a schematic of PASTE methodology using Bxb1 (Merrick, C. A. et al., *ACS Synth. Biol.* 2018, 7, 299-310).

Figure 7:
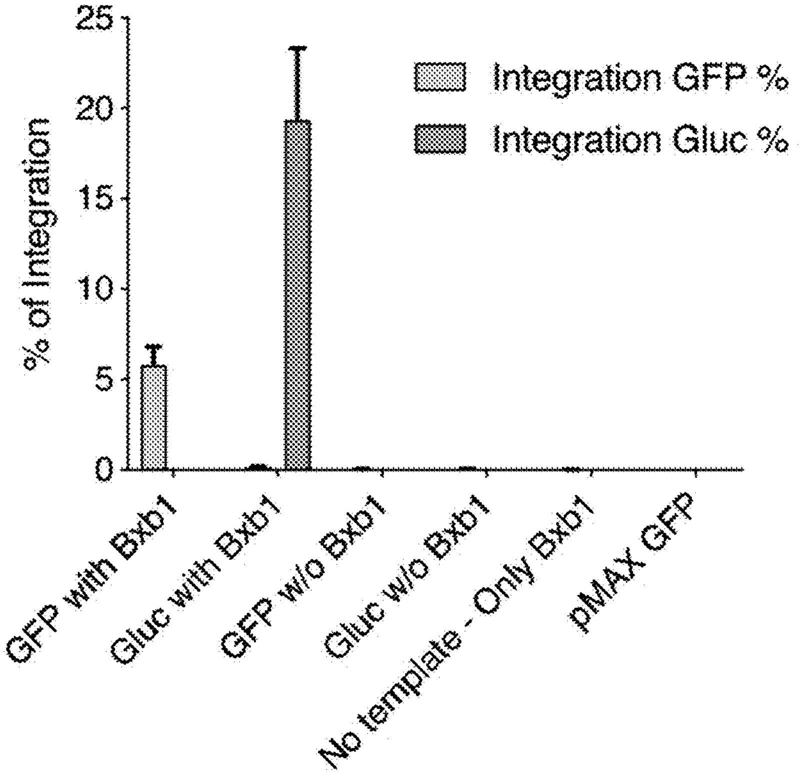
FIG. 7 shows the percent integration of GFP or Gluc into the attB locus using Bxb1 Programmable Addition via Site-Specific Targeting Elements (PASTE) according to embodiments of the present teachings.

To probe the efficiency of the Bxb1 integration system, a clonal HEK293FT cell line with attB Bxb1 site (SEQ ID NO: 3) integrated using lentivirus was developed. The modified HEK293FT cell line was then transferred with the following plasmids: (1) plus/minus Bxb1 expression plasmid and (2) plus/minus GFP (SEQ ID NO: 76) or G-Luc (SEQ ID NO: 77) minicircle template with attP Bxb1 site. After 72 hours, the integration of GFP or Gluc into the attB site in the HEK293FT genome was probed. The percent integrations of GFP or Gluc into the attB locus are shown in FIG. 7. It was observed that GFP and Gluc showed efficient integration into the attB site in HEK293FT cells.

Example 5

Addition of Bxb1 Site to Human Genome Using PRIME

Figure 8:
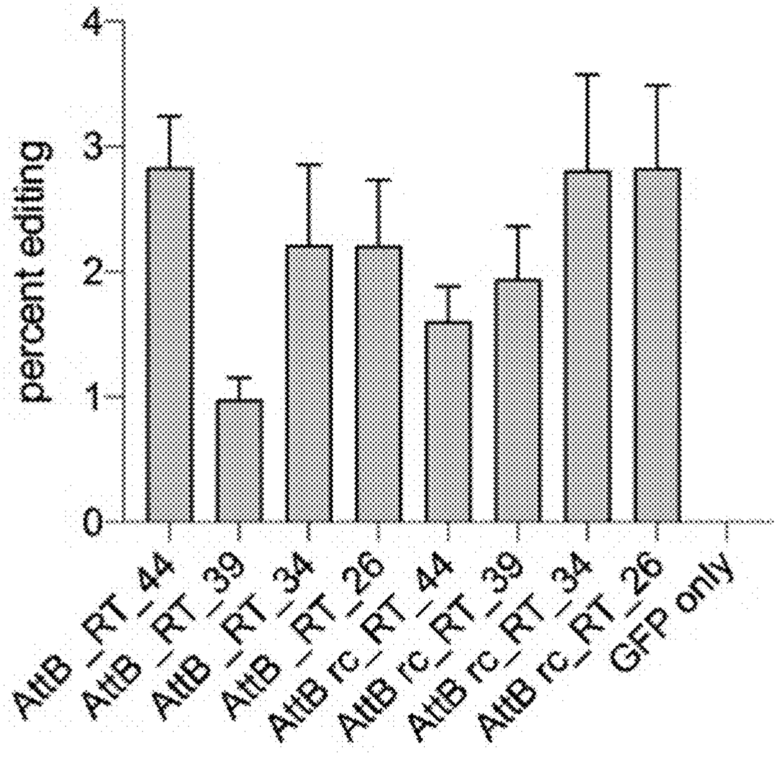
FIG. 8 shows the percent editing of various HEK3 targeting pegRNA Programmable Addition via Site-Specific Targeting Elements (PASTE) according to embodiments of the present teachings.
Figure 9A:
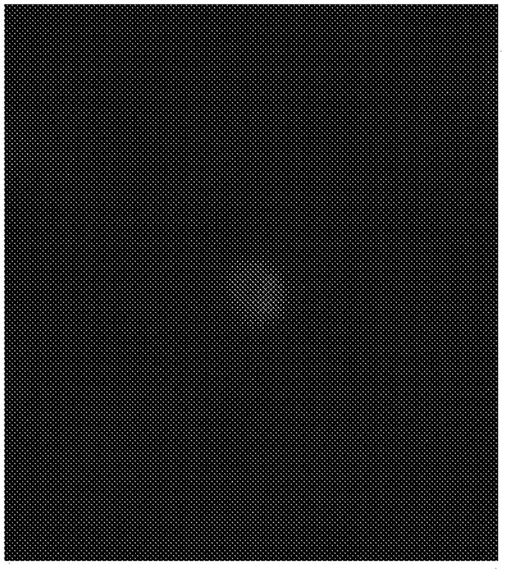
FIG. 9A shows a fluorescent image of cells wherein the SUPT16H marker is tagged with EGFP using PASTE according to embodiments of the present teachings.
Figure 9B:
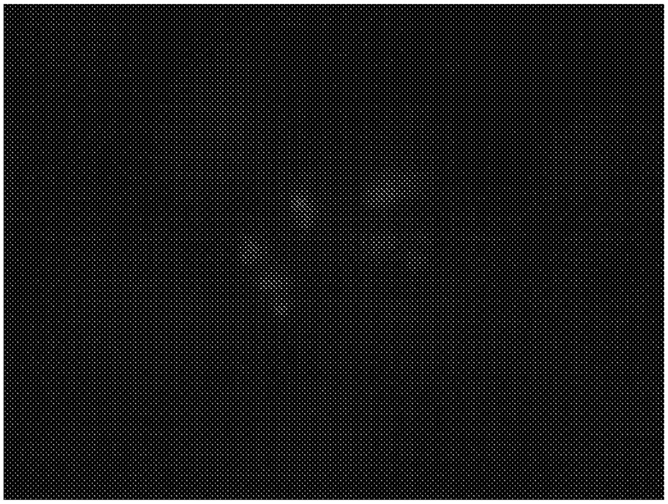
FIG. 9B shows a fluorescent image of cells wherein the SRRM2 marker is tagged with EGFP using Programmable Addition via Site-Specific Targeting Elements (PASTE) according to embodiments of the present teachings.
Figure 9C:
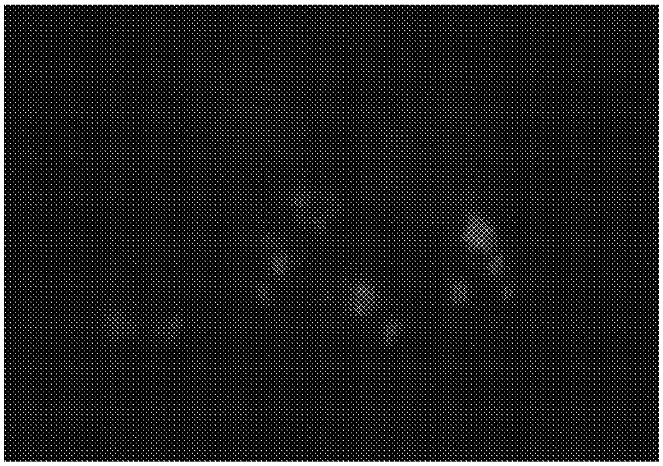
FIG. 9C shows a fluorescent image of cells wherein the LAMNB1 marker is tagged with EGFP using Programmable Addition via Site-Specific Targeting Elements (PASTE) according to embodiments of the present teachings.
Figure 9D:
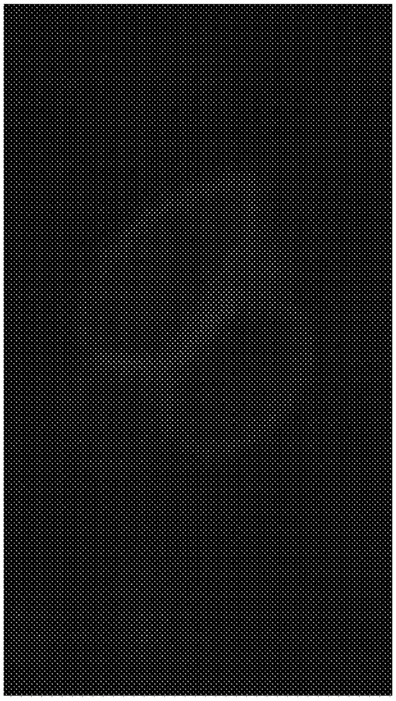
FIG. 9D shows a fluorescent image of cells wherein the NOLC1 marker is tagged with EGFP using Programmable Addition via Site-Specific Targeting Elements (PASTE) according to embodiments of the present teachings.
Figure 9E:
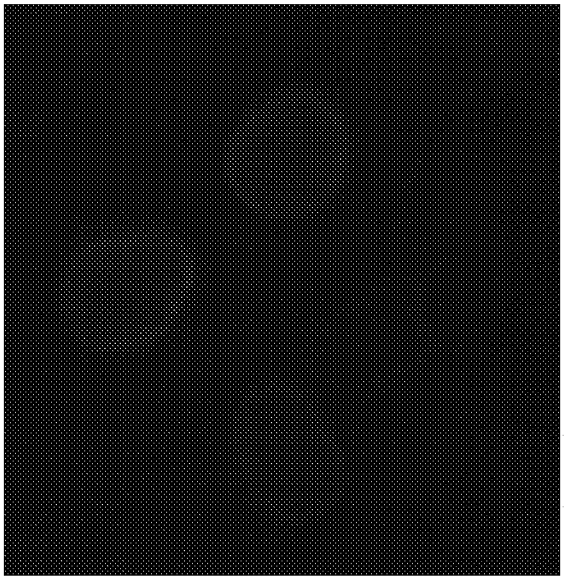
FIG. 9E shows a fluorescent image of cells wherein the NOLC1 marker is tagged with EGFP using Programmable Addition via Site-Specific Targeting Elements (PASTE) according to embodiments of the present teachings.
Figure 9F:
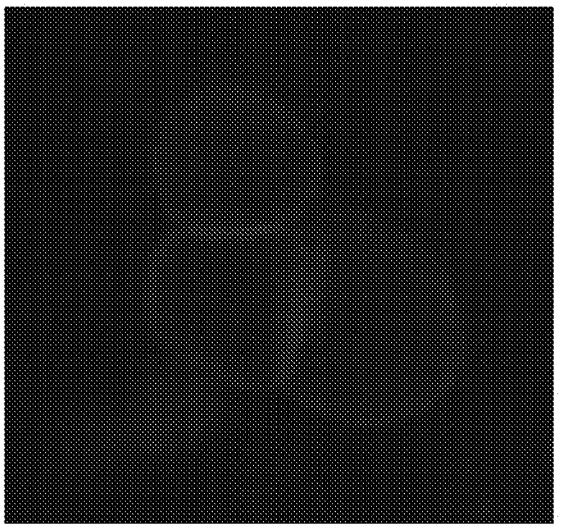
FIG. 9F shows a fluorescent image of cells wherein the NOLC1 marker is tagged with EGFP using Programmable Addition via Site-Specific Targeting Elements (PASTE) according to embodiments of the present teachings.
Figure 9G:
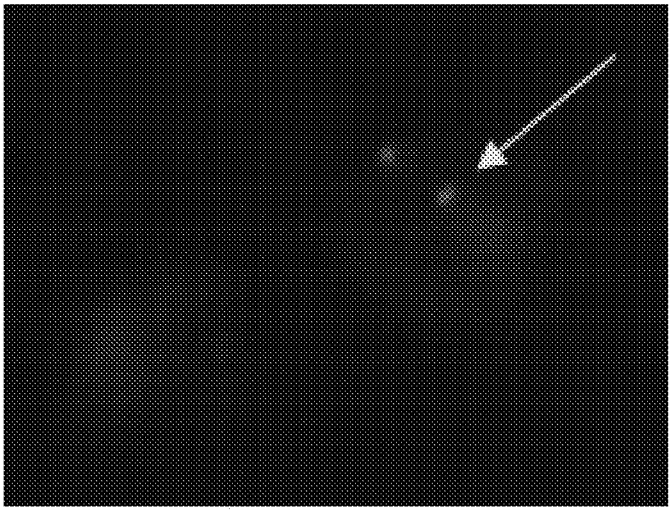
FIG. 9G shows a fluorescent image of cells wherein the DEPDC4 marker is tagged with EGFP using Programmable Addition via Site-Specific Targeting Elements (PASTE) according to embodiments of the present teachings.

The maximum length of attB that can be integrated into a HEK293FT cell line with the best efficiency was probed. To probe the best length of attB (SEQ ID NO: 3) or its reverse complement attP (SEQ ID NO: 4) for prime editing, pegRNAs having PBS length of 13 nt with varying RT homology length were used. The following plasmids were transfected in HEK293FT: (1) prime expression plasmid; (2) HEK3 targeting pegRNA design; and (3) HEK3 +90 nicking guide. After 72 hours, the percent integration of each of the attB construct was probed. FIG. 8 shows the percent editing in each HEK3 targeting pegRNA. It was observed that attB with 44, 34 and 26 base pairs and attB reverse complement with 34 and 26 base pairs showed the highest percent editing.

Integration PASTE was then tested with tagging cell-organelle marker proteins with GFP in HEK29FT cells. PASTE was used to tag SUPT16H, SRRM2, LAMNB1, NOLC1 and DEPDC4 with GFP in different cell-culture wells and to test the usefulness of PASTE in tracking protein localization within the cells using microscopy. FIGS. 9A-9G shows the fluorescent microscopy results for each of the organelles. SUPT16H-GFP was observed to be enriched in the nucleus, SRRM2-GFP was observed to be enriched in the nuclear speckles, LAMNB1-GFP was observed to be enriched in the nuclear membrane, NOLC1-GFP was observed to be enriched in the fibrillar center, and DEPDC4-GFP was observed to be enriched in the aggresome.

Figure 10A:
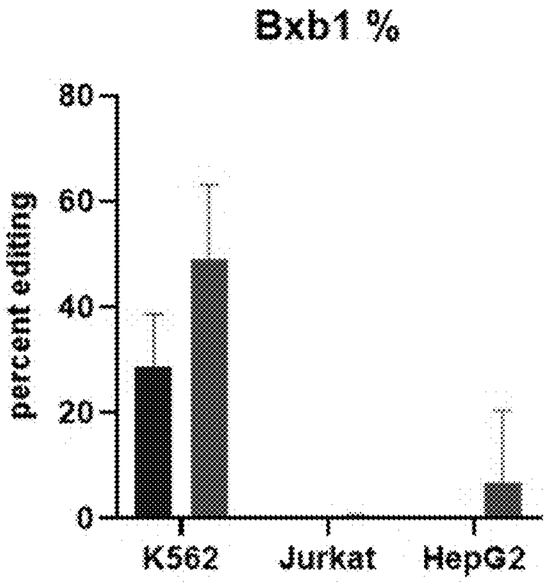
FIG. 10A shows comparisons of lipofectamine aided transfection in blue with electroporation aided transfection in red for the addition of the Bxb1 attB site at the ACTB N-terminal site in the genome using PASTE according to embodiments of the present teachings.
Figure 10B:
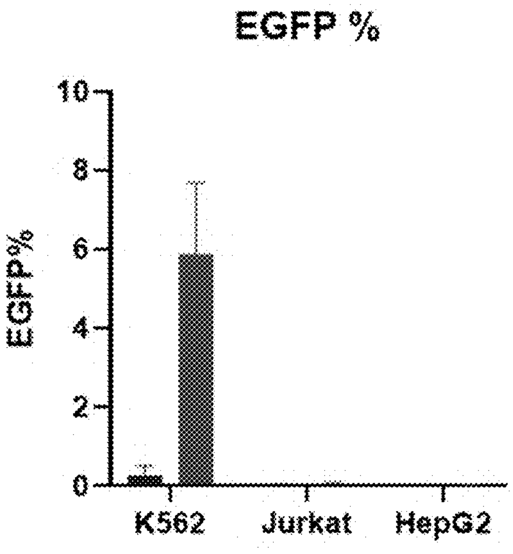
FIG. 10B shows comparisons of lipofectamine aided transfection in blue with electroporation aided transfection in red for EGFP integration at the ACTB N-terminal site in the genome using PASTE according to embodiments of the present teachings.

The transfection of the plasmids can be achieved using electroporation as illustrated in FIGS. 10A-10B.

Example 6

Programmable Integration of Genes with PASTE

The efficiency of gene integration of Gluc or EGFP with PASTE was tested. To enable gene integration with PASTE, the following HEK3 targeting pegRNAs were used: (1) 44 pegRNA: PBS of 13nt and RT homology of 44nt; (2) 34 pegRNA: PBS of 13nt and RT homology of 34nt; and (3) 26 pegRNA: PBS of 13nt and RT homology of 26nt.

Figure 11:
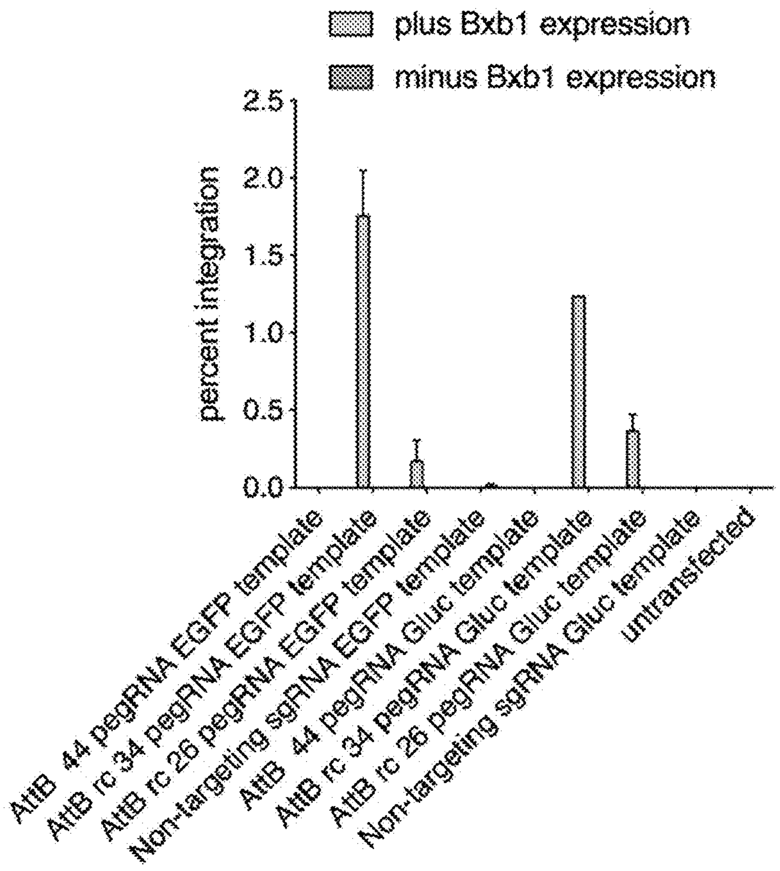
FIG. 11 shows a diagram of the integration of EGFP and Gluc with various HEK3 targeting pegRNAs according to embodiments of the present teachings.

A HEK293 cell line was transfected with following plasmids HEK293FT: (1) Prime expression plasmid; (2) Bxb1 expression plasmid; (3) HEK3 targeting pegRNA design; (4) HEK3 +90 nicking guide; and (5) EGFP or Gluc minicircle. After 72 hours, the percent integration of Gluc or EGFP was observed. FIG. 11 shows integration of EGFP and Gluc with each of the tested HEK3 targeting pegRNAs. It was observed that EGFP and Gluc were efficiently integrated using PASTE.

Example 7

PASTE for Integration of Multiple Genes

The PASTE technique for site-specific integration of multiple genes into a cell is facilitated with the use of orthogonal attB and attP sites. Central dinucleotide can be changed to GA from GT, and only GA containing attB/attP sites can interact and do not cross react with GT containing sequences. A screen of dinucleotide combinations to find orthogonal attB/attP pairs for multiplexed PASTE editing can be performed. It has been shown that many orthogonal dinucleotide combinations can be found using a Bxb1 reporter system.

Figure 14A:
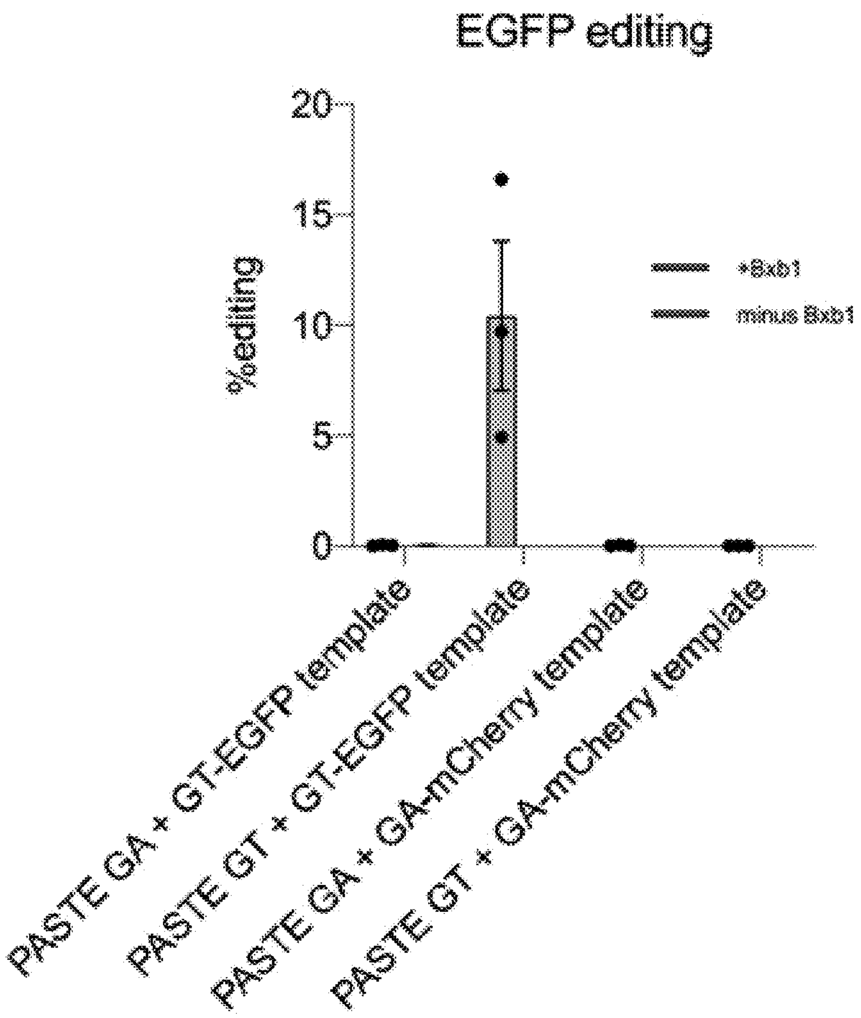
FIG. 14A shows a diagram of the orthogonal editing with the right GT-EGFP according to embodiments of the present teachings.
Figure 14B:
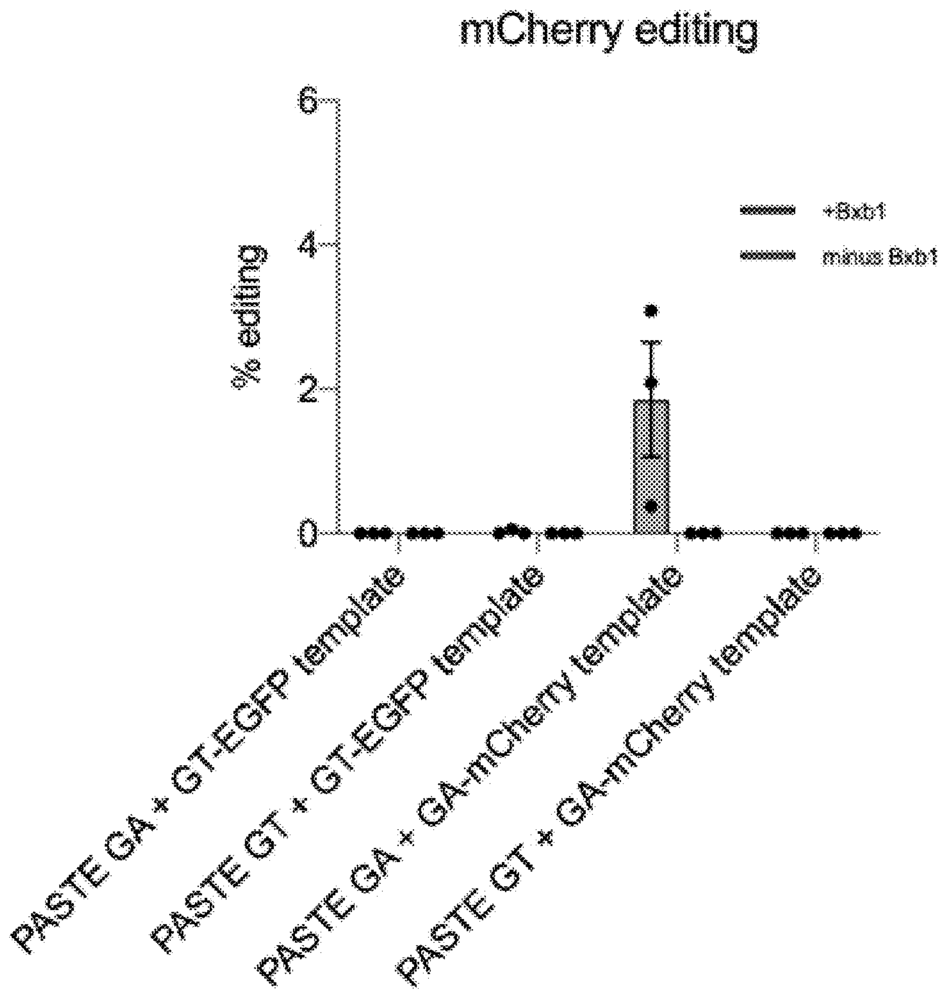
FIG. 14B shows a diagram of the orthogonal editing with the right GA-mCherry according to embodiments of the present teachings.

To test this, $attB^{GT}$ and $attB^{GA}$ dinucleotides for Bxb1 was added at a ACTB site by prime editing. A EGFP-$attP^{GT}$ DNA minicircle and a mCherry-$attP^{GA}$ DNA minicircle was introduced to test the percent EGFP and mCherry editing in the presence or absence of Bxb1. The results of EGFP and mCherry editing are shown in FIGS. 14A-14B.

Orthogonal editing with the right GT-EGFP and GA-mCherry pairs was achieved demonstrating the ability for multiplexed PASTE editing in cells.

Figure 15A:
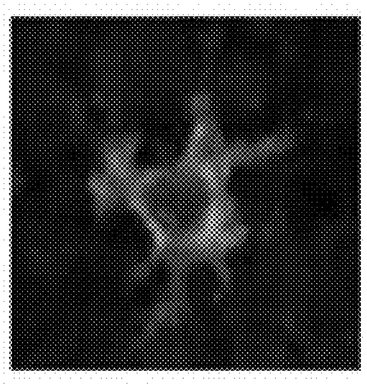
FIG. 15A shows a fluorescent image of a multiplexing of ACTB-EGFP and NOLC1-mCherry according to embodiments of the present teachings
Figure 15B:
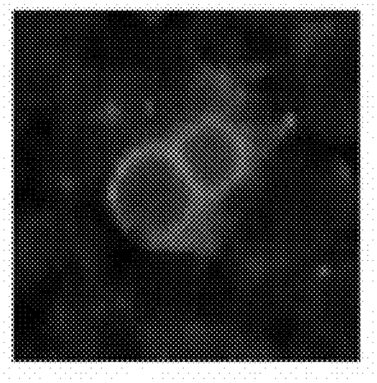
FIG. 15B shows a fluorescent image of a multiplexing of ACTB-EGFP and LAMNB1-mCherry according to embodiments of the present teachings.

Two genes were introduced in the same cell using multiplexed PASTE to tag two different genes in a single reaction. EGFP and mCherry were tagged into the loci of ACTB and NOLC1 in a x cell line, in a single reaction. Further, EGFP and mCherry were tagged into the loci of ACTB and LAMNB1. The cells were visualized using fluorescence microscopy. FIGS. 15A-15B show the results of fluorescent microscopy for multiplexed PASTE.

Figure 16A:
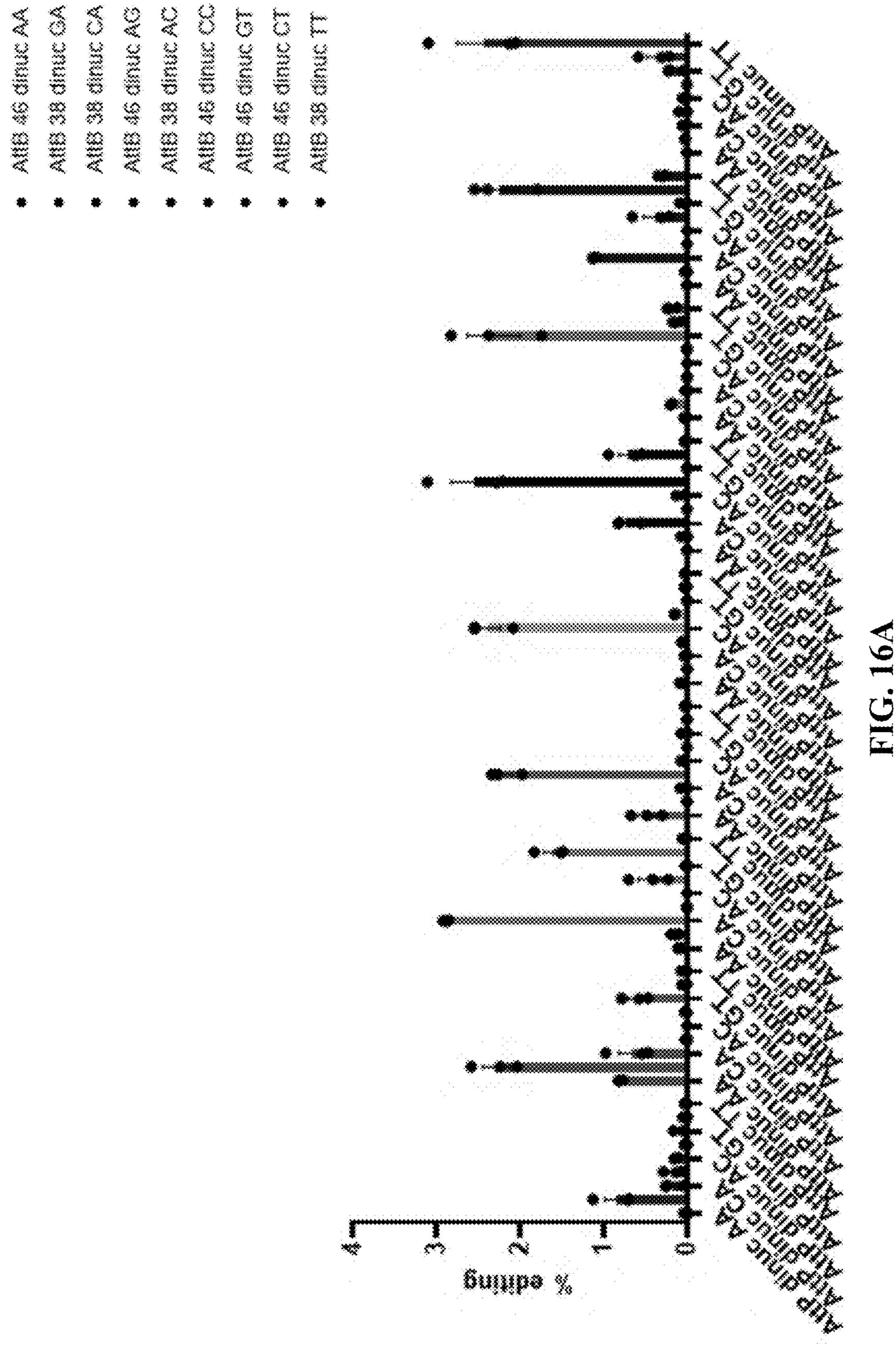
FIG. 16A shows next generation sequencing results of 9×9 attP and attB central dinucleotide variants and their edit percentage wherein the orthogonality of attB/attP combinations for potential multiplexing applications is shown according to embodiments of the present teachings.
Figure 16B:
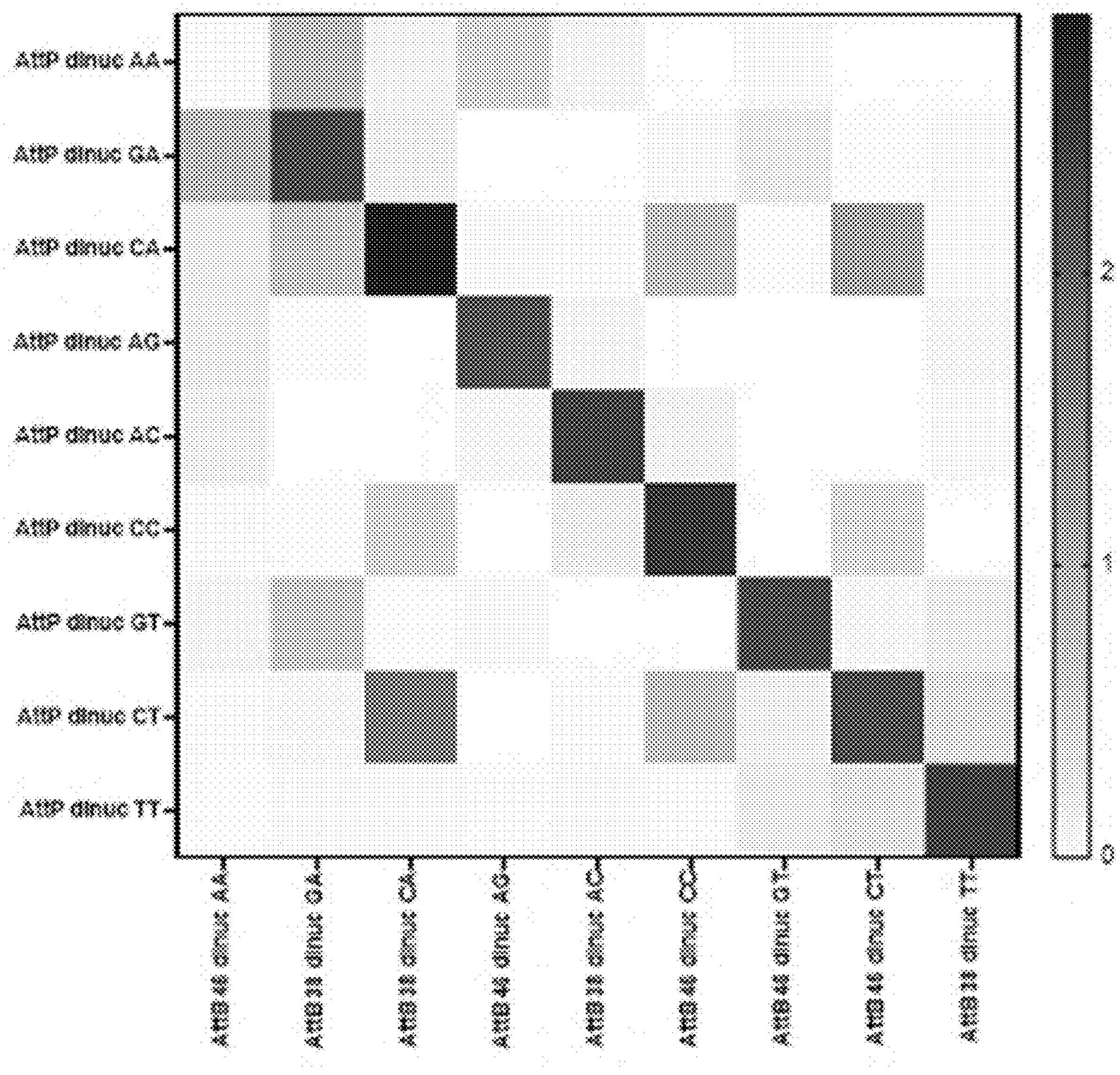
FIG. 16B shows an heatmap of 9×9 attP and attB central dinucleotide variants and their edit percentage according to embodiments of the present teachings.

The ability of multiplexing with 9-different attB and attP central dinucleotides—AA, GA, CA, AG, AC, CC, GT, CT and TT (SEQ ID NOs: 7, 8, 23, 24, 19, 20, 25, 26, 27, 28, 9, 10, 15, 16, 17, 18, 5 and 6)—in a 9×9 cross of attB and attP was tested. The edits were probed using next-generation sequencing. The results of the 9×9 cross of attB and attP central dinucleotides—AA, GA, CA, AG, AC, CC, GT, CT and TT—are shown in FIG. 16A. Only orthogonal pairs of attB and attP show the highest edit percentage. This result is also shown in the heat-map of FIG. 16B.

Example 8

Figure 17:
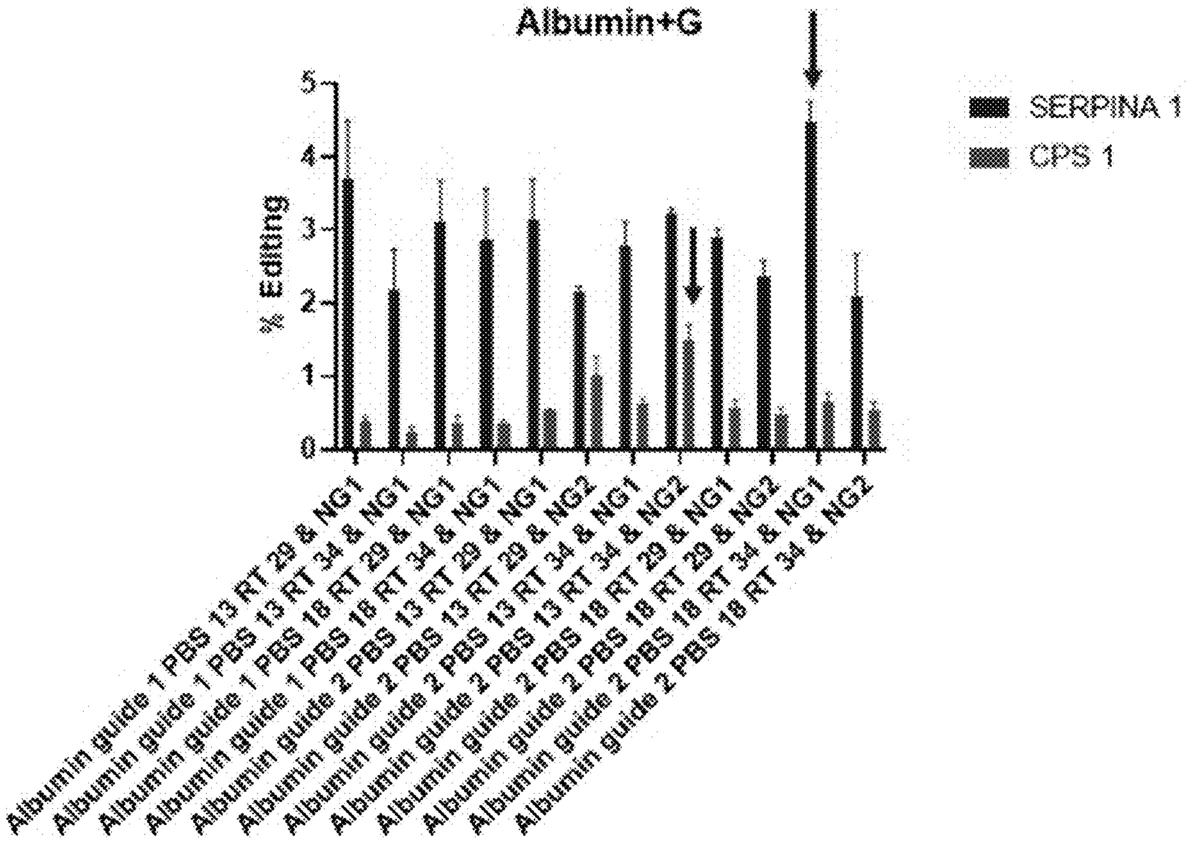
FIG. 17 shows integration of SERPINA and CPS1 into Albumin loci using Albumin guide-pegRNA in HEK293FT cells according to embodiments of the present teachings.

Integration of Albumin and CPS1 Into Albumin Locus 12 pegRNAs with albumin guide were linked to PBS and reverse transcriptase sequence of variable length, and different nicking guide RNAs were used to transfect HEK293FT cells. The percent editing in the albumin was probed using next-generation sequencing. The results of prime editing at the albumin locus are shown in FIG. 17. It was observed that SEQ ID NO: 79 showed the highest percent edits with SERPINA1 and SEQ ID NO: 80 showed the highest percent edits with CPS1.

Example 9

Engineering T-cells

Figure 18:
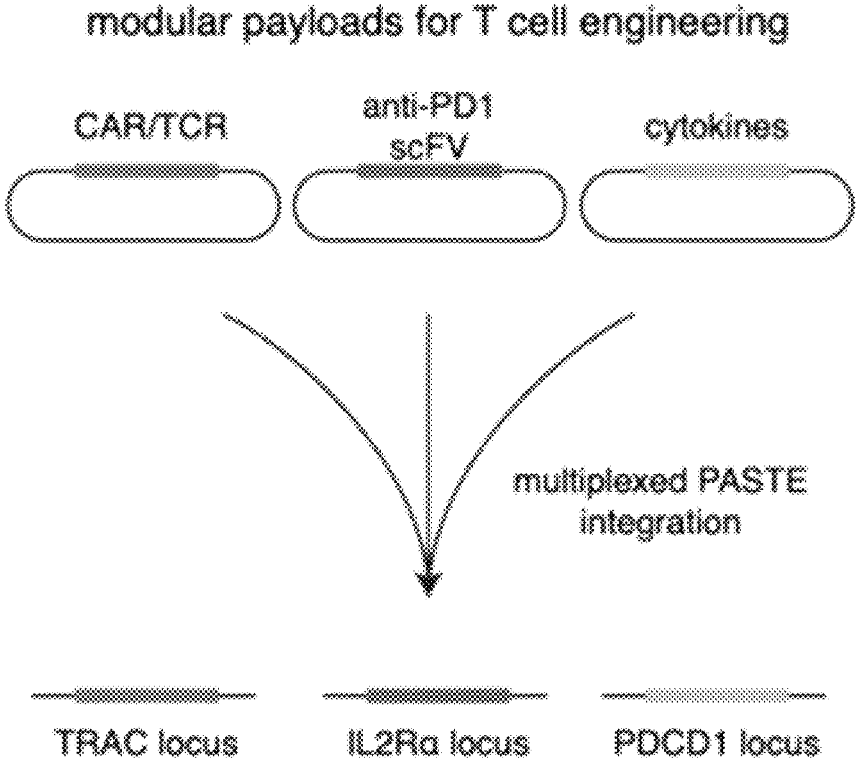
FIG. 18 shows schematics for different nucleic acids for engineering T-cells according to embodiments of the present teachings.

In order to engineer CD8+ T-cells, the efficiency of PASTE delivery and editing in T-cells can be evaluated (FIG. 18). ACTB targeting pegRNA can be used to insert an integration site with an EGFP insertion template. To deliver the PASTE components to CD8+ T-cells, electroporation can be used along with an optimized electroporation protocol for unstimulated T-cells. As multiple plasmids may reduce the efficiency of electroporation, the consolidated PASTE components that use fewer vectors can be applied.

Figure 19:
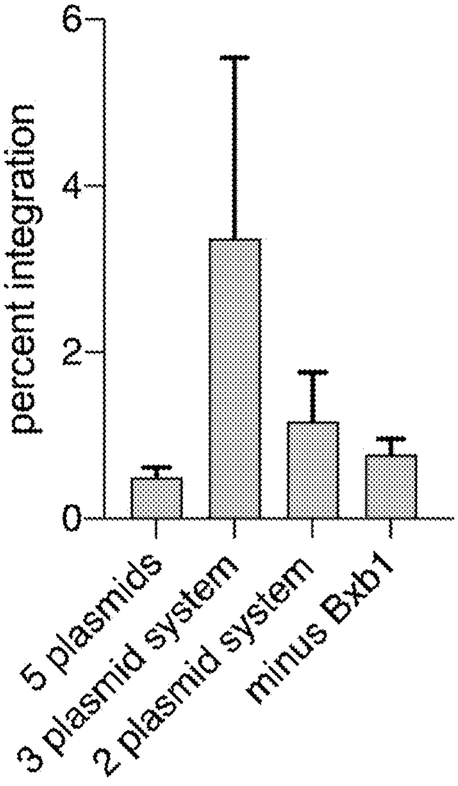
FIG. 19 shows the editing efficiency for EGFP integration at the ACTB locus in primary T-cells according to embodiments of the present teachings.
Figure 20:
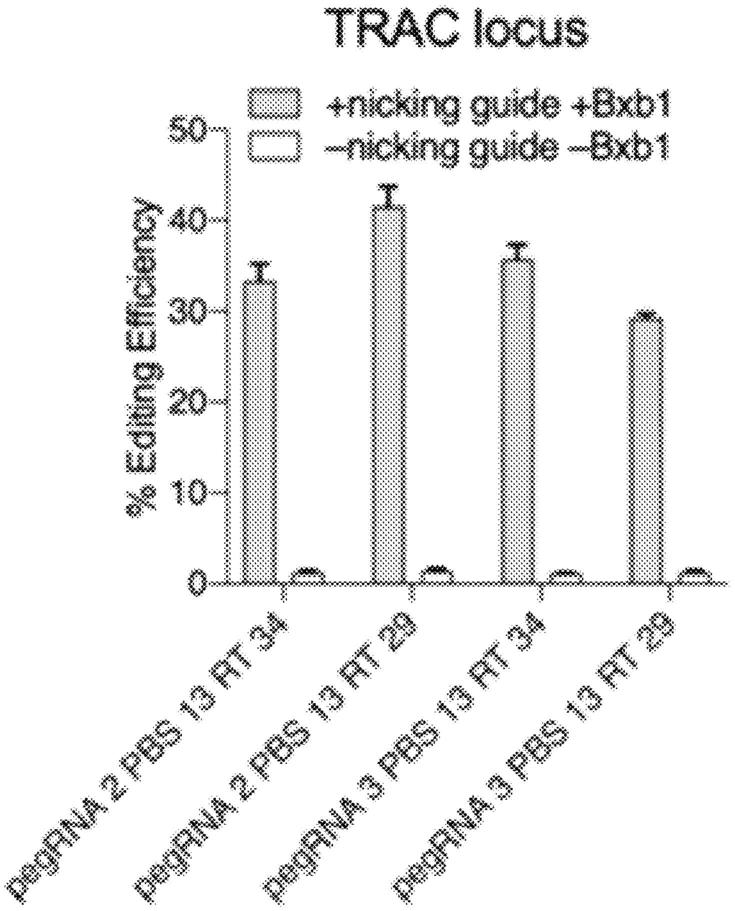
FIG. 20 shows editing in TRAC locus in HEK293FT with different pegRNA according to embodiments of the present teachings.

Five vectors, three vectors, and two vectors PASTE systems show that robust T-cell editing can be achieved with maximal editing using the three-vector approach (FIG. 19). Further, expanded sets of electroporation conditions, including the overall plasmid amounts, cell numbers, and voltage/amperage protocol can be tested. In addition, stimulation of T-cells may influence the efficiency of transduction and PASTE efficiency. Further, CD4+/CD8+ T cell mixtures stimulated with T-Activator CD3/CD28 ligands can have higher PASTE editing efficiency versus unstimulated cells. In order to separate efficiency of PASTE from the overall delivery rate, an mCherry expression cassette on PASTE vectors can be evaluated in order to sort successfully transfected T cells. Once optimized parameters are achieved, a panel of 10 insertion sites with PASTE in T cells, including the TRAC, IL2Rα, and PDCD1 loci, can be evaluated, using different insertions (e.g. EGFP, BFP, and YFP), both in single and multiplexed editing contexts. A tested subset of relevant sites in HEK293FT achieved greater than 40% editing for EGFP insertion (FIG. 20). The PASTE efficiency at TRAC locus with different TCR and CAR constructs can be evaluated. The T-cells can successfully be transfected to achieve insertion of CARs or TCRs.

Example 10

PASTE for CFTR

PASTE for the CFTR locus can be tested in HEK293FT cells to identify top performing pegRNA and nicking designs for human cells. Neuro-2A cells can also be tested to identify top performing pegRNA and nicking designs for mouse cells. The best constructs can be applied for testing in mouse air lung interface (ALI) organoids in vitro or for delivery in pre-clinical models of cystic fibrosis in mice. Table 12 shows the pegRNA, nicking guide and minicircle DNA characteristics for the CFTR gene modulation.

TABLE 12

| Variables | Characteristics |
|---|---|
| pegRNA | 38 bp shortened minimal attB and normal 46 bp attB sequence with:<br>a. PBS of 17, 13, and 9 nt length, and<br>b. RT of 20, 15, and 10 nt in length |
| Nicking guides | Nicking guide 1 +64 bp Nicking guide 2 +23 bp<br>Nicking guide 3 −60 bp Nicking guide 4 −78 bp<br>(distance is calculated from cut site of pegRNA) |
| Minicircle template | A. CFTR coding sequence alone (~4,454 pb in size)<br>B. CFTR coding sequence plus 5' and 3' UTRs (~6,011 bp in size)<br>(Both minicircles have attP site on them for integration by Bxbl and a bGH poly A signal) |

Example 11

AttB and EGPF Integration Using PASTE

Figure 21A:
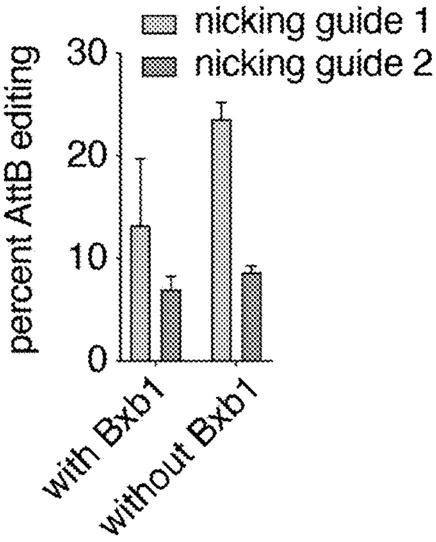
FIG. 21A shows the attB integration at the ACTB locus using nicking guides 1 and 2 according to embodiments of the present teachings.
Figure 21B:
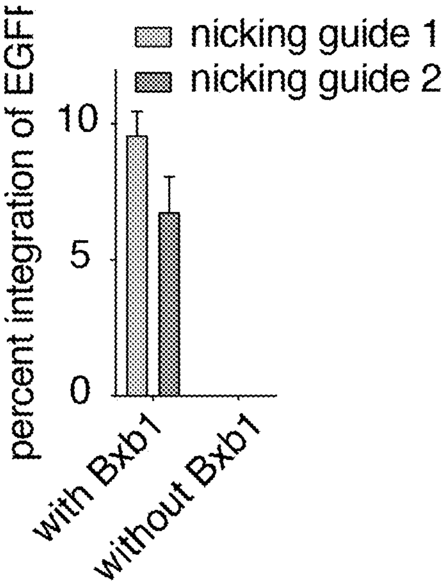
FIG. 21B shows the EGFP integration at the ACTB locus using nicking guides 1 and 2 according to embodiments of the present teachings.
Figure 21C:
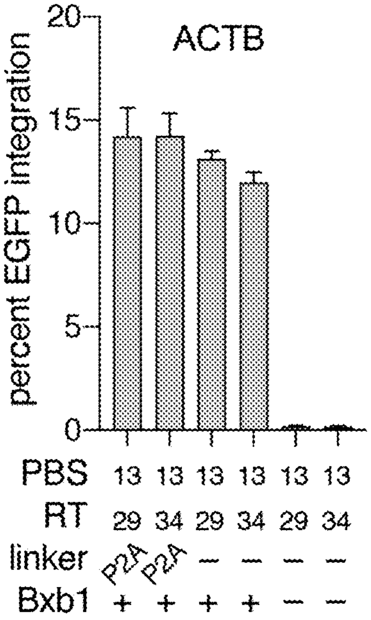
FIG. 21C shows the EGFP integration at an ACTB site according to embodiments of the present teachings.

The efficiency of the integration of attB and EGPF at the ACTB locus was evaluated (FIGS. 21A-21C). To investigate whether Bxb1 can add an EGFP template into this site, a delivery approach using a 5 plasmid system expressing each of the following component was deployed: 1) pegRNA expression, 2) nicking guide expression, 3) Prime expression (Cas9-RT), 4) Bxb1 expression and 5) the insertion template (in this case EGFP). This approach was found to yield editing efficiency of the attB site up to 24% and integration of EGFP ~10% in HEK293FT cells as measured by sequencing (FIGS. 21A-21B). Optimal activity is achieved in 3-4 days and can be performed as a single step transfection or electroporation of all components. Because the EGFP plasmid is designed as a minicircle, allowing removal of all undesired bacterial components, only the desired gene is inserted along with minimal scars from the Bxb1 recombined sites.

To make the tool simpler to use, the Bxb1 can be linked to Prime via a P2A linker to the Cas9-RT fusion, allowing for only a single plasmid to be used for PASTE protein expression rather than two. This optimization can maintain the same level of editing, making it easier to use the tool and deliver it (FIG. 21C).

Example 12

Programmable EGFP Integrations in Different Cell Types

Figure 22A:
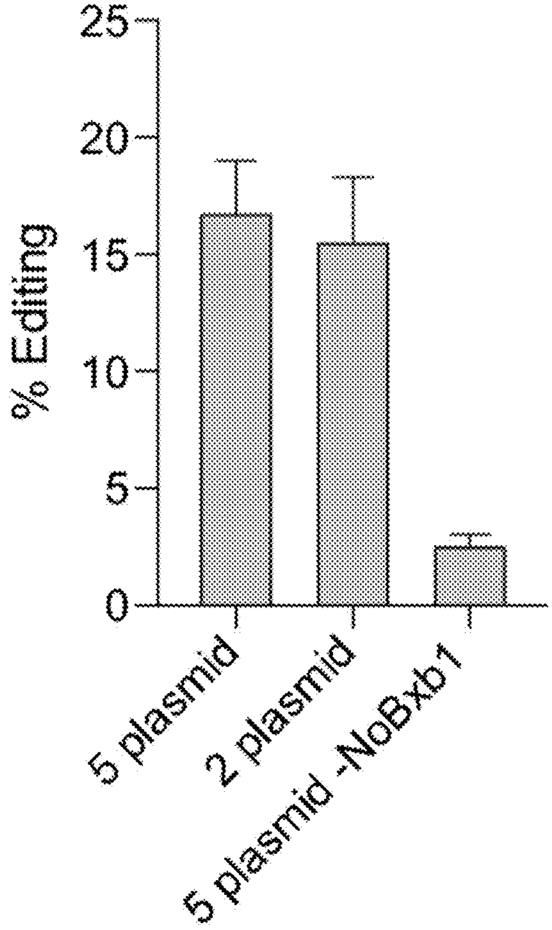
FIG. 22A shows PASTE editing in liver hepatocellular carcinoma cell line HEPG2 according to embodiments of the present teachings.
Figure 22B:
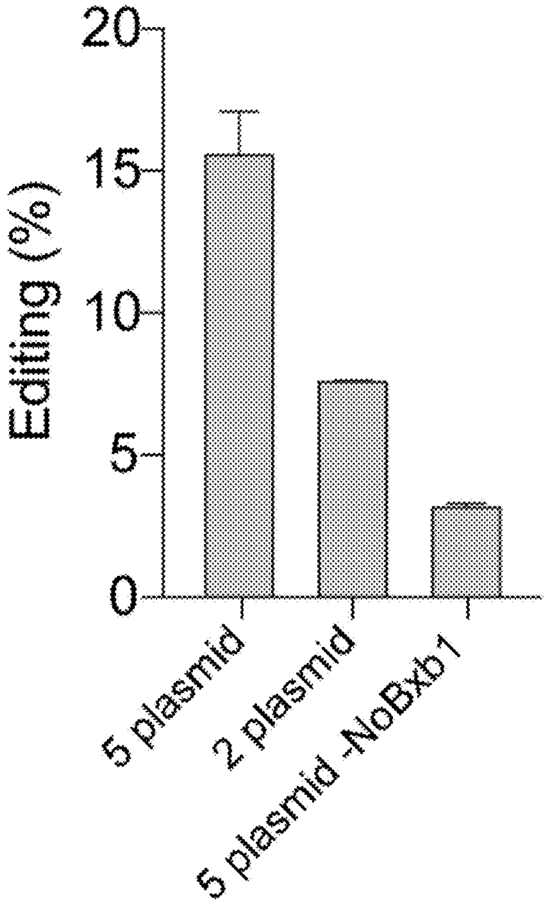
FIG. 22B shows PASTE editing of chronic myelogenous leukemia cell line K562 according to embodiments of the present teachings.

The programmable EGFP integration in liver hepatocellular carcinoma cell line HEPG2 (FIG. 22A) and chronic myelogenous leukemia cell line K562 (FIG. 22B) was evaluated. EGFP integration at the ACTB locus in K562 and HEPG2 cells of about 15% was observed, demonstrating robustness of the platform across cell types.

Example 13

Mutagenesis of Bxb1 for Enhanced PASTE Activity

Figure 23A:
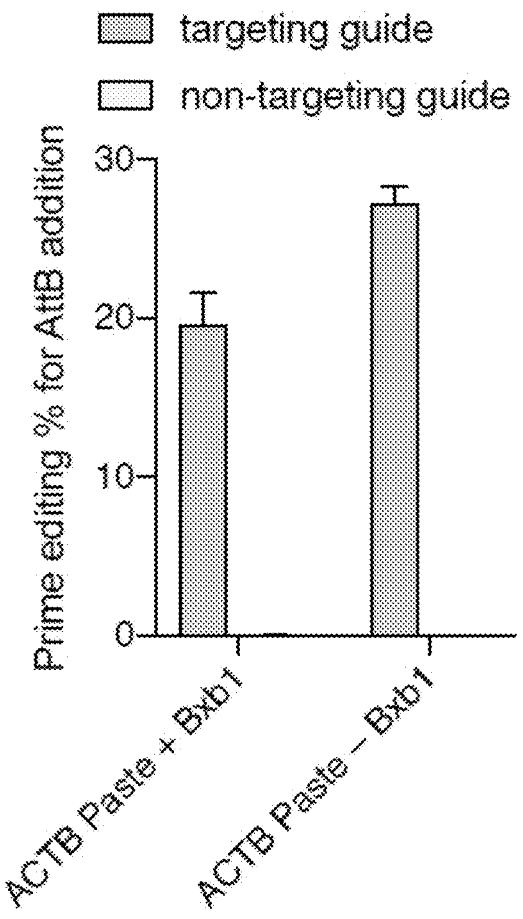
FIG. 23A shows the attB addition with targeting and non-targeting guides according to embodiments of the present teachings.
Figure 23B:
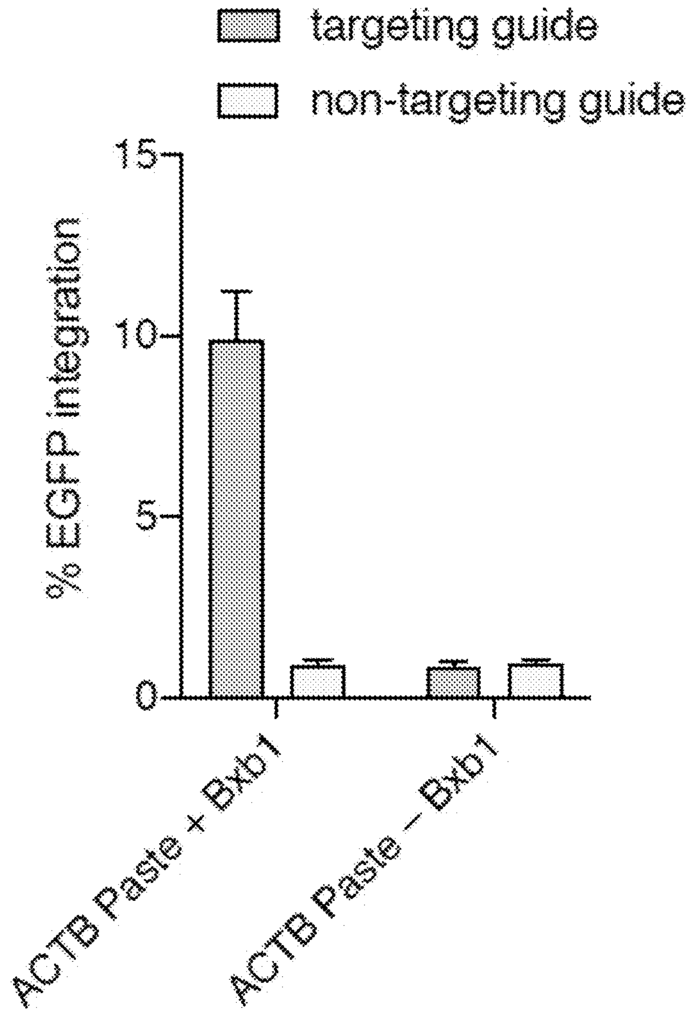
FIG. 23B shows the EGFP integration with targeting and non-targeting guides according to embodiments of the present teachings.
Figure 23C:
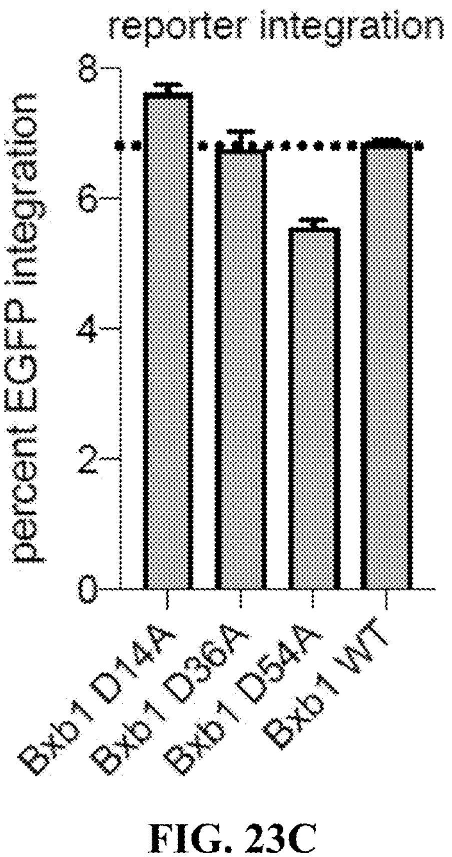
FIG. 23C shows the EGFP integration for mutagenized Bxb1 according to embodiments of the present teachings.

The mutagenesis of Bxb1 for enhanced PASTE activity was evaluated (FIGS. 23A-23C). Two levers for optimizing PASTE activity exist: 1) improving the activity of the integrase and 2) enhancing the Prime addition of the integration sequence. As illustrated in FIGS. 23A-23B, Bxb1 activity can be improved as only about 30% of Bxb1 attB sites that are added by PASTE are integrated into by Bxb1. This illustrates that if the Bxb1 efficiency can be improved, the PASTE can be improved. Furthermore, catalytic residues in the Bxb1 integrase were identified via conservation and structural analyses and Bxb1 mutants were generated to test as part of PASTE. As illustrated in FIG. 23B, the mutations can improve integration by about 20-30%.

Example 14

Figure 25A:
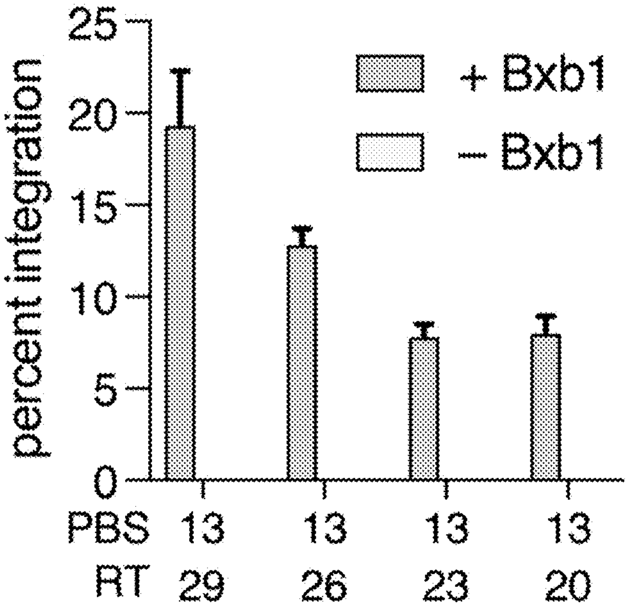
FIG. 25A shows the integration of EGFP at the ACTD locus with different PBS and RT lengths according to embodiments of the present teachings.
Figure 25B:
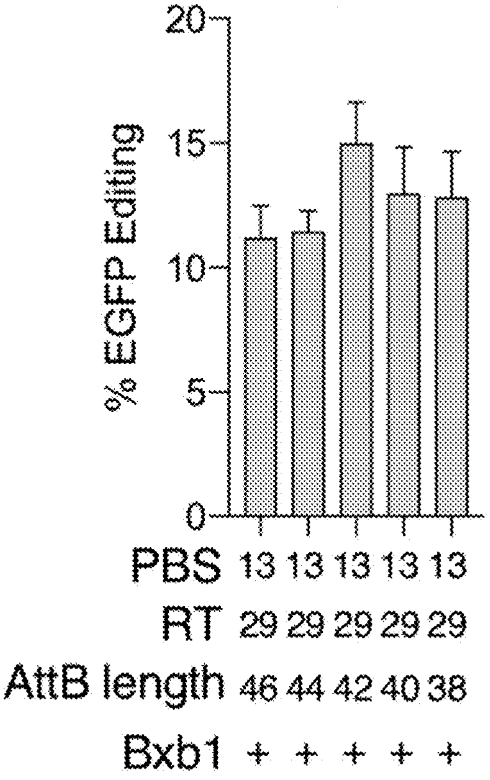
FIG. 25B shows the integration of EGFP at the LMNB1 loci with different PBS and RT lengths according to embodiments of the present teachings.
Figure 25C:
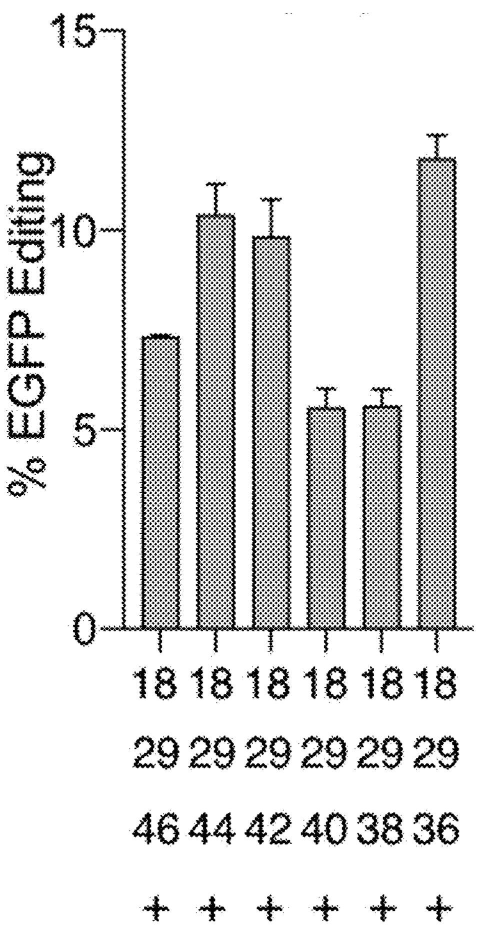
FIG. 25C shows the integration of EGFP at the NOLC1 loci with different PBS and RT lengths according to embodiments of the present teachings.
Figure 25D:
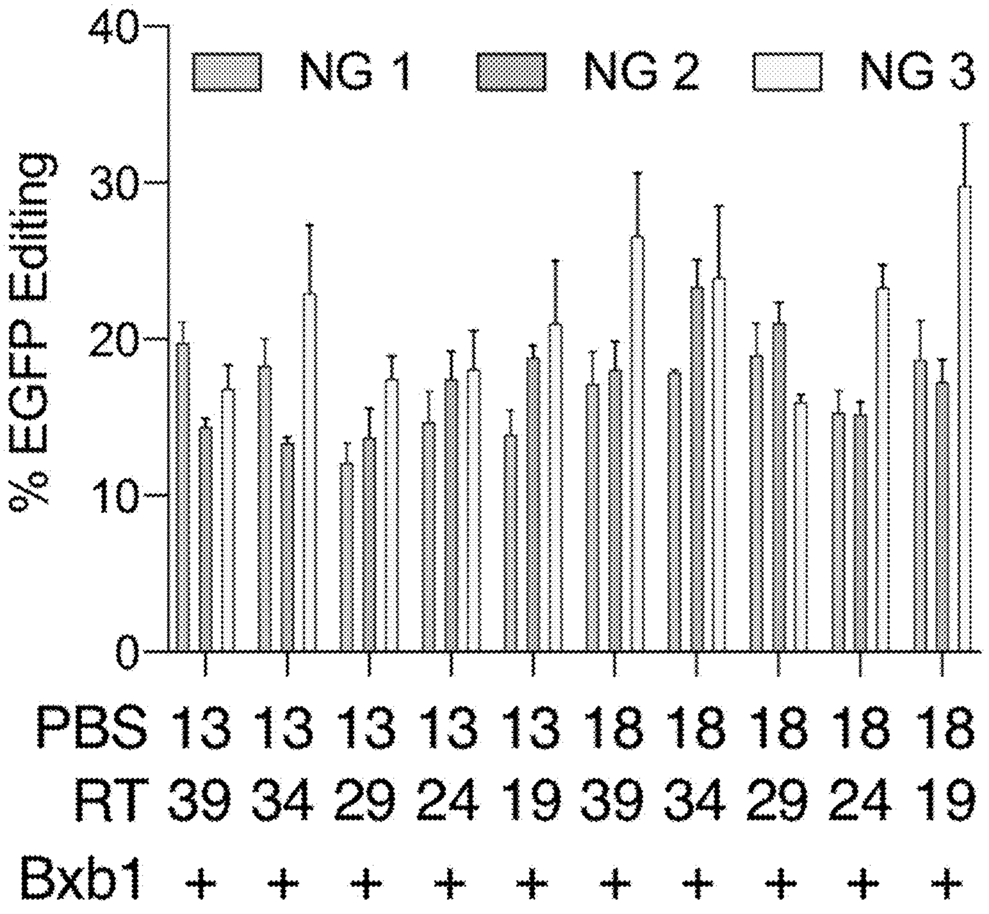
FIG. 25D shows the integration of EGFP at the GRSF1 locus with different PBS and RT lengths and different nicking guides according to embodiments of the present teachings.
Figure 25E:
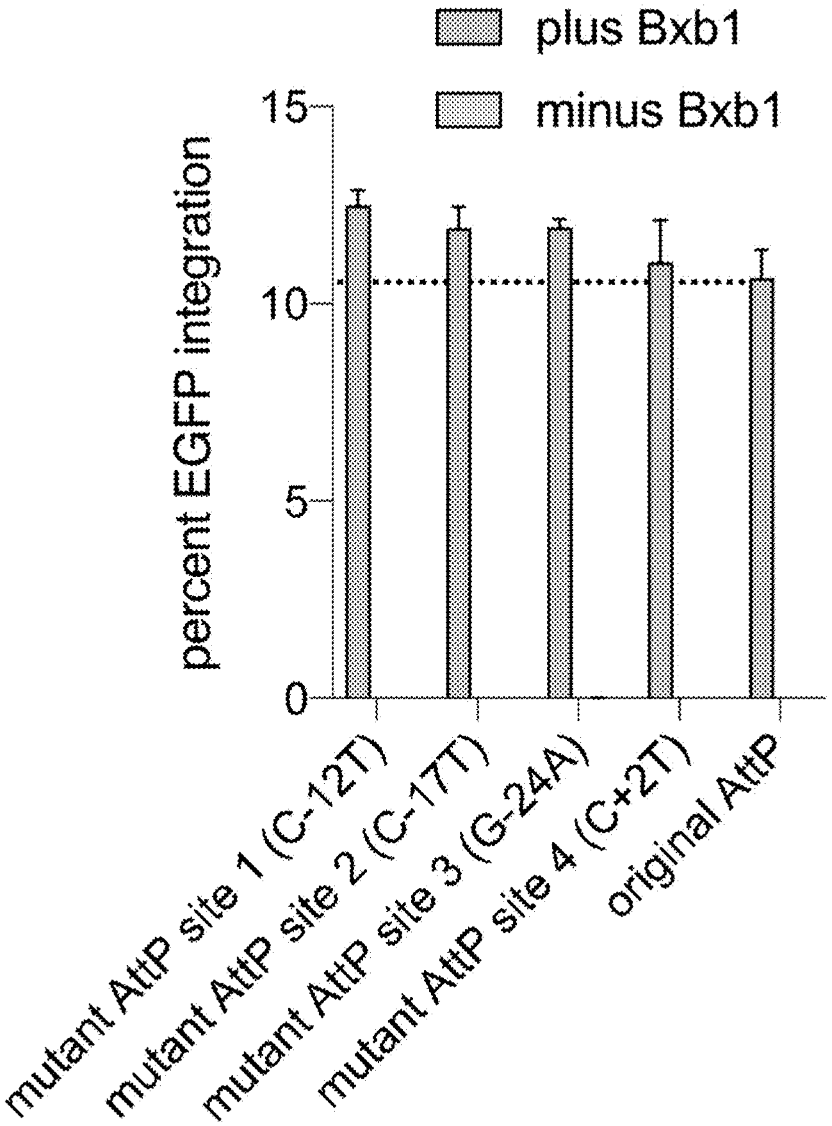
FIG. 25E shows EGFP integration with mutant attP sites according to embodiments of the present teachings.
Figure 25F:
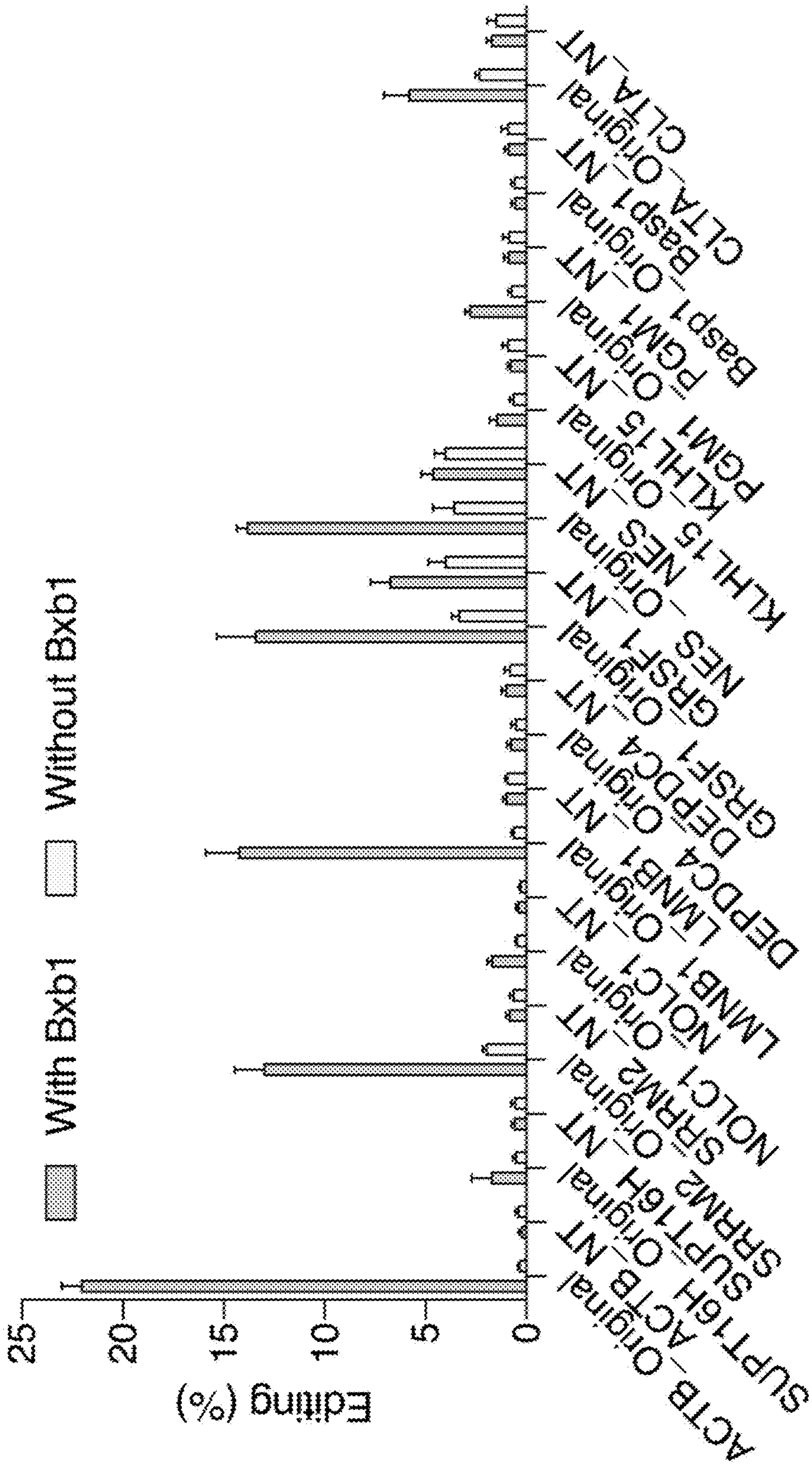
FIG. 25F shows the PASTE editing of an expanded panel of genes according to embodiments of the present teachings.

Effect of the pegRNA PBS and RT Lengths on the Prime Editing Integration Efficiency The effect of the pegRNA PBS and RT lengths on the prime editing integration efficiency was evaluated (FIGS. 25A-25F). It was found that PASTE can be optimized by tuning the PBS and RT lengths at the ACTB locus to achieve editing rates up to about 20% (FIG. 25A). It was found that shortening the attB site can help improve PASTE function as Prime is better at inserting shorter sequences. Further optimization of PBS, RT, and attB lengths showed that optimal designs can be found for insertion upstream of the LMNB1, NOLC1, and GRSF1 loci (FIGS. 25B, 25C, and 25D). Lengths as short as 36nt for attB were found to be still functional for integration into a reporter plasmid (FIGS. 25B and 25C). It was found that the reverse complemented version of the attB sequence was better integrated via Prime editing, suggesting that the sequence of what Prime is inserting matters. EGFP integrations with attP site mutants showed that certain mutants can improve integration efficiency significantly (FIG. 25E). PASTE was also performed with a large panel of genes, inserting EGFP at the N-terminus of ACTB, LMNB1, SUPT16H, SRRM2, NOLC1, KLHL15, GRSF1, DEPDC4, NES, PGM1, CLTA, BASP1, and DNAJC18 (FIG. 25F). Editing rates that are about 5%-40% were found using digital droplet PCR (ddPCR).

Example 15

Comparison of PASTE and HITI On-target and Off-target Activities

Figure 26A:
FIG. 26A shows the PASTE EGPF editing at the ACTB locus according to embodiments of the present teachings.
Figure 26B:
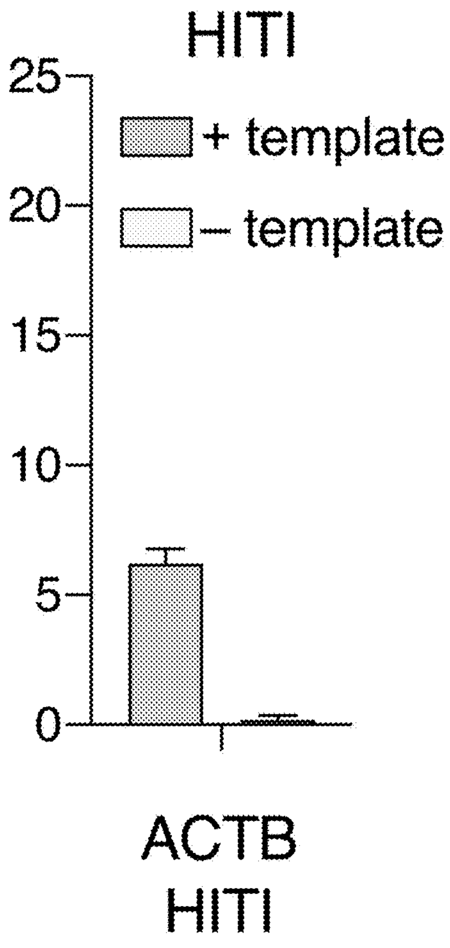
FIG. 26B shows the HITI EGPF editing at the ACTB locus according to embodiments of the present teachings.
Figure 26C:
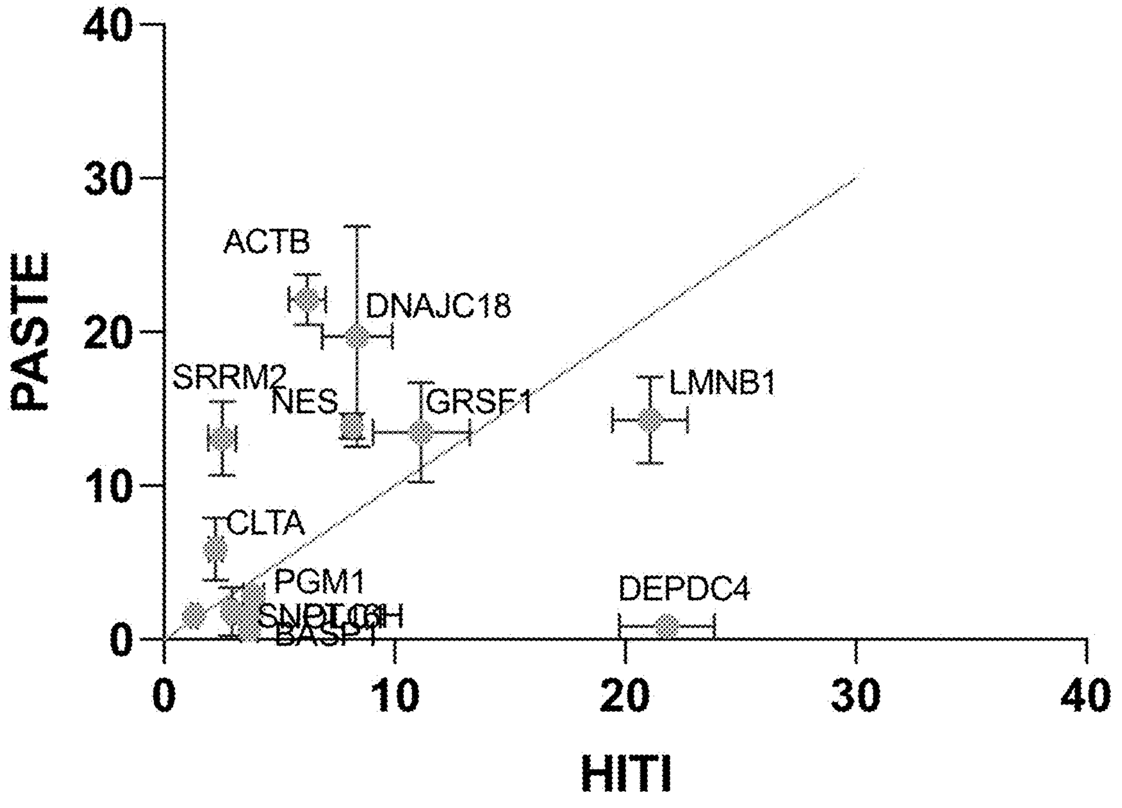
FIG. 26C shows the comparison between the PASTE and HITI editing a panel of 14 genes according to embodiments of the present teachings.
Figure 26D:
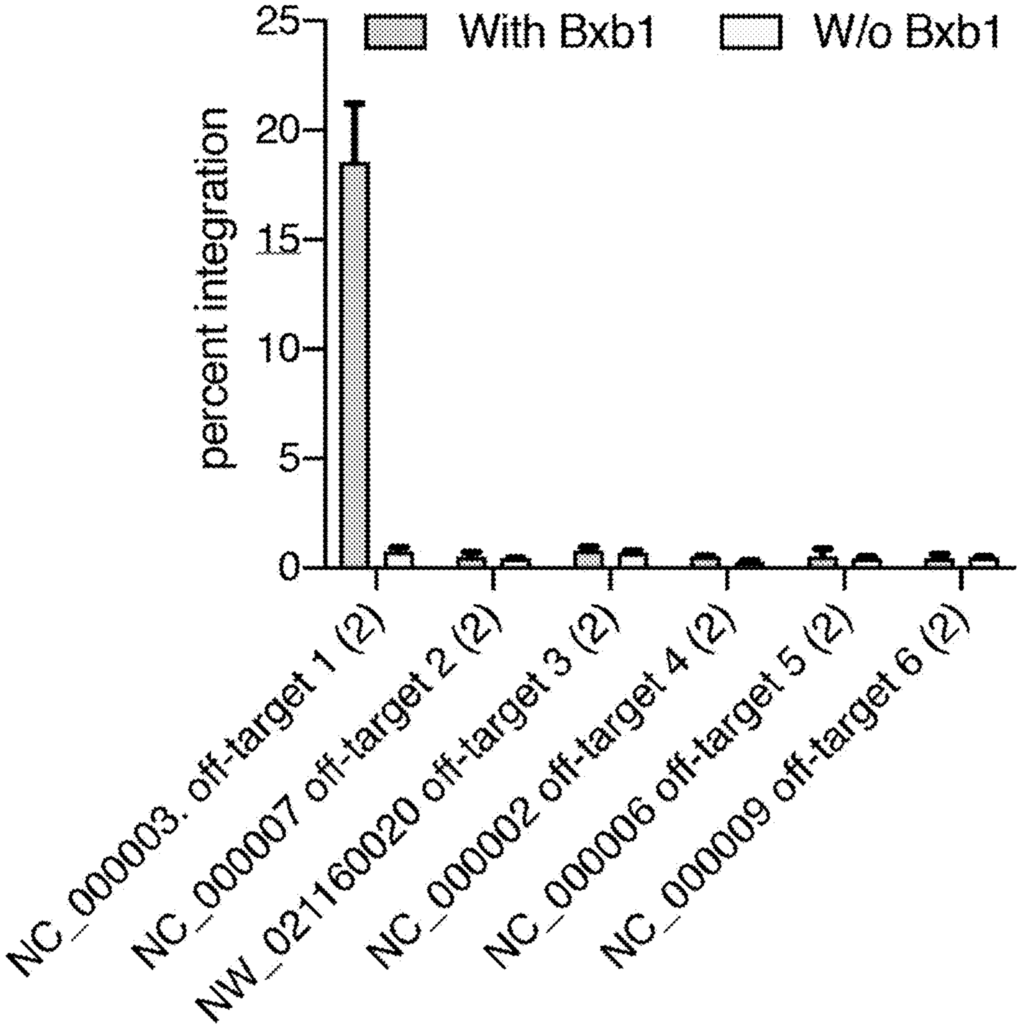
FIG. 26D shows PASTE Bxb1 off-target integrations according to embodiments of the present teachings.
Figure 26E:
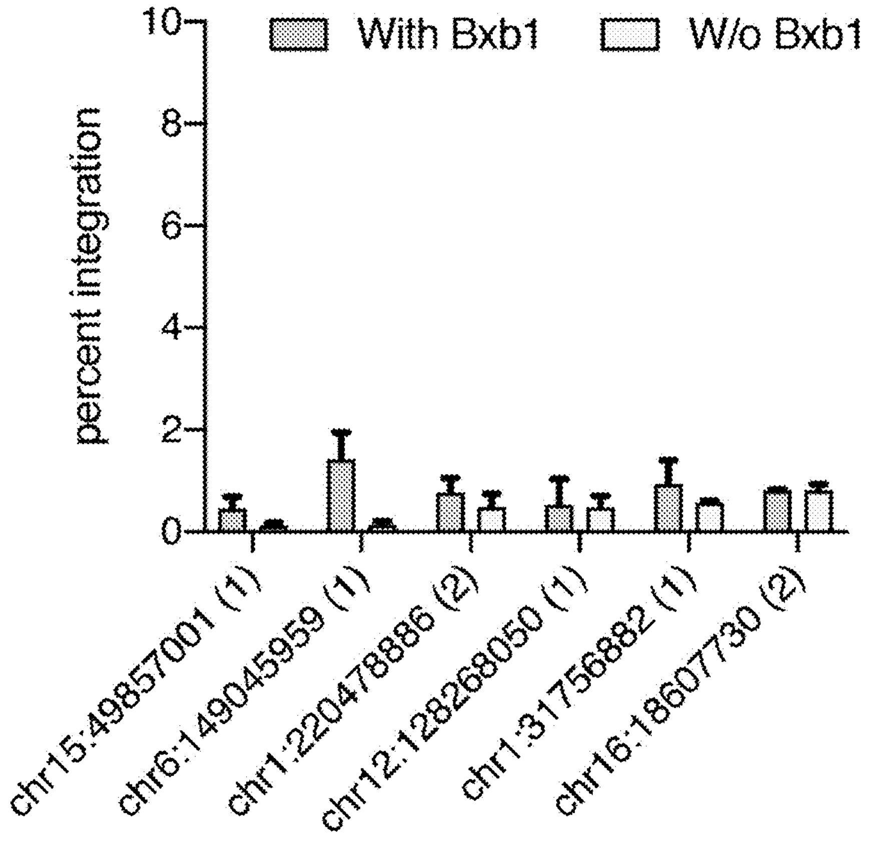
FIG. 26E shows PASTE Cas9 off-target integrations according to embodiments of the present teachings.
Figure 26F:
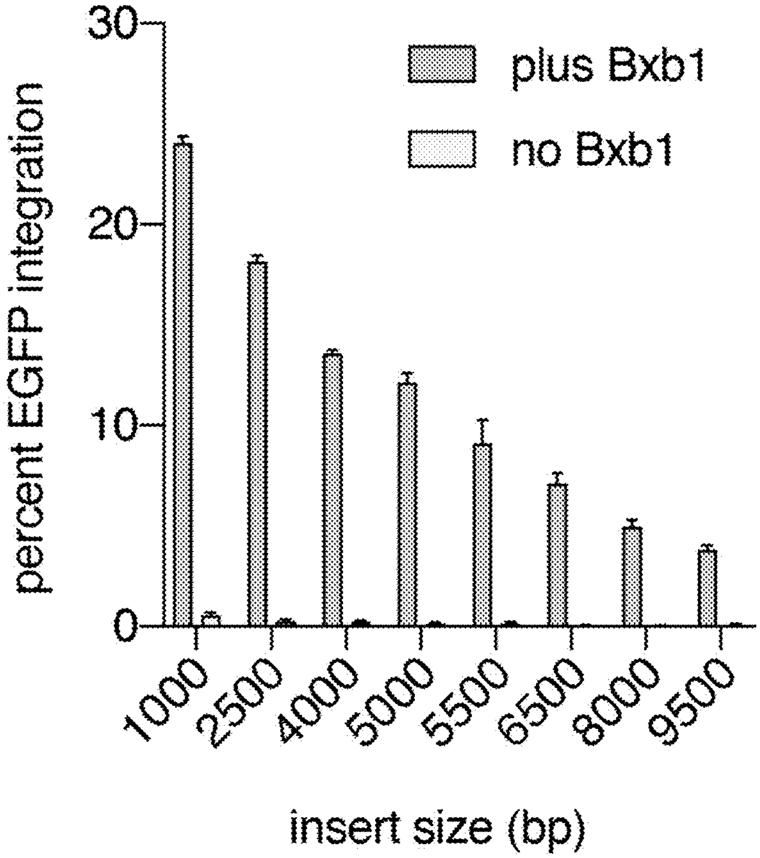
FIG. 26F shows the EGFP integration for gene inserts of different sizes according to embodiments of the present teachings.
Figure 27A:
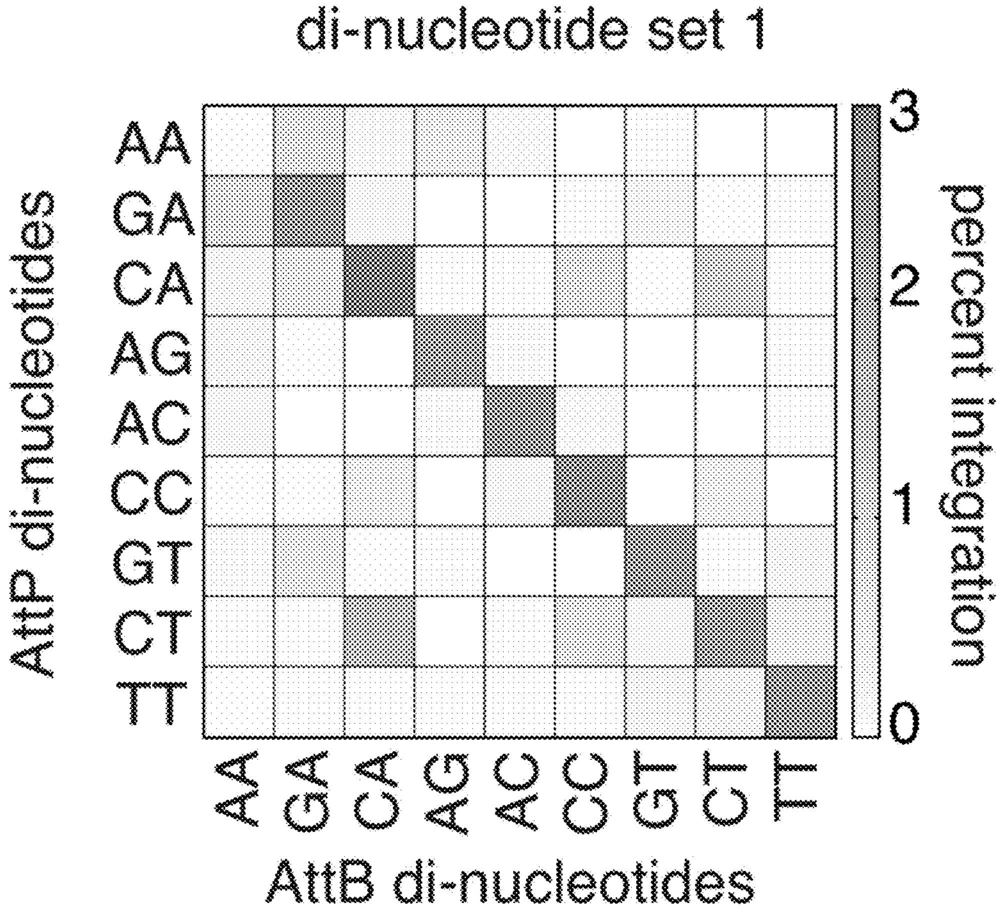
FIG. 27A shows the orthogonality between selected sets of attB and attP sites according to embodiments of the present teachings.
Figure 27B:
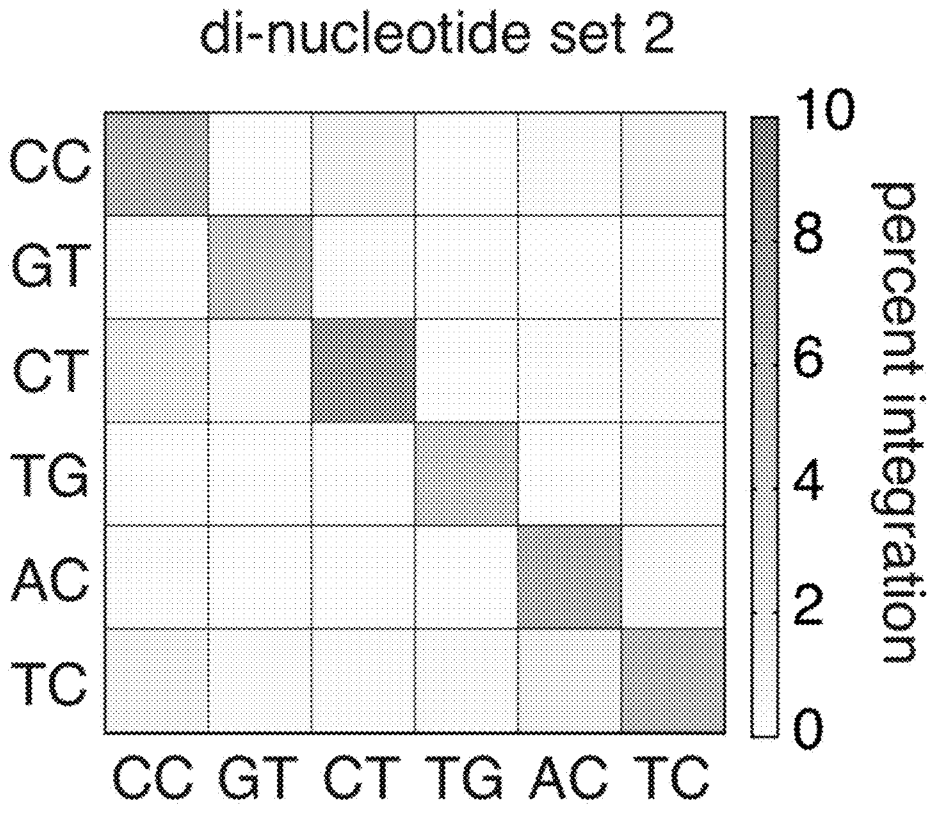
FIG. 27B shows the orthogonality between selected sets of attB and attP sites according to embodiments of the present teachings.
Figure 27C:
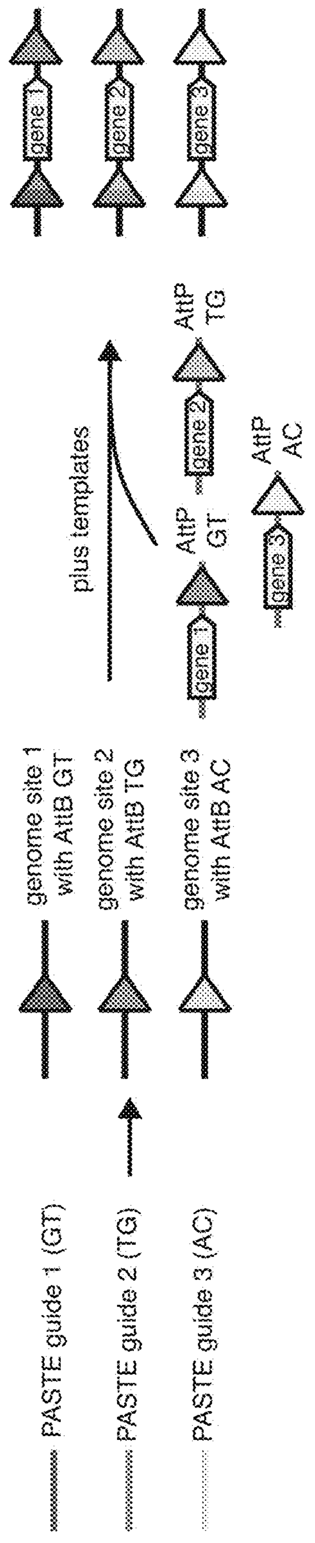
FIG. 27C shows a schematic for the orthogonal PASTE editing using engineered di-nucleotide combinations according to embodiments of the present teachings.

The PASTE and HITI on-target and off-target activities were compared (FIGS. 26A-26F). PASTE and HITI were found to have about 22% and 5% integration efficiencies respectively when using the same guide sequence (FIGS. 26A and 26B). PASTE was found to outperform HITI at most sites when analyzing the editing of 14 genes (FIG. 26C). Using a ddPCR based approach, it was found that PASTE was very specific with minimal off-target activity for Bxb1 off-targets integrations (FIG. 26D) and Cas9 off-targets integrations (FIG. 26E). The analysis of inserts of different sizes showed that PASTE can reliably insert sequences 1 kb-10 kb in size (FIG. 26F), revealing the wide range of sequence sizes PASTE is capable of working with. A decrease in insertion efficiency at larger sizes was also observed, which was likely due to the reduction in plasmid delivery to HEK293FT cells at larger plasmid sizes.

Example 16

Multiplexing with PASTE and Orthogonal Di-nucleotide attB and attP Sites

Figure 28A:
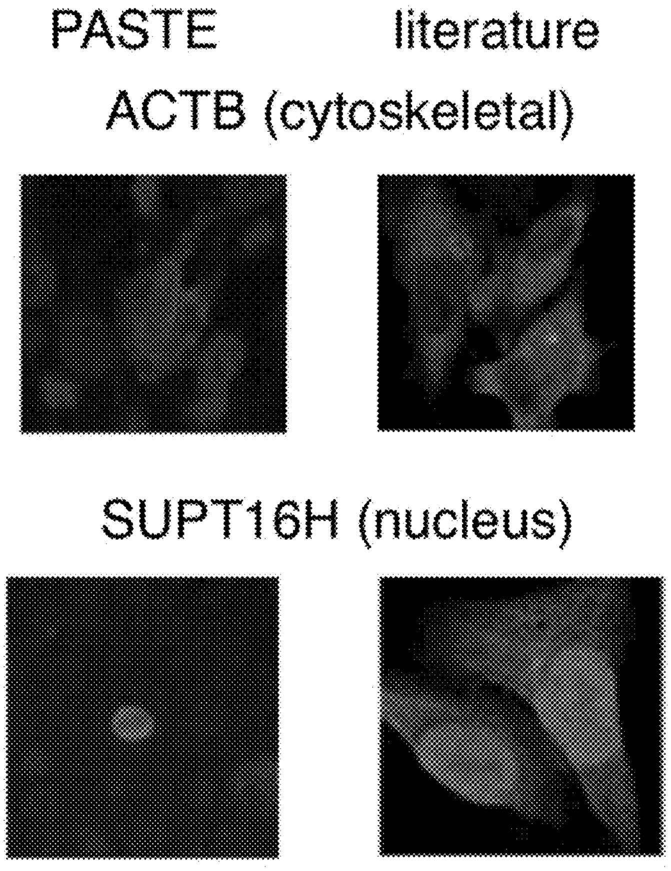
FIG. 28A shows fluorescent images of the GFP tagging of ACTB and SUPT16H genes with PASTE according to embodiments of the present teachings.
Figure 28B:
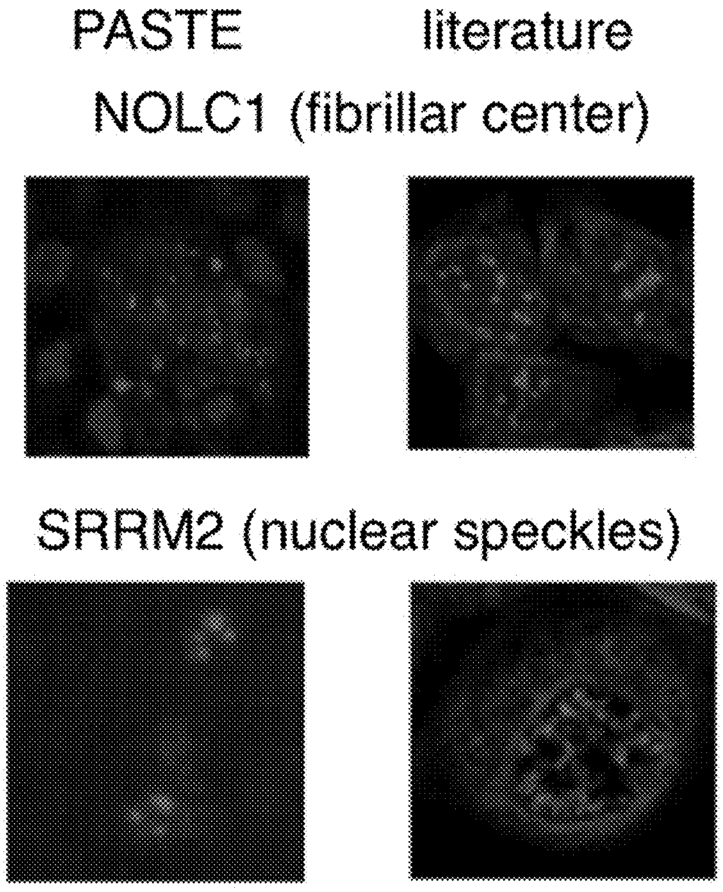
FIG. 28B shows fluorescent images of the GFP tagging of NOLC1 and SRRM2 genes with PASTE according to embodiments of the present teachings.
Figure 28C:
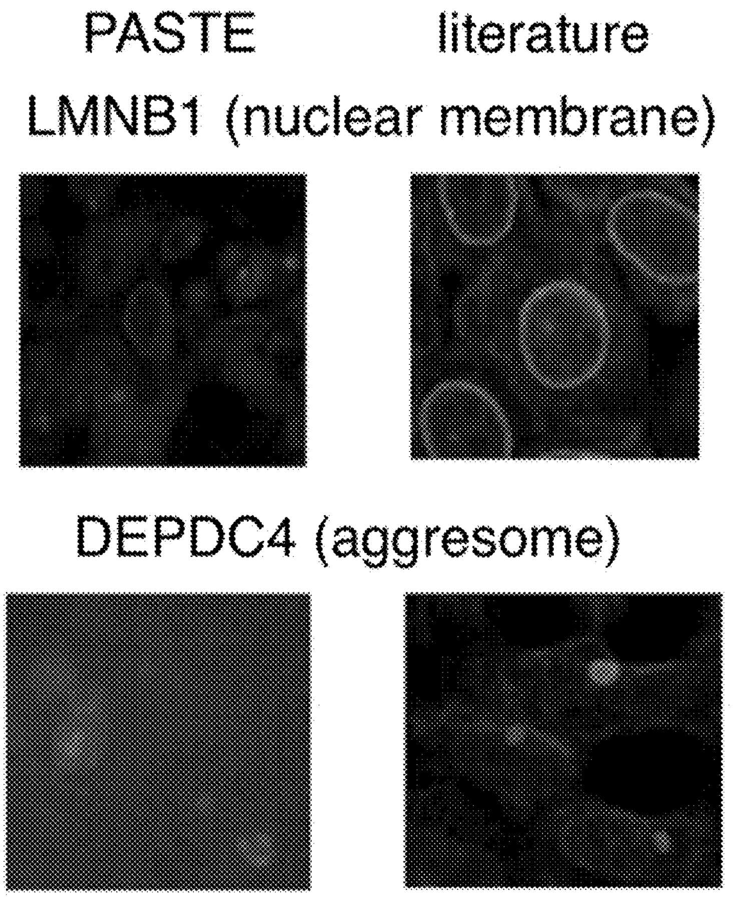
FIG. 28C shows fluorescent images of the GFP tagging of LMNB1 and DEPDC4 genes with PASTE according to embodiments of the present teachings.

Multiplexing with PASTE and orthogonal di-nucleotide attB and attP sites was evaluated (FIGS. 28A-28C). Multiple orthogonal combinations were found for mutants of the central di-nucleotide motif (FIGS. 28A and 28B). As illustrated in FIG. 28C, programmable multiplexed gene insertion can be achieved by using these orthogonal combinations with PASTE only delivering different pegRNAs and gene inserts while keeping the protein components the same (FIG. 8C).

Example 17

PASTE Multiplexed Integrations at Endogenous Sites

Figure 28D:
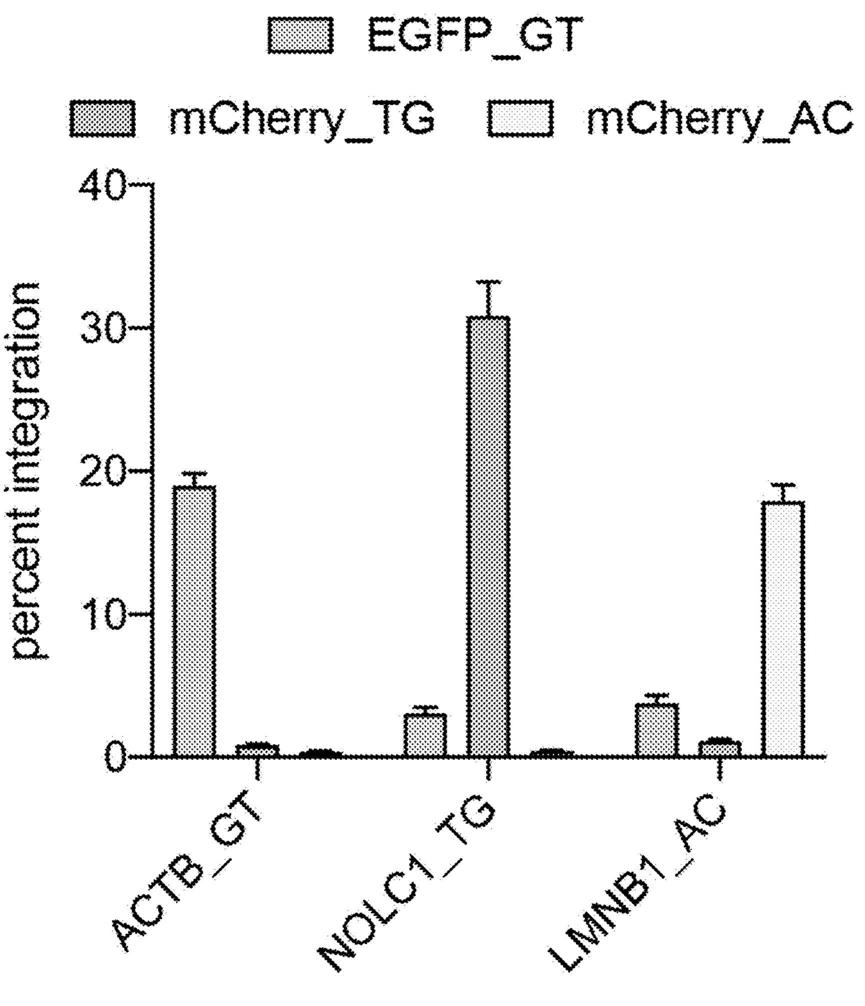
FIG. 28D shows the orthogonal gene integration at three endogenous sites with PASTE according to embodiments of the present teachings.
Figure 28E:
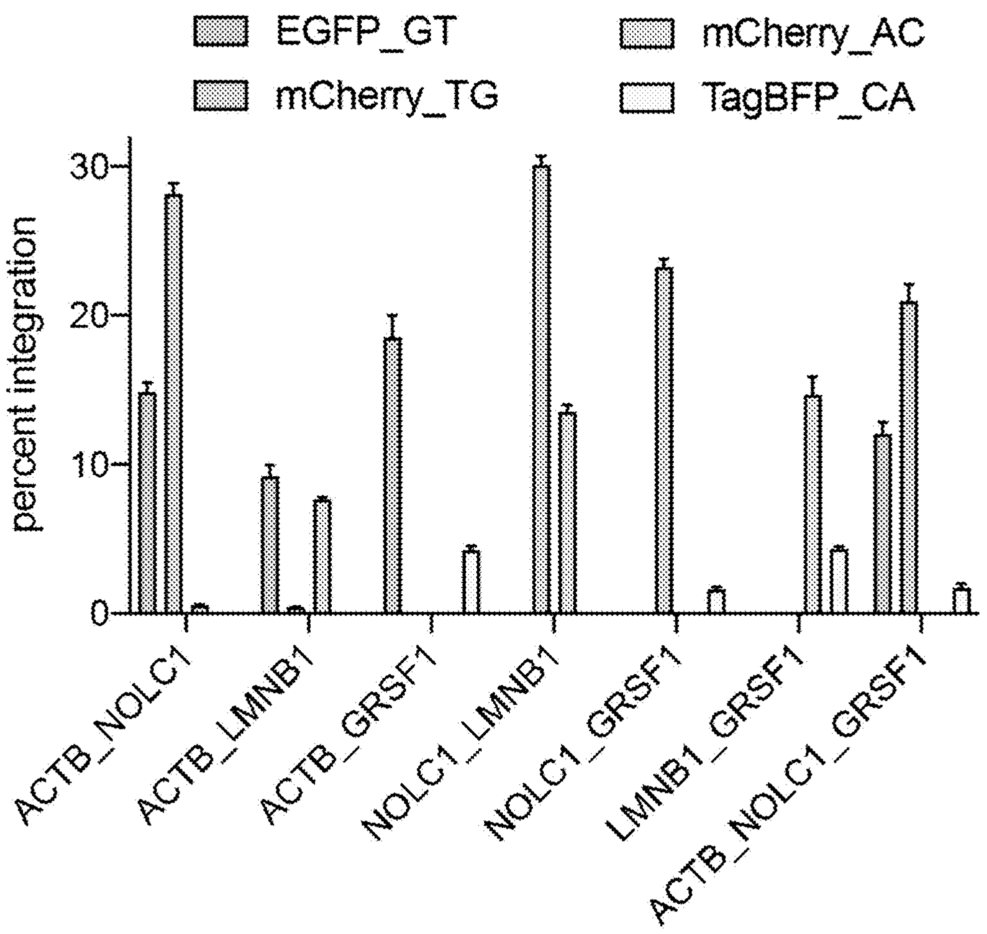
FIG. 28E shows the multiplexed insertion via one-plex, two-plex, and three-plex gene insertion at three endogenous sites via PASTE according to embodiments of the present teachings.
Figure 28F:
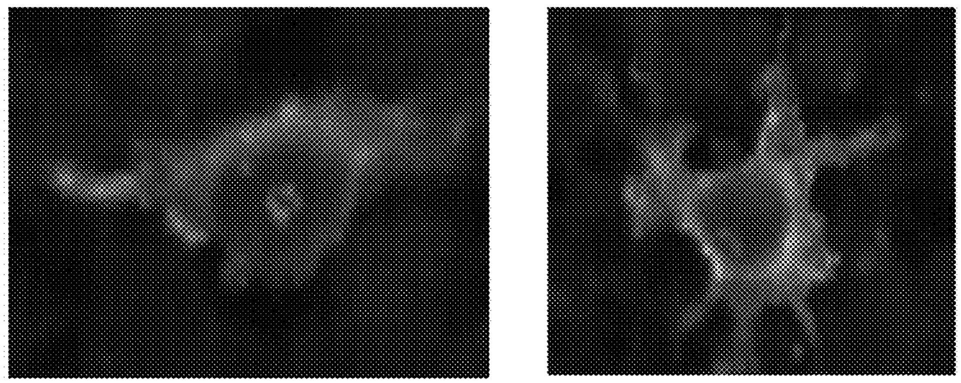
FIG. 28F shows fluorescent images of two single cells with multiplexed gene tagging of ACTB (EGFP) and NOLC1 (mCherry) using PASTE according to embodiments of the present teachings.
Figure 28G:
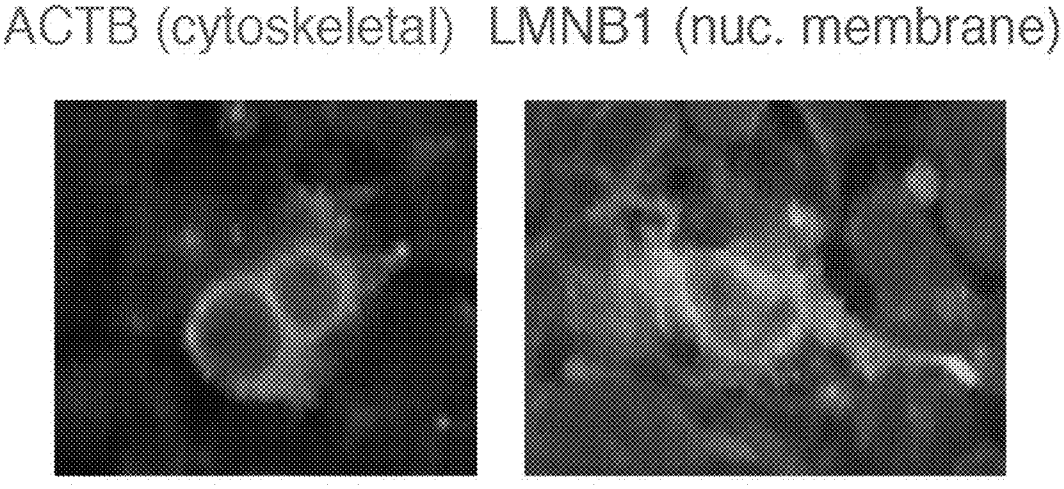
FIG. 28G shows fluorescent images two single cells with multiplexed gene tagging of ACTB (EGFP) and LMNB1 (mCherry) using PASTE according to embodiments of the present teachings.

PASTE multiplexed integrations at endogenous sites were evaluated (FIGS. 28A-28G). A reading frame for the attR scar that is left post-integration by Bxb1 that is ideal for a protein linker due to the enrichment of glycines, serines, and prolines in the sequence (GLSGQPPRSPSSGSSG (SEQ ID NO: 426)) was identified. PegRNAs were designed using this linker frame for the resolution of the attR for tagging a number of genes at the N-terminus with EGFP (ACTB, NOLC1, LMNB1, SUPT16H, SRRM2, and DEPDC4). As these genes all have distinct protein localization appearances, microscopy can be used for ascertaining proper gene tagging. PASTE was found to be capable of high-efficiency gene tagging with protein localizations that match the reference images and expected localization of the proteins in the cells (FIGS. 28A-28C). Genes were also tagged in multiplexed fashion to demonstrate the orthogonality of the engineered integration sites. ACTB, LMNB1, NOLC1, and GRSF were targeted with orthogonal pegRNAs carrying GT, TG, AC, and CA, respectively in HEK293FT in groups of single, dual-plexing, and triple-plexing (FIGS. 28D-28E). These dinucleotides were paired with templates carrying EGFP, BFP, and mCherry to allow for multicolor imaging of these labeled genes. The efficiencies of integration for these multiplexing experiments were found to range from about 5%-32%, revealing efficient multiplex integration with PASTE. Using confocal microscopy of these multiplexed integration experiments, cells were found with simultaneous labeling of these different proteins (FIGS. 28F-28G).

Example 18

Combination of CRISPR-Based Genome Editing and Site-Specific Integration

The combination of CRISPR-based genome editing and site-specific integration was evaluated.

Figure 29A:
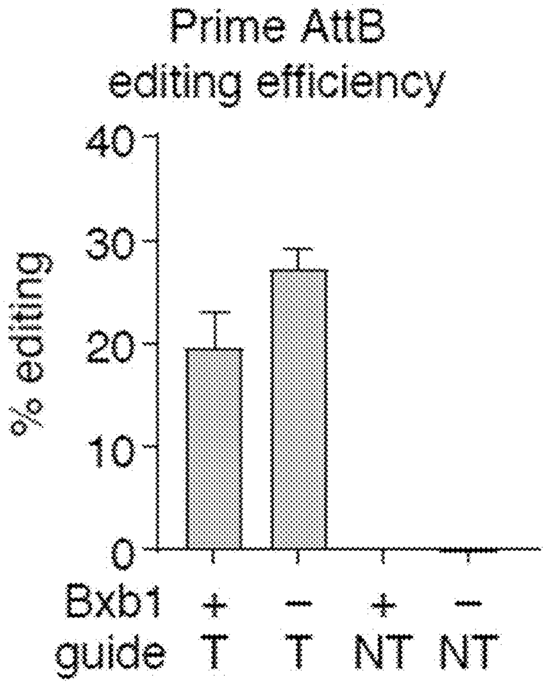
FIG. 29A shows the prime editing efficiency of Bxb1 attB site insertion at the ACTB locus according to embodiments of the present teachings.
Figure 29B:
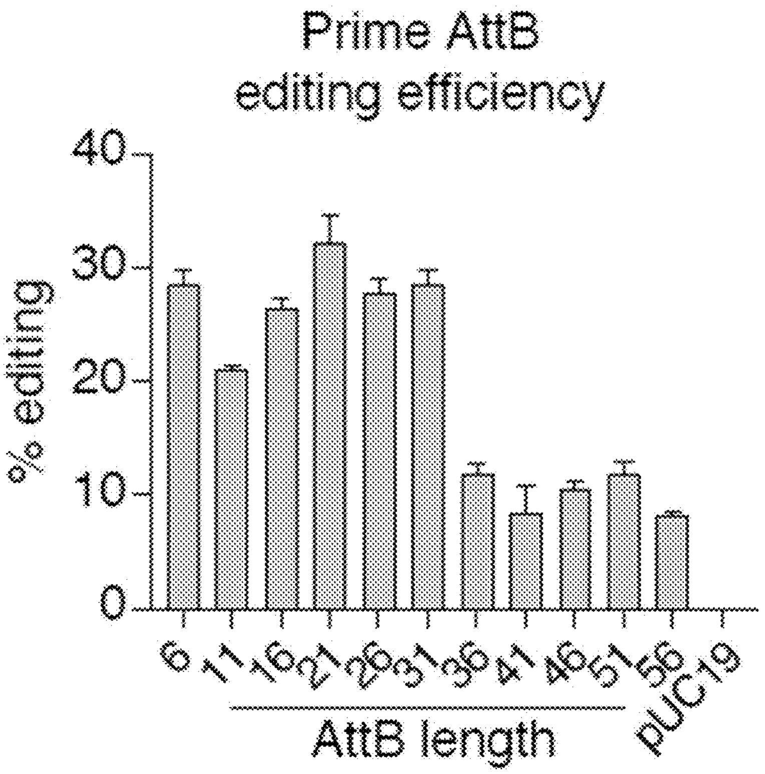
FIG. 29B shows the prime editing efficiency at inserting Bxb1 attB sites of different lengths at the ACTB locus according to embodiments of the present teachings.
Figure 29C:
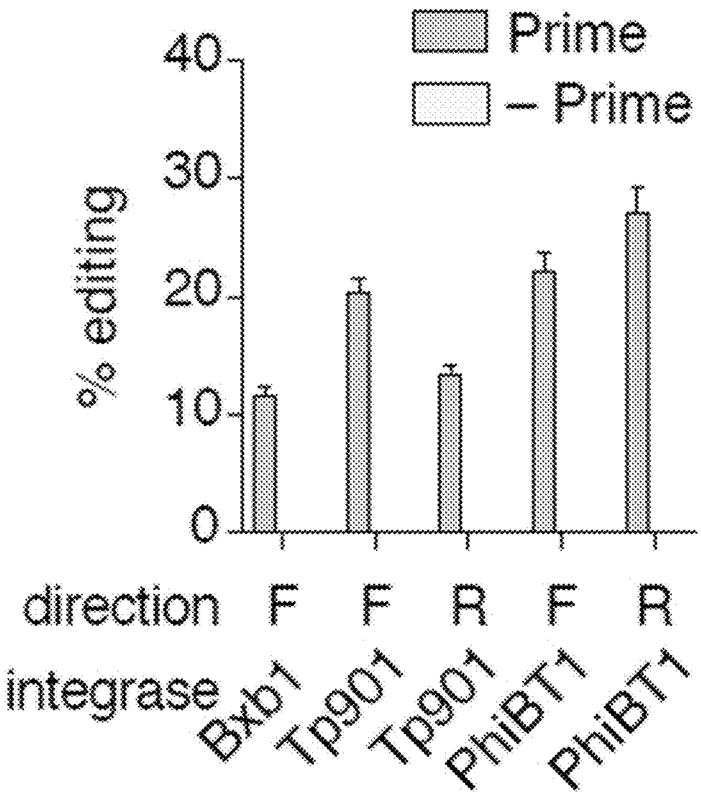
FIG. 29C shows the prime editing efficiency of inserting attB sequences from different integrases, wherein both orientations of landing sites are profiled (F, forward; and R, reverse) according to embodiments of the present teachings.
Figure 29D:
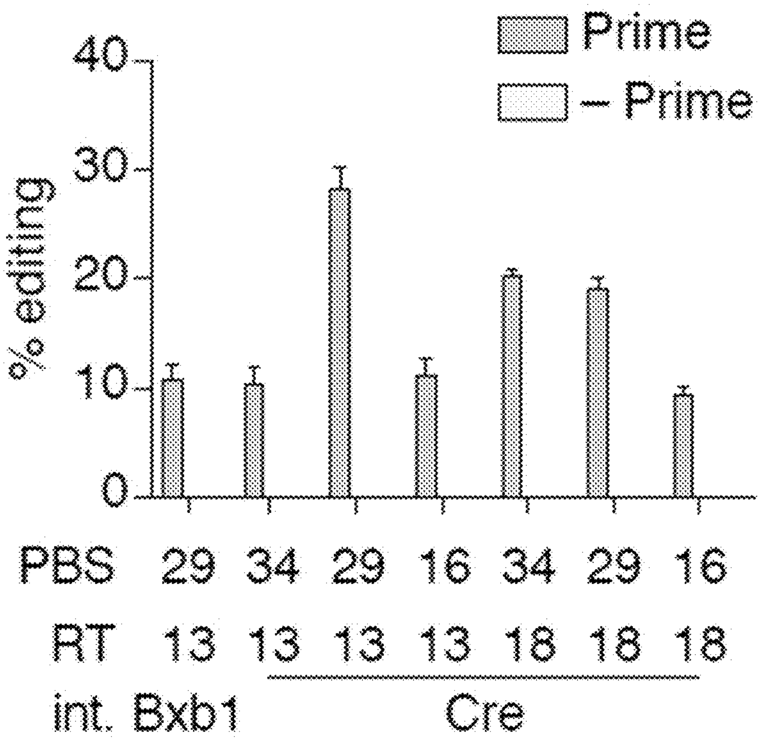
FIG. 29D shows the prime editing efficiency of inserting attB sequences from Bxb1 integrase and Cre recombinase, wherein both orientations of landing sites are profiled (F, forward; and R, reverse) according to embodiments of the present teachings.
Figure 29E:
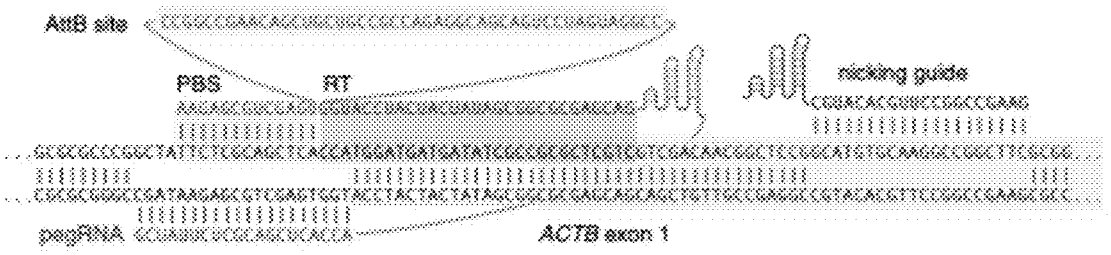
FIG. 29E shows a schematic of PASTE insertion at the ACTB locus showing guide and target sequences according to embodiments of the present teachings.
Figure 29F:
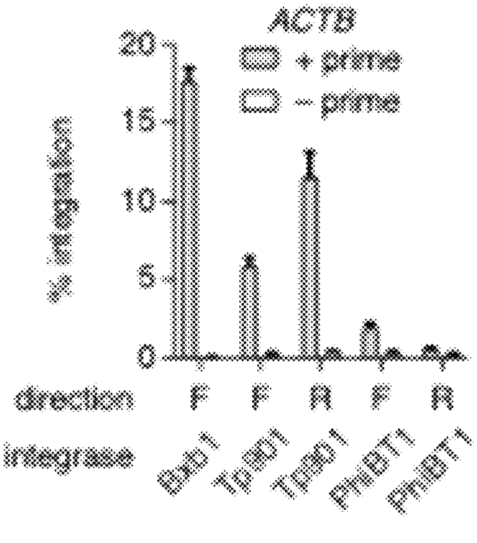
FIG. 29F shows a comparison of PASTE integration efficiency of GFP with a panel of integrases targeting the 5' end of the ACTB locus, wherein both orientations of landing sites are profiled (F, forward; and R, reverse) according to embodiments of the present teachings.
Figure 29G:
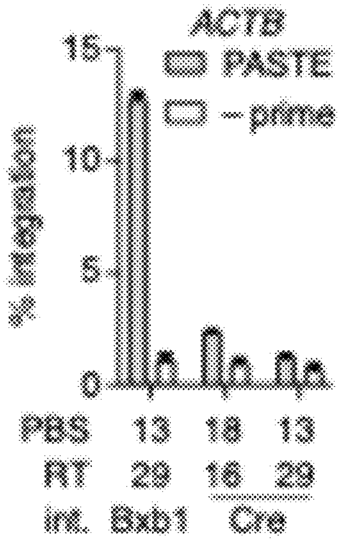
FIG. 29G shows a comparison of GFP cargo integration efficiency between Bxb1 integrases and Cre recombinase according to embodiments of the present teachings.
Figure 29H:
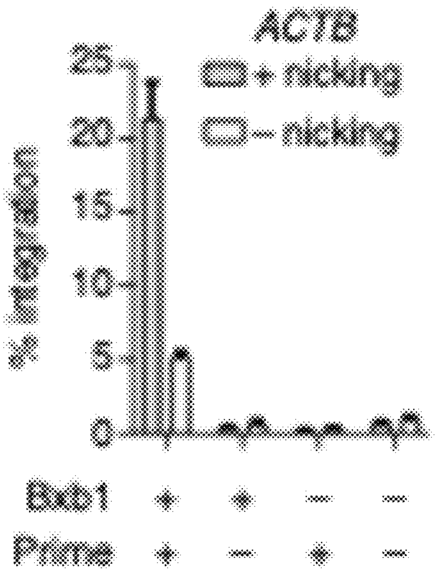
FIG. 29H shows the dependence of PASTE editing activity on different prime and integrase components according to embodiments of the present teachings.
Figure 29I:
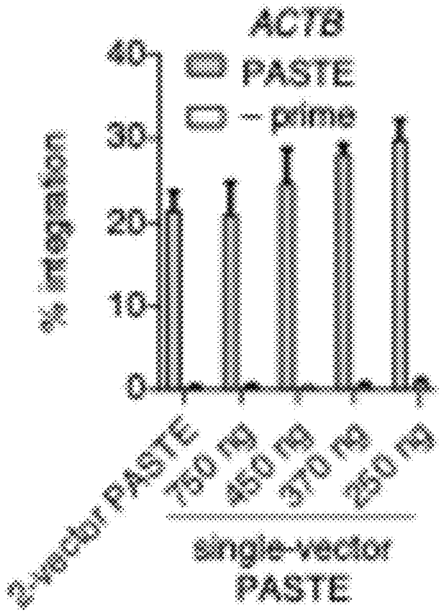
FIG. 29I shows a titration of a single vector PASTE system (SpCas9-RT-P2A-Bxb1) on integrase efficiency according to embodiments of the present teachings.
Figure 29J:
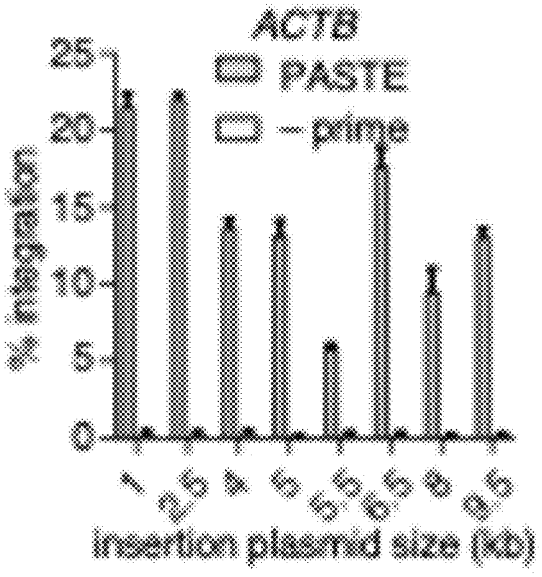
FIG. 29J shows the effect of cargo size on PASTE insertion efficiency at the endogenous ACTB target according to embodiments of the present teachings.
Figure 29K:
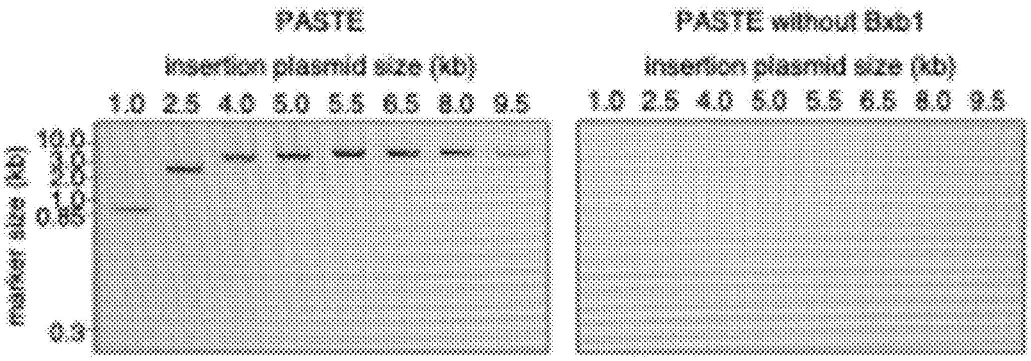
FIG. 29K shows a gel electrophoresis showing complete insertion by PASTE for multiple cargo sizes according to embodiments of the present teachings.
Figure 30A:
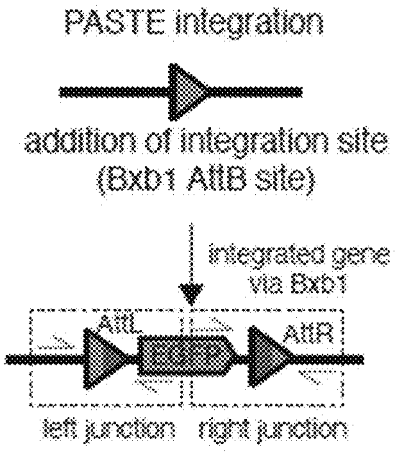
FIG. 30A shows a schematic of PASTE integration, including resulting attR and attL sites that are generated and PCR primers for assaying the integration junctions according to embodiments of the present teachings.
Figure 30B:
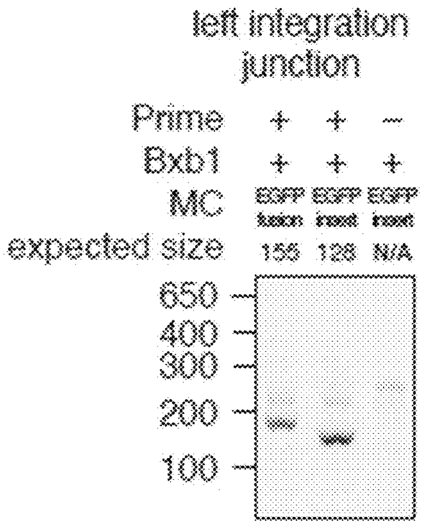
FIG. 30B shows a PCR and gel electrophoresis readout of left integration junction from PASTE insertion of GFP at the ACTB locus, wherein the insertion is analyzed for in-frame and out-of-frame GFP integration experiments as well as for a no prime control and expected sizes of the PCR fragments are shown using the primers shown in the schematic in subpanel FIG. 30A according to embodiments of the present teachings.
Figure 30C:
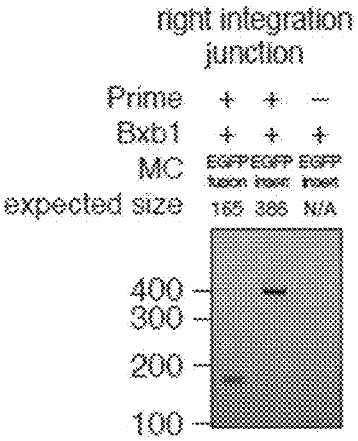
FIG. 30C shows a PCR and gel electrophoresis readout of right integration junction from PASTE insertion of GFP at the ACTB locus, wherein the insertion is analyzed for in-frame and out-of-frame GFP integration experiments as well as for a no prime control and the expected sizes of the PCR fragments are shown using the primers shown in the schematic in subpanel FIG. 30A according to embodiments of the present teachings.
Figure 30D:
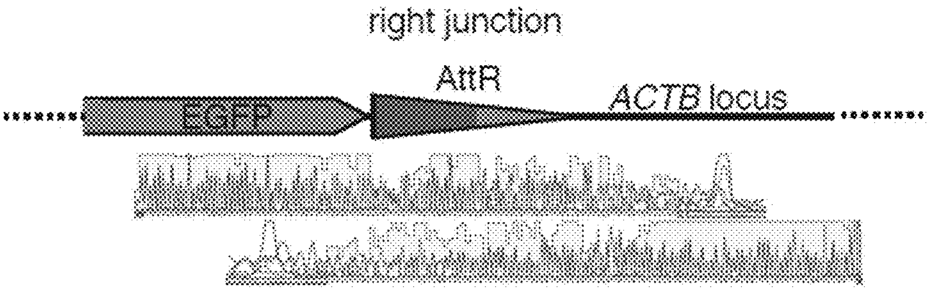
FIG. 30D shows a Sanger sequencing shown for the right integration junction for an in-frame fusion of GFP via PASTE to the N-terminus of ACTB according to embodiments of the present teachings.
Figure 30E:
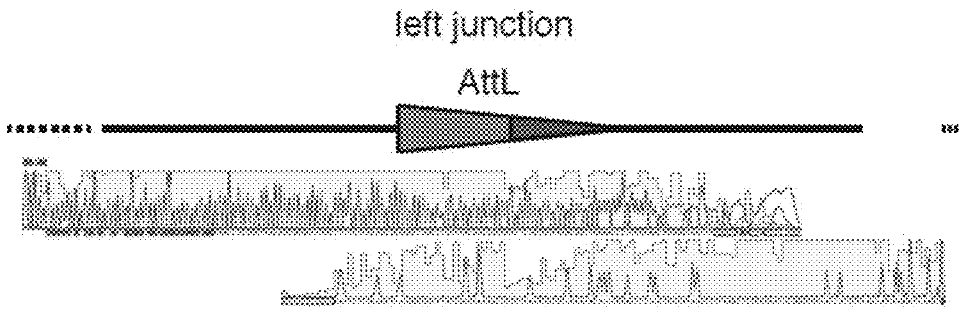
FIG. 30E shows a Sanger sequencing shown for the left integration junction for an in-frame fusion of GFP via PASTE to the N-terminus of ACTB according to embodiments of the present teachings.

PegRNAs containing different attB length truncations were assessed (FIG. 29A). Prime editing was found to be capable of inserting sequences up to 56 bp at the beta-actin (ACTB) gene locus, with higher efficiency at lengths below 31 bp (FIGS. 29A-B) The integration of cognate landing sites was tested for multiple insertion enzymes: Bxb1, TP901, and phiBT1 phage serine integrases and Cre recombinase. Prime editing successfully inserted all landing sites tested, with efficiencies between 10-30% (FIGS. 29C-D). To test the complete system, all components were combined and delivered in a single transfection: the prime editing vector, the landing site containing pegRNA, a nicking guide for stimulating prime editing, a mammalian expression vector for the corresponding integrase or recombinase and a 969 bp minicircle DNA cargo encoding green fluorescent protein (GFP) (FIG. 29E). GFP integration rates among the four integrases and recombinases were compared and Bxb1 integrase was found to have the highest integration rate (~20%) at the targeted ACTB locus and require the prime editing nicking guide for optimal performance (FIGS. 29F-H). Finally, to reduce the number of transfected components, Bxb1 was co-expressed with the SpCas9-M-MLV reverse transcriptase (PE2) fusion protein via a P2A protein cleavage site. This combination maintained high GFP insertion efficiency, up to 30% (FIG. 29E). The complete system, PASTE, achieved precise integration of templates as large as 9,500 bp with greater than 10% integration efficiency (FIGS. 29J-K and 26E), with complete integration of the full-length cargo confirmed by Sanger sequencing (FIG. 30A-E).

Example 19

Impact of Prime Editing and Integrase Parameters on PRIME Editing

The impact of prime editing and integrase parameters on the integration efficiency of PRIME editing was assessed.

Figure 31A:
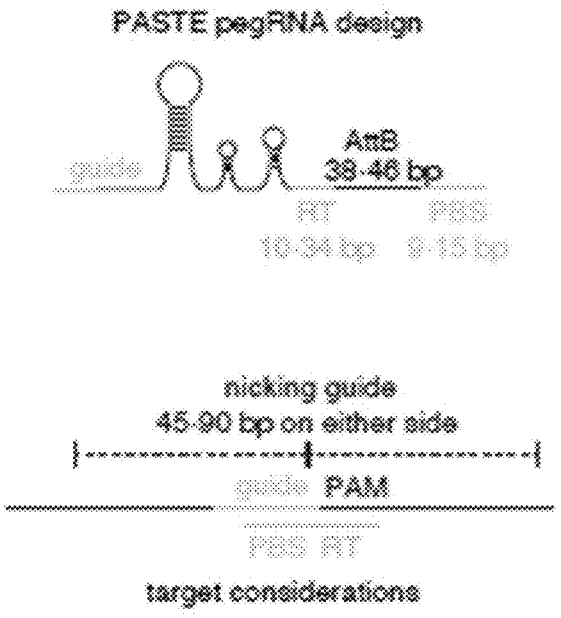
FIG. 31A shows a schematic of various parameters that affect PASTE integration of ~1 kb GFP insert, wherein on the pegRNA, the PBS, RT, and attB lengths can alter the efficiency of attB insertion, and nicking guide selection also affects overall gene integration efficiency according to embodiments of the present teachings.
Figure 31B:
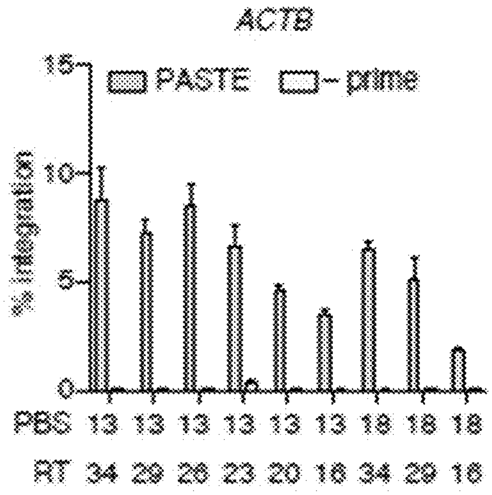
FIG. 31B shows the impact of PBS and RT length on PASTE integration of GFP at the ACTB locus according to embodiments of the present teachings.
Figure 31C:
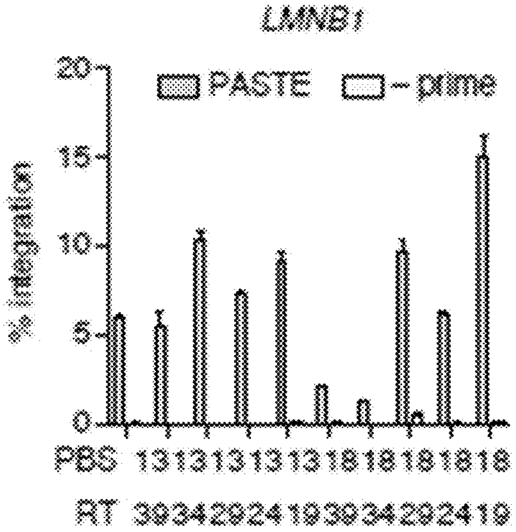
FIG. 31C shows the impact of PBS and RT length on PASTE integration of GFP at the LMNB1 locus according to embodiments of the present teachings.

Relevant pegRNA parameters for PASTE include the primer binding site (PBS), reverse transcription template (RT), and attB site lengths, as well as the relative locations and efficacy of the pegRNA spacer and nicking guide (FIG. 31A). A range of PBS and RT lengths were tested at two loci, ACTB and lamin B1 (LMNB1), and rules governing efficiency were found to vary between loci, with shorter PBS lengths and longer RT designs having higher editing at the ACTB locus (FIG. 31B) and longer PBS and shorter RT designs performing better at LMNB1 (FIG. 31C).

Figure 31D:
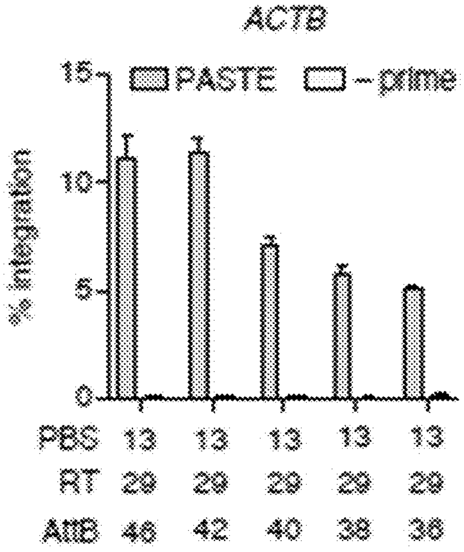
FIG. 31D shows the impact of attB length on PASTE integration of GFP at the ACTB locus according to embodiments of the present teachings.
Figure 31E:
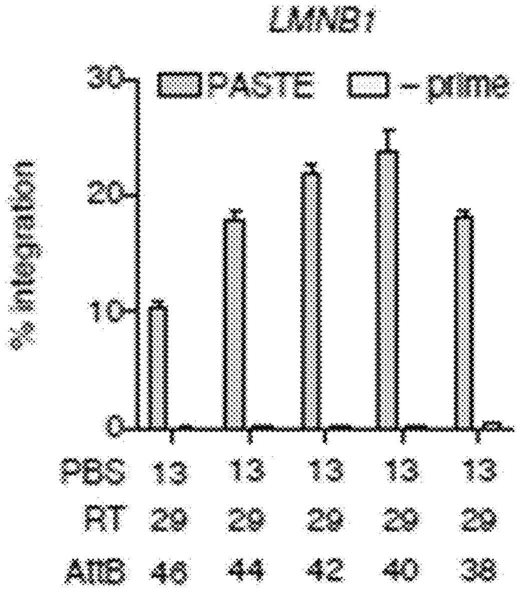
FIG. 31E shows the impact of attB length on PASTE integration of GFP at the LMNB1 locus according to embodiments of the present teachings.
Figure 31F:
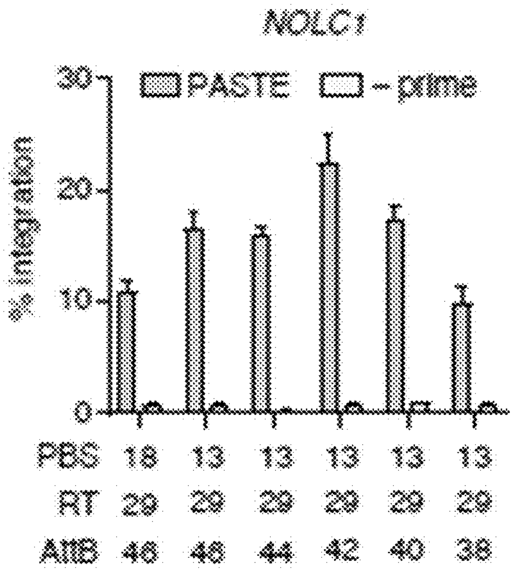
FIG. 31F shows the impact of attB length on PASTE integration of GFP at the NOLC1 locus according to embodiments of the present teachings.

The length of the attB landing site must balance two conflicting factors: the higher efficiency of prime editing for smaller inserts and reduced efficiency of Bxb1 integration at shorter attB lengths. AttB lengths were evaluated at ACTB, LMNB1, and nucleolar phosphoprotein p130 (NOLC1), and the optimal attB length was found to be locus dependent. At the ACTB locus, long attB lengths could be inserted by prime editing (FIG. 29B) and overall PASTE efficiencies for the insertion of GFP were highest for long attB lengths (FIG. 31*d*). In contrast, intermediate attB lengths had higher overall integration efficiencies (>20%) at LMNB1 (FIG. 31E) and NOLC1 (FIG. 31F), indicating that the increased efficiency of installing shorter attB sequences overcame the reduction of Bxb1 integration at these sites.

Figure 32A:
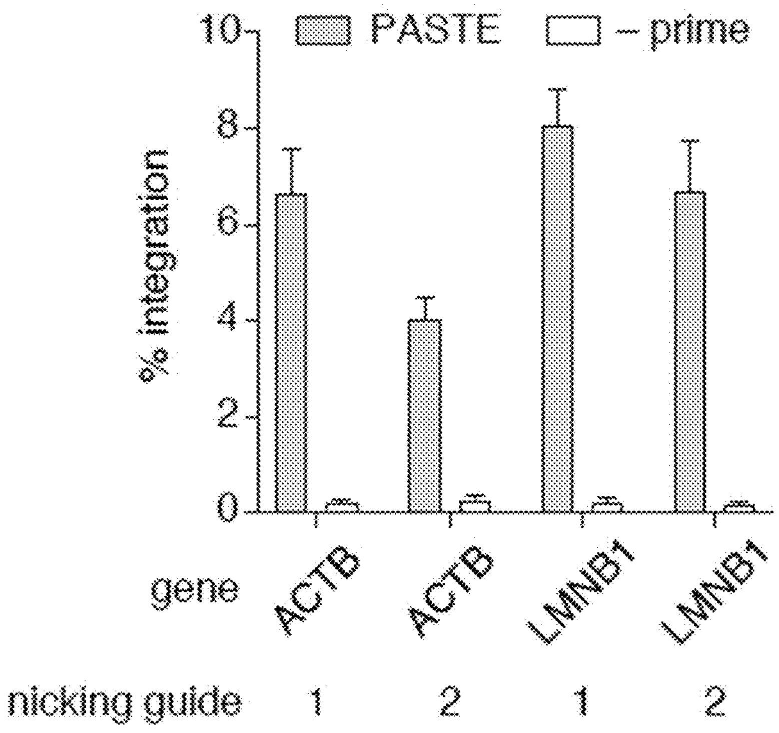
FIG. 32A shows the PASTE insertion efficiency at ACTB and LMNB1 loci with two different nicking guide designs according to embodiments of the present teachings.
Figure 32B:
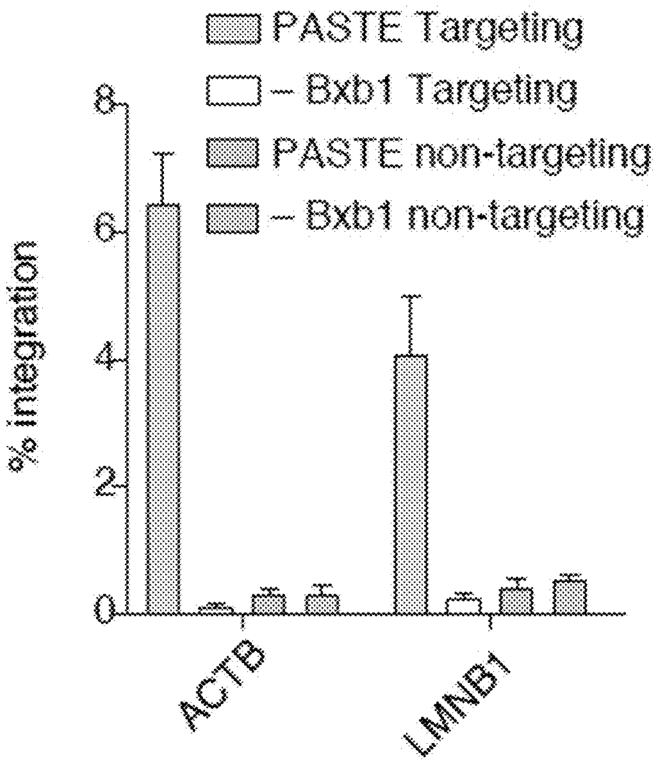
FIG. 32B shows the PASTE editing efficiency at ACTB and LMNB1 with target and non-targeting spacers and matched pegRNAs with and without Bxb1 expression according to embodiments of the present teachings.

The PE3 version of prime editing combines PE2 and an additional nicking guide to bias resolution of the flap intermediate towards insertion. To test the importance of nicking guide selection on PASTE editing, editing at ACTB and LMNB1 loci was tested with two nicking guide positions. Suboptimal nicking guide positions were found to reduce the PASTE efficiency up to 30% (FIG. 32A) in agreement with the 75% reduction of PASTE efficiency in the absence of nicking guide (FIG. 29G). The pegRNA spacer sequence was found to be necessary for PASTE editing, and substitution of the spacer sequence with a non-targeting guide was found to eliminate editing (FIG. 32B).

Figure 33A:
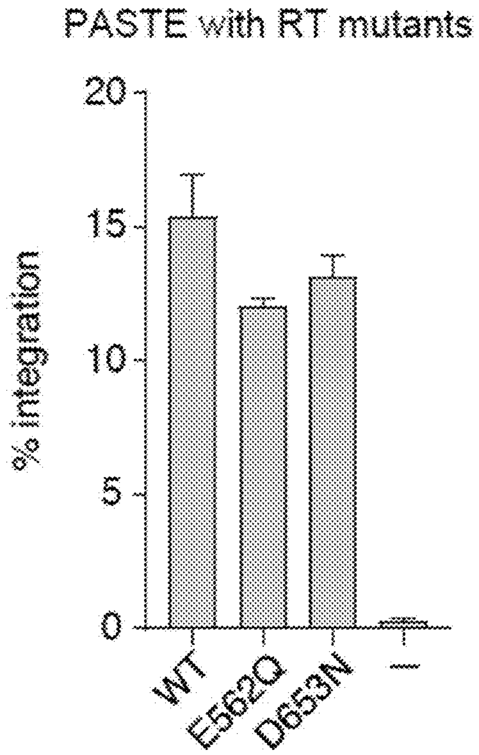
FIG. 33A shows the PASTE integration of GFP at the ACTB locus with different Bxb1 catalytic mutants according to embodiments of the present teachings.
Figure 33B:
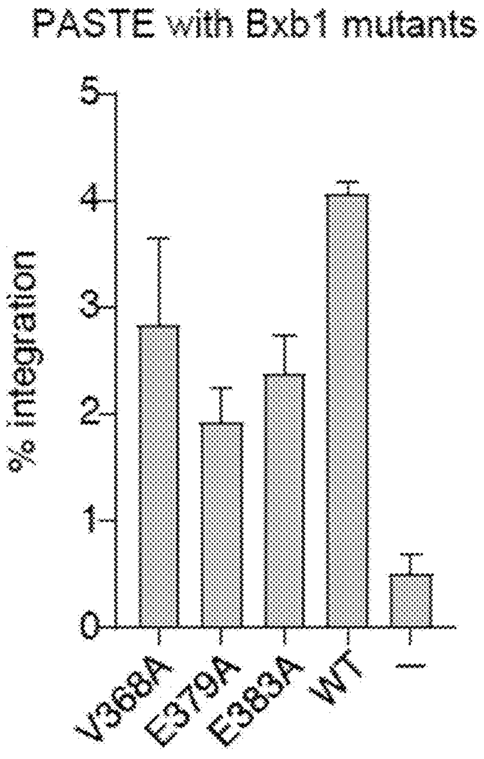
FIG. 33B shows the PASTE integration of GFP at the ACTB locus with different RT catalytic mutants according to embodiments of the present teachings.

Rational mutations were also introduced in both the Bxb1 integrase and reverse transcriptase domain of the PE2 construct to optimize PASTE further. While some of these mutations were well tolerated by PASTE (FIGS. 33A-B), none of them improved PASTE editing efficiency.

Figure 31G:
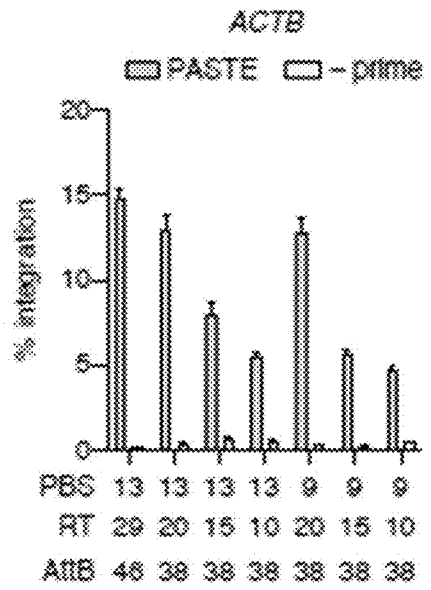
FIG. 31G shows the impact of minimal PBS, RT, and attB lengths on PASTE integration efficiency of GFP at the ACTB locus according to embodiments of the present teachings.
Figure 31H:
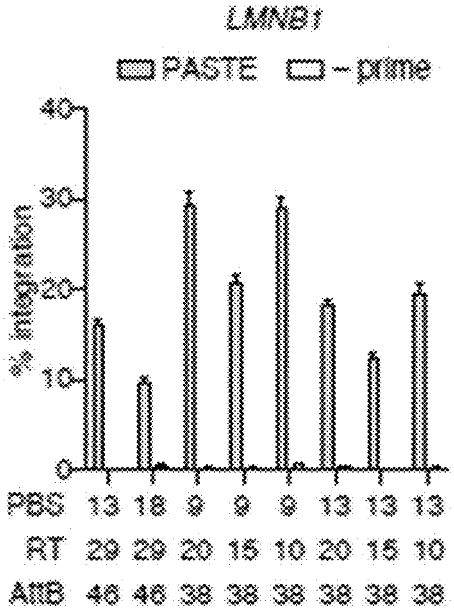
FIG. 31H shows the impact of minimal PBS, RT, and attB lengths on PASTE integration efficiency of GFP at the LMNB1 locus according to embodiments of the present teachings.
Figure 31I:
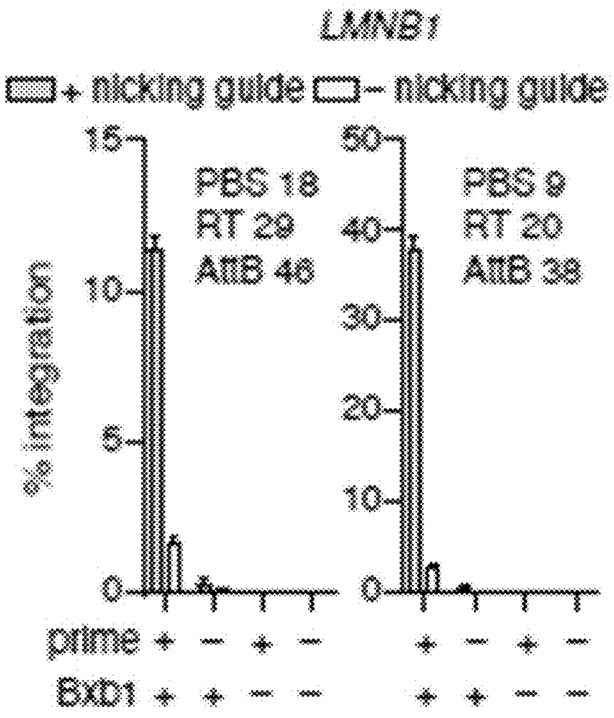
FIG. 31I shows the PASTE integration of GFP at the LMNB1 locus in the presence and absence of nicking guide, prime, and Bxb1 with a minimally compact pegRNA containing a 38 bp attB compared to a longer pegRNA design according to embodiments of the present teachings.

Short RT and PBS lengths can offer additional improvements for editing. A panel of shorter RT and PBS guides were tested at ACTB and LMNB1 loci and while shorter RT and PBS sequences did not increase editing at ACTB (FIG. 31G), it was found that they had improved editing at LMNB1 (FIG. 31H) with best performing guides reaching GFP insertion rates of ~40% (FIG. 31I).

Example 20

PASTE Tagging at Multiple Endogenous Genes

Figure 34A:
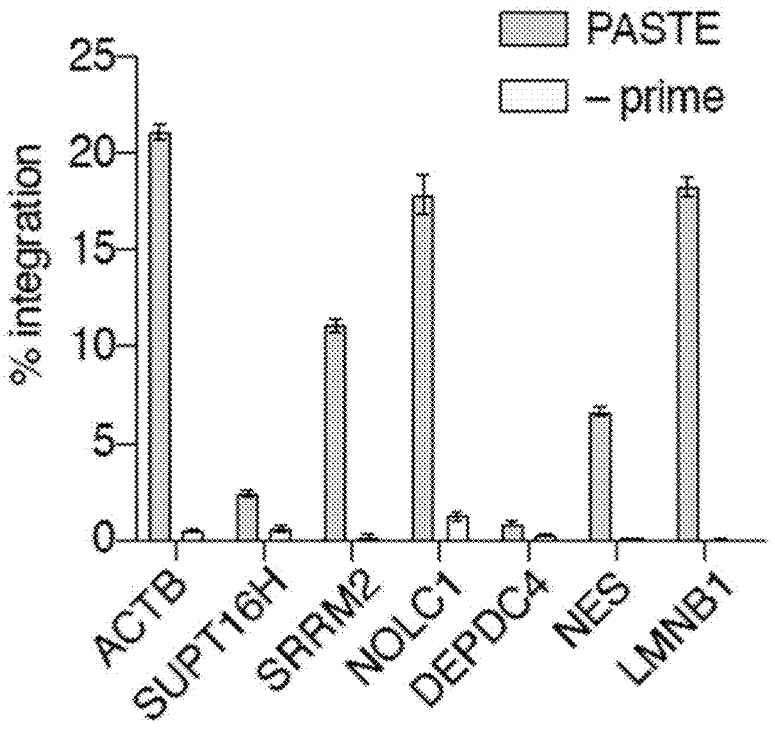
FIG. 34A shows the GFP integration by PASTE at a panel of endogenous genomic loci according to embodiments of the present teachings.
Figure 34B:
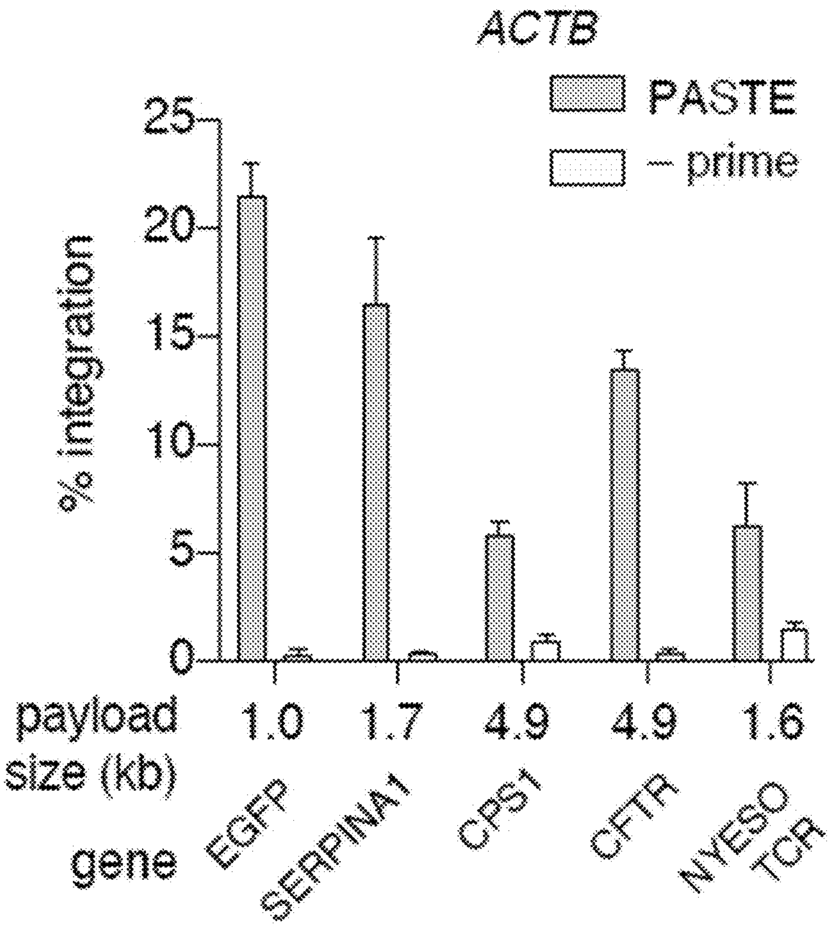
FIG. 34B shows the integration of a panel of different gene cargo at ACTB locus via PASTE according to embodiments of the present teachings.
Figure 34C:
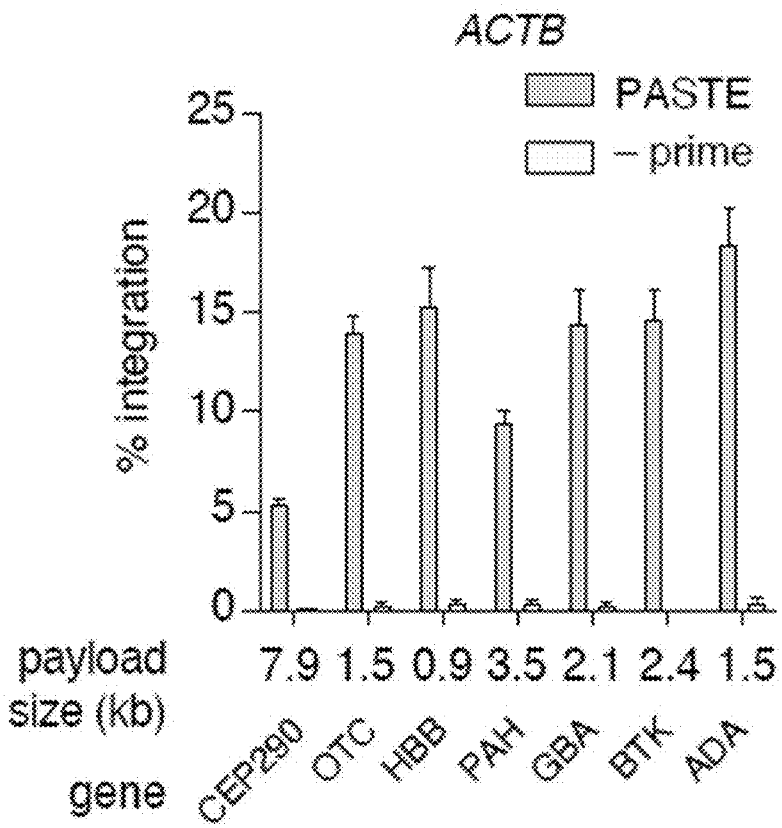
FIG. 34C shows the integration efficiency of therapeutically relevant genes at the ACTB locus according to embodiments of the present teachings.
Figure 35:
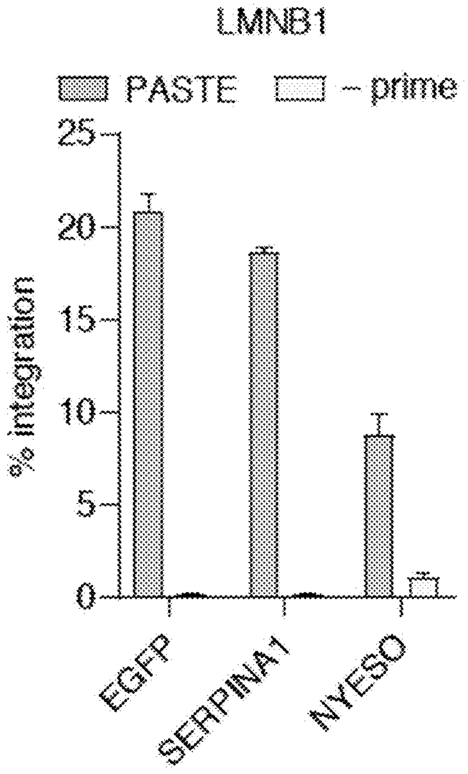
FIG. 35 shows the integration of a panel of different gene cargo at LMNB1 locus via PASTE according to embodiments of the present teachings.

GFP insertion efficiency was measured at seven different gene loci—ACTB, SUPT16H, SRM2, NOLC1, DEPDC4, NES, and LMNB1—to test the versatility of the PASTE programming. A range of integration rates up to 22% was found (FIG. 34A). Because PASTE does not require homology or sequence similarity on cargo plasmids, integration of diverse cargo sequences is modular and easily scaled across different loci. Six different gene cargos, varying in size from 969 bp to 4906 bp, were tested for insertion at ACTB and LMNB1 loci with PASTE. Integration frequencies between 5% and 22% depending on the gene and insertion locus were found (FIGS. 34B and 35). Additionally, a panel of seven common therapeutic genes, CEP290, OTC, HBB, PAH, GBA, BTK, and ADA was evaluated for insertion at the ACTB locus, and the efficient integration of these cargos were found between 5%-20% (FIG. 34C).

Figure 34D:
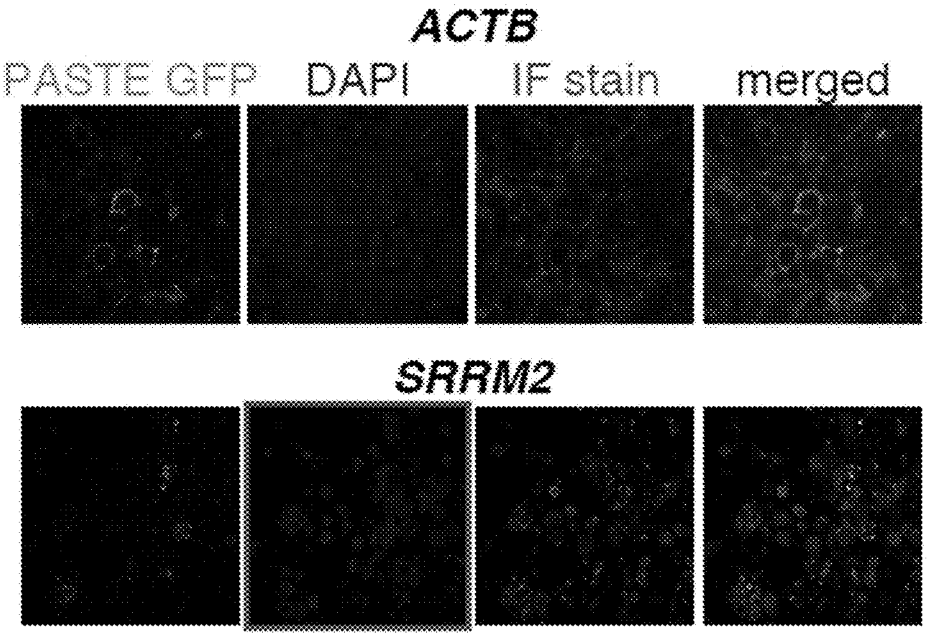
FIG. 34D shows the endogenous protein tagging with GFP via PASTE by in-frame endogenous gene tagging at the ACTB loci and SRRM2 loci according to embodiments of the present teachings.
Figure 34E:
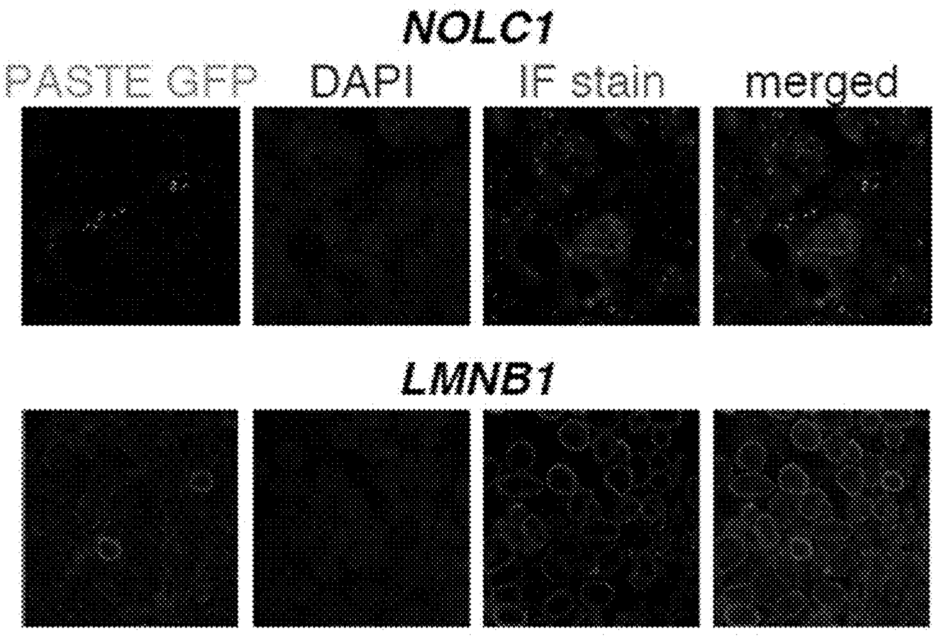
FIG. 34E shows the endogenous protein tagging with GFP via PASTE by in-frame endogenous gene tagging at the NOLC1 loci and LMNB1 loci according to embodiments of the present teachings.

The precise insertions of PASTE for in-frame protein tagging or expressing cargo without disruption of endogenous gene expression was assessed. As Bxb1 leaves residual sequences in the genome (termed attL and attR) after cargo integration, these genomic scars can serve as protein linkers. The frame of the attR sequence was positioned through strategic placement of the attP on the minicircle cargo, achieving a suitable protein linker, GGLSGQPPRSPSSGSSG (SEQ ID NO: 427). Using this linker, four genes (ACTB, SRRM2, NOLC1, and LMNB1) were tagged with GFP using PASTE. To assess correct gene tagging, the subcellular location of GFP was compared with the tagged gene product by immunofluorescence. For all four targeted loci, GFP co-localized with the tagged gene product, indicating successful tagging (FIGS. 34D-E).

Example 21

Orthogonal Sequence Preferences for Bxb1 Integration

Figure 36A:
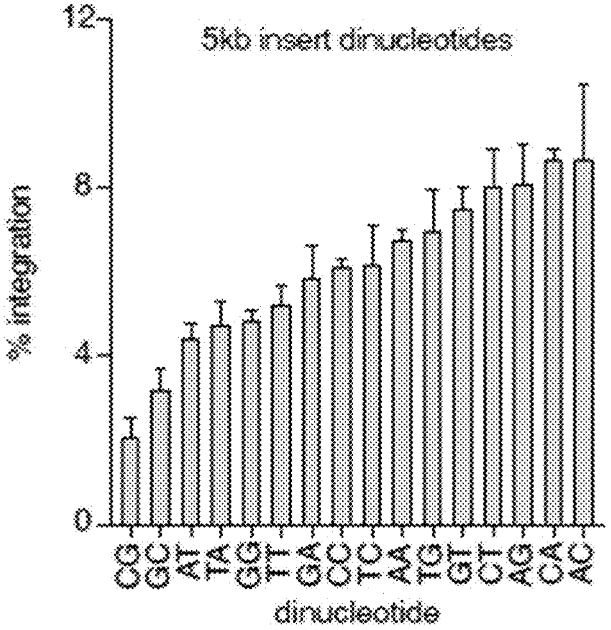
FIG. 36A shows the PASTE integration efficiency for all 16 central dinucleotide attB/attP sequence pairs with a 5 kb GFP template at the ACTB locus according to embodiments of the present teachings.

The central dinucleotide of Bxb1 is involved in the association of attB and attP sites for integration, and changing the matched central dinucleotide sequences can modify integrase activity and provide orthogonality for insertion of two genes. Expanding the set of attB/attP dinucleotides can enable multiplexed gene insertion with PASTE. The efficiency of GFP integration at the ACTB locus with PASTE across all 16 dinucleotide attB/attP sequence pairs was profiled to find optimal attB/attP dinucleotides for PASTE insertion. Several dinucleotides with integration efficiencies greater than the wild-type GT sequence were found (FIG. 36A). A majority of dinucleotides had 75% editing efficiency or greater compared to wild-type attB/attP efficiency, implying that these dinucleotides can be orthogonal channels for multiplexed gene insertion with PASTE.

Figure 36B:
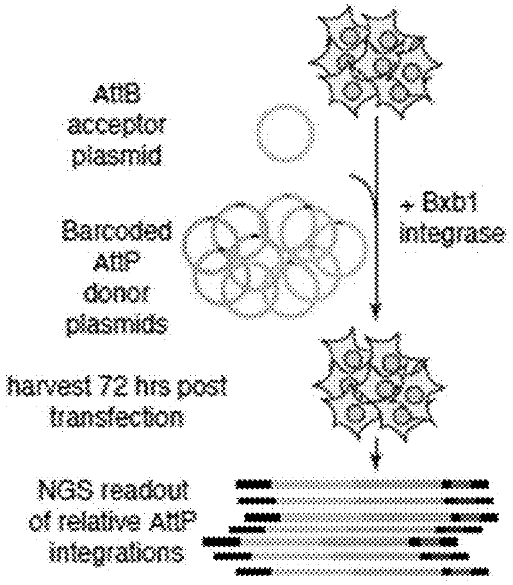
FIG. 36B shows a schematic of the pooled attB/attP dinucleotide orthogonality assay, wherein each attB dinucleotide sequence is co-transfected with a barcoded pool of all 16 attP dinucleotide sequences and Bxb1 integrase, relative integration efficiencies are determined by next generation sequencing of barcodes, and all 16 attB dinucleotides are profiled in an arrayed format with attP pools according to embodiments of the present teachings.
Figure 36C:
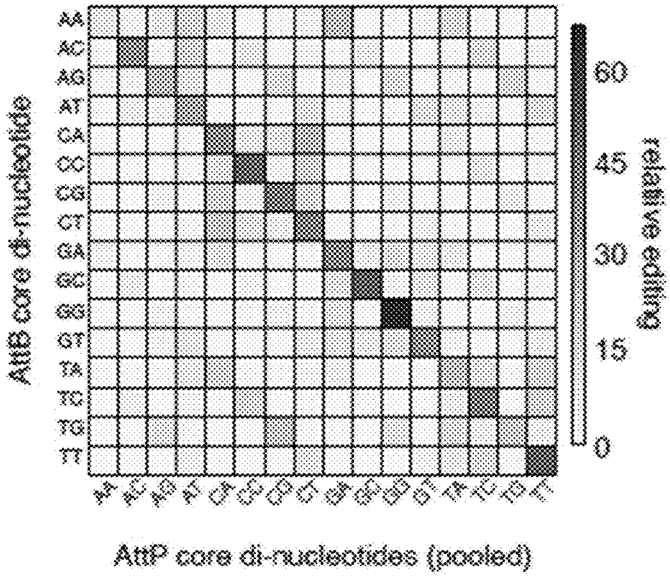
FIG. 36C shows the relative insertion preferences for all possible attB/attP dinucleotide pairs determined by the pooled orthogonality assay according to embodiments of the present teachings.
Figure 37:
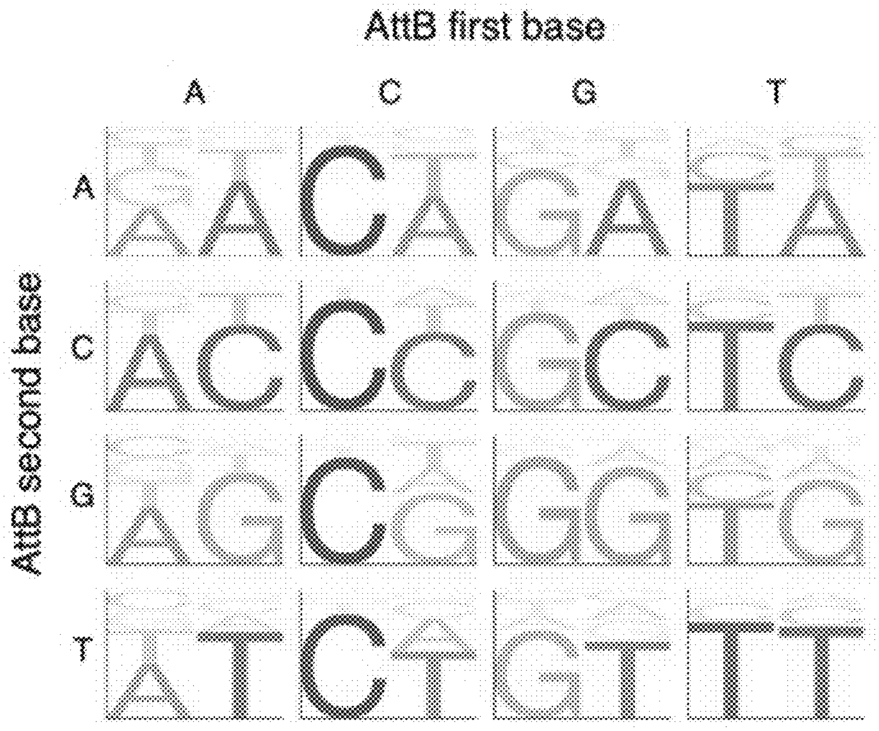
FIG. 37 shows the orthogonality of Bxb1 dinucleotides as measured by a pooled reporter assay, wherein each web logo motif shows the relative integration of different attP sequences in a pool at a denoted attB sequence with the listed dinucleotide according to embodiments of the present teachings.

The specificity of matched and unmatched attB/attP dinucleotide interactions was then assessed. The interactions between all dinucleotide combinations in a scalable fashion using a pooled assay to compare attB/attP integration were profiled (FIG. 36B). By barcoding 16 attP dinucleotide plasmids with unique identifiers, co-transfecting this attP pool with the Bxb1 integrase expression vector and a single attB dinucleotide acceptor plasmid, and sequencing the resulting integration products, the relative integration efficiencies of all possible attB/attP pairs were measured (FIG. 36C). Dinucleotide specificity was found to vary, with some dinucleotides (GG) exhibiting strong self-interaction with negligible crosstalk, and others (AA) showing minimal self-preference. Sequence logos of attP preferences (FIG. 37) revealed that dinucleotides with C or G in the first position have stronger preferences for attB dinucleotide sequences with shared first bases, while other attP dinucleotides, especially those with an A in the first position, have reduced specificity for the first attB base.

Figure 36D:
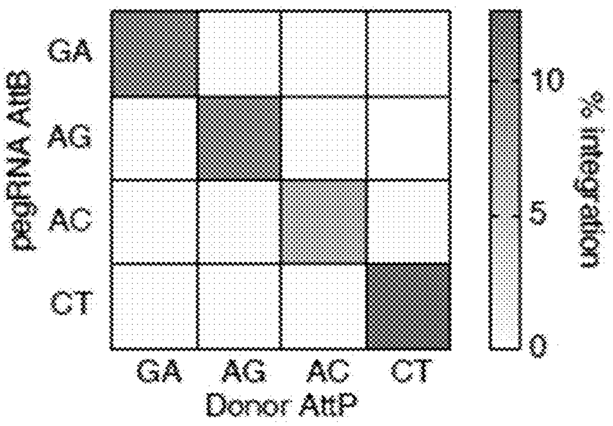
FIG. 36D shows the orthogonality of top 4 attB/attP dinucleotide pairs evaluated for GFP integration with PASTE at the ACTB locus according to embodiments of the present teachings.

GA, AG, AC, and CT dinucleotide pegRNAs were then tested for GFP integration at ACTB, either paired with their corresponding attP cargo or mispaired with the other three dinucleotide attP sequences. All four of the tested dinucleotides efficiently were found to integrate cargo only when paired with the corresponding attB/attP pair, with no detectable integration across mispaired combinations (FIG. 36D).

Example 22

Multiplex Gene Integration with PASTE

Figure 38A:
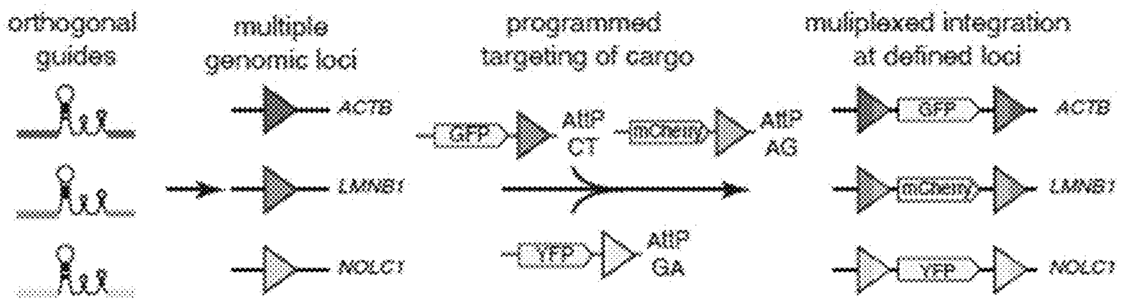
FIG. 38A shows a schematic of multiplexed integration of different cargo sets at specific genomic loci, wherein three fluorescent cargos (GFP, mCherry, and YFP) are inserted orthogonally at three different loci (ACTB, LMNB1, NOLC1) for in-frame gene tagging according to embodiments of the present teachings.
Figure 38B:
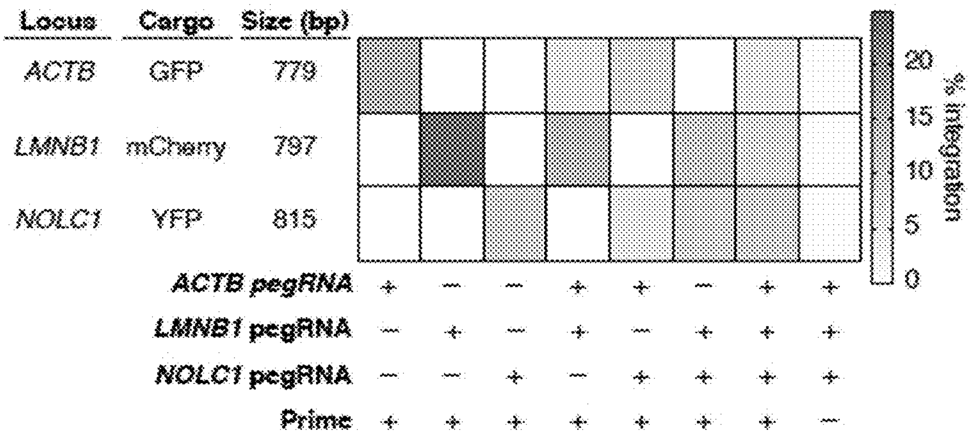
FIG. 38B shows the efficiency of multiplexed PASTE insertion of combinations of fluorophores at ACTB, LMNB1, and NOLC1 loci according to embodiments of the present teachings.

Multiplexing in cells by using orthogonal pegRNAs that direct a matched attP cargo to a specific site in the genome was assessed (FIG. 38A). Selecting the three top dinucleotide attachment site pairs (CT, AG, and GA), pegRNAs that target ACTB (CT), LMNB1 (AG), and NOLC1 (GA) and corresponding minicircle cargo containing GFP (CT), mCherry (AG), and YFP (GA) were designed. Upon co-delivering these reagents to cells, single-plex, dual-plex, and trip-plex editing of all possible combinations of these pegRNAs and cargo in the range of 5%-25% integration was found to be achieved (FIG. 38B).

An application for multiplexed gene integration is for labeling different proteins to visualize intracellular localization and interactions within the same cell. PASTE was used to simultaneously tag ACTB (GFP) and NOLC1 (mCherry) or ACTB (GFP) and LMNB1 (mCherry) in the same cell. No overlap of GFP and mCherry fluorescence was observed and tagged genes were confirmed to be visible in their appropriate cellular compartments, based on the known subcellular localizations of the ACTB, NOLC1 and LMNB1 protein products (FIGS. 15A-B).

Example 23

PASTE Efficiencies Compared With DSB-based Insertion Methods

PASTE efficiencies were found to exceed comparable DSB-based insertion methods.

Figure 39A:
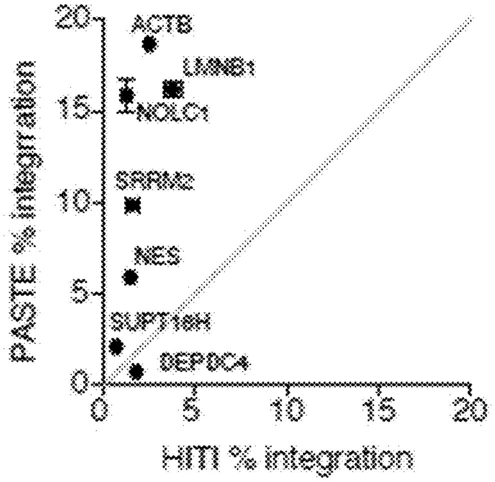
FIG. 39A shows the GFP integration efficiency at a panel of genomic loci by PASTE compared to insertion rates by homology-independent targeted integration (HITI) according to embodiments of the present teachings.
Figure 39B:
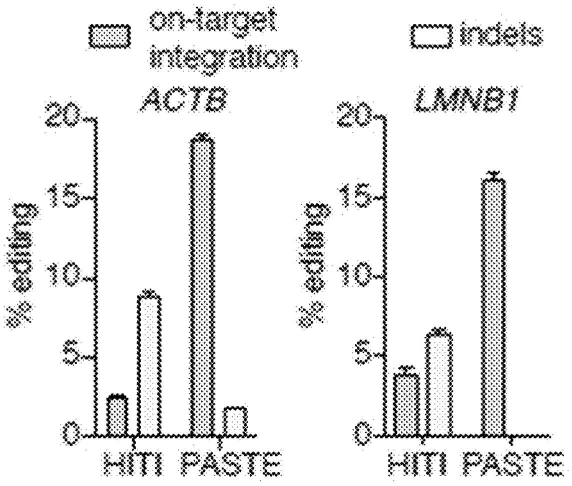
FIG. 39B shows a comparison of unintended indel generation by PASTE and HITI at the ACTB and LMNB1 target sites, wherein the on-target EGFP integration rate observed compared to unintended indels is shown according to embodiments of the present teachings.
Figure 39C:
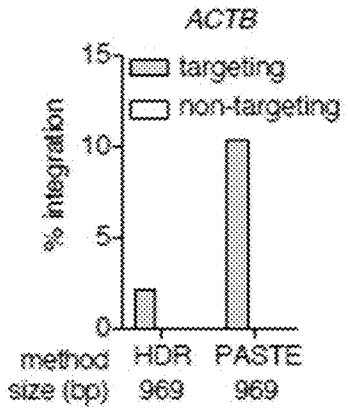
FIG. 39C shows the integration of a GFP template by PASTE at the ACTB locus compared to homology-directed repair (HDR) at the same target, wherein the quantification is by single-cell clone counting, wherein targeting and non-targeting guides were used for HDR insertion, and wherein for PASTE targeting and non-targeting refers to the presence or absence of the SpCas9-RT protein respectively according to embodiments of the present teachings.
Figure 39D:
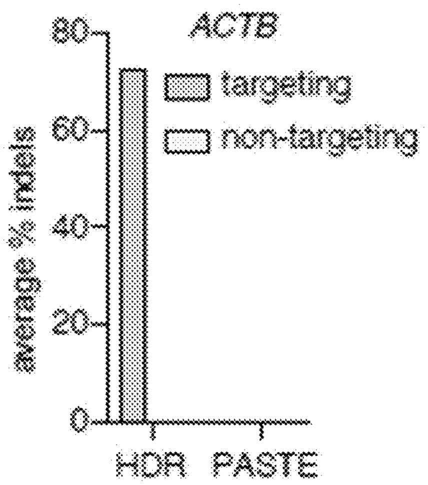
FIG. 39D shows the comparison of unintended indel generation by PASTE and HDR based EGFP insertion at the ACTB target site, wherein the average indel rate measured across all single-cell clones generated is showed according to embodiments of the present teachings.
Figure 40A:
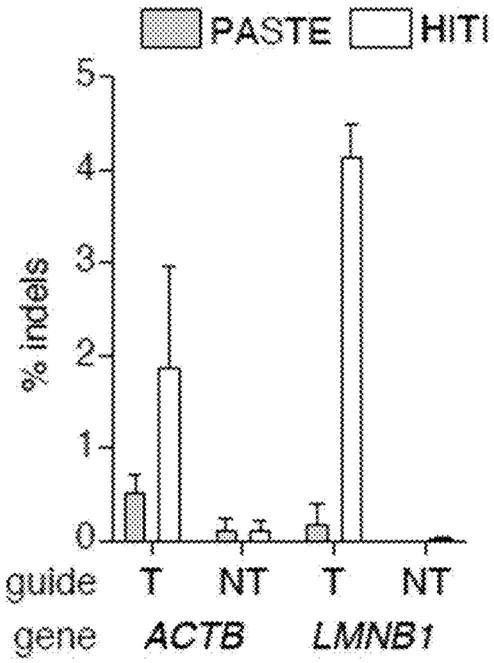
FIG. 40A shows a comparison of indel rates generated by PASTE and HITI mediated insertion of EGFP at the ACTB and LMNB1 loci in HepG2 cells according to embodiments of the present teachings.
Figure 40B:
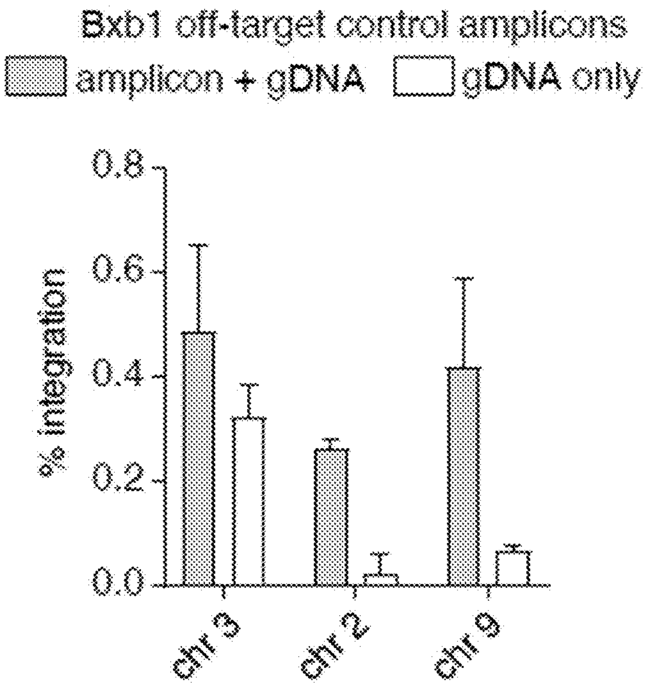
FIG. 40B shows the validation of ddPCR assays for detecting editing at predicted Bxb1 offtarget sites using synthetic amplicons according to embodiments of the present teachings.
Figure 40C:
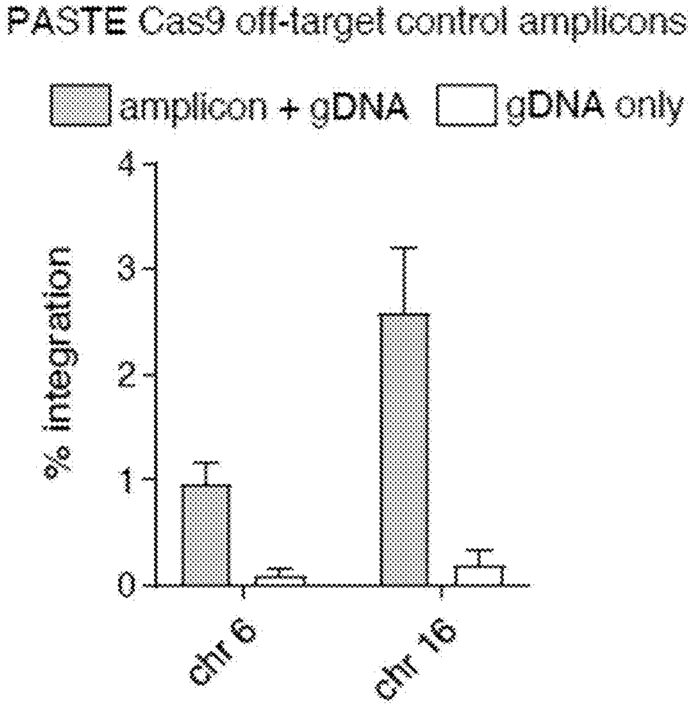
Figure 40D:
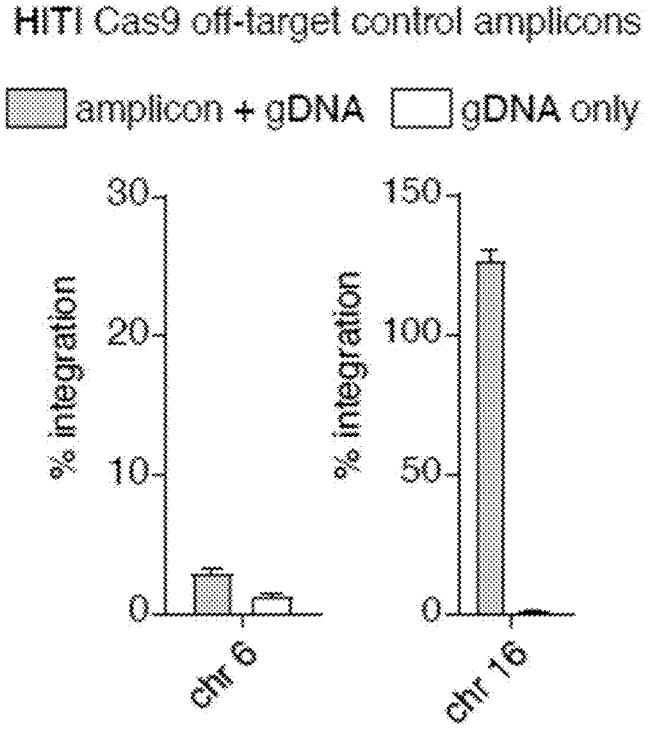

PASTE editing was assessed alongside DSB-dependent gene integration using either NHEJ (i.e., homology-independent targeted integration, HITI) or HDR pathways. PASTE had equivalent or better gene insertion efficiencies than either HITI (FIGS. 39A-B) or HDR (FIGS. 39C-D). On a panel of 7 different endogenous targets, PASTE exceeded HITI editing at 6 out of 7 genes, with similar efficiency for the 7th gene (FIG. 39A). As DSB generation can lead to insertions or deletions (indels) as an alternative and undesired editing outcome, the indel frequency of all three methods was assessed by next-generation sequencing, finding significantly fewer indels generated with PASTE than either HDR or HITI in both HEK293FT and HepG2 cells (FIGS. 39B, 39D and 40A), showcasing the high purity of gene integration outcomes with PASTE.

Example 24

Off-Target Characterization of PASTE and HITI Gene Integration

Figure 39E:
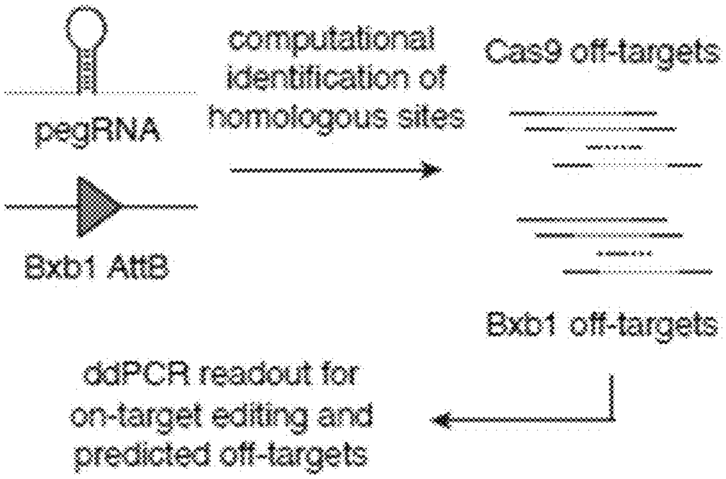
FIG. 39E shows a schematic for Bxb1 and Cas9 off-target identification and a detection assay according to embodiments of the present teachings.
Figure 39F:
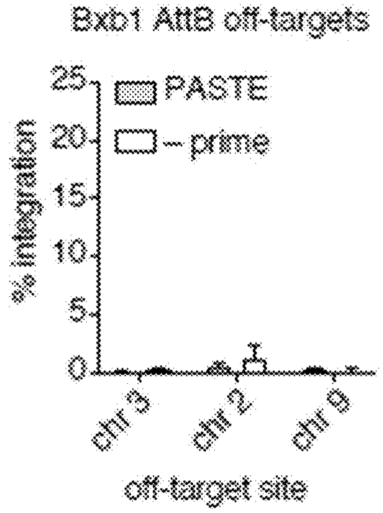
FIG. 39F shows the GFP integration activity at predicted Bxb1 off-target sites in the human genome according to embodiments of the present teachings.
Figure 39G:
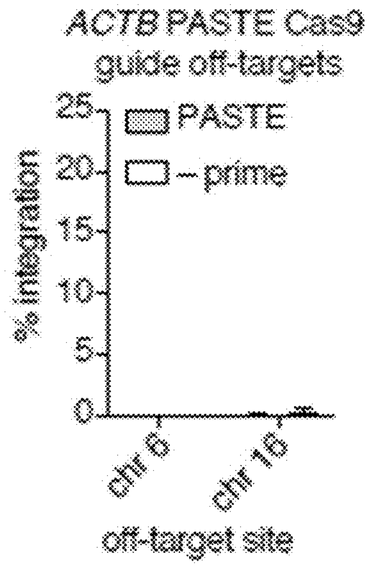
FIG. 39G shows the GFP integrations activity at predicted PASTE ACTB Cas9 guide off target sites according to embodiments of the present teachings.
Figure 39H:
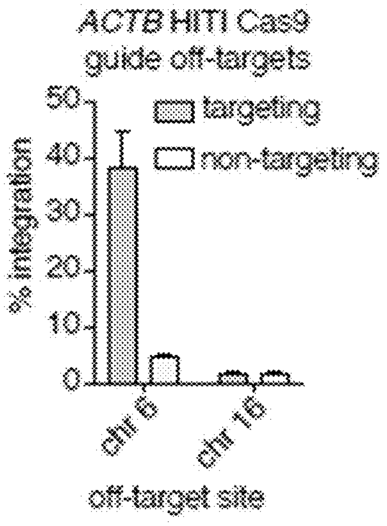
FIG. 39H shows the GFP integration activity at predicted HITI ACTB Cas9 guide off-target sites according to embodiments of the present teachings.

Off-target editing can be used in genome editing technologies. The specificity of PASTE at specific sites was assessed based on off-targets generated by Bxb1 integration into pseudo-attB sites in the human genome and off-targets generated via guide- and Cas9-dependent editing in the human genome (FIG. 39E). While Bxb1 lacks documented integration into the human genome at pseudo-attachment sites, potential sites with partial similarity to the natural Bxb1 attB core sequence were computationally identified. Bxb1 integration by ddPCR across these sites was tested and no off-target activity was found (FIGS. 39F and 40B-D). To assay Cas9 off-targets for the ACTB pegRNA, two potential off-target sites were identified via computational prediction and no off-target integration for PASTE was found (FIGS. 39G and 40A-D), but substantial off-target activity by HITI at one of the sites was found (FIGS. 39H and 40A-D).

Figure 39I:
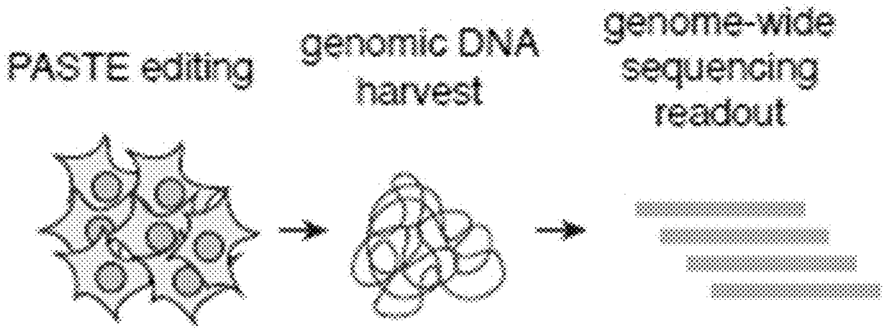
FIG. 39I shows a schematic of next-generation sequencing method to assay genome-wide off-target integration sites by PASTE according to embodiments of the present teachings.
Figure 39J:
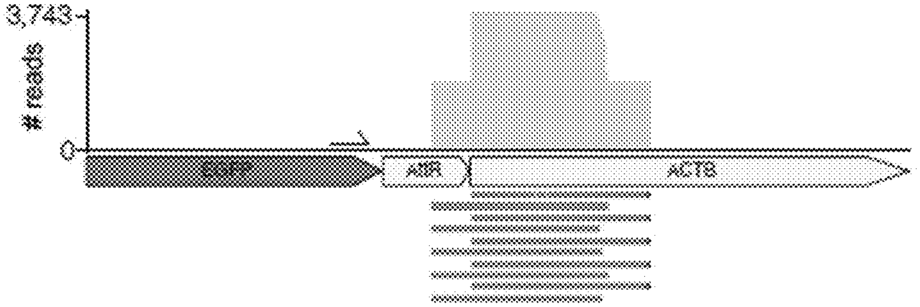
FIG. 39J shows the alignment of reads at the on-target ACTB site using a genome-wide integration assay, wherein expected on-target integration outcomes are shown according to embodiments of the present teachings.
Figure 39K:
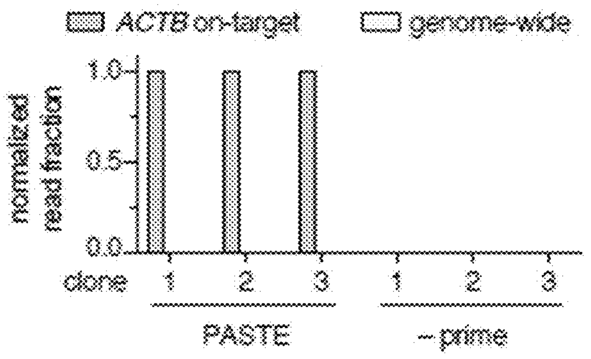
FIG. 39K shows the analysis of on-target and off-target integration events across 3 single-cell clones for PASTE and 3 single-cell clones for no prime condition according to embodiments of the present teachings.
Figure 39L:
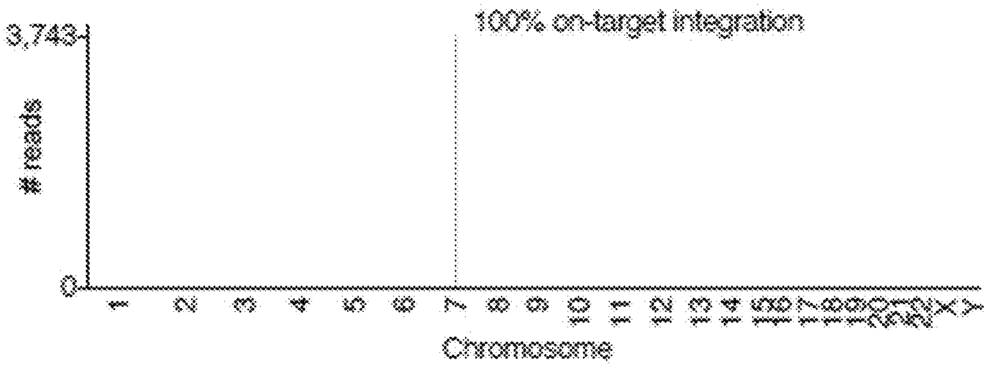
FIG. 39L shows a Manhattan plot of integration events for a representative single-cell clone with PASTE editing, wherein the on-target site is at the ACTB gene on chromosome 7 according to embodiments of the present teachings.

Genome-wide off-targets due to either Cas9 or Bxb1 through tagging and PCR amplification of insert-genomic junctions were additionally assessed (FIG. 39I). Single cell clones were isolated for conditions with PASTE editing and negative controls missing PE2, and deep sequencing of insert genomic junctions from these clones showed all reads aligning to the on-target ACTB site, confirming no off-target genomic insertions (FIGS. 39J-L).

Expression of reverse transcriptases and integrases involved in PASTE can have detrimental effects on cellular health. The complete PASTE system, the corresponding guides and cargo with only PE2, and the corresponding guides and cargo with only Bxb1 were transfected and compared to both GFP control transfections and guides without protein expression via transcriptome-wide RNA sequencing to determine the extent of these effects. While Bxb1 expression in the absence of Prime editing was found to have several significant off targets, the complete PASTE system had only one differentially regulated gene with more than a 1.5-fold change (FIGS. 41A-B). Genes upregulated by Bxb1 overexpression included stress response genes, such as TENT5C and DDIT3, but these changes were not seen in the expression of the PASTE system (FIG. 41C), potentially due to the decreased expression of Bxb1 from the P2A linker on the PASTE construct.

Example 25

PASTE Efficiency in Non-Dividing Cell

PASTE activity in non-dividing cells was assessed. Cas9 and HDR templates or PASTE were transfected into HEK293FT cells and cell division was arrested via aphidicolin treatment (FIG. 42A). In this model of blocked cell division, PASTE was found to maintain a GFP gene integration activity greater than 20% at the ACTB locus whereas HDR-mediated integration was abolished (FIGS. 42B and 43A).

Example 26

Production and Secretion of Therapeutic Transgene

PASTE with larger transgenes and in additional cell lines were assessed.

To evaluate the size limits for therapeutic transgenes, insertion of cargos up to 13.3 kb in length in both dividing and aphidicolin treated cells was assessed. Insertion efficiency greater than 10% was found (FIG. 42C), enabling insertion of ~99.7% of all full-length human cDNA transgenes. To overcome reduction of large insert delivery to cells because of delivery inefficiencies, delivering larger DNA amounts of insert was found to significantly improve gene integration efficiency (FIG. 43B). PASTE editing to additional cell types such as PASTE in the K562 lymphoblast line and in primary human T cells were also assessed. Both PE2-P2A-Bxb1 (PASTE) and separate delivery of PE2 and Bxb1 were found to result in efficient editing in both cell types (FIGS. 42D-E). Lastly, as therapeutic delivery of PASTE in vivo might require viral delivery of the DNA cargo, whether AAV could deliver an attP containing payload that could be integrated into the genome via Bxb1 was evaluated. Targeting the ACTB locus, AAV was found to be capable of delivering the appropriate template for integrase mediated insertion with rates up to 4% in a dose dependent fashion (FIGS. 42F and 43C).

To improve the efficiency of PASTE, PE2* NLS was incorporated for prime editing and improved PASTE integration at multiple loci was found (FIG. 44A). Furthermore, PE2* resulted in more robust integration at lower titrations of cargo plasmid, demonstrating integration at amounts as low as 8 ng of plasmid (FIG. 44B). To combat reductions in PASTE efficiency due to incomplete plasmid delivery, a puromycin resistance gene was co-delivered and found to increase the PASTE efficiency in the presence of drug selection (FIG. 45).

Programmable gene integration provides a modality for expression of therapeutic protein products, and protein production was assessed for therapeutically relevant proteins Alpha-1 antitrypsin (encoded by SERPINA1) and Carbamoyl phosphate synthetase I (encoded by CPS1), involved in the diseases Alpha-1 antitrypsin deficiency and CPS1 deficiency, respectively. By tagging gene products with the luminescent protein subunit HiBiT, the transgene production and secretion were assessed independently in response to PASTE treatment (FIG. 42G). PASTE was transfected with SERPINA1 or CPS1 cargo in HEK293FT cells and a human hepatocellular carcinoma cell line (HepG2) and efficient integration at the ACTB locus was found (FIG. 42H-I). This integration resulted in robust protein expression, intracellular accumulation of transgene products (FIGS. 42J and 46A-B), and secretion of proteins into the media (FIG. 42K).

Example 27

Optimized PASTE Constructs

To optimize complex activity, a panel of protein modifications were screened, including alternative reverse transcriptase fusions and mutations, various linkers between the reverse transcriptase domain and integrase and between the Cas9 and reverse transcriptase domain, and reverse transcriptase and BxbINT domain mutants (FIG. 47A and FIG. 49C-FIG. 49F). A number of protein modifications, including a 48 residue XTEN linker between the Cas9 and reverse transcriptase and the fusion of MMuLV to the Sto7d DNA binding domain (Oscorbin et al. FEBS Lett. 594. 4338-4356. 2020) improved editing efficiency (FIG. 47A and FIG. 49C-FIG. 49D). When these top modifications were combined with a GGGGS linker (SEQ ID NO: 420) between the reverse transcriptase-Sto7d domain and the BxbINT, they produced ~55% gene integration, highlighting the importance of directly recruiting the integrase to the target site (FIG. 47A). This optimized construct was referred to as SpCas9-(XTEN-48)-RT-Sto7d-(GGGGS)-BxbINT. The optimized contruct achieved precise integration of templates as large as 36,000 bp with ~20% integration efficiency (FIG. 47A), with complete integration of the full-length cargo confirmed by Sanger sequencing.

Additionally, pegRNAs containing different AttB length truncations were tested and found that prime editing was capable of inserting sequences up to 56 bp at the beta-actin (ACTB) gene locus, with higher efficiency at lengths below 31 bp (FIG. 48A-FIG. 48B). A panel of multiple enzymes was evaluated, including Bxb1 (i.e., BxbINT), TP901 (i.e., Tp9INT), and phiBT1 (i.e., Bt1INT) phage serine integrases. Prime editing successfully inserted all landing sites tested, with efficiencies between 10-30% (FIG. 48C-FIG. 48D)

Example 28

Viral Delivery & In Vivo Editing

In order to package the complete PASTE system in viral vectors, an AdV vector was utilized (FIG. 50B). Adenovirus was evaluated for if it could deliver a suitable template for BxbINT-mediated insertion along with plasmids for SpCas9-RT-BxbINT and guide expression, or AdV delivery of guides and BxbINT with plasmid delivery of SpCas9-RT, finding that 10-20% integration of the ~36 kb adenovirus genome carrying EGFP in HEK293FT and HepG2 cells was achieved (FIG. 50C). Upon packaging and delivering the cargo and PASTE system components across 3 AdV vectors, the complete PASTE system (Cas9-reverse transcriptase, integrase and guide RNAs, or cargo) could be substituted by adenoviral delivery, with integration of up to ~50-60% with viral-only delivery in HEK293FT and HepG2 cells (FIG. 50D).

To further demonstrate PASTE would be amenable for in vivo delivery, an mRNA version of the PASTE protein components was developed as well as chemically-modified synthetic atgRNA and nicking guide against the LMNB1 target (FIG. 50E). Electroporation of the mRNA and guides along with delivery of the template via adenovirus or plasmid yielded high efficiency integration up to ~23% (FIG. 50E-FIG. 50F). More sustained BxbINT expression could allow for integration into newly placed AttB sites in the genome, so circular mRNA expression was tested and found to boost the efficiency of integration to ~30% (FIG. 50G-FIG. 50I).

Example 29

Simultaneous Deletion & Insertion with PASTE

The PASTE system was used to simultaneously delete one sequence and insert another. 130 bp and 385 bp deletions of first exon of LMNB1 with combined insertion of AttB nucleic acid sequence was performed (FIG. 51A). This data shows that it is possible to replace DNA sequence using the PASTE system.

A130 bp deletion of the first exon of LMNB1 with combined insertion of a 967 bp cargo using the PASTE system was also performed.

One of two attP sequences were inserted using the mini circle template that has mutated AttP, as described above. This AttP mutants shows better integration kinetics and efficiency, especially for the shorter AttBs (38-44 bp). The LMNB1 AttB used in this experiment is 38 bp (FIG. 51B).

What is claimed is:

1. A method of site-specifically integrating an exogenous nucleic acid sequence into a mammalian cell genome or intracellular target nucleic acid, the method comprising:

(a) incorporating at least one integration sequence at a specific target site in the cell genome or intracellular target nucleic acid by introducing ex vivo into a mammalian cell:

(i) an expressible polynucleotide construct encoding an editing polypeptide, wherein the editing polypeptide comprises a DNA binding nuclease domain linked via a linker to a reverse transcriptase domain, wherein the DNA binding nuclease domain comprises a nickase activity; and (ii) a guide RNA (gRNA) comprising a targeting sequence, a primer binding sequence, and a complement of the at least one integration sequence, wherein the gRNA interacts with the expressed editing polypeptide to target direct the editing polypeptide to the specific target site of the cell genome or intracellular target nucleic acid, wherein the DNA binding nuclease domain nicks a strand of the cell genome or intracellular target nucleic acid to form a nicked site, and wherein the reverse transcriptase domain reverse transcribes the complement of the at least one integration sequence within the gRNA and thereby incorporates the at least one integration sequence into the nicked site, thereby incorporating the at least one integration sequence at the specific target site of the cell genome or intracellular target nucleic acid; and (b) integrating an exogenous nucleic acid sequence into the cell genome or intracellular target nucleic acid by introducing into the cell:

(i) the exogenous nucleic acid sequence linked to a sequence that is an integration cognate to the site-specifically incorporated-integration sequence; and (ii) an expressible polynucleotide construct encoding an integration enzyme, wherein the integration enzyme integrates the exogenous nucleic acid sequence into the cell genome or the intracellular target nucleic acid at the at least one site-specifically incorporated integration sequence, thereby site-specifically integrating the exogenous nucleic acid sequence into the cell genome or the intracellular target nucleic acid, wherein the expressible polynucleotide encoding the editing polypeptide, the gRNA, the expressible polynucleotide construct encoding the integration enzyme, and the exogenous nucleic acid sequence are introduced into the mammalian cell concurrently.

2. The method of claim 1, wherein the gRNA, the expressible polynucleotide construct encoding the editing polypeptide, and the expressible polynucleotide construct encoding the integration enzyme are introduced into the mammalian cell using a virus, a RNP, an mRNA, a lipid, or a polymeric nanoparticle.

3. The method of claim 1, wherein the gRNA hybridizes to a strand of the mammalian cell genome.

4. The method of claim 1, wherein the exogenous nucleic acid is introduced into the mammalian cell as an adeno-associated virus (AAV) or an adenovirus (AdV).

5. The method of claim 1, wherein the exogenous nucleic acid is introduced into the mammalian cell as a minicircle, a plasmid, mRNA, or a linear DNA.

6. The method of claim 5, wherein the minicircle does not comprise a sequence of a bacterial origin.

7. The method of claim 1, wherein the linker is cleavable.

8. The method of claim 1, wherein the linker is non-cleavable.

9. The method of claim 1, wherein the linker is two associating binding domains of the DNA binding nuclease linked to a reverse transcriptase.

10. The method of claim 1, wherein the integration enzyme is selected from the group consisting of Dre, Vika, Bxbl, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc 1, Tc3, Mariner Himar 1, Mariner mos 1, and Minos, and any mutants thereof.

11. The method of claim 1, wherein the integration sequence is an attB sequence, an attP sequence, an attL sequence, an attR sequence, a lox71 sequence, a Vox sequence, or a FRT sequence.

12. The method of claim 1, wherein the DNA binding nuclease domain comprising a nickase activity is selected from Cas9-D10A, Cas9-H840A, and Cas12a/b nickase.

13. The method of claim 1, wherein the reverse transcriptase domain comprises a mutation relative to a wild-type sequence.

14. The method of claim 1, wherein the reverse transcriptase domain is selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium* rectale maturase RT.

15. The method of claim 14, wherein the M-MLV reverse transcriptase domain comprises one or more mutations selected from the group consisting of D200N, T306K, W313F, T3301P, and L603W.

16. The method of claim 1, further comprising introducing a nicking guide RNA (ngRNA).

17. The method claim 1, wherein:

the exogenous nucleic acid is a reporter gene;

the exogenous nucleic acid is a degradation tag for programmable knockdown of proteins in the presence of small molecules;

the exogenous nucleic acid is a T-cell receptor (TCR), a chimeric antigen receptor (CAR), an interleukin, a cytokine, or an immune checkpoint gene and the mammalian cell is a T-cell or natural killer (NK) cell;

the exogenous nucleic acid is a beta hemoglobin (HBB) gene and the cell is a hematopoietic stem cell (HSC);

the exogenous nucleic acid is a metabolic gene; or the exogenous nucleic acid is a gene involved in an inherited disease or an inherited syndrome.

18. The method of claim 17, wherein the reporter gene is a fluorescent protein.

19. The method of claim 1, wherein the mammalian cell is a dividing cell or a non-dividing cell.

20. The method of claim 1, wherein:

the exogenous nucleic acid is between 1000 bp and 36,000 bp;

the exogenous nucleic acid is more than 36,000 bp; or the exogenous nucleic acid is less than 1000 bp.

21. The method of claim 17 wherein the inherited disease is cystic fibrosis, familial hypercholesterolemia, adenosine deaminase (ADA) deficiency, X-linked SCID (X-SCID), Wiskott-Aldrich syndrome (WAS), hemochromatosis, Tay- Sachs, fragile X syndrome, Huntington's disease, Marfan syndrome, phenylketonuria, or muscular dystrophy.

22. A method of site-specifically integrating an exogenous nucleic acid sequence into a mammalian cell genome or intracellular target nucleic acid, the method comprising:

(a) incorporating at least one integration sequence at a specific target site in the cell genome or intracellular target nucleic acid by introducing ex vivo into a mammalian cell:

(i) an expressible polynucleotide construct encoding an editing polypeptide, wherein the editing polypeptide comprises a DNA-binding nuclease domain linked via a linker to a reverse transcriptase domain, wherein the DNA-binding nuclease domain comprises a nickase activity; and (ii) an expressible polynucleotide construct encoding a guide RNA (gRNA) comprising a targeting sequence, a primer binding sequence, and a complement of the at least one integration sequence, wherein the gRNA interacts with the expressed editing polypeptide to direct the editing polypeptide to the specific target site of the cell genome or intracellular target nucleic acid, wherein the DNA-binding nuclease domain nicks a strand of the cell genome or intracellular target nucleic acid to form a nicked site, and wherein the reverse transcriptase domain reverse transcribes the complement of the at least one integration sequence and thereby incorporates the at least one integration sequence into the nicked site, thereby incorporating the at least one integration sequence at the specific target site of the cell genome or intracellular target nucleic acid; and (b) integrating the exogenous nucleic acid sequence into the cell genome or intracellular target nucleic acid by introducing into the mammalian cell:

(i) an exogenous nucleic acid sequence linked to a sequence that is an integration cognate to the site-specifically incorporated integration sequence; and (ii) an expressible polynucleotide construct encoding an integration enzyme, wherein the integration enzyme integrates the exogenous nucleic acid into the cell genome or intracellular target nucleic acid at the at least one site-specifically incorporated integration sequence, thereby site-specifically integrating the exogenous nucleic acid into the cell genome or the intracellular target nucleic acid, wherein the integration sequence is an attB sequence, an attP sequence, an attL sequence, an attR sequence, a lox71 sequence, a Vox sequence, or a FRT sequence, wherein the integration sequence is longer than 38 base-pairs, and wherein the expressible polynucleotide constructs encoding the editing polypeptide, the gRNA, and the integration enzyme, and the exogenous nucleic acid, are introduced into the mammalian cell concurrently.

23. The method of claim 22, wherein the integration sequence is 40, 42, 44, or 46 base pairs.

* * * * *

UNITED STATES PATENT AND TRADEMARK OFFICE

CERTIFICATE OF CORRECTION

PATENT NO. : 11,572,556 B2
APPLICATION NO. : 17/649308
DATED : February 7, 2023
INVENTOR(S) : Abudayyeh et al.

It is certified that error appears in the above-identified patent and that said Letters Patent is hereby corrected as shown below:

In the Specification

In Column 1, Lines 16-18, delete:
"This invention was made with government support under EB031057 by the National Institutes of Health. The government has certain rights in the invention."

And insert:
-- This invention was made with government support under EB031957 awarded by the National Institutes of Health. The government has certain rights in the invention. --

Signed and Sealed this
Eleventh Day of November, 2025

John A. Squires
*Director of the United States Patent and Trademark Office*

SEQUENCE LISTING

<160> NUMBER OF SEQ ID NOS: 431

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Lox71

<400> SEQUENCE: 1
ataacttcgt ataatgtatg ctatacgaac ggta 34

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Lox66

<400> SEQUENCE: 2
taccgttcgt ataatgtatg ctatacgaag ttat 34

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttB

<400> SEQUENCE: 3
ggccggcttg tcgacgacgg cggtctccgt cgtcaggatc atccgg 46

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttP

<400> SEQUENCE: 4
ccggatgatc ctgacgacgg agaccgccgt cgtcgacaag ccggcc 46

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttB-TT

<400> SEQUENCE: 5
ggcttgtcga cgacggcgtt ctccgtcgtc aggatcat 38

<210> SEQ ID NO 6

```
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-TT

<400> SEQUENCE: 6

gtggtttgtc tggtcaacca ccgcgttctc agtggtgtac ggtacaaacc ca            52


<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-AA

<400> SEQUENCE: 7

ggcttgtcga cgacggcgaa ctccgtcgtc aggatcat                            38


<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-AA

<400> SEQUENCE: 8

gtggtttgtc tggtcaacca ccgcgaactc agtggtgtac ggtacaaacc ca            52


<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-CC

<400> SEQUENCE: 9

ggcttgtcga cgacggcgcc ctccgtcgtc aggatcat                            38


<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-CC

<400> SEQUENCE: 10

gtggtttgtc tggtcaacca ccgcgccctc agtggtgtac ggtacaaacc ca            52


<210> SEQ ID NO 11
<211> LENGTH: 38
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: AttB-GG

<400> SEQUENCE: 11

ggcttgtcga cgacggcggg ctccgtcgtc aggatcat                            38


<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-GG

<400> SEQUENCE: 12

gtggtttgtc tggtcaacca ccgcgggctc agtggtgtac ggtacaaacc ca            52


<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-TG

<400> SEQUENCE: 13

ggcttgtcga cgacggcgtg ctccgtcgtc aggatcat                            38


<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-TG

<400> SEQUENCE: 14

gtggtttgtc tggtcaacca ccgcgtgctc agtggtgtac ggtacaaacc ca            52


<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-GT

<400> SEQUENCE: 15

ggcttgtcga cgacggcggt ctccgtcgtc aggatcat                            38


<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-GT
```

<400> SEQUENCE: 16
gtggtttgtc tggtcaacca ccgcggtctc agtggtgtac ggtacaaacc ca 52

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-CT

<400> SEQUENCE: 17
ggcttgtcga cgacggcgct ctccgtcgtc aggatcat 38

<210> SEQ ID NO 18
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttP-CT

<400> SEQUENCE: 18
gtggtttgtc tggtcaacca ccgcgctctc agtggtgtac ggtacaaacc ca 52

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-CA

<400> SEQUENCE: 19
ggcttgtcga cgacggcgca ctccgtcgtc aggatcat 38

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttP-CA

<400> SEQUENCE: 20
gtggtttgtc tggtcaacca ccgcgcactc agtggtgtac ggtacaaacc ca 52

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-TC

<400> SEQUENCE: 21
ggcttgtcga cgacggcgtc ctccgtcgtc aggatcat 38

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-TC

<400> SEQUENCE: 22
gtggtttgtc tggtcaacca ccgcgtcctc agtggtgtac ggtacaaacc ca 52

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-GA

<400> SEQUENCE: 23
ggcttgtcga cgacggcgga ctccgtcgtc aggatcat 38

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-GA

<400> SEQUENCE: 24
gtggtttgtc tggtcaacca ccgcggactc agtggtgtac ggtacaaacc ca 52

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttB-AG

<400> SEQUENCE: 25
ggcttgtcga cgacggcgag ctccgtcgtc aggatcat 38

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AttP-AG

<400> SEQUENCE: 26
gtggtttgtc tggtcaacca ccgcgagctc agtggtgtac ggtacaaacc ca 52

<210> SEQ ID NO 27
<211> LENGTH: 38

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-AC

<400> SEQUENCE: 27
ggcttgtcga cgacggcgac ctccgtcgtc aggatcat 38

<210> SEQ ID NO 28
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttP-AC

<400> SEQUENCE: 28
gtggtttgtc tggtcaacca ccgcgacctc agtggtgtac ggtacaaacc ca 52

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-AT

<400> SEQUENCE: 29
ggcttgtcga cgacggcgat ctccgtcgtc aggatcat 38

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttP-AT

<400> SEQUENCE: 30
gtggtttgtc tggtcaacca ccgcgatctc agtggtgtac ggtacaaacc ca 52

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-GC

<400> SEQUENCE: 31
ggcttgtcga cgacggcggc ctccgtcgtc aggatcat 38

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttP-GC

<400> SEQUENCE: 32
gtggtttgtc tggtcaacca ccgcggcctc agtggtgtac ggtacaaacc ca 52

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-CG

<400> SEQUENCE: 33
ggcttgtcga cgacggcgcg ctccgtcgtc aggatcat 38

<210> SEQ ID NO 34
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-CG

<400> SEQUENCE: 34
gtggtttgtc tggtcaacca ccgcgcgctc agtggtgtac ggtacaaacc ca 52

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttB-TA

<400> SEQUENCE: 35
ggcttgtcga cgacggcgta ctccgtcgtc aggatcat 38

<210> SEQ ID NO 36
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: AttP-TA

<400> SEQUENCE: 36
gtggtttgtc tggtcaacca ccgcgtactc agtggtgtac ggtacaaacc ca 52

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: C-31-B

<400> SEQUENCE: 37
tgcgggtgcc agggcgtgcc cttgggctcc ccgggcgcgt actcc 45

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: C31-P

<400> SEQUENCE: 38
gtgccccaac tggggtaacc tttgagttct ctcagttggg gg 42

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: R4-B

<400> SEQUENCE: 39
gcgcccaagt tgcccatgac catgccgaag cagtggtaga agggcaccgg cagacac 57

<210> SEQ ID NO 40
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: R4-P

<400> SEQUENCE: 40
aggcatgttc cccaaagcga taccacttga agcagtggta ctgcttgtgg gtacactctg 60
cgggtgatga 70

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: BT1-B

<400> SEQUENCE: 41
gtccttgacc aggtttttga cgaaagtgat ccagatgatc cagctccaca ccccgaacgc 60

<210> SEQ ID NO 42
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: BT1-P

<400> SEQUENCE: 42
ggtgctgggt tgttgtctct ggacagtgat ccatgggaaa ctactcagca ccaccaatgt 60
tcc 63

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Bxb-B

<400> SEQUENCE: 43
tcggccggct tgtcgacgac ggcggtctcc gtcgtcagga tcatccgggc 50

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Bxb-P

<400> SEQUENCE: 44
gtcgtggttt gtctggtcaa ccaccgcggt ctcagtggtg tacggtacaa accccgac 58

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: TG1-B

<400> SEQUENCE: 45
gatcagctcc gcgggcaaga ccttctcctt cacggggtgg aaggtc 46

<210> SEQ ID NO 46
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: TG1-P

<400> SEQUENCE: 46
tcaaccccgt tccagcccaa cagtgttagt ctttgctctt acccagttgg gcgggatagc 60
ctgcccg 67

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: C1-B

<400> SEQUENCE: 47
aacgattttc aaaggatcac tgaatcaaaa gtattgctca tccacgcgaa atttttc 57

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: C1-P

<400> SEQUENCE: 48
aatattttag gtatatgatt ttgtttatta gtgtaaataa cactatgtac ctaaaat 57

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: C370-B

<400> SEQUENCE: 49
tgtaaaggag actgataatg gcatgtacaa ctatactcgt cggtaaaaag gca 53

<210> SEQ ID NO 50
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: C370-P

<400> SEQUENCE: 50
taaaaaaata cagcgttttt catgtacaac tatactagtt gtagtgccta aa 52

<210> SEQ ID NO 51
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: K38-B

<400> SEQUENCE: 51
gagcgccgga tcagggagtg gacggcctgg gagcgctaca cgctgtggct gcggtc 56

<210> SEQ ID NO 52
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: K38-P

<400> SEQUENCE: 52
ccctaatacg caagtcgata actctcctgg gagcgttgac aacttgcgca ccctga 56

<210> SEQ ID NO 53

<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: RB-B

<400> SEQUENCE: 53
tctcgtggtg gtggaaggtg ttggtgcggg gttggccgtg gtcgaggtgg ggtggtggta 60
gccattcg 68

<210> SEQ ID NO 54
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: RV-P

<400> SEQUENCE: 54
gcacaggtgt agtgtatctc acaggtccac ggttggccgt ggactgctga agaacattcc 60
acgccagga 69

<210> SEQ ID NO 55
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: SPBC-B

<400> SEQUENCE: 55
agtgcagcat gtcattaata tcagtacaga taaagctgta tctcctgtga acacaatggg 60
tgcca 65

<210> SEQ ID NO 56
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: SPBC-P

<400> SEQUENCE: 56
aaagtagtaa gtatcttaaa aaacagataa agctgtatat taagatactt actac 55

<210> SEQ ID NO 57
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: TP901-B

<400> SEQUENCE: 57
tgataattgc caacacaatt aacatctcaa tcaaggtaaa tgctttttcg tttt 54

<210> SEQ ID NO 58
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: TP901-P

<400> SEQUENCE: 58
aattgcgagt ttttatttcg tttatttcaa ttaaggtaac taaaaaactc cttt 54

<210> SEQ ID NO 59
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Wbeta-B

<400> SEQUENCE: 59
aaggtagcgt caacgatagg tgtaactgtc gtgtttgtaa cggtacttcc aacagctggc 60
gtttcagt 68

<210> SEQ ID NO 60
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Wbeta-P

<400> SEQUENCE: 60
tagttttaaa gttggttatt agttactgtg atatttatca cggtacccaa taaccaatga 60
atatttga 68

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: A118-B

<400> SEQUENCE: 61
tgtaactttt tcggatcaag ctatgaagga cgcaaagagg gaactaaaca cttaatt 57

<210> SEQ ID NO 62
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: A118-P

<400> SEQUENCE: 62
ttgtttagtt cctcgttttc tctcgttgga agaagaagaa acgagaaact aaaatta 57

<210> SEQ ID NO 63
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: BL3-B

<400> SEQUENCE: 63
caacctgttg acatgtttcc acagacaact cacgtggagg tagtcacggc ttttacgtta 60
gtt 63

<210> SEQ ID NO 64
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: BL3-P

<400> SEQUENCE: 64
gagaatactg ttgaacaatg aaaaactagg catgtagaag ttgtttgtgc actaacttta 60
a 61

<210> SEQ ID NO 65
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: MR11-B

<400> SEQUENCE: 65
acaggtcaac acatcgcagt tatcgaacaa tcttcgaaaa tgtatggagg cacttgtatc 60
aatataggat gtataccttc gaagacactt gtacatgatg gattagaagg caaatccttt 120

<210> SEQ ID NO 66
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: MR11-P

<400> SEQUENCE: 66
caaaataaaa aacattgatt tttattaact tcttttgtgc ggaactacga acagttcatt 60
aatacgaagt gtacaaactt ccatacaaaa ataaccacga caattaagac gtggtttcta 120

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttL

<400> SEQUENCE: 67
attatttctc accctga 17

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AttR

<400> SEQUENCE: 68
atcatctccc acccgga 17

<210> SEQ ID NO 69
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Vox

<400> SEQUENCE: 69
aataggtctg agaacgccca ttctcagacg tatt 34

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: FRT

<400> SEQUENCE: 70
gaagttccta tactttctag agaataggaa cttc 34

<210> SEQ ID NO 71
<211> LENGTH: 5881
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cre Recombinase Expression Plasmid

<400> SEQUENCE: 71
ggtcgacatt gattattgac tagttattaa tagtaatcaa ttacggggtc attagttcat 60
agcccatata tggagttccg cgttacataa cttacggtaa atggcccgcc tggctgaccg 120
cccaacgacc cccgcccatt gacgtcaata atgacgtatg ttcccatagt aacgccaata 180
gggactttcc attgacgtca atgggtggag tatttacggt aaactgccca cttggcagta 240
catcaagtgt atcatatgcc aagtacgccc cctattgacg tcaatgacgg taaatggccc 300
gcctggcatt atgcccagta catgacctta tgggactttc ctacttggca gtacatctac 360
gtattagtca tcgctattac catggtcgag gtgagcccca cgttctgctt cactctcccc 420
atctcccccc cctccccacc cccaattttg tatttattta ttttttaatt attttgtgca 480
gcgatggggg cggggggggg gggggcgcgc gccaggcggg gggggggggg gggggggggg 540

```
gggggggggg gggcgggggg gggcggcggc agccaatcag agcggcgcgc tccgaaagtt    600
tccttttatg gcgaggcggc ggcggcggcg gccctataaa aagcgaagcg cgcggcgggc    660
gggagtcgct gcgcgctgcc ttcgccccgt gccccgctcc gccgccgcct cgcgccgccc    720
gccccggctc tgactgaccg cgttactccc acaggtgagc gggcgggacg gcccttctcc    780
tccgggctgt aattagcgct tggtttaatg acggcttgtt tcttttctgt ggctgcgtga    840
aagccttgag gggctccggg agggcccttt gtgcgggggg agcggctcgg ggggtgcgtg    900
cgtgtgtgtg tgcgtgggga gcgccgcgtg cggctccgcg ctgcccggcg gctgtgagcg    960
ctgcgggcgc ggcgcggggc tttgtgcgct ccgcagtgtg cgcgagggga gcgcggccgg   1020
gggcggtgcc ccgcggtgcg gggggggctg cgaggggaac aaaggctgcg tgcggggtgt   1080
gtgcgtgggg gggtgagcag ggggtgtggg cgcgtcggtc gggctgcaac ccccccctgca   1140
ccccccctccc cgagttgctg agcacggccc ggcttcgggt gcggggctcc gtacggggcg   1200
tggcgcgggg ctcgccgtgc cgggcggggg gtggcggcag gtgggggtgc cgggcggggc   1260
ggggccgcct cgggccgggg agggctcggg ggaggggcgc ggcggccccc ggagcgccgg   1320
cggctgtcga ggcgcggcga gccgcagcca ttgcctttta tggtaatcgt gcgagagggc   1380
gcagggactt cctttgtccc aaatctgtgc ggagccgaaa tctgggaggc gccgccgcac   1440
cccctctagc gggcgcgggg cgaagcggtg cggcgccggc aggaaggaaa tgggcgggga   1500
gggccttcgt gcgtcgccgc gccgccgtcc ccttctccct ctccagcctc ggggctgtcc   1560
gcggggggac ggctgccttc ggggggggacg gggcagggcg gggttcggct tctggcgtgt   1620
gaccggcggc tctagagcct ctgctaacca tgttcatgcc ttcttctttt tcctacagct   1680
cctgggcaac gtgctggtta ttgtgctgtc tcatcatttt ggcaaagaat tctgagccgc   1740
caccatggcc aatttactga ccgtacacca aaatttgcct gcattaccgg tcgatgcaac   1800
gagtgatgag gttcgcaaga acctgatgga catgttcagg gatcgccagg cgtttttctga   1860
gcatacctgg aaaatgcttc tgtccgtttg ccggtcgtgg gcggcatggt gcaagttgaa   1920
taaccggaaa tggtttcccg cagaacctga agatgttcgc gattatcttc tatatcttca   1980
ggcgcgcggt ctggcagtaa aaactatcca gcaacatttg ggccagctaa acatgcttca   2040
tcgtcggtcc gggctgccac gaccaagtga cagcaatgct gtttcactgg ttatgcggcg   2100
gatccgaaaa gaaaacgttg atgccggtga acgtgcaaaa caggctctag cgttcgaacg   2160
cactgatttc gaccaggttc gttcactcat ggaaaatagc gatcgctgcc aggatatacg   2220
taatctggca tttctggggga ttgcttataa caccctgtta cgtatagccg aaattgccag   2280
gatcagggtt aaagatatct cacgtactga cggtgggaga atgttaatcc atattggcag   2340
aacgaaaacg ctggttagca ccgcaggtgt agagaaggca cttagcctgg gggtaactaa   2400
actggtcgag cgatggattt ccgtctctgg tgtagctgat gatccgaata actacctgtt   2460
ttgccgggtc agaaaaaatg gtgttgccgc gccatctgcc accagccagc tatcaactcg   2520
cgccctggaa gggatttttg aagcaactca tcgattgatt tacggcgcta aggatgactc   2580
tggtcagaga tacctggcct ggtctggaca cagtgcccgt gtcggagccg cgcgagatat   2640
ggcccgcgct ggagtttcaa taccggagat catgcaagct ggtggctgga ccaatgtaaa   2700
tattgtcatg aactatatcc gtaacctgga tagtgaaaca ggggcaatgg tgcgcctgct   2760
ggaagatggc gatggaccgg tggaacaaaa acttatttct gaagaagatc tgtgatagcg   2820
gccgcactcc tcaggtgcag gctgcctatc agaaggtggt ggctggtgtg gccaatgccc   2880
```

-continued

```
tggctcacaa ataccactga gatctttttc cctctgccaa aaattatggg gacatcatga   2940
agccccttga gcatctgact tctggctaat aaaggaaatt tattttcatt gcaatagtgt   3000
gttggaattt tttgtgtctc tcactcggaa ggacatatgg gagggcaaat catttaaaac   3060
atcagaatga gtatttggtt tagagtttgg caacatatgc ccatatgctg gctgccatga   3120
acaaaggttg gctataaaga ggtcatcagt atatgaaaca gccccctgct gtccattcct   3180
tattccatag aaaagccttg acttgaggtt agattttttt tatattttgt tttgtgttat   3240
tttttctttt aacatcccta aaattttcct tacatgtttt actagccaga tttttcctcc   3300
tctcctgact actcccagtc atagctgtcc ctcttctctt atggagatcc ctcgacctgc   3360
agcccaagct tggcgtaatc atggtcatag ctgtttcctg tgtgaaattg ttatccgctc   3420
acaattccac acaacatacg agccggaagc ataaagtgta aagcctgggg tgcctaatga   3480
gtgagctaac tcacattaat tgcgttgcgc tcactgcccg ctttccagtc gggaaacctg   3540
tcgtgccagc ggatccgcat ctcaattagt cagcaaccat agtcccgccc ctaactccgc   3600
ccatcccgcc cctaactccg cccagttccg cccattctcc gccccatggc tgactaattt   3660
tttttattta tgcagaggcc gaggccgcct cggcctctga gctattccag aagtagtgag   3720
gaggcttttt tggaggccta ggcttttgca aaaagctaac ttgtttattg cagcttataa   3780
tggttacaaa taaagcaata gcatcacaaa tttcacaaat aaagcatttt tttcactgca   3840
ttctagttgt ggtttgtcca aactcatcaa tgtatcttat catgtctgga tccgctgcat   3900
taatgaatcg gccaacgcgc ggggagaggc ggtttgcgta ttgggcgctc ttccgcttcc   3960
tcgctcactg actcgctgcg ctcggtcgtt cggctgcggc gagcggtatc agctcactca   4020
aaggcggtaa tacggttatc cacagaatca ggggataacg caggaaagaa catgtgagca   4080
aaaggccagc aaaaggccag gaaccgtaaa aaggccgcgt tgctggcgtt tttccatagg   4140
ctccgccccc ctgacgagca tcacaaaaat cgacgctcaa gtcagaggtg gcgaaacccg   4200
acaggactat aaagatacca ggcgtttccc cctggaagct ccctcgtgcg ctctcctgtt   4260
ccgaccctgc cgcttaccgg atacctgtcc gcctttctcc cttcgggaag cgtggcgctt   4320
tctcatagct cacgctgtag gtatctcagt tcggtgtagg tcgttcgctc caagctgggc   4380
tgtgtgcacg aaccccccgt tcagcccgac cgctgcgcct tatccggtaa ctatcgtctt   4440
gagtccaacc cggtaagaca cgacttatcg ccactggcag cagccactgg taacaggatt   4500
agcagagcga ggtatgtagg cggtgctaca gagttcttga agtggtggcc taactacggc   4560
tacactagaa gaacagtatt tggtatctgc gctctgctga agccagttac cttcggaaaa   4620
agagttggta gctcttgatc cggcaaacaa accaccgctg gtagcggtgg tttttttgtt   4680
tgcaagcagc agattacgcg cagaaaaaaa ggatctcaag aagatccttt gatcttttct   4740
acggggtctg acgctcagtg gaacgaaaac tcacgttaag ggattttggt catgagatta   4800
tcaaaaagga tcttcaccta gatcctttta aattaaaaat gaagttttaa atcaatctaa   4860
agtatatatg agtaaacttg gtctgacagt taccaatgct taatcagtga ggcacctatc   4920
tcagcgatct gtctatttcg ttcatccata gttgcctgac tccccgtcgt gtagataact   4980
acgatacggg agggcttacc atctggcccc agtgctgcaa tgataccgcg agacccacgc   5040
tcaccggctc cagatttatc agcaataaac cagccagccg gaagggccga gcgcagaagt   5100
ggtcctgcaa ctttatccgc ctccatccag tctattaatt gttgccggga agctagagta   5160
agtagttcgc cagttaatag tttgcgcaac gttgttgcca ttgctacagg catcgtggtg   5220
tcacgctcgt cgtttggtat ggcttcattc agctccggtt cccaacgatc aaggcgagtt   5280
```

acatgatccc ccatgttgtg caaaaaagcg gttagctcct tcggtcctcc gatcgttgtc 5340
agaagtaagt tggccgcagt gttatcactc atggttatgg cagcactgca taattctctt 5400
actgtcatgc catccgtaag atgcttttct gtgactggtg agtactcaac caagtcattc 5460
tgagaatagt gtatgcggcg accgagttgc tcttgcccgg cgtcaatacg ggataatacc 5520
gcgccacata gcagaacttt aaaagtgctc atcattggaa aacgttcttc ggggcgaaaa 5580
ctctcaagga tcttaccgct gttgagatcc agttcgatgt aacccactcg tgcacccaac 5640
tgatcttcag catcttttac tttcaccagc gtttctgggt gagcaaaaac aggaaggcaa 5700
aatgccgcaa aaaagggaat aagggcgaca cggaaatgtt gaatactcat actcttcctt 5760
tttcaatatt attgaagcat ttatcagggt tattgtctca tgagcggata catatttgaa 5820
tgtatttaga aaaataaaca aataggggtt ccgcgcacat ttccccgaaa agtgccacct 5880
g 5881

<210> SEQ ID NO 72
<211> LENGTH: 4915
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GFP-Lox66-Cre expression plasmid

<400> SEQUENCE: 72
agctctgatc aagagacagg atgaggatcg tttcgcatga ttgaacaaga tggattgcac 60
gcaggttctc cggccgcttg ggtggagagg ctattcggct atgactgggc acaacagaca 120
atcggctgct ctgatgccgc cgtgttccgg ctgtcagcgc aggggcgccc ggttcttttt 180
gtcaagaccg acctgtccgg tgccctgaat gaactgcaag acgaggcagc gcggctatcg 240
tggctggcca cgacgggcgt tccttgcgca gctgtgctcg acgttgtcac tgaagcggga 300
agggactggc tgctattggg cgaagtgccg gggcaggatc tcctgtcatc tcaccttgc 360 ctcctgccga gaaagtatcc atcatggctg atgcaatgcg gcggctgcat acgcttgatc 420
cggctacctg cccattcgac caccaagcga aacatcgcat cgagcgagca cgtactcgga 480
tggaagccgg tcttgtcgat caggatgatc tggacgaaga gcatcagggg ctcgcgccag 540
ccgaactgtt cgccaggctc aaggcgagca tgcccgacgg cgaggatctc gtcgtgaccc 600
atggcgatgc ctgcttgccg aatatcatgg tggaaaatgg ccgcttttct ggattcatcg 660
actgtggccg gctgggtgtg gcggaccgct atcaggacat agcgttggct acccgtgata 720
ttgctgaaga gcttggcggc gaatgggctg accgcttcct cgtgctttac ggtatcgccg 780
ctcccgattc gcagcgcatc gccttctatc gccttcttga cgagttcttc tgaattatta 840
actcgagatc cactagagtg tggcggccgc attcttataa tcagcatcat gatgtggtac 900
cacatcatga tgctgattac ccccaactga gagaactcaa aggttacccc agttggggcg 960
ggcccacaaa taaagcaata gcatcacaaa tttcacaaat aaagcatttt tttcactgca 1020
ttctagttgt ggtttgtcca aactcatcga gctcgagatc tggcgaaggc gatgggggtc 1080
ttgaaggcgt gctggtactc cacgatgccc agctcggtgt tgctgtgcag ctcctccacg 1140
cggcggaagg cgaacatggg gcccccgttc tgcaggatgc tggggtggat ggcgctcttg 1200
aagtgcatgt ggctgtccac cacgaagctg tagtagccgc cgtcgcgcag gctgaaggtg 1260
cgggcgaagc tgcccaccag cacgttatcg cccatggggt gcaggtgctc cacggtggcg 1320
ttgctgcgga tgatcttgtc ggtgaagatc acgctgtcct cggggaagcc ggtgcccacc 1380
accttgaagt cgccgatcac gcggccggcc tcgtagcggt agctgaagct cacgtgcagc 1440
acgccgccgt cctcgtactt ctcgatgcgg gtgttggtgt agccgccgtt gttgatggcg 1500
tgcaggaagg ggttctcgta gccgctgggg taggtgccga agtggtagaa gccgtagccc 1560
atcacgtggc tcagcaggta ggggctgaag gtcagggcgc ctttggtgct cttcatcttg 1620
ttggtcatgc ggccctgctc gggggtgccc tctccgccgc ccaccagctc gaactccacg 1680
ccgttcaggg tgccggtgat gcggcactcg atcttcatgg cgggcatggt ggcgaccggt 1740
agcgctagcg gcttcggata acttcgtata gcatacatta tacgaacggt aagcgctacc 1800
gccggcatac ccaagtgaag ttgctcgcag cttatagtcg cgcccgggga gcccaagggc 1860
acgccctggc accgcggccg ctgagtctcg accatcatca tcatcatcat tgagtttatc 1920
tgggataaca gggtaatgtc atctagggat aacagggtat gtcatctggg ataacagggt 1980
aatgtatcta gggataacag ggtaatgtca tctgggataa cagggtaatg tcatctaggg 2040
ataacagggt atgtcatctg ggataacagg gtaatgtatc tagggataac agggtaatgt 2100
catctgggat aacagggtaa tgtcatctag ggataacagg gtatgtcatc tgggataaca 2160
gggtaatgta tctagggata acagggtaat gtcatctggg ataacagggt aatgtcatct 2220
agggataaca gggtatgtca tctgggataa cagggtaatg tatctaggga taacagggta 2280
atgtcatctg ggataacagg gtaatgtcat ctagggataa cagggtatgt catctgggat 2340
aacagggtaa tgtatctagg gataacaggg taatgtcatc tgggataaca gggtaatgtc 2400
atctagggat aacagggtat gtcatctggg ataacagggt aatgtatcta gggataacag 2460
ggtaatgtca tctgggataa cagggtaatg tcatctaggg ataacagggt aaatgtcatc 2520
tagggataac agggtaatgt catctaggga taacagggta atgtcatctg ggataacagg 2580
gtaatgtcat ctagggataa cagggtaatg tatcgccagc gtcgcacagc atgtttgctt 2640
gtcgccgtcg cgtctgtcac atcttttccg ccagcagtta gggattagcg tcttaagctg 2700
gcgcgaggac caacgtatca gccaggcgaa gctgcttttg agcaccaccc ggatgcctat 2760
cgccaccgtc ggtcgcaatg ttggttttga cgatcaactc tatttctcgc gggtatttaa 2820
aaaatgcacc ggggccagcc cgagcgagtt ccgtgccggt tgtgaagaaa aagtgaatga 2880
tgtagccgtc aagttgtcat aattggtaac gaatcagaca attgacggct tgacggagta 2940
gcatagggtt tgcagaatcc ctgcttcgtc catttgacag gcacattatg catgccgctt 3000
cgccttcgcg cgcgaattga tctgctgcct cgcgcgtttc ggtgatgacg gtgaaaacct 3060
ctgacacatg cagctcccgg agacggtcac agcttgtctg taagcggatg ccgggagcag 3120
acaagcccgt cagggcgcgt cagcgggtgt tggcgggtgt cggggcgcag ccatgaccca 3180
gtcacgtagc gatagcggag tgtatactgg cttaactatg cggcatcaga gcagattgta 3240
ctgagagtgc accatatgcg gtgtgaaata ccgcacagat gcgtaaggag aaaataccgc 3300
atcaggcgct cttccgcttc ctcgctcact gactcgctgc gctcggtcgt tcggctgcgg 3360
cgagcggtat cagctcactc aaaggcggta atacggttat ccacagaatc aggggataac 3420
gcaggaaaga acatgtgagc aaaaggccag caaaaggcca ggaaccgtaa aaaggccgcg 3480
ttgctggcgt ttttccatag gctccgcccc cctgacgagc atcacaaaaa tcgacgctca 3540
agtcagaggt ggcgaaaccc gacaggacta taaagatacc aggcgtttcc ccctggaagc 3600
tccctcgtgc gctctcctgt tccgaccctg ccgcttaccg gatacctgtc cgcctttctc 3660
ccttcgggaa gcgtggcgct ttctcatagc tcacgctgta ggtatctcag ttcggtgtag 3720
gtcgttcgct ccaagctggg ctgtgtgcac gaaccccccg ttcagcccga ccgctgcgcc 3780
ttatccggta actatcgtct tgagtccaac ccggtaagac acgacttatc gccactggca 3840
gcagccactg gtaacaggat tagcagagcg aggtatgtag gcggtgctac agagttcttg 3900
aagtggtggc ctaactacgg ctacactaga aggacagtat ttggtatctg cgctctgctg 3960
aagccagtta ccttcggaaa aagagttggt agctcttgat ccggcaaaca aaccaccgct 4020
ggtagcggtg gtttttttgt ttgcaagcag cagattacgc gcagaaaaaa aggatctcaa 4080
gaagatcctt tgatcttttc tacggggtct gacgctcagt ggaacgaaaa ctcacgttaa 4140
gggattttgg tcatgagcgg atacatattt gaatgtattt agaaaaataa acaaaagagt 4200
ttgtagaaac gcaaaaaggc catccgtcag gatggccttc tgcttaattt gatgcctggc 4260
agtttatggc gggcgtcctg cccgccaccc tccgggccgt tgcttcgcaa cgttcaaatc 4320
cgctcccggc ggatttgtcc tactcaggag agcgttcacc gacaaacaac agataaaacg 4380
aaaggcccag tctttcgact gagcctttcg ttttatttga tgcctggcag ttccctactc 4440
tcgcatgggg agaccccaca ctaccatcgg cgctacggcg tttcacttct gagttcggca 4500
tggggtcagg tgggaccacc gcgctactgc cgccaggcaa attctgtttt atcagaccgc 4560
ttctgcgttc tgatttaatc tgtatcaggc tgaaaatctt ctctcatccg ccaaaacagc 4620
caagctggag accgtttggc ccccctcgag cacgtagaaa gccagtccgc agaaacggtg 4680
ctgaccccgg atgaatgtca gctactgggc tatctggaca agggaaaacg caagcgcaaa 4740
gagaaagcag gtagcttgca gtgggcttac atggcgatag ctagactggg cggttttatg 4800
gacagcaagc gaaccggaat tgccagctgg ggcgccctct ggtaaggttg ggaagccctg 4860
caaagtaaac tggatggctt tctcgccgcc aaggatctga tggcgcaggg gatca 4915

<210> SEQ ID NO 73
<211> LENGTH: 10815
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: pCMV-PE2-P2A-Cre

<400> SEQUENCE: 73
acgcgttgac attgattatt gactagttat taatagtaat caattacggg gtcattagtt 60
catagcccat atatggagtt ccgcgttaca taacttacgg taaatggccc gcctggctga 120
ccgcccaacg acccccgccc attgacgtca ataatgacgt atgttcccat agtaacgcca 180
atagggactt tccattgacg tcaatgggtg gagtatttac ggtaaactgc ccacttggca 240
gtacatcaag tgtatcatat gccaagtacg ccccctattg acgtcaatga cggtaaatgg 300
cccgcctggc attatgccca gtacatgacc ttatgggact ttcctacttg gcagtacatc 360
tacgtattag tcatcgctat taccatggtg atgcggtttt ggcagtacat caatgggcgt 420
ggatagcggt ttgactcacg gggatttcca agtctccacc ccattgacgt caatgggagt 480
ttgttttggc accaaaatca acgggacttt ccaaaatgtc gtaacaactc cgccccattg 540
acgcaaatgg gcggtaggcg tgtacggtgg gaggtctata taagcagagc tggtttagtg 600
aaccgtcaga tccgctagag atccgcggcc gctaatacga ctcactatag ggagagccgc 660
caccatgaaa cggacagccg acggaagcga gttcgagtca ccaaagaaga agcggaaagt 720

-continued

```
cgacaagaag tacagcatcg gcctggacat cggcaccaac tctgtgggct gggccgtgat    780
caccgacgag tacaaggtgc ccagcaagaa attcaaggtg ctgggcaaca ccgaccggca    840
cagcatcaag aagaacctga tcggagccct gctgttcgac agcggcgaaa cagccgaggc    900
cacccggctg aagagaaccg ccagaagaag atacaccaga cggaagaacc ggatctgcta    960
tctgcaagag atcttcagca acgagatggc caaggtggac gacagcttct tccacagact   1020
ggaagagtcc ttcctggtgg aagaggataa gaagcacgag cggcacccca tcttcggcaa   1080
catcgtggac gaggtggcct accacgagaa gtaccccacc atctaccacc tgagaaagaa   1140
actggtggac agcaccgaca aggccgacct gcggctgatc tatctggccc tggcccacat   1200
gatcaagttc cggggccact tcctgatcga gggcgacctg aaccccgaca acagcgacgt   1260
ggacaagctg ttcatccagc tggtgcagac ctacaaccag ctgttcgagg aaaaccccat   1320
caacgccagc ggcgtggacg ccaaggccat cctgtctgcc agactgagca agagcagacg   1380
gctggaaaat ctgatcgccc agctgcccgg cgagaagaag aatggcctgt tcggaaacct   1440
gattgccctg agcctgggcc tgacccccaa cttcaagagc aacttcgacc tggccgagga   1500
tgccaaactg cagctgagca aggacaccta cgacgacgac ctggacaacc tgctggccca   1560
gatcggcgac cagtacgccg acctgtttct ggccgccaag aacctgtccg acgccatcct   1620
gctgagcgac atcctgagag tgaacaccga gatcaccaag gccccccctga gcgcctctat   1680
gatcaagaga tacgacgagc accaccagga cctgaccctg ctgaaagctc tcgtgcggca   1740
gcagctgcct gagaagtaca aagagatttt cttcgaccag agcaagaacg gctacgccgg   1800
ctacattgac ggcggagcca gccaggaaga gttctacaag ttcatcaagc ccatcctgga   1860
aaagatggac ggcaccgagg aactgctcgt gaagctgaac agagaggacc tgctgcggaa   1920
gcagcggacc ttcgacaacg gcagcatccc ccaccagatc cacctgggag agctgcacgc   1980
cattctgcgg cggcaggaag atttttaccc attcctgaag gacaaccggg aaaagatcga   2040
gaagatcctg accttccgca tcccctacta cgtgggccct ctggccaggg gaaacagcag   2100
attcgcctgg atgaccagaa agagcgagga aaccatcacc ccctggaact tcgaggaagt   2160
ggtggacaag ggcgcttccg cccagagctt catcgagcgg atgaccaact tcgataagaa   2220
cctgcccaac gagaaggtgc tgcccaagca cagcctgctg tacgagtact tcaccgtgta   2280
taacgagctg accaaagtga aatacgtgac cgagggaatg agaaagcccg ccttcctgag   2340
cggcgagcag aaaaaggcca tcgtggacct gctgttcaag accaaccgga aagtgaccgt   2400
gaagcagctg aaagaggact acttcaagaa aatcgagtgc ttcgactccg tggaaatctc   2460
cggcgtggaa gatcggttca acgcctccct gggcacatac cacgatctgc tgaaaattat   2520
caaggacaag gacttcctgg acaatgagga aaacgaggac attctggaag atatcgtgct   2580
gaccctgaca ctgtttgagg acagagagat gatcgaggaa cggctgaaaa cctatgccca   2640
cctgttcgac gacaaagtga tgaagcagct gaagcggcgg agatacaccg gctggggcag   2700
gctgagccgg aagctgatca acggcatccg ggacaagcag tccggcaaga caatcctgga   2760
tttcctgaag tccgacggct tcgccaacag aaacttcatg cagctgatcc acgacgacag   2820
cctgaccttt aaagaggaca tccagaaagc ccaggtgtcc ggccagggcg atagcctgca   2880
cgagcacatt gccaatctgg ccggcagccc cgccattaag aagggcatcc tgcagacagt   2940
gaaggtggtg gacgagctcg tgaaagtgat gggccggcac aagcccgaga acatcgtgat   3000
cgaaatggcc agagagaacc agaccaccca gaagggacag aagaacagcc gcgagagaat   3060
gaagcggatc gaagagggca tcaaagagct gggcagccag atcctgaaag aacaccccgt   3120
```

ggaaaacacc cagctgcaga acgagaagct gtacctgtac tacctgcaga atgggcggga 3180
tatgtacgtg gaccaggaac tggacatcaa ccggctgtcc gactacgatg tggacgctat 3240
cgtgcctcag agctttctga aggacgactc catcgacaac aaggtgctga ccagaagcga 3300
caagaaccgg ggcaagagcg acaacgtgcc ctccgaagag gtcgtgaaga agatgaagaa 3360
ctactggcgg cagctgctga acgccaagct gattacccag agaaagttcg acaatctgac 3420
caaggccgag agaggcggcc tgagcgaact ggataaggcc ggcttcatca agagacagct 3480
ggtggaaacc cggcagatca caaagcacgt ggcacagatc ctggactccc ggatgaacac 3540
taagtacgac gagaatgaca agctgatccg ggaagtgaaa gtgatcaccc tgaagtccaa 3600
gctggtgtcc gatttccgga aggatttcca gttttacaaa gtgcgcgaga tcaacaacta 3660
ccaccacgcc cacgacgcct acctgaacgc cgtcgtggga accgccctga tcaaaaagta 3720
ccctaagctg gaaagcgagt tcgtgtacgg cgactacaag gtgtacgacg tgcggaagat 3780
gatcgccaag agcgagcagg aaatcggcaa ggctaccgcc aagtacttct tctacagcaa 3840
catcatgaac tttttcaaga ccgagattac cctggccaac ggcgagatcc ggaagcggcc 3900
tctgatcgag acaaacggcg aaaccgggga gatcgtgtgg gataagggcc gggattttgc 3960
caccgtgcgg aaagtgctga gcatgcccca agtgaatatc gtgaaaaaga ccgaggtgca 4020
gacaggcggc ttcagcaaag agtctatcct gcccaagagg aacagcgata agctgatcgc 4080
cagaaagaag gactgggacc ctaagaagta cggcggcttc gacagcccca ccgtggccta 4140
ttctgtgctg gtggtggcca aagtggaaaa gggcaagtcc aagaaactga agagtgtgaa 4200
agagctgctg gggatcacca tcatggaaag aagcagcttc gagaagaatc ccatcgactt 4260
tctggaagcc aagggctaca aagaagtgaa aaaggacctg atcatcaagc tgcctaagta 4320
ctccctgttc gagctggaaa acggccggaa gagaatgctg gcctctgccg gcgaactgca 4380
gaagggaaac gaactggccc tgccctccaa atatgtgaac ttcctgtacc tggccagcca 4440
ctatgagaag ctgaagggct cccccgagga taatgagcag aaacagctgt ttgtggaaca 4500
gcacaagcac tacctggacg agatcatcga gcagatcagc gagttctcca agagagtgat 4560
cctggccgac gctaatctgg acaaagtgct gtccgcctac aacaagcacc gggataagcc 4620
catcagagag caggccgaga atatcatcca cctgtttacc ctgaccaatc tgggagcccc 4680
tgccgccttc aagtactttg acaccaccat cgaccggaag aggtacacca gcaccaaaga 4740
ggtgctggac gccaccctga tccaccagag catcaccggc ctgtacgaga cacggatcga 4800
cctgtctcag ctgggaggtg actctggagg atctagcgga ggatcctctg gcagcgagac 4860
accaggaaca agcgagtcag caacaccaga gagcagtggc ggcagcagcg gcggcagcag 4920
caccctaaat atagaagatg agtatcggct acatgagacc tcaaaagagc cagatgtttc 4980
tctagggtcc acatggctgt ctgattttcc tcaggcctgg gcggaaaccg gggggcatggg 5040 actggcagtt cgccaagctc ctctgatcat acctctgaaa gcaacctcta cccccgtgtc 5100
cataaaacaa taccccatgt cacaagaagc cagactgggg atcaagcccc acatacagag 5160
actgttggac cagggaatac tggtaccctg ccagtccccc tggaacacgc ccctgctacc 5220
cgttaagaaa ccagggacta atgattatag gcctgtccag gatctgagag aagtcaacaa 5280
gcgggtggaa gacatccacc ccaccgtgcc caaccccttac aacctcttga gcgggctccc 5340
accgtcccac cagtggtaca ctgtgcttga tttaaaggat gccttttttct gcctgagact 5400 ccaccccacc agtcagcctc tcttcgcctt tgagtggaga gatccagaga tgggaatctc 5460

-continued aggacaattg acctggacca gactcccaca gggtttcaaa aacagtccca ccctgtttaa 5520
tgaggcactg cacagagacc tagcagactt ccggatccag cacccagact tgatcctgct 5580
acagtacgtg gatgacttac tgctggccgc cacttctgag ctagactgcc aacaaggtac 5640
tcgggccctg ttacaaaccc tagggaacct cgggtatcgg gcctcggcca agaaagccca 5700
aatttgccag aaacaggtca agtatctggg gtatcttcta aaagagggtc agagatggct 5760
gactgaggcc agaaaagaga ctgtgatggg gcagcctact ccgaagaccc ctcgacaact 5820
aagggagttc ctagggaagg caggcttctg tcgcctcttc atccctgggt ttgcagaaat 5880
ggcagccccc ctgtaccctc tcaccaaacc ggggactctg tttaattggg gcccagacca 5940
acaaaaggcc tatcaagaaa tcaagcaagc tcttctaact gccccagccc tggggttgcc 6000
agatttgact aagccctttg aactctttgt cgacgagaag cagggctacg ccaaaggtgt 6060
cctaacgcaa aaactgggac cttggcgtcg gccggtggcc tacctgtcca aaaagctaga 6120
cccagtagca gctgggtggc cccccttgcct acggatggta gcagccattg ccgtactgac 6180
aaaggatgca ggcaagctaa ccatgggaca gccactagtc attctggccc cccatgcagt 6240
agaggcacta gtcaaacaac cccccgaccg ctggctttcc aacgcccgga tgactcacta 6300
tcaggccttg cttttggaca cggaccgggt ccagttcgga ccggtggtag ccctgaaccc 6360
ggctacgctg ctcccactgc ctgaggaagg gctgcaacac aactgccttg atatcctggc 6420
cgaagcccac ggaacccgac ccgacctaac ggaccagccg ctcccagacg ccgaccacac 6480
ctggtacacg gatggaagca gtctcttaca agagggacag cgtaaggcgg gagctgcggt 6540
gaccaccgag accgaggtaa tctgggctaa agccctgcca gccgggacat ccgctcagcg 6600
ggctgaactg atagcactca cccaggccct aaagatggca gaaggtaaga agctaaatgt 6660
ttatactgat agccgttatg cttttgctac tgcccatatc catggagaaa tatacagaag 6720
gcgtgggtgg ctcacatcag aaggcaaaga gatcaaaaat aaagacgaga tcttggccct 6780
actaaaagcc ctctttctgc ccaaaagact tagcataatc cattgtccag gacatcaaaa 6840
gggacacagc gccgaggcta gaggcaaccg gatggctgac caagcggccc gaaaggcagc 6900
catcacagag actccagaca cctctaccct cctcatagaa aattcatcac cctctggcgg 6960
ctcaaaaaga accgccgacg gcagcgaatt cgagcccaag aagaagagga aagtcggaag 7020
cggagctact aacttcagcc tgctgaagca ggctggcgac gtggaggaga accctggacc 7080
taatttactg accgtacacc aaaatttgcc tgcattaccg gtcgatgcaa cgagtgatga 7140
ggttcgcaag aacctgatgg acatgttcag ggatcgccag gcgttttctg agcatacctg 7200
gaaaatgctt ctgtccgttt gccggtcgtg ggcggcatgg tgcaagttga ataaccggaa 7260
atggtttccc gcagaacctg aagatgttcg cgattatctt ctatatcttc aggcgcgcgg 7320
tctggcagta aaaactatcc agcaacattt gggccagcta aacatgcttc atcgtcggtc 7380
cgggctgcca cgaccaagtg acagcaatgc tgtttcactg gttatgcggc ggatccgaaa 7440
agaaaacgtt gatgccggtg aacgtgcaaa acaggctcta gcgttcgaac gcactgattt 7500
cgaccaggtt cgttcactca tggaaaatag cgatcgctgc caggatatac gtaatctggc 7560
atttctgggg attgcttata acaccctgtt acgtatagcc gaaattgcca ggatcagggt 7620
taaagatatc tcacgtactg acggtgggag aatgttaatc catattggca gaacgaaaac 7680
gctggttagc accgcaggtg tagagaaggc acttagcctg gggtaacta aactggtcga 7740 gcgatggatt tccgtctctg gtgtagctga tgatccgaat aactacctgt tttgccgggt 7800
cagaaaaaat ggtgttgccg cgccatctgc caccagccag ctatcaactc gcgccctgga 7860
agggattttt gaagcaactc atcgattgat ttacggcgct aaggatgact ctggtcagag 7920
atacctggcc tggtctggac acagtgcccg tgtcggagcc gcgcgagata tggcccgcgc 7980
tggagtttca ataccggaga tcatgcaagc tggtggctgg accaatgtaa atattgtcat 8040
gaactatatc cgtaacctgg atagtgaaac aggggcaatg gtgcgcctgc tggaagatgg 8100
cgattaattt aaacccgctg atcagcctcg actgtgcctt ctagttgcca gccatctgtt 8160
gtttgcccct cccccgtgcc ttccttgacc ctggaaggtg ccactcccac tgtcctttcc 8220
taataaaatg agaaaattgc atcgcattgt ctgagtaggt gtcattctat tctggggggt 8280
ggggtggggc aggacagcaa gggggaggat tgggaagaca atagcaggca tgctggggat 8340
gcggtgggct ctatggcttc tgaggcggaa agaaccagct ggggctcgat accgtcgacc 8400
tctagctaga gcttggcgta atcatggtca tagctgtttc ctgtgtgaaa ttgttatccg 8460
ctcacaattc cacacaacat acgagccgga agcataaagt gtaaagccta gggtgcctaa 8520
tgagtgagct aactcacatt aattgcgttg cgctcactgc ccgctttcca gtcgggaaac 8580
ctgtcgtgcc agctgcatta atgaatcggc caacgcgcgg ggagaggcgg tttgcgtatt 8640
gggcgctctt ccgcttcctc gctcactgac tcgctgcgct cggtcgttcg gctgcggcga 8700
gcggtatcag ctcactcaaa ggcggtaata cggttatcca cagaatcagg ggataacgca 8760
ggaaagaaca tgtgagcaaa aggccagcaa aaggccagga accgtaaaaa ggccgcgttg 8820
ctggcgtttt tccataggct ccgcccccct gacgagcatc acaaaaatcg acgctcaagt 8880
cagaggtggc gaaacccgac aggactataa agataccagg cgtttccccc tggaagctcc 8940
ctcgtgcgct ctcctgttcc gaccctgccg cttaccggat acctgtccgc ctttctccct 9000
tcgggaagcg tggcgctttc tcatagctca cgctgtaggt atctcagttc ggtgtaggtc 9060
gttcgctcca agctgggctg tgtgcacgaa ccccccgttc agcccgaccg ctgcgcctta 9120
tccggtaact atcgtcttga gtccaacccg gtaagacacg acttatcgcc actggcagca 9180
gccactggta acaggattag cagagcgagg tatgtaggcg gtgctacaga gttcttgaag 9240
tggtggccta actacggcta cactagaaga acagtatttg gtatctgcgc tctgctgaag 9300
ccagttacct tcggaaaaag agttggtagc tcttgatccg gcaaacaaac caccgctggt 9360
agcggtggtt tttttgtttg caagcagcag attacgcgca gaaaaaaagg atctcaagaa 9420
gatcctttga tcttttctac ggggtctgac gctcagtgga acgaaaactc acgttaaggg 9480
attttggtca tgagattatc aaaaaggatc ttcacctaga tccttttaaa ttaaaaatga 9540
agttttaaat caatctaaag tatatatgag taaacttggt ctgacagtta ccaatgctta 9600
atcagtgagg cacctatctc agcgatctgt ctatttcgtt catccatagt tgcctgactc 9660
cccgtcgtgt agataactac gatacgggag ggcttaccat ctggccccag tgctgcaatg 9720
ataccgcgag acccacgctc accggctcca gatttatcag caataaacca gccagccgga 9780
agggccgagc gcagaagtgg tcctgcaact ttatccgcct ccatccagtc tattaattgt 9840
tgccgggaag ctagagtaag tagttcgcca gttaatagtt tgcgcaacgt tgttgccatt 9900
gctacaggca tcgtggtgtc acgctcgtcg tttggtatgg cttcattcag ctccggttcc 9960
caacgatcaa ggcgagttac atgatccccc atgttgtgca aaaaagcggt tagctccttc 10020
ggtcctccga tcgttgtcag aagtaagttg gccgcagtgt tatcactcat ggttatggca 10080
gcactgcata attctcttac tgtcatgcca tccgtaagat gcttttctgt gactggtgag 10140
tactcaacca agtcattctg agaatagtgt atgcggcgac cgagttgctc ttgcccggcg 10200
tcaatacggg ataataccgc gccacatagc agaactttaa aagtgctcat cattggaaaa 10260
cgttcttcgg ggcgaaaact ctcaaggatc ttaccgctgt tgagatccag ttcgatgtaa 10320
cccactcgtg cacccaactg atcttcagca tcttttactt tcaccagcgt ttctgggtga 10380
gcaaaaacag gaaggcaaaa tgccgcaaaa aagggaataa gggcgacacg gaaatgttga 10440
atactcatac tcttcctttt tcaatattat tgaagcattt atcagggtta ttgtctcatg 10500
agcggataca tatttgaatg tatttagaaa aataaacaaa taggggttcc gcgcacattt 10560
ccccgaaaag tgccacctga cgtcgacgga tcgggagatc gatctcccga tcccctaggg 10620
tcgactctca gtacaatctg ctctgatgcc gcatagttaa gccagtatct gctccctgct 10680
tgtgtgttgg aggtcgctga gtagtgcgcg agcaaaattt aagctacaac aaggcaaggc 10740
ttgaccgaca attgcatgaa gaatctgctt agggttaggc gttttgcgct gcttcgcgat 10800
gtacgggcca gatat 10815

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: +90ngRNA guide sequence

<400> SEQUENCE: 74
gtcaaccagt atcccggtgc 20

<210> SEQ ID NO 75
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: +90ngRNA

<400> SEQUENCE: 75
gtcaaccagt atcccggtgc gttttagagc tagaaatagc aagttaaaat aaggctagtc 60
cgttatcaac ttgaaaaagt ggcaccgagt cggtgc 96

<210> SEQ ID NO 76
<211> LENGTH: 4968
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: GFP minicircle template (before cleavage)

<400> SEQUENCE: 76
tgatcccctg cgccatcaga tccttggcgg cgagaaagcc atccagttta ctttgcaggg 60
cttcccaacc ttaccagagg gcgccccagc tggcaattcc ggttcgcttg ctgtccataa 120
aaccgcccag tctagctatc gccatgtaag cccactgcaa gctacctgct ttctctttgc 180
gcttgcgttt tcccttgtcc agatagccca gtagctgaca ttcatccggg gtcagcaccg 240
tttctgcgga ctggctttct acgtgctcga ggggggccaa acggtctcca gcttggctgt 300
tttggcggat gagagaagat tttcagcctg atacagatta aatcagaacg cagaagcggt 360

-continued

```
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atcctttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
cagggggaaa cgcctggtat ctttatagtc ctgtcgggtt tcgccacctc tgacttgagc   1380
gtcgattttt gtgatgctcg tcaggggggc ggagcctatg gaaaaacgcc agcaacgcgg   1440
cctttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cactttttct tcacaaccgg cacggaactc gctcgggctg gccccggtgc atttttttaaa   2100
tacccgcgag aaatagagtt gatcgtcaaa accaacattg cgaccgacgg tggcgatagg   2160
catccgggtg gtgctcaaaa gcagcttcgc ctggctgata cgttggtcct cgcgccagct   2220
taagacgcta atccctaact gctggcggaa aagatgtgac agacgcgacg gcgacaagca   2280
aacatgctgt gcgacgctgg cgatacatta ccctgttatc cctagatgac attaccctgt   2340
tatcccagat gacattaccc tgttatccct agatgacatt accctgttat ccctagatga   2400
catttaccct gttatcccta gatgacatta ccctgttatc ccagatgaca ttaccctgtt   2460
atccctagat acattaccct gttatcccag atgacatacc ctgttatccc tagatgacat   2520
taccctgtta tcccagatga cattaccctg ttatccctag atacattacc ctgttatccc   2580
agatgacata ccctgttatc cctagatgac attaccctgt tatcccagat gacattaccc   2640
tgttatccct agatacatta ccctgttatc ccagatgaca taccctgtta tccctagatg   2700
acattaccct gttatcccag atgacattac cctgttatcc ctagatacat taccctgtta   2760
```

tcccagatga cataccctgt tatccctaga tgacattacc ctgttatccc agatgacatt 2820
accctgttat ccctagatac attaccctgt tatcccagat gacataccct gttatcccta 2880
gatgacatta ccctgttatc ccagatgaca ttaccctgtt atccctagat acattaccct 2940
gttatcccag atgacatacc ctgttatccc tagatgacat taccctgtta tcccagataa 3000
actcaatgat gatgatgatg atggtcgaga ctcagcggcc gcggtgccag ggcgtgccct 3060
tgggctcccc gggcgcgact ataagctgcg agcaacttca cttgggtatg ccggcggtag 3120
cgcttaccgt tcgtataatg tatgctatac gaagttatcc gaagccgcta gcggtggttt 3180
gtctggtcaa ccaccgcggt ctcagtggtg tacggtacaa acccagctac cggtcgccac 3240
catgcccgcc atgaagatcg agtgccgcat caccggcacc ctgaacggcg tggagttcga 3300
gctggtgggc ggcggagagg gcacccccga gcagggccgc atgaccaaca agatgaagag 3360
caccaaaggc gccctgacct tcagccccta cctgctgagc cacgtgatgg gctacggctt 3420
ctaccacttc ggcacctacc ccagcggcta cgagaacccc ttcctgcacg ccatcaacaa 3480
cggcggctac accaacaccc gcatcgagaa gtacgaggac ggcggcgtgc tgcacgtgag 3540
cttcagctac cgctacgagg ccggccgcgt gatcggcgac ttcaaggtgg tgggcaccgg 3600
cttccccgag gacagcgtga tcttcaccga caagatcatc cgcagcaacg ccaccgtgga 3660
gcacctgcac cccatgggcg ataacgtgct ggtgggcagc ttcgcccgca ccttcagcct 3720
gcgcgacggc ggctactaca gcttcgtggt ggacagccac atgcacttca agagcgccat 3780
ccaccccagc atcctgcaga acgggggccc catgttcgcc ttccgccgcg tggaggagct 3840
gcacagcaac accgagctgg gcatcgtgga gtaccagcac gccttcaaga cccccatcgc 3900
cttcgccaga tctcgagctc gatgagtttg gacaaaccac aactagaatg cagtgaaaaa 3960
aatgctttat ttgtgaaatt tgtgatgcta ttgctttatt tgtgggcccg ccccaactgg 4020
ggtaaccttt gagttctctc agttgggggt aatcagcatc atgatgtggt accacatcat 4080
gatgctgatt ataagaatgc ggccgccaca ctctagtgga tctcgagtta ataattcaga 4140
agaactcgtc aagaaggcga tagaaggcga tgcgctgcga atcgggagcg gcgataccgt 4200
aaagcacgag gaagcggtca gcccattcgc cgccaagctc ttcagcaata tcacgggtag 4260
ccaacgctat gtcctgatag cggtccgcca cacccagccg gccacagtcg atgaatccag 4320
aaaagcggcc attttccacc atgatattcg gcaagcaggc atcgccatgg gtcacgacga 4380
gatcctcgcc gtcgggcatg ctcgccttga gcctggcgaa cagttcggct ggcgcgagcc 4440
cctgatgctc ttcgtccaga tcatcctgat cgacaagacc ggcttccatc cgagtacgtg 4500
ctcgctcgat gcgatgtttc gcttggtggt cgaatgggca ggtagccgga tcaagcgtat 4560
gcagccgccg cattgcatca gccatgatgg atactttctc ggcaggagca aggtgtagat 4620
gacatggaga tcctgccccg gcacttcgcc caatagcagc cagtcccttc ccgcttcagt 4680
gacaacgtcg agcacagctg cgcaaggaac gcccgtcgtg gccagccacg atagccgcgc 4740
tgcctcgtct tgcagttcat tcagggcacc ggacaggtcg gtcttgacaa aaagaaccgg 4800
gcgcccctgc gctgacagcc ggaacacggc ggcatcagag cagccgattg tctgttgtgc 4860
ccagtcatag ccgaatagcc tctccaccca agcggccgga gaacctgcgt gcaatccatc 4920
ttgttcaatc atgcgaaacg atcctcatcc tgtctcttga tcagagct 4968

<210> SEQ ID NO 77
<211> LENGTH: 4855
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: GLuc minicircle template

<400> SEQUENCE: 77
tgatcccctg cgccatcaga tccttggcgg cgagaaagcc atccagttta ctttgcaggg 60
cttcccaacc ttaccagagg gcgccccagc tggcaattcc ggttcgcttg ctgtccataa 120
aaccgcccag tctagctatc gccatgtaag cccactgcaa gctacctgct ttctctttgc 180
gcttgcgttt tcccttgtcc agatagccca gtagctgaca ttcatccggg gtcagcaccg 240
tttctgcgga ctggctttct acgtgctcga ggggggccaa acggtctcca gcttggctgt 300
tttggcggat gagagaagat tttcagcctg atacagatta aatcagaacg cagaagcggt 360
ctgataaaac agaatttgcc tggcggcagt agcgcggtgg tcccacctga ccccatgccg 420
aactcagaag tgaaacgccg tagcgccgat ggtagtgtgg ggtctcccca tgcgagagta 480
gggaactgcc aggcatcaaa taaaacgaaa ggctcagtcg aaagactggg cctttcgttt 540
tatctgttgt ttgtcggtga acgctctcct gagtaggaca aatccgccgg gagcggattt 600
gaacgttgcg aagcaacggc ccggagggtg gcgggcagga cgcccgccat aaactgccag 660
gcatcaaatt aagcagaagg ccatcctgac ggatggcctt tttgcgtttc tacaaactct 720
tttgtttatt tttctaaata cattcaaata tgtatccgct catgaccaaa atcccttaac 780
gtgagttttc gttccactga gcgtcagacc ccgtagaaaa gatcaaagga tcttcttgag 840
atcctttttt tctgcgcgta atctgctgct tgcaaacaaa aaaaccaccg ctaccagcgg 900
tggtttgttt gccggatcaa gagctaccaa ctctttttcc gaaggtaact ggcttcagca 960
gagcgcagat accaaatact gtccttctag tgtagccgta gttaggccac cacttcaaga 1020
actctgtagc accgcctaca tacctcgctc tgctaatcct gttaccagtg gctgctgcca 1080
gtggcgataa gtcgtgtctt accgggttgg actcaagacg atagttaccg gataaggcgc 1140
agcggtcggg ctgaacgggg ggttcgtgca cacagcccag cttggagcga acgacctaca 1200
ccgaactgag atacctacag cgtgagctat gagaaagcgc cacgcttccc gaagggagaa 1260
aggcggacag gtatccggta agcggcaggg tcggaacagg agagcgcacg agggagcttc 1320 caggggggaaa cgcctggtat ctttatagtc ctgtcgggtt tcgccacctc tgacttgagc 1380
gtcgattttt gtgatgctcg tcaggggggc ggagcctatg gaaaaacgcc agcaacgcgg 1440
cctttttacg gttcctggcc ttttgctggc cttttgctca catgttcttt cctgcgttat 1500
cccctgattc tgtggataac cgtattaccg cctttgagtg agctgatacc gctcgccgca 1560
gccgaacgac cgagcgcagc gagtcagtga gcgaggaagc ggaagagcgc ctgatgcggt 1620
attttctcct tacgcatctg tgcggtattt cacaccgcat atggtgcact ctcagtacaa 1680
tctgctctga tgccgcatag ttaagccagt atacactccg ctatcgctac gtgactgggt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagccg tcaattgtct gattcgttac caattatgac aacttgacgg ctacatcatt 2040
cactttttct tcacaaccgg cacggaactc gctcgggctg gccccggtgc atttttttaaa 2100

-continued tacccgcgag aaatagagtt gatcgtcaaa accaacattg cgaccgacgg tggcgatagg 2160
catccgggtg gtgctcaaaa gcagcttcgc ctggctgata cgttggtcct cgcgccagct 2220
taagacgcta atccctaact gctggcggaa aagatgtgac agacgcgacg gcgacaagca 2280
aacatgctgt gcgacgctgg cgatacatta ccctgttatc cctagatgac attaccctgt 2340
tatcccagat gacattaccc tgttatccct agatgacatt accctgttat ccctagatga 2400
catttaccct gttatcccta gatgacatta ccctgttatc ccagatgaca ttaccctgtt 2460
atccctagat acattaccct gttatcccag atgacatacc ctgttatccc tagatgacat 2520
taccctgtta tcccagatga cattaccctg ttatccctag atacattacc ctgttatccc 2580
agatgacata ccctgttatc cctagatgac attaccctgt tatcccagat gacattaccc 2640
tgttatccct agatacatta ccctgttatc ccagatgaca taccctgtta tccctagatg 2700
acattaccct gttatcccag atgacattac cctgttatcc ctagatacat taccctgtta 2760
tcccagatga cataccctgt tatccctaga tgacattacc ctgttatccc agatgacatt 2820
accctgttat ccctagatac attaccctgt tatcccagat gacataccct gttatcccta 2880
gatgacatta ccctgttatc ccagatgaca ttaccctgtt atccctagat acattaccct 2940
gttatcccag atgacatacc ctgttatccc tagatgacat taccctgtta tcccagataa 3000
actcaatgat gatgatgatg atggtcgaga ctcagcggcc gcggtgccag ggcgtgccct 3060
tgggctcccc gggcgcgact ataagctgcg agcaacttca cttgggtatg ccggcggtag 3120
cgcttaccgt tcgtataatg tatgctatac gaagttatcc gaagccgcta gcggtggttt 3180
gtctggtcaa ccaccgcggt ctcagtggtg tacggtacaa acccactacc ggtcgccacc 3240
atgggagtca aagttctgtt tgccctgatc tgcatcgctg tggccgaggc caagcccacc 3300
gagaacaacg aagacttcaa catcgtggcc gtggccagca acttcgcgac cacggatctc 3360
gatgctgacc gcgggaagtt gcccggcaag aagctgccgc tggaggtgct caaagagatg 3420
gaagccaatg cccggaaagc tggctgcacc aggggctgtc tgatctgcct gtcccacatc 3480
aagtgcacgc ccaagatgaa gaagttcatc ccaggacgct gccacaccta cgaaggcgac 3540
aaagagtccg cacagggcgg cataggcgag gcgatcgtcg acattcctga gattcctggg 3600
ttcaaggact tggagcccat ggagcagttc atcgcacagg tcgatctgtg tgtggactgc 3660
acaactggct gcctcaaagg gcttgccaac gtgcagtgtt ctgacctgct caagaagtgg 3720
ctgccgcaac gctgtgcgac ctttgccagc aagatccagg gccaggtgga caagatcaag 3780
ggggccggtg gtgactaagc ggagctcgat gagtttggac aaaccacaac tagaatgcag 3840
tgaaaaaaat gctttatttg tgaaatttgt gatgctattg ctttatttgt gggcccgccc 3900
caactggggt aacctttgag ttctctcagt tgggggtaat cagcatcatg atgtggtacc 3960
acatcatgat gctgattata agaatgcggc cgccacactc tagtggatct cgagttaata 4020
attcagaaga actcgtcaag aaggcgatag aaggcgatgc gctgcgaatc gggagcggcg 4080
ataccgtaaa gcacgaggaa gcggtcagcc cattcgccgc caagctcttc agcaatatca 4140
cgggtagcca acgctatgtc ctgatagcgg tccgccacac ccagccggcc acagtcgatg 4200
aatccagaaa agcggccatt ttccaccatg atattcggca agcaggcatc gccatgggtc 4260
acgacgagat cctcgccgtc gggcatgctc gccttgagcc tggcgaacag ttcggctggc 4320
gcgagcccct gatgctcttc gtccagatca tcctgatcga caagaccggc ttccatccga 4380
gtacgtgctc gctcgatgcg atgtttcgct tggtggtcga atgggcaggt agccggatca 4440
agcgtatgca gccgccgcat tgcatcagcc atgatggata ctttctcggc aggagcaagg 4500
tgtagatgac atggagatcc tgccccggca cttcgcccaa tagcagccag tcccttcccg 4560
cttcagtgac aacgtcgagc acagctgcgc aaggaacgcc cgtcgtggcc agccacgata 4620
gccgcgctgc ctcgtcttgc agttcattca gggcaccgga caggtcggtc ttgacaaaaa 4680
gaaccgggcg cccctgcgct gacagccgga acacggcggc atcagagcag ccgattgtct 4740
gttgtgccca gtcatagccg aatagcctct ccacccaagc ggccggagaa cctgcgtgca 4800
atccatcttg ttcaatcatg cgaaacgatc ctcatcctgt ctcttgatca gagct 4855

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: pseudo-attP

<400> SEQUENCE: 78
ccccaactgg ggtaaccttt gagttctctc agttgggg 38

<210> SEQ ID NO 79
<211> LENGTH: 194
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Albumin-pegRNA-SERPIN

<400> SEQUENCE: 79
gactgaaact tcacagaata gttttagagc tagaaatagc aagttaaaat aaggctagtc 60
cgttatcaac ttgaaaaagt ggcaccgagt cggtgcttgg gatagttatg aattcaatct 120
tcaaccctat ccggatgatc ctgacgacgg agaccgccgt cgtcgacaag ccggcctctg 180
tgaagtttca gtca 194

<210> SEQ ID NO 80
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Albumin-pegRNA-CPS1

<400> SEQUENCE: 80
gactgaaact tcacagaata gttttagagc tagaaatagc aagttaaaat aaggctagtc 60
cgttatcaac ttgaaaaagt ggcaccgagt cggtgcttgg gatagttatg aattcaatct 120
tcaaccctat ccggatgatc ctgacgacgg agaccgccgt cgtcgacaag ccggcctctg 180
tgaagtttc 189

<210> SEQ ID NO 81
<211> LENGTH: 177
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

<223> OTHER INFORMATION: 34bp lox71 pegRNA

<400> SEQUENCE: 81
ggcccagact gagcacgtga gttttagagc tagaaatagc aagttaaaat aaggctagtc 60
cgttatcaac ttgaaaaagt ggcaccgagt cggtgctgga ggaagcaggg cttcctttcc 120
tctgccatca taccgttcgt atagcataca ttatacgaag ttatcgtgct cagtctg 177

<210> SEQ ID NO 82
<211> LENGTH: 177
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 34bp lox66 pegRNA

<400> SEQUENCE: 82
ggcccagact gagcacgtga gttttagagc tagaaatagc aagttaaaat aaggctagtc 60
cgttatcaac ttgaaaaagt ggcaccgagt cggtgctgga ggaagcaggg cttcctttcc 120
tctgccatca ataacttcgt atagcataca ttatacgaac ggtacgtgct cagtctg 177

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: gRNA2

<400> SEQUENCE: 83
ggcccagact gagcacgtga 20

<210> SEQ ID NO 84
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggccgga tgatcctgac gacggagacc gccgtcgtcg acaagccggc ctgagctgcg 180
agaa 184

<210> SEQ ID NO 85
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
gctattctcg cagctcacca gttttagagc tagaaatagc aagttaaaat aaggctagtc 60
cgttatcaac ttgaaaaagt ggcaccgagt cggtgcgagt cggtgcgacg agcgcggcga 120
tatcatcatc catggcacaa ttaacatctc aatcaaggta aatgcttgag ctgcgagaa 179

<210> SEQ ID NO 86
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
gctattctcg cagctcacca gttttagagc tagaaatagc aagttaaaat aaggctagtc 60
cgttatcaac ttgaaaaagt ggcaccgagt cggtgcgagt cggtgcgacg agcgcggcga 120
tatcatcatc catggagcat ttaccttgat tgagatgtta attgtgtgag ctgcgagaa 179

<210> SEQ ID NO 87
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87
gctattctcg cagctcacca gttttagagc tagaaatagc aagttaaaat aaggctagtc 60
cgttatcaac ttgaaaaagt ggcaccgagt cggtgcgagt cggtgcgacg agcgcggcga 120
tatcatcatc catggcaggt ttttgacgaa agtgatccag atgatccagt gagctgcgag 180
aa 182

<210> SEQ ID NO 88
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 88
gctattctcg cagctcacca gttttagagc tagaaatagc aagttaaaat aaggctagtc 60
cgttatcaac ttgaaaaagt ggcaccgagt cggtgcgagt cggtgcgacg agcgcggcga 120
tatcatcatc catggctgga tcatctggat cactttcgtc aaaaacctgt gagctgcgag 180
aa 182

<210> SEQ ID NO 89
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
gaagccggcc ttgcacatgc gttttagagc tagaaatagc aagttaaaat aaggctagtc 60
cgttatcaac ttgaaaaagt ggcaccgagt cggtgc 96

<210> SEQ ID NO 90
<211> LENGTH: 164
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
gaagccggcc ttgcacatgc gttttagagc tagaaatagc aagttaaaat aaggctagtc 60
cgttatcaac ttgaaaaagt ggcaccgagt cggtgcatat catcatccat ggtaccgttc 120
gtatagcata cattatacga agttattgag ctgcgagaat agcc 164

<210> SEQ ID NO 91
<211> LENGTH: 172
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
gaagccggcc ttgcacatgc gttttagagc tagaaatagc aagttaaaat aaggctagtc 60
cgttatcaac ttgaaaaagt ggcaccgagt cggtgcgacg agcgcggcga tatcatcatc 120
catggtaccg ttcgtatagc atacattata cgaagttatt gagctgcgag aa 172

<210> SEQ ID NO 92
<211> LENGTH: 189
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
gctattctcg cagctcacca gttttagagc tagaaatagc aagttaaaat aaggctagtc 60
cgttatcaac ttgaaaaagt ggcaccgagt cggtgctcga cgacgagcgc ggcgatatca 120
tcatccatgg ccggatgatc ctgacgacgg agaccgccgt cgtcgacaag ccggcctgag 180
ctgcgagaa 189

<210> SEQ ID NO 93
<211> LENGTH: 181
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93
gctattctcg cagctcacca gttttagagc tagaaatagc aagttaaaat aaggctagtc 60
cgttatcaac ttgaaaaagt ggcaccgagt cggtgcgagc gcggcgatat catcatccat 120
ggccggatga tcctgacgac ggagaccgcc gtcgtcgaca agccggcctg agctgcgaga 180
a 181

<210> SEQ ID NO 94
<211> LENGTH: 178
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94
gctattctcg cagctcacca gttttagagc tagaaatagc aagttaaaat aaggctagtc 60
cgttatcaac ttgaaaaagt ggcaccgagt cggtgccgcg gcgatatcat catccatggc 120
cggatgatcc tgacgacgga gaccgccgtc gtcgacaagc cggcctgagc tgcgagaa 178

<210> SEQ ID NO 95
<211> LENGTH: 175
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95
gctattctcg cagctcacca gttttagagc tagaaatagc aagttaaaat aaggctagtc 60
cgttatcaac ttgaaaaagt ggcaccgagt cggtgcggcg atatcatcat ccatggccgg 120
atgatcctga cgacggagac cgccgtcgtc gacaagccgg cctgagctgc gagaa 175

<210> SEQ ID NO 96
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96
gctattctcg cagctcacca gttttagagc tagaaatagc aagttaaaat aaggctagtc 60
cgttatcaac ttgaaaaagt ggcaccgagt cggtgcatat catcatccat ggccggatga 120
tcctgacgac ggagaccgcc gtcgtcgaca agccggcctg agctgcgaga a 171

<210> SEQ ID NO 97
<211> LENGTH: 194
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gctattctcg cagctcacca gttttagagc tagaaatagc aagttaaaat aaggctagtc 60
cgttatcaac ttgaaaaagt ggcaccgagt cggtgctcga cgacgagcgc ggcgatatca 120
tcatccatgg ccggatgatc ctgacgacgg agaccgccgt cgtcgacaag ccggcctgag 180
ctgcgagaat agcc 194

<210> SEQ ID NO 98
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 98
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggccgga tgatcctgac gacggagacc gccgtcgtcg acaagccggc ctgagctgcg 180
agaatagcc 189

<210> SEQ ID NO 99
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 99
gctattctcg cagctcacca gttttagagc tagaaatagc aagttaaaat aaggctagtc 60
cgttatcaac ttgaaaaagt ggcaccgagt cggtgcatat catcatccat ggccggatga 120
tcctgacgac ggagaccgcc gtcgtcgaca agccggcctg agctgcgaga atagcc 176

<210> SEQ ID NO 100
<211> LENGTH: 194
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100
gctgtctccg ccgcccgcca gttttagagc tagaaatagc aagttaaaat aaggctagtc 60
cgttatcaac ttgaaaaagt ggcaccgagt cggtgcctgc ccatccgcgg cggcacgggg 120
gtcgcagtcg ccatgccgga tgatcctgac gacggagacc gccgtcgtcg acaagccggc 180
ccgggcggcg gaga 194

<210> SEQ ID NO 101
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 101
gctgtctccg ccgcccgcca gttttagagc tagaaatagc aagttaaaat aaggctagtc 60
cgttatcaac ttgaaaaagt ggcaccgagt cggtgccatc cgcggcggca cgggggtcgc 120
agtcgccatg ccggatgatc ctgacgacgg agaccgccgt cgtcgacaag ccggcccggg 180
cggcggaga 189

<210> SEQ ID NO 102
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 102
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgccgga tgatcctgac gacggagacc gccgtcgtcg acaagccggc ccgggcggcg 180
gaga 184

<210> SEQ ID NO 103
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
gctgtctccg ccgcccgcca gttttagagc tagaaatagc aagttaaaat aaggctagtc 60
cgttatcaac ttgaaaaagt ggcaccgagt cggtgcggca cgggggtcgc agtcgccatg 120
ccggatgatc ctgacgacgg agaccgccgt cgtcgacaag ccggcccggg cggcggaga 179

<210> SEQ ID NO 104
<211> LENGTH: 174
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 104
gctgtctccg ccgcccgcca gttttagagc tagaaatagc aagttaaaat aaggctagtc 60
cgttatcaac ttgaaaaagt ggcaccgagt cggtgcgggg gtcgcagtcg ccatgccgga 120
tgatcctgac gacggagacc gccgtcgtcg acaagccggc ccgggcggcg gaga 174

<210> SEQ ID NO 105
<211> LENGTH: 199
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
gctgtctccg ccgcccgcca gttttagagc tagaaatagc aagttaaaat aaggctagtc 60
cgttatcaac ttgaaaaagt ggcaccgagt cggtgcctgc ccatccgcgg cggcacgggg 120
gtcgcagtcg ccatgccgga tgatcctgac gacggagacc gccgtcgtcg acaagccggc 180
ccgggcggcg gagacagcg 199

<210> SEQ ID NO 106
<211> LENGTH: 194
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106
gctgtctccg ccgcccgcca gttttagagc tagaaatagc aagttaaaat aaggctagtc 60
cgttatcaac ttgaaaaagt ggcaccgagt cggtgccatc cgcggcggca cgggggtcgc 120
agtcgccatg ccggatgatc ctgacgacgg agaccgccgt cgtcgacaag ccggcccggg 180
cggcggagac agcg 194

<210> SEQ ID NO 107
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 107
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgccgga tgatcctgac gacggagacc gccgtcgtcg acaagccggc ccgggcggcg 180
gagacagcg 189

<210> SEQ ID NO 108
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 108
gctgtctccg ccgcccgcca gttttagagc tagaaatagc aagttaaaat aaggctagtc 60
cgttatcaac ttgaaaaagt ggcaccgagt cggtgcggca cgggggtcgc agtcgccatg 120
ccggatgatc ctgacgacgg agaccgccgt cgtcgacaag ccggcccggg cggcggagac 180
agcg 184

<210> SEQ ID NO 109
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 109
gctgtctccg ccgcccgcca gttttagagc tagaaatagc aagttaaaat aaggctagtc 60
cgttatcaac ttgaaaaagt ggcaccgagt cggtgcgggg gtcgcagtcg ccatgccgga 120
tgatcctgac gacggagacc gccgtcgtcg acaagccggc ccgggcggcg gagacagcg 179

<210> SEQ ID NO 110
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
gcgtggtggg gccgccagcg gttttagagc tagaaatagc aagttaaaat aaggctagtc 60
cgttatcaac ttgaaaaagt ggcaccgagt cggtgc 96

<210> SEQ ID NO 111
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 111
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggggatg atcctgacga cggagaccgc cgtcgtcgac aagccggtga gctgcgagaa 180

<210> SEQ ID NO 112
<211> LENGTH: 178
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 112
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catgggatga tcctgacgac ggagaccgcc gtcgtcgaca agccgtgagc tgcgagaa 178

<210> SEQ ID NO 113
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 113
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggatgat cctgacgacg gagaccgccg tcgtcgacaa gcctgagctg cgagaa 176

<210> SEQ ID NO 114
<211> LENGTH: 174
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 114
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggtgatc ctgacgacgg agaccgccgt cgtcgacaag ctgagctgcg agaa 174

<210> SEQ ID NO 115
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 115
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgcggat gatcctgacg acggagaccg ccgtcgtcga caagccggcc gggcggcgga 180
ga 182

<210> SEQ ID NO 116
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 116
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgggatg atcctgacga cggagaccgc cgtcgtcgac aagccggcgg gcggcggaga 180

<210> SEQ ID NO 117
<211> LENGTH: 178
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 117
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatggatga tcctgacgac ggagaccgcc gtcgtcgaca agccgcgggc ggcggaga 178

<210> SEQ ID NO 118
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgatgat cctgacgacg gagaccgccg tcgtcgacaa gcccgggcgg cggaga 176

<210> SEQ ID NO 119
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccccgga tgatcctgac gacggagacc gccgtcgtcg acaagccggc ctcctccagg 180
caatacgcg 189

<210> SEQ ID NO 120
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccccgga tgatcctgac gacggagacc gccgtcgtcg acaagccggc ctcctccagg 180
caat 184

<210> SEQ ID NO 121
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgcccggat gatcctgacg acggagaccg ccgtcgtcga caagccggct cctccaggca 180
at 182

<210> SEQ ID NO 122
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccggatg atcctgacga cggagaccgc cgtcgtcgac aagccggtcc tccaggcaat 180

<210> SEQ ID NO 123
<211> LENGTH: 178
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccgatga tcctgacgac ggagaccgcc gtcgtcgaca agccgtcctc caggcaat 178

<210> SEQ ID NO 124
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccatgat cctgacgacg gagaccgccg tcgtcgacaa gcctcctcca ggcaat 176

<210> SEQ ID NO 125
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
gagccgagca cgaggggata cgttttagag ctagaaatag caagttaaaa taaggctagt 60
ccgttatcaa cttgaaaaag tggcaccgag tcggtgc 97

<210> SEQ ID NO 126

<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gctattctcg cagctcacca gttttagagc tagaaatagc aagttaaaat aaggctagtc 60
cgttatcaac ttgaaaaagt ggcaccgagt cggtgcggcg atatcatcat ccatggatga 120
tcctgacgac ggagaccgcc gtcgtcgaca agcctgagct gcgagaa 167

<210> SEQ ID NO 127
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
gctattctcg cagctcacca gttttagagc tagaaatagc aagttaaaat aaggctagtc 60
cgttatcaac ttgaaaaagt ggcaccgagt cggtgctatc atcatccatg gatgatcctg 120
acgacggaga ccgccgtcgt cgacaagcct gagctgcgag aa 162

<210> SEQ ID NO 128
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
gctattctcg cagctcacca gttttagagc tagaaatagc aagttaaaat aaggctagtc 60
cgttatcaac ttgaaaaagt ggcaccgagt cggtgctcat ccatggatga tcctgacgac 120
ggagaccgcc gtcgtcgaca agcctgagct gcgagaa 157

<210> SEQ ID NO 129
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gctattctcg cagctcacca gttttagagc tagaaatagc aagttaaaat aaggctagtc 60
cgttatcaac ttgaaaaagt ggcaccgagt cggtgcggcg atatcatcat ccatggatga 120
tcctgacgac ggagaccgcc gtcgtcgaca agcctgagct gcg 163

<210> SEQ ID NO 130
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gctattctcg cagctcacca gttttagagc tagaaatagc aagttaaaat aaggctagtc 60

```
cgttatcaac ttgaaaaagt ggcaccgagt cggtgctatc atcatccatg gatgatcctg    120

acgacggaga ccgccgtcgt cgacaagcct gagctgcg                            158


<210> SEQ ID NO 131
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

gctattctcg cagctcacca gttttagagc tagaaatagc aagttaaaat aaggctagtc     60

cgttatcaac ttgaaaaagt ggcaccgagt cggtgctcat ccatggatga tcctgacgac    120

ggagaccgcc gtcgtcgaca agcctgagct gcg                                 153


<210> SEQ ID NO 132
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

gctgtctccg ccgcccgcca gttttagagc tagaaatagc aagttaaaat aaggctagtc     60

cgttatcaac ttgaaaaagt ggcaccgagt cggtgccggg ggtcgcagtc gccatgatga    120

tcctgacgac ggagaccgcc gtcgtcgaca agcccgggcg gcggaga                  167


<210> SEQ ID NO 133
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

gctgtctccg ccgcccgcca gttttagagc tagaaatagc aagttaaaat aaggctagtc     60

cgttatcaac ttgaaaaagt ggcaccgagt cggtgcgtcg cagtcgccat gatgatcctg    120

acgacggaga ccgccgtcgt cgacaagccc gggcggcgga ga                       162


<210> SEQ ID NO 134
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

gctgtctccg ccgcccgcca gttttagagc tagaaatagc aagttaaaat aaggctagtc     60

cgttatcaac ttgaaaaagt ggcaccgagt cggtgcagtc gccatgatga tcctgacgac    120

ggagaccgcc gtcgtcgaca agcccgggcg gcggaga                             157


<210> SEQ ID NO 135
<211> LENGTH: 163
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 135
gctgtctccg ccgcccgcca gttttagagc tagaaatagc aagttaaaat aaggctagtc 60
cgttatcaac ttgaaaaagt ggcaccgagt cggtgccggg ggtcgcagtc gccatgatga 120
tcctgacgac ggagaccgcc gtcgtcgaca agcccgggcg gcg 163

<210> SEQ ID NO 136
<211> LENGTH: 158
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 136
gctgtctccg ccgcccgcca gttttagagc tagaaatagc aagttaaaat aaggctagtc 60
cgttatcaac ttgaaaaagt ggcaccgagt cggtgcgtcg cagtcgccat gatgatcctg 120
acgacggaga ccgccgtcgt cgacaagccc gggcggcg 158

<210> SEQ ID NO 137
<211> LENGTH: 153
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 137
gctgtctccg ccgcccgcca gttttagagc tagaaatagc aagttaaaat aaggctagtc 60
cgttatcaac ttgaaaaagt ggcaccgagt cggtgcagtc gccatgatga tcctgacgac 120
ggagaccgcc gtcgtcgaca agcccgggcg gcg 153

<210> SEQ ID NO 138
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
gagaagcggc gtccggggct agttttagag ctagaaatag caagttaaaa taaggctagt 60
ccgttatcaa cttgaaaaag tggcaccgag tcggtgctct ttgtccagag tcacagccat 120
accggatgat cctgacgacg gagaccgccg tcgtcgacaa gccggccccc cggacgccgc 180

<210> SEQ ID NO 139
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
gggcacgggg ccatgtacaa gttttagagc tagaaatagc aagttaaaat aaggctagtc 60
cgttatcaac ttgaaaaagt ggcaccgagt cggtgcggcg tcggcagccc gatcccgttg 120
ccggatgatc ctgacgacgg agaccgccgt cgtcgacaag ccggcctaca tggccccgt 179

<210> SEQ ID NO 140
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 140
gtgtcaggtg gggcggggct agttttagag ctagaaatag caagttaaaa taaggctagt 60
ccgttatcaa cttgaaaaag tggcaccgag tcggtgcgct ggctcctccc ctggcaccat 120
accggatgat cctgacgacg gagaccgccg tcgtcgacaa gccggccccc cgccccacct 180
gacac 185

<210> SEQ ID NO 141
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141
gagtgggtca gacgagcagg agttttagag ctagaaatag caagttaaaa taaggctagt 60
ccgttatcaa cttgaaaaag tggcaccgag tcggtgcgat ggagggctgc atgggggagg 120
agtcgccgga tgatcctgac gacggagacc gccgtcgtcg acaagccggc ctgctcgtct 180
gacc 184

<210> SEQ ID NO 142
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
gcagccaccc gctctcggcc cgttttagag ctagaaatag caagttaaaa taaggctagt 60
ccgttatcaa cttgaaaaag tggcaccgag tcggtgc 97

<210> SEQ ID NO 143
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
gtgtagtcag gccgctcacc cgttttagag ctagaaatag caagttaaaa taaggctagt 60
ccgttatcaa cttgaaaaag tggcaccgag tcggtgc 97

<210> SEQ ID NO 144
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
gctgacaagt ctacggaacc tgttttagag ctagaaatag caagttaaaa taaggctagt 60
ccgttatcaa cttgaaaaag tggcaccgag tcggtgc 97

<210> SEQ ID NO 145
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
gctcctccag cgccttgacc gttttagagc tagaaatagc aagttaaaat aaggctagtc 60
cgttatcaac ttgaaaaagt ggcaccgagt cggtgc 96

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
gctattctcg cagctcacca 20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
agaagcggcg tccggggcta 20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
gggcacgggg ccatgtacaa 20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
gcgtattgcc tggaggatgg 20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
tgtcaggtgg ggcggggcta 20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
agtgggtcag acgagcagga 20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
gctgtctccg ccgcccgcca 20

<210> SEQ ID NO 153
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
gctattctcg cagctcacca gttttagagc tagaaatagc aagttaaaat aaggctagtc 60
cgttatcaac ttgaaaaagt ggcaccgagt cggtgc 96

<210> SEQ ID NO 154
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (148)..(149)
<223> OTHER INFORMATION: CG, GC, AT, TA, GG, TT, GA, AG, CC, TC, CT, AA,
TG, GT, CA, or AC

<400> SEQUENCE: 154
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggccgga tgatcctgac gacggagnnc gccgtcgtcg acaagccggc ctgagctgcg 180
agaa 184

<210> SEQ ID NO 155
<211> LENGTH: 183
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 155
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catgccggat gatcctgacg acggagaccg ccgtcgtcga caagccggcc tgagctgcga 180
gaa 183

<210> SEQ ID NO 156
<211> LENGTH: 183
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 156
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catgccggat gatcctgacg acggagagcg ccgtcgtcga caagccggcc tgagctgcga 180
gaa 183

<210> SEQ ID NO 157
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 157
gcgtattgcc tggaggatgg gttttagagc tagaaatagc aagttaaaat aaggctagtc 60
cgttatcaac ttgaaaaagt ggcaccgagt cggtgcgaac cacgcggcga atgccggcgt 120
ccgccccgga tgatcctgac gacggagtcc gccgtcgtcg acaagccggc ctcctccagg 180
caatacgcg 189

<210> SEQ ID NO 158
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 158
gctgtctccg ccgcccgcca gttttagagc tagaaatagc aagttaaaat aaggctagtc 60
cgttatcaac ttgaaaaagt ggcaccgagt cggtgcgcgg cggcacgggg gtcgcagtcg 120
ccatgccgga tgatcctgac gacggagctc gccgtcgtcg acaagccggc ccgggcggcg 180
gagacagcg 189

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
gtcacctcca atgactaggg 20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
gggcaaccac aaacccacga 20

<210> SEQ ID NO 161
<211> LENGTH: 194
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 161
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggctatg ccggatgatc ctgacgacgg agtccgccgt cgtcgacaag ccggccctag 180
ctgagctgcg agaa 194

<210> SEQ ID NO 162
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 162
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggtgccg gatgatcctg acgacggagt ccgccgtcgt cgacaagccg gccctatgag 180
ctgcgagaa 189

<210> SEQ ID NO 163
<211> LENGTH: 184
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 163
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggccgga tgatcctgac gacggagtcc gccgtcgtcg acaagccggc ctgagctgcg 180
agaa 184

<210> SEQ ID NO 164
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 164
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggggatg atcctgacga cggagtccgc cgtcgtcgac aagccgtgag ctgcgagaa 179

<210> SEQ ID NO 165
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggtgatc ctgacgacgg agtccgccgt cgtcgacaag ctgagctgcg agaa 174

<210> SEQ ID NO 166
<211> LENGTH: 169
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggatcct gacgacggag tccgccgtcg tcgacatgag ctgcgagaa 169

<210> SEQ ID NO 167
<211> LENGTH: 164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 167
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggcctga cgacggagtc cgccgtcgtc gtgagctgcg agaa 164

<210> SEQ ID NO 168
<211> LENGTH: 159
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggtgacg acggagtccg ccgtcgtgag ctgcgagaa 159

<210> SEQ ID NO 169
<211> LENGTH: 154

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 169
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggacgac ggagtccgcc gtgagctgcg agaa 154

<210> SEQ ID NO 170
<211> LENGTH: 149
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 170
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catgggacgg agtccgtgag ctgcgagaa 149

<210> SEQ ID NO 171
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 171
gctattctcg cagctcacca gttttagagc tagaaatagc aagttaaaat aaggctagtc 60
cgttatcaac ttgaaaaagt ggcaccgagt cggtgcgacg agcgcggcga tatcatcatc 120
catggcggag ttgagctgcg agaa 144

<210> SEQ ID NO 172
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 172
gaagccggcc ttgcacatgc gttttagagc tagaaatagc aagttaaaat aaggctagtc 60
cgttatcaac ttgaaaaagt ggcaccgagt cggtgctcga cgacgagcgc ggcgatatca 120
tcatccatgg taccgttcgt atagcataca ttatacgaag ttattgagct gcgagaatag 180
cc 182

<210> SEQ ID NO 173
<211> LENGTH: 177
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 173
gaagccggcc ttgcacatgc gttttagagc tagaaatagc aagttaaaat aaggctagtc 60
cgttatcaac ttgaaaaagt ggcaccgagt cggtgcgacg agcgcggcga tatcatcatc 120
catggtaccg ttcgtatagc atacattata cgaagttatt gagctgcgag aatagcc 177

<210> SEQ ID NO 174
<211> LENGTH: 177
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 174
gaagccggcc ttgcacatgc gttttagagc tagaaatagc aagttaaaat aaggctagtc 60
cgttatcaac ttgaaaaagt ggcaccgagt cggtgctcga cgacgagcgc ggcgatatca 120
tcatccatgg taccgttcgt atagcataca ttatacgaag ttattgagct gcgagaa 177

<210> SEQ ID NO 175
<211> LENGTH: 159
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 175
gaagccggcc ttgcacatgc gttttagagc tagaaatagc aagttaaaat aaggctagtc 60
cgttatcaac ttgaaaaagt ggcaccgagt cggtgcatat catcatccat ggtaccgttc 120
gtatagcata cattatacga agttattgag ctgcgagaa 159

<210> SEQ ID NO 176
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
ccccacgatg gaggggaaga gttttagagc tagaaatagc aagttaaaat aaggctagtc 60
cgttatcaac ttgaaaaagt ggcaccgagt cggtgc 96

<210> SEQ ID NO 177
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
ccttctcctg gagccgcgac gttttagagc tagaaatagc aagttaaaat aaggctagtc 60
cgttatcaac ttgaaaaagt ggcaccgagt cggtgc 96

<210> SEQ ID NO 178
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
gtggtttgtc tggtcaacca ccgcggtctc agtggtgtac ggtacaaacc ca 52

<210> SEQ ID NO 179
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
tgggtttgta ccgtacacca ctgagaccgc ggtggttgac cagacaaacc ac 52

<210> SEQ ID NO 180
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
gtggtttgtc tggtcaacca ccgcgcgctc agtggtgtac ggtacaaacc ca 52

<210> SEQ ID NO 181
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
tgggtttgta ccgtacacca ctgagcgcgc ggtggttgac cagacaaacc ac 52

<210> SEQ ID NO 182
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
gtggtttgtc tggtcaacca ccgcggcctc agtggtgtac ggtacaaacc ca 52

<210> SEQ ID NO 183
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
tgggtttgta ccgtacacca ctgaggccgc ggtggttgac cagacaaacc ac 52

<210> SEQ ID NO 184
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
gtggtttgtc tggtcaacca ccgcgatctc agtggtgtac ggtacaaacc ca 52

<210> SEQ ID NO 185
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
tgggtttgta ccgtacacca ctgagatcgc ggtggttgac cagacaaacc ac 52

<210> SEQ ID NO 186
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
gtggtttgtc tggtcaacca ccgcgtactc agtggtgtac ggtacaaacc ca 52

<210> SEQ ID NO 187
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
tgggtttgta ccgtacacca ctgagtacgc ggtggttgac cagacaaacc ac 52

<210> SEQ ID NO 188
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
gtggtttgtc tggtcaacca ccgcgggctc agtggtgtac ggtacaaacc ca 52

<210> SEQ ID NO 189
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
tgggtttgta ccgtacacca ctgagcccgc ggtggttgac cagacaaacc ac 52

<210> SEQ ID NO 190
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
gtggtttgtc tggtcaacca ccgcgttctc agtggtgtac ggtacaaacc ca 52

<210> SEQ ID NO 191
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
tgggtttgta ccgtacacca ctgagaacgc ggtggttgac cagacaaacc ac 52

<210> SEQ ID NO 192
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192
gtggtttgtc tggtcaacca ccgcggactc agtggtgtac ggtacaaacc ca 52

<210> SEQ ID NO 193
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
tgggtttgta ccgtacacca ctgagtccgc ggtggttgac cagacaaacc ac 52

<210> SEQ ID NO 194
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
gtggtttgtc tggtcaacca ccgcgagctc agtggtgtac ggtacaaacc ca 52

<210> SEQ ID NO 195
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
tgggtttgta ccgtacacca ctgagctcgc ggtggttgac cagacaaacc ac 52

<210> SEQ ID NO 196
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
gtggtttgtc tggtcaacca ccgcgccctc agtggtgtac ggtacaaacc ca 52

<210> SEQ ID NO 197
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
tgggtttgta ccgtacacca ctgagggcgc ggtggttgac cagacaaacc ac 52

<210> SEQ ID NO 198
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
gtggtttgtc tggtcaacca ccgcgtcctc agtggtgtac ggtacaaacc ca 52

<210> SEQ ID NO 199
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
tgggtttgta ccgtacacca ctgaggacgc ggtggttgac cagacaaacc ac 52

<210> SEQ ID NO 200
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
gtggtttgtc tggtcaacca ccgcgctctc agtggtgtac ggtacaaacc ca 52

<210> SEQ ID NO 201
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
tgggtttgta ccgtacacca ctgagagcgc ggtggttgac cagacaaacc ac 52

<210> SEQ ID NO 202
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
gtggtttgtc tggtcaacca ccgcgaactc agtggtgtac ggtacaaacc ca 52

<210> SEQ ID NO 203
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
tgggtttgta ccgtacacca ctgagttcgc ggtggttgac cagacaaacc ac 52

<210> SEQ ID NO 204
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
gtggtttgtc tggtcaacca ccgcgcactc agtggtgtac ggtacaaacc ca 52

<210> SEQ ID NO 205
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
tgggtttgta ccgtacacca ctgagtgcgc ggtggttgac cagacaaacc ac 52

<210> SEQ ID NO 206
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
gtggtttgtc tggtcaacca ccgcgacctc agtggtgtac ggtacaaacc ca 52

<210> SEQ ID NO 207
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
tgggtttgta ccgtacacca ctgaggtcgc ggtggttgac cagacaaacc ac 52

<210> SEQ ID NO 208
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
gtggtttgtc tggtcaacca ccgcgtgctc agtggtgtac ggtacaaacc ca 52

<210> SEQ ID NO 209

<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
tgggtttgta ccgtacacca ctgagcacgc ggtggttgac cagacaaacc ac 52

<210> SEQ ID NO 210
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 210
ggccggcttg tcgacgacgg cggtctccgt cgtcaggatc atccgg 46

<210> SEQ ID NO 211
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
ccggatgatc ctgacgacgg agaccgccgt cgtcgacaag ccggcc 46

<210> SEQ ID NO 212
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
ggccggcttg tcgacgacgg cgaactccgt cgtcaggatc atccgg 46

<210> SEQ ID NO 213
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
ccggatgatc ctgacgacgg agttcgccgt cgtcgacaag ccggcc 46

<210> SEQ ID NO 214
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
ggccggcttg tcgacgacgg cggactccgt cgtcaggatc atccgg 46

<210> SEQ ID NO 215
<211> LENGTH: 46

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
ccggatgatc ctgacgacgg agtccgccgt cgtcgacaag ccggcc 46

<210> SEQ ID NO 216
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
ggccggcttg tcgacgacgg cgcactccgt cgtcaggatc atccgg 46

<210> SEQ ID NO 217
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
ccggatgatc ctgacgacgg agtgcgccgt cgtcgacaag ccggcc 46

<210> SEQ ID NO 218
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
ggccggcttg tcgacgacgg cgtactccgt cgtcaggatc atccgg 46

<210> SEQ ID NO 219
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
ccggatgatc ctgacgacgg agtacgccgt cgtcgacaag ccggcc 46

<210> SEQ ID NO 220
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
ggccggcttg tcgacgacgg cgagctccgt cgtcaggatc atccgg 46

<210> SEQ ID NO 221
<211> LENGTH: 46
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 221
ccggatgatc ctgacgacgg agctcgccgt cgtcgacaag ccggcc 46

<210> SEQ ID NO 222
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 222
ggccggcttg tcgacgacgg cgggctccgt cgtcaggatc atccgg 46

<210> SEQ ID NO 223
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 223
ccggatgatc ctgacgacgg agcccgccgt cgtcgacaag ccggcc 46

<210> SEQ ID NO 224
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 224
ggccggcttg tcgacgacgg cgcgctccgt cgtcaggatc atccgg 46

<210> SEQ ID NO 225
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 225
ccggatgatc ctgacgacgg agcgcgccgt cgtcgacaag ccggcc 46

<210> SEQ ID NO 226
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 226
ggccggcttg tcgacgacgg cgtgctccgt cgtcaggatc atccgg 46

<210> SEQ ID NO 227
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ccggatgatc ctgacgacgg agcacgccgt cgtcgacaag ccggcc 46

<210> SEQ ID NO 228
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ggccggcttg tcgacgacgg cgacctccgt cgtcaggatc atccgg 46

<210> SEQ ID NO 229
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccggatgatc ctgacgacgg aggtcgccgt cgtcgacaag ccggcc 46

<210> SEQ ID NO 230
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ggccggcttg tcgacgacgg cggcctccgt cgtcaggatc atccgg 46

<210> SEQ ID NO 231
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ccggatgatc ctgacgacgg aggccgccgt cgtcgacaag ccggcc 46

<210> SEQ ID NO 232
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ggccggcttg tcgacgacgg cgccctccgt cgtcaggatc atccgg 46

<210> SEQ ID NO 233
<211> LENGTH: 46
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 233
ccggatgatc ctgacgacgg agggcgccgt cgtcgacaag ccggcc 46

<210> SEQ ID NO 234
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ggccggcttg tcgacgacgg cgtcctccgt cgtcaggatc atccgg 46

<210> SEQ ID NO 235
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccggatgatc ctgacgacgg aggacgccgt cgtcgacaag ccggcc 46

<210> SEQ ID NO 236
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ggccggcttg tcgacgacgg cgatctccgt cgtcaggatc atccgg 46

<210> SEQ ID NO 237
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ccggatgatc ctgacgacgg agatcgccgt cgtcgacaag ccggcc 46

<210> SEQ ID NO 238
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ggccggcttg tcgacgacgg cgctctccgt cgtcaggatc atccgg 46

<210> SEQ ID NO 239
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 239
ccggatgatc ctgacgacgg agagcgccgt cgtcgacaag ccggcc 46

<210> SEQ ID NO 240
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
ggccggcttg tcgacgacgg cgttctccgt cgtcaggatc atccgg 46

<210> SEQ ID NO 241
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
ccggatgatc ctgacgacgg agaacgccgt cgtcgacaag ccggcc 46

<210> SEQ ID NO 242
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
ggcttgtcga cgacggcggt ctccgtcgtc aggatcat 38

<210> SEQ ID NO 243
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
atgatcctga cgacggagac cgccgtcgtc gacaagcc 38

<210> SEQ ID NO 244
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 244
ggcttgtcga cgacggcgaa ctccgtcgtc aggatcat 38

<210> SEQ ID NO 245
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
atgatcctga cgacggagtt cgccgtcgtc gacaagcc 38

<210> SEQ ID NO 246
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 246
ggcttgtcga cgacggcgga ctccgtcgtc aggatcat 38

<210> SEQ ID NO 247
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
atgatcctga cgacggagtc cgccgtcgtc gacaagcc 38

<210> SEQ ID NO 248
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
ggcttgtcga cgacggcgca ctccgtcgtc aggatcat 38

<210> SEQ ID NO 249
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
atgatcctga cgacggagtg cgccgtcgtc gacaagcc 38

<210> SEQ ID NO 250
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
ggcttgtcga cgacggcgta ctccgtcgtc aggatcat 38

<210> SEQ ID NO 251
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
atgatcctga cgacggagta cgccgtcgtc gacaagcc 38

<210> SEQ ID NO 252
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 252
ggcttgtcga cgacggcgag ctccgtcgtc aggatcat 38

<210> SEQ ID NO 253
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253
atgatcctga cgacggagct cgccgtcgtc gacaagcc 38

<210> SEQ ID NO 254
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254
ggcttgtcga cgacggcggg ctccgtcgtc aggatcat 38

<210> SEQ ID NO 255
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 255
atgatcctga cgacggagcc cgccgtcgtc gacaagcc 38

<210> SEQ ID NO 256
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
ggcttgtcga cgacggcgcg ctccgtcgtc aggatcat 38

<210> SEQ ID NO 257
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 257
atgatcctga cgacggagcg cgccgtcgtc gacaagcc 38

<210> SEQ ID NO 258
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 258
ggcttgtcga cgacggcgtg ctccgtcgtc aggatcat 38

<210> SEQ ID NO 259
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 259
atgatcctga cgacggagca cgccgtcgtc gacaagcc 38

<210> SEQ ID NO 260
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 260
ggcttgtcga cgacggcgac ctccgtcgtc aggatcat 38

<210> SEQ ID NO 261
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 261
atgatcctga cgacggaggt cgccgtcgtc gacaagcc 38

<210> SEQ ID NO 262
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
ggcttgtcga cgacggcggc ctccgtcgtc aggatcat 38

<210> SEQ ID NO 263
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
atgatcctga cgacggaggc cgccgtcgtc gacaagcc 38

<210> SEQ ID NO 264
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 264
ggcttgtcga cgacggcgcc ctccgtcgtc aggatcat 38

<210> SEQ ID NO 265
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 265
atgatcctga cgacggaggg cgccgtcgtc gacaagcc 38

<210> SEQ ID NO 266
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 266
ggcttgtcga cgacggcgtc ctccgtcgtc aggatcat 38

<210> SEQ ID NO 267
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 267
atgatcctga cgacggagga cgccgtcgtc gacaagcc 38

<210> SEQ ID NO 268
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 268
ggcttgtcga cgacggcgat ctccgtcgtc aggatcat 38

<210> SEQ ID NO 269
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 269
atgatcctga cgacggagat cgccgtcgtc gacaagcc 38

<210> SEQ ID NO 270
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 270
ggcttgtcga cgacggcgct ctccgtcgtc aggatcat 38

<210> SEQ ID NO 271
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271
atgatcctga cgacggagag cgccgtcgtc gacaagcc 38

<210> SEQ ID NO 272
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 272
ggcttgtcga cgacggcgtt ctccgtcgtc aggatcat 38

<210> SEQ ID NO 273
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 273
atgatcctga cgacggagaa cgccgtcgtc gacaagcc 38

<210> SEQ ID NO 274
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 274
taccgttcgt ataatgtatg ctatacgaag ttat 34

<210> SEQ ID NO 275
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 275
ataacttcgt atagcataca ttatacgaac ggta 34

<210> SEQ ID NO 276
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 276
ataacttcgt ataatgtatg ctatacgaac ggta 34

<210> SEQ ID NO 277
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 277
taccgttcgt atagcataca ttatacgaag ttat 34

<210> SEQ ID NO 278
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 278
tttaccttga ttgagatgtt aattgtg 27

<210> SEQ ID NO 279
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 279
cacaattaac atctcaatca aggtaaa 27

<210> SEQ ID NO 280
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 280
gcgagttttt atttcgttta tttcaattaa ggtaactaaa aaactccttt 50

<210> SEQ ID NO 281
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
aaaggagttt tttagttacc ttaattgaaa taaacgaaat aaaaactcgc 50

<210> SEQ ID NO 282
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 282
ctggatcatc tggatcactt tcgtcaaaaa cctg 34

<210> SEQ ID NO 283
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
caggtttttg acgaaagtga tccagatgat ccag 34

<210> SEQ ID NO 284
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 284
ttcgggtgct gggttgttgt ctctggacag tgatccatgg gaaactactc agcacca 57

<210> SEQ ID NO 285
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 285
tggtgctgag tagtttccca tggatcactg tccagagaca acaacccagc acccgaa 57

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
aaaagtgtgg gctgcaggat ctga 24

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
ggagctggca gctgtcaatg cc 22

<210> SEQ ID NO 288

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 288
agtcaatgcc gctctcgtgg a 21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 289
cagcgggctc agctgatagc a 21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 290
cggatggcta accaagcggc c 21

<210> SEQ ID NO 291
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
cccggcttcc tttgtcc 17

<210> SEQ ID NO 292
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
gaactccacg ccgttca 17

<210> SEQ ID NO 293
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
cccggcttcc tttgtcc 17

<210> SEQ ID NO 294
<211> LENGTH: 22

<212> TYPE: DNA
<213> ORGANISM: Artificial Sequence
<220> FEATURE:
<223> OTHER INFORMATION: Description of Artificial Sequence: Synthetic
primer

<400> SEQUENCE: 294
aaccacaact agaatgcagt ga 22

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 295
cccggcttcc tttgtcc 17

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 296
gaactccacg ccgttca 17

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 297
cccggcttcc tttgtcc 17

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 298
aaccacaact agaatgcagt ga 22

<210> SEQ ID NO 299
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 299
cccggcttcc tttgtcc 17

<210> SEQ ID NO 300
<211> LENGTH: 17
<212> TYPE: DNA

<213> ORGANISM: Artificial Sequence
<220> FEATURE:
<223> OTHER INFORMATION: Description of Artificial Sequence: Synthetic primer

<400> SEQUENCE: 300
gaactccacg ccgttca 17

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 301
tccttatcac ggtcccgctc g 21

<210> SEQ ID NO 302
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 302
gaactccacg ccgttca 17

<210> SEQ ID NO 303
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 303
cgtcgacaac ggtagtg 17

<210> SEQ ID NO 304
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 304
gaactccacg ccgttca 17

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 305
tcgcgtgatt ctcggaac 18

<210> SEQ ID NO 306
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 306
gaactccacg ccgttca 17

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 307
gggcggtaag tggttagttt 20

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 308
gaactccacg ccgttca 17

<210> SEQ ID NO 309
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 309
aagaggcgga gccagta 17

<210> SEQ ID NO 310
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 310
gaactccacg ccgttca 17

<210> SEQ ID NO 311
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 311
ctcccttctc ccggtgccc 19

<210> SEQ ID NO 312
<211> LENGTH: 17
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 312
gaactccacg ccgttca                                                    17

<210> SEQ ID NO 313
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cccggcttcc tttgtcc                                                    17

<210> SEQ ID NO 314
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
gaactccacg ccgttca                                                    17

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
gggcggtaag tggttagttt                                                 20

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
gaactccacg ccgttca                                                    17

<210> SEQ ID NO 317
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cgtcgacaac ggtagtg                                                    17

<210> SEQ ID NO 318
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
gaactccacg ccgttca 17

<210> SEQ ID NO 319
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 319
aagaggcgga gccagta 17

<210> SEQ ID NO 320
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 320
gaactccacg ccgttca 17

<210> SEQ ID NO 321
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 321
ctcccttctc ccggtgccc 19

<210> SEQ ID NO 322
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 322
gaactccacg ccgttca 17

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 323
tccttatcac ggtcccgctc g 21

<210> SEQ ID NO 324
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 324
gaactccacg ccgttca 17

<210> SEQ ID NO 325
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 325
cccggcttcc tttgtcc 17

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 326
ggcctgccag caggagga 18

<210> SEQ ID NO 327
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
cccggcttcc tttgtcc 17

<210> SEQ ID NO 328
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
ggtgtgcagt cacattggta aagcc 25

<210> SEQ ID NO 329
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
cccggcttcc tttgtcc 17

<210> SEQ ID NO 330
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
gatgggtcta gtccagctaa ag 22

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 331
cccggcttcc tttgtcc 17

<210> SEQ ID NO 332
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 332
gagagacaag gctgcaca 18

<210> SEQ ID NO 333
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 333
ccaggtgaga gtcagggtag tgttca 26

<210> SEQ ID NO 334
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 334
gaactccacg ccgttca 17

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 335
agggaccttt gcctgtgtga gtc 23

<210> SEQ ID NO 336
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
gaactccacg ccgttca 17

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
tcagctctgt gctgaggcga a 21

<210> SEQ ID NO 338
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
gaactccacg ccgttca 17

<210> SEQ ID NO 339
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
aagccatctc ccagaatatc tgcttagaaa tg 32

<210> SEQ ID NO 340
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 340
gaactccacg ccgttca 17

<210> SEQ ID NO 341
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 341
gagaggagca acagtgagca tgatg 25

<210> SEQ ID NO 342
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 342
gaactccacg ccgttca 17

<210> SEQ ID NO 343
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 343
aagccatctc ccagaatatc tgcttagaaa tg 32

<210> SEQ ID NO 344
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 344
gaactccacg ccgttca 17

<210> SEQ ID NO 345
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 345
gagaggagca acagtgagca tgatg 25

<210> SEQ ID NO 346
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 346
gaactccacg ccgttca 17

<210> SEQ ID NO 347
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 347
cccggcttcc tttgtcc 17

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 348
ggctatgaac taatgacccc gt 22

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 349
cccggcttcc tttgtcc 17

<210> SEQ ID NO 350
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 350
ggcctgccag caggagga 18

<210> SEQ ID NO 351
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 351
cccggcttcc tttgtcc 17

<210> SEQ ID NO 352
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
ggtgtgcagt cacattggta aagcc 25

<210> SEQ ID NO 353
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
acactctttc cctacacgac gctcttccga tctccgacct cggctcacag cg 52

<210> SEQ ID NO 354
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354
acactctttc cctacacgac gctcttccga tctaccgacc tcggctcaca gcg 53

<210> SEQ ID NO 355
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 355
acactctttc cctacacgac gctcttccga tctgaccgac ctcggctcac agcg 54

<210> SEQ ID NO 356
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
acactctttc cctacacgac gctcttccga tcttgaccga cctcggctca cagcg 55

<210> SEQ ID NO 357
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
acactctttc cctacacgac gctcttccga tctctgaccg acctcggctc acagcg 56

<210> SEQ ID NO 358
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
acactctttc cctacacgac gctcttccga tctactgacc gacctcggct cacagcg 57

<210> SEQ ID NO 359
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
acactctttc cctacacgac gctcttccga tcttactgac cgacctcggc tcacagcg 58

<210> SEQ ID NO 360
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
acactctttc cctacacgac gctcttccga tctgtactga ccgacctcgg ctcacagcg 59

<210> SEQ ID NO 361
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
gtgactggag ttcagacgtg tgctcttccg atctccaccc agccagctcc c 51

<210> SEQ ID NO 362
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
acactctttc cctacacgac gctcttccga tctccggtgg cgcattgcca c 51

<210> SEQ ID NO 363
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
acactctttc cctacacgac gctcttccga tctaccggtg gcgcattgcc ac 52

<210> SEQ ID NO 364
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 364
acactctttc cctacacgac gctcttccga tctgaccggt ggcgcattgc cac 53

<210> SEQ ID NO 365
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 365
acactctttc cctacacgac gctcttccga tcttgaccgg tggcgcattg ccac 54

<210> SEQ ID NO 366
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
acactctttc cctacacgac gctcttccga tctctgaccg gtggcgcatt gccac 55

<210> SEQ ID NO 367

<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 367
acactctttc cctacacgac gctcttccga tctactgacc ggtggcgcat tgccac 56

<210> SEQ ID NO 368
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
acactctttc cctacacgac gctcttccga tcttactgac cggtggcgca ttgccac 57

<210> SEQ ID NO 369
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 369
acactctttc cctacacgac gctcttccga tctgtactga ccggtggcgc attgccac 58

<210> SEQ ID NO 370
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
gtgactggag ttcagacgtg tgctcttccg atctcagagt ccagcttggg ccca 54

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
gatattttcc cagctcacca 20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 372
tctattctcc cagctcccca 20

<210> SEQ ID NO 373
<211> LENGTH: 40

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
agcggcttct gtctctgtga gtgagctggc ggtctccgtc 40

<210> SEQ ID NO 374
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
gactagccca cgctccggtt ctgagccgcg acggcggtct ccg 43

<210> SEQ ID NO 375
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
cccagggtcc catgcgctcc ccggccctga cggcggtctc c 41

<210> SEQ ID NO 376
<211> LENGTH: 2560
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 376

```
Met Lys Arg Thr Ala Asp Gly Ser Glu Phe Glu Ser Pro Lys Lys Lys
1               5                   10                  15

Arg Lys Val Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
        115                 120                 125

Lys Lys His Glu Arg His Pro Ile Phe Gly Asn Ile Val Asp Glu Val
    130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175
```

```
Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590
```

```
Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
        675                 680                 685

Arg Asp Lys Gln Ser Gly Lys Thr Ile Leu Asp Phe Leu Lys Ser Asp
    690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
            740                 745                 750

Lys Gly Ile Leu Gln Thr Val Lys Val Val Asp Glu Leu Val Lys Val
        755                 760                 765

Met Gly Arg His Lys Pro Glu Asn Ile Val Ile Glu Met Ala Arg Glu
    770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp Ala Ile Val Pro Gln Ser Phe
    850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His  His Ala His Asp Ala  Tyr Leu Asn
        995                 1000                 1005

Ala Val  Val Gly Thr Ala Leu  Ile Lys Lys Tyr Pro  Lys Leu Glu
```

-continued

```
    1010                1015                1020

Ser Glu  Phe Val Tyr Gly Asp  Tyr Lys Val Tyr Asp  Val Arg Lys
    1025                1030                1035

Met Ile  Ala Lys Ser Glu Gln  Glu Ile Gly Lys Ala  Thr Ala Lys
    1040                1045                1050

Tyr Phe  Phe Tyr Ser Asn Ile  Met Asn Phe Phe Lys  Thr Glu Ile
    1055                1060                1065

Thr Leu  Ala Asn Gly Glu Ile  Arg Lys Arg Pro Leu  Ile Glu Thr
    1070                1075                1080

Asn Gly  Glu Thr Gly Glu Ile  Val Trp Asp Lys Gly  Arg Asp Phe
    1085                1090                1095

Ala Thr  Val Arg Lys Val Leu  Ser Met Pro Gln Val  Asn Ile Val
    1100                1105                1110

Lys Lys  Thr Glu Val Gln Thr  Gly Gly Phe Ser Lys  Glu Ser Ile
    1115                1120                1125

Leu Pro  Lys Arg Asn Ser Asp  Lys Leu Ile Ala Arg  Lys Lys Asp
    1130                1135                1140

Trp Asp  Pro Lys Lys Tyr Gly  Gly Phe Asp Ser Pro  Thr Val Ala
    1145                1150                1155

Tyr Ser  Val Leu Val Val Ala  Lys Val Glu Lys Gly  Lys Ser Lys
    1160                1165                1170

Lys Leu  Lys Ser Val Lys Glu  Leu Leu Gly Ile Thr  Ile Met Glu
    1175                1180                1185

Arg Ser  Ser Phe Glu Lys Asn  Pro Ile Asp Phe Leu  Glu Ala Lys
    1190                1195                1200

Gly Tyr  Lys Glu Val Lys Lys  Asp Leu Ile Ile Lys  Leu Pro Lys
    1205                1210                1215

Tyr Ser  Leu Phe Glu Leu Glu  Asn Gly Arg Lys Arg  Met Leu Ala
    1220                1225                1230

Ser Ala  Gly Glu Leu Gln Lys  Gly Asn Glu Leu Ala  Leu Pro Ser
    1235                1240                1245

Lys Tyr  Val Asn Phe Leu Tyr  Leu Ala Ser His Tyr  Glu Lys Leu
    1250                1255                1260

Lys Gly  Ser Pro Glu Asp Asn  Glu Gln Lys Gln Leu  Phe Val Glu
    1265                1270                1275

Gln His  Lys His Tyr Leu Asp  Glu Ile Ile Glu Gln  Ile Ser Glu
    1280                1285                1290

Phe Ser  Lys Arg Val Ile Leu  Ala Asp Ala Asn Leu  Asp Lys Val
    1295                1300                1305

Leu Ser  Ala Tyr Asn Lys His  Arg Asp Lys Pro Ile  Arg Glu Gln
    1310                1315                1320

Ala Glu  Asn Ile Ile His Leu  Phe Thr Leu Thr Asn  Leu Gly Ala
    1325                1330                1335

Pro Ala  Ala Phe Lys Tyr Phe  Asp Thr Thr Ile Asp  Arg Lys Arg
    1340                1345                1350

Tyr Thr  Ser Thr Lys Glu Val  Leu Asp Ala Thr Leu  Ile His Gln
    1355                1360                1365

Ser Ile  Thr Gly Leu Tyr Glu  Thr Arg Ile Asp Leu  Ser Gln Leu
    1370                1375                1380

Gly Gly  Asp Ser Gly Gly Ser  Ser Gly Gly Ser Ser  Gly Ser Glu
    1385                1390                1395

Thr Pro  Gly Thr Ser Glu Ser  Ala Thr Pro Glu Ser  Ser Gly Ser
    1400                1405                1410
```

```
Glu Thr  Pro Gly Thr Ser Glu  Ser Ala Thr Pro Glu  Ser Ser Gly
    1415                 1420                 1425

Ser Glu  Thr Pro Gly Thr Ser  Glu Ser Ala Thr Pro  Glu Ser Ser
    1430                 1435                 1440

Gly Gly  Ser Ser Gly Gly Ser  Ser Thr Leu Asn Ile  Glu Asp Glu
    1445                 1450                 1455

Tyr Arg  Leu His Glu Thr Ser  Lys Glu Pro Asp Val  Ser Leu Gly
    1460                 1465                 1470

Ser Thr  Trp Leu Ser Asp Phe  Pro Gln Ala Trp Ala  Glu Thr Gly
    1475                 1480                 1485

Gly Met  Gly Leu Ala Val Arg  Gln Ala Pro Leu Ile  Ile Pro Leu
    1490                 1495                 1500

Lys Ala  Thr Ser Thr Pro Val  Ser Ile Lys Gln Tyr  Pro Met Ser
    1505                 1510                 1515

Gln Glu  Ala Arg Leu Gly Ile  Lys Pro His Ile Gln  Arg Leu Leu
    1520                 1525                 1530

Asp Gln  Gly Ile Leu Val Pro  Cys Gln Ser Pro Trp  Asn Thr Pro
    1535                 1540                 1545

Leu Leu  Pro Val Lys Lys Pro  Gly Thr Asn Asp Tyr  Arg Pro Val
    1550                 1555                 1560

Gln Asp  Leu Arg Glu Val Asn  Lys Arg Val Glu Asp  Ile His Pro
    1565                 1570                 1575

Thr Val  Pro Asn Pro Tyr Asn  Leu Leu Ser Gly Pro  Pro Pro Ser
    1580                 1585                 1590

His Gln  Trp Tyr Thr Val Leu  Asp Leu Lys Asp Ala  Phe Phe Cys
    1595                 1600                 1605

Leu Arg  Leu His Pro Thr Ser  Gln Pro Leu Phe Ala  Phe Glu Trp
    1610                 1615                 1620

Arg Asp  Pro Glu Met Gly Ile  Ser Gly Gln Leu Thr  Trp Thr Arg
    1625                 1630                 1635

Leu Pro  Gln Gly Phe Lys Asn  Ser Pro Thr Leu Phe  Asn Glu Ala
    1640                 1645                 1650

Leu His  Arg Asp Leu Ala Asp  Phe Arg Ile Gln His  Pro Asp Leu
    1655                 1660                 1665

Ile Leu  Leu Gln Tyr Val Asp  Asp Leu Leu Leu Ala  Ala Thr Ser
    1670                 1675                 1680

Glu Leu  Asp Cys Gln Gln Gly  Thr Arg Ala Leu Leu  Gln Thr Leu
    1685                 1690                 1695

Gly Asn  Leu Gly Tyr Arg Ala  Ser Ala Lys Lys Ala  Gln Ile Cys
    1700                 1705                 1710

Gln Lys  Gln Val Lys Tyr Leu  Gly Tyr Leu Leu Lys  Glu Gly Gln
    1715                 1720                 1725

Arg Trp  Leu Thr Glu Ala Arg  Lys Glu Thr Val Met  Gly Gln Pro
    1730                 1735                 1740

Thr Pro  Lys Thr Pro Arg Gln  Leu Arg Glu Phe Leu  Gly Lys Ala
    1745                 1750                 1755

Gly Phe  Cys Arg Leu Phe Ile  Pro Gly Phe Ala Glu  Met Ala Ala
    1760                 1765                 1770

Pro Leu  Tyr Pro Leu Thr Lys  Pro Gly Thr Leu Phe  Asn Trp Gly
    1775                 1780                 1785

Pro Asp  Gln Gln Lys Ala Tyr  Gln Glu Ile Lys Gln  Ala Leu Leu
    1790                 1795                 1800
```

```
Thr Ala  Pro Ala Leu Gly Leu  Pro Asp Leu Thr Lys  Pro Phe Glu
    1805                 1810                 1815

Leu Phe  Val Asp Glu Lys Gln  Gly Tyr Ala Lys Gly  Val Leu Thr
    1820                 1825                 1830

Gln Lys  Leu Gly Pro Trp Arg  Arg Pro Val Ala Tyr  Leu Ser Lys
    1835                 1840                 1845

Lys Leu  Asp Pro Val Ala Ala  Gly Trp Pro Pro Cys  Leu Arg Met
    1850                 1855                 1860

Val Ala  Ala Ile Ala Val Leu  Thr Lys Asp Ala Gly  Lys Leu Thr
    1865                 1870                 1875

Met Gly  Gln Pro Leu Val Ile  Leu Ala Pro His Ala  Val Glu Ala
    1880                 1885                 1890

Leu Val  Lys Gln Pro Pro Asp  Arg Trp Leu Ser Asn  Ala Arg Met
    1895                 1900                 1905

Thr His  Tyr Gln Ala Leu Leu  Leu Asp Thr Asp Arg  Val Gln Phe
    1910                 1915                 1920

Gly Pro  Val Val Ala Leu Asn  Pro Ala Thr Leu Leu  Pro Leu Pro
    1925                 1930                 1935

Glu Glu  Gly Leu Gln His Asn  Cys Leu Asp Gly Thr  Gly Gly Gly
    1940                 1945                 1950

Gly Val  Thr Val Lys Phe Lys  Tyr Lys Gly Glu Glu  Leu Glu Val
    1955                 1960                 1965

Asp Ile  Ser Lys Ile Lys Lys  Val Trp Arg Val Gly  Lys Met Ile
    1970                 1975                 1980

Ser Phe  Thr Tyr Asp Asp Asn  Gly Lys Thr Gly Arg  Gly Ala Val
    1985                 1990                 1995

Ser Glu  Lys Asp Ala Pro Lys  Glu Leu Leu Gln Met  Leu Glu Lys
    2000                 2005                 2010

Ser Gly  Lys Lys Ser Gly Gly  Ser Lys Arg Thr Ala  Asp Gly Ser
    2015                 2020                 2025

Glu Phe  Glu Pro Lys Lys Lys  Arg Lys Val Gly Gly  Gly Gly Ser
    2030                 2035                 2040

Pro Lys  Lys Lys Arg Lys Val  Tyr Pro Tyr Asp Val  Pro Asp Tyr
    2045                 2050                 2055

Ala Gly  Ser Arg Ala Leu Val  Val Ile Arg Leu Ser  Arg Val Thr
    2060                 2065                 2070

Asp Ala  Thr Thr Ser Pro Glu  Arg Gln Leu Glu Ser  Cys Gln Gln
    2075                 2080                 2085

Leu Cys  Ala Gln Arg Gly Trp  Asp Val Val Gly Val  Ala Glu Asp
    2090                 2095                 2100

Leu Asp  Val Ser Gly Ala Val  Asp Pro Phe Asp Arg  Lys Arg Arg
    2105                 2110                 2115

Pro Asn  Leu Ala Arg Trp Leu  Ala Phe Glu Glu Gln  Pro Phe Asp
    2120                 2125                 2130

Val Ile  Val Ala Tyr Arg Val  Asp Arg Leu Thr Arg  Ser Ile Arg
    2135                 2140                 2145

His Leu  Gln Gln Leu Val His  Trp Ala Glu Asp His  Lys Lys Leu
    2150                 2155                 2160

Val Val  Ser Ala Thr Glu Ala  His Phe Asp Thr Thr  Thr Pro Phe
    2165                 2170                 2175

Ala Ala  Val Val Ile Ala Leu  Met Gly Thr Val Ala  Gln Met Glu
    2180                 2185                 2190

Leu Glu  Ala Ile Lys Glu Arg  Asn Arg Ser Ala Ala  His Phe Asn
```

```
    2195                2200                2205

Ile Arg  Ala Gly Lys Tyr Arg  Gly Ser Leu Pro Pro  Trp Gly Tyr
    2210                2215                2220

Leu Pro  Thr Arg Val Asp Gly  Glu Trp Arg Leu Val  Pro Asp Pro
    2225                2230                2235

Val Gln  Arg Glu Arg Ile Leu  Glu Val Tyr His Arg  Val Val Asp
    2240                2245                2250

Asn His  Glu Pro Leu His Leu  Val Ala His Asp Leu  Asn Arg Arg
    2255                2260                2265

Gly Val  Leu Ser Pro Lys Asp  Tyr Phe Ala Gln Leu  Gln Gly Arg
    2270                2275                2280

Glu Pro  Gln Gly Arg Glu Trp  Ser Ala Thr Ala Leu  Lys Arg Ser
    2285                2290                2295

Met Ile  Ser Glu Ala Met Leu  Gly Tyr Ala Thr Leu  Asn Gly Lys
    2300                2305                2310

Thr Val  Arg Asp Asp Asp Gly  Ala Pro Leu Val Arg  Ala Glu Pro
    2315                2320                2325

Ile Leu  Thr Arg Glu Gln Leu  Glu Ala Leu Arg Ala  Glu Leu Val
    2330                2335                2340

Lys Thr  Ser Arg Ala Lys Pro  Ala Val Ser Thr Pro  Ser Leu Leu
    2345                2350                2355

Leu Arg  Val Leu Phe Cys Ala  Val Cys Gly Glu Pro  Ala Tyr Lys
    2360                2365                2370

Phe Ala  Gly Gly Gly Arg Lys  His Pro Arg Tyr Arg  Cys Arg Ser
    2375                2380                2385

Met Gly  Phe Pro Lys His Cys  Gly Asn Gly Thr Val  Ala Met Ala
    2390                2395                2400

Glu Trp  Asp Ala Phe Cys Glu  Glu Gln Val Leu Asp  Leu Leu Gly
    2405                2410                2415

Asp Ala  Glu Arg Leu Glu Lys  Val Trp Val Ala Gly  Ser Asp Ser
    2420                2425                2430

Ala Val  Glu Leu Ala Glu Val  Asn Ala Glu Leu Val  Asp Leu Thr
    2435                2440                2445

Ser Leu  Ile Gly Ser Pro Ala  Tyr Arg Ala Gly Ser  Pro Gln Arg
    2450                2455                2460

Glu Ala  Leu Asp Ala Arg Ile  Ala Ala Leu Ala Ala  Arg Gln Glu
    2465                2470                2475

Glu Leu  Glu Gly Leu Glu Ala  Arg Pro Ser Gly Trp  Glu Trp Arg
    2480                2485                2490

Glu Thr  Gly Gln Arg Phe Gly  Asp Trp Trp Arg Glu  Gln Asp Thr
    2495                2500                2505

Ala Ala  Lys Asn Thr Trp Leu  Arg Ser Met Asn Val  Arg Leu Thr
    2510                2515                2520

Phe Asp  Val Arg Gly Gly Leu  Thr Arg Thr Ile Asp  Phe Gly Asp
    2525                2530                2535

Leu Gln  Glu Tyr Glu Gln His  Leu Arg Leu Gly Ser  Val Val Glu
    2540                2545                2550

Arg Leu  His Thr Gly Met Ser
    2555                2560
```

<210> SEQ ID NO 377
<211> LENGTH: 7680
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 377

```
atgaaacgga cagccgacgg aagcgagttc gagtcaccaa agaagaagcg gaaagtcgac     60

aagaagtaca gcatcggcct ggacatcggc accaactctg tgggctgggc cgtgatcacc    120

gacgagtaca aggtgcccag caagaaattc aaggtgctgg gcaacaccga ccggcacagc    180

atcaagaaga acctgatcgg agccctgctg ttcgacagcg gcgaaacagc cgaggccacc    240

cggctgaaga gaaccgccag aagaagatac accagacgga agaaccggat ctgctatctg    300

caagagatct tcagcaacga gatggccaag gtggacgaca gcttcttcca cagactggaa    360

gagtccttcc tggtggaaga ggataagaag cacgagcggc accccatctt cggcaacatc    420

gtggacgagg tggcctacca cgagaagtac cccaccatct accacctgag aaagaaactg    480

gtggacagca ccgacaaggc cgacctgcgg ctgatctatc tggccctggc ccacatgatc    540

aagttccggg gccacttcct gatcgagggc gacctgaacc ccgacaacag cgacgtggac    600

aagctgttca tccagctggt gcagacctac aaccagctgt tcgaggaaaa ccccatcaac    660

gccagcggcg tggacgccaa ggccatcctg tctgccagac tgagcaagag cagacggctg    720

gaaaatctga tcgcccagct gcccggcgag aagaagaatg gcctgttcgg aaacctgatt    780

gccctgagcc tgggcctgac ccccaacttc aagagcaact tcgacctggc cgaggatgcc    840

aaactgcagc tgagcaagga cacctacgac gacgacctgg acaacctgct ggcccagatc    900

ggcgaccagt acgccgacct gtttctggcc gccaagaacc tgtccgacgc catcctgctg    960

agcgacatcc tgagagtgaa caccgagatc accaaggccc ccctgagcgc ctctatgatc   1020

aagagatacg acgagcacca ccaggacctg accctgctga aagctctcgt gcggcagcag   1080

ctgcctgaga agtacaaaga gattttcttc gaccagagca agaacggcta cgccggctac   1140

attgacggcg gagccagcca ggaagagttc tacaagttca tcaagcccat cctggaaaag   1200

atggacggca ccgaggaact gctcgtgaag ctgaacagag aggacctgct gcggaagcag   1260

cggaccttcg acaacggcag catcccccac cagatccacc tgggagagct gcacgccatt   1320

ctgcggcggc aggaagattt ttacccattc ctgaaggaca accgggaaaa gatcgagaag   1380

atcctgacct tccgcatccc ctactacgtg ggccctctgg ccaggggaaa cagcagattc   1440

gcctggatga ccagaaagag cgaggaaacc atcacccccct ggaacttcga ggaagtggtg   1500

gacaagggcg cttccgccca gagcttcatc gagcggatga ccaacttcga taagaacctg   1560

cccaacgaga aggtgctgcc caagcacagc ctgctgtacg agtacttcac cgtgtataac   1620

gagctgacca aagtgaaata cgtgaccgag ggaatgagaa agcccgcctt cctgagcggc   1680

gagcagaaaa aggccatcgt ggacctgctg ttcaagacca accggaaagt gaccgtgaag   1740

cagctgaaag aggactactt caagaaaatc gagtgcttcg actccgtgga aatctccggc   1800

gtggaagatc ggttcaacgc ctccctgggc acataccacg atctgctgaa aattatcaag   1860

gacaaggact tcctggacaa tgaggaaaac gaggacattc tggaagatat cgtgctgacc   1920

ctgacactgt ttgaggacag agagatgatc gaggaacggc tgaaaaccta tgcccacctg   1980

ttcgacgaca aagtgatgaa gcagctgaag cggcggagat acaccggctg gggcaggctg   2040

agccggaagc tgatcaacgg catccgggac aagcagtccg gcaagacaat cctggatttc   2100

ctgaagtccg acggcttcgc caacagaaac ttcatgcagc tgatccacga cgacagcctg   2160

acctttaaag aggacatcca gaaagcccag gtgtccggcc agggcgatag cctgcacgag   2220
```

```
cacattgcca atctggccgg cagccccgcc attaagaagg gcatcctgca gacagtgaag   2280
gtggtggacg agctcgtgaa agtgatgggc cggcacaagc ccgagaacat cgtgatcgaa   2340
atggccagag agaaccagac cacccagaag ggacagaaga acagccgcga gagaatgaag   2400
cggatcgaag agggcatcaa agagctgggc agccagatcc tgaaagaaca ccccgtggaa   2460
aacacccagc tgcagaacga gaagctgtac ctgtactacc tgcagaatgg gcgggatatg   2520
tacgtggacc aggaactgga catcaaccgg ctgtccgact acgatgtgga cgctatcgtg   2580
cctcagagct ttctgaagga cgactccatc gacaacaagg tgctgaccag aagcgacaag   2640
aaccggggca agagcgacaa cgtgccctcc gaagaggtcg tgaagaagat gaagaactac   2700
tggcggcagc tgctgaacgc caagctgatt acccagagaa agttcgacaa tctgaccaag   2760
gccgagagag gcggcctgag cgaactggat aaggccggct tcatcaagag acagctggtg   2820
gaaacccggc agatcacaaa gcacgtggca cagatcctgg actcccggat gaacactaag   2880
tacgacgaga atgacaagct gatccgggaa gtgaaagtga tcaccctgaa gtccaagctg   2940
gtgtccgatt tccggaagga tttccagttt tacaaagtgc gcgagatcaa caactaccac   3000
cacgcccacg acgcctacct gaacgccgtc gtgggaaccg ccctgatcaa aaagtaccct   3060
aagctggaaa gcgagttcgt gtacggcgac tacaaggtgt acgacgtgcg gaagatgatc   3120
gccaagagcg agcaggaaat cggcaaggct accgccaagt acttcttcta cagcaacatc   3180
atgaactttt tcaagaccga gattaccctg gccaacggcg agatccggaa gcggcctctg   3240
atcgagacaa acggcgaaac cggggagatc gtgtgggata agggccggga ttttgccacc   3300
gtgcggaaag tgctgagcat gccccaagtg aatatcgtga aaaagaccga ggtgcagaca   3360
ggcggcttca gcaaagagtc tatcctgccc aagaggaaca gcgataagct gatcgccaga   3420
aagaaggact gggaccctaa gaagtacggc ggcttcgaca gccccaccgt ggcctattct   3480
gtgctggtgg tggccaaagt ggaaaagggc aagtccaaga aactgaagag tgtgaaagag   3540
ctgctgggga tcaccatcat ggaaagaagc agcttcgaga agaatcccat cgactttctg   3600
gaagccaagg gctacaaaga agtgaaaaag gacctgatca tcaagctgcc taagtactcc   3660
ctgttcgagc tggaaaacgg ccggaagaga atgctggcct ctgccggcga actgcagaag   3720
ggaaacgaac tggccctgcc ctccaaatat gtgaacttcc tgtacctggc cagccactat   3780
gagaagctga agggctcccc cgaggataat gagcagaaac agctgtttgt ggaacagcac   3840
aagcactacc tggacgagat catcgagcag atcagcgagt tctccaagag agtgatcctg   3900
gccgacgcta atctggacaa agtgctgtcc gcctacaaca agcaccggga taagcccatc   3960
agagagcagg ccgagaatat catccacctg tttaccctga ccaatctggg agcccctgcc   4020
gccttcaagt actttgacac caccatcgac cggaagaggt acaccagcac caaagaggtg   4080
ctggacgcca ccctgatcca ccagagcatc accggcctgt acgagacacg gatcgacctg   4140
tctcagctgg gaggtgactc tggaggatct agcggaggat cctctggcag cgagacacca   4200
ggaacaagcg agtcagcaac accagagagc tctggtagcg agacacccgg taccagtgaa   4260
agcgccacgc cagaaagcag tgggagtgag actccgggta catctgaatc agcgacaccg   4320
gaatcaagtg gcggcagcag cggcggcagc agcaccctaa atatagaaga tgagtatcgg   4380
ctacatgaga cctcaaaaga gccagatgtt tctctagggt ccacatggct gtctgatttt   4440
cctcaggcct gggcggaaac cgggggcatg ggactggcag ttcgccaagc tcctctgatc   4500
atacctctga aagcaacctc taccccgtg tccataaaac aataccccat gtcacaagaa   4560
```

```
gccagactgg ggatcaagcc ccacatacag agactgttgg accagggaat actggtaccc   4620
tgccagtccc cctggaacac gcccctgcta cccgttaaga aaccagggac taatgattat   4680
aggcctgtcc aggatctgag agaagtcaac aagcgggtgg aagacatcca ccccaccgtg   4740
cccaaccctt acaacctctt gagcgggccc ccaccgtccc accagtggta cactgtgctt   4800
gatttaaagg atgccttttt ctgcctgaga ctccacccca ccagtcagcc tctcttcgcc   4860
tttgagtgga gagatccaga gatgggaatc tcaggacaat tgacctggac cagactccca   4920
cagggtttca aaaacagtcc caccctgttt aatgaggcac tgcacagaga cctagcagac   4980
ttccggatcc agcacccaga cttgatcctg ctacagtacg tggatgactt actgctggcc   5040
gccacttctg agctagactg ccaacaaggt actcgggccc tgttacaaac cctagggaac   5100
ctcgggtatc gggcctcggc caagaaagcc caaatttgcc agaaacaggt caagtatctg   5160
gggtatcttc taaaagaggg tcagagatgg ctgactgagg ccagaaaaga gactgtgatg   5220
gggcagccta ctccgaagac ccctcgacaa ctaagggagt tcctagggaa ggcaggcttc   5280
tgtcgcctct tcatccctgg gtttgcagaa atggcagccc ccctgtaccc tctcaccaaa   5340
ccggggactc tgtttaattg gggcccagac caacaaaagg cctatcaaga aatcaagcaa   5400
gctcttctaa ctgccccagc cctggggttg ccagatttga ctaagccctt tgaactcttt   5460
gtcgacgaga agcagggcta cgccaaaggt gtcctaacgc aaaaactggg accttggcgt   5520
cggccggtgg cctacctgtc caaaaagcta gacccagtag cagctgggtg gcccccttgc   5580
ctacggatgg tagcagccat tgccgtactg acaaaggatg caggcaagct aaccatggga   5640
cagccactag tcattctggc cccccatgca gtagaggcac tagtcaaaca accccccgac   5700
cgctggcttt ccaacgcccg gatgactcac tatcaggcct tgcttttgga cacggaccgg   5760
gtccagttcg gaccggtggt agccctgaac ccggctacgc tgctcccact gcctgaggaa   5820
gggctgcaac acaactgcct tgatgggaca ggtggcggtg gtgtcaccgt caagttcaag   5880
tacaagggtg aggaacttga agttgatatt agcaaaatca agaaggtttg gcgcgttggt   5940
aaaatgatat cttttactta tgacgacaac ggcaagacag gtagaggggc agtgtctgag   6000
aaagacgccc ccaaggagct gttgcaaatg ttggaaaagt ctgggaaaaa gtctggcggc   6060
tcaaaaagaa ccgccgacgg cagcgaattc gagcccaaga agaagaggaa agtcggaggt   6120
ggcgggagcc caaaaaagaa aagaaaagtg tatccctatg atgtccccga ttatgccggt   6180
tcaagagccc tggtcgtgat tagactgagc cgagtgacag acgccaccac aagtcccgag   6240
agacagctgg aatcatgcca gcagctctgt gctcagcggg gttgggatgt ggtcggcgtg   6300
gcagaggatc tggacgtgag cggggccgtc gatccattcg acagaaagag gaggcccaac   6360
ctggcaagat ggctcgcttt cgaggaacag ccctttgatg tgatcgtcgc ctacagagtg   6420
gaccggctga cccgctcaat tcgacatctc cagcagctgg tgcattgggc tgaggaccac   6480
aagaaactgg tggtcagcgc aacagaagcc cacttcgata ctaccacacc ttttgccgct   6540
gtggtcatcg cactgatggg cactgtggcc cagatggagc tcgaagctat caaggagcga   6600
aacaggagcg cagcccattt caatattagg gccggtaaat acagaggctc cctgccccct   6660
tggggatatc tccctaccag ggtggatggg gagtggagac tggtgccaga ccccgtccag   6720
agagagcgga ttctggaagt gtaccacaga gtggtcgata accacgaacc actccatctg   6780
gtggcacacg acctgaatag acgcggcgtg ctctctccaa aggattattt tgctcagctg   6840
cagggaagag agccacaggg aagagaatgg agtgctactg cactgaagag atctatgatc   6900
agtgaggcta tgctgggtta cgcaacactc aatggcaaaa ctgtccggga cgatgacgga   6960
```

```
gcccctctgg tgagggctga gcctattctc accagagagc agctcgaagc tctgcgggca   7020

gaactggtca agactagtcg cgccaaacct gccgtgagca ccccaagcct gctcctgagg   7080

gtgctgttct gcgccgtctg tggagagcca gcatacaagt ttgccggcgg agggcgcaaa   7140

catccccgct atcgatgcag gagcatgggg ttccctaagc actgtggaaa cgggacagtg   7200

gccatggctg agtgggacgc cttttgcgag gaacaggtgc tggatctcct gggtgacgct   7260

gagcggctgg aaaaagtgtg ggtggcagga tctgactccg ctgtggagct ggcagaagtc   7320

aatgccgagc tcgtggatct gacttccctc atcggatctc ctgcatatag agctgggtcc   7380

ccacagagag aagctctgga cgcacgaatt gctgcactcg ctgctagaca ggaggaactg   7440

gagggcctgg aggccaggcc ctctggatgg gagtggcgag aaaccggaca gaggtttggg   7500

gattggtgga gggagcagga caccgcagcc aagaacacat ggctgagatc catgaatgtc   7560

cggctcacat tcgacgtgcg cggtggcctg actcgaacca tcgattttgg cgacctgcag   7620

gagtatgaac agcacctgag actggggtcc gtggtcgaaa gactgcacac tgggatgtcc   7680
```

<210> SEQ ID NO 378
<211> LENGTH: 1367
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 378

```
Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
```

-continued

```
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655
```

-continued

```
Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065
```

Gly Glu Ile Val Trp Asp Lys Gly Arg Asp Phe Ala Thr Val Arg
1070 1075 1080

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 379
<211> LENGTH: 576
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 379

Leu Asn Ile Glu Asp Glu Tyr Arg Leu His Glu Thr Ser Lys Glu Pro
1 5 10 15

Asp Val Ser Leu Gly Ser Thr Trp Leu Ser Asp Phe Pro Gln Ala Trp
20 25 30

Ala Glu Thr Gly Gly Met Gly Leu Ala Val Arg Gln Ala Pro Leu Ile
35 40 45

```
Ile Pro Leu Lys Ala Thr Ser Thr Pro Val Ser Ile Lys Gln Tyr Pro
    50                  55                  60

Met Ser Gln Glu Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Gly Pro Pro Pro Ser His Gln Trp
    130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asn Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
            260                 265                 270

Lys Glu Gly Gln Arg Trp Leu Thr Glu Ala Arg Lys Glu Thr Val Met
        275                 280                 285

Gly Gln Pro Thr Pro Lys Thr Pro Arg Gln Leu Arg Glu Phe Leu Gly
    290                 295                 300

Lys Ala Gly Phe Cys Arg Leu Phe Ile Pro Gly Phe Ala Glu Met Ala
305                 310                 315                 320

Ala Pro Leu Tyr Pro Leu Thr Lys Pro Gly Thr Leu Phe Asn Trp Gly
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
        355                 360                 365

Val Asp Glu Lys Gln Gly Tyr Ala Lys Gly Val Leu Thr Gln Lys Leu
    370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Leu Ala Pro His Ala Val Glu Ala Leu Val Lys Gln Pro Pro Asp
        435                 440                 445

Arg Trp Leu Ser Asn Ala Arg Met Thr His Tyr Gln Ala Leu Leu Leu
    450                 455                 460
```

Asp Thr Asp Arg Val Gln Phe Gly Pro Val Val Ala Leu Asn Pro Ala
465 470 475 480

Thr Leu Leu Pro Leu Pro Glu Glu Gly Leu Gln His Asn Cys Leu Asp
485 490 495

Gly Thr Gly Gly Gly Gly Val Thr Val Lys Phe Lys Tyr Lys Gly Glu
500 505 510

Glu Leu Glu Val Asp Ile Ser Lys Ile Lys Lys Val Trp Arg Val Gly
515 520 525

Lys Met Ile Ser Phe Thr Tyr Asp Asp Asn Gly Lys Thr Gly Arg Gly
530 535 540

Ala Val Ser Glu Lys Asp Ala Pro Lys Glu Leu Leu Gln Met Leu Glu
545 550 555 560

Lys Ser Gly Lys Lys Ser Gly Gly Ser Lys Arg Thr Ala Asp Gly Ser
565 570 575

<210> SEQ ID NO 380
<211> LENGTH: 500
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 380

Ser Arg Ala Leu Val Val Ile Arg Leu Ser Arg Val Thr Asp Ala Thr
1 5 10 15

Thr Ser Pro Glu Arg Gln Leu Glu Ser Cys Gln Gln Leu Cys Ala Gln
20 25 30

Arg Gly Trp Asp Val Val Gly Val Ala Glu Asp Leu Asp Val Ser Gly
35 40 45

Ala Val Asp Pro Phe Asp Arg Lys Arg Arg Pro Asn Leu Ala Arg Trp
50 55 60

Leu Ala Phe Glu Glu Gln Pro Phe Asp Val Ile Val Ala Tyr Arg Val
65 70 75 80

Asp Arg Leu Thr Arg Ser Ile Arg His Leu Gln Gln Leu Val His Trp
85 90 95

Ala Glu Asp His Lys Lys Leu Val Val Ser Ala Thr Glu Ala His Phe
100 105 110

Asp Thr Thr Thr Pro Phe Ala Ala Val Val Ile Ala Leu Met Gly Thr
115 120 125

Val Ala Gln Met Glu Leu Glu Ala Ile Lys Glu Arg Asn Arg Ser Ala
130 135 140

Ala His Phe Asn Ile Arg Ala Gly Lys Tyr Arg Gly Ser Leu Pro Pro
145 150 155 160

Trp Gly Tyr Leu Pro Thr Arg Val Asp Gly Glu Trp Arg Leu Val Pro
165 170 175

Asp Pro Val Gln Arg Glu Arg Ile Leu Glu Val Tyr His Arg Val Val
180 185 190

Asp Asn His Glu Pro Leu His Leu Val Ala His Asp Leu Asn Arg Arg
195 200 205

Gly Val Leu Ser Pro Lys Asp Tyr Phe Ala Gln Leu Gln Gly Arg Glu
210 215 220

Pro Gln Gly Arg Glu Trp Ser Ala Thr Ala Leu Lys Arg Ser Met Ile
225 230 235 240

Ser Glu Ala Met Leu Gly Tyr Ala Thr Leu Asn Gly Lys Thr Val Arg
245 250 255

```
Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Ser Arg Ala
        275                 280                 285

Lys Pro Ala Val Ser Thr Pro Ser Leu Leu Leu Arg Val Leu Phe Cys
    290                 295                 300

Ala Val Cys Gly Glu Pro Ala Tyr Lys Phe Ala Gly Gly Gly Arg Lys
305                 310                 315                 320

His Pro Arg Tyr Arg Cys Arg Ser Met Gly Phe Pro Lys His Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Glu Gln Asp Thr
        435                 440                 445

Ala Ala Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Thr Gly Met Ser
            500
```

<210> SEQ ID NO 381
<211> LENGTH: 11344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 381

```
ccgaaaagtg ccacctgacg tcgacggatc gggagatcga tctcccgatc ccctagggtc      60

gactctcagt acaatctgct ctgatgccgc atagttaagc cagtatctgc tccctgcttg     120

tgtgttggag gtcgctgagt agtgcgcgag caaaatttaa gctacaacaa ggcaaggctt     180

gaccgacaat tgcatgaaga atctgcttag ggttaggcgt tttgcgctgc ttcgcgatgt     240

acgggccaga tatacgcgtt gacattgatt attgactagt tattaatagt aatcaattac     300

ggggtcatta gttcatagcc catatatgga gttccgcgtt acataactta cggtaaatgg     360

cccgcctggc tgaccgccca acgacccccg cccattgacg tcaataatga cgtatgttcc     420

catagtaacg ccaataggga ctttccattg acgtcaatgg gtggagtatt tacggtaaac     480

tgcccacttg gcagtacatc aagtgtatca tatgccaagt acgcccccta ttgacgtcaa     540

tgacggtaaa tggcccgcct ggcattatgc ccagtacatg accttatggg actttcctac     600
```

-continued

```
ttggcagtac atctacgtat tagtcatcgc tattaccatg gtgatgcggt tttggcagta    660
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg gccgctaata cgactcacta    900
tagggagagc cgccaccatg aaacggacag ccgacggaag cgagttcgag tcaccaaaga    960
agaagcggaa agtcgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcggcagg aagattttta cccattcctg aaggacaacc   2280
gggaaaagat cgagaagatc ctgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
```

-continued

```
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aactttttca agaccgagat taccctggcc aacggcgaga   4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggcggcag cagcacccta aatatagaag atgagtatcg gctacatgag acctcaaaag   5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
```

```
ctacccccgt gtccataaaa caatacccca tgtcacaaga agccagactg gggatcaagc   5400
cccacataca gagactgttg gaccagggaa tactggtacc ctgccagtcc ccctggaaca   5460
cgcccctgct acccgttaag aaaccaggga ctaatgatta taggcctgtc caggatctga   5520
gagaagtcaa caagcgggtg gaagacatcc accccaccgt gcccaaccct tacaacctct   5580
tgagcgggct cccaccgtcc caccagtggt acactgtgct tgatttaaag gatgcctttt   5640
tctgcctgag actccacccc accagtcagc ctctcttcgc ctttgagtgg agagatccag   5700
agatgggaat ctcaggacaa ttgacctgga ccagactccc acagggtttc aaaaacagtc   5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctagggaa cctcgggtat cgggcctcgg   5940
ccaagaaagc ccaaatttgc cagaaacagg tcaagtatct ggggtatctt ctaaaagagg   6000
gtcagagatg gctgactgag gccagaaaag agactgtgat ggggcagcct actccgaaga   6060
cccctcgaca actaagggag ttcctaggga aggcaggctt ctgtcgcctc ttcatccctg   6120
ggtttgcaga aatggcagcc cccctgtacc ctctcaccaa accggggact ctgtttaatt   6180
ggggcccaga ccaacaaaag gcctatcaag aaatcaagca agctcttcta actgccccag   6240
ccctggggtt gccagatttg actaagccct ttgaactctt tgtcgacgag aagcagggct   6300
acgccaaagg tgtcctaacg caaaaactgg gaccttggcg tcggccggtg gcctacctgt   6360
ccaaaaagct agacccagta gcagctgggt ggcccccttg cctacggatg gtagcagcca   6420
ttgccgtact gacaaaggat gcaggcaagc taaccatggg acagccacta gtcattctgg   6480
ccccccatgc agtagaggca ctagtcaaac aacccccga ccgctggctt tccaacgccc   6540
ggatgactca ctatcaggcc ttgcttttgg acacggaccg ggtccagttc ggaccggtgg   6600
tagccctgaa cccggctacg ctgctcccac tgcctgagga agggctgcaa cacaactgcc   6660
ttgatatcct ggccgaagcc cacggaaccc gacccgacct aacggaccag ccgctcccag   6720
acgccgacca cacctggtac acggatggaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaaggta   6900
agaagctaaa tgtttatact gatagccgtt atgcttttgc tactgcccat atccatggag   6960
aaatatacag aaggcgtggg tggctcacat cagaaggcaa agagatcaaa aataaagacg   7020
agatcttggc cctactaaaa gccctctttc tgcccaaaag acttagcata atccattgtc   7080
caggacatca aaagggacac agcgccgagg ctagaggcaa ccggatggct gaccaagcgg   7140
cccgaaaggc agccatcaca gagactccag acacctctac cctcctcata gaaaattcat   7200
caccctctgg cggctcaaaa agaaccgccg acggcagcga attcgagccc aagaagaaga   7260
ggaaagtcgg aagcggagct actaacttca gcctgctgaa gcaggctggc gacgtggagg   7320
agaaccctgg acctccaaaa aagaaaagaa aagtgtatcc ctatgatgtc cccgattatg   7380
ccggttcaag agccctggtc gtgattagac tgagccgagt gacagacgcc accacaagtc   7440
ccgagagaca gctggaatca tgccagcagc tctgtgctca gcggggttgg gatgtggtcg   7500
gcgtggcaga ggatctggac gtgagcgggg ccgtcgatcc attcgacaga aagaggaggc   7560
ccaacctggc aagatggctc gctttcgagg aacagccctt tgatgtgatc gtcgcctaca   7620
gagtggaccg gctgacccgc tcaattcgac atctccagca gctggtgcat tgggctgagg   7680
```

-continued

```
accacaagaa actggtggtc agcgcaacag aagcccactt cgatactacc acaccttttg   7740
ccgctgtggt catcgcactg atgggcactg tggcccagat ggagctcgaa gctatcaagg   7800
agcgaaacag gagcgcagcc catttcaata ttagggccgg taaatacaga ggctccctgc   7860
ccccttgggg atatctccct accagggtgg atggggagtg gagactggtg ccagaccccg   7920
tccagagaga gcggattctg gaagtgtacc acagagtggt cgataaccac gaaccactcc   7980
atctggtggc acacgacctg aatagacgcg gcgtgctctc tccaaaggat tattttgctc   8040
agctgcaggg aagagagcca cagggaagag aatggagtgc tactgcactg aagagatcta   8100
tgatcagtga ggctatgctg ggttacgcaa cactcaatgg caaaactgtc cgggacgatg   8160
acggagcccc tctggtgagg gctgagccta ttctcaccag agagcagctc gaagctctgc   8220
gggcagaact ggtcaagact agtcgcgcca aacctgccgt gagcacccca agcctgctcc   8280
tgagggtgct gttctgcgcc gtctgtggag agccagcata caagtttgcc ggcggagggc   8340
gcaaacatcc ccgctatcga tgcaggagca tggggttccc taagcactgt ggaaacggga   8400
cagtggccat ggctgagtgg gacgcctttt gcgaggaaca ggtgctggat ctcctgggtg   8460
acgctgagcg gctggaaaaa gtgtgggtgg caggatctga ctccgctgtg gagctggcag   8520
aagtcaatgc cgagctcgtg gatctgactt ccctcatcgg atctcctgca tatagagctg   8580
ggtccccaca gagagaagct ctggacgcac gaattgctgc actcgctgct agacaggagg   8640
aactggaggg cctggaggcc aggccctctg gatgggagtg gcgagaaacc ggacagaggt   8700
ttggggattg gtggagggag caggacaccg cagccaagaa cacatggctg agatccatga   8760
atgtccggct cacattcgac gtgcgcggtg gcctgactcg aaccatcgat tttggcgacc   8820
tgcaggagta tgaacagcac ctgagactgg ggtccgtggt cgaaagactg cacactggga   8880
tgtcctaggt ttaaacccgc tgatcagcct cgactgtgcc ttctagttgc cagccatctg   8940
ttgtttgccc ctcccccgtg ccttccttga ccctggaagg tgccactccc actgtccttt   9000
cctaataaaa tgagaaaatt gcatcgcatt gtctgagtag gtgtcattct attctggggg   9060
gtggggtggg gcaggacagc aagggggagg attgggaaga caatagcagg catgctgggg   9120
atgcggtggg ctctatggct tctgaggcgg aaagaaccag ctggggctcg ataccgtcga   9180
cctctagcta gagcttggcg taatcatggt catagctgtt tcctgtgtga aattgttatc   9240
cgctcacaat tccacacaac atacgagccg gaagcataaa gtgtaaagcc tagggtgcct   9300
aatgagtgag ctaactcaca ttaattgcgt tgcgctcact gcccgctttc cagtcgggaa   9360
acctgtcgtg ccagctgcat taatgaatcg gccaacgcgc ggggagaggc ggtttgcgta   9420
ttgggcgctc ttccgcttcc tcgctcactg actcgctgcg ctcggtcgtt cggctgcggc   9480
gagcggtatc agctcactca aaggcggtaa tacggttatc cacagaatca ggggataacg   9540
caggaaagaa catgtgagca aaaggccagc aaaaggccag gaaccgtaaa aaggccgcgt   9600
tgctggcgtt tttccatagg ctccgccccc ctgacgagca tcacaaaaat cgacgctcaa   9660
gtcagaggtg gcgaaacccg acaggactat aaagatacca ggcgtttccc cctggaagct   9720
ccctcgtgcg ctctcctgtt ccgaccctgc cgcttaccgg atacctgtcc gcctttctcc   9780
cttcgggaag cgtggcgctt tctcatagct cacgctgtag gtatctcagt tcggtgtagg   9840
tcgttcgctc caagctgggc tgtgtgcacg aaccccccgt tcagcccgac cgctgcgcct   9900
tatccggtaa ctatcgtctt gagtccaacc cggtaagaca cgacttatcg ccactggcag   9960
cagccactgg taacaggatt agcagagcga ggtatgtagg cggtgctaca gagttcttga  10020
agtggtggcc taactacggc tacactagaa gaacagtatt tggtatctgc gctctgctga  10080
```

agccagttac cttcggaaaa agagttggta gctcttgatc cggcaaacaa accaccgctg 10140
gtagcggtgg tttttttgtt tgcaagcagc agattacgcg cagaaaaaaa ggatctcaag 10200
aagatccttt gatcttttct acggggtctg acgctcagtg gaacgaaaac tcacgttaag 10260
ggattttggt catgagatta tcaaaaagga tcttcaccta gatcctttta aattaaaaat 10320
gaagttttaa atcaatctaa agtatatatg agtaaacttg gtctgacagt taccaatgct 10380
taatcagtga ggcacctatc tcagcgatct gtctatttcg ttcatccata gttgcctgac 10440
tccccgtcgt gtagataact acgatacggg agggcttacc atctggcccc agtgctgcaa 10500
tgataccgcg agacccacgc tcaccggctc cagatttatc agcaataaac cagccagccg 10560
gaagggccga gcgcagaagt ggtcctgcaa ctttatccgc ctccatccag tctattaatt 10620
gttgccggga agctagagta agtagttcgc cagttaatag tttgcgcaac gttgttgcca 10680
ttgctacagg catcgtggtg tcacgctcgt cgtttggtat ggcttcattc agctccggtt 10740
cccaacgatc aaggcgagtt acatgatccc ccatgttgtg caaaaaagcg gttagctcct 10800
tcggtcctcc gatcgttgtc agaagtaagt tggccgcagt gttatcactc atggttatgg 10860
cagcactgca taattctctt actgtcatgc catccgtaag atgcttttct gtgactggtg 10920
agtactcaac caagtcattc tgagaatagt gtatgcggcg accgagttgc tcttgcccgg 10980
cgtcaatacg ggataatacc gcgccacata gcagaacttt aaaagtgctc atcattggaa 11040
aacgttcttc ggggcgaaaa ctctcaagga tcttaccgct gttgagatcc agttcgatgt 11100
aacccactcg tgcacccaac tgatcttcag catcttttac tttcaccagc gtttctgggt 11160
gagcaaaaac aggaaggcaa aatgccgcaa aaaagggaat aagggcgaca cggaaatgtt 11220
gaatactcat actcttcctt tttcaatatt attgaagcat ttatcagggt tattgtctca 11280
tgagcggata catatttgaa tgtatttaga aaaataaaca aataggggtt ccgcgcacat 11340
ttcc 11344

<210> SEQ ID NO 382
<211> LENGTH: 9753
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 382
ccgaaaagtg ccacctgacg tcgacggatc gggagatcga tctcccgatc ccctagggtc 60
gactctcagt acaatctgct ctgatgccgc atagttaagc cagtatctgc tccctgcttg 120
tgtgttggag gtcgctgagt agtgcgcgag caaaatttaa gctacaacaa ggcaaggctt 180
gaccgacaat tgcatgaaga atctgcttag ggttaggcgt tttgcgctgc ttcgcgatgt 240
acgggccaga tatacgcgtt gacattgatt attgactagt tattaatagt aatcaattac 300
ggggtcatta gttcatagcc catatatgga gttccgcgtt acataactta cggtaaatgg 360
cccgcctggc tgaccgccca acgacccccg cccattgacg tcaataatga cgtatgttcc 420
catagtaacg ccaataggga ctttccattg acgtcaatgg gtggagtatt tacggtaaac 480
tgcccacttg gcagtacatc aagtgtatca tatgccaagt acgcccccta ttgacgtcaa 540
tgacggtaaa tggcccgcct ggcattatgc ccagtacatg accttatggg actttcctac 600
ttggcagtac atctacgtat tagtcatcgc tattaccatg gtgatgcggt tttggcagta 660
catcaatggg cgtggatagc ggtttgactc acggggattt ccaagtctcc accccattga 720
cgtcaatggg agtttgtttt ggcaccaaaa tcaacgggac tttccaaaat gtcgtaacaa 780
ctccgcccca ttgacgcaaa tgggcggtag gcgtgtacgg tgggaggtct atataagcag 840
agctggttta gtgaaccgtc agatccgcta gagatccgcg gccgctaata cgactcacta 900
tagggagagc cgccaccatg aaacggacag ccgacggaag cgagttcgag tcaccaaaga 960
agaagcggaa agtcgacaag aagtacagca tcggcctgga catcggcacc aactctgtgg 1020
gctgggccgt gatcaccgac gagtacaagg tgcccagcaa gaaattcaag gtgctgggca 1080
acaccgaccg gcacagcatc aagaagaacc tgatcggagc cctgctgttc gacagcggcg 1140
aaacagccga ggccacccgg ctgaagagaa ccgccagaag aagatacacc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcacc 1320
ccatcttcgg caacatcgtg gacgaggtgg cctaccacga gaagtacccc accatctacc 1380
acctgagaaa gaaactggtg gacagcaccg acaaggccga cctgcggctg atctatctgg 1440
ccctggccca catgatcaag ttccggggcc acttcctgat cgagggcgac ctgaaccccg 1500
acaacagcga cgtggacaag ctgttcatcc agctggtgca gacctacaac cagctgttcg 1560
aggaaaaccc catcaacgcc agcggcgtgg acgccaaggc catcctgtct gccagactga 1620
gcaagagcag acggctggaa aatctgatcg cccagctgcc cggcgagaag aagaatggcc 1680
tgttcggaaa cctgattgcc ctgagcctgg gcctgacccc caacttcaag agcaacttcg 1740
acctggccga ggatgccaaa ctgcagctga gcaaggacac ctacgacgac gacctggaca 1800
acctgctggc ccagatcggc gaccagtacg ccgacctgtt tctggccgcc aagaacctgt 1860
ccgacgccat cctgctgagc gacatcctga gagtgaacac cgagatcacc aaggcccccc 1920
tgagcgcctc tatgatcaag agatacgacg agcaccacca ggacctgacc ctgctgaaag 1980
ctctcgtgcg gcagcagctg cctgagaagt acaaagagat tttcttcgac cagagcaaga 2040
acggctacgc cggctacatt gacggcggag ccagccagga agagttctac aagttcatca 2100
agcccatcct ggaaaagatg gacggcaccg aggaactgct cgtgaagctg aacagagagg 2160
acctgctgcg gaagcagcgg accttcgaca acggcagcat cccccaccag atccacctgg 2220
gagagctgca cgccattctg cggcggcagg aagattttta cccattcctg aaggacaacc 2280
gggaaaagat cgagaagatc ctgaccttcc gcatccccta ctacgtgggc cctctggcca 2340
ggggaaacag cagattcgcc tggatgacca gaaagagcga ggaaaccatc accccctgga 2400
acttcgagga agtggtggac aagggcgctt ccgcccagag cttcatcgag cggatgacca 2460
acttcgataa gaacctgccc aacgagaagg tgctgcccaa gcacagcctg ctgtacgagt 2520
acttcaccgt gtataacgag ctgaccaaag tgaaatacgt gaccgaggga atgagaaagc 2580
ccgccttcct gagcggcgag cagaaaaagg ccatcgtgga cctgctgttc aagaccaacc 2640
ggaaagtgac cgtgaagcag ctgaaagagg actacttcaa gaaaatcgag tgcttcgact 2700
ccgtggaaat ctccggcgtg gaagatcggt tcaacgcctc cctgggcaca taccacgatc 2760
tgctgaaaat tatcaaggac aaggacttcc tggacaatga ggaaaacgag gacattctgg 2820
aagatatcgt gctgaccctg acactgtttg aggacagaga gatgatcgag gaacggctga 2880
aaacctatgc ccacctgttc gacgacaaag tgatgaagca gctgaagcgg cggagataca 2940
ccggctgggg caggctgagc cggaagctga tcaacggcat ccgggacaag cagtccggca 3000
agacaatcct ggatttcctg aagtccgacg gcttcgccaa cagaaacttc atgcagctga 3060

-continued

```
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aactttttca agaccgagat taccctggcc aacggcgaga   4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggcggcag cagcacccta aatatagaag atgagtatcg gctacatgag acctcaaaag   5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
ctacccccgt gtccataaaa caataccca tgtcacaaga agccagactg gggatcaagc   5400
cccacataca gagactgttg gaccagggaa tactggtacc ctgccagtcc ccctggaaca   5460
```

```
cgcccctgct acccgttaag aaaccaggga ctaatgatta taggcctgtc caggatctga   5520
gagaagtcaa caagcgggtg gaagacatcc accccaccgt gcccaaccct tacaacctct   5580
tgagcgggct cccaccgtcc caccagtggt acactgtgct tgatttaaag gatgcctttt   5640
tctgcctgag actccacccc accagtcagc ctctcttcgc ctttgagtgg agagatccag   5700
agatgggaat ctcaggacaa ttgacctgga ccagactccc acagggtttc aaaaacagtc   5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctagggaa cctcgggtat cgggcctcgg   5940
ccaagaaagc ccaaatttgc cagaaacagg tcaagtatct ggggtatctt ctaaaagagg   6000
gtcagagatg gctgactgag gccagaaaag agactgtgat ggggcagcct actccgaaga   6060
cccctcgaca actaagggag ttcctaggga aggcaggctt ctgtcgcctc ttcatccctg   6120
ggtttgcaga aatggcagcc cccctgtacc ctctcaccaa accgggact ctgtttaatt   6180
ggggcccaga ccaacaaaag gcctatcaag aaatcaagca agctcttcta actgccccag   6240
ccctggggtt gccagatttg actaagccct ttgaactctt tgtcgacgag aagcagggct   6300
acgccaaagg tgtcctaacg caaaaactgg gaccttggcg tcggccggtg gcctacctgt   6360
ccaaaaagct agacccagta gcagctgggt ggcccccttg cctacggatg gtagcagcca   6420
ttgccgtact gacaaaggat gcaggcaagc taaccatggg acagccacta gtcattctgg   6480
ccccccatgc agtagaggca ctagtcaaac aacccccga ccgctggctt tccaacgccc   6540
ggatgactca ctatcaggcc ttgcttttgg acacggaccg ggtccagttc ggaccggtgg   6600
tagccctgaa cccggctacg ctgctcccac tgcctgagga agggctgcaa cacaactgcc   6660
ttgatatcct ggccgaagcc cacggaaccc gacccgacct aacggaccag ccgctcccag   6720
acgccgacca cacctggtac acggatggaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaaggta   6900
agaagctaaa tgtttatact gatagccgtt atgcttttgc tactgcccat atccatggag   6960
aaatatacag aaggcgtggg tggctcacat cagaaggcaa agagatcaaa aataaagacg   7020
agatcttggc cctactaaaa gccctctttc tgcccaaaag acttagcata atccattgtc   7080
caggacatca aaagggacac agcgccgagg ctagaggcaa ccggatggct gaccaagcgg   7140
cccgaaaggc agccatcaca gagactccag acacctctac cctcctcata gaaaattcat   7200
caccctctgg cggctcaaaa agaaccgccg acggcagcga attcgagccc aagaagaaga   7260
ggaaagtcta accggtcatc atcaccatca ccattgagtt taaacccgct gatcagcctc   7320
gactgtgcct tctagttgcc agccatctgt tgtttgcccc tcccccgtgc cttccttgac   7380
cctggaaggt gccactccca ctgtcctttc ctaataaaat gagaaaattg catcgcattg   7440
tctgagtagg tgtcattcta ttctgggggg tggggtgggg caggacagca agggggagga   7500
ttgggaagac aatagcaggc atgctgggga tgcggtgggc tctatggctt ctgaggcgga   7560
aagaaccagc tggggctcga taccgtcgac ctctagctag agcttggcgt aatcatggtc   7620
atagctgttt cctgtgtgaa attgttatcc gctcacaatt ccacacaaca tacgagccgg   7680
aagcataaag tgtaaagcct agggtgccta atgagtgagc taactcacat taattgcgtt   7740
gcgctcactg cccgctttcc agtcgggaaa cctgtcgtgc cagctgcatt aatgaatcgg   7800
```

ccaacgcgcg gggagaggcg gtttgcgtat tgggcgctct tccgcttcct cgctcactga 7860
ctcgctgcgc tcggtcgttc ggctgcggcg agcggtatca gctcactcaa aggcggtaat 7920
acggttatcc acagaatcag gggataacgc aggaaagaac atgtgagcaa aaggccagca 7980
aaaggccagg aaccgtaaaa aggccgcgtt gctggcgttt ttccataggc tccgcccccc 8040
tgacgagcat cacaaaaatc gacgctcaag tcagaggtgg cgaaacccga caggactata 8100
aagataccag gcgtttcccc ctggaagctc cctcgtgcgc tctcctgttc cgaccctgcc 8160
gcttaccgga tacctgtccg cctttctccc ttcgggaagc gtggcgcttt ctcatagctc 8220
acgctgtagg tatctcagtt cggtgtaggt cgttcgctcc aagctgggct gtgtgcacga 8280
accccccgtt cagcccgacc gctgcgcctt atccggtaac tatcgtcttg agtccaaccc 8340
ggtaagacac gacttatcgc cactggcagc agccactggt aacaggatta gcagagcgag 8400
gtatgtaggc ggtgctacag agttcttgaa gtggtggcct aactacggct acactagaag 8460
aacagtattt ggtatctgcg ctctgctgaa gccagttacc ttcggaaaaa gagttggtag 8520
ctcttgatcc ggcaaacaaa ccaccgctgg tagcggtggt ttttttgttt gcaagcagca 8580
gattacgcgc agaaaaaaag gatctcaaga agatcctttg atcttttcta cggggtctga 8640
cgctcagtgg aacgaaaact cacgttaagg gattttggtc atgagattat caaaaaggat 8700
cttcacctag atccttttaa attaaaaatg aagttttaaa tcaatctaaa gtatatatga 8760
gtaaacttgg tctgacagtt accaatgctt aatcagtgag gcacctatct cagcgatctg 8820
tctatttcgt tcatccatag ttgcctgact ccccgtcgtg tagataacta cgatacggga 8880
gggcttacca tctggcccca gtgctgcaat gataccgcga gacccacgct caccggctcc 8940
agatttatca gcaataaacc agccagccgg aagggccgag cgcagaagtg gtcctgcaac 9000
tttatccgcc tccatccagt ctattaattg ttgccgggaa gctagagtaa gtagttcgcc 9060
agttaatagt ttgcgcaacg ttgttgccat tgctacaggc atcgtggtgt cacgctcgtc 9120
gtttggtatg gcttcattca gctccggttc ccaacgatca aggcgagtta catgatcccc 9180
catgttgtgc aaaaaagcgg ttagctcctt cggtcctccg atcgttgtca gaagtaagtt 9240
ggccgcagtg ttatcactca tggttatggc agcactgcat aattctctta ctgtcatgcc 9300
atccgtaaga tgcttttctg tgactggtga gtactcaacc aagtcattct gagaatagtg 9360
tatgcggcga ccgagttgct cttgcccggc gtcaatacgg gataataccg cgccacatag 9420
cagaacttta aaagtgctca tcattggaaa acgttcttcg gggcgaaaac tctcaaggat 9480
cttaccgctg ttgagatcca gttcgatgta acccactcgt gcacccaact gatcttcagc 9540
atcttttact ttcaccagcg tttctgggtg agcaaaaaca ggaaggcaaa atgccgcaaa 9600
aaagggaata agggcgacac ggaaatgttg aatactcata ctcttccttt ttcaatatta 9660
ttgaagcatt tatcagggtt attgtctcat gagcggatac atatttgaat gtatttagaa 9720
aaataaacaa ataggggttc cgcgcacatt tcc 9753

<210> SEQ ID NO 383
<211> LENGTH: 11433
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 383
ccgaaaagtg ccacctgacg tcgacggatc gggagatcga tctcccgatc ccctagggtc 60

-continued

```
gactctcagt acaatctgct ctgatgccgc atagttaagc cagtatctgc tccctgcttg    120
tgtgttggag gtcgctgagt agtgcgcgag caaaatttaa gctacaacaa ggcaaggctt    180
gaccgacaat tgcatgaaga atctgcttag ggttaggcgt tttgcgctgc ttcgcgatgt    240
acgggccaga tatacgcgtt gacattgatt attgactagt tattaatagt aatcaattac    300
ggggtcatta gttcatagcc catatatgga gttccgcgtt acataactta cggtaaatgg    360
cccgcctggc tgaccgccca acgacccccg cccattgacg tcaataatga cgtatgttcc    420
catagtaacg ccaataggga ctttccattg acgtcaatgg gtggagtatt tacggtaaac    480
tgcccacttg gcagtacatc aagtgtatca tatgccaagt acgcccccta ttgacgtcaa    540
tgacggtaaa tggcccgcct ggcattatgc ccagtacatg accttatggg actttcctac    600
ttggcagtac atctacgtat tagtcatcgc tattaccatg gtgatgcggt tttggcagta    660
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg gccgctaata cgactcacta    900
tagggagagc cgccaccatg cccgcggcta agagggtgaa gcttgacggt ggaaaacgga    960
cagccgacgg aagcgagttc gagtcaccaa agaagaagcg gaaagtcgac aagaagtaca   1020
gcatcggcct ggacatcggc accaactctg tgggctgggc cgtgatcacc gacgagtaca   1080
aggtgcccag caagaaattc aaggtgctgg gcaacaccga ccggcacagc atcaagaaga   1140
acctgatcgg agccctgctg ttcgacagcg gcgaaacagc cgaggccacc cggctgaaga   1200
gaaccgccag aagaagatac accagacgga agaaccggat ctgctatctg caagagatct   1260
tcagcaacga gatggccaag gtggacgaca gcttcttcca cagactggaa gagtccttcc   1320
tggtggaaga ggataagaag cacgagcggc accccatctt cggcaacatc gtggacgagg   1380
tggcctacca cgagaagtac cccaccatct accacctgag aaagaaactg gtggacagca   1440
ccgacaaggc cgacctgcgg ctgatctatc tggccctggc ccacatgatc aagttccggg   1500
gccacttcct gatcgagggc gacctgaacc ccgacaacag cgacgtggac aagctgttca   1560
tccagctggt gcagacctac aaccagctgt tcgaggaaaa ccccatcaac gccagcggcg   1620
tggacgccaa ggccatcctg tctgccagac tgagcaagag cagacggctg gaaaatctga   1680
tcgcccagct gcccggcgag aagaagaatg gcctgttcgg aaacctgatt gccctgagcc   1740
tgggcctgac ccccaacttc aagagcaact tcgacctggc cgaggatgcc aaactgcagc   1800
tgagcaagga cacctacgac gacgacctgg acaacctgct ggcccagatc ggcgaccagt   1860
acgccgacct gtttctggcc gccaagaacc tgtccgacgc catcctgctg agcgacatcc   1920
tgagagtgaa caccgagatc accaaggccc ccctgagcgc ctctatgatc aagagatacg   1980
acgagcacca ccaggacctg accctgctga aagctctcgt gcggcagcag ctgcctgaga   2040
agtacaaaga gatttttcttc gaccagagca agaacggcta cgccggctac attgacggcg   2100
gagccagcca ggaagagttc tacaagttca tcaagcccat cctggaaaag atggacggca   2160
ccgaggaact gctcgtgaag ctgaacagag aggacctgct gcggaagcag cggaccttcg   2220
acaacggcag catcccccac cagatccacc tgggagagct gcacgccatt ctgcggcggc   2280
aggaagattt ttacccattc ctgaaggaca accgggaaaa gatcgagaag atcctgacct   2340
tccgcatccc ctactacgtg ggccctctgg ccaggggaaa cagcagattc gcctggatga   2400
ccagaaagag cgaggaaacc atcacccccct ggaacttcga ggaagtggtg gacaagggcg   2460
```

```
cttccgccca gagcttcatc gagcggatga ccaacttcga taagaacctg cccaacgaga   2520
aggtgctgcc caagcacagc ctgctgtacg agtacttcac cgtgtataac gagctgacca   2580
aagtgaaata cgtgaccgag ggaatgagaa agcccgcctt cctgagcggc gagcagaaaa   2640
aggccatcgt ggacctgctg ttcaagacca accggaaagt gaccgtgaag cagctgaaag   2700
aggactactt caagaaaatc gagtgcttcg actccgtgga aatctccggc gtggaagatc   2760
ggttcaacgc ctccctgggc acataccacg atctgctgaa aattatcaag gacaaggact   2820
tcctggacaa tgaggaaaac gaggacattc tggaagatat cgtgctgacc ctgacactgt   2880
ttgaggacag agagatgatc gaggaacggc tgaaaaccta tgcccacctg ttcgacgaca   2940
aagtgatgaa gcagctgaag cggcggagat acaccggctg ggcaggctg agccggaagc   3000
tgatcaacgg catccgggac aagcagtccg gcaagacaat cctggatttc ctgaagtccg   3060
acggcttcgc caacagaaac ttcatgcagc tgatccacga cgacagcctg acctttaaag   3120
aggacatcca gaaagcccag gtgtccggcc agggcgatag cctgcacgag cacattgcca   3180
atctggccgg cagccccgcc attaagaagg gcatcctgca gacagtgaag gtggtggacg   3240
agctcgtgaa agtgatgggc cggcacaagc ccgagaacat cgtgatcgaa atggccagag   3300
agaaccagac cacccagaag ggacagaaga acagccgcga gagaatgaag cggatcgaag   3360
agggcatcaa agagctgggc agccagatcc tgaaagaaca ccccgtggaa aacacccagc   3420
tgcagaacga gaagctgtac ctgtactacc tgcagaatgg gcgggatatg tacgtggacc   3480
aggaactgga catcaaccgg ctgtccgact acgatgtgga cgctatcgtg cctcagagct   3540
ttctgaagga cgactccatc gacaacaagg tgctgaccag aagcgacaag aaccggggca   3600
agagcgacaa cgtgccctcc gaagaggtcg tgaagaagat gaagaactac tggcggcagc   3660
tgctgaacgc caagctgatt acccagagaa agttcgacaa tctgaccaag gccgagagag   3720
gcggcctgag cgaactggat aaggccggct tcatcaagag acagctggtg gaaacccggc   3780
agatcacaaa gcacgtggca cagatcctgg actcccggat gaacactaag tacgacgaga   3840
atgacaagct gatccgggaa gtgaaagtga tcaccctgaa gtccaagctg gtgtccgatt   3900
tccggaagga tttccagttt tacaaagtgc gcgagatcaa caactaccac cacgcccacg   3960
acgcctacct gaacgccgtc gtgggaaccg ccctgatcaa aaagtaccct aagctggaaa   4020
gcgagttcgt gtacggcgac tacaaggtgt acgacgtgcg gaagatgatc gccaagagcg   4080
agcaggaaat cggcaaggct accgccaagt acttcttcta cagcaacatc atgaactttt   4140
tcaagaccga gattaccctg gccaacggcg agatccggaa gcggcctctg atcgagacaa   4200
acggcgaaac cggggagatc gtgtgggata agggccggga ttttgccacc gtgcggaaag   4260
tgctgagcat gccccaagtg aatatcgtga aaaagaccga ggtgcagaca ggcggcttca   4320
gcaaagagtc tatcctgccc aagaggaaca gcgataagct gatcgccaga aagaaggact   4380
gggaccctaa gaagtacggc ggcttcgaca gccccaccgt ggcctattct gtgctggtgg   4440
tggccaaagt ggaaaagggc aagtccaaga aactgaagag tgtgaaagag ctgctgggga   4500
tcaccatcat ggaaagaagc agcttcgaga agaatcccat cgactttctg gaagccaagg   4560
gctacaaaga agtgaaaaag gacctgatca tcaagctgcc taagtactcc ctgttcgagc   4620
tggaaaacgg ccggaagaga atgctggcct ctgccggcga actgcagaag ggaaacgaac   4680
tggccctgcc ctccaaatat gtgaacttcc tgtacctggc cagccactat gagaagctga   4740
agggctcccc cgaggataat gagcagaaac agctgtttgt ggaacagcac aagcactacc   4800
```

tggacgagat catcgagcag atcagcgagt tctccaagag agtgatcctg gccgacgcta 4860
atctggacaa agtgctgtcc gcctacaaca agcaccggga taagcccatc agagagcagg 4920
ccgagaatat catccacctg tttaccctga ccaatctggg agcccctgcc gccttcaagt 4980
actttgacac caccatcgac cggaagaggt acaccagcac caaagaggtg ctggacgcca 5040
ccctgatcca ccagagcatc accggcctgt acgagacacg gatcgacctg tctcagctgg 5100
gaggtgactc tggaggatct agcggaggat cctctggcag cgagacacca ggaacaagcg 5160
agtcagcaac accagagagc agtggcggca gcagcggcgg cagcagcacc ctaaatatag 5220
aagatgagta tcggctacat gagacctcaa aagagccaga tgtttctcta gggtccacat 5280
ggctgtctga ttttcctcag gcctgggcgg aaaccggggg catgggactg gcagttcgcc 5340
aagctcctct gatcataccc ctgaaagcaa cctctacccc cgtgtccata aaacaatacc 5400
ccatgtcaca agaagccaga ctggggatca agccccacat acagagactg ttggaccagg 5460
gaatatggta ccctgccagt cccccctggaa cacgcccctg ctacccgtta agaaaccagg 5520
gactaatgat tataggcctg tccaggatct gagagaagtc aacaagcggg tggaagacat 5580
ccaccccacc gtgcccaacc cttacaacct cttgagcggg ctcccaccgt cccaccagtg 5640
gtacactgtg cttgatttaa aggatgcctt tttctgcctg agactccacc cccaccagtca 5700 gcctctcttc gcctttgagt ggagagatcc agagatggga atctcaggac aattgacctg 5760
gaccagactc ccacagggtt tcaaaaacag tcccaccctg tttaatgagg cactgcacag 5820
agacctagca gacttccgga tccagcaccc agacttgatc ctgctacagt acgtggatga 5880
cttactgctg gccgccactt ctgagctaga ctgccaacaa ggtactcggg ccctgttaca 5940
aaccctaggg aacctcgggt atcgggcctc ggccaagaaa gcccaaattt gccagaaaca 6000
ggtcaagtat ctggggtatc ttctaaaaga gggtcagaga tggctgactg aggccagaaa 6060
agagactgtg atggggcagc ctactccgaa gacccctcga caactaaggg agttcctagg 6120
gaaggcaggc ttctgtcgcc tcttcatccc tgggtttgca gaaatggcag ccccccctgta 6180 ccctctcacc aaaccgggga ctctgtttaa ttggggccca gaccaacaaa aggcctatca 6240
agaaatcaag caagctcttc taactgcccc agccctgggg ttgccagatt tgactaagcc 6300
ctttgaactc tttgtcgacg agaagcaggg ctacgccaaa ggtgtcctaa cgcaaaaact 6360
gggaccttgg cgtcggccgg tggcctacct gtccaaaaag ctagacccag tagcagctgg 6420 gtggcccccct tgcctacgga tggtagcagc cattgccgta ctgacaaagg atgcaggcaa 6480
gctaaccatg ggacagccac tagtcattct ggccccccat gcagtagagg cactagtcaa 6540
acaacccccc gaccgctggc tttccaacgc ccggatgact cactatcagg ccttgctttt 6600
ggacacggac cgggtccagt tcggaccggt ggtagccctg aacccggcta cgctgctccc 6660
actgcctgag gaagggctgc aacacaactg ccttgatatc ctggccgaag cccacggaac 6720
ccgacccgac ctaacggacc agccgctccc agacgccgac cacacctggt acacggatgg 6780
aagcagtctc ttacaagagg gacagcgtaa ggcgggagct gcggtgacca ccgagaccga 6840
ggtaatctgg gctaaagccc tgccagccgg gacatccgct cagcgggctg aactgatagc 6900
actcacccag gccctaaaga tggcagaagg taagaagcta aatgtttata ctgatagccg 6960
ttatgctttt gctactgccc atatccatgg agaaatatac agaaggcgtg ggtggctcac 7020
atcagaaggc aaagagatca aaaataaaga cgagatcttg gccctactaa aagccctctt 7080
tctgcccaaa agacttagca taatccattg tccaggacat caaaagggac acagcgccga 7140
ggctagaggc aaccggatgg ctgaccaagc ggcccgaaag gcagccatca cagagactcc 7200
agacacctct accctcctca tagaaaattc atcaccctct ggcggctcaa aaagaaccgc 7260
cgacggcagc gaaaaaagaa ccgctgactc tcaacattcc acacctccaa aaaccaagcg 7320
aaaagtggaa ttcgagccca agaagaagag gaaagtcgga agcggagcta ctaacttcag 7380
cctgctgaag caggctggcg acgtggagga gaaccctgga cctccaaaaa agaaaagaaa 7440
agtgtatccc tatgatgtcc ccgattatgc cggttcaaga gccctggtcg tgattagact 7500
gagccgagtg acagacgcca ccacaagtcc cgagagacag ctggaatcat gccagcagct 7560
ctgtgctcag cggggttggg atgtggtcgg cgtggcagag gatctggacg tgagcggggc 7620
cgtcgatcca ttcgacagaa agaggaggcc caacctggca agatggctcg ctttcgagga 7680
acagcccttt gatgtgatcg tcgcctacag agtggaccgg ctgacccgct caattcgaca 7740
tctccagcag ctggtgcatt gggctgagga ccacaagaaa ctggtggtca gcgcaacaga 7800
agcccacttc gatactacca caccttttgc cgctgtggtc atcgcactga tgggcactgt 7860
ggcccagatg gagctcgaag ctatcaagga gcgaaacagg agcgcagccc atttcaatat 7920
tagggccggt aaatacagag gctccctgcc cccttgggga tatctcccta ccagggtgga 7980
tggggagtgg agactggtgc cagaccccgt ccagagagag cggattctgg aagtgtacca 8040
cagagtggtc gataaccacg aaccactcca tctggtggca cacgacctga atagacgcgg 8100
cgtgctctct ccaaaggatt attttgctca gctgcaggga agagagccac agggaagaga 8160
atggagtgct actgcactga agagatctat gatcagtgag gctatgctgg gttacgcaac 8220
actcaatggc aaaactgtcc gggacgatga cggagcccct ctggtgaggg ctgagcctat 8280
tctcaccaga gagcagctcg aagctctgcg ggcagaactg gtcaagacta gtcgcgccaa 8340
acctgccgtg agcaccccaa gcctgctcct gagggtgctg ttctgcgccg tctgtggaga 8400
gccagcatac aagtttgccg gcggagggcg caaacatccc cgctatcgat gcaggagcat 8460
ggggttccct aagcactgtg gaaacgggac agtggccatg gctgagtggg acgccttttg 8520
cgaggaacag gtgctggatc tcctgggtga cgctgagcgg ctggaaaaag tgtgggtggc 8580
aggatctgac tccgctgtgg agctggcaga agtcaatgcc gagctcgtgg atctgacttc 8640
cctcatcgga tctcctgcat atagagctgg gtccccacag agagaagctc tggacgcacg 8700
aattgctgca ctcgctgcta gacaggagga actggagggc ctggaggcca ggccctctgg 8760
atgggagtgg cgagaaaccg gacagaggtt tggggattgg tggagggagc aggacaccgc 8820
agccaagaac acatggctga gatccatgaa tgtccggctc acattcgacg tgcgcggtgg 8880
cctgactcga accatcgatt ttggcgacct gcaggagtat gaacagcacc tgagactggg 8940
gtccgtggtc gaaagactgc acactgggat gtcctaggtt taaacccgct gatcagcctc 9000
gactgtgcct tctagttgcc agccatctgt tgtttgcccc tcccccgtgc cttccttgac 9060
cctggaaggt gccactccca ctgtcctttc ctaataaaat gagaaaattg catcgcattg 9120
tctgagtagg tgtcattcta ttctgggggg tggggtgggg caggacagca agggggagga 9180
ttgggaagac aatagcaggc atgctgggga tgcggtgggc tctatggctt ctgaggcgga 9240
aagaaccagc tggggctcga taccgtcgac ctctagctag agcttggcgt aatcatggtc 9300
atagctgttt cctgtgtgaa attgttatcc gctcacaatt ccacacaaca tacgagccgg 9360
aagcataaag tgtaaagcct agggtgccta atgagtgagc taactcacat taattgcgtt 9420
gcgctcactg cccgctttcc agtcgggaaa cctgtcgtgc cagctgcatt aatgaatcgg 9480
ccaacgcgcg gggagaggcg gtttgcgtat tgggcgctct tccgcttcct cgctcactga 9540
ctcgctgcgc tcggtcgttc ggctgcggcg agcggtatca gctcactcaa aggcggtaat 9600
acggttatcc acagaatcag gggataacgc aggaaagaac atgtgagcaa aaggccagca 9660
aaaggccagg aaccgtaaaa aggccgcgtt gctggcgttt ttccataggc tccgcccccc 9720
tgacgagcat cacaaaaatc gacgctcaag tcagaggtgg cgaaacccga caggactata 9780
aagataccag gcgtttcccc ctggaagctc cctcgtgcgc tctcctgttc cgaccctgcc 9840
gcttaccgga tacctgtccg cctttctccc ttcgggaagc gtggcgcttt ctcatagctc 9900
acgctgtagg tatctcagtt cggtgtaggt cgttcgctcc aagctgggct gtgtgcacga 9960
accccccgtt cagcccgacc gctgcgcctt atccggtaac tatcgtcttg agtccaaccc 10020
ggtaagacac gacttatcgc cactggcagc agccactggt aacaggatta gcagagcgag 10080
gtatgtaggc ggtgctacag agttcttgaa gtggtggcct aactacggct acactagaag 10140
aacagtattt ggtatctgcg ctctgctgaa gccagttacc ttcggaaaaa gagttggtag 10200
ctcttgatcc ggcaaacaaa ccaccgctgg tagcggtggt ttttttgttt gcaagcagca 10260
gattacgcgc agaaaaaaag gatctcaaga agatcctttg atcttttcta cggggtctga 10320
cgctcagtgg aacgaaaact cacgttaagg gattttggtc atgagattat caaaaaggat 10380
cttcacctag atccttttaa attaaaaatg aagttttaaa tcaatctaaa gtatatatga 10440
gtaaacttgg tctgacagtt accaatgctt aatcagtgag gcacctatct cagcgatctg 10500
tctatttcgt tcatccatag ttgcctgact ccccgtcgtg tagataacta cgatacggga 10560
gggcttacca tctggcccca gtgctgcaat gataccgcga gacccacgct caccggctcc 10620
agatttatca gcaataaacc agccagccgg aagggccgag cgcagaagtg gtcctgcaac 10680
tttatccgcc tccatccagt ctattaattg ttgccgggaa gctagagtaa gtagttcgcc 10740
agttaatagt ttgcgcaacg ttgttgccat tgctacaggc atcgtggtgt cacgctcgtc 10800
gtttggtatg gcttcattca gctccggttc ccaacgatca aggcgagtta catgatcccc 10860
catgttgtgc aaaaaagcgg ttagctcctt cggtcctccg atcgttgtca gaagtaagtt 10920
ggccgcagtg ttatcactca tggttatggc agcactgcat aattctctta ctgtcatgcc 10980
atccgtaaga tgcttttctg tgactggtga gtactcaacc aagtcattct gagaatagtg 11040
tatgcggcga ccgagttgct cttgcccggc gtcaatacgg gataataccg cgccacatag 11100
cagaacttta aaagtgctca tcattggaaa acgttcttcg gggcgaaaac tctcaaggat 11160
cttaccgctg ttgagatcca gttcgatgta acccactcgt gcacccaact gatcttcagc 11220
atcttttact ttcaccagcg tttctgggtg agcaaaaaca ggaaggcaaa atgccgcaaa 11280
aaagggaata agggcgacac ggaaatgttg aatactcata ctcttccttt ttcaatatta 11340
ttgaagcatt tatcagggtt attgtctcat gagcggatac atatttgaat gtatttagaa 11400
aaataaacaa ataggggttc cgcgcacatt tcc 11433

<210> SEQ ID NO 384
<211> LENGTH: 11056
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 384
ccgaaaagtg ccacctgacg tcgacggatc gggagatcga tctcccgatc ccctagggtc 60
gactctcagt acaatctgct ctgatgccgc atagttaagc cagtatctgc tccctgcttg 120

```
tgtgttggag gtcgctgagt agtgcgcgag caaaatttaa gctacaacaa ggcaaggctt    180
gaccgacaat tgcatgaaga atctgcttag ggttaggcgt tttgcgctgc ttcgcgatgt    240
acgggccaga tatacgcgtt gacattgatt attgactagt tattaatagt aatcaattac    300
ggggtcatta gttcatagcc catatatgga gttccgcgtt acataactta cggtaaatgg    360
cccgcctggc tgaccgccca acgacccccg cccattgacg tcaataatga cgtatgttcc    420
catagtaacg ccaataggga ctttccattg acgtcaatgg gtggagtatt tacggtaaac    480
tgcccacttg gcagtacatc aagtgtatca tatgccaagt acgcccccta ttgacgtcaa    540
tgacggtaaa tggcccgcct ggcattatgc ccagtacatg accttatggg actttcctac    600
ttggcagtac atctacgtat tagtcatcgc tattaccatg gtgatgcggt tttggcagta    660
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg gccgctaata cgactcacta    900
tagggagagc cgccaccatg aaacggacag ccgacggaag cgagttcgag tcaccaaaga    960
agaagcggaa agtcgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcggcagg aagattttta cccattcctg aaggacaacc   2280
gggaaaagat cgagaagatc ctgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
```

```
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aactttttca agaccgagat taccctggcc aacggcgaga   4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
```

accgggataa gcccatcaga gagcaggccg agaatatcat ccacctgttt accctgacca 4920
atctgggagc ccctgccgcc ttcaagtact ttgacaccac catcgaccgg aagaggtaca 4980
ccagcaccaa agaggtgctg gacgccaccc tgatccacca gagcatcacc ggcctgtacg 5040
agacacggat cgacctgtct cagctgggag gtgactctgg aggatctagc ggaggatcct 5100
ctggcagcga gacaccagga acaagcgagt cagcaacacc agagagctct ggtagcgaga 5160 caccccggtac cagtgaaagc gccacgccag aaagcagtgg gagtgagact ccgggtacat 5220
ctgaatcagc gacaccggaa tcaagtggcg gcagcagcgg cggcagcagc accctaaata 5280
tagaagatga gtatcggcta catgagacct caaaagagcc agatgtttct ctagggtcca 5340
catggctgtc tgattttcct caggcctggg cggaaaccgg gggcatggga ctggcagttc 5400
gccaagctcc tctgatcata cctctgaaag caacctctac ccccgtgtcc ataaaacaat 5460
accccatgtc acaagaagcc agactgggga tcaagcccca catacagaga ctgttggacc 5520
agggaatact ggtaccctgc cagtccccct ggaacacgcc cctgctaccc gttaagaaac 5580
cagggactaa tgattatagg cctgtccagg atctgagaga agtcaacaag cgggtggaag 5640
acatccaccc caccgtgccc aacccttaca acctcttgag cgggccccca ccgtcccacc 5700
agtggtacac tgtgcttgat ttaaaggatg cctttttctg cctgagactc caccccacca 5760
gtcagcctct cttcgccttt gagtggagag atccagagat gggaatctca ggacaattga 5820
cctggaccag actcccacag ggtttcaaaa acagtcccac cctgtttaat gaggcactgc 5880
acagagacct agcagacttc cggatccagc acccagactt gatcctgcta cagtacgtgg 5940
atgacttact gctggccgcc acttctgagc tagactgcca acaaggtact cgggccctgt 6000
tacaaaccct agggaacctc gggtatcggg cctcggccaa gaaagcccaa atttgccaga 6060
aacaggtcaa gtatctgggg tatcttctaa aagagggtca gagatggctg actgaggcca 6120
gaaaagagac tgtgatgggg cagcctactc cgaagacccc tcgacaacta agggagttcc 6180
tagggaaggc aggcttctgt cgcctcttca tccctgggtt tgcagaaatg gcagcccccc 6240
tgtaccctct caccaaaccg gggactctgt ttaattgggg cccagaccaa caaaaggcct 6300
atcaagaaat caagcaagct cttctaactg ccccagccct ggggttgcca gatttgacta 6360 agcccttttga actctttgtc gacgagaagc agggctacgc caaaggtgtc ctaacgcaaa 6420
aactgggacc ttggcgtcgg ccggtggcct acctgtccaa aaagctagac ccagtagcag 6480
ctgggtggcc cccttgccta cggatggtag cagccattgc cgtactgaca aaggatgcag 6540
gcaagctaac catgggacag ccactagtca ttctggcccc ccatgcagta gaggcactag 6600
tcaaacaacc ccccgaccgc tggctttcca acgcccggat gactcactat caggccttgc 6660
ttttggacac ggaccgggtc cagttcggac cggtggtagc cctgaacccg gctacgctgc 6720
tcccactgcc tgaggaaggg ctgcaacaca actgccttga tgggacaggt ggcggtggtg 6780
tcaccgtcaa gttcaagtac aagggtgagg aacttgaagt tgatattagc aaaatcaaga 6840
aggtttggcg cgttggtaaa atgatatctt ttacttatga cgacaacggc aagacaggta 6900
gaggggcagt gtctgagaaa gacgccccca aggagctgtt gcaaatgttg gaaaagtctg 6960
ggaaaaagtc tggcggctca aaaagaaccg ccgacggcag cgaattcgag cccaagaaga 7020
agaggaaagt cggaggtggc gggagcccaa aaaagaaaag aaaagtgtat ccctatgatg 7080
tccccgatta tgccggttca agagccctgg tcgtgattag actgagccga gtgacagacg 7140
ccaccacaag tcccgagaga cagctggaat catgccagca gctctgtgct cagcggggtt 7200
gggatgtggt cggcgtggca gaggatctgg acgtgagcgg ggccgtcgat ccattcgaca 7260

-continued

```
gaaagaggag gcccaacctg gcaagatggc tcgctttcga ggaacagccc tttgatgtga   7320
tcgtcgccta cagagtggac cggctgaccc gctcaattcg acatctccag cagctggtgc   7380
attgggctga ggaccacaag aaactggtgg tcagcgcaac agaagcccac ttcgatacta   7440
ccacaccttt tgccgctgtg gtcatcgcac tgatgggcac tgtggcccag atggagctcg   7500
aagctatcaa ggagcgaaac aggagcgcag cccatttcaa tattagggcc ggtaaataca   7560
gaggctccct gccccccttgg ggatatctcc ctaccagggt ggatggggag tggagactgg   7620
tgccagaccc cgtccagaga gagcggattc tggaagtgta ccacagagtg gtcgataacc   7680
acgaaccact ccatctggtg gcacacgacc tgaatagacg cggcgtgctc tctccaaagg   7740
attattttgc tcagctgcag ggaagagagc cacagggaag agaatggagt gctactgcac   7800
tgaagagatc tatgatcagt gaggctatgc tgggttacgc aacactcaat ggcaaaactg   7860
tccgggacga tgacggagcc cctctggtga gggctgagcc tattctcacc agagagcagc   7920
tcgaagctct gcgggcagaa ctggtcaaga ctagtcgcgc caaacctgcc gtgagcaccc   7980
caagcctgct cctgagggtg ctgttctgcg ccgtctgtgg agagccagca tacaagtttg   8040
ccggcggagg gcgcaaacat ccccgctatc gatgcaggag catggggttc cctaagcact   8100
gtggaaacgg gacagtggcc atggctgagt gggacgcctt ttgcgaggaa caggtgctgg   8160
atctcctggg tgacgctgag cggctggaaa aagtgtgggt ggcaggatct gactccgctg   8220
tggagctggc agaagtcaat gccgagctcg tggatctgac ttccctcatc ggatctcctg   8280
catatagagc tgggtcccca cagagagaag ctctggacgc acgaattgct gcactcgctg   8340
ctagacagga ggaactggag ggcctggagg ccaggccctc tggatgggag tggcgagaaa   8400
ccggacagag gtttggggat tggtggaggg agcaggacac cgcagccaag aacacatggc   8460
tgagatccat gaatgtccgg ctcacattcg acgtgcgcgg tggcctgact cgaaccatcg   8520
attttggcga cctgcaggag tatgaacagc acctgagact ggggtccgtg gtcgaaagac   8580
tgcacactgg gatgtcctag gtttaaaccc gctgatcagc ctcgactgtg ccttctagtt   8640
gccagccatc tgttgtttgc ccctcccccg tgccttcctt gaccctggaa ggtgccactc   8700
ccactgtcct ttcctaataa aatgagaaaa ttgcatcgca ttgtctgagt aggtgtcatt   8760
ctattctggg gggtggggtg gggcaggaca gcaaggggga ggattgggaa gacaatagca   8820
ggcatgctgg ggatgcggtg ggctctatgg cttctgaggc ggaaagaacc agctggggct   8880
cgataccgtc gacctctagc tagagcttgg cgtaatcatg gtcatagctg tttcctgtgt   8940
gaaattgtta tccgctcaca attccacaca acatacgagc cggaagcata aagtgtaaag   9000
cctagggtgc ctaatgagtg agctaactca cattaattgc gttgcgctca ctgcccgctt   9060
tccagtcggg aaacctgtcg tgccagctgc attaatgaat cggccaacgc gcggggagag   9120
gcggtttgcg tattgggcgc tcttccgctt cctcgctcac tgactcgctg cgctcggtcg   9180
ttcggctgcg gcgagcggta tcagctcact caaaggcggt aatacggtta tccacagaat   9240
caggggataa cgcaggaaag aacatgtgag caaaaggcca gcaaaaggcc aggaaccgta   9300
aaaaggccgc gttgctggcg tttttccata ggctccgccc ccctgacgag catcacaaaa   9360
atcgacgctc aagtcagagg tggcgaaacc cgacaggact ataaagatac caggcgtttc   9420
cccctggaag ctccctcgtg cgctctcctg ttccgaccct gccgcttacc ggatacctgt   9480
ccgcctttct cccttcggga agcgtggcgc tttctcatag ctcacgctgt aggtatctca   9540
gttcggtgta ggtcgttcgc tccaagctgg gctgtgtgca cgaacccccc gttcagcccg   9600
```

accgctgcgc cttatccggt aactatcgtc ttgagtccaa cccggtaaga cacgacttat 9660
cgccactggc agcagccact ggtaacagga ttagcagagc gaggtatgta ggcggtgcta 9720
cagagttctt gaagtggtgg cctaactacg gctacactag aagaacagta tttggtatct 9780
gcgctctgct gaagccagtt accttcggaa aaagagttgg tagctcttga tccggcaaac 9840
aaaccaccgc tggtagcggt ggtttttttg tttgcaagca gcagattacg cgcagaaaaa 9900
aaggatctca agaagatcct ttgatctttt ctacggggtc tgacgctcag tggaacgaaa 9960
actcacgtta agggattttg gtcatgagat tatcaaaaag gatcttcacc tagatccttt 10020
taaattaaaa atgaagtttt aaatcaatct aaagtatata tgagtaaact tggtctgaca 10080
gttaccaatg cttaatcagt gaggcaccta tctcagcgat ctgtctattt cgttcatcca 10140
tagttgcctg actccccgtc gtgtagataa ctacgatacg ggagggctta ccatctggcc 10200
ccagtgctgc aatgataccg cgagacccac gctcaccggc tccagattta tcagcaataa 10260
accagccagc cggaagggcc gagcgcagaa gtggtcctgc aactttatcc gcctccatcc 10320
agtctattaa ttgttgccgg gaagctagag taagtagttc gccagttaat agtttgcgca 10380
acgttgttgc cattgctaca ggcatcgtgg tgtcacgctc gtcgtttggt atggcttcat 10440
tcagctccgg ttcccaacga tcaaggcgag ttacatgatc ccccatgttg tgcaaaaaag 10500
cggttagctc cttcggtcct ccgatcgttg tcagaagtaa gttggccgca gtgttatcac 10560
tcatggttat ggcagcactg cataattctc ttactgtcat gccatccgta agatgctttt 10620
ctgtgactgg tgagtactca accaagtcat tctgagaata gtgtatgcgg cgaccgagtt 10680
gctcttgccc ggcgtcaata cgggataata ccgcgccaca tagcagaact ttaaaagtgc 10740
tcatcattgg aaaacgttct tcggggcgaa aactctcaag gatcttaccg ctgttgagat 10800
ccagttcgat gtaacccact cgtgcaccca actgatcttc agcatctttt actttcacca 10860
gcgtttctgg gtgagcaaaa acaggaaggc aaaatgccgc aaaaaaggga ataagggcga 10920
cacggaaatg ttgaatactc atactcttcc tttttcaata ttattgaagc atttatcagg 10980
gttattgtct catgagcgga tacatatttg aatgtattta gaaaaataaa caaatagggg 11040
ttccgcgcac atttcc 11056

<210> SEQ ID NO 385
<211> LENGTH: 2367
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 385
tgttgagatc cagttcgatg taacccactc gtgcacccaa ctgatcttca gcatctttta 60
ctttcaccag cgtttctggg tgagcaaaaa caggaaggca aaatgccgca aaaaagggaa 120
taagggcgac acggaaatgt tgaatactca tactcttcct ttttcaatat tattgaagca 180
tttatcaggg ttattgtctc atgagcggat acatatttga atgtatttag aaaaataaac 240
aaataggggt tccgcgcaca tttccccgaa aagtgccacc tgacgtcgct agctgtacaa 300
aaaagcaggc tttaaaggaa ccaattcagt cgactggatc cggtaccaag gtcgggcagg 360
aagagggcct atttcccatg attccttcat atttgcatat acgatacaag gctgttagag 420
agataattag aattaatttg actgtaaaca caaagatatt agtacaaaat acgtgacgta 480
gaaagtaata atttcttggg tagtttgcag ttttaaaatt atgttttaaa atggactatc 540
atatgcttac cgtaacttga aagtatttcg atttcttggc tttatatatc ttgtggaaag 600
gacgaaacac cgctattctc gcagctcacc agttttagag ctagaaatag caagttaaaa 660
taaggctagt ccgttatcaa cttgaaaaag tggcaccgag tcggtgcgac gagcgcggcg 720
atatcatcat ccatggccgg atgatcctga cgacggagac cgccgtcgtc gacaagccgg 780
cctgagctgc gagaattttt ttaagcttgg gccgctcgag gtacctctct acatatgaca 840
tgtgagcaaa aggccagcaa aaggccagga accgtaaaaa ggccgcgttg ctggcgtttt 900
tccataggct ccgcccccct gacgagcatc acaaaaatcg acgctcaagt cagaggtggc 960
gaaacccgac aggactataa agataccagg cgtttccccc tggaagctcc ctcgtgcgct 1020
ctcctgttcc gaccctgccg cttaccggat acctgtccgc ctttctccct tcgggaagcg 1080
tggcgctttc tcatagctca cgctgtaggt atctcagttc ggtgtaggtc gttcgctcca 1140
agctgggctg tgtgcacgaa ccccccgttc agcccgaccg ctgcgcctta tccggtaact 1200
atcgtcttga gtccaacccg gtaagacacg acttatcgcc actggcagca gccactggta 1260
acaggattag cagagcgagg tatgtaggcg gtgctacaga gttcttgaag tggtggccta 1320
actacggcta cactagaaga acagtatttg gtatctgcgc tctgctgaag ccagttacct 1380
tcggaaaaag agttggtagc tcttgatccg gcaaacaaac caccgctggt agcggtggtt 1440
tttttgtttg caagcagcag attacgcgca gaaaaaaagg atctcaagaa gatcctttga 1500
tcttttctac ggggtctgac gctcagtgga acgaaaactc acgttaaggg attttggtca 1560
tgagattatc aaaaaggatc ttcacctaga tccttttaaa ttaaaaatga agttttaaat 1620
caatctaaag tatatatgag taaacttggt ctgacagtta ccaatgctta atcagtgagg 1680
cacctatctc agcgatctgt ctatttcgtt catccatagt tgcctgactc cccgtcgtgt 1740
agataactac gatacgggag ggcttaccat ctggccccag tgctgcaatg ataccgcgag 1800
atccacgctc accggctcca gatttatcag caataaacca gccagccgga agggccgagc 1860
gcagaagtgg tcctgcaact ttatccgcct ccatccagtc tattaattgt tgccgggaag 1920
ctagagtaag tagttcgcca gttaatagtt tgcgcaacgt tgttgccatt gctacaggca 1980
tcgtggtgtc acgctcgtcg tttggtatgg cttcattcag ctccggttcc caacgatcaa 2040
ggcgagttac atgatccccc atgttgtgca aaaaagcggt tagctccttc ggtcctccga 2100
tcgttgtcag aagtaagttg gccgcagtgt tatcactcat ggttatggca gcactgcata 2160
attctcttac tgtcatgcca tccgtaagat gcttttctgt gactggtgag tactcaacca 2220
agtcattctg agaatagtgt atgcggcgac cgagttgctc ttgcccggcg tcaatacggg 2280
ataataccgc gccacatagc agaactttaa aagtgctcat cattggaaaa cgttcttcgg 2340
ggcgaaaact ctcaaggatc ttaccgc 2367

<210> SEQ ID NO 386
<211> LENGTH: 2280
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 386
ctccatccag tctattaatt gttgccggga agctagagta agtagttcgc cagttaatag 60
tttgcgcaac gttgttgcca ttgctacagg catcgtggtg tcacgctcgt cgtttggtat 120
ggcttcattc agctccggtt cccaacgatc aaggcgagtt acatgatccc ccatgttgtg 180
caaaaaagcg gttagctcct tcggtcctcc gatcgttgtc agaagtaagt tggccgcagt 240
gttatcactc atggttatgg cagcactgca taattctctt actgtcatgc catccgtaag 300
atgcttttct gtgactggtg agtactcaac caagtcattc tgagaatagt gtatgcggcg 360
accgagttgc tcttgcccgg cgtcaatacg ggataatacc gcgccacata gcagaacttt 420
aaaagtgctc atcattggaa aacgttcttc ggggcgaaaa ctctcaagga tcttaccgct 480
gttgagatcc agttcgatgt aacccactcg tgcacccaac tgatcttcag catcttttac 540
tttcaccagc gtttctgggt gagcaaaaac aggaaggcaa aatgccgcaa aaaagggaat 600
aagggcgaca cggaaatgtt gaatactcat actcttcctt tttcaatatt attgaagcat 660
ttatcagggt tattgtctca tgagcggata catatttgaa tgtatttaga aaaataaaca 720
aataggggtt ccgcgcacat ttccccgaaa agtgccacct gacgtcgcta gctgtacaaa 780
aaagcaggct ttaaaggaac caattcagtc gactggatcc ggtaccaagg tcgggcagga 840
agagggccta tttcccatga ttccttcata tttgcatata cgatacaagg ctgttagaga 900
gataattaga attaatttga ctgtaaacac aaagatatta gtacaaaata cgtgacgtag 960
aaagtaataa tttcttgggt agtttgcagt tttaaaatta tgttttaaaa tggactatca 1020
tatgcttacc gtaacttgaa agtatttcga tttcttggct ttatatatct tgtggaaagg 1080
acgaaacacc gaagccggcc ttgcacatgc gttttagagc tagaaatagc aagttaaaat 1140
aaggctagtc cgttatcaac ttgaaaaagt ggcaccgagt cggtgcgttt ttttaagctt 1200
gggccgctcg aggtacctct ctacatatga catgtgagca aaaggccagc aaaaggccag 1260
gaaccgtaaa aaggccgcgt tgctggcgtt tttccatagg ctccgccccc ctgacgagca 1320
tcacaaaaat cgacgctcaa gtcagaggtg gcgaaacccg acaggactat aaagatacca 1380
ggcgtttccc cctggaagct ccctcgtgcg ctctcctgtt ccgaccctgc cgcttaccgg 1440
atacctgtcc gcctttctcc cttcgggaag cgtggcgctt tctcatagct cacgctgtag 1500
gtatctcagt tcggtgtagg tcgttcgctc caagctgggc tgtgtgcacg aaccccccgt 1560
tcagcccgac cgctgcgcct tatccggtaa ctatcgtctt gagtccaacc cggtaagaca 1620
cgacttatcg ccactggcag cagccactgg taacaggatt agcagagcga ggtatgtagg 1680
cggtgctaca gagttcttga agtggtggcc taactacggc tacactagaa gaacagtatt 1740
tggtatctgc gctctgctga agccagttac cttcggaaaa agagttggta gctcttgatc 1800
cggcaaacaa accaccgctg gtagcggtgg tttttttgtt tgcaagcagc agattacgcg 1860
cagaaaaaaa ggatctcaag aagatccttt gatcttttct acggggtctg acgctcagtg 1920
gaacgaaaac tcacgttaag ggattttggt catgagatta tcaaaaagga tcttcaccta 1980
gatcctttta aattaaaaat gaagttttaa atcaatctaa agtatatatg agtaaacttg 2040
gtctgacagt taccaatgct taatcagtga ggcacctatc tcagcgatct gtctatttcg 2100
ttcatccata gttgcctgac tccccgtcgt gtagataact acgatacggg agggcttacc 2160
atctggcccc agtgctgcaa tgataccgcg agatccacgc tcaccggctc cagatttatc 2220
agcaataaac cagccagccg gaagggccga gcgcagaagt ggtcctgcaa ctttatccgc 2280

<210> SEQ ID NO 387
<211> LENGTH: 6386
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 387

```
tgagcgcaac gcaattaatg tgagttagct cactcattag gcaccccagg ctttacactt     60
tatgcttccg gctcgtatgt tgtgtggaat tgtgagcgga taacaatttc acacaggaaa    120
cagctatgac catgaggcgc gccggattcg acattgatta ttgactagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caatagggac tttccattga cgtcaatggg tggagtattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat gggggcgggg gggggggggg ggcgcgcgcc    660
rggsggggsg gggsggggsg rggggsgggg sggggsgagg cggagaggtg cggcggcagc    720
caatcagagc ggcgcgctcc gaaagtttcc ttttatggcg aggcggcggc ggcggcggcc    780
ctataaaaag cgaagcgcgc ggcgggcggg agtcgctgcg cgctgccttc gccccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgtttct tttctgtggc tgcgtgaaag ccttgagggg ctccgggagg gccctttgtg   1020
cggggggagc ggctcggggg gtgcgtgcgt gtgtgtgtgc gtggggagcg ccgcgtgcgg   1080
ctccgcgctg cccggcggct gtgagcgctg cgggcgcggc gcggggcttt gtgcgctccg   1140
cagtgtgcgc gaggggagcg cggccggggg cggtgccccg cggtgcgggg ggggctgcga   1200
ggggaacaaa ggctgcgtgc ggggtgtgtg cgtgggggggg tgagcagggg gtgtgggcgc   1260
gtcggtcggg ctgcaacccc ccctgcaccc ccctccccga gttgctgagc acggcccggc   1320
ttcgggtgcg gggctccgta cggggcgtgg cgcggggctc gccgtgccgg gcgggggggtg   1380
gcggcaggtg ggggtgccgg gcggggcggg gccgcctcgg gccggggagg gctcggggga   1440
ggggcgcggc ggcccccgga gcgccggcgg ctgtcgaggc gcggcgagcc gcagccattg   1500
ccttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcggggaggg ccttcgtgcg tcgccgcgcc gccgtcccct   1680
tctccctctc cagcctcggg gctgtccgcg gggggacggc tgccttcggg ggggacgggg   1740
cagggcgggg ttcggcttct ggcgtgtgac cggcggctct agagcctctg ctaaccatgt   1800
tcatgccttc ttcttttttcc tacagatcct taattaataa tacgactcac tatagggggt   1860
cgacccgcca ccatgccaaa aaagaaaaga aaagtgtatc cctatgatgt ccccgattat   1920
gccggttcaa gagccctggt cgtgattaga ctgagccgag tgacagacgc caccacaagt   1980
cccgagagac agctggaatc atgccagcag ctctgtgctc agcggggttg ggatgtggtc   2040
ggcgtggcag aggatctgga cgtgagcggg gccgtcgatc cattcgacag aaagaggagg   2100
cccaacctgg caagatggct cgctttcgag gaacagccct ttgatgtgat cgtcgcctac   2160
agagtggacc ggctgacccg ctcaattcga catctccagc agctggtgca ttgggctgag   2220
gaccacaaga aactggtggt cagcgcaaca gaagcccact tcgatactac cacacctttt   2280
gccgctgtgg tcatcgcact gatgggcact gtggcccaga tggagctcga agctatcaag   2340
```

-continued

```
gagcgaaaca ggagcgcagc ccatttcaat attagggccg gtaaatacag aggctccctg   2400
ccccccttggg gatatctccc taccagggtg gatggggagt ggagactggt gccagacccc   2460
gtccagagag agcggattct ggaagtgtac cacagagtgg tcgataacca cgaaccactc   2520
catctggtgg cacacgacct gaatagacgc ggcgtgctct ctccaaagga ttattttgct   2580
cagctgcagg gaagagagcc acagggaaga gaatggagtg ctactgcact gaagagatct   2640
atgatcagtg aggctatgct gggttacgca acactcaatg gcaaaactgt ccgggacgat   2700
gacggagccc ctctggtgag ggctgagcct attctcacca gagagcagct cgaagctctg   2760
cgggcagaac tggtcaagac tagtcgcgcc aaacctgccg tgagcacccc aagcctgctc   2820
ctgagggtgc tgttctgcgc cgtctgtgga gagccagcat acaagtttgc cggcggaggg   2880
cgcaaacatc cccgctatcg atgcaggagc atggggttcc ctaagcactg tggaaacggg   2940
acagtggcca tggctgagtg ggacgccttt tgcgaggaac aggtgctgga tctcctgggt   3000
gacgctgagc ggctggaaaa agtgtgggtg gcaggatctg actccgctgt ggagctggca   3060
gaagtcaatg ccgagctcgt ggatctgact tccctcatcg gatctcctgc atatagagct   3120
gggtccccac agagagaagc tctggacgca cgaattgctg cactcgctgc tagacaggag   3180
gaactggagg gcctggaggc caggccctct ggatgggagt ggcgagaaac cggacagagg   3240
tttggggatt ggtggaggga gcaggacacc gcagccaaga acacatggct gagatccatg   3300
aatgtccggc tcacattcga cgtgcgcggt ggcctgactc gaaccatcga ttttggcgac   3360
ctgcaggagt atgaacagca cctgagactg gggtccgtgg tcgaaagact gcacactggg   3420
atgtcctagg tcagagctcg ctgatcagcc tcgactgtgc cttctagttg ccagccatct   3480
gttgtttgcc cctcccccgt gccttccttg accctggaag gtgccactcc cactgtcctt   3540
tcctaataaa atgaggaaat tgcatcgcat tgtctgagta ggtgtcattc tattctgggg   3600
ggtggggtgg ggcaggacag caagggggag gattgggaag acaatagcag gcatgctggg   3660
gatgcggtgg gctctatggc ttctgaggcg gaaagaacca gctggggctc gagatccact   3720
agttctagcc tcgaggctag agcggccgcc actggccgtc gttttacaac gtcgtgactg   3780
ggaaaaccct ggcgttaccc aacttaatcg ccttgcagca catcccccctt tcgccagctg   3840
gcgtaatagc gaagaggccc gcaccgatcg cccttcccaa cagttgcgca gcctgaatgg   3900
cgaatgggac gcgccctgta gcggcgcatt aagcgcggcg ggtgtggtgg ttacgcgcag   3960
cgtgaccgct acacttgcca gcgccctagc gcccgctcct ttcgctttct tcccttcctt   4020
tctcgccacg ttcgccggct ttccccgtca agctctaaat cgggggctcc ctttagggtt   4080
ccgatttagt gctttacggc acctcgaccc caaaaaactt gattagggtg atggttcacg   4140
tagtgggcca tcgccctgat agacggtttt tcgccctttg acgttggagt ccacgttctt   4200
taatagtgga ctcttgttcc aaactggaac aacactcaac cctatctcgg tctattcttt   4260
tgatttataa gggattttgc cgatttcggc ctattggtta aaaaatgagc tgatttaaca   4320
aaaatttaac gcgaatttta acaaaatatt aacgcttacr mktymsrtks smcwttymgg   4380
sgaaatgtgc gcggaacccc tatttgttta tttttctaaa tacattcaaa tatgtatccg   4440
ctcatgagac aataaccctg ataaatgctt caataatatt gaaaaaggaa gagtatgagt   4500
attcaacatt tccgtgtcgc ccttattccc ttttttgcgg cattttgcct tcctgttttt   4560
gctcacccag aaacgctggt gaaagtaaaa gatgctgaag atcagttggg tgcacgagtg   4620
ggttacatcg aactggatct caacagcggt aagatccttg agagttttcg ccccgaagaa   4680
```

cgttttccaa tgatgagcac ttttaaagtt ctgctatgtg gcgcggtatt atcccgtatt 4740
gacgccgggc aagagcaact cggtcgccgc atacactatt ctcagaatga cttggttgag 4800
tactcaccag tcacagaaaa gcatcttacg gatggcatga cagtaagaga attatgcagt 4860
gctgccataa ccatgagtga taacactgcg gccaacttac ttctgacaac gatcggagga 4920
ccgaaggagc taaccgcttt tttgcacaac atgggggatc atgtaactcg ccttgatcgt 4980
tgggaaccgg agctgaatga agccatacca aacgacgagc gtgacaccac gatgcctgta 5040
gcaatggcaa caacgttgcg caaactatta actggcgaac tacttactct agcttcccgg 5100
caacaattaa tagactggat ggaggcggat aaagttgcag gaccacttct gcgctcggcc 5160
cttccggctg gctggtttat tgctgataaa tctggagccg gtgagcgtgg gtctcgcggt 5220
atcattgcag cactggggcc agatggtaag ccctcccgta tcgtagttat ctacacgacg 5280
gggagtcagg caactatgga tgaacgaaat agacagatcg ctgagatagg tgcctcactg 5340
attaagcatt ggtaactgtc agaccaagtt tactcatata tactttagat tgatttaaaa 5400
cttcattttt aatttaaaag gatctaggtg aagatccttt ttgataatct catgaccaaa 5460
atcccttaac gtgagttttc gttccactga gcgtcagacc ccgtagaaaa gatcaaagga 5520
tcttcttgag atcctttttt tctgcgcgta atctgctgct tgcaaacaaa aaaaccaccg 5580
ctaccagcgg tggtttgttt gccggatcaa gagctaccaa ctctttttcc gaaggtaact 5640
ggcttcagca gagcgcagat accaaatact gttcttctag tgtagccgta gttaggccac 5700
cacttcaaga actctgtagc accgcctaca tacctcgctc tgctaatcct gttaccagtg 5760
gctgctgcca gtggcgataa gtcgtgtctt accgggttgg actcaagacg atagttaccg 5820
gataaggcgc agcggtcggg ctgaacgggg ggttcgtgca cacagcccag cttggagcga 5880
acgacctaca ccgaactgag atacctacag cgtgagctat gagaaagcgc cacgcttccc 5940
gaagggagaa aggcggacag gtatccggta agcggcaggg tcggaacagg agagcgcacg 6000
agggagcttc cagggggaaa cgcctggtat ctttatagtc ctgtcgggtt tcgccacctc 6060
tgacttgagc gtcgattttt gtgatgctcg tcaggggggc ggagcctatg gaaaaacgcc 6120
agcaacgcgg cctttttacg gttcctggcc ttttgctggc cttttgctca catgttcttt 6180
cctgcgttat cccctgattc tgtggataac cgtattaccg cctttgagtg agctgatacc 6240
gctcgccgca gccgaacgac cgagcgcagc gagtcagtga gcgaggaagc ggaagagcgc 6300
ccaatacgca aaccgcctct ccccgcgcgt tggccgattc attaatgcag ctggcacgac 6360
aggtttcccg actggaaagc gggcag 6386

<210> SEQ ID NO 388
<211> LENGTH: 6317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 388
gattcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga gtatttacgg taaactgccc acttggcagt 240
acatcaagtg tatcatatgc caagtacgcc ccctattgac gtcaatgacg gtaaatggcc 300

-continued

```
cgcctggcat tatgcccagt acatgacctt atgggacttt cctacttggc agtacatcta    360
cgtattagtc atcgctatta ccatggtcga ggtgagcccc acgttctgct tcactctccc    420
catctccccc ccctccccac ccccaatttt gtatttattt atttttttaat tattttgtgc    480
agcgatgggg gcgggggggg gggggggggcg cgcgccrggs ggggsggggs ggggsgrggg    540
gsggggsggg gsgaggcgga gaggtgcggc ggcagccaat cagagcggcg cgctccgaaa    600
gtttcctttt atggcgaggc ggcggcggcg gcggccctat aaaaagcgaa gcgcgcggcg    660
ggcgggagtc gctgcgcgct gccttcgccc cgtgccccgc tccgccgccg cctcgcgccg    720
cccgccccgg ctctgactga ccgcgttact cccacaggtg agcgggcggg acggcccttc    780
tcctccgggc tgtaattagc gcttggttta atgacggctt gtttcttttc tgtggctgcg    840
tgaaagcctt gaggggctcc gggagggccc tttgtgcggg gggagcggct cggggggtgc    900
gtgcgtgtgt gtgtgcgtgg ggagcgccgc gtgcggctcc gcgctgcccg gcggctgtga    960
gcgctgcggg cgcggcgcgg ggctttgtgc gctccgcagt gtgcgcgagg ggagcgcggc   1020
cgggggcggt gccccgcggt gcgggggggg ctgcgagggg aacaaaggct gcgtgcgggg   1080
tgtgtgcgtg ggggggtgag cagggggtgt gggcgcgtcg gtcgggctgc aaccccccct   1140
gcacccccct ccccgagttg ctgagcacgg cccggcttcg ggtgcggggc tccgtacggg   1200
gcgtggcgcg gggctcgccg tgccgggcgg ggggtggcgg caggtggggg tgccgggcgg   1260
ggcggggccg cctcgggccg ggggagggctc gggggagggg cgcggcggcc cccggagcgc   1320
cggcggctgt cgaggcgcgg cgagccgcag ccattgcctt ttatggtaat cgtgcgagag   1380
ggcgcaggga cttcctttgt cccaaatctg tgcggagccg aaatctggga ggcgccgccg   1440
caccccctct agcgggcgcg ggcgaagcg gtgcggcgcc ggcaggaagg aaatgggcgg   1500
ggagggcctt cgtgcgtcgc cgcgccgccg tccccttctc cctctccagc ctcggggctg   1560
tccgcggggg gacggctgcc ttcggggggg acggggcagg gcggggttcg gcttctggcg   1620
tgtgaccggc ggctctagag cctctgctaa ccatgttcat gccttcttct ttttcctaca   1680
gatccttaat taataatacg actcactata gggggtcgac ccgccaccat gacagcgcca   1740
aagaaaaaga ggaaggtcat gaccaagaaa gtggccatct atactagagt gagcacaacg   1800
aatcaggccg aggaggggtt ctctattgac gagcaaatcg atcgtctgac caagtacgcg   1860
gaagcaatgg gctggcaagt cagcgacact tacaccgatg ctgggttctc cggcgccaaa   1920
ctggaaaggc ctgccatgca gcggctgatt aacgacattg agaacaaggc ctttgataca   1980
gtgctcgtat acaagctcga caggctcagc cgatctgtgc gggacacgct ttacctcgta   2040
aaggatgttt tcactaagaa taaaatcgac ttcattagcc tgaacgaatc cattgacacc   2100
agctcagcta tgggctctct gttcctgacc atcctgagcg ctatcaatga gtttgagagg   2160
gagaatataa aggagcgcat gacaatggga aagctgggta gagcgaagtc cgggaaatct   2220
atgatgtgga ccaagaccgc ttttggatac taccacaata ggaagacggg cattctggag   2280
atcgtgccct tgcaggcaac catcgttgag cagatcttca ccgactacct gagcggaata   2340
tctctcacga agttgcgaga taagctgaat gagagcggac acattggcaa ggatattcct   2400
tggtcatata gaaccctccg ccaaactctg gataatccgg tgtactgcgg ttacatcaag   2460
ttcaaagaca gcctcttcga gggaatgcat aaacctatca ttccatacga gacatacctg   2520
aaagtccaaa aggaactcga agagcgccag caacagactt acgaacggaa taataatccc   2580
aggcctttcc aggccaaata tatgctgtcc ggcatggcaa gatgcggata ctgcggggca   2640
ccactcaaga ttgtgcttgg ccataaacgg aaggatggaa gcagaaccat gaaatatcac   2700
```

tgcgcaaacc gctttccaag gaaaacgaag ggattaccg tgtacaatga caacaaaaaa 2760
tgtgatagcg gaacctacga tctgtccaac ttggaaaaca ccgtcattga caatttaatt 2820
ggatttcagg aaaataatga cagccttctg aagattatca acgggaacaa tcagccgatt 2880
ctggacactt catctttcaa aaaacagatc tctcagattg ataagaaaat tcagaaaaat 2940
tccgatttat acctcaatga tttcataacg atggatgagc tgaaggaccg gaccgacagt 3000
ttgcaggccg agaagaaact gctgaaagca aagatctccg agaacaagtt caatgacagt 3060
accgatgtct tcgagttggt gaagacccag ctgggtagta tcccaatcaa cgagttgagc 3120
tatgacaata agaagaagat tgttaataac ctggtgagca aagtggacgt gaccgctgat 3180
aacgtggata ttatcttcaa gttccagctg gcctgagtca gagctcgctg atcagcctcg 3240
actgtgcctt ctagttgcca gccatctgtt gtttgcccct cccccgtgcc ttccttgacc 3300
ctggaaggtg ccactcccac tgtcctttcc taataaaatg aggaaattgc atcgcattgt 3360
ctgagtaggt gtcattctat tctggggggt ggggtggggc aggacagcaa gggggaggat 3420
tgggaagaca atagcaggca tgctggggat gcggtgggct ctatggcttc tgaggcggaa 3480
agaaccagct ggggctcgag atccactagt tctagcctcg aggctagagc ggccgccact 3540
ggccgtcgtt ttacaacgtc gtgactggga aaaccctggc gttacccaac ttaatcgcct 3600
tgcagcacat ccccctttcg ccagctggcg taatagcgaa gaggcccgca ccgatcgccc 3660
ttcccaacag ttgcgcagcc tgaatggcga atgggacgcg ccctgtagcg gcgcattaag 3720
cgcggcgggt gtggtggtta cgcgcagcgt gaccgctaca cttgccagcg ccctagcgcc 3780
cgctcctttc gctttcttcc cttcctttct cgccacgttc gccggctttc cccgtcaagc 3840
tctaaatcgg gggctccctt tagggttccg atttagtgct ttacggcacc tcgaccccaa 3900
aaaacttgat tagggtgatg gttcacgtag tgggccatcg ccctgataga cggtttttcg 3960
ccctttgacg ttggagtcca cgttctttaa tagtggactc ttgttccaaa ctggaacaac 4020
actcaaccct atctcggtct attcttttga tttataaggg attttgccga tttcggccta 4080
ttggttaaaa aatgagctga tttaacaaaa atttaacgcg aattttaaca aaatattaac 4140
gcttacrmkt ymsrtkssmc wttymggsga aatgtgcgcg gaacccctat ttgtttattt 4200
ttctaaatac attcaaatat gtatccgctc atgagacaat aaccctgata aatgcttcaa 4260
taatattgaa aaaggaagag tatgagtatt caacatttcc gtgtcgccct tattcccttt 4320
tttgcggcat tttgccttcc tgtttttgct cacccagaaa cgctggtgaa agtaaaagat 4380
gctgaagatc agttgggtgc acgagtgggt tacatcgaac tggatctcaa cagcggtaag 4440
atccttgaga gttttcgccc cgaagaacgt tttccaatga tgagcacttt taaagttctg 4500
ctatgtggcg cggtattatc ccgtattgac gccgggcaag agcaactcgg tcgccgcata 4560
cactattctc agaatgactt ggttgagtac tcaccagtca cagaaaagca tcttacggat 4620
ggcatgacag taagagaatt atgcagtgct gccataacca tgagtgataa cactgcggcc 4680
aacttacttc tgacaacgat cggaggaccg aaggagctaa ccgctttttt gcacaacatg 4740
ggggatcatg taactcgcct tgatcgttgg gaaccggagc tgaatgaagc cataccaaac 4800
gacgagcgtg acaccacgat gcctgtagca atggcaacaa cgttgcgcaa actattaact 4860
ggcgaactac ttactctagc ttcccggcaa caattaatag actggatgga ggcggataaa 4920
gttgcaggac cacttctgcg ctcggccctt ccggctggct ggtttattgc tgataaatct 4980
ggagccggtg agcgtgggtc tcgcggtatc attgcagcac tggggccaga tggtaagccc 5040
tcccgtatcg tagttatcta cacgacgggg agtcaggcaa ctatggatga acgaaataga 5100
cagatcgctg agataggtgc ctcactgatt aagcattggt aactgtcaga ccaagtttac 5160
tcatatatac tttagattga tttaaaactt catttttaat ttaaaaggat ctaggtgaag 5220
atcctttttg ataatctcat gaccaaaatc ccttaacgtg agttttcgtt ccactgagcg 5280
tcagaccccg tagaaaagat caaaggatct tcttgagatc ctttttttct gcgcgtaatc 5340
tgctgcttgc aaacaaaaaa accaccgcta ccagcggtgg tttgtttgcc ggatcaagag 5400
ctaccaactc tttttccgaa ggtaactggc ttcagcagag cgcagatacc aaatactgtt 5460
cttctagtgt agccgtagtt aggccaccac ttcaagaact ctgtagcacc gcctacatac 5520
ctcgctctgc taatcctgtt accagtggct gctgccagtg gcgataagtc gtgtcttacc 5580
gggttggact caagacgata gttaccggat aaggcgcagc ggtcgggctg aacggggggt 5640
tcgtgcacac agcccagctt ggagcgaacg acctacaccg aactgagata cctacagcgt 5700
gagctatgag aaagcgccac gcttcccgaa gggagaaagg cggacaggta tccggtaagc 5760
ggcagggtcg gaacaggaga gcgcacgagg gagcttccag ggggaaacgc ctggtatctt 5820
tatagtcctg tcgggtttcg ccacctctga cttgagcgtc gatttttgtg atgctcgtca 5880
ggggggcgga gcctatggaa aaacgccagc aacgcggcct ttttacggtt cctggccttt 5940
tgctggcctt ttgctcacat gttctttcct gcgttatccc ctgattctgt ggataaccgt 6000
attaccgcct ttgagtgagc tgataccgct cgccgcagcc gaacgaccga gcgcagcgag 6060
tcagtgagcg aggaagcgga agagcgccca atacgcaaac cgcctctccc cgcgcgttgg 6120
ccgattcatt aatgcagctg gcacgacagg tttcccgact ggaaagcggg cagtgagcgc 6180
aacgcaatta atgtgagtta gctcactcat taggcacccc aggctttaca ctttatgctt 6240
ccggctcgta tgttgtgtgg aattgtgagc ggataacaat ttcacacagg aaacagctat 6300
gaccatgagg cgcgccg 6317

<210> SEQ ID NO 389
<211> LENGTH: 6638
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 389
gattcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga gtatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatggtcga ggtgagcccc acgttctgct tcactctccc 420
catctccccc ccctccccac ccccaatttt gtatttattt atttttaat tattttgtgc 480 agcgatgggg gcgggggggg gggggggcg cgcgccrggs ggggsgggs ggggsgrggg 540 gsggggsggg gsgaggcgga gaggtgcggc ggcagccaat cagagcggcg cgctccgaaa 600
gtttcctttt atggcgaggc ggcggcggcg gcggccctat aaaaagcgaa gcgcgcggcg 660
ggcgggagtc gctgcgcgct gccttcgccc cgtgccccgc tccgccgccg cctcgcgccg 720
cccgccccgg ctctgactga ccgcgttact cccacaggtg agcgggcggg acggcccttc 780
tcctccgggc tgtaattagc gcttggttta atgacggctt gtttcttttc tgtggctgcg 840
tgaaagcctt gaggggctcc gggagggccc tttgtgcggg gggagcggct cggggggtgc 900
gtgcgtgtgt gtgtgcgtgg ggagcgccgc gtgcggctcc gcgctgcccg gcggctgtga 960
gcgctgcggg cgcggcgcgg ggctttgtgc gctccgcagt gtgcgcgagg ggagcgcggc 1020
cgggggcggt gccccgcggt gcgggggggg ctgcgagggg aacaaaggct gcgtgcgggg 1080
tgtgtgcgtg ggggggtgag cagggggtgt gggcgcgtcg gtcgggctgc aacccccccct 1140 gcacccccct ccccgagttg ctgagcacgg cccggcttcg ggtgcggggc tccgtacggg 1200
gcgtggcgcg gggctcgccg tgccgggcgg ggggtggcgg caggtggggg tgccgggcgg 1260
ggcggggccg cctcgggccg gggagggctc gggggagggg cgcggcggcc cccggagcgc 1320
cggcggctgt cgaggcgcgg cgagccgcag ccattgcctt ttatggtaat cgtgcgagag 1380
ggcgcaggga cttcctttgt cccaaatctg tgcggagccg aaatctggga ggcgccgccg 1440 cacccccctct agcgggcgcg ggcgaagcg gtgcggcgcc ggcaggaagg aaatgggcgg 1500
ggagggcctt cgtgcgtcgc cgcgccgccg tccccttctc cctctccagc ctcggggctg 1560
tccgcggggg gacggctgcc ttcggggggg acggggcagg gcggggttcg gcttctggcg 1620
tgtgaccggc ggctctagag cctctgctaa ccatgttcat gccttcttct ttttcctaca 1680
gatccttaat taataatacg actcactata gggggtcgac ccgccaccat gcccaagaag 1740
aaacggaaag tgatgagccc ctttatcgcc ccggacgtgc ccgagcacct cctggacact 1800
gtgcgcgtct ttctgtacgc ccgtcagagt aaaggacggt cagatggatc tgacgtgtcc 1860
accgaagcac agctcgctgc cggacgggcc cttgttgcct caagaaacgc acaaggggga 1920
gctagatggg tggtggcggg cgaattcgtg gatgtgggca gatcagggtg ggacccgaat 1980
gtgacacgcg ccgacttcga aagaatgatg ggcgaggtgc gcgccggtga gggagacgta 2040
gtggtggtta atgaactgag tcgccttacg aggaagggcg cccacgacgc tctggagatc 2100
gataacgaac tcaaaaaaca cggtgtgcgg ttcatgagcg tgctggaacc attcctggat 2160
accagcaccc caatcggtgt cgcgatcttt gccctgattg ccgcgctcgc taaacaggat 2220
tcagacctta aagctgagcg gctgaagggg gctaaagatg agatcgctgc cttgggggt 2280 gtgcacagct catctgcgcc attcggcatg agggcggtca gaaagaaagt ggataacctg 2340
gtcatatctg ttctggagcc tgatgaggac aacccggacc acgttgagct tgtggaacgg 2400
atggctaaga tgtctttcga aggcgtcagc gataacgcaa ttgccacaac atttgagaag 2460
gagaaaatcc cctctccggg gatggctgag agacgagcca cggagaagag gcttgcttct 2520
attaaggcac ggaggctcaa tggcgccgaa aagccgatca tgtggcgggc gcagacagtt 2580
agatggattc ttaaccatcc cgcgattggt ggattcgcat tcgagcgggt gaaacacgga 2640
aaagcccaca tcaacgtgat acgaagagat cccggcggca aaccccttac ccctcacact 2700
ggtatcctgt ctggatccaa gtggttggaa ctccaggaga agagaagcgg gaaaaatctc 2760
tccgaccgca aaccaggtgc cgaagtggaa cctacgctgc tttccgggtg gagatttctg 2820
ggatgtcgga tatgcggtgg gtcaatgggc cagtcccaag gggggccgtaa gaggaatggg 2880 gacttggctg agggcaatta catgtgtgca aacccaaagg ggcacggcgg tctgagcgtc 2940
aagaggtctg agcttgatga attcgtggca tcaaaagtct gggccaggtt gcgcacggct 3000
gacatggagg atgaacatga ccaagcatgg attgcagctg cagctgaacg gtttgctttg 3060
cagcacgacc tggcgggggt agctgacgag cgacgggagc aacaagctca cctggataac 3120
gttcggagat caataaaaga tctccaggcg gataggaagg caggtctcta cgtgggacgc 3180
gaagaactgg agacctggcg cagtaccgtc ctgcaatata ggagctacga ggctgagtgt 3240
actactaggt tggctgagct ggatgaaaaa atgaatggat ccacccgggt gccttcagaa 3300
tggtttagcg gcgaggaccc aaccgcggaa ggaggcatat gggcgagctg ggatgtctat 3360
gagcgccggg agtttctcag cttttttttg gactccgtaa tggttgacag ggcagacat 3420
cctgaaacca agaaatatat accattgaaa gaccgggtga ccttaaagtg ggcggagctg 3480
ttaaaggaag aggatgaagc aagcgaggcc acagaacggg agctggcagc tctttaggtc 3540
agagctcgct gatcagcctc gactgtgcct tctagttgcc agccatctgt tgtttgcccc 3600
tcccccgtgc cttccttgac cctggaaggt gccactccca ctgtcctttc ctaataaaat 3660
gaggaaattg catcgcattg tctgagtagg tgtcattcta ttctgggggg tggggtgggg 3720
caggacagca agggggagga ttgggaagac aatagcaggc atgctgggga tgcggtgggc 3780
tctatggctt ctgaggcgga aagaaccagc tggggctcga gatccactag ttctagcctc 3840
gaggctagag cggccgccac tggccgtcgt tttacaacgt cgtgactggg aaaaccctgg 3900
cgttacccaa cttaatcgcc ttgcagcaca tccccctttc gccagctggc gtaatagcga 3960
agaggcccgc accgatcgcc cttcccaaca gttgcgcagc ctgaatggcg aatgggacgc 4020
gccctgtagc ggcgcattaa gcgcggcggg tgtggtggtt acgcgcagcg tgaccgctac 4080
acttgccagc gccctagcgc ccgctccttt cgctttcttc ccttcctttc tcgccacgtt 4140
cgccggcttt ccccgtcaag ctctaaatcg ggggctccct ttagggttcc gatttagtgc 4200
tttacggcac ctcgacccca aaaaacttga ttagggtgat ggttcacgta gtgggccatc 4260
gccctgatag acggtttttc gccctttgac gttggagtcc acgttcttta atagtggact 4320
cttgttccaa actggaacaa cactcaaccc tatctcggtc tattcttttg atttataagg 4380
gattttgccg atttcggcct attggttaaa aaatgagctg atttaacaaa aatttaacgc 4440
gaattttaac aaaatattaa cgcttacrmk tymsrtkssm cwttymggsg aaatgtgcgc 4500
ggaaccccta tttgtttatt tttctaaata cattcaaata tgtatccgct catgagacaa 4560
taaccctgat aaatgcttca ataatattga aaaaggaaga gtatgagtat tcaacatttc 4620
cgtgtcgccc ttattccctt ttttgcggca ttttgccttc ctgtttttgc tcacccagaa 4680
acgctggtga aagtaaaaga tgctgaagat cagttgggtg cacgagtggg ttacatcgaa 4740
ctggatctca acagcggtaa gatccttgag agttttcgcc ccgaagaacg ttttccaatg 4800
atgagcactt ttaaagttct gctatgtggc gcggtattat cccgtattga cgccgggcaa 4860
gagcaactcg gtcgccgcat acactattct cagaatgact tggttgagta ctcaccagtc 4920
acagaaaagc atcttacgga tggcatgaca gtaagagaat tatgcagtgc tgccataacc 4980
atgagtgata acactgcggc caacttactt ctgacaacga tcggaggacc gaaggagcta 5040
accgcttttt tgcacaacat gggggatcat gtaactcgcc ttgatcgttg ggaaccggag 5100
ctgaatgaag ccataccaaa cgacgagcgt gacaccacga tgcctgtagc aatggcaaca 5160
acgttgcgca aactattaac tggcgaacta cttactctag cttcccggca acaattaata 5220
gactggatgg aggcggataa agttgcagga ccacttctgc gctcggccct tccggctggc 5280
tggtttattg ctgataaatc tggagccggt gagcgtgggt ctcgcggtat cattgcagca 5340
ctggggccag atggtaagcc ctcccgtatc gtagttatct acacgacggg gagtcaggca 5400
actatggatg aacgaaatag acagatcgct gagataggtg cctcactgat taagcattgg 5460

-continued taactgtcag accaagttta ctcatatata ctttagattg atttaaaact tcatttttaa 5520
tttaaaagga tctaggtgaa gatccttttt gataatctca tgaccaaaat cccttaacgt 5580
gagttttcgt tccactgagc gtcagacccc gtagaaaaga tcaaaggatc ttcttgagat 5640
cctttttttc tgcgcgtaat ctgctgcttg caaacaaaaa aaccaccgct accagcggtg 5700
gtttgtttgc cggatcaaga gctaccaact ctttttccga aggtaactgg cttcagcaga 5760
gcgcagatac caaatactgt tcttctagtg tagccgtagt taggccacca cttcaagaac 5820
tctgtagcac cgcctacata cctcgctctg ctaatcctgt taccagtggc tgctgccagt 5880
ggcgataagt cgtgtcttac cgggttggac tcaagacgat agttaccgga taaggcgcag 5940
cggtcgggct gaacgggggg ttcgtgcaca cagcccagct tggagcgaac gacctacacc 6000
gaactgagat acctacagcg tgagctatga gaaagcgcca cgcttcccga agggagaaag 6060
gcggacaggt atccggtaag cggcagggtc ggaacaggag agcgcacgag ggagcttcca 6120
gggggaaacg cctggtatct ttatagtcct gtcgggtttc gccacctctg acttgagcgt 6180
cgatttttgt gatgctcgtc aggggggcgg agcctatgga aaaacgccag caacgcggcc 6240
tttttacggt tcctggcctt ttgctggcct tttgctcaca tgttctttcc tgcgttatcc 6300
cctgattctg tggataaccg tattaccgcc tttgagtgag ctgataccgc tcgccgcagc 6360
cgaacgaccg agcgcagcga gtcagtgagc gaggaagcgg aagagcgccc aatacgcaaa 6420
ccgcctctcc ccgcgcgttg gccgattcat taatgcagct ggcacgacag gtttcccgac 6480
tggaaagcgg gcagtgagcg caacgcaatt aatgtgagtt agctcactca ttaggcaccc 6540
caggctttac actttatgct tccggctcgt atgttgtgtg gaattgtgag cggataacaa 6600
tttcacacag gaaacagcta tgaccatgag gcgcgccg 6638

<210> SEQ ID NO 390
<211> LENGTH: 9530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 390
taatcagcat catgatgtgg taccacatca tgatgctgat tataagaatg cggccgccac 60
actctagtgg atctcgagtt aataattcag aagaactcgt caagaaggcg atagaaggcg 120
atgcgctgcg aatcgggagc ggcgataccg taaagcacga ggaagcggtc agcccattcg 180
ccgccaagct cttcagcaat atcacgggta gccaacgcta tgtcctgata gcggtccgcc 240
acacccagcc ggccacagtc gatgaatcca gaaaagcggc cattttccac catgatattc 300
ggcaagcagg catcgccatg ggtcacgacg agatcctcgc cgtcgggcat gctcgccttg 360
agcctggcga acagttcggc tggcgcgagc ccctgatgct cttcgtccag atcatcctga 420
tcgacaagac cggcttccat ccgagtacgt gctcgctcga tgcgatgttt cgcttggtgg 480
tcgaatgggc aggtagccgg atcaagcgta tgcagccgcc gcattgcatc agccatgatg 540
gatactttct cggcaggagc aaggtgtaga tgacatggag atcctgcccc ggcacttcgc 600
ccaatagcag ccagtccctt cccgcttcag tgacaacgtc gagcacagct gcgcaaggaa 660
cgcccgtcgt ggccagccac gatagccgcg ctgcctcgtc ttgcagttca ttcagggcac 720
cggacaggtc ggtcttgaca aaaagaaccg ggcgcccctg cgctgacagc cggaacacgg 780
cggcatcaga gcagccgatt gtctgttgtg cccagtcata gccgaatagc ctctccaccc 840

-continued

```
aagcggccgg agaacctgcg tgcaatccat cttgttcaat catgcgaaac gatcctcatc    900
ctgtctcttg atcagagctt gatcccctgc gccatcagat ccttggcggc gagaaagcca    960
tccagtttac tttgcagggc ttcccaacct taccagaggg cgccccagct ggcaattccg   1020
gttcgcttgc tgtccataaa accgcccagt ctagctatcg ccatgtaagc ccactgcaag   1080
ctacctgctt tctctttgcg cttgcgtttt cccttgtcca gatagcccag tagctgacat   1140
tcatccgggg tcagcaccgt ttctgcggac tggctttcta cgtgctcgag gggggccaaa   1200
cggtctccag cttggctgtt ttggcggatg agagaagatt ttcagcctga tacagattaa   1260
atcagaacgc agaagcggtc tgataaaaca gaatttgcct ggcggcagta gcgcggtggt   1320
cccacctgac cccatgccga actcagaagt gaaacgccgt agcgccgatg gtagtgtggg   1380
gtctccccat gcgagagtag ggaactgcca ggcatcaaat aaaacgaaag gctcagtcga   1440
aagactgggc ctttcgtttt atctgttgtt tgtcggtgaa cgctctcctg agtaggacaa   1500
atccgccggg agcggatttg aacgttgcga agcaacggcc cggagggtgg cgggcaggac   1560
gcccgccata aactgccagg catcaaatta agcagaaggc catcctgacg gatggccttt   1620
ttgcgtttct acaaactctt ttgtttattt ttctaaatac attcaaatat gtatccgctc   1680
atgaccaaaa tcccttaacg tgagttttcg ttccactgag cgtcagaccc cgtagaaaag   1740
atcaaaggat cttcttgaga tccttttttt ctgcgcgtaa tctgctgctt gcaaacaaaa   1800
aaaccaccgc taccagcggt ggtttgtttg ccggatcaag agctaccaac tctttttccg   1860
aaggtaactg gcttcagcag agcgcagata ccaaatactg tccttctagt gtagccgtag   1920
ttaggccacc acttcaagaa ctctgtagca ccgcctacat acctcgctct gctaatcctg   1980
ttaccagtgg ctgctgccag tggcgataag tcgtgtctta ccgggttgga ctcaagacga   2040
tagttaccgg ataaggcgca gcggtcgggc tgaacggggg gttcgtgcac acagcccagc   2100
ttggagcgaa cgacctacac cgaactgaga tacctacagc gtgagctatg agaaagcgcc   2160
acgcttcccg aagggagaaa ggcggacagg tatccggtaa gcggcagggt cggaacagga   2220
gagcgcacga gggagcttcc agggggaaac gcctggtatc tttatagtcc tgtcgggttt   2280
cgccacctct gacttgagcg tcgatttttg tgatgctcgt caggggggcg gagcctatgg   2340
aaaaacgcca gcaacgcggc ctttttacgg ttcctggcct tttgctggcc ttttgctcac   2400
atgttctttc ctgcgttatc ccctgattct gtggataacc gtattaccgc ctttgagtga   2460
gctgataccg ctcgccgcag ccgaacgacc gagcgcagcg agtcagtgag cgaggaagcg   2520
gaagagcgcc tgatgcggta ttttctcctt acgcatctgt gcggtatttc acaccgcata   2580
tggtgcactc tcagtacaat ctgctctgat gccgcatagt taagccagta tacactccgc   2640
tatcgctacg tgactgggtc atggctgcgc cccgacaccc gccaacaccc gctgacgcgc   2700
cctgacgggc ttgtctgctc ccggcatccg cttacagaca agctgtgacc gtctccggga   2760
gctgcatgtg tcagaggttt tcaccgtcat caccgaaacg cgcgaggcag cagatcaatt   2820
cgcgcgcgaa ggcgaagcgg catgcataat gtgcctgtca aatggacgaa gcagggattc   2880
tgcaaaccct atgctactcc gtcaagccgt caattgtctg attcgttacc aattatgaca   2940
acttgacggc tacatcattc actttttctt cacaaccggc acggaactcg ctcgggctgg   3000
ccccggtgca tttttaaat acccgcgaga aatagagttg atcgtcaaaa ccaacattgc   3060
gaccgacggt ggcgataggc atccgggtgg tgctcaaaag cagcttcgcc tggctgatac   3120
gttggtcctc gcgccagctt aagacgctaa tccctaactg ctggcggaaa agatgtgaca   3180
gacgcgacgg cgacaagcaa acatgctgtg cgacgctggc gatacattac cctgttatcc   3240
```

```
ctagatgaca ttaccctgtt atcccagatg acattaccct gttatcccta gatgacatta   3300
ccctgttatc cctagatgac atttaccctg ttatccctag atgacattac cctgttatcc   3360
cagatgacat taccctgtta tccctagata cattaccctg ttatcccaga tgacataccc   3420
tgttatccct agatgacatt accctgttat cccagatgac attaccctgt tatccctaga   3480
tacattaccc tgttatccca gatgacatac cctgttatcc ctagatgaca ttaccctgtt   3540
atcccagatg acattaccct gttatcccta gatacattac cctgttatcc cagatgacat   3600
accctgttat ccctagatga cattaccctg ttatcccaga tgacattacc ctgttatccc   3660
tagatacatt accctgttat cccagatgac ataccctgtt atccctagat gacattaccc   3720
tgttatccca gatgacatta ccctgttatc cctagataca ttaccctgtt atcccagatg   3780
acataccctg ttatccctag atgacattac cctgttatcc cagatgacat taccctgtta   3840
tccctagata cattaccctg ttatcccaga tgacataccc tgttatccct agatgacatt   3900
accctgttat cccagataaa ctcaatgatg atgatgatga tggtcgagac tcagcggccg   3960
cggtgccagg gcgtgccctt gggctccccg ggcgcgacta taagctgcga gcaacttcac   4020
ttgggtatgc cggcggtagc gctgagggcc tatttcccat gattccttca tatttgcata   4080
tacgatacaa ggctgttaga gagataattg gaattaattt gactgtaaac acaaagatat   4140
tagtacaaaa tacgtgacgt agaaagtaat aatttcttgg gtagtttgca gttttaaaat   4200
tatgttttaa aatggactat catatgctta ccgtaacttg aaagtatttc gatttcttgg   4260
ctttatatat cttgtggaaa ggacgaaaca ccgggtcttc gagaagacct gttttagagc   4320
tagaaatcgt ggttcgcacc gactcggtgc cacagcaagt taaaataagg ctagtccgtt   4380
atcaacttga aaaagtggca ccgagtcggt gctttttttga attcgctagc taggtcttga   4440
aaggagtggg aattggctcc ggtgcccgtc agtgggcaga gcgcacatcg cccacagtcc   4500
ccgagaagtt ggggggaggg gtcggcaatt gatccggtgc ctagagaagg tggcgcgggg   4560
taaactggga aagtgatgtc gtgtactggc tccgcctttt tcccgagggt gggggagaac   4620
cgtatataag tgcagtagtc gccgtgaacg ttcttttttcg caacgggttt gccgccagaa   4680
cacaggaccg gttctagagc gctgccacca tggacaagaa gtacagcatc ggcctggaca   4740
tcggcaccaa ctctgtgggc tggggccgtga tcaccgacga gtacaaggtg cccagcaaga   4800
aattcaaggt gctgggcaac accgaccggc acagcatcaa gaagaacctg atcggagccc   4860
tgctgttcga cagcggcgaa acagccgagg ccacccggct gaagagaacc gccagaagaa   4920
gatacaccag acggaagaac cggatctgct atctgcaaga gatcttcagc aacgagatgg   4980
ccaaggtgga cgacagcttc ttccacagac tggaagagtc cttcctggtg gaagaggata   5040
agaagcacga gcggcacccc atcttcggca acatcgtgga cgaggtggcc taccacgaga   5100
agtaccccac catctaccac ctgagaaaga aactggtgga cagcaccgac aaggccgacc   5160
tgcggctgat ctatctggcc ctggcccaca tgatcaagtt ccggggccac ttcctgatcg   5220
agggcgacct gaaccccgac aacagcgacg tggacaagct gttcatccag ctggtgcaga   5280
cctacaacca gctgttcgag gaaaacccca tcaacgccag cggcgtggac gccaaggcca   5340
tcctgtctgc cagactgagc aagagcagac ggctggaaaa tctgatcgcc cagctgcccg   5400
gcgagaagaa gaatggcctg ttcggaaacc tgattgccct gagcctgggc ctgaccccca   5460
acttcaagag caacttcgac ctggccgagg atgccaaact gcagctgagc aaggacacct   5520
acgacgacga cctggacaac ctgctggccc agatcggcga ccagtacgcc gacctgtttc   5580
```

tggccgccaa gaacctgtcc gacgccatcc tgctgagcga catcctgaga gtgaacaccg 5640
agatcaccaa ggcccccctg agcgcctcta tgatcaagag atacgacgag caccaccagg 5700
acctgaccct gctgaaagct ctcgtgcggc agcagctgcc tgagaagtac aaagagattt 5760
tcttcgacca gagcaagaac ggctacgccg gctacattga cggcggagcc agccaggaag 5820
agttctacaa gttcatcaag cccatcctgg aaaagatgga cggcaccgag gaactgctcg 5880
tgaagctgaa cagagaggac ctgctgcgga agcagcggac cttcgacaac ggcagcatcc 5940
cccaccagat ccacctggga gagctgcacg ccattctgcg gcggcaggaa gatttttacc 6000
cattcctgaa ggacaaccgg gaaaagatcg agaagatcct gaccttccgc atcccctact 6060
acgtgggccc tctggccagg ggaaacagca gattcgcctg gatgaccaga aagagcgagg 6120
aaaccatcac cccctggaac ttcgaggaag tggtggacaa gggcgcttcc gcccagagct 6180
tcatcgagcg gatgaccaac ttcgataaga acctgcccaa cgagaaggtg ctgcccaagc 6240
acagcctgct gtacgagtac ttcaccgtgt ataacgagct gaccaaagtg aaatacgtga 6300
ccgagggaat gagaaagccc gccttcctga gcggcgagca gaaaaaggcc atcgtggacc 6360
tgctgttcaa gaccaaccgg aaagtgaccg tgaagcagct gaaagaggac tacttcaaga 6420
aaatcgagtg cttcgactcc gtggaaatct ccggcgtgga agatcggttc aacgcctccc 6480
tgggcacata ccacgatctg ctgaaaatta tcaaggacaa ggacttcctg gacaatgagg 6540
aaaacgagga cattctggaa gatatcgtgc tgaccctgac actgtttgag gacagagaga 6600
tgatcgagga acggctgaaa acctatgccc acctgttcga cgacaaagtg atgaagcagc 6660
tgaagcggcg gagatacacc ggctggggca ggctgagccg gaagctgatc aacggcatcc 6720
gggacaagca gtccggcaag acaatcctgg atttcctgaa gtccgacggc ttcgccaaca 6780
gaaacttcat gcagctgatc cacgacgaca gcctgacctt taaagaggac atccagaaag 6840
cccaggtgtc cggccagggc gatagcctgc acgagcacat tgccaatctg gccggcagcc 6900
ccgccattaa gaagggcatc ctgcagacag tgaaggtggt ggacgagctc gtgaaagtga 6960
tgggccggca caagcccgag aacatcgtga tcgaaatggc cagagagaac cagaccaccc 7020
agaagggaca gaagaacagc cgcgagagaa tgaagcggat cgaagagggc atcaaagagc 7080
tgggcagcca gatcctgaaa gaacaccccg tggaaaacac ccagctgcag aacgagaagc 7140
tgtacctgta ctacctgcag aatgggcggg atatgtacgt ggaccaggaa ctggacatca 7200
accggctgtc cgactacgat gtggaccata tcgtgcctca gagctttctg aaggacgact 7260
ccatcgacaa caaggtgctg accagaagcg acaagaaccg gggcaagagc gacaacgtgc 7320
cctccgaaga ggtcgtgaag aagatgaaga actactggcg gcagctgctg aacgccaagc 7380
tgattaccca gagaaagttc gacaatctga ccaaggccga gagaggcggc ctgagcgaac 7440
tggataaggc cggcttcatc aagagacagc tggtggaaac ccggcagatc acaaagcacg 7500
tggcacagat cctggactcc cggatgaaca ctaagtacga cgagaatgac aagctgatcc 7560
gggaagtgaa agtgatcacc ctgaagtcca agctggtgtc cgatttccgg aaggatttcc 7620
agttttacaa agtgcgcgag atcaacaact accaccacgc ccacgacgcc tacctgaacg 7680
ccgtcgtggg aaccgccctg atcaaaaagt accctaagct ggaaagcgag ttcgtgtacg 7740
gcgactacaa ggtgtacgac gtgcggaaga tgatcgccaa gagcgagcag gaaatcggca 7800
aggctaccgc caagtacttc ttctacagca acatcatgaa ctttttcaag accgagatta 7860
ccctggccaa cggcgagatc cggaagcggc ctctgatcga gacaaacggc gaaaccgggg 7920
agatcgtgtg ggataagggc cgggattttg ccaccgtgcg gaaagtgctg agcatgcccc 7980
aagtgaatat cgtgaaaaag accgaggtgc agacaggcgg cttcagcaaa gagtctatcc 8040
tgcccaagag gaacagcgat aagctgatcg ccagaaagaa ggactgggac cctaagaagt 8100
acggcggctt cgacagcccc accgtggcct attctgtgct ggtggtggcc aaagtggaaa 8160
agggcaagtc caagaaactg aagagtgtga aagagctgct ggggatcacc atcatggaaa 8220
gaagcagctt cgagaagaat cccatcgact ttctggaagc caagggctac aaagaagtga 8280
aaaaggacct gatcatcaag ctgcctaagt actccctgtt cgagctggaa aacggccgga 8340
agagaatgct ggcctctgcc ggcgaactgc agaagggaaa cgaactggcc ctgccctcca 8400
aatatgtgaa cttcctgtac ctggccagcc actatgagaa gctgaagggc tcccccgagg 8460
ataatgagca gaaacagctg tttgtggaac agcacaagca ctacctggac gagatcatcg 8520
agcagatcag cgagttctcc aagagagtga tcctggccga cgctaatctg gacaaagtgc 8580
tgtccgccta caacaagcac cgggataagc ccatcagaga gcaggccgag aatatcatcc 8640
acctgtttac cctgaccaat ctgggagccc ctgccgcctt caagtacttt gacaccacca 8700
tcgaccggaa gaggtacacc agcaccaaag aggtgctgga cgccaccctg atccaccaga 8760
gcatcaccgg cctgtacgag acacggatcg acctgtctca gctgggaggc gacaagcgac 8820
ctgccgccac aaagaaggct ggacaggcta agaagaagaa agattacaaa gacgatgacg 8880
ataagtaact agagctcgct gatcagcctc gactgtgcct tctagttgcc agccatctgt 8940
tgtttgcccc tcccccgtgc cttccttgac cctggaaggt gccactccca ctgtcctttc 9000
ctaataaaat gaggaaattg catcgcattg tctgagtagg tgtcattcta ttctgggggg 9060
tggggtgggg caggacagca agggggagga ttgggaagag aatagcaggc atgctgggga 9120
ctgaggcgga aagaaccagc tgtggaatgt gtgtcagtta gggtgtggaa agtccccagg 9180
ctccccagca ggcagaagta tgcaaagcat gcatctcaat tagtcagcaa ccaggtgtgg 9240
aaagtcccca ggctccccag caggcagaag tatgcaaagc atgcatctca attagtcagc 9300
aaccatagtc ccgcccctaa ctccgcccat cccgccccta actccgccca gttccgccca 9360
ttctccgccc catggctgac taattttttt tatttatgca gaggccgagg ccgcctcggc 9420
ctctgagcta ttccagaagt agtgaggagg cttttttgga ggcctaggct tttgcaaaaa 9480
gcttgggccc gccccaactg gggtaacctt tgagttctct cagttggggg 9530

<210> SEQ ID NO 391
<211> LENGTH: 5722
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 391
tgatcccctg cgccatcaga tccttggcgg cgagaaagcc atccagttta ctttgcaggg 60
cttcccaacc ttaccagagg gcgccccagc tggcaattcc ggttcgcttg ctgtccataa 120
aaccgcccag tctagctatc gccatgtaag cccactgcaa gctacctgct ttctctttgc 180
gcttgcgttt tcccttgtcc agatagccca gtagctgaca ttcatccggg gtcagcaccg 240
tttctgcgga ctggctttct acgtgctcga gggggggccaa acggtctcca gcttggctgt 300
tttggcggat gagagaagat tttcagcctg atacagatta aatcagaacg cagaagcggt 360
ctgataaaac agaatttgcc tggcggcagt agcgcggtgg tcccacctga ccccatgccg 420
aactcagaag tgaaacgccg tagcgccgat ggtagtgtgg ggtctcccca tgcgagagta 480

```
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atcctttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
caggggggaaa cgcctggtat ctttatagtc ctgtcgggtt tcgccacctc tgacttgagc   1380
gtcgattttt gtgatgctcg tcaggggggc ggagcctatg gaaaaacgcc agcaacgcgg   1440
cctttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cactttttct tcacaaccgg cacggaactc gctcgggctg gccccggtgc atttttttaaa   2100
tacccgcgag aaatagagtt gatcgtcaaa accaacattg cgaccgacgg tggcgatagg   2160
catccgggtg gtgctcaaaa gcagcttcgc ctggctgata cgttggtcct cgcgccagct   2220
taagacgcta atccctaact gctggcggaa aagatgtgac agacgcgacg gcgacaagca   2280
aacatgctgt gcgacgctgg cgatacatta ccctgttatc cctagatgac attaccctgt   2340
tatcccagat gacattaccc tgttatccct agatgacatt accctgttat ccctagatga   2400
catttaccct gttatcccta gatgacatta ccctgttatc ccagatgaca ttaccctgtt   2460
atccctagat acattaccct gttatcccag atgacatacc ctgttatccc tagatgacat   2520
taccctgtta tcccagatga cattaccctg ttatccctag atacattacc ctgttatccc   2580
agatgacata ccctgttatc cctagatgac attaccctgt tatcccagat gacattaccc   2640
tgttatccct agatacatta ccctgttatc ccagatgaca taccctgtta tccctagatg   2700
acattaccct gttatcccag atgacattac cctgttatcc ctagatacat taccctgtta   2760
tcccagatga cataccctgt tatccctaga tgacattacc ctgttatccc agatgacatt   2820
```

accctgttat ccctagatac attaccctgt tatcccagat gacataccct gttatcccta 2880
gatgacatta ccctgttatc ccagatgaca ttaccctgtt atccctagat acattaccct 2940
gttatcccag atgacatacc ctgttatccc tagatgacat taccctgtta tcccagataa 3000
actcaatgat gatgatgatg atggtcgaga ctcagcggcc gcggtgccag ggcgtgccct 3060
tgggctcccc gggcgcggtc ctttgggcgc taactgcgtg cgcgctggga attggcgcta 3120
attgcgcgtg cgcgctggga ctcaaggcgc taactgcgcg tgcgttctgg ggcccggggt 3180
gccgcggcct gggctggggc gaaggcgggc tcggccggaa ggggtggggt cgccgcggct 3240
cccgggcgct tgcgcgcact tcctgcccga gccgctggcc gcccgagggt gtggccgctg 3300
cgtgcgcgcg cgccgacccg gcgctgtttg aaccgggcgg aggcggggct ggcgcccggt 3360
tgggaggggg ttggggcctg gcttcctgcc gcgcgccgcg gggacgcctc cgaccagtgt 3420
ttgcctttta tggtaataac gcggccggcc cggcttcctt tgtccccaat ctgggcgcgc 3480
gccggcgccc cctggcggcc taaggactcg gcgcgccgga agtggccagg gcgggggcga 3540
cctcggctca cagcgcgccc ggctattctc gcagctcgcc accatgcccg ccatgaagat 3600
cgagtgccgc atcaccggca ccctgaacgg cgtggagttc gagctggtgg gcggcggaga 3660
gggcaccccc gagcagggcc gcatgaccaa caagatgaag agcaccaaag gcgccctgac 3720
cttcagcccc tacctgctga gccacgtgat gggctacggc ttctaccact tcggcaccta 3780
ccccagcggc tacgagaacc ccttcctgca cgccatcaac aacggcggct acaccaacac 3840
ccgcatcgag aagtacgagg acggcggcgt gctgcacgtg agcttcagct accgctacga 3900
ggccggccgc gtgatcggcg acttcaaggt ggtgggcacc ggcttccccg aggacagcgt 3960
gatcttcacc gacaagatca tccgcagcaa cgccaccgtg gagcacctgc accccatggg 4020
cgataacgtg ctggtgggca gcttcgcccg caccttcagc ctgcgcgacg gcggctacta 4080
cagcttcgtg gtggacagcc acatgcactt caagagcgcc atccacccca gcatcctgca 4140
gaacgggggc cccatgttcg ccttccgccg cgtggaggag ctgcacagca acaccgagct 4200
gggcatcgtg gagtaccagc acgccttcaa gacccccatc gccttcgcca gatctcgagc 4260
tcgaaccatg gatgatgata tcgccgcgct cgtcgtcgac aacggctccg gcatgtgcaa 4320
ggccggcttc gcgggcgacg atgccccccg ggccgtcttc ccctccatcg tggggcgccc 4380
caggcaccag gtaggggagc tggctgggtg gggcagcccc gggagcgggc gggaggcaag 4440
ggcgctttct ctgcacagga gcctcccggt ttccggggtg gggctgcgc ccgtgctcag 4500 ggcttcttgt cctttccttc ccagggcgtg atggtgggca tgggtcagaa ggattcctat 4560
gtgggcgacg aggcccagag caagagaggc atcctcaccc tgaagtaccc catcgagcac 4620
ggcatcgtca ccaactggga cgacatggag aaaatctggc accacacctt ctacaatgag 4680
ctgcgtgtgg ctcccgagga gcaccccgtg ctgctgaccg aggcccccct gaaccccaag 4740
gccaaccgcg agaagatgac ccagccccaa ctggggtaac ctttgagttc tctcagttgg 4800
gggtaatcag catcatgatg tggtaccaca tcatgatgct gattataaga atgcggccgc 4860
cacactctag tggatctcga gttaataatt cagaagaact cgtcaagaag gcgatagaag 4920
gcgatgcgct gcgaatcggg agcggcgata ccgtaaagca cgaggaagcg gtcagcccat 4980
tcgccgccaa gctcttcagc aatatcacgg gtagccaacg ctatgtcctg atagcggtcc 5040
gccacaccca gccggccaca gtcgatgaat ccagaaaagc ggccattttc caccatgata 5100
ttcggcaagc aggcatcgcc atgggtcacg acgagatcct cgccgtcggg catgctcgcc 5160
ttgagcctgg cgaacagttc ggctggcgcg agcccctgat gctcttcgtc cagatcatcc 5220
tgatcgacaa gaccggcttc catccgagta cgtgctcgct cgatgcgatg tttcgcttgg 5280
tggtcgaatg ggcaggtagc cggatcaagc gtatgcagcc gccgcattgc atcagccatg 5340
atggatactt tctcggcagg agcaaggtgt agatgacatg gagatcctgc cccggcactt 5400
cgcccaatag cagccagtcc cttcccgctt cagtgacaac gtcgagcaca gctgcgcaag 5460
gaacgcccgt cgtggccagc cacgatagcc gcgctgcctc gtcttgcagt tcattcaggg 5520
caccggacag gtcggtcttg acaaaaagaa ccgggcgccc ctgcgctgac agccggaaca 5580
cggcggcatc agagcagccg attgtctgtt gtgcccagtc atagccgaat agcctctcca 5640
cccaagcggc cggagaacct gcgtgcaatc catcttgttc aatcatgcga aacgatcctc 5700
atcctgtctc ttgatcagag ct 5722

<210> SEQ ID NO 392
<211> LENGTH: 15424
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 392
tcgacggtat cgataagctt gatatcgaat tcctgcagcc cgggggatcc actagttcta 60
gagcggccgc caccgcggtg gagctccagc ttttgttccc tttagtgagg gttaatttcg 120
agcttggcgt aatcatggtc atagctgttt cctgtgtgaa attgttatcc gctcacaatt 180
ccacacaaca tacgagccgg aagcataaag tgtaaagcct ggggtgccta atgagtgagc 240
taactcacat taattgcgtt gcgctcactg cccgctttcc agtcgggaaa cctgtcgtgc 300
cagctgcatt aatgaatcgg ccaacgcgcg gggagaggcg gtttgcgtat tgggcgctct 360
tccgcttcct cgctcactga ctcgctgcgc tcggtcgttc ggctgcggcg agcggtatca 420
gctcactcaa aggcggtaat acggttatcc acagaatcag gggataacgc aggaaagaac 480
atgtgagcaa aaggccagca aaaggccagg aaccgtaaaa aggccgcgtt gctggcgttt 540
ttccataggc tccgcccccc tgacgagcat cacaaaaatc gacgctcaag tcagaggtgg 600
cgaaacccga caggactata aagataccag gcgtttcccc ctggaagctc cctcgtgcgc 660
tctcctgttc cgaccctgcc gcttaccgga tacctgtccg cctttctccc ttcgggaagc 720
gtggcgcttt ctcatagctc acgctgtagg tatctcagtt cggtgtaggt cgttcgctcc 780
aagctgggct gtgtgcacga accccccgtt cagcccgacc gctgcgcctt atccggtaac 840
tatcgtcttg agtccaaccc ggtaagacac gacttatcgc cactggcagc agccactggt 900
aacaggatta gcagagcgag gtatgtaggc ggtgctacag agttcttgaa gtggtggcct 960
aactacggct acactagaag gacagtattt ggtatctgcg ctctgctgaa gccagttacc 1020
ttcggaaaaa gagttggtag ctcttgatcc ggcaaacaaa ccaccgctgg tagcggtggt 1080 tttttgttt gcaagcagca gattacgcgc agaaaaaaag gatctcaaga agatcctttg 1140
atcttttcta cggggtctga cgctcagtgg aacgaaaact cacgttaagg gattttggtc 1200
atgagattat caaaaaggat cttcacctag atccttttaa attaaaaatg aagttttaaa 1260
tcaatctaaa gtatatatga gtaaacttgg tctgacagtt accaatgctt aatcagtgag 1320
gcacctatct cagcgatctg tctatttcgt tcatccatag ttgcctgact ccccgtcgtg 1380
tagataacta cgatacggga gggcttacca tctggcccca gtgctgcaat gataccgcga 1440
gacccacgct caccggctcc agatttatca gcaataaacc agccagccgg aagggccgag 1500
cgcagaagtg gtcctgcaac tttatccgcc tccatccagt ctattaattg ttgccgggaa 1560
gctagagtaa gtagttcgcc agttaatagt ttgcgcaacg ttgttgccat tgctacaggc 1620
atcgtggtgt cacgctcgtc gtttggtatg gcttcattca gctccggttc ccaacgatca 1680
aggcgagtta catgatcccc catgttgtgc aaaaaagcgg ttagctcctt cggtcctccg 1740
atcgttgtca gaagtaagtt ggccgcagtg ttatcactca tggttatggc agcactgcat 1800
aattctctta ctgtcatgcc atccgtaaga tgcttttctg tgactggtga gtactcaacc 1860
aagtcattct gagaatagtg tatgcggcga ccgagttgct cttgcccggc gtcaatacgg 1920
gataataccg cgccacatag cagaacttta aaagtgctca tcattggaaa acgttcttcg 1980
gggcgaaaac tctcaaggat cttaccgctg ttgagatcca gttcgatgta acccactcgt 2040
gcacccaact gatcttcagc atcttttact ttcaccagcg tttctgggtg agcaaaaaca 2100
ggaaggcaaa atgccgcaaa aaagggaata agggcgacac ggaaatgttg aatactcata 2160
ctcttccttt ttcaatatta ttgaagcatt tatcagggtt attgtctcat gagcggatac 2220
atatttgaat gtatttagaa aaataaacaa ataggggttc cgcgcacatt tccccgaaaa 2280
gtgccacctg acgtctaaga aaccattatt atcatgacat taacctataa aaataggcgt 2340
atcacgaggc cctttcgtct tcaagaattc tcatgtttga cagcttatca tcgataagct 2400
ttaatgcggt agtttatcac agttaaattg ctaacgcagt caggcaccgt gtatgaaatc 2460
taacaatgcg ctcatcgtca tcctcggcac cgtcaccctg gatgctgtag gcataggctt 2520
ggttatgccg gtactgccgg gcctcttgcg ggatatcgtc cattccgaca gcatcgccag 2580
tcactatggc gtgctgctag cgctatatgc gttgatgcaa tttctatgcg cacccgttct 2640
cggagcactg tccgaccgct ttggccgccg cccagtcctg ctcgcttcgc tacttggagc 2700
cactatcgac tacgcgatca tggcgaccac acccgtcctg tggatccggc gcacaccaaa 2760
aacgtcactt ttgccacatc cgtcgcttac atgtgttccg ccacacttgc aacatcacac 2820
ttccgccaca ctactacgtc acccgccccg ttcccacgcc ccgcgccacg tcacaaactc 2880
caccccctca ttatcatatt ggcttcaatc caaaataaat catcaataat ataccttatt 2940
ttggattgaa gccaatatga taatgagggg gtggagtttg tgacgtggcg cggggcgtgg 3000
gaacggggcg ggtgacgtag gttttagggc ggagtaactt gtatgtgttg ggaattgtag 3060
ttttcttaaa atgggaagtt acgtaacgtg ggaaaacgga agtgacgatt tgaggaagtt 3120
gtgggttttt tggctttcgt ttctgggcgt aggttcgcgt gcggttttct gggtgttttt 3180
tgtggacttt aaccgttacg tcattttttta gtcctatata tactcgctct gcacttggcc 3240 ctttttttaca ctgtgactga ttgagctggt gccgtgtcga gtggtgtttt tttaataggt 3300 tttcttttt actggtaagg ctgactgtta ggctgccgct gtgaagcgct gtatgttgtt 3360
ctggagcggg agggtgctat tttgcctagg caggagggtt tttcaggtgt ttatgtgttt 3420
ttctctccta ttaattttgt tatacctcct atgggggctg taatgttgtc tctacgcctg 3480
cgggtatgta ttcccccggg ctatttcggt cgctttttag cactgaccga tgaatcaacc 3540
tgatgtgttt accgagtctt acattatgac tccggacatg accgaggagc tgtcggtggt 3600
gctttttaat cacggtgacc agtttttta cggtcacgcc ggcatggccg tagtccgtct 3660
tatgcttata agggttgttt ttcctgttgt aagacaggct tctaatgttt aaatgttttt 3720
ttgttatttt attttgtgtt tatgcagaaa cccgcagaca tgtttgagag aaaaatggtg 3780
tctttttctg tggtggttcc ggagcttacc tgcctttatc tgcatgagca tgactacgat 3840

```
gtgctttctt ttttgcgcga ggctttgcct gattttttga gcagcacctt gcattttata    3900

tcgccgccca tgcaacaaag cttacatcgg ggctacgctg gttagcatag ctccgagtat    3960

gcgtgtcata atcagtgtgg gttcttttgt caaggttcct ggcggggaag tggccgcgct    4020

ggtccgtgca gacctgcacg attatgttca gctggccctg cgaagggacc tacgggatcg    4080

cggtattttt gttaatgttc cgcttttgaa tcttatacag gtctgtgagg aacctgaatt    4140

tttgcaatca tgattcgctg cttgaggctg aaggtggagg gcgctctgga gcagattttt    4200

acaatggccg gacttaatat tcgggatttg cttagagata tattgagaag gtggcgagat    4260

gagaattatt tgggcatggt tgaaggtgct ggaatgttta tagaggagat tcaccctgaa    4320

gggtttagcc tttacgtcca cttggacgtg agggccgttt gccttttgga agccattgtg    4380

caacatctta caaatgccat tatctgttct ttggctgtag agtttgacca cgccaccgga    4440

ggggagcgcg ttcacttaat agatcttcat tttgaggttt tggataatct tttggaataa    4500

aaaaaaaaac atggttcttc cagctcttcc cgctcctccc gtgtgtgact cgcagaacga    4560

atgtgtaggt tggctgggtg tggcttattc tgcggtggtg gatgttatca gggcagcggc    4620

gcatgaagga gtttacatag aacccgaagc caggggcgc ctggatgctt tgagagagtg    4680

gatatactac aactactaca cagagcgatc taagcggcga gaccggagac gcagatctgt    4740

ttgtcacgcc cgcacctggt tttgcttcag gaaatatgac tacgtccggc gttccatttg    4800

gcatgacact acgaccaaca cgatctcggt tgtctcggcg cactccgtac agtagggatc    4860

gtctacctcc ttttgagaca gaaacccgcg ctaccatact ggaggatcat ccgctgctgc    4920

ccgaatgtaa cactttgaca atgcacaacg tgagttacgt gcgaggtctt ccctgcagtg    4980

tgggatttac gctgattcag gaatgggttg ttccctggga tatggttcta acgcgggagg    5040

agcttgtaat cctgaggaag tgtatgcacg tgtgcctgtg ttgtgccaac attgatatca    5100

tgacgagcat gatgatccat ggttacgagt cctgggctct ccactgtcat tgttccagtc    5160

ccggttccct gcagtgtata gccggcgggc aggttttggc cagctggttt aggatggtgg    5220

tggatggcgc catgtttaat cagaggttta tatggtaccg ggaggtggtg aattacaaca    5280

tgccaaaaga ggtaatgttt atgtccagcg tgtttatgag gggtcgccac ttaatctacc    5340

tgcgcttgtg gtatgatggc cacgtgggtt ctgtggtccc cgccatgagc tttggataca    5400

gcgccttgca ctgtgggatt ttgaacaata ttgtggtgct gtgctgcagt tactgtgctg    5460

atttaagtga gatcagggtg cgctgctgtg cccggaggac aaggcgcctt atgctgcggg    5520

cggtgcgaat catcgctgag gagaccactg ccatgttgta ttcctgcagg acggagcggc    5580

ggcggcagca gtttattcgc gcgctgctgc agcaccaccg ccctatcctg atgcacgatt    5640

atgactctac ccccatgtag gcgtggactt ctccttcgcc gcccgttaag caaccgcaag    5700

ttggacagca gcctgtggct cagcagctgg acagcgacat gaacttaagt gagctgcccg    5760

gggagtttat taatatcact gatgagcgtt tggctcgaca ggaaaccgtg tggaatataa    5820

cacctaagaa tatgtctgtt acccatgata tgatgctttt taaggccagc cggggagaaa    5880

ggactgtgta ctctgtgtgt tgggagggag gtggcaggtt gaatactagg gttctgtgag    5940

tttgattaag gtacggtgat ctgtataagc tatgtggtgg tggggctata ctactgaatg    6000

aaaaatgact tgaaattttc tgcaattgaa aaataaacac gttgaaacat aacacaaacg    6060

attctttatt cttgggcaat gtatgaaaaa gtgtaagagg atgtggcaaa tatttcatta    6120

atgtagttgt ggccagacca gtcccatgaa aatgacatag agtatgcact tggagttgtg    6180

tctcctgttt cctgtgtacc gtttagtgta atggttagtg ttacaggttt agttttgtct    6240
```

ccgtttaagt aaacttgact gacaatgtta cttttggcag ttttaccgtg agattttgga 6300
taagctgata ggttaggcat aaatccaaca gcgtttgtat aggctgtgcc ttcagtaaga 6360
tctccatttc taaagttcca atattctggg tccaggaagg aattgtttag tagcactcca 6420
ttttcgtcaa atcttataat aagatgagca ctttgaactg ttccagatat tggagccaaa 6480
ctgcctttaa cagccaaaac tgaaactgta gcaagtattt gactgccaca ttttgttaag 6540
accaaagtga gtttagcatc tttctctgca tttagtctac agttaggaga tggagctggt 6600
gtggtccaca aagttagctt atcattattt ttgtttccta ctgtaatggc acctgtgctg 6660
tcaaaactaa ggccagttcc tagtttagga accatagcct tgtttgaatc aaattctagg 6720
ccatggccaa tttttgtttt gaggggattt gtgtttggtg cattaggtga accaaattca 6780
agcccatctc ctgcattaat ggctatggct gtagcgtcaa acatcaaccc cttggcagtg 6840
cttaggttaa cctcaagctt tttggaattg tttgaagctg taaacaagta aaggcctttg 6900
ttgtagttaa tatccaagtt gtgggctgag tttataaaaa gagggccctg tcctagtctt 6960
agatttagtt ggttttgagc atcaaacgga taactaacat caagtataag gcgtctgttt 7020
tgagaatcaa tccttagtcc tcctgctaca ttaagttgca tattgccttg tgaatcaaaa 7080
cccaaggctc cagtaacttt agtttgcaag gaagtattat taatagtcac acctggacca 7140
gttgctacgg tcaaagtgtt taggtcgtct gttacatgca aaggagcccc gtactttagt 7200
cctagtttc catttttgtgt ataaatgggc tctttcaagt caatgcccaa gctaccagtg 7260
gcagtagtta gagggggtga ggcagtgata gtaagggtac tgctatcggt ggtggtgagg 7320
gggcctgatg tttgcagggc tagctttcct tctgacactg tgaggggtcc ttgggtggca 7380
atgctaagtt tggagtcgtg cacggttagc ggggcctgtg attgcatggt gagtgtgttg 7440
cccgcgacca ttagaggtgc ggcggcagcc acagttaggg cttctgaggt aactgtgagg 7500
ggtgcagata tttccaggtt tatgtttgac ttggtttttt tgagaggtgg gctcacagtg 7560
gttacatttt gggaggtaag gttgccggcc tcgtccagag agaggccgtt gcccattttg 7620
agcgcaagca tgccattgga ggtaactaga ggttcggata ggcgcaaaga gagtacccca 7680
gggggactct cttgaaaccc attgggggat acaaagggag gagtaagaaa aggcacagtt 7740
ggaggaccgg tttccgtgtc atatggatac acggggttga aggtatcttc agacggtctt 7800
gcgcgcttca tctgcaacaa catgaagata gtgggtgcgg atggacagga acaggaggaa 7860
actgacattc catttagatt gtggagaaag tttgcagcca ggaggaagct gcaataccag 7920
agctgggagg agggcaagga ggtgctgctg aataaactgg acagaaattt gctaactgat 7980
tttaagtaag tgatgcttta ttattttttt ttattagtta aagggaataa gatccccggg 8040
tactctagtt aattaactag aggatcttga tgtaatccaa ggttaggaca gttgcaaatc 8100
acagtgagaa cacagggtcc cctgtcccgc tcaactagca gggggcgctg ggtaaactcc 8160
cgaatcaggc tacgggcaag ctctccctgg gcggtaagcc ggacgccgtg cgccgggccc 8220
tcgatatgat cctcgggcaa ttcaaagtag caaaactcac cggagtcgcg ggcaaagcac 8280
ttgtggcggc gacagtggac caggtgtttc aggcgcagtt gctctgcctc tccacttaac 8340
attcagtcgt agccgtccgc cgagtccttt accgcgtcaa agttaggaat aaattgatcc 8400
ggatagtggc cgggaggtcc cgagaagggg ttaaagtaga ccgatggcac aaactcctca 8460
ataaattgca gagttccaat gcctccagag cgcggctcag aggacgaggt ctgcagagtt 8520
aggattgcct gacgaggcgt gaatgaagga cggccggcgc cgccgatctg aaatgtcccg 8580
tccggacgga gaccaagcga ggagctcacc gactcgtcgt tgagctgaat acctcgccct 8640
ctgattgtca ggtgagttat accctgcccg ggcgaccgca ccctgtgacg aaagccgccc 8700
gcaagctgcg cccctgagtt agtcatctga acttcggcct gggcgtctct gggaagtacc 8760
acagtggtgg gagcgggact ttcctggtac accagggcag cgggccaact acggggatta 8820
aggttattac gaggtgtggt ggtaatagcc gcctgttcca agagaattcg gtttcggtgg 8880
gcgcggattc cgttgacccg ggatatcatg tggggtcccg cgctcatgta gtttattcgg 8940
gttgagtagt cttgggcagc tccagccgca agtcccattt gtggctggta actccacatg 9000
tagggcgtgg gaatttcctt gctcataatg gcgctgacga caggtgctgg cgccgggtgt 9060
ggccgctgga gatgacgtag ttttcgcgct taaatttgag aaagggcgcg aaactagtcc 9120
ttaagagtca gcgcgcagta tttactgaag agagcctccg cgtcttccag cgtgcgccga 9180
agctgatctt cgcttttgtg atacaggcag ctgcgggtga gggatcgcag agacctgttt 9240
tttattttca gctcttgttc ttggcccctg ctctgttgaa atatagcata cagagtggga 9300
aaaatcctgt ttctaagctc gcgggtcgat acgggttcgt tgggcgccag acgcagcgct 9360
cctcctcctg ctgctgccgc cgctgtggat ttcttgggct ttgtcagagt cttgctatcc 9420
ggtcgccttt gcttctgtgt ggccgctgct gttgctgccg ctgccgctgc cgccggtgca 9480
gtatgggctg tagagatgac ggtagtaatg caggatgtta cgggggaagg ccacgccgtg 9540
atggtagaga agaaagcggc gggcgaagga gatgttgccc ccacagtctt gcaagcaagc 9600
aactatggcg ttcttgtgcc cgcgccatga gcggtagcct tggcgctgtt gttgctcttg 9660
ggctaacggc ggcggctgct tggacttacc ggccctggtt ccagtggtgt cccatctacg 9720
gttgggtcgg cgaacgggca gtgccggcgg cgcctgagga gcggaggttg tagccatgct 9780
ggaaccggtt gccgatttct ggggcgccgg cgaggggaat gcgaccgagg gtgacggtgt 9840
ttcgtctgac acctcttcga cctcggaagc ttcctcgtct aggctctccc agtcttccat 9900
catgtcctcc tcctcctcgt ccaaaacctc ctctgcctga ctgtcccagt attcctcctc 9960
gtccgtgggt ggcggcggca gctgcagctt ctttttgggt gccatcctgg gaagcaaggg 10020
cccgcggctg ctgctgatag ggctgcggcg gcggggggat tgggttgagc tcctcgccgg 10080
actgggggtc caagtaaacc ccccgtccct ttcgtagcag aaactcttgg cgggctttgt 10140
tgatggcttg caattggcca agaatgtggc cctgggtaat gacgcaggcg gtaagctccg 10200
catttggcgg gcgggattgg tcttcgtaga acctaatctc gtgggcgtgg tagtcctcag 10260
gtacaaattt gcgaaggtaa gccgacgtcc acagccccgg agtgagtttc aaccccggag 10320
ccgcggactt ttcgtcaggc gagggaccct gcagctcaaa ggtaccgata atttgacttt 10380
cgttaagcag ctgcgaattg caaaccaggg agcggtgcgg ggtgcatagg ttgcagcgac 10440
agtgacactc cagtagaccg tcaccgctca cgtcttccat tatgtcagag tggtaggcaa 10500
ggtagttggc tagctgcaga aggtagcagt ggccccaaag cggcggaggg cattcgcggt 10560
acttaatggg cacaaagtcg ctaggaagtg cacagcaggt ggcgggcaag attcctgagc 10620
gctctaggat aaagttccta aagttctgca acatgctttg actggtgaag tctggcagac 10680
cctgttgcag ggttttaagc aggcgttcgg ggaaaatgat gtccgccagg tgcgcggcca 10740
cggagcgctc gttgaaggcc gtccataggt ccttcaagtt ttgctttagc agtttctgca 10800
gctccttgag gttgcactcc tccaagcact gctgccaaac gcccatggcc gtctgccagg 10860
tgtagcatag aaataagtaa acgcagtcgc ggacgtagtc gcggcgcgcc tcgcccttga 10920
gcgtggaatg aagcacgttt tgcccaaggc ggttttcgtg caaaattcca aggtaggaga 10980
ccaggttgca gagctccacg ttggagatct tgcaggcctg gcgtacgtag ccctgtcgaa 11040
aggtgtagtg caatgtttcc tctagcttgc gctgcatctc cgggtcagca aagaaccgct 11100
gcatgcactc aagctccacg gtaacgagca ctgcggccat cattagtttg cgtcgctcct 11160
ccaagtcggc aggctcgcgc gtttgaagcc agcgcgctag ctgctcgtcg ccaactgcgg 11220
gtaggccctc ctctgtttgt tcttgcaaat ttgcatccct ctccaggggc tgcgcacggc 11280
gcacgatcag ctcactcatg actgtgctca tgaccttggg ggtaggttta agtgccgggt 11340
aggcaaagtg ggtgacctcg atgctgcgtt ttagtacggc taggcgcgcg ttgtcaccct 11400
cgagttccac caacactcca gagtgacttt cattttcgct gttttcctgt tgcagagcgt 11460
ttgccgcgcg cttctcgtcg cgtccaagac cctcaaagat tttggcact tcgttgagcg 11520
aggcgatatc aggtatgaca gcgccctgcc gcaaggccag ctgcttgtcc gctcggctgc 11580
ggttggcacg gcaggatagg ggtatcttgc agttttggaa aaagatgtga taggtggcaa 11640
gcacctctgg cacggcaaat acggggtaga agttgaggcg cgggttgggc tcgcatgtgc 11700
cgttttcttg gcgtttgggg ggtacgcgcg gtgagaatag gtggcgttcg taggcaaggc 11760
tgacatccgc tatggcgagg ggcacatcgc tgcgctcttg caacgcgtcg cagataatgg 11820
cgcactggcg ctgcagatgc ttcaacagca cgtcgtctcc cacatctagg tagtcgccat 11880
gcctttcgtc cccccgcccg acttgttcct cgtttgcctc tgcgttgtcc tggtcttgct 11940
ttttatcctc tgttggtact gagcggtcct cgtcgtcttc gcttacaaaa cctgggtcct 12000
gctcgataat cacttcctcc tcctcaagcg gggtgcctc gacggggaag gtggtaggcg 12060
cgttggcggc atcggtggag gcggtggtgg cgaactcaga gggggcggtt aggctgtcct 12120
tcttctcgac tgactccatg atctttttct gcctatagga gaaggaaatg gccagtcggg 12180
aagaggagca gcgcgaaacc acccccgagc gcggacgcgg tgcggcgcga cgtcccccaa 12240
ccatggagga cgtgtcgtcc ccgtccccgt cgccgccgcc tccccgggcg cccccaaaaa 12300
agcggatgag gcggcgtatc gagtccgagg acgaggaaga ctcatcacaa gacgcgctgg 12360
tgccgcgcac acccagcccg cggccatcga cctcggcggc ggatttggcc attgcgccca 12420
agaagaaaaa gaagcgccct tctcccaagc ccgagcgccc gccatcacca gaggtaatcg 12480
tggacagcga ggaagaaaga gaagatgtgg cgctacaaat ggtgggtttc agcaacccac 12540
cggtgctaat caagcatggc aaaggaggta agcgcacagt gcggcggctg aatgaagacg 12600
acccagtggc gcgtggtatg cggacgcaag aggaagagga agagcccagc gaagcggaaa 12660
gtgaaattac ggtgatgaac ccgctgagtg tgccgatcgt gtctgcgtgg gagaagggca 12720
tggaggctgc gcgcgcgctg atggacaagt accacgtgga taacgatcta aaggcgaact 12780
tcaaactact gcctgaccaa gtggaagctc tggcggccgt atgcaagacc tggctgaacg 12840
aggagcaccg cgggttgcag ctgaccttca ccagcaacaa gacctttgtg acgatgatgg 12900
ggcgattcct gcaggcgtac ctgcagtcgt ttgcagaggt gacctacaag catcacgagc 12960
ccacgggctg cgcgttgtgg ctgcaccgct gcgctgagat cgaaggcgag cttaagtgtc 13020
tacacggaag cattatgata aataaggagc acgtgattga aatggatgtg acgagcgaaa 13080
acgggcagcg cgcgctgaag gagcagtcta gcaaggccaa gatcgtgaag aaccggtggg 13140
gccgaaatgt ggtgcagatc tccaacaccg acgcaaggtg ctgcgtgcac gacgcggcct 13200
gtccggccaa tcagttttcc ggcaagtctt gcggcatgtt cttctctgaa ggcgcaaagg 13260
ctcaggtggc ttttaagcag atcaaggctt ttatgcaggc gctgtatcct aacgcccaga 13320
ccgggcacgg tcaccttttg atgccactac ggtgcgagtg caactcaaag cctgggcacg 13380
cgccctttttt gggaaggcag ctaccaaagt tgactccgtt cgccctgagc aacgcggagg 13440
acctggacgc ggatctgatc tccgacaaga gcgtgctggc cagcgtgcac cacccggcgc 13500
tgatagtgtt ccagtgctgc aaccctgtgt atcgcaactc gcgcgcgcag ggcggaggcc 13560
ccaactgcga cttcaagata tcggcgcccg acctgctaaa cgcgttggtg atggtgcgca 13620
gcctgtggag tgaaaacttc accgagctgc cgcggatggt tgtgcctgag tttaagtgga 13680
gcactaaaca ccagtatcgc aacgtgtccc tgccagtggc gcatagcgat gcgcggcaga 13740
accccttga tttttaaacg gcgcagacgg caagggtggg ggtaaataat cacccgagag 13800
tgtacaaata aaagcatttg cctttattga aagtgtctct agtacattat ttttacatgt 13860
ttttcaagtg acaaaaagaa gtggcgctcc taatctgcgc actgtggctg cggaagtagg 13920
gcgagtggcg ctccaggaag ctgtagagct gttcctggtt gcgacgcagg gtgggctgta 13980
cctggggact gttgagcatg gagttgggta ccccggtaat aaggttcatg gtggggttgt 14040
gatccatggg agtttggggc cagttggcaa aggcgtggag aaacatgcag cagaatagtc 14100
cacaggcggc cgagttgggc ccctgtacgc tttgggtgga cttttccagc gttatacagc 14160
ggtcggggga agaagcaatg gcgctacggc gcaggagtga ctcgtactca aactggtaaa 14220
cctgcttgag tcgctggtca gaaaagccaa agggctcaaa gaggtagcat gtttttgagt 14280
gcgggttcca ggcaaaggcc atccagtgta cgcccccagt ctcggtccga gactcgaacc 14340
gggggtcccg cgactcaacc cttggaaaat aaccctccgg ctacagggag cgagccactt 14400
aatgctttcg ctttccagcc taaccgctta cgctgcgcgc ggccagtggc caaaaaagct 14460
agcgcagcag ccgccgcgcc tggaaggaag ccaaaaggag cactccccccg ttgtctgacg 14520
tcgcacacct gggttcgaca cgcgggcggt aaccgcatgg atcacggcgg acggccggat 14580
acggggctcg aaccccggtc gtccgccatg ataccccttgc gaatttatcc accagaccac 14640
ggaagagtgc ccgcttacag gctctccttt tgcacggtag agcgtcaacg attgcgcgcg 14700
cctgaccggc cagagcgtcc cgaccatgga gcactttttg ccgctgcgca acatctggaa 14760
ccgcgtccgc gactttccgc gcgcctccac caccgccgcc ggcatcacct ggatgtccag 14820
gtacatctac ggatatcatc gccttatgtt ggaagatctc gcccccggag ccccggccac 14880
cctacgctgg cccctctacc gccagccgcc gccgcacttt ttggtgggat accagtacct 14940
ggtgcggact tgcaacgact acgtatttga ctcgagggct tactcgcgtc tcaggtacac 15000
cgagctctcg cagccgggtc accagaccgt taactggtcc gttatggcca actgcactta 15060
caccatcaac acgggcgcat accaccgctt tgtggacatg gatgacttcc agtctaccct 15120
cacgcaggtg cagcaggcca tattagccga gcgcgttgtc gccgacctag ccctgcttca 15180
gccgatgagg ggcttcgggg tcacacgcat gggaggaaga gggcgccacc tacggccaaa 15240
ctccgccgcc gccgcagcga tagatgcaag agatgcagga caagaggaag gagaagaaga 15300
agtgccggta gaaaggctca tgcaagacta ctacaaagac ctgcgccgat gtcaaaacga 15360
agcctggggc atggccgacc gcctgcgcat tcagcaggcc ggacccaagg acatggtgct 15420
tctg 15424

<210> SEQ ID NO 393
<211> LENGTH: 3849
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 393
cggcgtcaat acgggataat accgcgccac atagcagaac tttaaaagtg ctcatcattg 60
gaaaacgttc ttcggggcga aaactctcaa ggatcttacc gctgttgaga tccagttcga 120
tgtaacccac tcgtgcaccc aactgatctt cagcatcttt tactttcacc agcgtttctg 180
ggtgagcaaa aacaggaagg caaaatgccg caaaaaaggg aataagggcg acacggaaat 240
gttgaatact catactcttc ctttttcaat attattgaag catttatcag ggttattgtc 300
tcatgagcgg atacatattt gaatgtattt agaaaaataa acaaataggg gttccgcgca 360
catttccccg aaaagtgcca cctaaattgt aagcgttaat attttgttaa aattcgcgtt 420
aaatttttgt taaatcagct cattttttaa ccaataggcc gaaatcggca aaatccctta 480
taaatcaaaa gaatagaccg agatagggtt gagtgttgtt ccagtttgga acaagagtcc 540
actattaaag aacgtggact ccaacgtcaa agggcgaaaa accgtctatc agggcgatgg 600
cccactacgt gaaccatcac cctaatcaag ttttttgggg tcgaggtgcc gtaaagcact 660
aaatcggaac cctaaaggga gcccccgatt tagagcttga cggggaaagc cggcgaacgt 720
ggcgagaaag gaagggaaga aagcgaaagg agcgggcgct agggcgctgg caagtgtagc 780
ggtcacgctg cgcgtaacca ccacacccgc cgcgcttaat gcgccgctac agggcgcgtc 840
ccattcgcca ttcaggctgc gcaactgttg ggaagggcga tcggtgcggg cctcttcgct 900
attacgccag ctgcgcgctc gctcgctcac tgaggccgcc cgggcaaagc ccgggcgtcg 960
ggcgaccttt ggtcgcccgg cctcagtgag cgagcgagcg cgcagagagg gagtggccaa 1020
ctccatcact aggggttcct tgtagttaat gattaacccg ccatgctact tatctacgta 1080
gccatgctct aggaagagta ccattgacgt caataatgac gtatgttccc atagtaacgc 1140
caatagggac tttccattga cgtcaatggg tggagtattt acggtaaact gcccacttgg 1200
cagtacatca agtgtatcag tggtttgtct ggtcaaccac cgcggtctca gtggtgtacg 1260
gtacaaaccc agctaccggt cgccaccatg cccgccatga agatcgagtg ccgcatcacc 1320
ggcaccctga acggcgtgga gttcgagctg gtgggcggcg gagagggcac ccccgagcag 1380
ggccgcatga ccaacaagat gaagagcacc aaaggcgccc tgaccttcag cccctacctg 1440
ctgagccacg tgatgggcta cggcttctac cacttcggca cctaccccag cggctacgag 1500
aacccettcc tgcacgccat caacaacggc ggctacacca acacccgcat cgagaagtac 1560
gaggacggcg gcgtgctgca cgtgagcttc agctaccgct acgaggccgg ccgcgtgatc 1620
ggcgacttca aggtggtggg caccggcttc cccgaggaca gcgtgatctt caccgacaag 1680
atcatccgca gcaacgccac cgtggagcac ctgcacccca tgggcgataa cgtgctggtg 1740
ggcagcttcg cccgcacctt cagcctgcgc gacggcggct actacagctt cgtggtggac 1800
agccacatgc acttcaagag cgccatccac cccagcatcc tgcagaacgg gggccccatg 1860
ttcgccttcc gccgcgtgga ggagctgcac agcaacaccg agctgggcat cgtggagtac 1920
cagcacgcct tcaagacccc catcgccttc gccagatctc gagctcgatg agtttggaca 1980
aaccacaact agaatgcagt gaaaaaaatg ctttatttgt gaaatttgtg atgctattgc 2040
tttatttgtg ggcccgggat cttcctagag catggctacg tagataagta gcatggcggg 2100
ttaatcatta actacaagga acccctagtg atggagttgg ccactccctc tctgcgcgct 2160
cgctcgctca ctgaggccgg gcgaccaaag gtcgcccgac gcccgggctt tgcccgggcg 2220
gcctcagtga gcgagcgagc gcgcagctgc attaatgaat cggccaacgc gcggggagag 2280
gcggtttgcg tattgggcgc tcttccgctt cctcgctcac tgactcgctg cgctcggtcg 2340
ttcggctgcg gcgagcggta tcagctcact caaaggcggt aatacggtta tccacagaat 2400
caggggataa cgcaggaaag aacatgtgag caaaaggcca gcaaaaggcc aggaaccgta 2460
aaaaggccgc gttgctggcg tttttccata ggctccgccc ccctgacgag catcacaaaa 2520
atcgacgctc aagtcagagg tggcgaaacc cgacaggact ataaagatac caggcgtttc 2580
cccctggaag ctccctcgtg cgctctcctg ttccgaccct gccgcttacc ggatacctgt 2640
ccgcctttct cccttcggga agcgtggcgc tttctcatag ctcacgctgt aggtatctca 2700
gttcggtgta ggtcgttcgc tccaagctgg gctgtgtgca cgaacccccc gttcagcccg 2760
accgctgcgc cttatccggt aactatcgtc ttgagtccaa cccggtaaga cacgacttat 2820
cgccactggc agcagccact ggtaacagga ttagcagagc gaggtatgta ggcggtgcta 2880
cagagttctt gaagtggtgg cctaactacg gctacactag aagaacagta tttggtatct 2940
gcgctctgct gaagccagtt accttcggaa aaagagttgg tagctcttga tccggcaaac 3000
aaaccaccgc tggtagcggt ggtttttttg tttgcaagca gcagattacg cgcagaaaaa 3060
aaggatctca agaagatcct ttgatctttt ctacggggtc tgacgctcag tggaacgaaa 3120
actcacgtta agggattttg gtcatgagat tatcaaaaag gatcttcacc tagatccttt 3180
taaattaaaa atgaagtttt aaatcaatct aaagtatata tgagtaaact tggtctgaca 3240
gttaccaatg cttaatcagt gaggcaccta tctcagcgat ctgtctattt cgttcatcca 3300
tagttgcctg actccccgtc gtgtagataa ctacgatacg ggagggctta ccatctggcc 3360
ccagtgctgc aatgataccg cgagacccac gctcaccggc tccagattta tcagcaataa 3420
accagccagc cggaagggcc gagcgcagaa gtggtcctgc aactttatcc gcctccatcc 3480
agtctattaa ttgttgccgg gaagctagag taagtagttc gccagttaat agtttgcgca 3540
acgttgttgc cattgctaca ggcatcgtgg tgtcacgctc gtcgtttggt atggcttcat 3600
tcagctccgg ttcccaacga tcaaggcgag ttacatgatc ccccatgttg tgcaaaaaag 3660
cggttagctc cttcggtcct ccgatcgttg tcagaagtaa gttggccgca gtgttatcac 3720
tcatggttat ggcagcactg cataattctc ttactgtcat gccatccgta agatgctttt 3780
ctgtgactgg tgagtactca accaagtcat tctgagaata gtgtatgcgg cgaccgagtt 3840
gctcttgcc 3849

<210> SEQ ID NO 394
<211> LENGTH: 7336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 394
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggctct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420

```
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
caacctctct gagggcattc gcgagtggtg ggcgctgaaa cctggagccc cgaagcccaa   1980
agccaaccag caaaagcagg acgacggccg gggtctggtg cttcctggct acaagtacct   2040
cggacccttc aacggactcg acaaggggga gcccgtcaac gcggcggacg cagcggccct   2100
cgagcacgac aaggcctacg accagcagct gcaggcgggt gacaatccgt acctgcggta   2160
taaccacgcc gacgccgagt ttcaggagcg tctgcaagaa gatacgtctt ttgggggcaa   2220
cctcgggcga gcagtcttcc aggccaagaa gcgggttctc gaacctctcg gtctggttga   2280
ggaaggcgct aagacggctc ctggaaagaa gagaccggta gagccatcac cccagcgttc   2340
tccagactcc tctacgggca tcggcaagaa aggccaacag cccgccagaa aaagactcaa   2400
ttttggtcag actggcgact cagagtcagt tccagaccct caacctctcg gagaacctcc   2460
agcagcgccc tctggtgtgg gacctaatac aatggctgca ggcggtggcg caccaatggc   2520
agacaataac gaaggcgccg acggagtggg tagttcctcg ggaaattggc attgcgattc   2580
cacatggctg ggcgacagag tcatcaccac cagcacccga acctgggccc tgcccaccta   2640
caacaaccac ctctacaagc aaatctccaa cgggacatcg ggaggagcca ccaacgacaa   2700
cacctacttc ggctacagca ccccctgggg gtattttgac tttaacagat tccactgcca   2760
```

-continued

```
cttttcacca cgtgactggc agcgactcat caacaacaac tggggattcc ggcccaagag   2820
actcagcttc aagctcttca acatccaggt caaggaggtc acgcagaatg aaggcaccaa   2880
gaccatcgcc aataacctca ccagcaccat ccaggtgttt acggactcgg agtaccagct   2940
gccgtacgtt ctcggctctg cccaccaggg ctgcctgcct ccgttcccgg cggacgtgtt   3000
catgattccc cagtacggct acctaacact caacaacggt agtcaggccg tgggacgctc   3060
ctccttctac tgcctggaat actttccttc gcagatgctg agaaccggca acaacttcca   3120
gtttacttac accttcgagg acgtgccttt ccacagcagc tacgcccaca gccagagctt   3180
ggaccggctg atgaatcctc tgattgacca gtacctgtac tacttgtctc ggactcaaac   3240
aacaggaggc acggcaaata cgcagactct gggcttcagc caaggtgggc ctaatacaat   3300
ggccaatcag gcaaagaact ggctgccagg accctgttac cgccaacaac gcgtctcaac   3360
gacaaccggg caaaacaaca atagcaactt tgcctggact gctgggacca aataccatct   3420
gaatggaaga aattcattgg ctaatcctgg catcgctatg gcaacacaca aagacgacga   3480
ggagcgtttt tttcccagta acgggatcct gatttttggc aaacaaaatg ctgccagaga   3540
caatgcggat tacagcgatg tcatgctcac cagcgaggaa gaaatcaaaa ccactaaccc   3600
tgtggctaca gaggaatacg gtatcgtggc agataacttg cagcagcaaa acacggctcc   3660
tcaaattgga actgtcaaca gccagggggc cttacccggt atggtctggc agaaccggga   3720
cgtgtacctg cagggtccca tctgggccaa gattcctcac acggacggca acttccaccc   3780
gtctccgctg atgggcggct ttggcctgaa acatcctccg cctcagatcc tgatcaagaa   3840
cacgcctgta cctgcggatc ctccgaccac cttcaaccag tcaaagctga actctttcat   3900
cacgcaatac agcaccggac aggtcagcgt ggaaattgaa tgggagctgc agaaggaaaa   3960
cagcaagcgc tggaaccccg agatccagta cacctccaac tactacaaat ctacaagtgt   4020
ggactttgct gttaatacag aaggcgtgta ctctgaaccc cgccccattg gcacccgtta   4080
cctcacccgt aatctgtaat tgcctgttaa tcaataaacc ggttgattcg tttcagttga   4140
actttggtct ctgcgaaggg cgaattcgtt taaacctgca ggactagagg tcctgtatta   4200
gaggtcacgt gagtgttttg cgacattttg cgacaccatg tggtcacgct gggtatttaa   4260
gcccgagtga gcacgcaggg tctccatttt gaagcgggag gtttgaacgc gcagccgcca   4320
agccgaattc tgcagatatc catcacactg gcggccgctc gactagagcg gccgccaccg   4380
cggtggagct ccagcttttg ttccctttag tgagggttaa ttgcgcgctt ggcgtaatca   4440
tggtcatagc tgtttcctgt gtgaaattgt tatccgctca caattccaca caacatacga   4500
gccggaagca taaagtgtaa agcctggggt gcctaatgag tgagctaact cacattaatt   4560
gcgttgcgct cactgcccgc tttccagtcg ggaaacctgt cgtgccagct gcattaatga   4620
atcggccaac gcgcggggag aggcggtttg cgtattgggc gctcttccgc ttcctcgctc   4680
actgactcgc tgcgctcggt cgttcggctg cggcgagcgg tatcagctca ctcaaaggcg   4740
gtaatacggt tatccacaga atcaggggat aacgcaggaa agaacatgtg agcaaaaggc   4800
cagcaaaagg ccaggaaccg taaaaaggcc gcgttgctgg cgtttttcca taggctccgc   4860
cccccctgacg agcatcacaa aaatcgacgc tcaagtcaga ggtggcgaaa cccgacagga   4920
ctataaagat accaggcgtt tccccctgga agctccctcg tgcgctctcc tgttccgacc   4980
ctgccgctta ccggatacct gtccgccttt ctcccttcgg gaagcgtggc gctttctcat   5040
agctcacgct gtaggtatct cagttcggtg taggtcgttc gctccaagct gggctgtgtg   5100
cacgaacccc ccgttcagcc cgaccgctgc gccttatccg gtaactatcg tcttgagtcc   5160
```

aacccggtaa gacacgactt atcgccactg gcagcagcca ctggtaacag gattagcaga 5220
gcgaggtatg taggcggtgc tacagagttc ttgaagtggt ggcctaacta cggctacact 5280
agaagaacag tatttggtat ctgcgctctg ctgaagccag ttaccttcgg aaaaagagtt 5340
ggtagctctt gatccggcaa acaaaccacc gctggtagcg gtggtttttt tgtttgcaag 5400
cagcagatta cgcgcagaaa aaaaggatct caagaagatc ctttgatctt ttctacgggg 5460
tctgacgctc agtggaacga aaactcacgt taagggattt tggtcatgag attatcaaaa 5520
aggatcttca cctagatcct tttaaattaa aaatgaagtt ttaaatcaat ctaaagtata 5580
tatgagtaaa cttggtctga cagttaccaa tgcttaatca gtgaggcacc tatctcagcg 5640
atctgtctat ttcgttcatc catagttgcc tgactccccg tcgtgtagat aactacgata 5700
cgggagggct taccatctgg ccccagtgct gcaatgatac cgcgagaccc acgctcaccg 5760
gctccagatt tatcagcaat aaaccagcca gccggaaggg ccgagcgcag aagtggtcct 5820
gcaactttat ccgcctccat ccagtctatt aattgttgcc gggaagctag agtaagtagt 5880
tcgccagtta atagtttgcg caacgttgtt gccattgcta caggcatcgt ggtgtcacgc 5940
tcgtcgtttg gtatggcttc attcagctcc ggttcccaac gatcaaggcg agttacatga 6000
tcccccatgt tgtgcaaaaa agcggttagc tccttcggtc ctccgatcgt tgtcagaagt 6060
aagttggccg cagtgttatc actcatggtt atggcagcac tgcataattc tcttactgtc 6120
atgccatccg taagatgctt ttctgtgact ggtgagtact caaccaagtc attctgagaa 6180
tagtgtatgc ggcgaccgag ttgctcttgc ccggcgtcaa tacgggataa taccgcgcca 6240
catagcagaa ctttaaaagt gctcatcatt ggaaaacgtt cttcggggcg aaaactctca 6300
aggatcttac cgctgttgag atccagttcg atgtaaccca ctcgtgcacc caactgatct 6360
tcagcatctt ttactttcac cagcgtttct gggtgagcaa aaacaggaag gcaaaatgcc 6420
gcaaaaaagg gaataagggc gacacggaaa tgttgaatac tcatactctt cctttttcaa 6480
tattattgaa gcatttatca gggttattgt ctcatgagcg gatacatatt tgaatgtatt 6540
tagaaaaata aacaaatagg ggttccgcgc acatttcccc gaaaagtgcc acctaaattg 6600
taagcgttaa tattttgtta aaattcgcgt taaatttttg ttaaatcagc tcatttttta 6660
accaataggc cgaaatcggc aaaatccctt ataaatcaaa agaatagacc gagatagggt 6720
tgagtgttgt tccagtttgg aacaagagtc cactattaaa gaacgtggac tccaacgtca 6780
aagggcgaaa aaccgtctat cagggcgatg gcccactacg tgaaccatca ccctaatcaa 6840 gtttttttggg gtcgaggtgc cgtaaagcac taaatcggaa ccctaaaggg agcccccgat 6900
ttagagcttg acggggaaag ccggcgaacg tggcgagaaa ggaagggaag aaagcgaaag 6960
gagcgggcgc tagggcgctg gcaagtgtag cggtcacgct gcgcgtaacc accacacccg 7020
ccgcgcttaa tgcgccgcta cagggcgcgt cccattcgcc attcaggctg cgcaactgtt 7080
gggaagggcg atcggtgcgg gcctcttcgc tattacgcca gctggcgaaa gggggatgtg 7140
ctgcaaggcg attaagttgg gtaacgccag ggttttccca gtcacgacgt tgtaaaacga 7200
cggccagtga gcgcgcgtaa tacgactcac tatagggcga attgggtacc gggccccccc 7260
tcgatcgagg tcgacggtat cgggggagct cgcagggtct ccattttgaa gcgggaggtt 7320
tgaacgcgca gccgcc 7336

<210> SEQ ID NO 395
<211> LENGTH: 969
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 395
ccccaactgg ggtaaccttt gggctccccg ggcgcgacta taagctgcga gcaacttcac 60
ttgggtatgc cggcggtagc gcttaccgtt cgtataatgt atgctatacg aagttatccg 120
aagccgctag cggtggtttg tctggtcaac caccgcggtc tcagtggtgt acggtacaaa 180
cccagctacc ggtcgccacc atgcccgcca tgaagatcga gtgccgcatc accggcaccc 240
tgaacggcgt ggagttcgag ctggtgggcg gcggagaggg cacccccgag cagggccgca 300
tgaccaacaa gatgaagagc accaaaggcg ccctgacctt cagcccctac ctgctgagcc 360
acgtgatggg ctacggcttc taccacttcg gcacctaccc cagcggctac gagaacccct 420
tcctgcacgc catcaacaac ggcggctaca ccaacacccg catcgagaag tacgaggacg 480
gcggcgtgct gcacgtgagc ttcagctacc gctacgaggc cggccgcgtg atcggcgact 540
tcaaggtggt gggcaccggc ttccccgagg acagcgtgat cttcaccgac aagatcatcc 600
gcagcaacgc caccgtggag cacctgcacc ccatgggcga taacgtgctg gtgggcagct 660
tcgcccgcac cttcagcctg cgcgacggcg gctactacag cttcgtggtg gacagccaca 720
tgcacttcaa gagcgccatc caccccagca tcctgcagaa cgggggcccc atgttcgcct 780
tccgccgcgt ggaggagctg cacagcaaca ccgagctggg catcgtggag taccagcacg 840
ccttcaagac ccccatcgcc ttcgccagat ctcgagctcg atgagtttgg acaaaccaca 900
actagaatgc agtgaaaaaa atgctttatt tgtgaaattt gtgatgctat tgctttattt 960
gtgggcccg 969

<210> SEQ ID NO 396
<211> LENGTH: 4769
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 396
tgatcccctg cgccatcaga tccttggcgg cgagaaagcc atccagttta ctttgcaggg 60
cttcccaacc ttaccagagg gcgccccagc tggcaattcc ggttcgcttg ctgtccataa 120
aaccgcccag tctagctatc gccatgtaag cccactgcaa gctacctgct ttctctttgc 180
gcttgcgttt tcccttgtcc agatagccca gtagctgaca ttcatccggg gtcagcaccg 240
tttctgcgga ctggctttct acgtgctcga ggggggccaa acggtctcca gcttggctgt 300
tttggcggat gagagaagat tttcagcctg atacagatta aatcagaacg cagaagcggt 360
ctgataaaac agaatttgcc tggcggcagt agcgcggtgg tcccacctga ccccatgccg 420
aactcagaag tgaaacgccg tagcgccgat ggtagtgtgg ggtctcccca tgcgagagta 480
gggaactgcc aggcatcaaa taaaacgaaa ggctcagtcg aaagactggg cctttcgttt 540
tatctgttgt ttgtcggtga acgctctcct gagtaggaca aatccgccgg gagcggattt 600
gaacgttgcg aagcaacggc ccggagggtg gcgggcagga cgcccgccat aaactgccag 660
gcatcaaatt aagcagaagg ccatcctgac ggatggcctt tttgcgtttc tacaaactct 720
tttgtttatt tttctaaata cattcaaata tgtatccgct catgaccaaa atcccttaac 780
gtgagttttc gttccactga gcgtcagacc ccgtagaaaa gatcaaagga tcttcttgag 840 atccttttt tctgcgcgta atctgctgct tgcaaacaaa aaaaccaccg ctaccagcgg 900
tggtttgttt gccggatcaa gagctaccaa ctctttttcc gaaggtaact ggcttcagca 960
gagcgcagat accaaatact gtccttctag tgtagccgta gttaggccac cacttcaaga 1020
actctgtagc accgcctaca tacctcgctc tgctaatcct gttaccagtg gctgctgcca 1080
gtggcgataa gtcgtgtctt accgggttgg actcaagacg atagttaccg gataaggcgc 1140
agcggtcggg ctgaacgggg ggttcgtgca cacagcccag cttggagcga acgacctaca 1200
ccgaactgag atacctacag cgtgagctat gagaaagcgc cacgcttccc gaagggagaa 1260
aggcggacag gtatccggta agcggcaggg tcggaacagg agagcgcacg agggagcttc 1320
caggggggaaa cgcctggtat ctttatagtc ctgtcgggtt tcgccacctc tgacttgagc 1380
gtcgattttt gtgatgctcg tcaggggggc ggagcctatg gaaaaacgcc agcaacgcgg 1440
cctttttacg gttcctggcc ttttgctggc cttttgctca catgttcttt cctgcgttat 1500
cccctgattc tgtggataac cgtattaccg cctttgagtg agctgatacc gctcgccgca 1560
gccgaacgac cgagcgcagc gagtcagtga gcgaggaagc ggaagagcgc ctgatgcggt 1620
attttctcct tacgcatctg tgcggtattt cacaccgcat atggtgcact ctcagtacaa 1680
tctgctctga tgccgcatag ttaagccagt atacactccg ctatcgctac gtgactgggt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagccg tcaattgtct gattcgttac caattatgac aacttgacgg ctacatcatt 2040
cactttttct tcacaaccgg cacggaactc gctcgggctg gccccggtgc atttttttaaa 2100
tacccgcgag aaatagagtt gatcgtcaaa accaacattg cgaccgacgg tggcgatagg 2160
catccgggtg gtgctcaaaa gcagcttcgc ctggctgata cgttggtcct cgcgccagct 2220
taagacgcta atccctaact gctggcggaa aagatgtgac agacgcgacg gcgacaagca 2280
aacatgctgt gcgacgctgg cgatacatta ccctgttatc cctagatgac attaccctgt 2340
tatcccagat gacattaccc tgttatccct agatgacatt accctgttat ccctagatga 2400
catttaccct gttatcccta gatgacatta ccctgttatc ccagatgaca ttaccctgtt 2460
atccctagat acattaccct gttatcccag atgacatacc ctgttatccc tagatgacat 2520
taccctgtta tcccagatga cattaccctg ttatccctag atacattacc ctgttatccc 2580
agatgacata ccctgttatc cctagatgac attaccctgt tatcccagat gacattaccc 2640
tgttatccct agatacatta ccctgttatc ccagatgaca taccctgtta tccctagatg 2700
acattaccct gttatcccag atgacattac cctgttatcc ctagatacat taccctgtta 2760
tcccagatga cataccctgt tatccctaga tgacattacc ctgttatccc agatgacatt 2820
accctgttat ccctagatac attaccctgt tatcccagat gacataccct gttatcccta 2880
gatgacatta ccctgttatc ccagatgaca ttaccctgtt atccctagat acattaccct 2940
gttatcccag atgacatacc ctgttatccc tagatgacat taccctgtta tcccagataa 3000
actcaatgat gatgatgatg atggtcgaga ctcagcggcc gcggtgccag ggcgtgccct 3060
tgggctcccc gggcgcgatg cccgccatga agatcgagtg ccgcatcacc ggcaccctga 3120
acggcgtgga gttcgagctg gtgggcggcg gagagggcac ccccgagcag ggccgcatga 3180
ccaacaagat gaagagcacc aaaggcgccc tgaccttcag cccctacctg ctgagccacg 3240
tgatgggcta cggcttctac cacttcggca cctaccccag cggctacgag aaccccttcc 3300
tgcacgccat caacaacggc ggctacacca acacccgcat cgagaagtac gaggacggcg 3360
gcgtgctgca cgtgagcttc agctaccgct acgaggccgg ccgcgtgatc ggcgacttca 3420
aggtggtggg caccggcttc cccgaggaca gcgtgatctt caccgacaag atcatccgca 3480
gcaacgccac cgtggagcac ctgcacccca tgggcgataa cgtgctggtg ggcagcttcg 3540
cccgcacctt cagcctgcgc gacggcggct actacagctt cgtggtggac agccacatgc 3600
acttcaagag cgccatccac cccagcatcc tgcagaacgg gggccccatg ttcgccttcc 3660
gccgcgtgga ggagctgcac agcaacaccg agctgggcat cgtggagtac cagcacgcct 3720
tcaagacccc catcgccttc gccagatctc gagctcgagg tggtttgtct ggtcaaccac 3780
cgcggtctca gtggtgtacg gtacaaaccc accccaactg ggtaaccttt tgagttctct 3840
cagttggggg taatcagcat catgatgtgg taccacatca tgatgctgat tataagaatg 3900
cggccgccac actctagtgg atctcgagtt aataattcag aagaactcgt caagaaggcg 3960
atagaaggcg atgcgctgcg aatcgggagc ggcgataccg taaagcacga ggaagcggtc 4020
agcccattcg ccgccaagct cttcagcaat atcacgggta gccaacgcta tgtcctgata 4080
gcggtccgcc acacccagcc ggccacagtc gatgaatcca gaaaagcggc cattttccac 4140
catgatattc ggcaagcagg catcgccatg ggtcacgacg agatcctcgc cgtcgggcat 4200
gctcgccttg agcctggcga acagttcggc tggcgcgagc ccctgatgct cttcgtccag 4260
atcatcctga tcgacaagac cggcttccat ccgagtacgt gctcgctcga tgcgatgttt 4320
cgcttggtgg tcgaatgggc aggtagccgg atcaagcgta tgcagccgcc gcattgcatc 4380
agccatgatg gatactttct cggcaggagc aaggtgtaga tgacatggag atcctgcccc 4440
ggcacttcgc ccaatagcag ccagtccctt cccgcttcag tgacaacgtc gagcacagct 4500
gcgcaaggaa cgcccgtcgt ggccagccac gatagccgcg ctgcctcgtc ttgcagttca 4560
ttcagggcac cggacaggtc ggtcttgaca aaaagaaccg ggcgcccctg cgctgacagc 4620
cggaacacgg cggcatcaga gcagccgatt gtctgttgtg cccagtcata gccgaatagc 4680
ctctccaccc aagcggccgg agaacctgcg tgcaatccat cttgttcaat catgcgaaac 4740
gatcctcatc ctgtctcttg atcagagct 4769

<210> SEQ ID NO 397
<211> LENGTH: 797
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 397
ccccaactgg ggtaaccttt gggctccccg ggcgcgatgg tgagcaaggg cgaggaggat 60
aacatggcca tcatcaagga gttcatgcgc ttcaaggtgc acatggaggg ctccgtgaac 120
ggccacgagt tcgagatcga gggcgagggc gagggccgcc cctacgaggg cacccagacc 180
gccaagctga aggtgaccaa gggtggcccc ctgcccttcg cctgggacat cctgtcccct 240
cagttcatgt acggctccaa ggcctacgtg aagcaccccg ccgacatccc cgactacttg 300
aagctgtcct tccccgaggg cttcaagtgg gagcgcgtga tgaacttcga ggacggcggc 360
gtggtgaccg tgacccagga ctcctccctg caggacggcg agttcatcta caaggtgaag 420
ctgcgcggca ccaacttccc ctccgacggc cccgtaatgc agaagaagac catgggctgg 480
gaggcctcct ccgagcggat gtaccccgag gacggcgccc tgaagggcga gatcaagcag 540
aggctgaagc tgaaggacgg cggccactac gacgctgagg tcaagaccac ctacaaggcc 600
aagaagcccg tgcagctgcc cggcgcctac aacgtcaaca tcaagttgga catcacctcc 660
cacaacgagg actacaccat cgtggaacag tacgaacgcg ccgagggccg ccactccacc 720
ggcggcatgg acgagctgta caagggtggt ttgtctggtc aaccaccgcg agctcagtgg 780
tgtacggtac aaaccca 797

<210> SEQ ID NO 398
<211> LENGTH: 815
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398
ccccaactgg ggtaaccttt gggctccccg ggcgcggccg ccaccatggt gtccaagggt 60
gaggaacttt ttaccggagt ggtgccgata ctggtagagc tggatggcga cgtaaacggg 120
cacaagttca gtgtacgggg agagggcgag ggcgacgcta cgaatgggaa attgactttg 180
aaatttattt gcaccacggg caaattgccg gtcccgtggc caactttggt tacgaccttg 240
acctatggcg ttcagtgttt ctcacggtac ccagaccaca tgaaacagca tgactttttt 300
aagtcagcga tgccggaggg atatgtgcaa gaacggacta tctcatttaa agatgatggc 360
acatataaga caagagcgga agtcaaattc gaaggggaca ccctcgtcaa tcgaatagaa 420
ctcaagggaa tagacttcaa agaagatggt aatatactgg ggcacaaact cgaatacaat 480
ttcaacagtc ataacgtcta catcactgcc gacaaacaaa aaaatgggat caaagcgaac 540
ttcaaaatcc gacataatgt cgaggatggg agcgtccaac tggcagacca ttaccagcaa 600
aatactccaa taggtgatgg tccagtgctt ttgccagata atcattatct tagctatcag 660
agcaagttga gtaaggatcc gaatgaaaag cgagatcaca tggtcttgct ggagtttgtt 720
acggcggctg gtatcacact tggtatggat gaattgtaca agggtggttt gtctggtcaa 780
ccaccgcgga ctcagtggtg tacggtacaa accca 815

<210> SEQ ID NO 399
<211> LENGTH: 1660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 399
ccccaactgg ggtaaccttt gggctccccg ggcgcggcca ccatgaaatg ggttactttc 60
atatctctgt tgtttttgtt ttcctctagt tccagggcca tgccgtcttc tgtctcgtgg 120
ggcatcctcc tgctggcagg cctgtgctgc ctggtccctg tctccctggc tgaggatccc 180
cagggagatg ctgcccagaa gacagataca tcccaccatg atcaggatca cccaaccttc 240
aacaagatca cccccaacct ggctgagttc gccttcagcc tataccgcca gctggcacac 300
cagtccaaca gcaccaatat cttcttctcc ccagtgagca tcgctacagc ctttgcaatg 360
ctctccctgg ggaccaaggc tgacactcac gatgaaatcc tggagggcct gaatttcaac 420
ctcacggaga ttccggaggc tcagatccat gaaggcttcc aggaactcct ccgtaccctc 480
aaccagccag acagccagct ccagctgacc accggcaatg gcctgttcct cagcgagggc 540
ctgaagctag tggataagtt tttggaggat gttaaaaagt tgtaccactc agaagccttc 600
actgtcaact tcggggacac cgaagaggcc aagaaacaga tcaacgatta cgtggagaag 660
ggtactcaag ggaaaattgt ggatttggtc aaggagcttg acagagacac agtttttgct 720
ctggtgaatt acatcttctt taaaggcaaa tgggagagac cctttgaagt caaggacacc 780
gaggaagagg acttccacgt ggaccaggtg accaccgtga aggtgcctat gatgaagcgt 840
ttaggcatgt ttaacatcca gcactgtaag aagctgtcca gctgggtgct gctgatgaaa 900
tacctgggca atgccaccgc catcttcttc ctgcctgatg aggggaaact acagcacctg 960
gaaaatgaac tcacccacga tatcatcacc aagttcctgg aaaatgaaga cagaaggtct 1020
gccagcttac atttacccaa actgtccatt actggaacct atgatctgaa gagcgtcctg 1080
ggtcaactgg gcatcactaa ggtcttcagc aatggggctg acctctccgg ggtcacagag 1140
gaggcacccc tgaagctctc caaggccgtg cataaggctg tgctgaccat cgacgagaaa 1200
gggactgaag ctgctggggc catgttttta gaggccatac ccatgtctat cccccccgag 1260
gtcaagttca acaaaccctt tgtcttctta atgattgaac aaaataccaa gtctcccctc 1320
ttcatgggaa aagtggtgaa tcccacccaa aaataagaat tctaactaga gctcgctgat 1380
cagcctcgac tgtgccttct agttgccagc catctgttgt ttgcccctcc cccgtgcctt 1440
ccttgaccct ggaaggtgcc actcccactg tcctttccta ataaaatgag gaaattgcat 1500
cgcattgtct gagtaggtgt cattctattc tggggggtgg ggtggggcag gacagcaagg 1560
gggaggattg ggaagagaat agcaggcatg ctggggagcg agctcgaggt ggtttgtctg 1620
gtcaaccacc gcggtctcag tggtgtacgg tacaaaccca 1660

<210> SEQ ID NO 400
<211> LENGTH: 4906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 400
ccccaactgg ggtaaccttt gggctccccg ggcgcggcca ccatgaaatg ggttactttc 60
atatctctgt tgtttttgtt ttcctctagt tccagggcca tgacgaggat tttgacagct 120
ttcaaagtgg tgaggacact gaagactggt tttggcttta ccaatgtgac tgcacaccaa 180
aaatggaaat tttcaagacc tggcatcagg ctcctttctg tcaaggcaca gacagcacac 240
attgtcctgg aagatggaac taagatgaaa ggttactcct ttggccatcc atcctctgtt 300
gctggtgaag tggtttttaa tactggcctg ggagggtacc cagaagctat tactgaccct 360
gcctacaaag gacagattct cacaatggcc aaccctatta ttgggaatgg tggagctcct 420
gatactactg ctctggatga actgggactt agcaaatatt tggagtctaa tggaatcaag 480
gtttcaggtt tgctggtgct ggattatagt aaagactaca accactggct ggctaccaag 540
agtttagggc aatggctaca ggaagaaaag gttcctgcaa tttatggagt ggacacaaga 600
atgctgacta aaataattcg ggataagggt accatgcttg ggaagattga atttgaaggt 660
cagcctgtgg attttgtgga tccaaataaa cagaatttga ttgctgaggt ttcaaccaag 720
gatgtcaaag tgtacggcaa aggaaacccc acaaaagtgg tagctgtaga ctgtgggatt 780
aaaaacaatg taatccgcct gctagtaaag cgaggagctg aagtgcactt agttccctgg 840

-continued

```
aaccatgatt tcaccaagat ggagtatgat gggattttga tcgcgggagg accggggaac    900
ccagctcttg cagaaccact aattcagaat gtcagaaaga ttttggagag tgatcgcaag    960
gagccattgt ttggaatcag tacaggaaac ttaataacag gattggctgc tggtgccaaa   1020
acctacaaga tgtccatggc caacagaggg cagaatcagc ctgttttgaa tatcacaaac   1080
aaacaggctt tcattactgc tcagaatcat ggctatgcct tggacaacac cctccctgct   1140
ggctggaaac cactttttgt gaatgtcaac gatcaaacaa atgaggggat tatgcatgag   1200
agcaaaccct tcttcgctgt gcagttccac ccagaggtca ccccggggcc aatagacact   1260
gagtacctgt ttgattcctt tttctcactg ataaagaaag gaaaagctac caccattaca   1320
tcagtcttac cgaagccagc actagttgca tctcgggttg aggtttccaa agtccttatt   1380
ctaggatcag gaggtctgtc cattggtcag gctggagaat ttgattactc aggatctcaa   1440
gctgtaaaag ccatgaagga agaaaatgtc aaaactgttc tgatgaaccc aaacattgca   1500
tcagtccaga ccaatgaggt gggcttaaag caagcggata ctgtctactt tcttcccatc   1560
acccctcagt ttgtcacaga ggtcatcaag gcagaacagc cagatgggtt aattctgggc   1620
atgggtggcc agacagctct gaactgtgga gtggaactat tcaagagagg tgtgctcaag   1680
gaatatggtg tgaaagtcct gggaacttca gttgagtcca ttatggctac ggaagacagg   1740
cagctgtttt cagataaact aaatgagatc aatgaaaaga ttgctccaag ttttgcagtg   1800
gaatcgattg aggatgcact gaaggcagca gacaccattg gctacccagt gatgatccgt   1860
tccgcctatg cactgggtgg gttaggctca ggcatctgtc ccaacagaga gactttgatg   1920
gacctcagca caaaggcctt tgctatgacc aaccaaattc tggtggagaa gtcagtgaca   1980
ggttggaaag aaatagaata tgaagtggtt cgagatgctg atgacaattg tgtcactgtc   2040
tgtaacatgg aaaatgttga tgccatgggt gttcacacag gtgactcagt tgttgtggct   2100
cctgcccaga cactctccaa tgccgagttt cagatgttga gacgtacttc aatcaatgtt   2160
gttcgccact tgggcattgt gggtgaatgc aacattcagt ttgcccttca tcctacctca   2220
atggaatact gcatcattga agtgaatgcc agactgtccc gaagctctgc tctggcctca   2280
aaagccactg gctacccatt ggcattcatt gctgcaaaga ttgccctagg aatcccactt   2340
ccagaaatta agaacgtcgt atccgggaag acatcagcct gttttgaacc tagcctggat   2400
tacatggtca ccaagattcc ccgctgggat cttgaccgtt ttcatggaac atctagccga   2460
attggtagct ctatgaaaag tgtaggagag gtcatggcta ttggtcgtac ctttgaggag   2520
agtttccaga aagctttacg gatgtgccac ccatctatag aaggtttcac tccccgtctc   2580
ccaatgaaca aagaatggcc atctaattta gatcttagaa aagagttgtc tgaaccaagc   2640
agcacgcgta tctatgccat tgccaaggcc attgatgaca acatgtccct tgatgagatt   2700
gagaagctca catacattga caagtggttt ttgtataaga tgcgtgatat tttaaacatg   2760
gaaaagacac tgaaaggcct caacagtgag tccatgacag aagaaaccct gaaaagggca   2820
aaggagattg ggttctcaga taagcagatt tcaaaatgcc ttgggctcac tgaggcccag   2880
acaagggagc tgaggttaaa gaaaaacatc cacccttggg ttaaacagat tgatacactg   2940
gctgcagaat acccatcagt aacaaactat ctctatgtta cctacaatgg tcaggagcat   3000
gatgtcaatt ttgatgacca tggaatgatg gtgctaggct gtggtccata tcacattggc   3060
agcagtgtgg aatttgattg gtgtgctgtc tctagtatcc gcacactgcg tcaacttggc   3120
aagaagacgg tggtggtgaa ttgcaatcct gagactgtga gcacagactt tgatgagtgt   3180
```

```
gacaaactgt actttgaaga gttgtccttg gagagaatcc tagacatcta ccatcaggag   3240

gcatgtggtg gctgcatcat atcagttgga ggccagattc caaacaacct ggcagttcct   3300

ctatacaaga atggtgtcaa gatcatgggc acaagccccc tgcagatcga cagggctgag   3360

gatcgctcca tcttctcagc tgtcttggat gagctgaagg tggctcaggc accttggaaa   3420

gctgttaata ctttgaatga agcactggaa tttgcaaagt ctgtggacta cccctgcttg   3480

ttgaggcctt cctatgtttt gagtgggtct gctatgaatg tggtattctc tgaggatgag   3540

atgaaaaaat tcctagaaga ggcgactaga gtttctcagg agcacccagt ggtgctgaca   3600

aaatttgttg aaggggcccg agaagtagaa atggacgctg ttggcaaaga tggaagggtt   3660

atctctcatg ccatctctga acatgttgaa gatgcaggtg tccactcggg agatgccact   3720

ctgatgctgc ccacacaaac catcagccaa ggggccattg aaaaggtgaa ggatgctacc   3780

cggaagattg caaaggcttt tgccatctct ggtccattca acgtccaatt tcttgtcaaa   3840

ggaaatgatg tcttggtgat tgagtgtaac ttgagagctt ctcgatcctt cccctttgtt   3900

tccaagactc ttggggttga cttcattgat gtggccacca aggtgatgat tggagagaat   3960

gttgatgaga aacatcttcc aacattggac catcccataa ttcctgctga ctatgttgca   4020

attaaggctc ccatgttttc ctggccccgg ttgagggatg ctgaccccat tctgagatgt   4080

gagatggctt ccactggaga ggtggcttgc tttggtgaag gtattcatac agccttccta   4140

aaggcaatgc tttccacagg atttaagata ccccagaaag gcatcctgat aggcatccag   4200

caatcattcc ggccaagatt ccttggtgtg gctgaacaat tacacaatga aggtttcaag   4260

ctgtttgcca cggaagccac atcagactgg ctcaacgcca acaatgtccc tgccacccca   4320

gtggcatggc cgtctcaaga aggacagaat cccagcctct cttccatcag aaaattgatt   4380

agagatggca gcattgacct agtgattaac cttcccaaca acaacactaa atttgtccat   4440

gataattatg tgattcggag gacagctgtt gatagtggaa tccctctcct cactaatttt   4500

caggtgacca aactttttgc tgaagctgtg cagaaatctc gcaaggtgga ctccaagagt   4560

cttttccact acaggcagta cagtgctgga aaagcagcat aggaattcta actagagctc   4620

gctgatcagc ctcgactgtg ccttctagtt gccagccatc tgttgtttgc ccctcccccg   4680

tgccttcctt gaccctggaa ggtgccactc ccactgtcct ttcctaataa aatgaggaaa   4740

ttgcatcgca ttgtctgagt aggtgtcatt ctattctggg gggtggggtg gggcaggaca   4800

gcaaggggga ggattgggaa gagaatagca ggcatgctgg ggagcgagct cgaggtggtt   4860

tgtctggtca accaccgcgg tctcagtggt gtacggtaca aaccca                  4906
```

<210> SEQ ID NO 401
<211> LENGTH: 4882
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 401

```
ccccaactgg ggtaaccttt gggctccccg ggcgcgacta taagctgcga gcaacttcac     60

ttgggtatgc cggcggtagc gcttaccgtt cgtataatgt atgctatacg aagttatccg    120

aagccgctag cggtggtttg tctggtcaac caccgcggtc tcagtggtgt acggtacaaa    180

cccacccgag agaccatgca gaggtcgcct ctggaaaagg ccagcgttgt ctccaaactt    240

ttctttagct ggactagacc catccttcgt aaaggataca gacagcgcct ggaattgtca    300
```

```
gacatatacc aaatcccttc tgttgattct gctgacaatc tatctgaaaa attggaaaga    360
gaatgggata gagagctggc ttcaaagaaa aatcctaaac tcattaatgc ccttcggcga    420
tgtttttttct ggagatttat gttctatgga atctttttat atttagggga agtcaccaaa   480
gcagtacagc ctctcttact gggaagaatc atagcttcct atgacccgga taacaaggag    540
gaacgctcta tcgcgattta tctaggcata ggcttatgcc ttctctttat tgtgaggaca    600
ctgctcctac acccagccat ttttggcctt catcacattg gaatgcagat gagaatagct    660
atgtttagtt tgatttataa gaagacttta aagctgtcaa gccgtgttct agataaaata    720
agtattggac aacttgttag tctcctttcc aacaacctga acaaatttga tgaaggactt    780
gcattggcac atttcgtgtg gatcgctcct ttgcaagtgg cactcctcat ggggctaatc    840
tgggagttgt tacaggcgtc tgccttctgt ggacttggtt tcctgatagt ccttgccctt    900
tttcaggctg ggctagggag aatgatgatg aagtacagag atcagagagc tgggaagatc    960
agtgaaagac ttgtgattac ctcagaaatg attgaaaata tccaatctgt taaggcatac   1020
tgctgggaag aagcaatgga aaaaatgatt gaaaacttaa gacaaacaga actgaaactg   1080
actcggaagg cagcctatgt gagatacttc aatagctcag ccttcttctt ctcagggttc   1140
tttgtggtgt ttttatctgt gcttccctat gcactaatca aaggaatcat cctccggaaa   1200
atattcacca ccatctcatt ctgcattgtt ctgcgcatgg cggtcactcg gcaatttccc   1260
tgggctgtac aaacatggta tgactctctt ggagcaataa acaaaataca ggatttctta   1320
caaaagcaag aatataagac attggaatat aacttaacga ctacagaagt agtgatggag   1380
aatgtaacag ccttctggga ggagggattt ggggaattat ttgagaaagc aaaacaaaac   1440
aataacaata gaaaaacttc taatggtgat gacagcctct tcttcagtaa tttctcactt   1500
cttggtactc ctgtcctgaa agatattaat ttcaagatag aaagaggaca gttgttggcg   1560
gttgctggat ccactggagc aggcaagact tcacttctaa tggtgattat gggagaactg   1620
gagccttcag agggtaaaat taagcacagt ggaagaattt cattctgttc tcagttttcc   1680
tggattatgc ctggcaccat taaagaaaat atcatctttg gtgtttccta tgatgaatat   1740
agatacagaa gcgtcatcaa agcatgccaa ctagaagagg acatctccaa gtttgcagag   1800
aaagacaata tagttcttgg agaaggtgga atcacactga gtggaggtca acgagcaaga   1860
atttctttag caagagcagt atacaaagat gctgatttgt atttattaga ctctcctttt   1920
ggatacctag acgtattgac tgagaaggag atcttcgagt cctgcgtttg caagcttatg   1980
gccaataaga caagaatcct ggttacaagt aagatggagc acctgaagaa ggccgataag   2040
attctgatcc tgcacgaggg atcttcatac ttctacggca ctttcagcga gcttcagaac   2100
ttgcaacctg atttctctag caagcttatg ggctgcgact cctttgatca gttctctgcc   2160
gagcgtcgca actccattct gaccgaaaca ctgcataggt tttccctcga gggcgacgca   2220
ccagtgtctt ggactgagac taagaagcag agcttcaagc aaaccggcga attcggtgag   2280
aagagaaaga acagtatcct gaaccccatt aattcaattc ggaagttcag tatcgttcag   2340
aaaacgcctc ttcagatgaa cgggattgag gaagactcag acgaaccgct tgaaaggcga   2400
ctctcattgg ttcctgacag tgaacaaggg gaagctattc tcccccggat ttcagtaatt   2460
tccacaggtc cgactctgca agcccggaga agacaatccg tgttgaatct tatgacccat   2520
tccgtgaatc aggggcaaaa tatccataga aagactactg cctctacgag gaaggtatcc   2580
cttgcacccc aagccaatct gacggagctc gacatctact ctcgccgcct gtcccaggag   2640
acaggactgg agattagcga ggagatcaat gaagaggatc tgaaagaatg tttcttcgac   2700
```

-continued gacatggaat ccatccctgc cgtcacgacg tggaatacct atttgcgtta catcacggta 2760
cataaaagtc tgatattcgt cctgatctgg tgtcttgtga tcttcctcgc tgaagtcgca 2820
gccagcctgg tcgttctttg gctgctcggg aatacccccct tgcaggataa gggaaactcc 2880
acccactctc ggaacaatag ttacgccgtc atcattactt ccacttcctc atactacgta 2940
ttctatatat atgtcggggt cgctgataca ctgctggcca tgggcttctt tcgcggcctg 3000
ccgctcgtcc acacgctgat aactgtctcc aagatcttgc atcataagat gctgcactca 3060
gtgctgcagg ctccaatgag tacactgaat actcttaagg ctggcggcat cctgaaccgc 3120
tttagtaagg acatcgccat acttgacgat ctcttgcccc tgacaatctt cgattttatt 3180
caactccttt tgatcgttat cggggcgatc gctgtggttg ctgtgttgca gccatatata 3240
ttcgtagcta ctgttcccgt catcgtcgcg ttcatcatgc tccgtgccta ctttctgcag 3300
acgtcccaac agctgaagca gctcgagagc gagggacggt cccccatatt tacgcacttg 3360
gtaactagtc tgaaggggct gtggactctg agagcatttg gtcgacaacc atatttcgag 3420
accctctttc ataaggccct caacctgcac accgcgaatt ggtttctgta tttgagtacg 3480
ttgcggtggt ttcagatgcg catcgagatg atattcgtga tattctttat cgcagtcaca 3540
tttatcagca tcctgactac gggcgaggga gagggtcgcg tgggcatcat actcacgctc 3600
gctatgaaca ttatgagcac cctgcaatgg gccgtgaata gctctatcga cgttgacagt 3660
cttatgcgat ctgtgagccg agtctttaag ttcattgaca tgccaacaga aggtaaacct 3720
accaagtcaa ccaaaccata caagaatggc caactctcga aagttatgat tattgagaat 3780
tcacacgtga agaaagatga catctggccc tcagggggcc aaatgactgt caaagatctc 3840
acagcaaaat acacagaagg tggaaatgcc atattagaga acatttcctt ctcaataagt 3900
cctggccaga gggtgggcct cttgggaaga actggatcag ggaagagtac tttgttatca 3960 gctttttga gactactgaa cactgaagga gaaatccaga tcgatggtgt gtcttgggat 4020
tcaataactt tgcaacagtg gaggaaagcc tttggagtga taccacagaa agtatttatt 4080
ttttctggaa catttagaaa aaacttggat ccctatgaac agtggagtga tcaagaaata 4140
tggaaagttg cagatgaggt tgggctcaga tctgtgatag aacagtttcc tgggaagctt 4200
gactttgtcc ttgtggatgg gggctgtgtc ctaagccatg gccacaagca gttgatgtgc 4260
ttggctagat ctgttctcag taaggcgaag atcttgctgc ttgatgaacc cagtgctcat 4320
ttggatccag taacatacca aataattaga agaactctaa aacaagcatt tgctgattgc 4380
acagtaattc tctgtgaaca caggatagaa gcaatgctgg aatgccaaca atttttggtc 4440
atagaagaga acaaagtgcg gcagtacgat tccatccaga aactgctgaa cgagaggagc 4500
ctcttccggc aagccatcag cccctccgac agggtgaagc tctttcccca ccggaactca 4560
agcaagtgca agtctaagcc ccagattgct gctctgaaag aggagacaga agaagaggtg 4620
caagatacaa ggctttagac ccgctgatca gcctcgactg tgccttctag ttgccagcca 4680
tctgttgttt gcccctcccc cgtgccttcc ttgaccctgg aaggtgccac tcccactgtc 4740
ctttcctaat aaaatgagaa aattgcatcg cattgtctga gtaggtgtca ttctattctg 4800
gggggtgggg tggggcagga cagcaagggg gaggattggg aagacaatag caggcatgct 4860
ggggatgcgg tgggctctat gg 4882

<210> SEQ ID NO 402
<211> LENGTH: 1594
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 402
ccccaactgg ggtaaccttt gggctccccg ggcgcggttc cggatccgga gagggcaggg 60
gatctctcct tacttgtggc gacgtggagg agaaccccgg ccccatgagc atcggcctcc 120
tgtgctgtgc agccttgtct ctcctgtggg caggtccagt gaatgctggt gtcactcaga 180
ccccaaaatt ccaggtcctg aagacaggac agagcatgac actgcagtgt gcccaggata 240
tgaaccatga atacatgtcc tggtatcgac aagacccagg catggggctg aggctgattc 300
attactcagt tggtgctggt atcactgacc aaggagaagt ccccaatggc tacaatgtct 360
ccagatcaac cacagaggat ttcccgctca ggctgctgtc ggctgctccc tcccagacat 420
ctgtgtactt ctgtgccagc agttacgtcg ggaacaccgg ggagctgttt tttggagaag 480
gctctaggct gaccgtactg gaggacctga aaaacgtgtt cccacccgag gtcgctgtgt 540
ttgagccatc agaagcagag atctcccaca cccaaaaggc cacactggta tgcctggcca 600
caggcttcta ccccgaccac gtggagctga gctggtgggt gaatgggaag gaggtgcaca 660
gtggggtcag cacagacccg cagcccctca aggagcagcc cgccctcaat gactccagat 720
actgcctgag cagccgcctg agggtctcgg ccaccttctg gcagaacccc cgcaaccact 780
tccgctgtca agtccagttc tacgggctct cggagaatga cgagtggacc caggataggg 840
ccaaacccgt cacccagatc gtcagcgccg aggcctgggg tagagcagac tgtggcttca 900
cctccgagtc ttaccagcaa ggggtcctgt ctgccaccat cctctatgag atcttgctag 960
ggaaggccac cttgtatgcc gtgctggtca gtgccctcgt gctgatggct atggtcaaga 1020
gaaaggattc cagaggccgg gccaagcggt ccggatccgg agccaccaac ttcagcctgc 1080
tgaagcaggc cggcgacgtg gaggagaacc ccggccccat ggagaccctc ttgggcctgc 1140
ttatcctttg gctgcagctg caatgggtga gcagcaaaca ggaggtgacg cagattcctg 1200
cagctctgag tgtcccagaa ggagaaaact tggttctcaa ctgcagtttc actgatagcg 1260
ctatttacaa cctccagtgg tttaggcagg accctgggaa aggtctcaca tctctgttgc 1320
ttattcagtc aagtcagaga gagcaaacaa gtggaagact taatgcctcg ctggataaat 1380
catcaggacg tagtacttta tacattgcag cttctcagcc tggtgactca gccacctacc 1440
tctgtgctgt gaggcccctg tacggaggaa gctacatacc tacatttgga agaggaacca 1500
gccttattgt tcatccgtat atccagaacc ctgaccctgc gggtggtttg tctggtcaac 1560
caccgcggtc tcagtggtgt acggtacaaa ccca 1594

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 403
ttgagcgggc ccccaccgt 19

<210> SEQ ID NO 404
<211> LENGTH: 393
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 404
atgactcact atcaggcctt gcttttggac acggaccggg tccagttcgg accggtggta     60
gccctgaacc cggctacgct gctcccactg cctgaggaag ggctgcaaca caactgcctt    120
gatgggacag gtggcggtgg tgtcaccgtc aagttcaagt acaagggtga ggaacttgaa    180
gttgatatta gcaaaatcaa gaaggtttgg cgcgttggta aaatgatatc ttttacttat    240
gacgacaacg gcaagacagg tagaggggca gtgtctgaga aagacgcccc caaggagctg    300
ttgcaaatgt tggaaaagtc tgggaaaaag tctggcggct caaaaagaac cgccgacggc    360
agcgaattcg agcccaagaa gaagaggaaa gtc                                 393

<210> SEQ ID NO 405
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 405
cgacgacggc g                                                          11

<210> SEQ ID NO 406
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
tttatttgtg ggcccg                                                     16

<210> SEQ ID NO 407
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
tcgagtgccg catca                                                      15

<210> SEQ ID NO 408
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 408
aaagtggtga ggacact                                                    17

<210> SEQ ID NO 409
<211> LENGTH: 15
<212> TYPE: DNA
<213> ORGANISM: Artificial Sequence
<220> FEATURE:
<223> OTHER INFORMATION: Description of Artificial Sequence: Synthetic probe

<400> SEQUENCE: 409
aacccacccg agaga 15

<210> SEQ ID NO 410
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
ggaagcggag ctactaactt cagcctgctg aagcaggctg gcgacgtgga ggagaaccct 60
ggacct 66

<210> SEQ ID NO 411
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 411
gggggaggag gttctggagg cggaggctcc ggaggcggag ggtca 45

<210> SEQ ID NO 412
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 412
ggaggtggcg ggagc 15

<210> SEQ ID NO 413
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 413
cccgcaccag cgcct 15

<210> SEQ ID NO 414
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 414
gaggcagctg ccaaggaagc cgctgccaag gaggcggccg caaag 45

<210> SEQ ID NO 415
<211> LENGTH: 48
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 415

agtgggagcg agacccctgg gactagcgag tcagctacac ccgaaagc                48

<210> SEQ ID NO 416
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416

ggggggtcag gtggatccgg cggaagtggc ggatccggtg gatctggcgg cagt          54

<210> SEQ ID NO 417
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417

gaagctgctg ctaag                                                     15

<210> SEQ ID NO 418
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Gly Gly Gly Ser Gly Gly Gly Gly Ser Gly Gly Gly Gly Ser
1               5                   10                  15

<210> SEQ ID NO 420
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gly Gly Gly Gly Ser
1               5
```

<210> SEQ ID NO 421
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 421

Pro Ala Pro Ala Pro
1 5

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Glu Ala Ala Ala Lys Glu Ala Ala Ala Lys Glu Ala Ala Ala Lys
1 5 10 15

<210> SEQ ID NO 423
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Ser Gly Ser Glu Thr Pro Gly Thr Ser Glu Ser Ala Thr Pro Glu Ser
1 5 10 15

<210> SEQ ID NO 424
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Gly Gly Ser Gly Gly Ser Gly Gly Ser Gly Gly Ser Gly Gly Ser Gly
1 5 10 15

Gly Ser

<210> SEQ ID NO 425
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Glu Ala Ala Ala Lys
1 5

<210> SEQ ID NO 426
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 426

Gly Leu Ser Gly Gln Pro Pro Arg Ser Pro Ser Ser Gly Ser Ser Gly
1               5                   10                  15

<210> SEQ ID NO 427
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Gly Gly Leu Ser Gly Gln Pro Pro Arg Ser Pro Ser Ser Gly Ser Ser
1               5                   10                  15

Gly

<210> SEQ ID NO 428
<211> LENGTH: 88
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 428
gacgagcgcg gcgauaucau cauccauggc cggaugaucc ugacgacgga gaccgccguc     60
gucgacaagc cggccugagc ugcgagaa                                        88

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
gaagccggcc uugcacaugc                                                 20

<210> SEQ ID NO 430
<211> LENGTH: 95
<212> TYPE: DNA
<213> ORGANISM: Homo sapiens

<400> SEQUENCE: 430
gcgcgcccgg ctattctcgc agctcaccat ggatgatgat atcgccgcgc tcgtcgtcga     60
caacggctcc ggcatgtgca aggccggctt cgcgg                                95

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 431
accacucgac gcucuuaucg                                                 20